United States Patent
Lee et al.

(10) Patent No.: US 11,028,090 B2
(45) Date of Patent: Jun. 8, 2021

(54) [1,2,4]TRIAZOLO[4,3-A]QUINOXALINE DERIVATIVE, METHOD FOR PREPARING SAME, AND PHARMACEUTICAL COMPOSITION FOR PREVENTING OR TREATING BET PROTEIN-RELATED DISEASES, CONTAINING SAME AS ACTIVE INGREDIENT

(71) Applicants: Dong Wha Pharm. Co., Ltd., Seoul (KR); Korea Research Institute of Chemical Technology, Daejeon (KR)

(72) Inventors: Kwangho Lee, Daejeon (KR); Gildon Choi, Daejeon (KR); Imran Ali, Daejeon (KR); Joo Yun Lee, Daejeon (KR); Jin Soo Lee, Gyeonggi-do (KR); Whui Jung Park, Gyeonggi-do (KR); Yong Tae Kim, Gyeonggi-do (KR); Seung Hwan Kim, Gyeonggi-do (KR); Jung Hwan Kim, Gyeonggi-do (KR); Jae-Kyung Lim, Gyeonggi-do (KR)

(73) Assignees: Dong Wha Pharm. Co., Ltd., Seoul (KR); Korea Research Institute of Chemical Technology, Daejeon (KR)

( * ) Notice: Subject to any disclaimer, the term of this patent is extended or adjusted under 35 U.S.C. 154(b) by 19 days.

(21) Appl. No.: 16/480,908

(22) PCT Filed: Jan. 25, 2018

(86) PCT No.: PCT/KR2018/001128
§ 371 (c)(1),
(2) Date: Jul. 25, 2019

(87) PCT Pub. No.: WO2018/139876
PCT Pub. Date: Aug. 2, 2018

(65) Prior Publication Data
US 2020/0039984 A1    Feb. 6, 2020

(30) Foreign Application Priority Data

Jan. 26, 2017 (KR) .................. 10-2017-0012823

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ............................. C07D 487/04; C07D 519/00
USPC ......................................................... 544/346
See application file for complete search history.

(56) References Cited

U.S. PATENT DOCUMENTS

| 4,780,464 A | 10/1988 | Trivedi |
| 2011/0257137 A1 | 10/2011 | Borchardt |

FOREIGN PATENT DOCUMENTS

| JP | 2000-319277 A | 11/2000 | |
| JP | 2000319277 | * 11/2000 | ........... C07D 487/04 |
| KR | 20110095857 | 9/2009 | |
| KR | 10-2014-0090984 A | 7/2014 | |

OTHER PUBLICATIONS

International Search Report issued in PCT/KR2018/001128 dated May 8, 2018.
Wagle, et al. "Synthesis of Some New 4-styryltetrazolo[1,5-a]quinoxaline and 1-substituted-4-styryl,[1,2,4]triazolo[4,3-a]quinoxaline derivatives as potent anticonvultants" European Journal of Medicinal Chemistry, 2009, vol. 44, pp. 1135-1143.
French, et al. "BRD-NUT oncoproteins: a family of closely related nuclear proteins that block epithelial differentiation and maintain the growth of carcinoma cells" Oncogene 2008, vol. 27, pp. 2237-2242.
Reinhard et al. "4-Amino[1,2,4]triazolo[4,3-a]quinoxalines. A novel Class of Potent Adenosine Receptor Antagonists and Potential Rapid-Onset Antidepressants" J. Med. Chem. 1990, 33, 2240-2254.

* cited by examiner

*Primary Examiner* — Jeffrey H Murray
(74) *Attorney, Agent, or Firm* — Workman Nydegger

(57) ABSTRACT

Provided are a novel [1,2,4]triazolo[4,3-a]quinoxaline derivative, a method for preparing the same, and a pharmaceutical composition for preventing or treating bromodomain extra-terminal (BET) protein-related diseases including cancer and autoimmune diseases, containing the same as an active ingredient.

6 Claims, No Drawings

[1,2,4]TRIAZOLO[4,3-A]QUINOXALINE DERIVATIVE, METHOD FOR PREPARING SAME, AND PHARMACEUTICAL COMPOSITION FOR PREVENTING OR TREATING BET PROTEIN-RELATED DISEASES, CONTAINING SAME AS ACTIVE INGREDIENT

CROSS-REFERENCE TO RELATED APPLICATIONS

This application claims priority to PCT Application No. PCT/KR2018/001128 filed Jan. 25, 2018, entitled "NOVEL [1,2,4]TRIAZOLO[4,3-A]QUINOXALINE DERIVATIVE, METHOD FOR PREPARING SAME, AND PHARMACEUTICAL COMPOSITION FOR PREVENTING OR TREATING BET PROTEIN-RELATED DISEASES, CONTAINING SAME AS ACTIVE INGREDIENT," which claims the benefit of and priority to Korean Patent Application No. 10-2017-0012823, filed on Jan. 26, 2017. All the aforementioned applications are incorporated by reference herein in their entirety.

BACKGROUND OF THE INVENTION

1. Field of the Invention

The present invention relates to a novel [1,2,4]triazolo[4,3-a]quinoxaline derivative, a method for preparing the same, and a pharmaceutical composition for preventing or treating bromodomain extra-terminal (BET) protein-related diseases including cancer and autoimmune diseases, containing the same as an active ingredient.

2. Description of the Related Art

Histone is a basic protein ionically binding to genomic DNA, which commonly exists in the nucleus of eukaryotic cells from human and other multicellular organisms to unicellular organisms represented by Eumycetes (fungus, yeast). In general, histone is composed of 5 components (H1, H2A, H2B, H3 and H4), and is highly similar in all species. Genomic DNA is stacked by regular binding with histone, and the complex of both forms a basic structural unit called nucleosome. Chromatin structure of chromosome is formed by the aggregation of the said nucleosome.

Histone is modified by acetylation, methylation, phosphorylation, ubiquitination, and sumoylation at the N-terminus of histone tail. By the modification above, the reactions that occur in chromosomal DNA such as gene expression, DNA duplication and DNA repair are controlled by maintaining the chromatin structure or specifically converting the structure.

In particular, acetylation of histone is closely related to the activation of gene transcription. This is because the modification caused by histone acetylation changes static electricity, so that the interaction between DNA and histone octomer becomes loose and thereby transcription is induced efficiently. In addition to these physical changes, a specific protein binds to acetylated lysine residues in histone, by which the protein is involved in gene transcription. Such a specific protein contains bromodomain.

Among those proteins containing bromodomain, BET (bromodomain extra-terminal) family includes the following 4 proteins, BRD2, BRD3, BRD4 and BRDT, 2 bromodomains and 1 extra-terminal domain. The said BET family plays an important role in immune response and inflammatory response.

For example, BRD4 protein stimulates NF-κB (Nuclear Factor-kappa B) involved in inflammatory response or auto-immunity to cause auto-immune diseases including rheumatoid arthritis, systemic lupus erythematosus, multiple sclerosis, type 1 diabetes, hyperthyroidism, myasthenia, Crohn's disease, ankylosing spondylitis, psoriasis, autoimmune malignant anemia, Sjogren's syndrome, and the like.

Particularly, the NF-κB protein is a transcription factor protein regulating various signal transmission systems involved in inflammatory response, immune function, aging and tumor. In the absence of external stimuli, it binds to an inhibitory molecule called IκB (inhibitory KB), and is present in the cytoplasm in the inactive state. However, when external stimuli are present, IκB is phosphorylated and inactivated by IκB kinase (IKK) via intracellular signaling. Accordingly, NF-κB separated from IκB becomes activated and then moves into the nucleus, and thereby transcription of a target gene is induced.

In addition, BET protein has been reported to play an important role in various types of tumors.

In particular, BRD4 and BRD3 bind to NUT (nucleoprotein in testis) in malignant epithelial tumors to form BRD3-NUT or BRD4-NUT, a novel fusion oncogene, according to the previous reports. BRD-NUT fusion protein has been reported to prevent cell differentiation, promote proliferation and contribute to carcinogenesis (Oncogene 2008, 27, 2237-2242). In addition, amplification of DNA region containing BRD4 gene was detected in breast tumor. In the transgenic mice over-expressing BRD2 in B cells, the development of B cell lymphoma and leukemia was reported.

Further, BET protein plays an important role in cell growth and cell cycle and also relates to viral infection.

Therefore, the said BET protein has been on the spotlight as a target for the treatment of various diseases.

SUMMARY OF THE INVENTION

It is an object of the present invention to provide a novel [1,2,4]triazolo[4,3-a]quinoxaline derivative, an optical isomer thereof or a pharmaceutically acceptable salt thereof.

It is another object of the present invention to provide a preparation method of the novel [1,2,4]triazolo[4,3-a]quinoxaline derivative.

It is also an object of the present invention to provide a pharmaceutical composition comprising the novel [1,2,4]triazolo[4,3-a]quinoxaline derivative as an active ingredient for the prevention or treatment of BET (bromodomain extra-terminal) protein related diseases.

To achieve the above objects, according to an aspect of the present invention, the present invention provides a compound represented by formula 1 below, an optical isomer thereof or a pharmaceutically acceptable salt thereof:

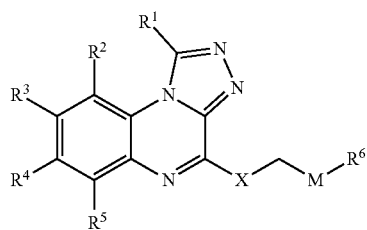

[Formula 1]

(In formula 1, $R^1$ is hydrogen, $C_{1-20}$ straight or branched alkyl nonsubstituted or substituted with one or more halogens, or $C_{6-20}$ aryl;

$R^2$ is hydrogen, $C_{1-20}$ straight or branched alkyl, or $C_{1-20}$ straight or branched alkoxy;

$R^3$ is hydrogen, nitro, halogen, nonsubstituted or substituted $C_{1-20}$ straight or branched alkyl, nonsubstituted or substituted $C_{1-20}$ straight or branched alkoxy, 5-10 membered heteroaryl nonsubstituted or substituted with one or more methyl groups containing one or more heteroatoms selected from the group consisting of N, O and S,

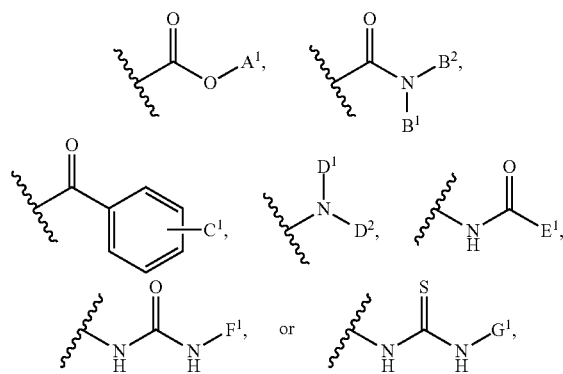

which forms 6 membered cycloalkyl containing one or more heteroatoms selected from the group consisting of S and O along with $R^4$, wherein, the substituted $C_{1-20}$ straight or branched alkyl and the substituted $C_{1-20}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, $A^1$ is hydrogen, or $C_{1-20}$ straight or branched alkyl, $B^1$ and $B^2$ are independently hydrogen, $C_{1-20}$ straight or branched alkyl, $diC_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-20}$ straight or branched alkyl, or $C_{1-20}$ straight or branched alkoxy, $D^1$ and $D^2$ are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl, $E^1$ is $C_{1-20}$ straight or branched alkyl, or $C_{6-10}$ aryl $C_{1-5}$ straight or branched alkyl, $F^1$ is $C_{1-20}$ straight or branched alkyl, or $C_{6-10}$ aryl, $G^1$ is $C_{1-20}$ straight or branched alkyl, or $C_{6-10}$ aryl;

$R^4$ is hydrogen, hydroxy, halogen, nitro, $C_{1-20}$ straight or branched alkyl nonsubstituted or substituted with one or more =S groups, $C_{1-20}$ straight or branched alkylsulfanyl nonsubstituted or substituted with one or more oxo (=O) groups, $C_{1-20}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-20}$ straight or branched alkoxy,

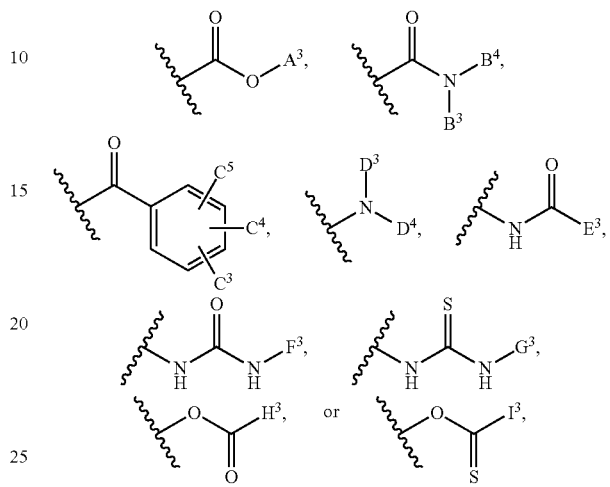

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-20}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

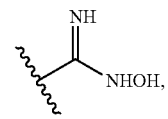

$C_{1-5}$ straight or branched alkoxycarbonyl, and 5-8 membered heteroaryl nonsubstituted or substituted with one or more N groups, $A^3$ is hydrogen, or $C_{1-20}$ straight or branched alkyl, $B^3$ and $B^4$ are independently hydrogen, $C_{1-20}$ straight or branched alkyl, $diC_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-20}$ straight or branched alkyl, or $C_{1-20}$ straight or branched alkoxy, $D^3$ and $D^4$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-20}$ straight or branched alkyl, or $C_{6-10}$ aryl $C_{1-5}$ straight or branched alkyl, $F^3$ is $C_{1-20}$ straight or branched alkyl, or $C_{6-10}$ aryl, $G^3$ is $C_{1-20}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is $diC_{1-3}$ straight or branched alkylamino;

$R^5$ is hydrogen, halogen, $C_{1-20}$ straight or branched alkyl nonsubstituted or substituted with one or more halogens, or $C_{1-20}$ straight or branched alkoxy;

$R^6$ is hydroxy,

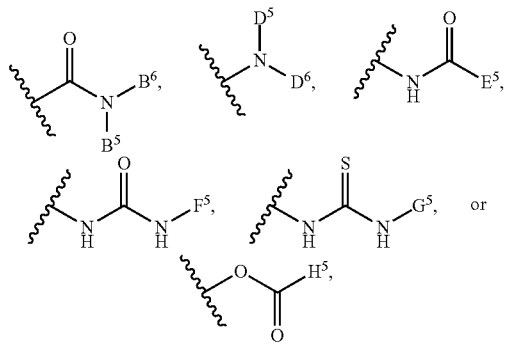

$B^5$ and $B^6$ are independently hydrogen, $C_{1-20}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, $E^5$ is $C_{1-20}$ straight or branched alkyl saturated or containing one or more carbon=carbon unsaturated bonds, $C_{1-20}$ straight or branched alkoxy saturated or containing one or more carbon=carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-20}$ straight or branched alkylsulfanyl, nonsubstituted or substituted $C_{6-10}$ aryl, $diC_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-20}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

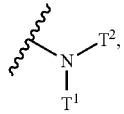

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-20}$ straight or branched alkyl, $C_{3-10}$ cycloalkyl, or $C_{6-10}$ aryl nonsubstituted or substituted with one or more halogens, $G^5$ is $C_{1-20}$ straight or branched alkyl, $H^5$ is $C_{1-20}$ straight or branched alkyl, or $C_{6-10}$ aryl nonsubstituted or substituted with one or more halogens;

M is $C_{1-20}$ straight or branched alkylene; and

X is —NH—, or —O—).

According to another aspect of the present invention, the present invention also provides a preparation method of the compound represented by formula 1 comprising the following steps, as shown in reaction formula 1 below:

preparing the compound represented by formula 4 by reacting the compound represented by formula 2 with the compound represented by formula 3 (step 1); and preparing the compound represented by formula 1 by reacting the compound represented by formula 4 prepared in step 1 above with the compound represented by formula 5 (step 2):

[Reaction Formula 1]

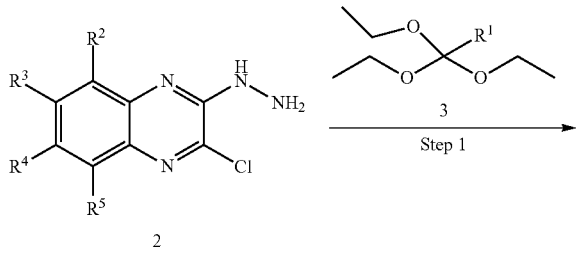

-continued

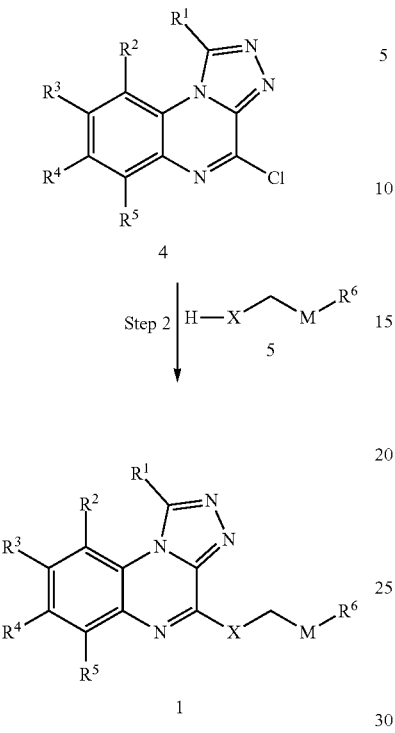

(In reaction formula 1,
R¹~R⁶, M and X are independently as defined in formula 1 above)

According to another aspect of the present invention, the present invention also provides a preparation method of the compound represented by formula 1 comprising the following steps, as shown in reaction formula 2 below:

preparing the compound represented by formula 8 by reacting the compound represented by formula 7 with the compound represented by formula 5 (step 1);

preparing the compound represented by formula 9 by reacting the compound represented by formula 8 prepared in step 1 above with hydrazine hydrate (step 2); and preparing the compound represented by formula 1 by reacting the compound represented by formula 9 prepared in step 2 above with the compound represented by formula 3 (step 3):

[Reaction Formula 2]

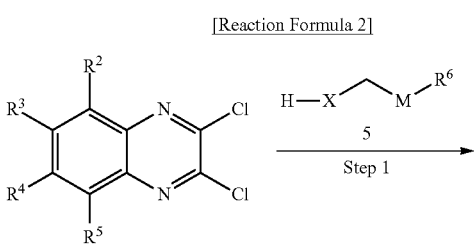

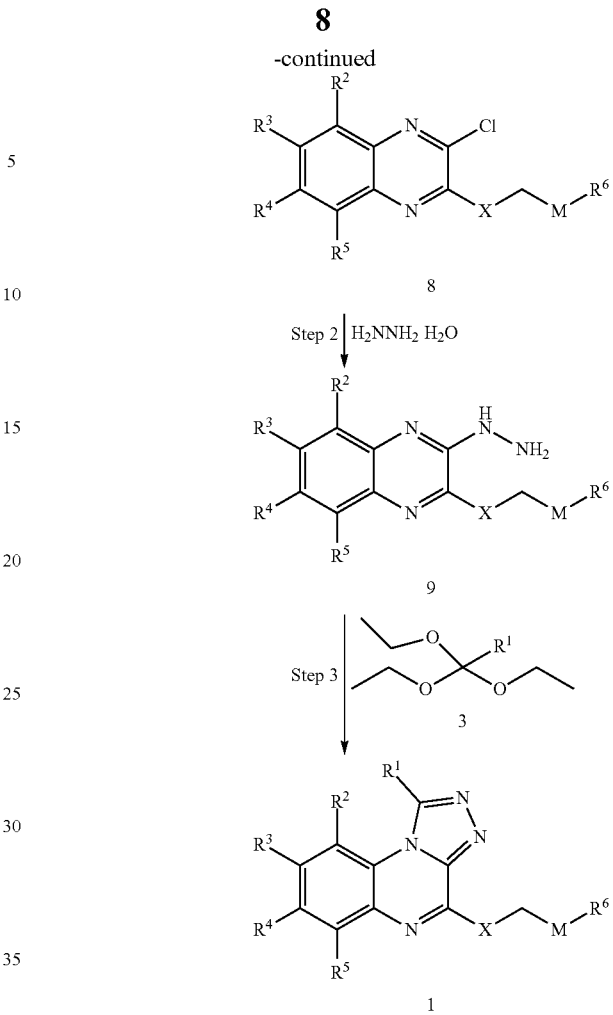

(In reaction formula 2,
R¹~R⁶, M and X are independently as defined in formula 1 above).

According to another aspect of the present invention, the present invention provides a pharmaceutical composition comprising the compound represented by formula 1, the optical isomer thereof or the pharmaceutically acceptable salt thereof as an active ingredient for the prevention or treatment of BET (bromodomain extra-terminal) protein related diseases.

According to another aspect of the present invention, the present invention provides a method for preventing, ameliorating or treating BET (bromodomain extra-terminal) protein related diseases which comprises a step of administering the pharmaceutical composition comprising the compound represented by formula 1, the optical isomer thereof or the pharmaceutically acceptable salt thereof as an active ingredient to a subject.

In addition, according to another aspect of the present invention, the present invention provides a use of the pharmaceutical composition comprising the compound represented by formula 1, the optical isomer thereof or the pharmaceutically acceptable salt thereof as an active ingredient.

Advantageous Effect

The novel [1,2,4]triazolo[4,3-a]quinoxaline derivative provided in an aspect of the present invention, inhibits the binding of BRD4, one of BET protein family, at a low concentration, and displays excellent cytotoxicity in tumor cells, so that it can be used as a pharmaceutical composition for the prevention or treatment of BET protein related diseases including cancer and autoimmune disease.

DESCRIPTION OF THE PREFERRED EMBODIMENTS

Hereinafter, the present invention is described in detail.

In an aspect of the present invention, the present invention provides a compound represented by formula 1, an optical isomer thereof or a pharmaceutically acceptable salt thereof:

[Formula 1]

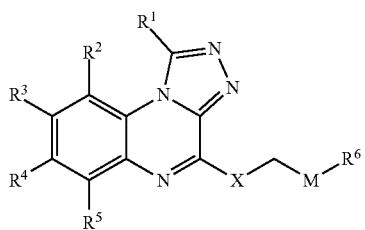

(In formula 1, $R^1$ is hydrogen, $C_{1-20}$ straight or branched alkyl nonsubstituted or substituted with one or more halogens, or $C_{6-20}$ aryl;

$R^2$ is hydrogen, $C_{1-20}$ straight or branched alkyl, or $C_{1-20}$ straight or branched alkoxy;

$R^3$ is hydrogen, nitro, halogen, nonsubstituted or substituted $C_{1-20}$ straight or branched alkyl, nonsubstituted or substituted $C_{1-20}$ straight or branched alkoxy, 5-10 membered heteroaryl nonsubstituted or substituted with one or more methyl groups containing one or more heteroatoms selected from the group consisting of N, O and S,

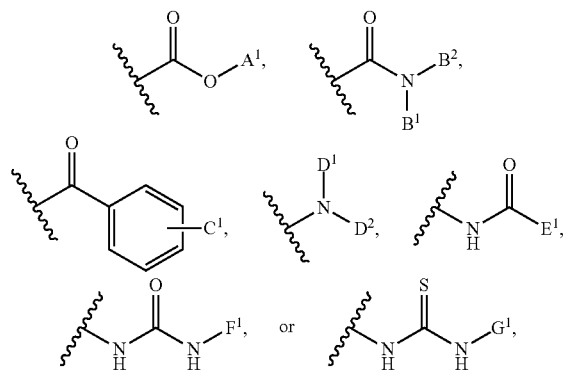

which forms 6 membered cycloalkyl containing one or more heteroatoms selected from the group consisting of S and O along with $R^4$, wherein, the substituted $C_{1-20}$ straight or branched alkyl and the substituted $C_{1-20}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, $A^1$ is hydrogen, or $C_{1-20}$ straight or branched alkyl, $B^1$ and $B^2$ are independently hydrogen, $C_{1-20}$ straight or branched alkyl, $diC_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-20}$ straight or branched alkyl, or $C_{1-20}$ straight or branched alkoxy, $D^1$ and $D^2$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl, $E^1$ is $C_{1-20}$ straight or branched alkyl, or $C_{6-10}$ aryl $C_{1-5}$ straight or branched alkyl, $F^1$ is $C_{1-20}$ straight or branched alkyl, or $C_{6-10}$ aryl, $G^1$ is $C_{1-20}$ straight or branched alkyl, or $C_{6-10}$ aryl;

$R^4$ is hydrogen, hydroxy, halogen, nitro, $C_{1-20}$ straight or branched alkyl nonsubstituted or substituted with one or more =S groups, $C_{1-20}$ straight or branched alkylsulfanyl nonsubstituted or substituted with one or more oxo (=O) groups, $C_{1-20}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-20}$ straight or branched alkoxy,

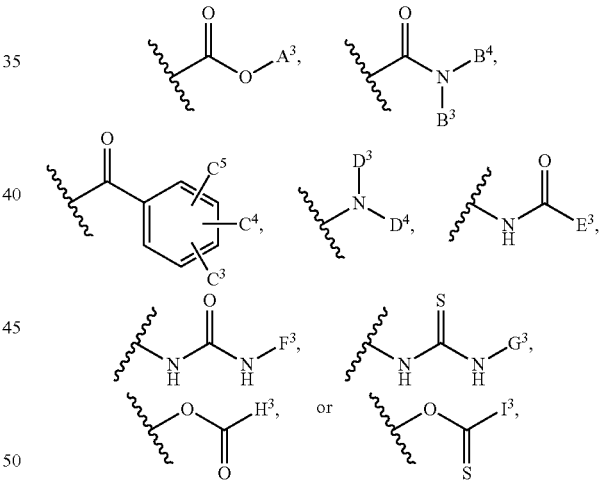

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-20}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

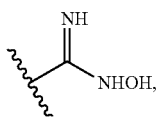

C$_{1-5}$ straight or branched alkoxycarbonyl, and 5-8 membered heteroaryl nonsubstituted or substituted with one or more N groups, A$^3$ is hydrogen, or C$_{1-20}$ straight or branched alkyl, B$^3$ and B$^4$ are independently hydrogen, C$_{1-20}$ straight or branched alkyl, diC$_{1-3}$ straight or branched alkylamino C$_{1-3}$ straight or branched alkyl, nonsubstituted or substituted C$_{6-10}$ aryl, nonsubstituted or substituted C$_{6-10}$ aryl C$_{1-3}$ straight or branched alkyl, and B$^3$ and B$^4$ are linked to each other to form 5-10 membered heterocycloalkyl nonsubstituted or substituted with one or more benzyl groups containing one or more heteroatoms selected from the group consisting of N, O and S, wherein, the substituted C$_{6-10}$ aryl can be substituted with one or more substituents selected from the group consisting of amine, halogen, C$_{1-5}$ straight or branched alkyl and C$_{1-5}$ straight or branched alkoxy, C$^3$, C$^4$ and C$^5$ are independently hydrogen, amine, halogen, C$_{1-20}$ straight or branched alkyl, or C$_{1-20}$ straight or branched alkoxy, D$^3$ and D$^4$ are independently hydrogen, hydroxy, C$_{1-20}$ straight or branched alkyl saturated or containing one or more carbon≡carbon unsaturated bonds, C$_{1-20}$ straight or branched alkyl nonsubstituted or substituted with one or more cyano groups, or C$_{1-20}$ straight or branched alkylsulfonyl nonsubstituted or substituted with one or more halogens, and D$^3$ and D$^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, E$^3$ is C$_{1-20}$ straight or branched alkyl, or C$_{6-10}$ aryl C$_{1-5}$ straight or branched alkyl, F$^3$ is C$_{1-20}$ straight or branched alkyl, or C$_{6-10}$ aryl, G$^3$ is C$_{1-20}$ straight or branched alkyl, or C$_{6-10}$ aryl, H$^3$ is C$_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, I$^3$ is diC$_{1-3}$ straight or branched alkylamino;

R$^5$ is hydrogen, halogen, C$_{1-20}$ straight or branched alkyl nonsubstituted or substituted with one or more halogens, or C$_{1-20}$ straight or branched alkoxy;

R$^6$ is hydroxy,

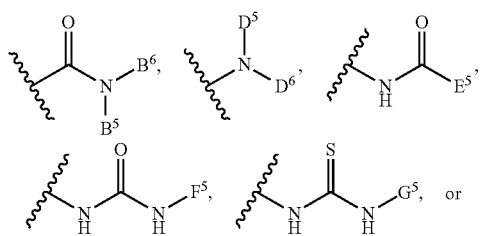

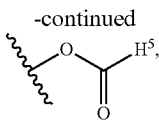

B$^5$ and B$^6$ are independently hydrogen, C$_{1-20}$ straight or branched alkyl, C$_{6-10}$ aryl C$_{1-3}$ straight or branched alkyl, or 5-10 membered heteroaryl C$_{1-3}$ straight or branched alkyl containing one or more heteroatoms selected from the group consisting of N, O and S, D$^5$ and D$^6$ are independently hydrogen, hydroxy, C$_{1-20}$ straight or branched alkyl saturated or containing one or more carbon≡carbon unsaturated bonds, C$_{1-20}$ straight or branched alkyl nonsubstituted or substituted with one or more cyano groups, or C$_{1-20}$ straight or branched alkylsulfonyl nonsubstituted or substituted with one or more halogens, E$^5$ is C$_{1-20}$ straight or branched alkyl saturated or containing one or more carbon≡carbon unsaturated bonds, C$_{1-20}$ straight or branched alkoxy saturated or containing one or more carbon≡carbon unsaturated bonds, C$_{3-10}$ cycloalkyloxy, C$_{3-10}$ cycloalkyl C$_{1-3}$ straight or branched alkyl, C$_{3-10}$ cycloalkyl, C$_{6-10}$ aryloxy, C$_{6-10}$ aryl C$_{1-3}$ straight or branched alkoxy, C$_{1-20}$ straight or branched alkylsulfanyl, nonsubstituted or substituted C$_6$ 10 aryl, diC$_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted C$_{1-20}$ straight or branched alkyl can be substituted with one or more substituents selected from the group consisting of hydroxy, halogen, C$_{1-3}$ straight or branched alkoxy, C$_{1-3}$ straight or branched alkylcarbonyloxy, C$_{1-3}$ straight or branched alkoxycarbonyl, hydroxycarbonyl, C$_{6-10}$ aryl nonsubstituted or substituted with one or more hydroxyl groups, 5-10 membered heteroaryl containing one or more heteroatoms selected from the group consisting of N, O and S, and

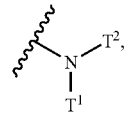

T$^1$ and T$^2$ are independently hydrogen, C$_{1-5}$ straight or branched alkyl, C$_{1-5}$ straight or branched alkoxycarbonyl, C$_{1-5}$ straight or branched alkylcarbonyl nonsubstituted or substituted with one or more halogens or hydroxyl groups, and T$^1$ and T$^2$ are linked to each other to form heterocycloalkyl nonsubstituted or substituted with one or more hydroxyl groups or C$_{1-3}$ straight or branched alkyl groups containing one S group and one or more heteroatoms selected from the group consisting of N, O and S, wherein, the substituted C$_{6-10}$ aryl and the substituted 5-10 membered heteroaryl can be independently substituted with one or more substituents selected from the group consisting of halogen, nitro, C$_{1-5}$ straight or branched alkyl and C$_{1-5}$ straight or branched alkoxy, F$^5$ is C$_{1-20}$ straight or branched alkyl, C$_{3-10}$ cycloalkyl, or C$_{6-10}$ aryl nonsubstituted or substituted with one or more halogens, G$^5$ is C$_{1-20}$ straight or branched alkyl, H$^5$ is C$_{1-20}$ straight or branched alkyl, or C$_{6-10}$ aryl nonsubstituted or substituted with one or more halogens;

M is C$_{1-20}$ straight or branched alkylene; and

X is —NH—, or —O—).

Preferable examples of the substituent according to formula 1 above are as follows:

The compound, the optical isomer thereof or the pharmaceutically acceptable salt thereof wherein:

$R^1$ is hydrogen, $C_{1-10}$ straight or branched alkyl nonsubstituted or substituted with one or more halogens, or $C_{6-10}$ aryl;

$R^2$ is hydrogen, $C_{1-10}$ straight or branched alkyl, or $C_{1-10}$ straight or branched alkoxy;

$R^3$ is hydrogen, nitro, halogen, nonsubstituted or substituted $C_{1-10}$ straight or branched alkyl, nonsubstituted or substituted $C_{1-10}$ straight or branched alkoxy, 5-10 membered heteroaryl nonsubstituted or substituted with one or more methyl groups containing one or more heteroatoms selected from the group consisting of N, O and S,

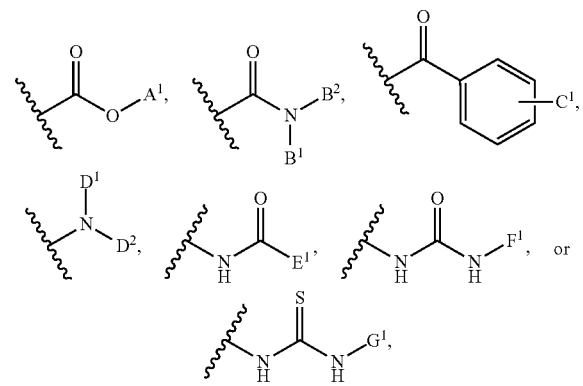

which forms 6 membered cycloalkyl containing one or more heteroatoms selected from the group consisting of S and O along with $R^4$, wherein, the substituted $C_{1-10}$ straight or branched alkyl and the substituted $C_{1-10}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_6$ aryl nonsubstituted or substituted with one or more nitro groups, $A^1$ is hydrogen, or $C_{1-10}$ straight or branched alkyl, $B^1$ and $B^2$ are independently hydrogen, $C_{1-10}$ straight or branched alkyl, $diC_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-10}$ straight or branched alkyl, or $C_{1-10}$ straight or branched alkoxy, $D^1$ and $D^2$ are independently hydrogen, hydroxy, $C_{1-10}$ straight or branched alkyl saturated or containing one or more carbon≡carbon unsaturated bonds, $C_{1-10}$ straight or branched alkyl nonsubstituted or substituted with one or more cyano groups, or $C_{1-10}$ straight or branched alkylsulfonyl, $E^1$ is $C_{1-10}$ straight or branched alkyl, or $C_{6-10}$ aryl $C_{1-5}$ straight or branched alkyl, $F^1$ is $C_{1-10}$ straight or branched alkyl, or $C_{6-10}$ aryl, $G^1$ is $C_{1-10}$ straight or branched alkyl, or $C_{6-10}$ aryl;

$R^4$ is hydrogen, hydroxy, halogen, nitro, $C_{1-10}$ straight or branched alkyl nonsubstituted or substituted with one or more =S groups, $C_{1-10}$ straight or branched alkylsulfanyl nonsubstituted or substituted with one or more oxo (=O) groups, $C_{1-10}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-10}$ straight or branched alkoxy,

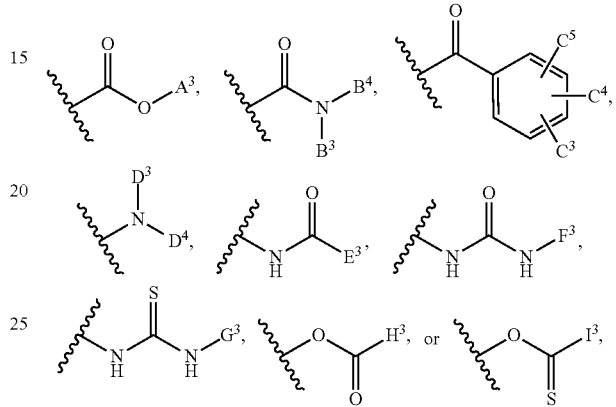

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-10}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_6$ 10 aryl can be independently substituted with one or more substituents selected from the group consisting of cyano,

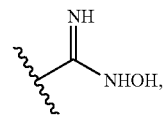

$C_{1-5}$ straight or branched alkoxycarbonyl, and 5-8 membered heteroaryl nonsubstituted or substituted with one or more N groups, $A^3$ is hydrogen, or $C_{1-10}$ straight or branched alkyl, $B^3$ and $B^4$ are independently hydrogen, $C_{1-10}$ straight or branched alkyl, $diC_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-10}$ straight or branched alkyl, or $C_{1-10}$ straight or branched alkoxy, $D^3$ and $D^4$ are independently hydrogen, hydroxy, $C_{1-10}$ straight or branched alkyl saturated or containing one or more carbon≡carbon unsaturated bonds, $C_{1-10}$ straight or branched alkyl nonsubstituted or substituted with one or more cyano groups, or $C_{1-10}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-10}$ straight or branched alkyl, or $C_{6-10}$ aryl $C_{1-5}$ straight or branched alkyl, $F^3$ is $C_{1-10}$ straight or branched alkyl, or $C_{6-10}$ aryl, $G^3$ is $C_{1-10}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is di$C_{1-3}$ straight or branched alkylamino;

$R^5$ is hydrogen, halogen, $C_{1-10}$ straight or branched alkyl nonsubstituted or substituted with one or more halogens, or $C_{1-10}$ straight or branched alkoxy;

$R^6$ is hydroxy,

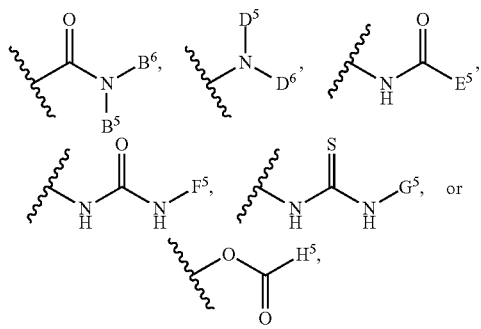

$B^5$ and $B^6$ are independently hydrogen, $C_{1-10}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-10}$ straight or branched alkyl saturated or containing one or more carbon≡carbon unsaturated bonds, $C_{1-10}$ straight or branched alkyl nonsubstituted or substituted with one or more cyano groups, or $C_{1-10}$ straight or branched alkylsulfonyl nonsubstituted or substituted with one or more halogens, $E^5$ is $C_{1-10}$ straight or branched alkyl saturated or containing one or more carbon≡carbon unsaturated bonds, $C_{1-10}$ straight or branched alkoxy saturated or containing one or more carbon≡carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-10}$ straight or branched alkylsulfanyl, nonsubstituted or substituted $C_{6-10}$ aryl, di$C_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-10}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

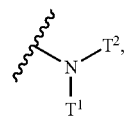

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-10}$ straight or branched alkyl, $C_{3-10}$ cycloalkyl, or $C_6$ 10 aryl nonsubstituted or substituted with one or more halogens, $G^5$ is $C_{1-10}$ straight or branched alkyl, $H^5$ is $C_{1-10}$ straight or branched alkyl, or $C_{6-10}$ aryl nonsubstituted or substituted with one or more halogens;

M is $C_{1-10}$ straight or branched alkylene; and

X is —NH—, or —O—.

More preferable examples of the substituent according to formula 1 above are as follows:

The compound, the optical isomer thereof or the pharmaceutically acceptable salt thereof wherein:

$R^1$ is —H, —CH$_3$, —CH$_2$CH$_3$, —CF$_3$,

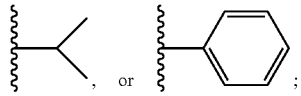

$R^2$ is —H, —CH$_3$, or —OCH$_3$;

$R^3$ is —H, —Cl, —F, —CH$_3$, —CF$_3$, —OCH$_3$, —OCF$_3$, —NO$_2$, —NH$_2$,

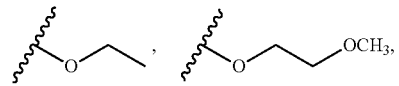

-continued
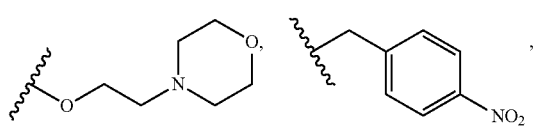
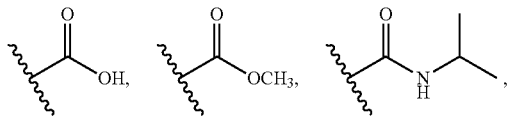
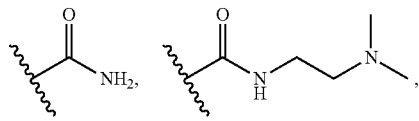
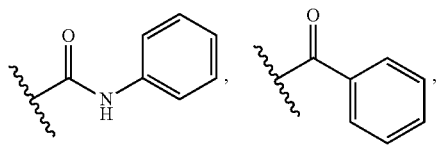
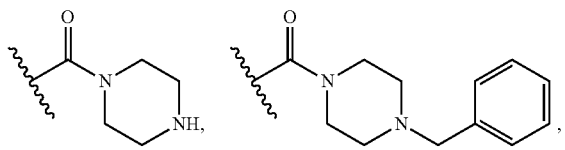
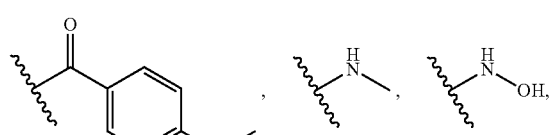
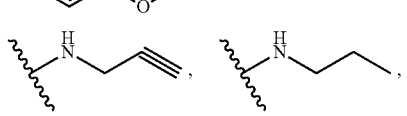
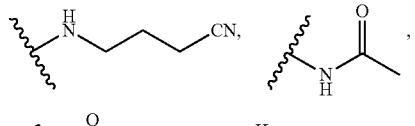
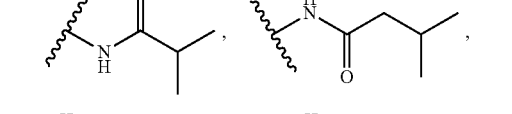
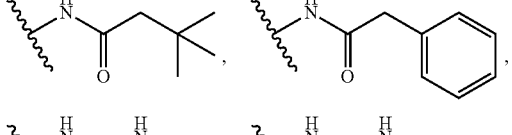
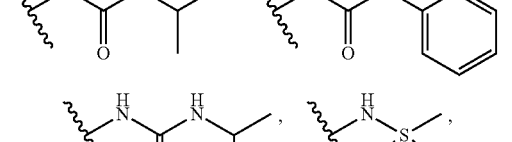
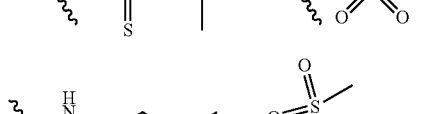
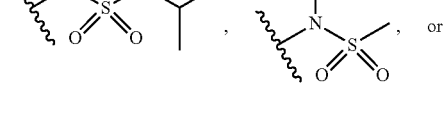
-continued
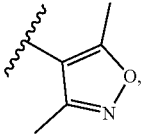
which forms
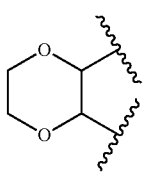 [SMILES: *C1OCCOC1*]
along with $R^4$;
$R^4$ is —H, —OH, —Cl, —F, —CH$_3$, —OCH$_3$, —SCH$_3$, —OCF$_3$, —NO$_2$, —NH$_2$,
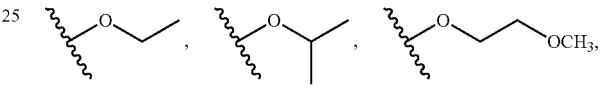
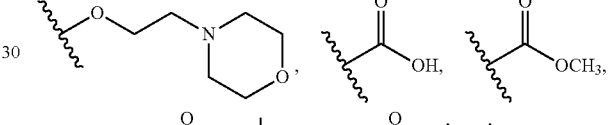
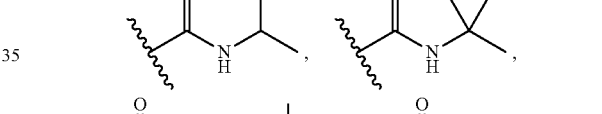
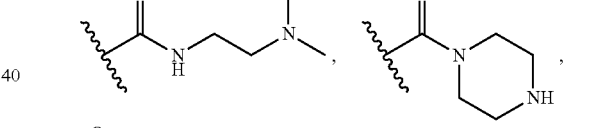
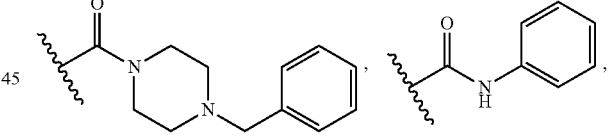
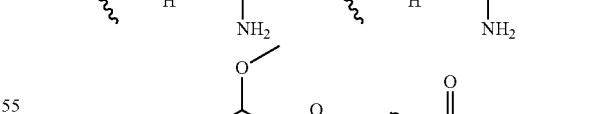
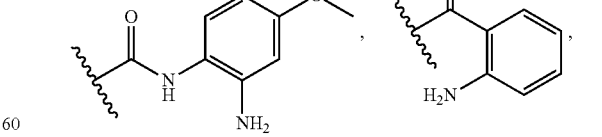
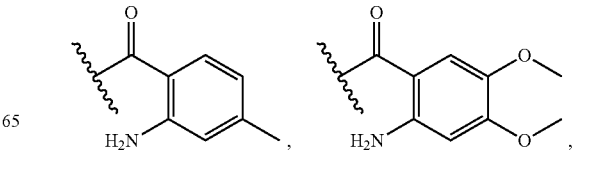

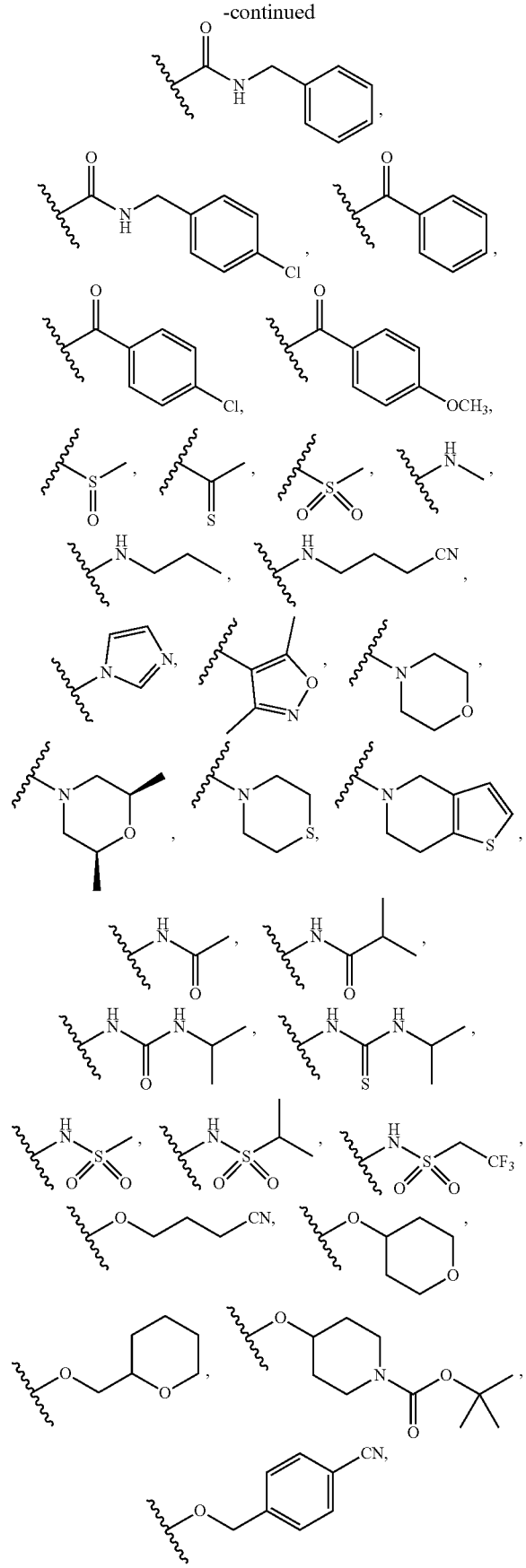
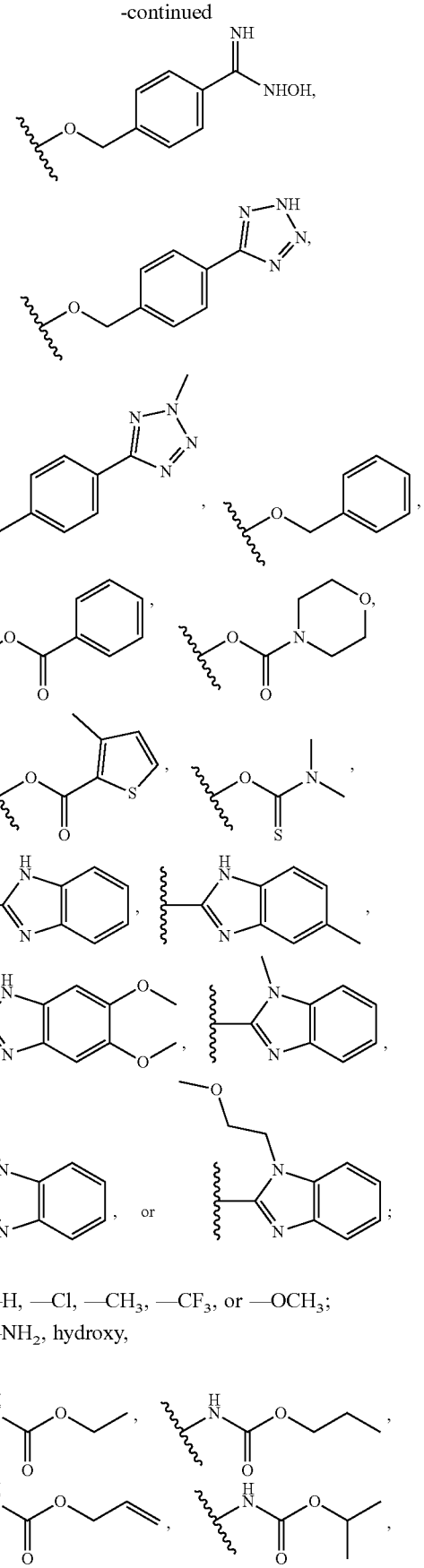
$R^5$ is —H, —Cl, —CH$_3$, —CF$_3$, or —OCH$_3$;
$R^6$ is —NH$_2$, hydroxy,
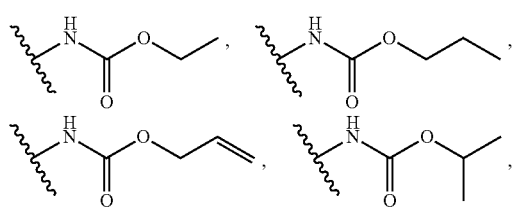

-continued
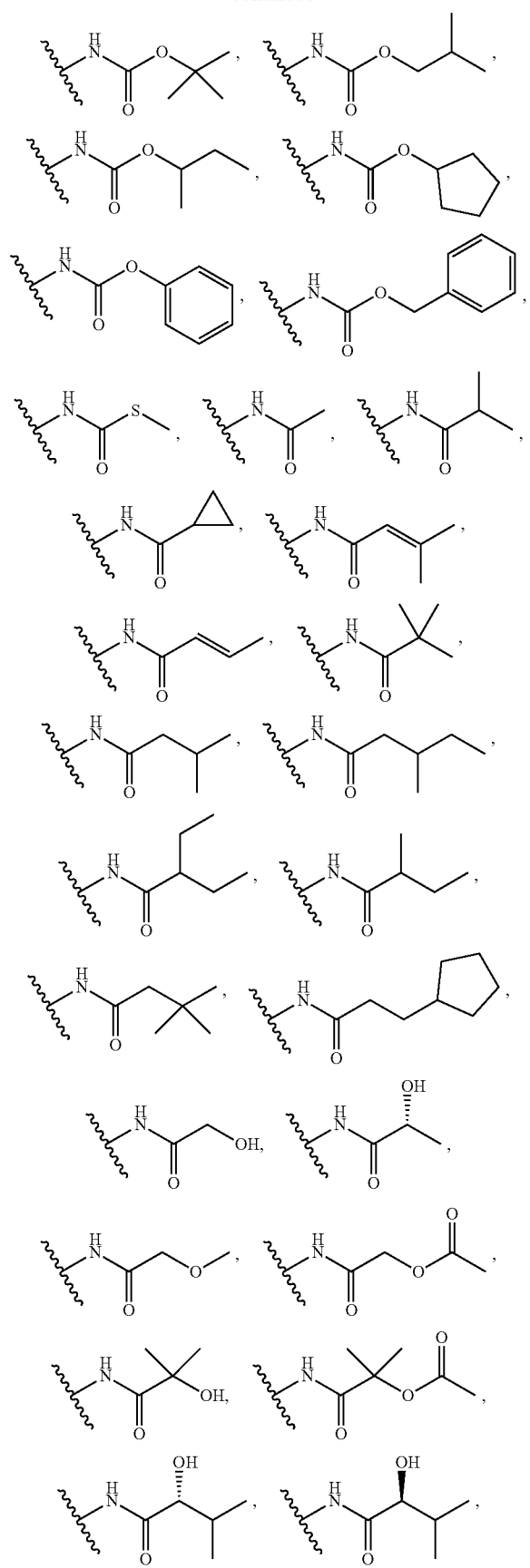
-continued
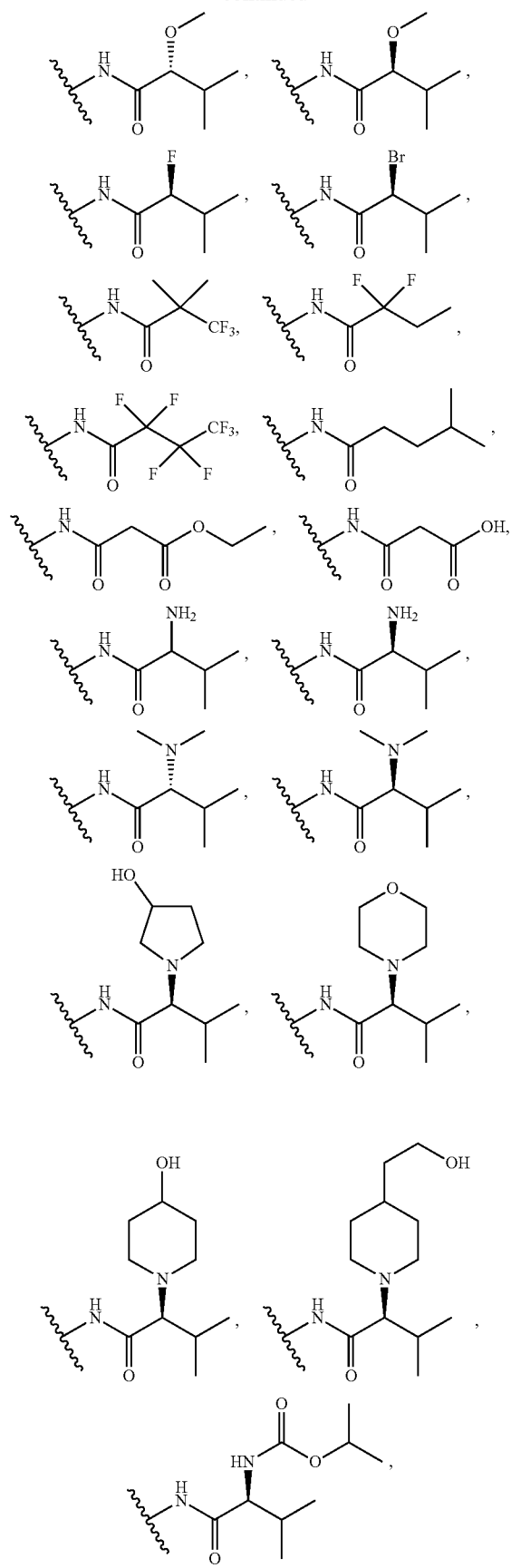

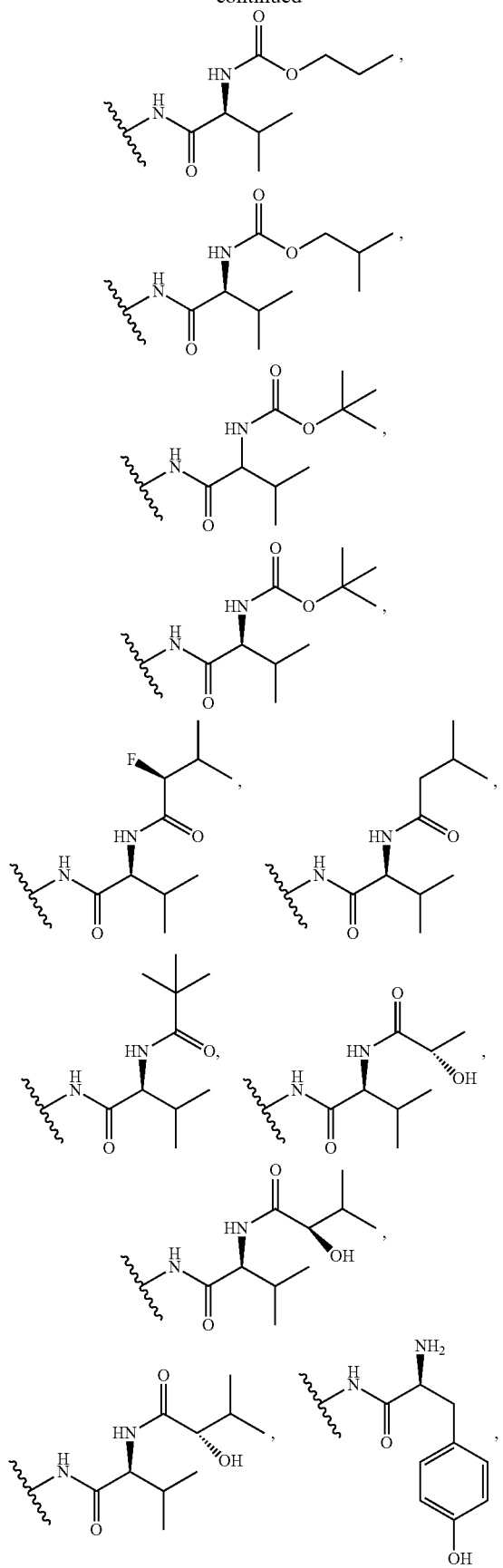
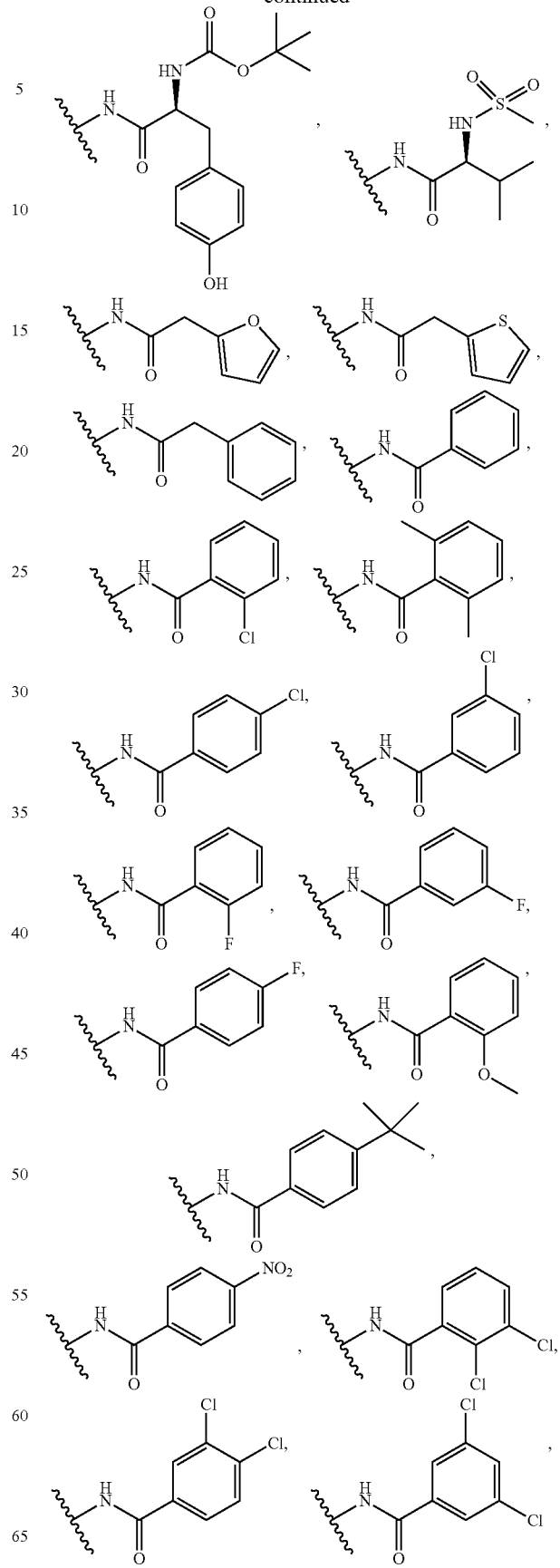

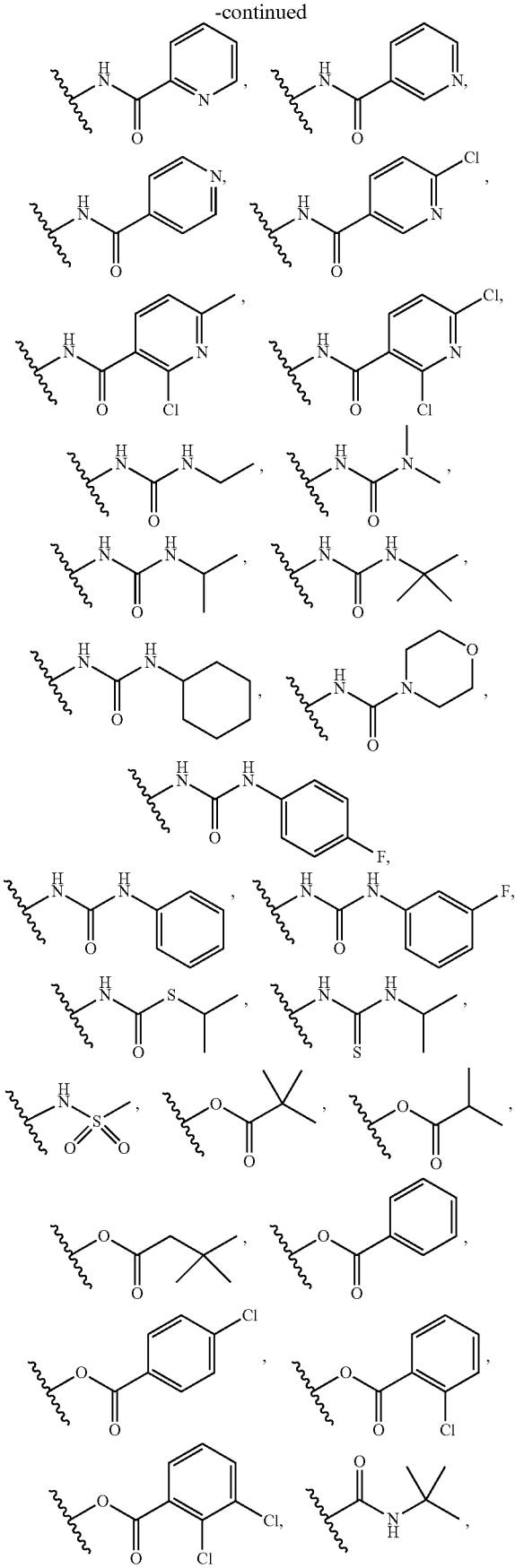
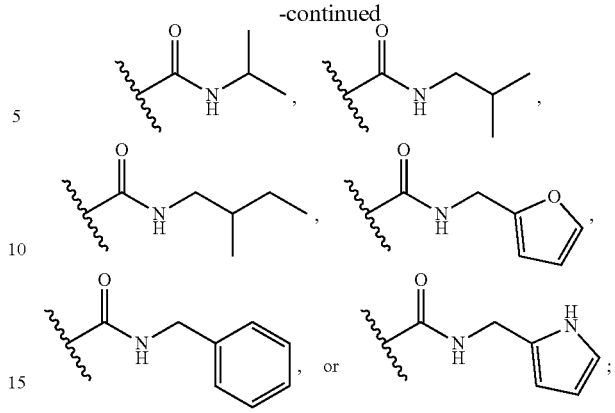

M is $C_{3-4}$ straight or branched alkylene; and
X is —NH—, or —O—.

Most preferable examples of the substituent according to formula 1 above are as follows:

(1) [4-(1-methyl-[1,2,4]triazolo[4,3-a]quinoxaline-4-ylamino)-butyl]-carbamic acid-tert-butylester;
(2) $N^1$-(1-methyl-[1,2,4]triazolo[4,3-a]quinoxaline-4-yl)-butane-1,4-diamine dihydrochloride;
(3) 2,2-dimethyl-N-[4-(1-methyl-[1,2,4]triazolo[4,3-a]quinoxaline-4-ylamino)-butyl]-propionamide;
(4) [4-(1-methyl-[1,2,4]triazolo[4,3-a]quinoxaline-4-ylamino)-butyl]-carbamic acid isopropylester;
(5) [4-(1-methyl-[1,2,4]triazolo[4,3-a]quinoxaline-4-ylamino)-butyl]-acetamide;
(6) [4-(1-methyl-[1,2,4]triazolo[4,3-a]quinoxaline-4-ylamino)-butyl]-isobutyramide;
(7) 3-methyl-N-[4-(1-methyl-[1,2,4]triazolo[4,3-a]quinoxaline-4-ylamino)-butyl]-butyramide;
(8) 3,3-dimethyl-N-[4-(1-methyl-[1,2,4]triazolo[4,3-a]quinoxaline-4-ylamino)-butyl]-butyramide;
(9) 2-(R)-hydroxy-N-[4-(1-methyl-[1,2,4]triazolo[4,3-a]quinoxaline-4-ylamino)-butyl]-3-methyl-butyramide;
(10) 2-(S)-hydroxy-N-[4-(1-methyl-[1,2,4]triazolo[4,3-a]quinoxaline-4-ylamino)-butyl]-3-methyl-butyramide;
(11) N-[4-(1-methyl-[1,2,4]triazolo[4,3-a]quinoxaline-4-ylamino)-butyl]-benzamide;
(12) 2-chloro-N-[4-(1-methyl-[1,2,4]triazolo[4,3-a]quinoxaline-4-ylamino)-butyl]-benzamide;
(13) 2,6-dimethyl-N-[4-(1-methyl-[1,2,4]triazolo[4,3-a]quinoxaline-4-ylamino)-butyl]-benzamide;
(14) 4-chloro-N-[4-(1-methyl-[1,2,4]triazolo[4,3-a]quinoxaline-4-ylamino)-butyl]-benzamide;
(15) 3-chloro-N-[4-(1-methyl-[1,2,4]triazolo[4,3-a]quinoxaline-4-ylamino)-butyl]-benzamide;
(16) 3,4-dichloro-N-[4-(1-methyl-[1,2,4]triazolo[4,3-a]quinoxaline-4-ylamino)-butyl]-benzamide;
(17) 2,3-dichloro-N-[4-(1-methyl-[1,2,4]triazolo[4,3-a]quinoxaline-4-ylamino)-butyl]-benzamide;
(18) 3,5-dichloro-N-[4-(1-methyl-[1,2,4]triazolo[4,3-a]quinoxaline-4-ylamino)-butyl]-benzamide;
(19) 2,6-dichloro-N-[4-(1-methyl-[1,2,4]triazolo[4,3-a]quinoxaline-4-ylamino)-butyl]-nicotinamide;
(20) 6-chloro-N-[4-(1-methyl-[1,2,4]triazolo[4,3-a]quinoxaline-4-ylamino)-butyl]-nicotinamide;
(21) 2-chloro-6-methyl-N-[4-(1-methyl-[1,2,4]triazolo[4,3-a]quinoxaline-4-ylamino)-butyl]-nicotinamide;
(22) 1-tert-butyl-3-[4-(1-methyl-[1,2,4]triazolo[4,3-a]quinoxaline-4-ylamino)-butyl]-urea;

(23) 1-(4-fluoro-phenyl)-3-[4-(1-methyl-[1,2,4]triazolo[4,3-a]quinoxaline-4-ylamino)-butyl]-urea;
(24) 1-(3-fluoro-phenyl)-3-[4-(1-methyl-[1,2,4]triazolo[4,3-a]quinoxaline-4-ylamino)-butyl]-urea;
(25) [4-(1-methyl-[1,2,4]triazolo[4,3-a]quinoxaline-4-ylamino)-butyl]-carbamic acid benzylester;
(26) [4-(7,8-dichloro-1-methyl-[1,2,4]triazolo[4,3-a]quinoxaline-4-ylamino)-butyl]-carbamic acid-tert-butylester;
(27) $N^1$-(7,8-dichloro-1-methyl-[1,2,4]triazolo[4,3-a]quinoxaline-4-yl)butane-1,4-diamine ditrifluoroacetic acid;
(28) N-[4-(7,8-dichloro-1-methyl-[1,2,4]triazolo[4,3-a]quinoxaline-4-ylamino)-butyl]-2,2-dimethyl-propionamide;
(29) N-[4-(7,8-dichloro-1-methyl-[1,2,4]triazolo[4,3-a]quinoxaline-4-ylamino)-butyl]-isobutyramide;
(30) N-[4-(7,8-dichloro-1-methyl-[1,2,4]triazolo[4,3-a]quinoxaline-4-ylamino)-butyl]-3-methyl-butyramide;
(31) N-[4-(7,8-dichloro-1-methyl-[1,2,4]triazolo[4,3-a]quinoxaline-4-ylamino)-butyl]-benzamide;
(32) 2-chloro-N-[4-(7,8-dichloro-1-methyl-[1,2,4]triazolo[4,3-a]quinoxaline-4-ylamino)-butyl]-benzamide;
(33) 6-chloro-N-[4-(7,8-dichloro-1-methyl-[1,2,4]triazolo[4,3-a]quinoxaline-4-ylamino)-butyl]-nicotinamide;
(34) [4-(1,7,8-trimethyl-[1,2,4]triazolo[4,3-a]quinoxaline-4-ylamino)-butyl]-carbamic acid-tert-butylester;
(35) [4-(7,8-difluoro-1-methyl-[1,2,4]triazolo[4,3-a]quinoxaline-4-ylamino)-butyl]-carbamic acid-tert-butylester;
(36) $N^1$-(7,8-difluoro-1-methyl-[1,2,4]triazolo[4,3-a]quinoxaline-4-yl)-butane-1,4-diamine ditrifluoroacetic acid;
(37) N-[4-(7,8-difluoro-1-methyl-[1,2,4]triazolo[4,3-a]quinoxaline-4-ylamino)-butyl]-3-methyl-butyramide;
(38) N-[4-(7,8-difluoro-1-methyl-[1,2,4]triazolo[4,3-a]quinoxaline-4-ylamino)-butyl]-2-(R)-hydroxy-3-methyl-butyramide;
(39) N-[4-(7,8-difluoro-1-methyl-[1,2,4]triazolo[4,3-a]quinoxaline-4-ylamino)-butyl]-2-(S)-hydroxy-3-methyl-butyramide;
(40) [4-(1,8-dimethyl-[1,2,4]triazolo[4,3-a]quinoxaline-4-ylamino)-butyl]-carbamic acid-tert-butylester;
(41) [4-(1,8-dimethyl-[1,2,4]triazolo[4,3-a]quinoxaline-4-ylamino)-butane]-1,4-diamine dihydrochloride;
(42) N-[4-(1,8-dimethyl-[1,2,4]triazolo[4,3-a]quinoxaline-4-ylamino)-butyl]-2,2-dimethyl-propionamide;
(43) N-[4-(1,8-dimethyl-[1,2,4]triazolo[4,3-a]quinoxaline-4-ylamino)-butyl]-isobutyramide;
(44) 1-tert-butyl-3-[4-(1,8-dimethyl-[1,2,4]triazolo[4,3-a]quinoxaline-4-ylamino)-butyl]-urea;
(45) N-[4-(1,8-dimethyl-[1,2,4]triazolo[4,3-a]quinoxaline-4-ylamino)-butyl]-benzamide;
(46) 1-[4-(1,8-dimethyl-[1,2,4]triazolo[4,3-a]quinoxaline-4-ylamino)-butyl]-3-phenyl-urea;
(47) [4-(8-fluoro-1-methyl-[1,2,4]triazolo[4,3-a]quinoxaline-4-ylamino)-butyl]-carbamic acid-tert-butylester;
(48) [4-(8-fluoro-1-methyl-[1,2,4]triazolo[4,3-a]quinoxaline-4-ylamino)-butyl]-1,4-diamine dihydrochloride;
(49) N-[4-(8-fluoro-1-methyl-[1,2,4]triazolo[4,3-a]quinoxaline-4-ylamino)-butyl]-2,2-dimethyl-propionamide;
(50) [4-(8-fluoro-1-methyl-[1,2,4]triazolo[4,3-a]quinoxaline-4-ylamino)-butyl]-isobutyramide;
(51) N-[4-(8-fluoro-1-methyl-[1,2,4]triazolo[4,3-a]quinoxaline-4-ylamino)-butyl]-benzamide;
(52) 1-tert-butyl-3-[4-(8-fluoro-1-methyl-[1,2,4]triazolo[4,3-a]quinoxaline-4-ylamino)-butyl]-urea;
(53) 1-[4-(8-fluoro-1-methyl-[1,2,4]triazolo[4,3-a]quinoxaline-4-ylamino)-butyl]-3-phenyl-urea;
(54) [4-(8-chloro-1-methyl-[1,2,4]triazolo[4,3-a]quinoxaline-4-ylamino)-butyl]-carbamic acid-tert-butylester;
(55) $N^1$-(8-chloro-1-methyl-[1,2,4]triazolo[4,3-a]quinoxaline-4-yl)butane-1,4-diamine hydrochloride;
(56) N-[4-(8-chloro-1-methyl-[1,2,4]triazolo[4,3-a]quinoxaline-4-ylamino)-butyl]-benzamide;
(57) [4-(7,8-dimethoxy-1-methyl-[1,2,4]triazolo[4,3-a]quinoxaline-4-ylamino)-butyl]-carbamic acid-tert-butylester;
(58) $N^1$-(7,8-dimethoxy-1-methyl-[1,2,4]triazolo[4,3-a]quinoxaline-4-yl)-butane-1,4-diamine ditrifluoroacetic acid;
(59) N-[4-(7,8-dimethoxy-1-methyl-[1,2,4]quinoxaline-4-ylamino)-butyl]-2,2-dimethyl-propionamide;
(60) [4-(7,8-dimethoxy-1-methyl-[1,2,4]triazolo[4,3-a]quinoxaline-4-ylamino)-butyl]-carbamic acid isopropylester;
(61) [4-(7,8-dimethoxy-1-methyl-[1,2,4]triazolo[4,3-a]quinoxaline-4-ylamino)-butyl]-carbamic acid ethylester;
(62) [4-(7,8-dimethoxy-1-methyl-[1,2,4]triazolo[4,3-a]quinoxaline-4-ylamino)-butyl]-carbamic acid isobutylester;
(63) [4-(7,8-dimethoxy-1-methyl-[1,2,4]triazolo[4,3-a]quinoxaline-4-ylamino)-butyl]-carbamic acid-sec-butylester;
(64) [4-(7,8-dimethoxy-1-methyl-[1,2,4]triazolo[4,3-a]quinoxaline-4-ylamino)-butyl]-carbamic acid propylester;
(65) [4-(7,8-dimethoxy-1-methyl-[1,2,4]triazolo[4,3-a]quinoxaline-4-ylamino)-butyl]-carbamic acid allylester;
(66) [4-(7,8-dimethoxy-1-methyl-[1,2,4]triazolo[4,3-a]quinoxaline-4-ylamino)-butyl]-carbamic acid cyclopentylester;
(67) [4-(7,8-dimethoxy-1-methyl-[1,2,4]triazolo[4,3-a]quinoxaline-4-ylamino)-butyl]-carbamic acid phenylester;
(68) [4-(7,8-dimethoxy-1-methyl-[1,2,4]triazolo[4,3-a]quinoxaline-4-ylamino)-butyl]-carbamic acid benzylester;
(69) N-[4-(7,8-dimethoxy-1-methyl-[1,2,4]triazolo[4,3-a]quinoxaline-4-ylamino)-butyl]-acetamide;
(70) N-[4-(7,8-dimethoxy-1-methyl-[1,2,4]triazolo[4,3-a]quinoxaline-4-ylamino)-butyl]-isobutyramide;
(71) 3-methyl-buten-2-oic acid-[4-(7,8-dimethoxy-1-methyl-[1,2,4]triazolo[4,3-a]quinoxaline-4-ylamino)-butyl]-amide;
(72) butene-2-oic acid-[4-(7,8-dimethoxy-1-methyl-[1,2,4]triazolo[4,3-a]quinoxaline-4-ylamino)-butyl]-amide;
(73) 3-methyl-pentanoic acid-[4-(7,8-dimethoxy-1-methyl-[1,2,4]triazolo[4,3-a]quinoxaline-4-ylamino)-butyl]-amide;
(74) N-[4-(7,8-dimethoxy-1-methyl-[1,2,4]triazolo[4,3-a]quinoxaline-4-ylamino)-butyl]-3-methyl-butyramide;
(75) N-[4-(7,8-dimethoxy-1-methyl-[1,2,4]triazolo[4,3-a]quinoxaline-4-ylamino)-butyl]-3,3-dimethyl-butyramide;
(76) cyclopropanecarboxylic acid-[4-(7,8-dimethoxy-1-methyl-[1,2,4]triazolo[4,3-a]quinoxaline-4-ylamino)-butyl]-amide;
(77) N-[4-(7,8-dimethoxy-1-methyl-[1,2,4]triazolo[4,3-a]quinoxaline-4-ylamino)-butyl]-2-methyl-butyramide;
(78) N-[4-(7,8-dimethoxy-1-methyl-[1,2,4]triazolo[4,3-a]quinoxaline-4-ylamino)-butyl]-2-ethyl-butyramide;
(79) 4-methyl-pentanoic acid-[4-(7,8-dimethoxy-1-methyl-[1,2,4]triazolo[4,3-a]quinoxaline-4-ylamino)-butyl]-amide;
(80) N-[4-(7,8-dimethoxy-1-methyl-[1,2,4]triazolo[4,3-a]quinoxaline-4-ylamino)-butyl]-2-methoxy-acetamide;
(81) 3-cyclopentyl-N-[4-(7,8-dimethoxy-1-methyl-[1,2,4]triazolo[4,3-a]quinoxaline-4-ylamino)-butyl]-propionamide;
(82) N-[4-(7,8-dimethoxy-1-methyl-[1,2,4]triazolo[4,3-a]quinoxaline-4-ylamino)-butyl]-2-(R)-hydroxy-3-methyl-butyramide;

(83) N-[4-(7,8-dimethoxy-1-methyl-[1,2,4]triazolo[4,3-a]quinoxaline-4-ylamino)-butyl]-2-(S)-hydroxy-3-methyl-butyramide;
(84) N-[4-(7,8-dimethoxy-1-methyl-[1,2,4]triazolo[4,3-a]quinoxaline-4-ylamino)-butyl]-2-thiophene-2-yl-acetamide;
(85) N-[4-(7,8-dimethoxy-1-methyl-[1,2,4]triazolo[4,3-a]quinoxaline-4-ylamino)-butyl]-2-furan-2-yl-acetamide;
(86) N-[4-(7,8-dimethoxy-1-methyl-[1,2,4]triazolo[4,3-a]quinoxaline-4-ylamino)-butyl]-2-phenyl-acetamide;
(87) acetic acid-[4-(7,8-dimethoxy-1-methyl-[1,2,4]triazolo[4,3-a]quinoxaline-4-ylamino)-butyl-carbamoyl]-methylester;
(88) 1-tert-butyl-3-[4-(7,8-dimethoxy-1-methyl-[1,2,4]triazolo[4,3-a]quinoxaline-4-ylamino)-butyl]-urea;
(89) 1-[4-(7,8-dimethoxy-1-methyl-[1,2,4]triazolo[4,3-a]quinoxaline-4-ylamino)-butyl]-3-ethyl-urea;
(90) 1-[4-(7,8-dimethoxy-1-methyl-[1,2,4]triazolo[4,3-a]quinoxaline-4-ylamino)-3-isopropyl-urea;
(91) 3-[4-(7,8-dimethoxy-1-methyl-[1,2,4]triazolo[4,3-a]quinoxaline-4-ylamino)-butyl]-1,1-dimethyl-urea;
(92) morpholine-4-carboxylic acid-[4-(7,8-dimethoxy-1-methyl-[1,2,4]triazolo[4,3-a]quinoxaline-4-ylamino)-butyl]-amide;
(93) 1-cyclohexyl-3-[4-(7,8-dimethoxy-1-methyl-[1,2,4]triazolo[4,3-a]quinoxaline-4-ylamino)-butyl]-urea;
(94) 1-[4-(7,8-dimethoxy-1-methyl-[1,2,4]triazolo[4,3-a]quinoxaline-4-ylamino)-butyl]-3-phenyl-urea;
(95) N-[4-(7,8-dimethoxy-1-methyl-[1,2,4]triazolo[4,3-a]quinoxaline-4-ylamino)-butyl]-benzamide;
(96) 4-tert-butyl-N-[4-(7,8-dimethoxy-1-methyl-[1,2,4]triazolo[4,3-a]quinoxaline-4-ylamino)-butyl]-benzamide;
(97) N-[4-(7,8-dimethoxy-1-methyl-[1,2,4]triazolo[4,3-a]quinoxaline-4-ylamino)-butyl]-2-methoxy-benzamide;
(98) N-[4-(7,8-dimethoxy-1-methyl-[1,2,4]triazolo[4,3-a]quinoxaline-4-ylamino)-butyl]-4-fluoro-benzamide;
(99) 2-chloro-N-[4-(7,8-dimethoxy-1-methyl-[1,2,4]triazolo[4,3-a]quinoxaline-4-ylamino)-butyl]-benzamide;
(100) 4-chloro-N-[4-(7,8-dimethoxy-1-methyl-[1,2,4]triazolo[4,3-a]quinoxaline-4-ylamino)-butyl]-benzamide;
(101) N-[4-(7,8-dimethoxy-1-methyl-[1,2,4]triazolo[4,3-a]quinoxaline-4-ylamino)-butyl]-4-nitro-benzamide;
(102) 2,3-dichloro-N-[4-(7,8-dimethoxy-1-methyl-[1,2,4]triazolo[4,3-a]quinoxaline-4-ylamino)-butyl]-benzamide;
(103) N-[4-(7,8-dimethoxy-1-methyl-[1,2,4]triazolo[4,3-a]quinoxaline-4-ylamino)-butyl]-isonicotinamide;
(104) N-[4-(7,8-dimethoxy-1-methyl-[1,2,4]triazolo[4,3-a]quinoxaline-4-ylamino)-butyl]-nicotinamide;
(105) pyridine-2-carboxylic acid-[4-(7,8-dimethoxy-1-methyl-[1,2,4]triazolo[4,3-a]quinoxaline-4-ylamino)-butyl]-amide;
(106) N-[4-(7,8-dimethoxy-1-methyl-[1,2,4]triazolo[4,3-a]quinoxaline-4-ylamino)-butyl]-2-fluoro-benzamide;
(107) 6-chloro-N-[4-(7,8-dimethoxy-1-methyl-[1,2,4]triazolo[4,3-a]quinoxaline-4-ylamino)-butyl]-nicotinamide;
(108) 2-chloro-N-[4-(7,8-dimethoxy-1-methyl-[1,2,4]triazolo[4,3-a]quinoxaline-4-ylamino)-butyl]-6-methyl-nicotinamide;
(109) N-[4-(7,8-dimethoxy-1-methyl-[1,2,4]triazolo[4,3-a]quinoxaline-4-ylamino)-butyl]-methanesulfonamide;
(110) [4-(7,8-dimethoxy-1-methyl-[1,2,4]triazolo[4,3-a]quinoxaline-4-ylamino)-butyl]-thiocarbamic acid-S-isopropylester;
(111) [4-(8-fluoro-1-methyl-6-trifluoromethyl-[1,2,4]triazolo[4,3-a]quinoxaline-4-ylamino)-butyl]-carbamic acid-tert-butylester;
(112) $N^1$-(8-fluoro-1-methyl-6-trifluoromethyl-[1,2,4]triazolo[4,3-a]quinoxaline-4-yl)-butane-1,4-diamine dihydrochloride;
(113) N-[4-(8-fluoro-1-methyl-6-trifluoromethyl-[1,2,4]triazolo[4,3-a]quinoxaline-4-ylamino)-butyl]-2,2-dimethyl-propionamide;
(114) [4-(8-fluoro-1-methyl-6-trifluoromethyl-[1,2,4]triazolo[4,3-a]quinoxaline-4-ylamino)-butyl]-carbamic acid isopropylester;
(115) [4-(8-fluoro-1-methyl-6-trifluoromethyl-[1,2,4]triazolo[4,3-a]quinoxaline-4-ylamino)-butyl]-carbamic acid isobutylester;
(116) N-[4-(8-fluoro-1-methyl-6-trifluoromethyl-[1,2,4]triazolo[4,3-a]quinoxaline-4-ylamino)-butyl]-3,3-dimethyl-butyramide;
(117) [4-(6-methoxy-1-methyl-[1,2,4]triazolo[4,3-a]quinoxaline-4-ylamino)-butyl]-carbamic acid-tert-butylester;
(118) $N^1$-(6-methoxy-1-methyl-[1,2,4]triazolo[4,3-a]quinoxaline-4-yl)-butane-1,4-diamine dihydrochloride;
(119) N-[4-(6-methoxy-1-methyl-[1,2,4]triazolo[4,3-a]quinoxaline-4-ylamino)-butyl]-2,2-dimethyl-propionamide;
(120) N-[4-(6-methoxy-1-methyl-[1,2,4]triazolo[4,3-a]quinoxaline-4-ylamino)-butyl]-carbamic acid isobutylester;
(121) [4-(8-methoxy-1-methyl-[1,2,4]triazolo[4,3-a]quinoxaline-4-ylamino)-butyl]-carbamic acid-tert-butylester;
(122) $N^1$-(8-methoxy-1-methyl-[1,2,4]triazolo[4,3-a]quinoxaline-4-yl)-butane-1,4-diamine ditrifluoroacetic acid;
(123) N-[4-(8-methoxy-1-methyl-[1,2,4]triazolo[4,3-a]quinoxaline-4-ylamino)-butyl]-2,2-dimethyl-propionamide;
(124) [4-(8-methoxy-1-methyl-[1,2,4]triazolo[4,3-a]quinoxaline-4-ylamino)-butyl]-3,3-dimethyl-butyramide;
(125) 2-(R)-hydroxy-N-[4-(8-methoxy-1-methyl-[1,2,4]triazolo[4,3-a]quinoxaline-4-ylamino)-butyl]-3-methyl-butyramide;
(126) 2-(S)-hydroxy-N-[4-(8-methoxy-1-methyl-[1,2,4]triazolo[4,3-a]quinoxaline-4-ylamino)-butyl]-3-methyl-butyramide;
(127) N-[4-(8-methoxy-1-methyl-[1,2,4]triazolo[4,3-a]quinoxaline-4-ylamino)-butyl]-benzamide;
(128) 2-chloro-N-[4-(8-methoxy-1-methyl-[1,2,4]triazolo[4,3-a]quinoxaline-4-ylamino)-butyl]-benzamide;
(129) 2-chloro-N-[4-(8-methoxy-1-methyl-[1,2,4]triazolo[4,3-a]quinoxaline-4-ylamino)-6-methyl-nicotinamide;
(130) {4-[6-methoxy-1,7-dimethyl-[1,2,4]triazolo[4,3-a]quinoxaline-4-ylamino]-butyl}-carbamic acid-tert-butylester;
(131) $N^1$-(6-methoxy-1,7-dimethyl-[1,2,4]triazolo[4,3-a]quinoxaline-4-yl)-butane-1,4-diamine ditrifluoroacetic acid;
(132) [4-(6-methoxy-1,7-dimethyl-[1,2,4]triazolo[4,3-a]quinoxaline-4-ylamino)-butyl]-2,2-dimethyl-propionamide;
(133) [4-(6-methoxy-1,7-dimethyl-[1,2,4]triazolo[4,3-a]quinoxaline-4-ylamino)-butyl]-carbamic acid isopropylester;
(134) [4-(6-methoxy-1,7-dimethyl-[1,2,4]triazolo[4,3-a]quinoxaline-4-ylamino)-butyl]-carbamic acid isobutylester;
(135) N-[4-(6-methoxy-1,7-dimethyl-[1,2,4]triazolo[4,3-a]quinoxaline-4-ylamino)-butyl]-3-methyl-butyramide;
(136) 2-(R)-hydroxy-N-[4-(6-methoxy-1,7-dimethyl-[1,2,4]triazolo[4,3-a]quinoxaline-4-ylamino)-butyl]-3-methyl-butyramide;

(137) 2-(S)-hydroxy-N-[4-(6-methoxy-1,7-dimethyl-[1,2,4]triazolo[4,3-a]quinoxaline-4-ylamino)-butyl]-3-methyl-butyramide;
(138) N-[4-(6-methoxy-1,7-dimethyl-[1,2,4]triazolo[4,3-a]quinoxaline-4-ylamino)-butyl]-benzamide;
(139) 2-fluoro-N-[4-(6-methoxy-1,7-dimethyl-[1,2,4]triazolo[4,3-a]quinoxaline-4-ylamino)-butyl]-benzamide;
(140) 2-chloro-N-[4-(6-methoxy-1,7-dimethyl-[1,2,4]triazolo[4,3-a]quinoxaline-4-ylamino)-butyl]-benzamide;
(141) 2-chloro-N-[4-(6-methoxy-1,7-dimethyl-[1,2,4]triazolo[4,3-a]quinoxaline-4-ylamino)-butyl]-6-methyl-nicotinamide;
(142) [4-(6-methoxy-1-methyl-8-trifluoromethyl-[1,2,4]triazolo[4,3-a]quinoxaline-4-ylamino)-butyl]-carbamic acid-tert-butylester;
(143) $N^1$-(6-methoxy-1-methyl-8-trifluoromethyl-[1,2,4]triazolo[4,3-a]quinoxaline-4-yl)-butane-1,4-diamine ditrifluoroacetic acid;
(144) [4-(6-methoxy-1-methyl-8-trifluoromethyl-[1,2,4]triazolo[4,3-a]quinoxaline-4-ylamino)-butyl]-carbamic acid isopropylester;
(145) N-[4-(6-methoxy-1-methyl-8-trifluoromethyl-[1,2,4]triazolo[4,3-a]quinoxaline-4-ylamino)-butyl]-3-methyl-butyramide;
(146) [4-(8-methoxy-1,7-dimethyl-[1,2,4]triazolo[4,3-a]quinoxaline-4-ylamino)-butyl]-carbamic acid-tert-butylester;
(147) $N^1$-(8-methoxy-1,7-dimethyl-[1,2,4]triazolo[4,3-a]quinoxaline-4-yl)-butane-1,4-diamine ditrifluoroacetic acid;
(148) N-[4-(8-methoxy-1,7-dimethyl-[1,2,4]triazolo[4,3-a]quinoxaline-4-ylamino)-butyl]-2,2-dimethyl-propionamide;
(149) [4-(8-methoxy-1,7-dimethyl-[1,2,4]triazolo[4,3-a]quinoxaline-4-ylamino)-butyl]-carbamic acid isopropylester;
(150) [4-(8-methoxy-1,7-dimethyl-[1,2,4]triazolo[4,3-a]quinoxaline-4-ylamino)-butyl]-carbamic acid isobutylester;
(151) N-[4-(8-methoxy-1,7-dimethyl-[1,2,4]triazolo[4,3-a]quinoxaline-4-ylamino)-butyl]-3-methyl-butyramide;
(152) 2-(R)-hydroxy-N-[4-(8-methoxy-1,7-dimethyl-[1,2,4]triazolo[4,3-a]quinoxaline-4-ylamino)-butyl]-3-methyl-butyramide;
(153) 2-(S)-hydroxy-N-[4-(8-methoxy-1,7-dimethyl-[1,2,4]triazolo[4,3-a]quinoxaline-4-ylamino)-butyl]-3-methyl-butyramide;
(154) N-[4-(8-methoxy-1,7-dimethyl-[1,2,4]triazolo[4,3-a]quinoxaline-4-ylamino)-butyl]-benzamide;
(155) 2-fluoro-N-[4-(8-methoxy-1,7-dimethyl-[1,2,4]triazolo[4,3-a]quinoxaline-4-ylamino)-butyl]-benzamide;
(156) 2-chloro-N-[4-(8-methoxy-1,7-dimethyl-[1,2,4]triazolo[4,3-a]quinoxaline-4-ylamino)-butyl]-benzamide;
(157) 2-chloro-N-[4-(8-methoxy-1,7-dimethyl-[1,2,4]triazolo[4,3-a]quinoxaline-4-ylamino)-butyl]-6-methyl-nicotinamide;
(158) [4-(8-methoxy-1,6-dimethyl-[1,2,4]triazolo[4,3-a]quinoxaline-4-ylamino)-butyl]-carbamic acid-tert-butylester;
(159) $N^1$-(8-methoxy-1,6-dimethyl-[1,2,4]triazolo[4,3-a]quinoxaline-4-yl)-butane-1,4-diamine difluoroacetic acid;
(160) N-[4-(8-methoxy-1,6-dimethyl-[1,2,4]triazolo[4,3-a]quinoxaline-4-ylamino)-butyl]-3-methyl-butyramide;
(161) [4-(8-methoxy-1,6-dimethyl-[1,2,4]triazolo[4,3-a]quinoxaline-4-ylamino)-butyl]-carbamic acid isopropylester;
(162) {4-[7,8-bis-(2-methoxy-ethoxy)-1-methyl-[1,2,4]triazolo[4,3-a]quinoxaline-4-ylamino]-butyl}-carbamic acid-tert-butylester;
(163) $N^1$-[7,8-bis-(2-methoxy-ethoxy)-1-methyl-[1,2,4]triazolo[4,3-a]quinoxaline-4-yl]-butane-1,4-diamine ditrifluoroacetic acid;
(164) N-{4-[7,8-bis-(2-methoxy-ethoxy)-1-methyl-[1,2,4]triazolo[4,3-a]quinoxaline-4-ylamino]-butyl}-2,2-dimethyl-propionamide;
(165) {4-[7,8-bis-(2-methoxy-ethoxy)-1-methyl-[1,2,4]triazolo[4,3-a]quinoxaline-4-ylamino]-butyl}-carbamic acid isopropylester;
(166) N-{4-[7,8-bis-(2-methoxy-ethoxy)-1-methyl-[1,2,4]triazolo[4,3-a]quinoxaline-4-ylamino]-butyl}-3-methyl-butyramide;
(167) N-{4-[7,8-bis-(2-methoxy-ethoxy)-1-methyl-[1,2,4]triazolo[4,3-a]quinoxaline-4-ylamino]-butyl}-3,3-dimethyl-butyramide;
(168) {4-[7,8-bis-(2-methoxy-ethoxy)-1-methyl-[1,2,4]triazolo[4,3-a]quinoxaline-4-ylamino]-butyl}-carbamic acid isobutylester;
(169) 1-{4-[7,8-bis-(2-methoxy-ethoxy)-1-methyl-[1,2,4]triazolo[4,3-a]quinoxaline-4-ylamino]-butyl}-3-tert-butyl-urea;
(170) N-{4-[7,8-bis-(2-methoxy-ethoxy)-1-methyl-[1,2,4]triazolo[4,3-a]quinoxaline-4-ylamino]-butyl}-benzamide;
(171) N-{4-[7,8-bis-(2-methoxy-ethoxy)-1-methyl-[1,2,4]triazolo[4,3-a]quinoxaline-4-ylamino]-butyl}-2-chloro-benzamide;
(172) N-{4-[7,8-bis-(2-methoxy-ethoxy)-1-methyl-[1,2,4]triazolo[4,3-a]quinoxaline-4-ylamino]-butyl}-2-chloro-6-methyl-nicotinamide;
(173) [4-(7,8-diethoxy-1-methyl-[1,2,4]triazolo[4,3-a]quinoxaline-4-ylamino)-butyl-carbamic acid-tert-butylester;
(174) $N^1$-(7,8-diethoxy-1-methyl-[1,2,4]triazolo[4,3-a]quinoxaline-4-yl)-butane-1,4-diamine ditrifluoroacetic acid;
(175) [4-(7,8-diethoxy-1-methyl-[1,2,4]triazolo[4,3-a]quinoxaline-4-ylamino)-butyl]-carbamic acid isopropylester;
(176) [4-(7,8-diethoxy-1-methyl-[1,2,4]triazolo[4,3-a]quinoxaline-4-ylamino)-butyl]-carbamic acid isobutylester;
(177) N-[4-(7,8-diethoxy-1-methyl-[1,2,4]triazolo[4,3-a]quinoxaline-4-ylamino)-butyl-3-methyl-butyramide;
(178) [4-(1-methyl-8,9-dihydro-7,10-dioxa-2,3,5,11b-tetraaza-cyclopenta[a]anthracene-4-ylamino)-butyl]-carbamic acid-tert-butylester;
(179) $N^1$-(1-methyl-8,9-dihydro-7,10-dioxa-2,3,5,11b-tetraaza-cyclopenta[a]anthracene-4-yl)-butane-1,4-diamine ditrifluoroacetic acid;
(180) 2,2-dimethyl-N-[4-(1-methyl-8,9-dihydro-7,10-dioxa-2,3,5,11b-tetraaza-cyclopenta[a]anthracene-4-ylamino)-butyl]-propionamide;
(181) 3-methyl-N-[4-(1-methyl-8,9-dihydro-7,10-dioxa-2,3,5,11b-tetraaza-cyclopenta[a]anthracene-4-ylamino)-butyl]-butyramide;
(182) 2-(R)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide;
(183) 2-(S)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide;
(184) acetic acid-[4-(1-methyl-8,9-dihydro-7,10-dioxa-2,3,5,11b-tetraaza-cyclopenta[a]anthracene-4-ylamino)-butyl]-carbamoyl]-methylester;
(185) N-[4-(1-methyl-8,9-dihydro-7,10-dioxa-2,3,5,11b-tetraaza-cyclopenta[a]anthracene-4-ylamino)-butyl]-2-thiophene-2-yl-acetamide;

(186) N-[4-(1-methyl-8,9-dihydro-7,10-dioxa-2,3,5,11b-tetraaza-cyclopenta[a]anthracene-4-ylamino)-butyl]-benzamide;
(187) 2-chloro-N-[4-(1-methyl-8,9-dihydro-7,10-dioxa-2,3,5,11b-tetraaza-cyclopenta[a]anthracene-4-ylamino)-butyl]-benzamide;
(188) [4-(1-methyl-8,9-dihydro-7,10-dioxa-2,3,5,11b-tetraaza-cyclopenta[a]anthracene-4-ylamino)-butyl]-carbamic acid isopropylester;
(189) [4-(1-methyl-8,9-dihydro-7,10-dioxa-2,3,5,11b-tetraaza-cyclopenta[a]anthracene-4-ylamino)-butyl]-carbamic acid isobutylester;
(190) [4-(1-methyl-8,9-dihydro-7,10-dioxa-2,3,5,11b-tetraaza-cyclopenta[a]anthracene-4-ylamino)-butyl]-carbamic acid cyclopentylester;
(191) [4-(1-methyl-8,9-dihydro-7,10-dioxa-2,3,5,11b-tetraaza-cyclopenta[a]anthracene-4-ylamino)-butyl]-carbamic acid phenylester;
(192) 1-isopropyl-3-[4-(1-methyl-8,9-dihydro-7,10-dioxa-2,3,5,11b-tetraaza-cyclopenta[a]anthracene-4-ylamino)-butyl]-urea;
(193) [4-(6,7,8-trimethoxy-1-methyl-[1,2,4]triazolo[4,3-a]quinoxaline-4-ylamino)-butyl]-carbamic acid-tert-butylester;
(194) $N^1$-(6,7,8-trimethoxy-1-methyl-[1,2,4]triazolo[4,3-a]quinoxaline-4-yl)-butane-1,4-diamine ditrifluoroacetic acid;
(195) 3-methyl-N-[4-(6,7,8-trimethoxy-1-methyl-[1,2,4]triazolo[4,3-a]quinoxaline-4-ylamino)-butyl]-butyramide;
(196) 3-methyl-pentanoic acid-[4-(6,7,8-trimethoxy-1-methyl-[1,2,4]triazolo[4,3-a]quinoxaline-4-ylamino)-butyl]-amide;
(197) 4-(4-tert-butoxycarbamoylamino-butylamino)-1-methyl-[1,2,4]triazolo[4,3-a]quinoxaline-7-carboxylic acid methylester;
(198) 4-(4-amino-butylamino)-1-methyl-[1,2,4]triazolo[4,3-a]quinoxaline-7-carboxylic acid methylester ditrifluoroacetic acid;
(199) 1-methyl-4-[4-(3-methyl-butyrylamino)-butylamino]-[1,2,4]triazolo[4,3-a]quinoxaline-7-carboxylic acid methylester;
(200) 4-[(4-tert-butoxycarbamoylamino)-butylamino]-1-methyl-[1,2,4]triazolo[4,3-a]quinoxaline-7-carboxylic acid;
(201) 1-methyl-4-[4-(3-methyl-butyrylamino)-butylamino]-[1,2,4]triazolo[4,3-a]quinoxaline-7-carboxylic acid;
(202) [4-(7-isopropylcarbamoyl-1-methyl-[1,2,4]triazolo[4,3-a]quinoxaline-4-ylamino)-butyl]-carbamic acid-tert-butylester;
(203) [4-(7-tert-butylcarbamoyl-1-methyl-[1,2,4]triazolo[4,3-a]quinoxaline-4-ylamino)-butyl]-carbamic acid-tert-butylester;
(204) 4-(4-isobutyramido-butylamino)-1-methyl-[1,2,4]triazolo[4,3-a]quinoxaline-7-carboxylic acid isopropylamide;
(205) 4-(4-benzoylamino-butylamino)-1-methyl-[1,2,4]triazolo[4,3-a]quinoxaline-7-carboxylic acid isopropylamide;
(206) {4-[7-(2-dimethylamino-ethylcarbamoyl)-1-methyl-[1,2,4]triazolo[4,3-a]quinoxaline-4-ylamino]-butyl}-carbamic acid-tert-butylester;
(207) 4-(4-benzoylamino-butylamino)-1-methyl-[1,2,4]triazolo[4,3-a]quinoxaline-7-carboxylic acid-(2-dimethylamino-ethyl)-amide;
(208) N-{4-[7-(4-benzyl-piperazine-1-carbonyl)-1-methyl-[1,2,4]triazolo[4,3-a]quinoxaline-4-ylamino]-butyl}-benzamide;
(209) N-{4-[1-methyl-7-(piperazine-1-carbonyl)-[1,2,4]triazolo[4,3-a]quinoxaline-4-ylamino]-butyl}-benzamide;
(210) [4-(7-benzylcarbamoyl-1-methyl-[1,2,4]triazolo[4,3-a]quinoxaline-4-ylamino)-butyl]-carbamic acid-tert-butylester;
(211) {4-[7-(4-chloro-benzylcarbamoyl)-1-methyl-[1,2,4]triazolo[4,3-a]quinoxaline-4-ylamino]-butyl}-carbamic acid-tert-butylester;
(212) [4-(1-methyl-7-phenylcarbamoyl-[1,2,4]triazolo[4,3-a]quinoxaline-4-ylamino)-butyl]-carbamic acid-tert-butylester;
(213) {4-[7-(2-amino-phenylcarbamoyl)-1-methyl-[1,2,4]triazolo[4,3-a]quinoxaline-4-ylamino]-butyl}-carbamic acid-tert-butylester;
(214) {4-[7-(2-amino-4-methyl-phenylcarbamoyl)-1-methyl-[1,2,4]triazolo[4,3-a]quinoxaline-4-ylamino]-butyl}-carbamic acid-tert-butylester;
(215) 1-methyl-4-[4-(3-methyl-butyrylamino)-butylamino]-[1,2,4]triazolo[4,3-a]quinoxaline-7-carboxylic acid-(2-amino-phenyl)-amide;
(216) 1-methyl-4-[4-(3-methyl-butyrylamino)-butylamino]-[1,2,4]triazolo[4,3-a]quinoxaline-7-carboxylic acid-(2-amino-4-methyl-phenyl)-amide;
(217) 1-methyl-4-[4-(3-methyl-butyrylamino)-butylamino]-[1,2,4]triazolo[4,3-a]quinoxaline-7-carboxylic acid-(2-amino-4,5-dimethoxy-phenyl)-amide;
(218) {4-[7-(1H-benzoimidazole-2-yl)-1-methyl-[1,2,4]triazolo[4,3-a]quinoxaline-4-ylamino]-butyl}-carbamic acid-tert-butylester;
(219) {4-[1-methyl-7-(5-methyl-1H-benzoimidazole-2-yl)-[1,2,4]triazolo[4,3-a]quinoxaline-4-ylamino]-butyl}-carbamic acid-tert-butylester;
(220) {4-[1-methyl-7-(1-methyl-1H-benzoimidazole-2-yl)-[1,2,4]triazolo[4,3-a]quinoxaline-4-ylamino]-butyl}-carbamic acid-tert-butylester;
(221) $N^1$-[1-methyl-7-(1-methyl-1H-benzoimidazole-2-yl)-[1,2,4]triazolo[4,3-a]quinoxaline-4-yl]-butane-1,4-diamine ditrifluoroacetic acid;
(222) 3-methyl-N-{4-[1-methyl-7-(1-methyl-1H-benzoimidazole-2-yl)-[1,2,4]triazolo[4,3-a]quinoxaline-4-ylamino]-butyl}-butyramide;
(223) 3-methyl-N-{4-[1-methyl-7-(5-methyl-1H-benzoimidazole-2-yl)-[1,2,4]triazolo[4,3-a]quinoxaline-4-ylamino]-butyl}-butyramide;
(224) N-{4-[7-(1H-benzoimidazole-2-yl)-1-methyl-[1,2,4]triazolo[4,3-a]quinoxaline-4-ylamino]-butyl}-3-methyl-butyramide;
(225) N-{4-[7-(1H-benzoimidazole-2-yl)-1-methyl-[1,2,4]triazolo[4,3-a]quinoxaline-4-ylamino]-butyl}-2-(S)-hydroxy-3-methyl-butyramide;
(226) N-{4-[7-(1H-benzoimidazole-2-yl)-1-methyl-[1,2,4]triazolo[4,3-a]quinoxaline-4-ylamino]-butyl}-2-(R)-hydroxy-3-methyl-butyramide;
(227) N-{4-[7-(5,6-dimethoxy-1H-benzoimidazole-2-yl)-1-methyl-[1,2,4]triazolo[4,3-a]quinoxaline-4-ylamino]-butyl}-3-methyl-butyramide;
(228) {4-[1-methyl-7-(1-methyl-H-benzoimidazole-2-yl)-[1,2,4]triazolo[4,3-a]quinoxaline-4-ylamino]-butyl}-carbamic acid propylester;
(229) {4-[1-methyl-7-(1-methyl-1H-benzoimidazole-2-yl)-[1,2,4]triazolo[4,3-a]quinoxaline-4-ylamino]-butyl}-carbamic acid cyclopentylester;
(230) 2,2-dimethyl-N-{4-[1-methyl-7-(1-methyl-1H-benzoimidazole-2-yl)-[1,2,4]triazolo[4,3-a]quinoxaline-4-ylamino]-butyl}-propionamide;

(231) acetic acid-1-{4-[7-(1-methyl-1H-benzoimidazole-2-yl)-1-methyl-[1,2,4]triazolo[4,3-a]quinoxaline-4-ylamino]-butylcarbamoyl}-1-methyl-ethylester;

(232) 2-hydroxy-N-{4-(7-(1-methyl-1H-benzoimidazole-2-yl)-1-methyl-[1,2,4]triazolo[4,3-a]quinoxaline-4-ylamino)-butyl}-2-methyl-propionamide;

(233) 2,2-difluoro-N-{4-[1-methyl-7-(1-methyl-1H-benzoimidazole-2-yl)-[1,2,4]triazolo[4,3-a]quinoxaline-4-ylamino]-butyl}-butyramide;

(234) 2-(S)-hydroxy-3-methyl-N-{4-[1-methyl-7-(1-methyl-1H-benzoimidazole-2-yl)-[1,2,4]triazolo[4,3-a]quinoxaline-4-ylamino]-butyl}-butyramide;

(235) 2-(R)-hydroxy-3-methyl-N-{4-[1-methyl-7-(1-methyl-1H-benzimidazole-2-yl)-[1,2,4]triazolo[4,3-a]quinoxaline-4-ylamino]-butyl}-butyramide;

(236) 4-methyl-pentanoic acid-{4-[1l-methyl-7-(1-methyl-1H-benzoimidazole-2-yl)-[1,2,4]triazolo[4,3-a]quinoxaline-4-ylamino]-butyl}-amide;

(237) 2-methoxy-N-{4-[1-methyl-7-(1-methyl-1H-benzoimidazole-2-yl)-[1,2,4]triazolo[4,3-a]quinoxaline-4-ylamino]-butyl}-benzamide;

(238) 1-isopropyl-3-{4-[1-methyl-7-(1-methyl-1H-benzoimidazole-2-yl)-[1,2,4]triazolo[4,3-a]quinoxaline-4-ylamino]-butyl}-urea;

(239) 1-cyclohexyl-3-{4-[1-methyl-7-(1-methyl-1H-benzoimidazole-2-yl)-[1,2,4]triazolo[4,3-a]quinoxaline-4-ylamino]-butyl}-urea;

(240) 3-methyl-N-{4-[1-methyl-7-(1-propyl-1H-benzoimidazole-2-yl)-[1,2,4]triazolo[4,3-a]quinoxaline-4-ylamino]-butyl}-butyramide;

(241) N-(4-{7-[1-(2-methoxy-ethyl)-1H-benzoimidazole-2-yl]-1-methyl-[1,2,4]triazolo[4,3-a]quinoxaline-4-ylamino}-butyl)-3-methyl-butyramide;

(242) [4-(1-methyl-7-nitro-[1,2,4]triazolo[4,3-a]quinoxaline-4-ylamino)-butyl]-carbamic acid-tert-butylester;

(243) [4-(7-amino-1-methyl-[1,2,4]triazolo[4,3-a]quinoxaline-4-ylamino)-butyl]-carbamic acid-tert-butylester;

(244) 3-methyl-N-[4-(1-methyl-8-nitro-[1,2,4]triazolo[4,3-a]quinoxaline-4-ylamino)-butyl]-butyramide;

(245) N-[4-(7-amino-1-methyl-[1,2,4]triazolo[4,3-a]quinoxaline-4-ylamino)-butyl]-3-methyl-butyramide;

(246) [4-(7-isobutyramido-1-methyl-[1,2,4]triazolo[4,3-a]quinoxaline-4-ylamino)-butyl]-carbamic acid-tert-butylester;

(247) N-[4-(7-isobutyramido-1-methyl-[1,2,4]triazolo[4,3-a]quinoxaline-4-ylamino)-butyl]-2,2-dimethyl-propionamide;

(248) N-[4-(7-isobutyramido-1-methyl-[1,2,4]triazolo[4,3-a]quinoxaline-4-ylamino)-butyl]-benzamide;

(249) [4-(7-acetylamino-methyl-[1,2,4]triazolo[4,3-a]quinoxaline-4-ylamino)-butyl]-carbamic acid-tert-butylester;

(250) N-[4-(7-acetylamino-methyl-[1,2,4]triazolo[4,3-a]quinoxaline-4-ylamino)-butyl]-2,2-dimethyl-propionamide;

(251) N-[4-(7-acetylamino-methyl-[1,2,4]triazolo[4,3-a]quinoxaline-4-ylamino)-butyl]-benzamide;

(252) 3-methyl-N-[4-(1-methyl-7-methylamino-[1,2,4]triazolo[4,3-a]quinoxaline-4-ylamino)-butyl]-butyramide;

(253) 3-methyl-N-[4-(1-methyl-7-propylamino-[1,2,4]triazolo[4,3-a]quinoxaline-4-ylamino)-butyl]-butyramide;

(254) N-{4-[7-(3-cyano-propylamino)-1-methyl-[1,2,4]triazolo[4,3-a]quinoxaline-4-ylamino]-butyl}-3-methyl-butyramide;

(255) N-{4-[7-(3-isopropyl-ureido)-1-methyl-[1,2,4]triazolo[4,3-a]quinoxaline-4-ylamino]-butyl}-3-methyl-butyramide;

(256) N-{4-[7-(3-isopropyl-thioureido)-1-methyl-[1,2,4]triazolo[4,3-a]quinoxaline-4-ylamino]-butyl}-3-methyl-butyramide;

(257) N-[4-(7-methanesulfonylamino-1-methyl-[1,2,4]triazolo[4,3-a]quinoxaline-4-ylamino)-butyl]-3-methyl-butyramide;

(258) 3-methyl-N-{4-[1-methyl-7-(2,2,2-trifluoro-ethanesulfonylamino)-[1,2,4]triazolo[4,3-a]quinoxaline-4-ylamino]-butyl}-butyramide;

(259) 3-methyl-N-{4-[1-methyl-7-(propane-2-sulfonylamino)-[1,2,4]triazolo[4,3-a]quinoxaline-4-ylamino]-butyl}-butyramide;

(260) [4-(7-benzoyl-1-methyl-[1,2,4]triazolo[4,3-a]quinoxaline-4-ylamino)-butyl]-carbamic acid-tert-butylester;

(261) {4-[7-(4-chloro-benzoyl)-1-methyl-[1,2,4]triazolo[4,3-a]quinoxaline-4-ylamino]-butyl}-carbamic acid-tert-butylester;

(262) {4-[7-(4-methoxy-benzoyl)-1-methyl-[1,2,4]triazolo[4,3-a]quinoxaline-4-ylamino]-butyl}-carbamic acid-tert-butylester;

(263) [4-(1-methyl-8-trifluoromethoxy-[1,2,4]triazolo[4,3-a]quinoxaline-4-ylamino)-butyl]-carbamic acid-tert-butylester;

(264) $N^1$-(1-methyl-8-trifluoromethoxy-[1,2,4]triazolo[4,3-a]quinoxaline-4-yl)-butane-1,4-diamine ditrifluoroacetic acid;

(265) 2,2-dimethyl-N-[4-(1-methyl-8-trifluoromethoxy-[1,2,4]triazolo[4,3-a]quinoxaline-4-ylamino)-butyl]-propionamide;

(266) 3,3-dimethyl-N-[4-(1-methyl-8-trifluoromethoxy-[1,2,4]triazolo[4,3-a]quinoxaline-4-ylamino)-butyl]-butyramide;

(267) N-[4-(1-methyl-8-trifluoromethoxy-[1,2,4]triazolo[4,3-a]quinoxaline-4-ylamino)-butyl]-benzamide;

(268) 2-chloro-N-[4-(1-methyl-8-trifluoromethoxy-[1,2,4]triazolo[4,3-a]quinoxaline-4-ylamino)-butyl]-benzamide;

(269) [4-(1-methyl-7-trifluoromethoxy-[1,2,4]triazolo[4,3-a]quinoxaline-4-ylamino)-butyl]-carbamic acid-tert-butylester;

(270) $N^1$-(1-methyl-7-trifluoromethoxy-[1,2,4]triazolo[4,3-a]quinoxaline-4-yl)-butane-1,4-diamine ditrifluoroacetic acid;

(271) 2,2-dimethyl-N-[4-(1-methyl-7-trifluoromethoxy-[1,2,4]triazolo[4,3-a]quinoxaline-4-ylamino)-butyl]-propionamide;

(272) 3,3-dimethyl-N-[4-(1-methyl-7-trifluoromethoxy-[1,2,4]triazolo[4,3-a]quinoxaline-4-ylamino)-butyl]-butyramide;

(273) N-[4-(1-methyl-7-trifluoromethoxy-[1,2,4]triazolo[4,3-a]quinoxaline-4-ylamino)-butyl]-benzamide;

(274) 2-chloro-N-[4-(1-methyl-7-trifluoromethoxy-[1,2,4]triazolo[4,3-a]quinoxaline-4-ylamino)-butyl]-benzamide;

(275) [4-(7-methoxy-1-methyl-[1,2,4]triazolo[4,3-a]quinoxaline-4-ylamino)-butyl]-carbamic acid-tert-butylester;

(276) $N^1$-(7-methoxy-1-methyl-[1,2,4]triazolo[4,3-a]quinoxaline-4-yl)-butane-1,4-diamine ditrifluoroacetic acid;

(277) N-[4-(7-methoxy-1-methyl-[1,2,4]triazolo[4,3-a]quinoxaline-4-ylamino)-butyl]-2,2-dimethyl-propionamide;

(278) [4-(7-methoxy-1-methyl-[1,2,4]triazolo[4,3-a]quinoxaline-4-ylamino)-butyl]-carbamic acid isopropylester;

(279) [4-(7-methoxy-1-methyl-[1,2,4]triazolo[4,3-a]quinoxaline-4-ylamino)-butyl]-carbamic acid isobutylester;

(280) [4-(7-methoxy-1-methyl-[1,2,4]triazolo[4,3-a]quinoxaline-4-ylamino)-butyl]-carbamic acid-sec-butylester;

(281) N-[4-(7-methoxy-1-methyl-[1,2,4]triazolo[4,3-a]quinoxaline-4-ylamino)-butyl]-isobutyramide;
(282) cyclopropanecarboxylic acid-[4-(7-methoxy-1-methyl-[1,2,4]triazolo[4,3-a]quinoxaline-4-ylamino)-butyl]-amide;
(283) butene-2-oic acid-[4-(7-methoxy-1-methyl-[1,2,4]triazolo[4,3-a]quinoxaline-4-ylamino)-butyl]-amide;
(284) 3-methyl-butene-2-oic acid-[4-(7-methoxy-1-methyl-[1,2,4]triazolo[4,3-a]quinoxaline-4-ylamino)-butyl]-amide;
(285) N-[4-(7-methoxy-1-methyl-[1,2,4]triazolo[4,3-a]quinoxaline-4-ylamino)-butyl]-3-methyl-butyramide;
(286) 2-(S)-fluoro-N-[4-(7-methoxy-1-methyl-[1,2,4]triazolo[4,3-a]quinoxaline-4-ylamino)-butyl]-3-methyl-butyramide;
(287) N-[4-(7-methoxy-1-methyl-[1,2,4]triazolo[4,3-a]quinoxaline-4-ylamino)-butyl]-3,3-dimethyl-butyramide;
(288) 4-methyl-pentanoic acid-[4-(7-methoxy-1-methyl-[1,2,4]triazolo[4,3-a]quinoxaline-4-ylamino)-butyl]-amide;
(289) 3-methyl-pentanoic acid-[4-(7-methoxy-1-methyl-[1,2,4]triazolo[4,3-a]quinoxaline-4-ylamino)-butyl]-amide;
(290) 2-ethyl-N-[4-(7-methoxy-1-methyl-[1,2,4]triazolo[4,3-a]quinoxaline-4-ylamino)-butyl]-butyramide;
(291) N-[4-(7-methoxy-1-methyl-[1,2,4]triazolo[4,3-a]quinoxaline-4-ylamino)-butyl]-2-methyl-butyramide;
(292) 2,2,3,3,4,4-heptafluoro-N-[4-(7-methoxy-1-methyl-[1,2,4]triazolo[4,3-a]quinoxaline-4-ylamino)-butyl]-butyramide;
(293) 3,3,3-trifluoro-N-[4-(7-methoxy-1-methyl-[1,2,4]triazolo[4,3-a]quinoxaline-4-ylamino)-butyl]-2,2-dimethyl-propaneamide;
(294) 2,2-difluoro-N-[4-(7-methoxy-1-methyl-[1,2,4]triazolo[4,3-a]quinoxaline-4-ylamino)-butyl]-butyramide;
(295) 2-(R)-hydroxy-N-[4-(7-methoxy-1-methyl-[1,2,4]triazolo[4,3-a]quinoxaline-4-ylamino)-butyl]-propane-amide;
(296) acetic acid-1-[4-(7-methoxy-1-methyl-[1,2,4]triazolo[4,3-a]quinoxaline-4-ylamino)-butylcarbamoyl]-1-methyl-ethylester;
(297) 2-hydroxy-N-[4-(7-methoxy-1-methyl-[1,2,4]triazolo[4,3-a]quinoxaline-4-ylamino)-butyl]-2-methyl-propionamide;
(298) 2-(R)-hydroxy-N-[4-(7-methoxy-1-methyl-[1,2,4]triazolo[4,3-a]quinoxaline-4-ylamino)-butyl]-3-methyl-butyramide;
(299) 2-(S)-hydroxy-N-[4-(7-methoxy-1-methyl-[1,2,4]triazolo[4,3-a]quinoxaline-4-ylamino)-butyl]-3-methyl-butyramide;
(300) 2-(R)-methoxy-N-[4-(7-methoxy-1-methyl-[1,2,4]triazolo[4,3-a]quinoxaline-4-ylamino)-butyl]-3-methyl-butyramide;
(301) 2-(S)-methoxy-N-[4-(7-methoxy-1-methyl-[1,2,4]triazolo[4,3-a]quinoxaline-4-ylamino)-butyl]-3-methyl-butyramide;
(302) 2-(S)-bromo-N-[4-(7-methoxy-1-methyl-[1,2,4]triazolo[4,3-a]quinoxaline-4-ylamino)-butyl]-3-methyl-butyramide;
(303) acetic acid-[4-(7-methoxy-1-methyl-[1,2,4]triazolo[4,3-a]quinoxaline-4-ylamino)-butylcarbamoyl]-methyl-ester;
(304) 2-hydroxy-N-[4-(7-methoxy-1-methyl-[1,2,4]triazolo[4,3-a]quinoxaline-4-ylamino)-butyl]-acetamide;
(305) N-[4-(7-methoxy-1-methyl-[1,2,4]triazolo[4,3-a]quinoxaline-4-ylamino)-butyl]-malonamic acid ethylester;
(306) N-[4-(7-methoxy-1-methyl-[1,2,4]triazolo[4,3-a]quinoxaline-4-ylamino)-butyl]-malonamic acid;
(307) N-[4-(7-methoxy-1-methyl-[1,2,4]triazolo[4,3-a]quinoxaline-4-ylamino)-butyl]-2-thiophene-2-yl-acetamide;
(308) 2-furan-2-yl-N-[4-(7-methoxy-1-methyl-[1,2,4]triazolo[4,3-a]quinoxaline-4-ylamino)-butyl]-acetamide;
(309) 3-cyclopentyl-N-[4-(7-methoxy-1-methyl-[1,2,4]triazolo[4,3-a]quinoxaline-4-ylamino)-butyl]-propionamide;
(310) {-[4-(7-methoxy-1-methyl-[1,2,4]triazolo[4,3-a]quinoxaline-4-ylamino)-butylcarbamoyl]-2-methyl-propyl}-carbamic acid-tert-butylester;
(311) 2-amino-N-[4-(7-methoxy-1-methyl-[1,2,4]triazolo[4,3-a]quinoxaline-4-ylamino)-butyl]-3-methyl-butyramide;
(312) 2-(R)-dimethylamino-N-[4-(7-methoxy-1-methyl-[1,2,4]triazolo[4,3-a]quinoxaline-4-ylamino)-butyl]-3-methyl-butyramide;
(313) 2-(S)-dimethylamino-N-[4-(7-methoxy-1-methyl-[1,2,4]triazolo[4,3-a]quinoxaline-4-ylamino)-butyl]-3-methyl-butyramide;
(314) N-[4-(7-methoxy-1-methyl-[1,2,4]triazolo[4,3-a]quinoxaline-4-ylamino)-butyl]-3-methyl-2-(S)-morpholine-4-yl-butyramide;
(315) 2-(S)-(3-hydroxy-pyrrolidine-1-yl)-N-[4-(7-methoxy-1-methyl-[1,2,4]triazolo[4,3-a]quinoxaline-4-ylamino)-butyl]-3-methyl-butyramide;
(316) 2-(S)-(4-hydroxy-piperidine-1-yl)-N-[4-(7-methoxy-1-methyl-[1,2,4]triazolo[4,3-a]quinoxaline-4-ylamino)-butyl]-3-methyl-butyramide;
(317) 2-(S)-[4-(2-hydroxy-ethyl)-piperidine-1-yl]-N-[4-(7-methoxy-1-methyl-[1,2,4]triazolo[4,3-a]quinoxaline-4-ylamino)-butyl]-3-methyl-butyramide;
(318) (S)-{1-[4-(7-methoxy-1-methyl-[1,2,4]triazolo[4,3-a]quinoxaline-4-ylamino)-butylcarbamoyl]-2-methyl-propyl}-carbamic acid isobutylester;
(319) (S)-{1-[4-(7-methoxy-1-methyl-[1,2,4]triazolo[4,3-a]quinoxaline-4-ylamino)-butylcarbamoyl]-2-methyl-propyl}-carbamic acid propylester;
(320) (S)-{1-[4-(7-methoxy-1-methyl-[1,2,4]triazolo[4,3-a]quinoxaline-4-ylamino)-butylcarbamoyl]-2-methyl-propyl}-carbamic acid isopropylester;
(321) (S)-2-(S)-fluoro-N-{1-[4-(7-methoxy-1-methyl-[1,2,4]triazolo[4,3-a]quinoxaline-4-ylamino)-butyl carbamoyl]-2-methyl-propyl}-3-methyl-butyramide;
(322) (S)—N-[4-(7-methoxy-1-methyl-[1,2,4]triazolo[4,3-a]quinoxaline-4-ylamino)-butyl]-3-methyl-2-(3-methyl-butyrylamino)-butyramide;
(323) (S)-2-(2,2-dimethyl-propionylamino)-N-[4-(7-methoxy-1-methyl-[1,2,4]triazolo[4,3-a]quinoxaline-4-ylamino)-butyl]-3-methyl-butyramide;
(324) 2-(S)-(2 (S)-hydroxy-propionylamino)-N-[4-(7-methoxy-1-methyl-[1,2,4]triazolo[4,3-a]quinoxaline-4-ylamino)-butyl]-3-methyl-butyramide;
(325) {2-(S)-(4-hydroxy-phenyl)-1-[4-(7-methoxy-1-methyl-[1,2,4]triazolo[4,3-a]quinoxaline-4-ylamino)-butylcarbamoyl]-ethyl}-carbamic acid-tert-butylester;
(326) 2-(S)-amino-3-(4-hydroxy-phenyl)-N-[4-(7-methoxy-1-methyl-[1,2,4]triazolo[4,3-a]quinoxaline-4-ylamino)-butyl]-propionamide;
(327) 2-(S)-methanesulfonylamino-N-[4-(7-methoxy-1-methyl-[1,2,4]triazolo[4,3-a]quinoxaline-4-ylamino)-butyl]-3-methyl-butyramide;
(328) 2-fluoro-N-[4-(7-methoxy-1-methyl-[1,2,4]triazolo[4,3-a]quinoxaline-4-ylamino)-butyl]-benzamide;
(329) N-[4-(7-methoxy-1-methyl-[1,2,4]triazolo[4,3-a]quinoxaline-4-ylamino)-butyl]-2-phenyl-acetamide;
(330) 1-isopropyl-3-[4-(7-methoxy-1-methyl-[1,2,4]triazolo[4,3-a]quinoxaline-4-ylamino)-butyl]-urea;

(331) 1-tert-butyl-3-[4-(7-methoxy-1-methyl-[1,2,4]triazolo[4,3-a]quinoxaline-4-ylamino)-butyl]-urea;
(332) [4-(7-methoxy-1-methyl-[1,2,4]triazolo[4,3-a]quinoxaline-4-ylamino)-butyl]-carbamic acid cyclopentylester;
(333) [4-(7-methoxy-1-methyl-[1,2,4]triazolo[4,3-a]quinoxaline-4-ylamino)-butyl]-carbamic acid phenylester;
(334) 3-[4-(7-methoxy-1-methyl-[1,2,4]triazolo[4,3-a]quinoxaline-4-ylamino)-butyl]-1,1-dimethyl-urea;
(335) 1-cyclohexyl-3-[4-(7-methoxy-1-methyl-[1,2,4]triazolo[4,3-a]quinoxaline-4-ylamino)-butyl]-urea;
(336) [4-(7-methoxy-1-methyl-[1,2,4]triazolo[4,3-a]quinoxaline-4-ylamino)-butyl]-thiocarbamic acid-S-isopropylester;
(337) 1-isopropyl-3-[4-(7-methoxy-1-methyl-[1,2,4]triazolo[4,3-a]quinoxaline-4-ylamino)-butyl]-thiourea;
(338) N-[4-(7-methoxy-1-methyl-[1,2,4]triazolo[4,3-a]quinoxaline-4-ylamino)-butyl]-methanesulfonamide;
(339) N-{4-[7-methoxy-1-methyl-8-(4-nitro-benzyl)-[1,2,4]triazolo[4,3-a]quinoxaline-4-ylamino]-butyl}-3-methyl-butyramide;
(340) N-[4-(7-hydroxy-1-methyl-[1,2,4]triazolo[4,3-a]quinoxaline-4-ylamino)-butyl]-3-methyl-butyramide;
(341) N-{4-[7-(4-cyano-benzyloxy)-1-methyl-[1,2,4]triazolo[4,3-a]quinoxaline-4-ylamino]-butyl}-3-methyl-butyramide;
(342) N-{4-[7-(3-cyano-propoxy)-1-methyl-[1,2,4]triazolo[4,3-a]quinoxaline-4-ylamino]-butyl}-3-methyl-butyramide;
(343) 3-methyl-N-{4-[1-methyl-7-(tetrahydro-pyran-2-ylmethoxy)-[1,2,4]triazolo[4,3-a]quinoxaline-4-ylamino]-butyl}-butyramide;
(344) 3-methyl-N-{4-[1-methyl-7-(tetrahydro-pyran-4-yloxy)-[1,2,4]triazolo[4,3-a]quinoxaline-4-ylamino]-butyl}-butyramide;
(345) 4-{1-methyl-4-[4-(3-methyl-butylamino)-butylamino]-[1,2,4]triazolo[4,3-a]quinoxaline-7-yloxy}-piperidine-1-carboxylic acid-tert-butylester;
(346) N-[4-(7-benzyloxy-1-methyl-[1,2,4]triazolo[4,3-a]quinoxaline-4-ylamino)-butyl]-3-methyl-butyramide;
(347) N-(4-{7-[4-(N-hydroxycarbamimidoyl)-benzoyl]-1-methyl-[1,2,4]triazolo[4,3-a]quinoxaline-4-ylamino}-butyl)-3-methyl-butyramide;
(348) 3-methyl-N-(4-{1-methyl-7-[4-(2H-tetrazol-5-yl)-benzyloxy]-[1,2,4]triazolo[4,3-a]quinoxaline-4-ylamino}-butyl)-butyramide;
(349) 3-methyl-N-(4-{1l-methyl-7-[4-(2-methyl-2H-tetrazolo-5-yl)-benzyloxy]-[1,2,4]triazolo[4,3-a]quinoxaline-4-ylamino}-butyl)-butyramide;
(350) benzoic acid-1-methyl-4-[4-(3-methyl-butylamino)-butylamino]-[1,2,4]triazolo[4,3-a]quinoxaline-7-yl-ester;
(351) morpholine-4-carboxylic acid-1-methyl-4-[4-(3-methyl-butylamino)-butylamino]-[1,2,4]triazolo[4,3-a]quinoxaline-7-yl-ester;
(352) 3-methyl-thiophene-2-carboxylic acid-1-methyl-4-[4-(3-methyl-butylamino)-butylamino]-[1,2,4]triazolo[4,3-a]quinoxaline-7-yl-ester;
(353) dimethyl-thiocarbamic acid-O-{1l-methyl-4-[4-(3-methyl-butylamino)-butylamino]-[1,2,4]triazolo[4,3-a]quinoxaline-7-yl}-ester;
(354) [4-(1-methyl-7-methylsulfanyl-[1,2,4]triazolo[4,3-a]quinoxaline-4-ylamino)-butyl]-carbamic acid-tert-butylester;
(355) N$^1$-(1-methyl-(7-methylsulfanyl-[1,2,4]triazolo[4,3-a]quinoxaline-4-yl)-butane-1,4-diamine ditrifluoroacetic acid;
(356) 3-methyl-N-[4-(1-methyl-7-methylsulfanyl-[1,2,4]triazolo[4,3-a]quinoxaline-4-ylamino)-butyl]-butyramide;
(357) 2-(S)-fluoro-3-methyl-N-[4-(1-methyl-7-methylsulfanyl-[1,2,4]triazolo[4,3-a]quinoxaline-4-ylamino)-butyl]-butyramide;
(358) 2-(S)-hydroxy-3-methyl-N-[4-(1-methyl-7-methylsulfanyl-[1,2,4]triazolo[4,3-a]quinoxaline-4-ylamino)-butyl]-butyramide;
(359) N-[4-(7-methanesulfinyl-1-methyl-[1,2,4]triazolo[4,3-a]quinoxaline-4-ylamino)-butyl]-3-methyl-butyramide;
(360) N-[4-(7-methanesulfonyl-1-methyl-[1,2,4]triazolo[4,3-a]quinoxaline-4-ylamino)-butyl]-3-methyl-butyramide;
(361) [4-(7-fluoro-1-methyl-[1,2,4]triazolo[4,3-a]quinoxaline-4-ylamino)-butyl]-carbamic acid-tert-butylester;
(362) 4-(7-chloro-1-methyl-[1,2,4]triazolo[4,3-a]quinoxaline-4-ylamino)-carbamic acid-tert-butylester;
(363) {4-[7-(2-methoxy-ethoxy)-1-methyl-[1,2,4]triazolo[4,3-a]quinoxaline-4-ylamino]-butyl}-carbamic acid-tert-butylester;
(364) N$^1$-[7-(2-methoxy-ethoxy)-1-methyl-[1,2,4]triazolo[4,3-a]quinoxaline-4-yl]-butane-1,4-diamine ditrifluoroacetic acid;
(365) N-{4-[7-(2-methoxy-ethoxy)-1-methyl-[1,2,4]triazolo[4,3-a]quinoxaline-4-ylamino]-butyl}-3-methyl-butyramide;
(366) {4-[7-(2-methoxy-ethoxy)-1-methyl-[1,2,4]triazolo[4,3-a]quinoxaline-4-ylamino]-butyl}-carbamic acid isopropylester;
(367) {4-[7-(2-methoxy-ethoxy)-1-methyl-[1,2,4]triazolo[4,3-a]quinoxaline-4-ylamino]-butyl}-carbamic acid propylester;
(368) {4-[7-(2-methoxy-ethoxy)-1-methyl-[1,2,4]triazolo[4,3-a]quinoxaline-4-ylamino]-butyl}-carbamic acid-sec-butylester;
(369) {4-[7-(2-methoxy-ethoxy)-1-methyl-[1,2,4]triazolo[4,3-a]quinoxaline-4-ylamino]-butyl}-carbamic acid isobutylester;
(370) {4-[7-(2-methoxy-ethoxy)-1-methyl-[1,2,4]triazolo[4,3-a]quinoxaline-4-ylamino]-butyl}-carbamic acid allylester;
(371) {4-[7-(2-methoxy-ethoxy)-1-methyl-[1,2,4]triazolo[4,3-a]quinoxaline-4-ylamino]-butyl}-carbamic acid cyclopentylester;
(372) {4-[7-(2-methoxy-ethoxy)-1-methyl-[1,2,4]triazolo[4,3-a]quinoxaline-4-ylamino]-butyl}-carbamic acid phenylester;
(373) {4-[7-(2-methoxy-ethoxy)-1-methyl-[1,2,4]triazolo[4,3-a]quinoxaline-4-ylamino]-butyl}-carbamic acid benzylester;
(374) {4-[7-(2-methoxy-ethoxy)-1-methyl-[1,2,4]triazolo[4,3-a]quinoxaline-4-ylamino]-butyl}-acetamide;
(375) {4-[7-(2-methoxy-ethoxy)-1-methyl-[1,2,4]triazolo[4,3-a]quinoxaline-4-ylamino]-butyl}-2,2-dimethyl-propionamide;
(376) {4-[7-(2-methoxy-ethoxy)-1-methyl-[1,2,4]triazolo[4,3-a]quinoxaline-4-ylamino]-butyl}-isobutyramide;
(377) cyclopropanecarboxylic acid-{4-[7-(2-methoxy-ethoxy)-1-methyl-[1,2,4]triazolo[4,3-a]quinoxaline-4-ylamino]-butyl}-amide;
(378) 3-methyl-butene-2-oic acid-{4-[7-(2-methoxy-ethoxy)-1-methyl-[1,2,4]triazolo[4,3-a]quinoxaline-4-ylamino]-butyl}-amide;
(379) butene-2-oic acid-{4-[7-(2-methoxy-ethoxy)-1-methyl-[1,2,4]triazolo[4,3-a]quinoxaline-4-ylamino]-butyl}-amide;

(380) N-{4-[7-(2-methoxy-ethoxy)-1-methyl-[1,2,4]triazolo[4,3-a]quinoxaline-4-ylamino]-butyl}-2-methyl-butyramide;
(381) 2-ethyl-N-{4-[7-(2-methoxy-ethoxy)-1-methyl-[1,2,4]triazolo[4,3-a]quinoxaline-4-ylamino]-butyl}-butyramide;
(382) N-{4-[7-(2-methoxy-ethoxy)-1-methyl-[1,2,4]triazolo[4,3-a]quinoxaline-4-ylamino]-butyl}-3,3-dimethyl-butyramide;
(383) 4-methyl-pentanoic acid-{4-[7-(2-methoxy-ethoxy)-1-methyl-[1,2,4]triazolo[4,3-a]quinoxaline-4-ylamino]-butyl}-amide;
(384) acetic acid-1-{4-[7-(2-methoxy-ethoxy)-1-methyl-[1,2,4]triazolo[4,3-a]quinoxaline-4-ylamino]-butylcarbamoyl}-1-methyl-ethylester;
(385) 2-hydroxy-N-{4-(7-(2-methoxy-ethoxy)-1-methyl-[1,2,4]triazolo[4,3-a]quinoxaline-4-ylamino)-butyl}-2-methyl-propionamide;
(386) acetic acid-{4-[7-(2-methoxy-ethoxy)-1-methyl-[1,2,4]triazolo[4,3-a]quinoxaline-4-ylamino]-butylcarbamoyl}-methylester;
(387) 2-hydroxy-N-{4-[7-(2-methoxy-ethoxy)-1-methyl-[1,2,4]triazolo[4,3-a]quinoxaline-4-ylamino]-butyl}-acetamide;
(388) 2-(R)-hydroxy-N-{4-[7-(2-methoxy-ethoxy)-1-methyl-[1,2,4]triazolo[4,3-a]quinoxaline-4-ylamino]-butyl}-3-methyl-butyramide;
(389) 2-(S)-hydroxy-N-{4-[7-(2-methoxy-ethoxy)-1-methyl-[1,2,4]triazolo[4,3-a]quinoxaline-4-ylamino]-butyl}-3-methyl-butyramide;
(390) 2-(R)-methoxy-N-{4-[7-(2-methoxy-ethoxy)-1-methyl-[1,2,4]triazolo[4,3-a]quinoxaline-4-ylamino]-butyl}-3-methyl-butyramide;
(391) 2,2-difluoro-N-{4-[7-(2-methoxy-ethoxy)-1-methyl-[1,2,4]triazolo[4,3-a]quinoxaline-4-ylamino]-butyl}-butyramide;
(392) 3,3,3-trifluoro-N-{4-[7-(2-methoxy-ethoxy)-1-methyl-[1,2,4]triazolo[4,3-a]quinoxaline-4-ylamino]-butyl}-2,2-dimethyl-propionamide;
(393) 3-cyclopentyl-N-{4-[7-(2-methoxy-ethoxy)-1-methyl-[1,2,4]triazolo[4,3-a]quinoxaline-4-ylamino]-butyl}-propionamide;
(394) N-{4-[7-(2-methoxy-ethoxy)-1-methyl-[1,2,4]triazolo[4,3-a]quinoxaline-4-ylamino]-butyl}-malonamic acid ethylester;
(395) N-{4-[7-(2-methoxy-ethoxy)-1-methyl-[1,2,4]triazolo[4,3-a]quinoxaline-4-ylamino]-butyl}-malonamic acid;
(396) (1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid-tert-butylester;
(397) 2-amino-N-{4-[7-(2-methoxy-ethoxy)-1-methyl-[1,2,4]triazolo[4,3-a]quinoxaline-4-ylamino]-butyl}-3-methyl-butyramide;
(398) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid isobutylester;
(399) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid propylester;
(400) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid isopropylester;
(401) (S)—N-{4-[7-(2-methoxy-ethoxy)-1-methyl-[1,2,4]triazolo[4,3-a]quinoxaline-4-ylamino]-butyl}-3-methyl-2-(3-methyl-butyrylamino)-butyramide;
(402) (S)-2-(2,2-dimethyl-propionylamino)-N-{4-[7-(2-methoxy-ethoxy)-1-methyl-[1,2,4]triazolo[4,3-a]quinoxaline-4-ylamino]-butyl}-3-methyl-butyramide;
(403) 2-(S,R)-hydroxy-N-(1-{4-[7-(2-methoxy-ethoxy)-1-methyl-[1,2,4]triazolo[4,3-a]quinoxaline-4-ylamino]-butylcarbamoyl}-2-methyl-propyl)-3-methyl-butyramide;
(404) 2-(S,S)-hydroxy-N-(1-{4-[7-(2-methoxy-ethoxy)-1-methyl-[1,2,4]triazolo[4,3-a]quinoxaline-4-ylamino]-butylcarbamoyl}-2-methyl-propyl)-3-methyl-butyramide;
(405) 2-(S)-methanesulfonylamino-{4-[7-(2-methoxy-ethoxy)-1-methyl-[1,2,4]triazolo[4,3-a]quinoxaline-4-ylamino]-butyl}-3-methyl-butyramide;
(406) N-{4-[7-(2-methoxy-ethoxy)-1-methyl-[1,2,4]triazolo[4,3-a]quinoxaline-4-ylamino]-butyl}-2-thiophene-2-yl-acetamide;
(407) 2-furan-2-yl-N-{4-[7-(2-methoxy-ethoxy)-1-methyl-[1,2,4]triazolo[4,3-a]quinoxaline-4-ylamino]-butyl}-acetamide;
(408) N-{4-[7-(2-methoxy-ethoxy)-1-methyl-[1,2,4]triazolo[4,3-a]quinoxaline-4-ylamino]-butyl}-benzamide;
(409) 2-fluoro-N-{4-[7-(2-methoxy-ethoxy)-1-methyl-[1,2,4]triazolo[4,3-a]quinoxaline-4-ylamino]-butyl}-benzamide;
(410) 3-fluoro-N-{4-[7-(2-methoxy-ethoxy)-1-methyl-[1,2,4]triazolo[4,3-a]quinoxaline-4-ylamino]-butyl}-benzamide;
(411) 2-chloro-N-{4-[7-(2-methoxy-ethoxy)-1-methyl-[1,2,4]triazolo[4,3-a]quinoxaline-4-ylamino]-butyl}-benzamide;
(412) 2-chloro-N-{4-[7-(2-methoxy-ethoxy)-1-methyl-[1,2,4]triazolo[4,3-a]quinoxaline-4-ylamino]-butyl}-benzamide;
(413) 2,3-dichloro-N-{4-[7-(2-methoxy-ethoxy)-1-methyl-[1,2,4]triazolo[4,3-a]quinoxaline-4-ylamino]-butyl}-benzamide;
(414) 2-methoxy-N-{4-[7-(2-methoxy-ethoxy)-1-methyl-[1,2,4]triazolo[4,3-a]quinoxaline-4-ylamino]-butyl}-benzamide;
(415) N-{4-[7-(2-methoxy-ethoxy)-1-methyl-[1,2,4]triazolo[4,3-a]quinoxaline-4-ylamino]-butyl}-4-nitro-butyramide;
(416) pyridine-2-carboxylic acid-{4-[7-(2-methoxy-ethoxy)-1-methyl-[1,2,4]triazolo[4,3-a]quinoxaline-4-ylamino]-butyl}-amide;
(417) N-{4-[7-(2-methoxy-ethoxy)-1-methyl-[1,2,4]triazolo[4,3-a]quinoxaline-4-ylamino]-butyl}-nicotinamide;
(418) N-{4-[7-(2-methoxy-ethoxy)-1-methyl-[1,2,4]triazolo[4,3-a]quinoxaline-4-ylamino]-butyl}-isonicotinamide;
(419) 6-chloro-N-{4-[7-(2-methoxy-ethoxy)-1-methyl-[1,2,4]triazolo[4,3-a]quinoxaline-4-ylamino]-butyl}-nicotinamide;
(420) N-{4-[7-(2-methoxy-ethoxy)-1-methyl-[1,2,4]triazolo[4,3-a]quinoxaline-4-ylamino]-butyl}-2-phenyl-acetamide;
(421) 3-{4-[7-(2-methoxy-ethoxy)-1-methyl-[1,2,4]triazolo[4,3-a]quinoxaline-4-ylamino]-butyl}-1,1-dimethyl-urea;
(422) 1-isopropyl-3-{4-[7-(2-methoxy-ethoxy)-1-methyl-[1,2,4]triazolo[4,3-a]quinoxaline-4-ylamino]-butyl}-urea;
(423) 1-ethyl-3-{4-[7-(2-methoxy-ethoxy)-1-methyl-[1,2,4]triazolo[4,3-a]quinoxaline-4-ylamino]-butyl}-urea;
(424) 1-tert-butyl-3-{4-[7-(2-methoxy-ethoxy)-1-methyl-[1,2,4]triazolo[4,3-a]quinoxaline-4-ylamino]-butyl}-urea;
(425) morpholine-4-carboxylic acid-{4-[7-(2-methoxy-ethoxy)-1-methyl-[1,2,4]triazolo[4,3-a]quinoxaline-4-ylamino]-butyl}-amide;

(426) 1-cyclohexyl-3-{4-[7-(2-methoxy-ethoxy)-1-methyl-[1,2,4]triazolo[4,3-a]quinoxaline-4-ylamino]-butyl}-urea;
(427) 3-{4-[7-(2-methoxy-ethoxy)-1-methyl-[1,2,4]triazolo[4,3-a]quinoxaline-4-ylamino]-butyl}-1-phenyl-urea;
(428) {4-[7-(2-methoxy-ethoxy)-1-methyl-[1,2,4]triazolo[4,3-a]quinoxaline-4-ylamino]-butyl}-thiocarbamic acid-S-isopropylester;
(429) N-{4-[7-(2-methoxy-ethoxy)-1-methyl-[1,2,4]triazolo[4,3-a]quinoxaline-4-ylamino]-butyl}-methanesulfonamide;
(430) {4-[1-methyl-7-(2-morpholine-4-yl-ethoxy)-[1,2,4]triazolo[4,3-a]quinoxaline-4-ylamino]-butyl}-carbamic acid-tert-butylester;
(431) $N^1$-{4-[1-methyl-7-(2-morpholine-4-yl-ethoxy)-[1,2,4]triazolo[4,3-a]quinoxaline-4-yl]-butane-1,4-diamine trifluoroacetic acid;
(432) 3-methyl-N-{4-[1-methyl-7-(2-morpholine-4-yl-ethoxy)-[1,2,4]triazolo[4,3-a]quinoxaline-4-ylamino]-butyl}-butyramide;
(433) 2,2-dimethyl-N-{4-[1-methyl-7-(2-morpholine-4-yl-ethoxy)-[1,2,4]triazolo[4,3-a]quinoxaline-4-ylamino]-butyl}-propionamide;
(434) 2-(R)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide;
(435) 2-(S)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide;
(436) {4-[1-methyl-7-(2-morpholine-4-yl-ethoxy)-[1,2,4]triazolo[4,3-a]quinoxaline-4-ylamino]-butyl}-carbamic acid isopropylester;
(437) {4-[1-methyl-7-(2-morpholine-4-yl-ethoxy)-[1,2,4]triazolo[4,3-a]quinoxaline-4-ylamino]-butyl}-carbamic acid cyclopentylester;
(438) N-{4-[1-methyl-7-(2-morpholine-4-yl-ethoxy)-[1,2,4]triazolo[4,3-a]quinoxaline-4-ylamino]-butyl}-2-thiophene-2-yl-acetamide;
(439) 2-chloro-N-{4-[1-methyl-7-(2-morpholine-4-yl-ethoxy)-[1,2,4]triazolo[4,3-a]quinoxaline-4-ylamino]-butyl}-benzamide;
(440) [4-(7-ethoxy-1-methyl-[1,2,4]triazolo[4,3-a]quinoxaline-4-ylamino)-butyl]-carbamic acid-tert-butylester;
(441) $N^1$-(7-ethoxy-1-methyl-[1,2,4]triazolo[4,3-a]quinoxaline-4-yl)-butane-1,4-diamine dihydrochloride;
(442) N-[4-(7-ethoxy-1-methyl-[1,2,4]triazolo[4,3-a]quinoxaline-4-ylamino)-butyl]-3-methyl-butyramide;
(443) [4-(7-ethoxy-1-methyl-[1,2,4]triazolo[4,3-a]quinoxaline-4-ylamino)-butyl]-carbamic acid isopropylester;
(444) [4-(7-ethoxy-1-methyl-[1,2,4]triazolo[4,3-a]quinoxaline-4-ylamino)-butyl]-carbamic acid isobutylester;
(445) [4-(7-ethoxy-1-methyl-[1,2,4]triazolo[4,3-a]quinoxaline-4-ylamino)-butyl]-carbamic acid cyclopentylester;
(446) N-[4-(7-ethoxy-1-methyl-[1,2,4]triazolo[4,3-a]quinoxaline-4-ylamino)-butyl]-2-thiophene-2-yl-acetamide;
(447) [4-(7-isopropoxy-1-methyl-[1,2,4]triazolo[4,3-a]quinoxaline-4-ylamino)-butyl]-carbamic acid-tert-butylester;
(448) $N^1$-(7-isopropoxy-1-methyl-[1,2,4]triazolo[4,3-a]quinoxaline-4-yl)-butane-1,4-diamine ditrifluoroacetic acid;
(449) N-[-(7-isopropoxy-1-methyl-[1,2,4]triazolo[4,3-a]quinoxaline-4-ylamino)-butyl]-3-methyl-butyramide;
(450) N-[4-(7-isopropoxy-1-methyl-[1,2,4]triazolo[4,3-a]quinoxaline-4-ylamino)-butyl]-2-methyl-butyramide;
(451) N-[4-(7-isopropoxy-1-methyl-[1,2,4]triazolo[4,3-a]quinoxaline-4-ylamino)-butyl]-2-thiophene-2-yl-acetamide;
(452) [4-(7-isopropoxy-1-methyl-[1,2,4]triazolo[4,3-a]quinoxaline-4-ylamino)-butyl]-carbamic acid isopropylester;
(453) [4-(7-isopropoxy-1-methyl-[1,2,4]triazolo[4,3-a]quinoxaline-4-ylamino)-butyl]-carbamic acid cyclopentylester;
(454) 2-chloro-N-[4-(7-isopropoxy-1-methyl-[1,2,4]triazolo[4,3-a]quinoxaline-4-ylamino)-butyl]-benzamide;
(455) [4-(7-methoxy-1,9-dimethyl-[1,2,4]triazolo[4,3-a]quinoxaline-4-ylamino)-butyl]-carbamic acid-tert-butylester;
(456) $N^1$-(7-methoxy-1,9-dimethyl-[1,2,4]triazolo[4,3-a]quinoxaline-4-yl)-butane-1,4-diamine ditrifluoroacetic acid;
(457) [4-(7-methoxy-1,9-dimethyl-[1,2,4]triazolo[4,3-a]quinoxaline-4-ylamino)-butyl]-carbamic acid isopropylester;
(458) [4-(7-methoxy-1,9-dimethyl-[1,2,4]triazolo[4,3-a]quinoxaline-4-ylamino)-butyl]-3-methyl-butyramide;
(459) [4-(6-chloro-7-methoxy-1-methyl-[1,2,4]triazolo[4,3-a]quinoxaline-4-ylamino)-butyl]-carbamic acid-tert-butylester;
(460) [4-(6-chloro-7-methoxy-1-methyl-[1,2,4]triazolo[4,3-a]quinoxaline-4-yl)-butane-1,4-diamine dihydrochloride;
(461) [4-(6-chloro-7-methoxy-1-methyl-[1,2,4]triazolo[4,3-a]quinoxaline-4-ylamino)-butyl]-3-methyl-butyramide;
(462) [4-(6-chloro-7-methoxy-1-methyl-[1,2,4]triazolo[4,3-a]quinoxaline-4-ylamino)-butyl]-carbamic acid isobutylester;
(463) N-[4-(6-chloro-7-methoxy-1-methyl-[1,2,4]triazolo[4,3-a]quinoxaline-4-ylamino)-butyl]-2-thiophene-2-yl-acetamide;
(464) [4-(7-methoxy-1,8-dimethyl-[1,2,4]triazolo[4,3-a]quinoxaline-4-ylamino)-butyl]-carbamic acid-tert-butylester;
(465) $N^1$-(7-methoxy-1,8-dimethyl-[1,2,4]triazolo[4,3-a]quinoxaline-4-yl)-butane-1,4-diamine ditrifluoroacetic acid;
(466) N-[4-(7-methoxy-1,8-dimethyl-[1,2,4]triazolo[4,3-a]quinoxaline-4-ylamino)-butyl]-2,2-dimethyl-propionamide;
(467) [4-(7-methoxy-1,8-dimethyl-[1,2,4]triazolo[4,3-a]quinoxaline-4-ylamino)-butyl]-carbamic acid isopropylester;
(468) [4-(7-methoxy-1,8-dimethyl-[1,2,4]triazolo[4,3-a]quinoxaline-4-ylamino)-butyl]-carbamic acid isobutylester;
(469) N-[4-(7-methoxy-1,8-dimethyl-[1,2,4]triazolo[4,3-a]quinoxaline-4-ylamino)-butyl]-3-methyl-butyramide;
(470) 2-chloro-N-[4-(7-methoxy-1,8-dimethyl-[1,2,4]triazolo[4,3-a]quinoxaline-4-ylamino)-butyl]-benzamide;
(471) [4-(7-methoxy-1-methyl-8-trifluoromethyl-[1,2,4]triazolo[4,3-a]quinoxaline-4-ylamino)-butyl]-carbamic acid-tert-butylester;
(472) $N^1$-(7-methoxy-1-methyl-8-trifluoromethyl-[1,2,4]triazolo[4,3-a]quinoxaline-4-yl)-butane-1,4-diamine ditrifluoroacetic acid;
(473) [4-(7-methoxy-1-methyl-8-trifluoromethyl-[1,2,4]triazolo[4,3-a]quinoxaline-4-ylamino)-butyl]-carbamic acid isopropylester;
(474) [4-(7-methoxy-1-methyl-8-trifluoromethyl-[1,2,4]triazolo[4,3-a]quinoxaline-4-ylamino)-butyl]-carbamic acid isobutylester;
(475) [4-(7-methoxy-1-methyl-8-trifluoromethyl-[1,2,4]triazolo[4,3-a]quinoxaline-4-ylamino)-butyl]-carbamic acid cyclopentylester;

(476) N-[4-(7-methoxy-1-methyl-8-trifluoromethyl-[1,2,4]triazolo[4,3-a]quinoxaline-4-ylamino)-butyl]-3-methyl-butyramide;
(477) N-[4-(7-methoxy-1-methyl-8-trifluoromethyl-[1,2,4]triazolo[4,3-a]quinoxaline-4-ylamino)-butyl]-2,2-dimethyl-propionamide;
(478) 2-(R)-hydroxy-N-[4-(7-methoxy-1-methyl-8-trifluoromethyl-[1,2,4]triazolo[4,3-a]quinoxaline-4-ylamino)-butyl]-3-methyl-butyramide;
(479) 2-(S)-hydroxy-N-[4-(7-methoxy-1-methyl-8-trifluoromethyl-[1,2,4]triazolo[4,3-a]quinoxaline-4-ylamino)-butyl]-3-methyl-butyramide;
(480) N-[4-(7-methoxy-1-methyl-8-trifluoromethyl-[1,2,4]triazolo[4,3-a]quinoxaline-4-ylamino)-butyl]-2-thiophene-2-yl-acetamide;
(481) 2-chloro-N-[4-(7-methoxy-1-methyl-8-trifluoromethyl-[1,2,4]triazolo[4,3-a]quinoxaline-4-ylamino)-butyl]-benzamide;
(482) 1-cyclohexyl-3-[4-(7-methoxy-1-methyl-8-trifluoromethyl-[1,2,4]triazolo[4,3-a]quinoxaline-4-ylamino)-butyl]-urea;
(483) {4-[7-methoxy-8-(2-methoxy-ethoxy)-1-methyl-[1,2,4]triazolo[4,3-a]quinoxaline-4-ylamino]-butyl}-carbamic acid-tert-butylester;
(484) N-[7-methoxy-8-(2-methoxy-ethoxy)-1-methyl-[1,2,4]triazolo[4,3-a]quinoxaline-4-yl]-butane-1,4-diamine ditrifluoroacetic acid;
(485) N-{4-[7-methoxy-8-(2-methoxy-ethoxy)-1-methyl-[1,2,4]triazolo[4,3-a]quinoxaline-4-ylamino]-butyl}-3-methyl-butyramide;
(486) [4-(7,8,9-trimethoxy-1-methyl-[1,2,4]triazolo[4,3-a]quinoxaline-4-ylamino)-butyl]-carbamic acid-tert-butylester;
(487) $N^1$-(7,8,9-trimethoxy-1-methyl-[1,2,4]triazolo[4,3-a]quinoxaline-4-yl)-butane-1,4-diamine ditrifluoroacetic acid;
(488) 3-methyl-N-[4-(7,8,9-trimethoxy-1-methyl-[1,2,4]triazolo[4,3-a]quinoxaline-4-ylamino)-butyl]-butyramide;
(489) 3-methyl-pentanoic acid-[4-(6,8,9-trimethoxy-1-methyl-[1,2,4]triazolo[4,3-a]quinoxaline-4-ylamino)-butyl]-amide;
(490) [4-(7-imidazole-1-yl-1-methyl-[1,2,4]triazolo[4,3-a]quinoxaline-4-ylamino)-butyl]-carbamic acid-tert-butylester;
(491) $N^1$-(7-imidazole-1-yl-1-methyl-[1,2,4]triazolo[4,3-a]quinoxaline-4-yl)-butane-1,4-diamine dihydrochloride;
(492) N-[4-(7-imidazole-1-yl-1-methyl-[1,2,4]triazolo[4,3-a]quinoxaline-4-ylamino)-butyl]-3-methyl-butyramide;
(493) [4-(7-imidazole-1-yl-1-methyl-[1,2,4]triazolo[4,3-a]quinoxaline-4-ylamino)-butyl]-carbamic acid isobutylester;
(494) [4-(7-imidazole-1-yl-1-methyl-[1,2,4]triazolo[4,3-a]quinoxaline-4-ylamino)-butyl]-carbamic acid isopropylester;
(495) 3-methyl-pentanoic acid-[4-(7-imidazole-1-yl-1-methyl-[1,2,4]triazolo[4,3-a]quinoxaline-4-ylamino)-butyl]-amide;
(496) N-[4-(7-imidazole-1-yl-1-methyl-[1,2,4]triazolo[4,3-a]quinoxaline-4-ylamino)-butyl]-2-thiophene-2-yl-acetamide;
(497) [4-(1-methyl-7-morpholine-4-yl-[1,2,4]triazolo[4,3-a]quinoxaline-4-ylamino)-butyl]-carbamic acid-tert-butylester;
(498) $N^1$-(1-methyl-7-morpholine-4-yl-[1,2,4]triazolo[4,3-a]quinoxaline-4-yl)-butane-1,4-diamine dihydrochloride;
(499) 3-methyl-N-[4-(1-methyl-7-morpholine-4-yl-[1,2,4]triazolo[4,3-a]quinoxaline-4-ylamino)-butyl]-butyramide;
(500) 2-(S)-fluoro-3-methyl-N-[4-(1-methyl-7-morpholine-4-yl-[1,2,4]triazolo[4,3-a]quinoxaline-4-ylamino)-butyl]-butyramide;
(501) 3-methyl-pentanoic acid-[4-(1-methyl-7-morpholine-4-yl-[1,2,4]triazolo[4,3-a]quinoxaline-4-ylamino)-butyl]-amide;
(502) (S)-{2-methyl-1-[4-(1-methyl-7-morpholine-4-yl-[1,2,4]triazolo[4,3-a]quinoxaline-4-ylamino)-butylcarbamoyl]-propyl}-carbamic acid-tert-butylester;
(503) 2-(S)-amino-3-methyl-N-[4-(1-methyl-7-morpholine-4-yl-[1,2,4]triazolo[4,3-a]quinoxaline-4-ylamino)-butyl]-butyramide hydrochloride;
(504) (S)-2-(2-(S)-hydroxy-propionylamino)-3-methyl-N-[4-(1-methyl-7-morpholine-4-yl-[1,2,4]triazolo[4,3-a]quinoxaline-4-ylamino)-butyl]-butyramide hydrochloride;
(505) 2-(S)-methanesulfonylamino-3-methyl-N-[4-(1-methyl-7-morphonyl-4-yl-[1,2,4]triazolo[4,3-a]quinoxaline-4-ylamino)-butyl]-butyramide;
(506) [4-(1-methyl-7-morpholine-4-yl-[1,2,4]triazolo[4,3-a]quinoxaline-4-ylamino)-butyl]-carbamic acid isopropylester;
(507) N-[4-(1-methyl-7-morpholine-4-yl-[1,2,4]triazolo[4,3-a]quinoxaline-4-ylamino)-butyl]-2-thiophene-2-yl-acetamide;
(508) {4-[7-(2,6-dimethyl-morphonyl-4-yl)-1-methyl-[1,2,4]triazolo[4,3-a]quinoxaline-4-ylamino]-butyl}-carbamic acid-tert-butylester;
(509) $N^1$-[7-(2,6-dimethyl-morphonyl-4-yl)-1-methyl-[1,2,4]triazolo[4,3-a]quinoxaline-4-yl]-butane-1,4-diamine ditrifluoroacetic acid;
(510) N-{4-[7-(2,6-dimethyl-morpholine-4-yl)-1-methyl-[1,2,4]triazolo[4,3-a]quinoxaline-4-ylamino]-butyl}-3-methyl-butyramide;
(511) N-{4-[7-(2,6-dimethyl-morphonyl-4-yl)-1-methyl-[1,2,4]triazolo[4,3-a]quinoxaline-4-ylamino]-butyl}-2-(S)-fluoro-3-methyl-butyramide;
(512) N-{4-[7-(2,6-dimethyl-morpholine-4-yl)-1-methyl-[1,2,4]triazolo[4,3-a]quinoxaline-4-ylamino]-butyl}-2-(R)-hydroxy-3-methyl-butyramide;
(513) (S)-(2-methyl-1-{4-[1-methyl-7-(2,6-dimethyl-morpholine-4-yl)-[1,2,4]triazolo[4,3-a]quinoxaline-4-ylamino]-butylcarbamoyl}-propyl)-carbamic acid-tert-butylester;
(514) 2-(S)-amino-N-{4-[7-(2,6-dimethyl-morpholine-4-yl)-1-methyl-[1,2,4]triazolo[4,3-a]quinoxaline-4-ylamino]-butyl}-3-methyl-butyramide hydrochloride;
(515) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isobutylester;
(516) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid propylester;
(517) (S)—$N^1$-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-2-(S)-fluoro-3-methyl-butyramide;
(518) (S)—N-{4-[7-(2,6-dimethyl-morpholine-4-yl)-1-methyl-[1,2,4]triazolo[4,3-a]quinoxaline-4-ylamino]-butyl}-3-methyl-2-(3-methyl-butyrylamino)-butyramide;

(519) (S)—N-{4-[7-(2,6-dimethyl-morpholine-4-yl)-1-methyl-[1,2,4]triazolo[4,3-a]quinoxaline-4-ylamino]-butyl}-2-(2,2-dimethyl-propionylamino)-3-methyl-butyramide;
(520) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isopropylester;
(521) {[4-(1-methyl-7-thiomorpholine-4-yl)-[1,2,4]triazolo[4,3-a]quinoxaline-4-ylamino]-butyl}-carbamic acid-tert-butylester;
(522) $N^1$-(1-methyl-7-thiomorphonyl-4-yl-[1,2,4]triazolo[4,3-a]quinoxaline-4-yl)-butane-1,4-diamine ditrifluoroacetic acid;
(523) 3-methyl-N-[4-(1-methyl-7-thiomorpholine-4-yl-[1,2,4]triazolo[4,3-a]quinoxaline-4-ylamino)-butyl]-butyramide;
(524) N-[4-(7-thiomorphonyl-4-yl-1-methyl-[1,2,4]triazolo[4,3-a]quinoxaline-4-ylamino)-butyl]-2-(R)-hydroxy-3-methyl-butyramide;
(525) N-[4-(7-thiomorphonyl-4-yl-1-methyl-[1,2,4]triazolo[4,3-a]quinoxaline-4-ylamino)-butyl]-2-(S)-hydroxy-3-methyl-butyramide;
(526) {4-[7-(6,7-dihydro-4H-thiano[3,2-c]pyridine-5-yl)-1-methyl-[1,2,4]triazolo[4,3-a]quinoxaline-4-ylamino]-butyl}-carbamic acid-tert-butylester;
(527) $N^1$-[7-(6,7-dihydro-4H-thiano[3,2-c]pyridine-5-yl)-1-methyl-[1,2,4]triazolo[4,3-a]quinoxaline-4-yl]-butane-1,4-diamine ditrifluoroacetic acid;
(528) N-{4-[7-(6,7-dihydro-4H-thiano[3,2-c]pyridine-5-yl)-1-methyl-[1,2,4]triazolo[4,3-a]quinoxaline-4-ylamino]-butyl}-3-methyl-butyramide;
(529) N-{4-[7-(6,7-dihydro-4H-thiano[3,2-c]pyridine-5-yl)-1-methyl-[1,2,4]triazolo[4,3-a]quinoxaline-4-ylamino]-butyl}-2-(S)-fluoro-3-methyl-butyramide;
(530) 4-(4-tert-butoxycarbonylamino-butylamino)-1-methyl-[1,2,4]triazolo[4,3-a]quinoxaline-8-carboxylic acid methylester;
(531) 4-(4-tert-butoxycarbonylamino-butylamino)-1-methyl-[1,2,4]triazolo[4,3-a]quinoxaline-8-carboxylic acid;
(532) [4-(8-isopropylcarbamoyl-1-methyl-[1,2,4]triazolo[4,3-a]quinoxaline-4-ylamino)-butyl]-carbamic acid-tert-butylester;
(533) [4-(8-carbamoyl-1-methyl-[1,2,4]triazolo[4,3-a]quinoxaline-4-ylamino)-butyl]-carbamic acid-tert-butylester;
(534) 4-(4-isobutyramido-butylamino)-1-methyl-[1,2,4]triazolo[4,3-a]quinoxaline-8-carboxylic acid isopropylamide;
(535) 4-(4-benzylamino-butylamino)-1-methyl-[1,2,4]triazolo[4,3-a]quinoxaline-8-carboxylic acid isopropylamide;
(536) {4-[8-(2-dimethylamino-ethylcarbamoyl)-1-methyl-[1,2,4]triazolo[4,3-a]quinoxaline-4-ylamino]-butyl}-carbamic acid-tert-butylester;
(537) 4-(4-benzoylamino)-1-methyl-[1,2,4]triazolo[4,3-a]quinoxaline-8-carboxylic acid-(2-dimethylamino-ethyl)-amide;
(538) [4-(1-methyl-8-phenylcarbamoyl-[1,2,4]triazolo[4,3-a]quinoxaline-4-ylamino)-butyl]-carbamic acid-tert-butylester;
(539) N-{4-[8-(4-benzyl-piperazine-1-carbonyl)-1-methyl-[1,2,4]triazolo[4,3-a]quinoxaline-4-ylamino]-butyl}-benzamide;
(540) N-{4-[1-methyl-8-(piperazine-1-carbonyl)-[1,2,4]triazolo[4,3-a]quinoxaline-4-ylamino]-butyl}-benzamide;
(541) [4-(1-methyl-8-nitro-[1,2,4]triazolo[4,3-a]quinoxaline-4-ylamino)-butyl]-carbamic acid-tert-butylester;
(542) [4-(8-amino-1-methyl-[1,2,4]triazolo[4,3-a]quinoxaline-4-ylamino)-butyl]-carbamic acid-tert-butylester;
(543) [4-(8-isobutyramido-1-methyl-[1,2,4]triazolo[4,3-a]quinoxaline-4-ylamino)-butyl]-carbamic acid-tert-butylester;
(544) N-[4-(4-aminobutylamino)-1-methyl-[1,2,4]triazolo[4,3-a]quinoxaline-8-yl]-isobutyramide ditrifluoroacetic acid;
(545) N-[4-(8-isobutyramido-1-methyl-[1,2,4]triazolo[4,3-a]quinoxaline-4-ylamino)-butyl]-2,2-dimethyl-propionamide;
(546) [4-(8-acetamino-1-methyl-[1,2,4]triazolo[4,3-a]quinoxaline-4-ylamino)-butyl]-carbamic acid-tert-butylester;
(547) N-[4-(8-acetamino-1-methyl-[1,2,4]triazolo[4,3-a]quinoxaline-4-ylamino)-butyl]-2,2-dimethyl-propionamide;
(548) N-[4-(8-acetamino-1-methyl-[1,2,4]triazolo[4,3-a]quinoxaline-4-ylamino)-butyl]-benzamide;
(549) N-[4-(8-isobutyramido-1-methyl-[1,2,4]triazolo[4,3-a]quinoxaline-4-ylamino)-butyl]-benzamide;
(550) 3-methyl-N-[4-(1-methyl-8-nitro-[1,2,4]triazolo[4,3-a]quinoxaline-4-ylamino)-butyl]-butyramide;
(551) N-[4-(8-amino-1-methyl-[1,2,4]triazolo[4,3-a]quinoxaline-4-ylamino)-butyl]-3-methyl-butyramide;
(552) 3-methyl-N-[4-(1-methyl-8-propylamino-[1,2,4]triazolo[4,3-a]quinoxaline-4-ylamino)-butyl]-butyramide;
(553) N-{4-[8-(3-cyano-propylamino)-1-methyl-[1,2,4]triazolo[4,3-a]quinoxaline-4-ylamino]-butyl}-3-methyl-butyramide;
(554) N-{4-[8-(3-ethyl-thioureido)-1-methyl-[1,2,4]triazolo[4,3-a]quinoxaline-4-ylamino]-butyl}-3-methyl-butyramide;
(555) N-[4-(7-methoxy-1-methyl-8-nitro-[1,2,4]triazolo[4,3-a]quinoxaline-4-ylamino)-butyl]-3-methyl-butyramide;
(556) N-[4-(8-amino-7-methoxy-1-methyl-[1,2,4]triazolo[4,3-a]quinoxaline-4-ylamino)-butyl]-3-methyl-butyramide;
(557) N-[4-(7-methoxy-1-methyl-8-methylamino-[1,2,4]triazolo[4,3-a]quinoxaline-4-ylamino)-butyl]-3-methyl-butyramide;
(558) N-[4-(8-hydroxyamino-7-methoxy-1-methyl-[1,2,4]triazolo[4,3-a]quinoxaline-4-ylamino)-butyl]-3-methyl-butyramide;
(559) N-[4-(7-methoxy-1-methyl-8-propylamino-[1,2,4]triazolo[4,3-a]quinoxaline-4-ylamino)-butyl]-3-methyl-butyramide;
(560) N-[4-(7-methoxy-1-methyl-8-prop-2-ylamino-[1,2,4]triazolo[4,3-a]quinoxaline-4-ylamino)-butyl]-3-methyl-butyramide;
(561) N-{4-[8-(3-isopropyl-ureido)-7-methoxy-1-methyl-[1,2,4]triazolo[4,3-a]quinoxaline-4-ylamino]-butyl}-3-methyl-butyramide;
(562) N-{4-[7-methoxy-1-methyl-8-(3-methyl-butyrylamino)-[1,2,4]triazolo[4,3-a]quinoxaline-4-ylamino]-butyl}-3-methyl-butyramide;
(563) N-{7-methoxy-1-methyl-4-[4-(3-methyl-butyrylamino)-[1,2,4]triazolo[4,3-a]quinoxaline-8-ylamino]-butyl}-3,3-dimethyl-butyramide;
(564) N-{4-[7-methoxy-1-methyl-8-(3-phenyl-ureido)-[1,2,4]triazolo[4,3-a]quinoxaline-4-ylamino]-butyl}-3-methyl-butyramide;
(565) N-[4-(8-methanesulfonylamino-7-methoxy-1-methyl-[1,2,4]triazolo[4,3-a]quinoxaline-4-ylamino]-butyl]-3-methyl-butyramide;

(566) N-[4-(8-dimethanesulfonylamino-7-methoxy-1-methyl-[1,2,4]triazolo[4,3-a]quinoxaline-4-ylamino)-butyl]-3-methyl-butyramide;
(567) N-{4-[7-methoxy-1-methyl-8-(2-methyl-propane-1-sulfonylamino)-[1,2,4]triazolo[4,3-a]quinoxaline-4-ylamino]-butyl}-3-methyl-butyramide;
(568) N-{4-[7-methoxy-1-methyl-8-(3-phenyl-ureido)-[1,2,4]triazolo[4,3-a]quinoxaline-4-ylamino]-butyl}-3-methyl-butyramide;
(569) N-{4-[8-(3-isopropyl-thioureido)-7-methoxy-1-methyl-[1,2,4]triazolo[4,3-a]quinoxaline-4-ylamino]-butyl}-3-methyl-butyramide;
(570) {4-[8-(4-methoxy-benzoyl)-1-methyl-[1,2,4]triazolo[4,3-a]quinoxaline-4-ylamino]-butyl}-carbamic acid-tert-butylester;
(571) [4-(8-benzoyl-1-methyl-[1,2,4]triazolo[4,3-a]quinoxaline-4-ylamino)-butyl]-carbamic acid-tert-butylester;
(572) [4-(8-fluoro-7-methoxy-1-methyl-[1,2,4]triazolo[4,3-a]quinoxaline-4-ylamino)-butyl]-carbamic acid-tert-butylester;
(573) [4-(7-fluoro-8-methoxy-1-methyl-[1,2,4]triazolo[4,3-a]quinoxaline-4-ylamino)-butyl]-carbamic acid-tert-butylester;
(574) N-[4-(8-fluoro-7-methoxy-1-methyl-[1,2,4]triazolo[4,3-a]quinoxaline-4-ylamino)-butyl]-3-methyl-butyramide;
(575) N-[4-(7-fluoro-8-methoxy-1-methyl-[1,2,4]triazolo[4,3-a]quinoxaline-4-ylamino)-butyl]-3-methyl-butyramide;
(576) N-{4-[7-methoxy-1-methyl-8-(2-morpholine-4-yl-ethoxy)-[1,2,4]triazolo[4,3-a]quinoxaline-4-ylamino]-butyl}-3-methyl-butyramide;
(577) N-{4-[8-methoxy-1-methyl-7-(2-morpholine-4-yl-ethoxy)-[1,2,4]triazolo[4,3-a]quinoxaline-4-ylamino]-butyl}-3-methyl-butyramide;
(578) {4-[8-(3,5-dimethyl-isoxazol-4-yl)-1-methyl-[1,2,4]triazolo[4,3-a]quinoxaline-4-ylamino]-butyl}-carbamic acid-tert-butylester;
(579) $N^1$-[8-(3,5-dimethyl-isoxazol-4-yl)-1-methyl-[1,2,4]triazolo[4,3-a]quinoxaline-4-yl]-butane-1,4-diamine ditrifluoroacetic acid;
(580) N-{4-[8-(3,5-dimethyl-isoxazol-4-yl)-1-methyl-[1,2,4]triazolo[4,3-a]quinoxaline-4-ylamino]-butyl}-3-methyl-butyramide;
(581) N-{4-[8-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide;
(582) N-{4-[8-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide;
(583) {4-[7-(3,5-dimethyl-isoxazol-4-yl)-1-methyl-[1,2,4]triazolo[4,3-a]quinoxaline-4-ylamino]-butyl}-carbamic acid-tert-butylester;
(584) $N^1$-[7-(3,5-dimethyl-isoxazol-4-yl)-1-methyl-[1,2,4]triazolo[4,3-a]quinoxaline-4-yl]-butane-1,4-diamine ditrifluoroacetic acid;
(585) N-{4-[7-(3,5-dimethyl-isoxazol-4-yl)-1-methyl-[1,2,4]triazolo[4,3-a]quinoxaline-4-ylamino]-butyl}-3-methyl-butyramide;
(586) N-{4-[7-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide;
(587) N-{4-[7-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide;
(588) $N^1$-[7-methoxy-1-trifluoromethyl-[1,2,4]triazolo[4,3-a]quinoxaline-4-yl]-butane-1,4-diamine ditrifluoroacetic acid;
(589) [4-(7-methoxy-1-trifluoromethyl-[1,2,4]triazolo[4,3-a]quinoxaline-4-ylamino)-butyl]-carbamic acid isopropylester;
(590) N-[4-(7-methoxy-1-trifluoromethyl-[1,2,4]triazolo[4,3-a]quinoxaline-4-ylamino)-butyl]-3-methyl-butyramide;
(591) 3-methyl-pentanoic acid-[4-(7-methoxy-1-trifluoromethyl-[1,2,4]triazolo[4,3-a]quinoxaline-4-ylamino)-butyl]-amide;
(592) $N^1$-(7,8-dimethoxy-1-trifluoromethyl-[1,2,4]triazolo[4,3-a]quinoxaline-4-yl)-butane-1,4-diamine ditrifluoroacetic acid;
(593) N-[4-(7,8-dimethoxy-1-trifluoromethyl-[1,2,4]triazolo[4,3-a]quinoxaline-4-ylamino)-butyl]-3-methyl-butyramide;
(594) [4-(1-ethyl-7,8-dimethoxy-[1,2,4]triazolo[4,3-a]quinoxaline-4-ylamino)-butyl]-carbamic acid-tert-butylester;
(595) $N^1$-(1-ethyl-7,8-dimethoxy-[1,2,4]triazolo[4,3-a]quinoxaline-4-yl)-butane-1,4-diamine ditrifluoroacetic acid;
(596) [4-(1-ethyl-7,8-dimethoxy-[1,2,4]triazolo[4,3-a]quinoxaline-4-ylamino)-butyl]-carbamic acid isopropylester;
(597) N-[4-(1-ethyl-7,8-dimethoxy-[1,2,4]triazolo[4,3-a]quinoxaline-4-ylamino)-butyl]-3-methyl-butyramide;
(598) [4-(1-ethyl-7,8-dimethoxy-[1,2,4]triazolo[4,3-a]quinoxaline-4-ylamino)-butyl]-carbamic acid isobutylester;
(599) [4-(1-isopropyl-7,8-dimethoxy-[1,2,4]triazolo[4,3-a]quinoxaline-4-ylamino)-butyl]-carbamic acid-tert-butylester;
(600) $N^1$-(1-isopropyl-7,8-dimethoxy-[1,2,4]triazolo[4,3-a]quinoxaline-4-yl)-butane-1,4-diamine ditrifluoroacetic acid;
(601) [4-(1-isopropyl-7,8-dimethoxy-[1,2,4]triazolo[4,3-a]quinoxaline-4-ylamino)-butyl]-carbamic acid isopropylester;
(602) [4-(1-isopropyl-7,8-dimethoxy-[1,2,4]triazolo[4,3-a]quinoxaline-4-ylamino)-butyl]-carbamic acid isobutylester;
(603) N-[4-(1-isopropyl-7,8-dimethoxy-[1,2,4]triazolo[4,3-a]quinoxaline-4-ylamino)-butyl]-3-methyl-butyramide;
(604) [4-(1-phenyl-7,8-dimethoxy-[1,2,4]triazolo[4,3-a]quinoxaline-4-ylamino)-butyl]-carbamic acid-tert-butylester;
(605) $N^1$-(1-phenyl-7,8-dimethoxy-[1,2,4]triazolo[4,3-a]quinoxaline-4-yl)-butane-1,4-diamine ditrifluoroacetic acid;
(606) [4-(1-phenyl-7,8-dimethoxy-[1,2,4]triazolo[4,3-a]quinoxaline-4-ylamino)-butyl]-carbamic acid isopropylester;
(607) [4-(1-phenyl-7,8-dimethoxy-[1,2,4]triazolo[4,3-a]quinoxaline-4-ylamino)-butyl]-carbamic acid isobutylester;
(608) N-[4-(1-phenyl-7,8-dimethoxy-[1,2,4]triazolo[4,3-a]quinoxaline-4-ylamino)-butyl]-3-methyl-butyramide;
(609) [4-([1,2,4]triazolo[4,3-a]quinoxaline-4-ylamino)-butyl]-carbamic acid-tert-butylester;
(610) [4-(1-trifluoromethyl-[1,2,4]triazolo[4,3-a]quinoxaline-4-ylamino)-butyl]-carbamic acid-tert-butylester;
(611) $N^1$-(1-trifluoromethyl-[1,2,4]triazolo[4,3-a]quinoxaline-4-yl)-butane-1,4-diamine;
(612) N-[4-(1-trifluoromethyl-[1,2,4]triazolo[4,3-a]quinoxaline-4-ylamino)-butyl]-acetamide;
(613) [4-(1-ethyl-[1,2,4]triazolo[4,3-a]quinoxaline-4-ylamino)-butyl]-carbamic acid-tert-butylester;
(614) $N^1$-(1-ethyl-[1,2,4]triazolo[4,3-a]quinoxaline-4-yl)-butane-1,4-diamine;
(615) [4-(1-isopropyl-[1,2,4]triazolo[4,3-a]quinoxaline-4-ylamino)-butyl]-carbamic acid-tert-butylester;
(616) $N^1$-(1-isopropyl-[1,2,4]triazolo[4,3-a]quinoxaline-4-yl)-butane-1,4-diamine;

(617) [4-(1-phenyl-[1,2,4]triazolo[4,3-a]quinoxaline-4-ylamino)-butyl]-carbamic acid-tert-butylester;
(618) $N^1$-(1-phenyl-[1,2,4]triazolo[4,3-a]quinoxaline-4-yl)-butane-1,4-diamine;
(619) N-[4-(1-phenyl-[1,2,4]triazolo[4,3-a]quinoxaline-4-ylamino)-butyl]-acetamide;
(620) [4-(7-methoxy-1-ethyl-[1,2,4]triazolo[4,3-a]quinoxaline-4-ylamino)-butyl]-carbamic acid-tert-butylester;
(621) $N^1$-(7-methoxy-1-ethyl-[1,2,4]triazolo[4,3-a]quinoxaline-4-yl)-butane-1,4-diamine ditrifluoroacetic acid;
(622) [4-(7-methoxy-1-ethyl-[1,2,4]triazolo[4,3-a]quinoxaline-4-ylamino)-butyl]-3-methyl-butyramide;
(623) [4-(7-methoxy-1-ethyl-[1,2,4]triazolo[4,3-a]quinoxaline-4-ylamino)-butyl]-carbamic acid isopropylester;
(624) [4-(7-methoxy-1-ethyl-[1,2,4]triazolo[4,3-a]quinoxaline-4-ylamino)-butyl]-carbamic acid isobutylester;
(625) [4-(7-methoxy-1-isopropyl-[1,2,4]triazolo[4,3-a]quinoxaline-4-ylamino)-butyl]-carbamic acid-tert-butylester;
(626) $N^1$-(7-methoxy-1-isopropyl-[1,2,4]triazolo[4,3-a]quinoxaline-4-yl)-butane-1,4-diamine ditrifluoroacetic acid;
(627) [4-(1-isopropyl-7-methoxy-[1,2,4]triazolo[4,3-a]quinoxaline-4-ylamino)-butyl]-3-methyl-butyramide;
(628) [4-(1-isopropyl-7-methoxy-[1,2,4]triazolo[4,3-a]quinoxaline-4-ylamino)-butyl]-carbamic acid isopropylester;
(629) [4-(1-isopropyl-7-methoxy-[1,2,4]triazolo[4,3-a]quinoxaline-4-ylamino)-butyl]-carbamic acid isobutylester;
(630) 4-(1-methyl-[1,2,4]triazolo[4,3-a]quinoxaline-4-ylamino)-butan-1-ol;
(631) 2,2-dimethyl-propionic acid-4-(1-methyl-[1,2,4]triazolo[4,3-a]quinoxaline-4-ylamino)-butylester;
(632) isobutyric acid-4-(1-methyl-[1,2,4]triazolo[4,3-a]quinoxaline-4-ylamino)-butyl]-ester;
(633) 3,3-dimethyl-butyric acid-4-(1-methyl-[1,2,4]triazolo[4,3-a]quinoxaline-4-ylamino)-butyl]-ester;
(634) benzoic acid-4-(1-methyl-[1,2,4]triazolo[4,3-a]quinoxaline-4-ylamino)-butylester;
(635) 4-chloro-benzoic acid-4-(1-methyl-[1,2,4]triazolo[4,3-a]quinoxaline-4-ylamino)-butylester;
(636) 2,3-dichloro-benzoic acid-4-(1-methyl-[1,2,4]triazolo[4,3-a]quinoxaline-4-ylamino)-butylester;
(637) 2-chloro-benzoic acid-4-(1-methyl-[1,2,4]triazolo[4,3-a]quinoxaline-4-ylamino)-butylester;
(638) 4-(7-methoxy-1-methyl-[1,2,4]triazolo[4,3-a]quinoxaline-4-yloxy)-butyl-carbamic acid-tert-butylester;
(639) 4-(7-methoxy-1-methyl-[1,2,4]triazolo[4,3-a]quinoxaline-4-yloxy)-butylamine ditrifluoroacetic acid;
(640) N-[4-(7-methoxy-1-methyl-[1,2,4]triazolo[4,3-a]quinoxaline-4-yloxy)-butyl]-3-methyl-butyramide;
(641) tert-butyl(2-((1-methyl-[1,2,4]triazolo[4,3-a]quinoxaline-4-yl)amino)pentyl)carbamate;
(642) [5-(7,8-dimethoxy-1-methyl-[1,2,4]triazolo[4,3-a]quinoxaline-4-ylamino)-pentyl]-carbamic acid-tert-butylester;
(643) $N^1$-(7,8-dimethoxy-1-methyl-[1,2,4]triazolo[4,3-a]quinoxaline-4-yl)-pentane-1,5-diamine ditrifluoroacetic acid;
(644) [5-(7,8-dimethoxy-1-methyl-[1,2,4]triazolo[4,3-a]quinoxaline-4-ylamino)-pentyl]-carbamic acid isopropylester;
(645) N-[5-(7,8-dimethoxy-1-methyl-[1,2,4]triazolo[4,3-a]quinoxaline-4-ylamino)-pentyl]-2,2-dimethyl-propionamide;
(646) 5-(7,8-dimethoxy-1-methyl-[1,2,4]triazolo[4,3-a]quinoxaline-4-ylamino)-pentanoic acid-tert-butylamide;
(647) 5-(7,8-dimethoxy-1-methyl-[1,2,4]triazolo[4,3-a]quinoxaline-4-ylamino)-pentanoic acid isopropylamide;
(648) 5-(7,8-dimethoxy-1-methyl-[1,2,4]triazolo[4,3-a]quinoxaline-4-ylamino)-pentanoic acid isobutylamide;
(649) 5-(7,8-dimethoxy-1-methyl-[1,2,4]triazolo[4,3-a]quinoxaline-4-ylamino)-pentanoic acid-(2-methyl-butyl)-amide;
(650) 5-(7,8-dimethoxy-1-methyl-[1,2,4]triazolo[4,3-a]quinoxaline-4-ylamino)-pentanoic acid-(furan-2-yl-methyl)-amide;
(651) 5-(7,8-dimethoxy-1-methyl-[1,2,4]triazolo[4,3-a]quinoxaline-4-ylamino)-pentanoic acid benzylamide;
(652) 5-(7,8-dimethoxy-1-methyl-[1,2,4]triazolo[4,3-a]quinoxaline-4-ylamino)-pentanoic acid-(1H-pyrrole-2-yl-methyl)-amide;
(653) 5-(7-methoxy-1-methyl-[1,2,4]triazolo[4,3-a]quinoxaline-4-ylamino)-pentanoic acid-tert-butylamide;
(654) 5-(7-methoxy-1-methyl-[1,2,4]triazolo[4,3-a]quinoxaline-4-ylamino)-pentanoic acid isopropylamide;
(655) 5-(7-methoxy-1-methyl-[1,2,4]triazolo[4,3-a]quinoxaline-4-ylamino)-pentanoic acid isobutylamide;
(656) 5-(7-methoxy-1-methyl-[1,2,4]triazolo[4,3-a]quinoxaline-4-ylamino)-pentanoic acid-(2-methyl-butyl)-amide;
(657) 5-(7-methoxy-1-methyl-[1,2,4]triazolo[4,3-a]quinoxaline-4-ylamino)-pentanoic acid-(furan-2-yl-methyl)-amide;
(658) 5-(7-methoxy-1-methyl-[1,2,4]triazolo[4,3-a]quinoxaline-4-ylamino)-pentanoic acid-benzamide;
(659) 5-(1-methyl-[1,2,4]triazolo[4,3-a]quinoxaline-4-ylamino)-pentanoic acid isopropylamide;
(660) 5-(1-methyl-[1,2,4]triazolo[4,3-a]quinoxaline-4-ylamino)-pentanoic acid isobutylamide;
(661) 6-(1-methyl-[1,2,4]triazolo[4,3-a]quinoxaline-4-ylamino)-hexanoic acid isopropylamide; and
(662) 6-(1-methyl-[1,2,4]triazolo[4,3-a]quinoxaline-4-ylamino)-hexanoic acid isobutylamide.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

In another aspect of the present invention, the present invention also provides a preparation method of the compound represented by formula 1 comprising the following steps, as shown in reaction formula 1 below:

preparing the compound represented by formula 4 by reacting the compound represented by formula 2 with the compound represented by formula 3 (step 1); and preparing the compound represented by formula 1 by reacting the compound represented by formula 4 prepared in step 1 above with the compound represented by formula 5 (step 2):

[Reaction Formula 1]

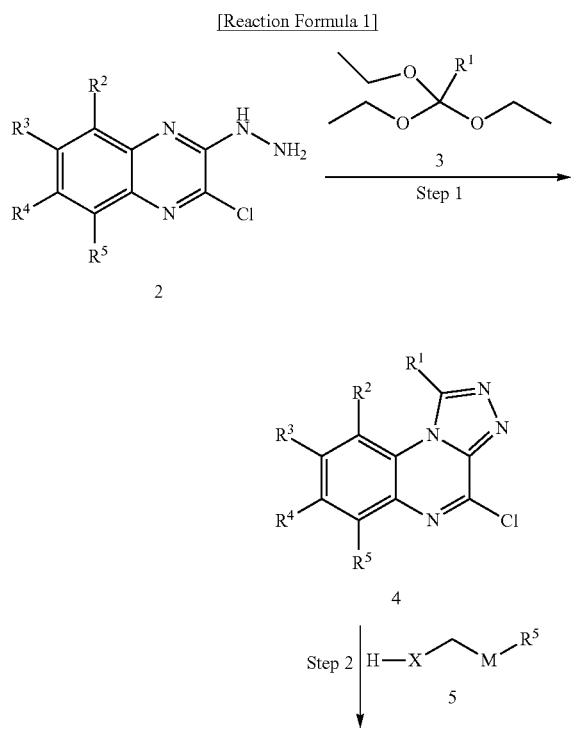

-continued

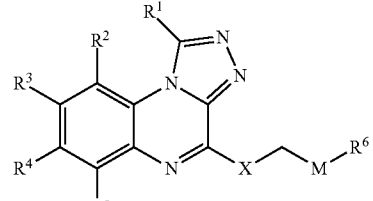

(In reaction formula 1, $R^1$~$R^6$, M and X are independently as defined in formula 1 above)

Hereinafter, the preparation method of the compound represented by formula 1 of the present invention is described in more detail, step by step.

In the preparation method of the compound represented by formula 1 of the present invention, step 1 is to prepare the compound represented by formula 4 by reacting the compound represented by formula 2 with the compound represented by formula 3.

In the step above, the reaction temperature is not particularly limited, but the reaction can be performed at 60~160° C., preferably at 80~140° C., more preferably at 90~120° C., and most preferably at 100° C.

In addition, the reaction time is not particularly limited, but the reaction can be performed for 0.2~4 hours, preferably for 0.5~3 hours, more preferably for 0.8~2 hours, and most preferably for 1 hour.

In the preparation method of the compound represented by formula 1 according to the present invention, step 2 is to prepare the compound represented by formula 1 by reacting the compound represented by formula 4 prepared in step 1 above with the compound represented by formula 5.

In the step above, the reaction temperature is not particularly limited, but the reaction can be performed at 10~100° C., preferably at 50~100° C., more preferably at 60~90° C., and most preferably at 80° C.

In addition, the reaction time is not particularly limited, but the reaction can be performed for 1~24 hours, preferably for 12~24 hours, more preferably for 16~20 hours, and most preferably for 18 hours.

In another aspect of the present invention, the present invention also provides a preparation method of the compound represented by formula 1 comprising the following steps, as shown in reaction formula 2 below:

preparing the compound represented by formula 8 by reacting the compound represented by formula 7 with the compound represented by formula 5 (step 1);

preparing the compound represented by formula 9 by reacting the compound represented by formula 8 prepared in step 1 above with hydrazine hydrate (step 2); and preparing the compound represented by formula 1 by reacting the compound represented by formula 9 prepared in step 2 above with the compound represented by formula 3 (step 3):

[Reaction Formula 2]

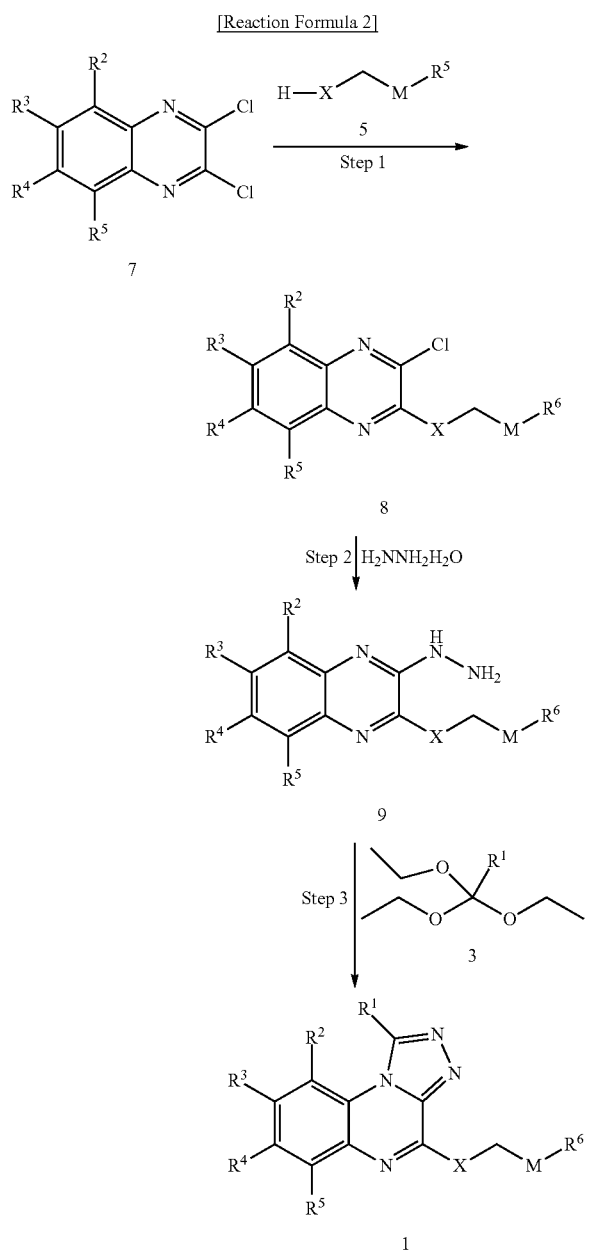

(In reaction formula 2, $R^1$~$R^6$, M and X are independently as defined in formula 1 above).

Hereinafter, the preparation method of the compound represented by formula 1 of the present invention is described in more detail, step by step.

In the preparation method of the compound represented by formula 1 of the present invention, step 1 is to prepare the compound represented by formula 8 by reacting the compound represented by formula 7 with the compound represented by formula 5.

In the step above, the reaction temperature is not particularly limited, but the reaction can be performed at 10~100° C., preferably at 20~100° C., more preferably at 20~90° C., and most preferably at 80° C.

In addition, the reaction time is not particularly limited, but the reaction can be performed for 1~24 hours, preferably for 12~24 hours, more preferably for 16~20 hours, and most preferably for 18 hours.

In the preparation method of the compound represented by formula 1 according to the present invention, step 2 is to prepare the compound represented by formula 9 by reacting the compound represented by formula 8 prepared in step 1 above with hydrazine hydrate.

As an example, the compound represented by formula 8 prepared in the step 1 and hydrazine hydrate were dissolved in ethanol, refluxed and stirred. Upon completion of the reaction, the solvent was distilled under reduced pressure. Moisture was eliminated over magnesium sulfate, followed by distillation and drying under reduced pressure. As a result, the compound represented by formula 9 was obtained.

In the step above, the reaction temperature is not particularly limited, but the reaction can be performed at 10~80° C., preferably at 25~80° C., more preferably at 40~80° C., and most preferably at 80° C.

In addition, the reaction time is not particularly limited, but the reaction can be performed for 1~6 hours, preferably for 1.5~5 hours, more preferably for 2~4 hours, and most preferably for 3 hours.

In the preparation method of the compound represented by formula 1 according to the present invention, step 3 is to prepare the compound represented by formula 1 by reacting the compound represented by formula 9 prepared in step 2 above with the compound represented by formula 3.

In the step above, the reaction temperature is not particularly limited, but the reaction can be performed at 60~160° C., preferably at 80~140° C., more preferably at 90~120° C., and most preferably at 100° C.

In addition, the reaction time is not particularly limited, but the reaction can be performed for 0.2~4 hours, preferably for 0.5~3 hours, more preferably for 0.8~2 hours, and most preferably for 1 hour.

In an aspect of the present invention, the present invention provides a pharmaceutical composition comprising the compound represented by formula 1, the optical isomer thereof or the pharmaceutically acceptable salt thereof as an active ingredient for the prevention or treatment of BET (bromodomain extra-terminal) protein related diseases.

Herein, the BET (bromodomain extra-terminal) protein related disease above is characterized by cancer, which is preferably exemplified by thymus cancer, blood cancer, ovarian cancer, cervical cancer, breast cancer, colorectal cancer, liver cancer, stomach cancer, pancreatic cancer, colon cancer, peritoneal metastatic cancer, bladder cancer, prostate cancer, thyroid cancer, lung cancer, osteosarcoma, fibroid tumor and brain tumor.

In addition, the BET (bromodomain extra-terminal) protein related disease above is characterized by autoimmune disease, which is preferably exemplified by rheumatoid arthritis, systemic lupus erythematosus, multiple sclerosis, type 1 diabetes, hyperthyroidism, myasthenia, Crohn's disease, ankylosing spondylitis, psoriasis, autoimmune malignant anemia and Sjogren's syndrome.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by formula 1 as an active ingredient can be administered parenterally and the parenteral administration includes subcutaneous injection, intravenous injection, intramuscular injection and intrathoracic injection.

To prepare the composition as a formulation for parenteral administration, the compound represented by formula 1 or the pharmaceutically acceptable salt thereof are mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the compound represented by formula 1 of the present invention can vary depending on the patient's age, weight, gender, administration form, health condition and disease severity. Based on an adult patient weighing 70 kg, the dosage is generally 0.1~1000 mg/day, and preferably 1~500 mg/day. The compound of the present invention can be administered once or several times a day at a predetermined time interval according to the judgment of a doctor or a pharmacist.

The novel [1,2,4]triazolo[4,3-a]quinoxaline derivative according to the present invention can inhibit the binding of BRD4, one of BET protein family, at a low concentration, and displays excellent cytotoxicity in tumor cells, so that it can be used as a pharmaceutical composition for the prevention or treatment of BET protein related diseases including cancer and autoimmune disease, which is supported by the following experimental results.

In an aspect of the present invention, the present invention provides a method for preventing, ameliorating or treating BET (bromodomain extra-terminal) protein related diseases which comprises a step of administering the pharmaceutical composition comprising the compound represented by formula 1, the optical isomer thereof or the pharmaceutically acceptable salt thereof as an active ingredient to a subject.

In addition, in another aspect of the present invention, the present invention provides a use of the pharmaceutical composition comprising the compound represented by formula 1, the optical isomer thereof or the pharmaceutically acceptable salt thereof as an active ingredient.

Practical and presently preferred embodiments of the present invention are illustrative as shown in the following Examples and Experimental Examples.

However, it will be appreciated that those skilled in the art, on consideration of this disclosure, may make modifications and improvements within the spirit and scope of the present invention.

<Preparative Example 1> Preparation of 4-chloro-1-methyl-[1,2,4]triazolo[4,3-a]quinoxaline

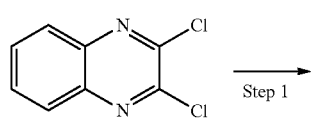

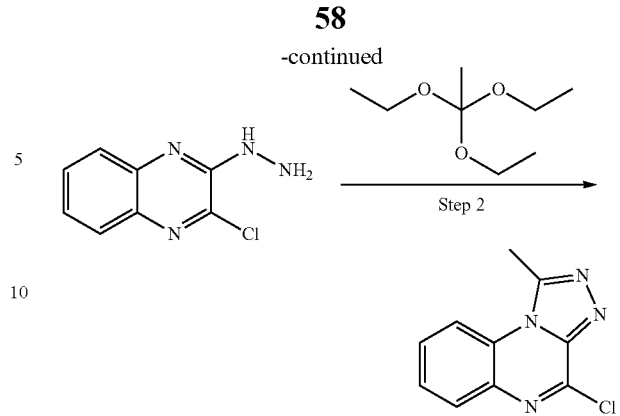

Step 1: Preparation of 2-chloro-3-hydrazinylquinoxaline

Hydrazine hydrate (2.77 g, 55.3 mmol) was added dropwise to ethanol containing 2,3-dichloroquinoxaline (5.00 g, 25.1 mmol) at room temperature, followed by stirring at 25° C. for 16 hours. The resulting precipitate was collected by filtration, washed with ethanol and dried. As a result, a target compound 2-chloro-3-hydrazinylquinoxaline was obtained (95% yield) as pale yellow powder.

Mass (M+H$^+$): 195.0

Step 2: Preparation of 4-chloro-1-methyl-[1,2,4]triazolo[4,3-a]quinoxaline

2-Chloro-3 hydrazinylquinoxaline (5.00 g, 25.7 mmol) obtained in step 1 of Preparative Example 1 was refluxed in triethylorthoacetate solvent at 100° C. for 1 hour. The reaction mixture was cooled down at room temperature and the resulting precipitate was filtered, washed with normal hexane and dried under reduced pressure. As a result, a target compound was obtained (91% yield) as a light grey solid.

Mass (M+H$^+$): 219.0

$^1$H NMR (300 MHz, DMSO-d6): δ3.11 (s, 3H), 7.72 (t, J=7.41 Hz, 1H), 7.81 (t, J=7.56 Hz, 1H), 8.03 (d, J=7.74 Hz, 1H), 8.37 (d, J=8.28 Hz, 1H).

<Example 1> Preparation of [4-(1-methyl-[1,2,4]triazolo[4,3-a]quinoxaline-4-ylamino)-butyl]-carbamic acid-tert-butylester

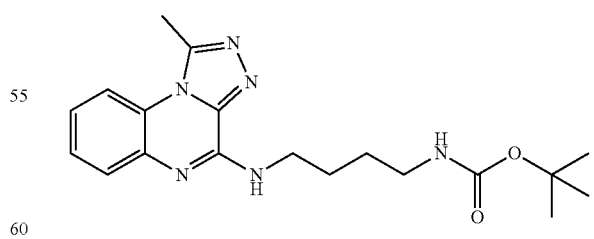

Tert-butyl(4-aminobutyl)carbamate (2.50 g, 13.7 mmol) and N,N-diisopropylethylamine (DIPEA, 4.79 ml, 27.mmol) were dissolved in isopropyl alcohol. 4-Chloro-1-methyl-[1,2,4]triazolo[4,3-a]quinoxaline (2.00 g, 9.15 mmol) obtained in step 2 of Preparative Example 1 was added thereto at room temperature. The reaction mixture was stirred at 40° C. for 1.5 hours. The reaction mixture was cooled down at room temperature and the resulting white precipitate was collected by filtration, washed with isopropyl alcohol and dried. As a result, a target compound was obtained (89% yield).

Mass (M+H$^+$): 371.2

$^1$H NMR (300 MHz, DMSO-d6): δ1.36 (s, 9H), 1.45-1.51 (m, 2H), 1.63-1.68 (m, 2H), 2.93-3.02 (m, 2H), 3.02 (s, 3H), 3.50-3.57 (m, 2H), 7.29 (t, J=7.35 Hz, 1H), 7.44 (t, J=7.68 Hz, 1H), 7.60 (d, J=7.89 Hz, 1H), 8.07-8.11 (m, 2H).

<Example 2> Preparation of N$^1$-(1-methyl-[1,2,4]triazolo[4,3-a]quinoxaline-4-yl)-butane-1,4-diamine dihydrochloride

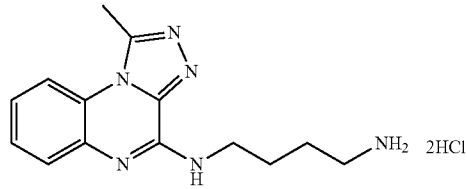 [SMILES: Cc1nnc2c(NCCCCN)nc3ccccc3n12]

[4-(1-Methyl-[1,2,4]triazolo[4,3-a]quinoxaline-4-ylamino)-butyl]-carbamic acid-tert-butylester obtained in Example 1 was dissolved in ethylacetate, to which excessive amount of 4 M HCl and dioxane were added. The reaction mixture was stirred at room temperature for 4 hours. The reaction mixture was concentrated to give a target compound in the status of hydrochloride (quantitative yield), which was used in the next step without any further purification process.

Mass (M+H$^+$): 271.2

$^1$H NMR (500 MHz, DMSO-d6): δ1.62-1.68 (m, 2H), 1.73-1.77 (m, 2H), 2.83-2.90 (m, 2H), 3.05 (s, 3H), 3.58-3.61 (m, 2H), 7.33-7.36 (m, 1H), 7.47-7.50 (m, 1H), 7.64 (dd, J=8.15, 1.00 Hz, 1H), 7.72 (brs, 2H), 8.13 (d, J=8.1 Hz, 2H), 8.37 (brs, 1H).

<Example 3> Preparation of 2,2-dimethyl-N-[4-(1-methyl-[1,2,4]triazolo[4,3-a]quinoxaline-4-ylamino)-butyl]-propionamide

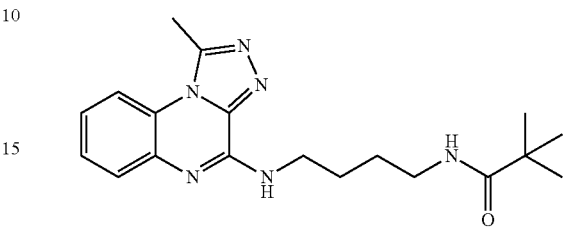

N$^1$-(1-methyl-[1,2,4]triazolo[4,3-a]quinoxaline-4-yl)-butane-1,4-diamine dihydrochloride obtained in Example 2 and DIPEA (4 eq.) were dissolved in acetonitrile, to which trimethylacetylchloride (1.10-1.50 eq.) was slowly added at 0° C. The reaction mixture was warmed to room temperature, followed by stirring at room temperature for 1 hour. The reaction mixture was concentrated, diluted in sodium bicarbonate solution and extracted with ethylacetate three times. The organic layer was washed with brine, dried over magnesium sulfate, concentrated and purified using MPLC (isopropylalcohol/dimethylchloride). As a result, a target compound was obtained (63% yield).

Mass (M+H$^+$): 355.2

$^1$H NMR (300 MHz, DMSO-d6): δ1.06 (s, 9H), 1.46-1.54 (m, 2H), 1.60-1.68 (m, 2H), 3.02 (s, 3H), 3.05-3.11 (m, 2H), 3.51-3.57 (m, 2H), 7.27-7.32 (m, 1H), 7.39-7.46 (m, 2H), 7.59 (dd, 1H), 8.07-8.12 (m, 2H).

The compounds shown in Table 1 below were prepared by the same manner as described in Example 3.

TABLE 1

| Example | Structure | Name | Data |
|---------|-----------|------|------|
| Example 4 | 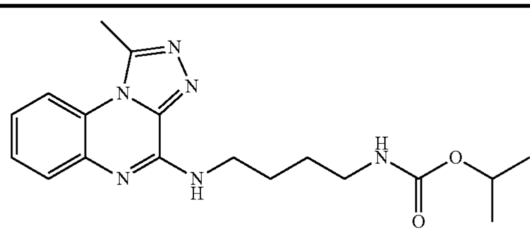 | [4-(1-methyl-[1,2,4]triazolo[4,3-a]quinoxaline-4-ylamino)-butyl]-carbamic acid isopropylester | Mass (M + H$^+$): 356.1; $^1$H NMR (500 MHz, DMSO-d6): δ1.14 (d, J = 6.25 Hz, 6H), 1.46-1.52 (m, 2H), 1.63-1.69 (m, 2H), 3.00-3.03 (m, 2H), 3.04 (s, 3H), 3.53-3.57 (m, 2H), 4.70-4.75 (m, 1H), 7.00 (t, J = 5.15 Hz, 1H), 7.31 (t, J = 7.35 Hz, 1H), 7.45 (t, J = 7.65 Hz, 1H), 7.62 (d, J = 7.85 Hz, 1H), 8.10-8.14 (m, 2H). |
| Example 5 | 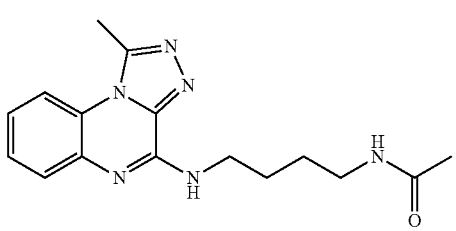 [SMILES: CC(=O)NCCCCNc1nc2ccccc2n2c(C)nnc12] | [4-(1-methyl-[1,2,4]triazolo[4,3-a]quinoxaline-4-ylamino)-butyl]-acetamide | Mass (M + H$^+$): 313.2; $^1$H NMR (500 MHz, DMSO-d6): δ1.44-1.53 (m, 2H), 1.63-1.73 (m, 2H), 1.78 (s, 3H), 3.03 (s, 3H), 3.04-3.11 (m, 2H), 3.54-3.61 (m, 2H), 7.34 (t, J = 7.26 Hz, 1H), 7.48 (t, J = 7.53 Hz, |

TABLE 1-continued

| Example | Structure | Name | Data |
|---|---|---|---|
| | | | 1H), 7.65 (d, J = 7.95 Hz, 1H), 7.82 (t, J = 4.29 Hz, 1H), 8.11 (d, J = 8.19 Hz, 1H), 8.52 (brs, 1H). |
| Example 6 | 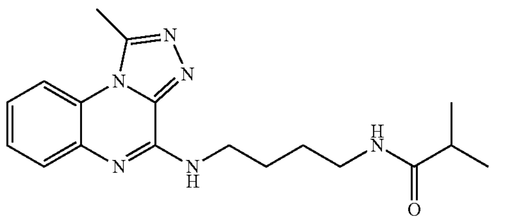 [SMILES: Cc1nnc2c(NCCCCNC(=O)C(C)C)nc3ccccc3n12] | [4-(1-methyl-[1,2,4]triazolo[4,3-a]quinoxaline-4-ylamino)-butyl]-isobutyramide | Mass (M + H⁺): 341.2; $^1$H NMR (500 MHz, DMSO-d6): δ0.97 (d, J = 6.85 Hz, 6H), 1.46-1.52 (m, 2H), 1.64-1.70 (m, 2H), 2.29-2.34 (m, 1H), 3.04 (s, 3H), 3.06-3.10 (m, 2H), 3.53-3.57 (m, 2H), 7.29-7.33 (m, 1H), 7.45 (t, J = 7.20 Hz, 1H), 7.60 (dd, J = 7.90 Hz, 0.80 Hz, 1H), 7.70 (t, J = 5.05 Hz, 1H), 8.10 (d, J = 8.15 Hz, 1H), 8.14 (t, J = 5.60 Hz, 1H). |
| Example 7 | 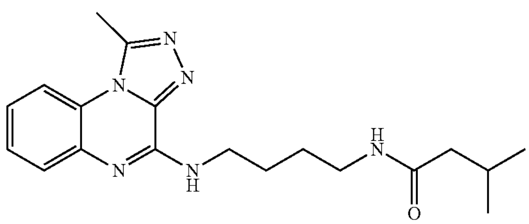 [SMILES: Cc1nnc2c(NCCCCNC(=O)CC(C)C)nc3ccccc3n12] | 3-methyl-N-[4-(1-methyl-[1,2,4]triazolo[4,3-a]quinoxaline-4-ylamino)-butyl]-butyramide | Mass (M + H⁺): 355.2; $^1$H NMR (300 MHz, DMSO-d6): δ0.83 (d, J = 6.15 Hz, 6H), 1.46-1.52 (m, 2H), 1.65-1.71 (m, 2H), 1.91-1.97 (m, 3H), 3.04 (s, 3H), 3.07-3.11 (m, 2H), 3.53-3.57 (m, 2H), 7.31 (t, J = 7.50 Hz, 1H), 7.45 (t, J = 7.65 Hz, 1H), 7.61 (d, J = 7.95 Hz, 1H), 7.75 (t, J = 5.25 Hz, 1H), 8.10 (d, J = 8.30 Hz, 1H), 8.14 (t, J = 5.70 Hz, 1H). |
| Example 8 | 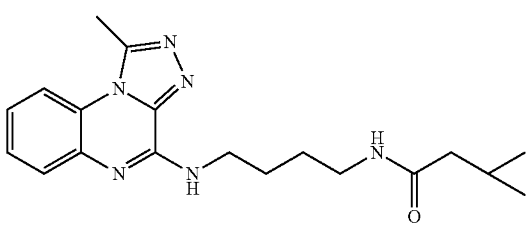 | 3,3-dimethyl-N-[4-(1-methyl-[1,2,4]triazolo[4,3-a]quinoxaline-4-ylamino)-butyl]-butyramide | Mass (M + H⁺): 369.2; $^1$H NMR (300 MHz, DMSO-d6): δ0.92 (s, 9H),1.43-1.53 (m, 2H), 1.63-1.72 (m, 2H), 1.92 (s, 2H), 3.03-3.11 (m, 5H), 3.51-3.58 (m, 2H), 7.27-7.33 (m, 1H), 7.44 (t, J = 7.38 Hz, 1H), 7.59-7.62 (m, 1H), 7.69 (t, J = 5.28 Hz, 1H), 8.08-8.14 (m, 2H). |
| Example 9 | 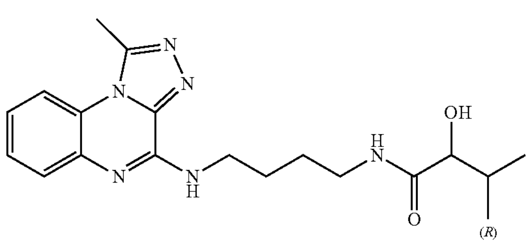 | 2-(R)-hydroxy-N-[4-(1-methyl-[1,2,4]triazolo[4,3-a]quinoxaline-4-ylamino)-butyl]-3-methyl-butyramide | Mass (M + H⁺): 371.2; $^1$H NMR (500 MHz, DMSO-d6): δ0.68 (d, 3H), 0.83 (d, 3H), 1.49 (m, 2H), 1.62 (m, 2H), 1.90 (m, 1H), 2.98 (s, 3H), 3.13 (m, 2H), 3.51 (q, 2H), 3.59 (d, 1H), 5.23 (d, 1H), 7.26 (q, 1H), 7.39 (q, 1H), 7.54 (d, 1H), 7.65 (t, 1H), 8.03 (d, 1H), 8.08 (t, 1H). |

TABLE 1-continued

| Example | Structure | Name | Data |
|---|---|---|---|
| Example 10 | 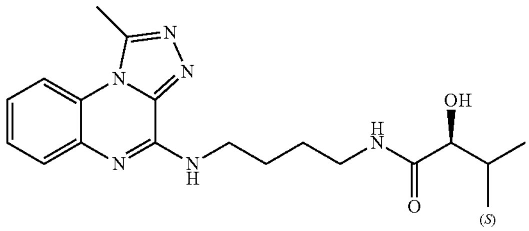 | 2-(S)-hydroxy-N-[4-(1-methyl-[1,2,4]triazolo[4,3-a]quinoxaline-4-ylamino)-butyl]-3-methyl-butyramide | Mass (M + H⁺): 371.2; ¹H NMR (500 MHz, DMSO-d6): δ0.68 (d, 3H), 0.83 (d, 3H), 1.49 (m, 2H), 1.62 (m, 2H), 1.90 (m, 1H), 2.98 (s, 3H), 3.13 (m, 2H), 3.51 (q, 2H), 3.59 (d, 1H), 5.23 (d, 1H), 7.26 (q, 1H), 7.39 (q, 1H), 7.54 (d, 1H), 7.65 (t, 1H), 8.03 (d, 1H), 8.08 (t, 1H). |
| Example 11 | 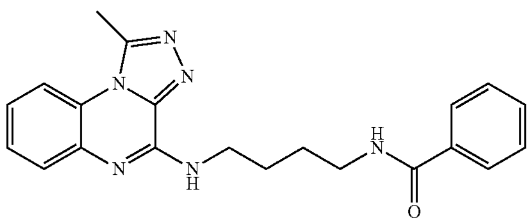 [SMILES: Cc1nnc2c(NCCCCNC(=O)c3ccccc3)nc3ccccc3n12] | N-[4-(1-methyl-[1,2,4]triazolo[4,3-a]quinoxaline-4-ylamino)-butyl]-benzamide | Mass (M + H⁺): 374.5; ¹H NMR (500 MHz, DMSO-d6): δ1.63-1.66 (m, 2H), 1.75-1.78 (m, 2H), 3.04 (s, 3H), 3.31-3.35 (m, 2H), 3.62-3.64 (m, 2H), 7.36-7.39 (m, 1H), 7.44 (t, J = 7.20 Hz, 2H), 7.48-7.52 (m, 1H), 7.68 (d, J = 7.95 Hz, 1H), 7.82-7.83 (m, 2H), 8.12 (d, J = 8.10 Hz, 1H), 8.48 (t, J = 5.50 Hz, 1H), 8.83 (brs, 1H). |
| Example 12 | 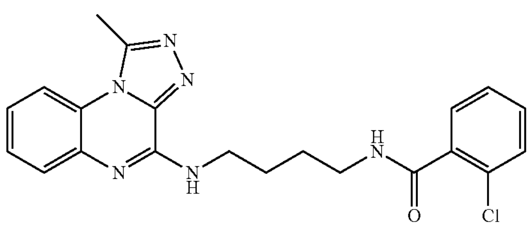 [SMILES: Cc1nnc2c(NCCCCNC(=O)c3ccccc3Cl)nc3ccccc3n12] | 2-chloro-N-[4-(1-methyl-[1,2,4[triazolo[4,3-a]quinoxaline-4-ylamino)-butyl]-benzamide | Mass (M + H⁺): 409.2; ¹H NMR (300 MHz, DMSO-d6): δ1.57-1.66 (m, 2H), 1.72-1.82 (m, 2H), 3.03 (s, 3H), 3.25-3.31 (m, 2H), 3.56-3.62 (m, 2H), 7.28-7.52 (m, 7H), 7.61 (dd, J = 8.07, 1.14 Hz, 1H), 8.09-8.16 (m, 2H), 8.40 (t, J = 5.46 Hz,1H). |
| Example 13 | 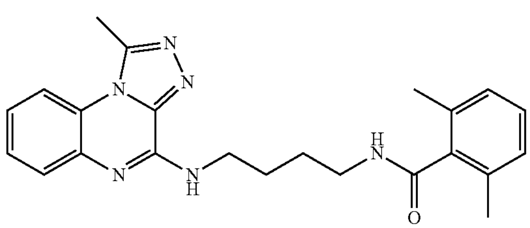 [SMILES: Cc1cccc(C)c1C(=O)NCCCCNc1nc2ccccc2n2c(C)nnc12] | 2,6-dimethyl-N-[4-(1-methyl-[1,2,4]triazolo[4,3-a]quinoxaline-4-ylamino)-butyl]-benzamide | Mass (M + H⁺): 403.2; ¹H NMR (300 MHz, DMSO-d6): δ1.58-1.66 (m, 2H), 1.71-1.78 (m, 2H), 2.17 (s, 6H), 3.03 (s, 3H), 3.25-3.31 (m, 2H), 3.55-3.61 (m, 2H), 6.99 (d, J = 7.56 Hz, 2H), 7.13 (t, J = 7.65 Hz, 1H), 7.31 (t, J = 7.23 Hz, 1H), 7.45 (t, J = 7.41 Hz, 1H), 7.60 (d, J = 7.95 Hz, 1H), 8.10 (d, J = 8.22 Hz, 1H), 8.15 (t, J = 5.67 Hz, 1H), 8.25 (t, J = 5.19 Hz, 1H). |

TABLE 1-continued

| Example | Structure | Name | Data |
|---|---|---|---|
| Example 14 | 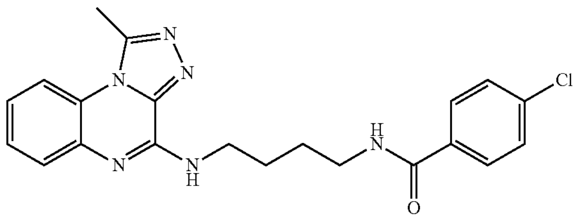 | 4-chloro-N-[4-(1-methyl-[1,2,4]triazolo[4,3-a]quinoxaline-4-ylamino)-butyl]-benzamide | Mass (M + H$^+$): 409.2; $^1$H NMR (300 MHz, DMSO-d6): δ1.59-1.76 (m, 4H), 3.02 (s, 3H), 3.28-3.34 (m, 2H), 3.55-3.61 (m, 2H), 7.27-7.32 (m, 1H), 7.43 (t, J = 7.41 Hz, 1H), 7.50 (d, J = 8.4 Hz, 2H), 7.57 (d, J = 7.95 Hz, 1H), 7.83 (d, J = 8.49 Hz, 2H), 8.07-8.13 (m, 2H), 8.51 (t, J = 5.37 Hz, 1H). |
| Example 15 | 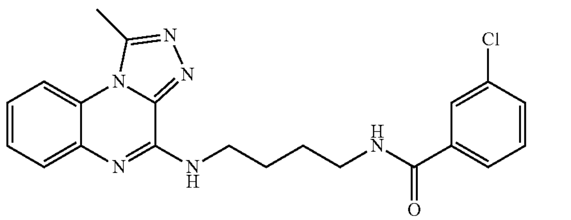 [SMILES: Cc1nnc2c(NCCCCNC(=O)c3cccc(Cl)c3)nc3ccccc3n12] | 3-chloro-N-[4-(1-methyl-[1,2,4]triazolo[4,3-a]quinoxaline-4-ylamino)-butyl]-benzamide | Mass (M + H$^+$): 409.2; $^1$H NMR (300 MHz, DMSO-d6): δ1.60-1.76 (m, 4H), 3.02 (s, 3H), 3.28-3.35 (m, 2H), 3.55-3.61 (m, 2H), 7.26-7.32 (m, 1H), 7.40-7.49 (m, 2H), 7.58 (d, J = 7.95 Hz, 2H), 7.85 (brs, 1H), 8.07-8.13 (m, 2H), 8.58 (t, J = 5.28 Hz, 1H). |
| Example 16 | 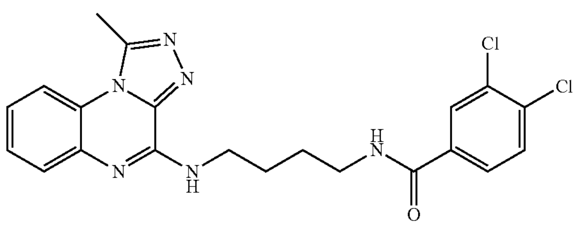 [SMILES: Cc1nnc2c(NCCCCNC(=O)c3ccc(Cl)c(Cl)c3)nc3ccccc3n12] | 3,4-dichloro-N-[4-(1-methyl-[1,2,4]triazolo[4,3-a]quinoxaline-4-ylamino)-butyl]-benzamide | Mass (M + H$^+$): 443.1; $^1$H NMR (300 MHz, DMSO-d6): δ1.60-1.77 (m, 4H), 3.03 (s, 3H), 3.31-3.35 (m, 2H), 3.55-3.61 (m, 2H), 7.27-7.33 (m, 1H), 7.40-7.45 (m, 1H), 7.55-7.58 (m, 1H), 7.71 (d, J = 8.97 Hz, 1H), 7.79 (dd, J = 8.40 Hz, 1.65 Hz, 1H), 7.04 (d, J = 1.86 Hz, 1H), 8.08-8.14 (m, 2H), 8.63 (t, J = 5.37 Hz, 1H). |
| Example 17 | 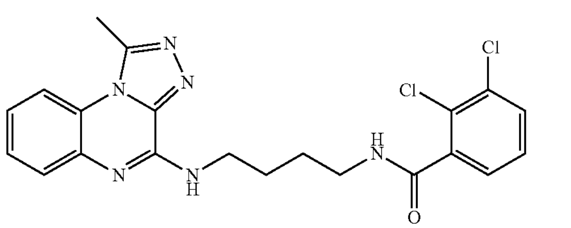 [SMILES: Cc1nnc2c(NCCCCNC(=O)c3cccc(Cl)c3Cl)nc3ccccc3n12] | 2,3-dichloro-N-[4-(1-methyl-[1,2,4]triazolo[4,3-a]quinoxaline-4-ylamino)-butyl]-benzamide | Mass (M + H$^+$): 443.1; $^1$H NMR (300 MHz, DMSO-d6): δ1.58-1.65 (m, 2H), 1.72-1.77 (m, 2H), 3.03 (s, 3H), 3.25-3.32 (m, 2H), 3.55-3.62 (m, 2H), 7.28-7.39 (m, 3H), 7.45 (t, J = 7.80 Hz, 1H), 7.60 (d, J = 7.92 Hz, 1H), 7.67 (dd, J = 6.63 Hz, 2.79 Hz, 1H), 8.10 (d, J = 8.22 Hz, 1H), 8.16 (t, J = 5.52 Hz, 1H), 8.51 (t, J = 5.43 Hz, 1H). |

TABLE 1-continued

| Example | Structure | Name | Data |
|---|---|---|---|
| Example 18 | 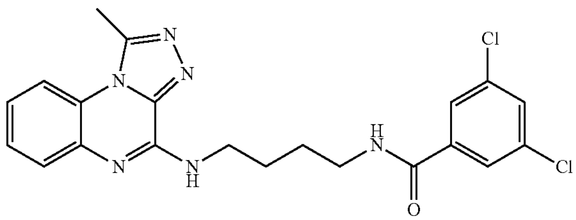 [SMILES: Cc1nnc2c(NCCCCNC(=O)c3cc(Cl)cc(Cl)c3)nc3ccccc3n12] | 3,5-dichloro-N-[4-(1-methyl-[1,2,4]triazolo[4,3-a]quinoxaline-4-ylamino)-butyl]-benzamide | Mass (M + H⁺): 443.1; ¹H NMR (300 MHz, DMSO-d6): δ1.58-1.79 (m, 4H), 3.03 (s, 3H), 3.29-3.33 (m, 2H), 3.55-3.61 (m, 2H), 7.27-7.32 (m, 1H), 7.43 (t, J= 7.68 Hz, 1H), 7.57 (d, J =7.95 Hz, 1H), 7.77 (d, J = 1.56 Hz, 1H), 7.85 (d, J = 1.68 Hz, 2H), 8.08-8.16 (m, 2H), 8.75 (t, J = 5.19 Hz, 1H). |
| Example 19 | 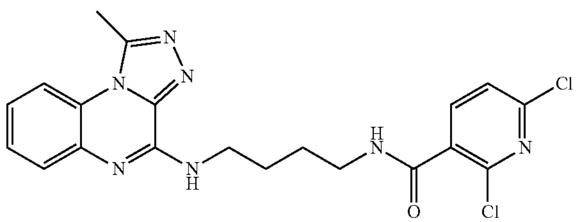 [SMILES: Cc1nnc2c(NCCCCNC(=O)c3ccc(Cl)nc3Cl)nc3ccccc3n12] | 2,6-dichloro-N-[4-(1-methyl-[1,2,4]triazolo[4,3-a]quinoxaline-4-ylamino)-butyl]-nicotinamide | Mass (M + H⁺): 444.1; ¹H NMR (500 MHz, DMSO-d6): δ1.58 (m, 2H), 1.72 (m, 2H), 3.99 (s, 3H), 3.24 (m, 2H), 3.54 (q, 2H), 7.27 (t, 1H), 7.41 (t, 1H), 7.57 (d, 2H), 7.89 (s, 1H), 8.06 (d, 1H), 8.12 (t, 1H), 8.57 (t, 1H). |
| Example 20 | 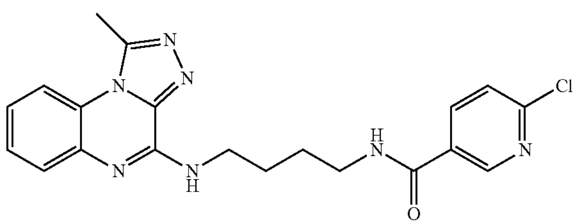 | 6-chloro-N-[4-(1-methyl-[1,2,4]triazolo[4,3-a]quinoxaline-4-ylamino)-butyl]-nicotinamide | Mass (M + H⁺): 410.1; ¹H NMR (500 MHz, DMSO-d6): δ1.50 (m, 2H), 1.70 (m, 2H), 2.98 (s, 3H), 3.30 (q, 2H), 3.54 (q, 2H), 7.26 (t, 1H), 7.38 (t, 1H), 7.52 (d, 1H), 7.56 (d, 1H), 8.06 (d, 1H), 8.10 (t, 1H), 8.16 (d, 1H), 8.66 (t, 1H), 8.76 (s, 1H). |
| Example 21 | 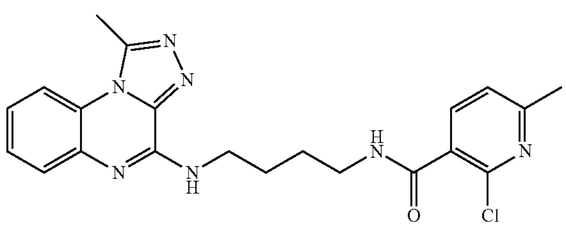 [SMILES: Cc1ccc(C(=O)NCCCCNc2nc3ccccc3n3c(C)nnc23)c(Cl)n1] | 2-chloro-6-methyl-N-[4-(1-methyl-[1,2,4]triazolo[4,3-a]quinoxaline-4-ylamino)-butyl]-nicotinamide | Mass (M + H⁺): 424.2; ¹NMR (500 MHz, DMSO-d6): δ1.57 (m, 2H), 1.72 (m, 2H), 2.42 (s, 3H), 7.24 (d, 1H), 7.27 (t, 1H), 7.42 (t, 1H), 7.56 (d, 1H), 7.68 (d, 1H), 8.06 (d, 1H), 8.11 (t, 1H), 8.44 (t, 1H). |
| Example 22 | 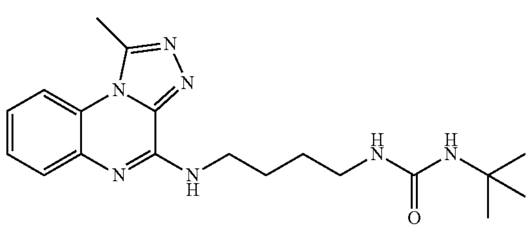 [SMILES: Cc1nnc2c(NCCCCNC(=O)NC(C)(C)C)nc3ccccc3n12] | 1-tert-butyl-3-[4-(1-methyl-[1,2,4]triazolo[4,3-a]quinoxaline-4-ylamino)-butyl]-urea | Mass (M + H⁺): 370.1; ¹H NMR (500 MHz, DMSO-d6): δ1.15 (s, 9H), 1.39 (m, 2H), 1.61 (m, 2H), 2.94 (q, 2H), 2.99 (s, 3H), 3.51 (q, 2H), 5.48 (s, 1H), 5.56 (t, 1H), 7.26 (t, 1H), 7.40 (t, 1H), 7.56 (d, 1H), 8.06 (d, 1H), 8.09 (m, 1H). |

TABLE 1-continued

| Example | Structure | Name | Data |
|---|---|---|---|
| Example 23 | 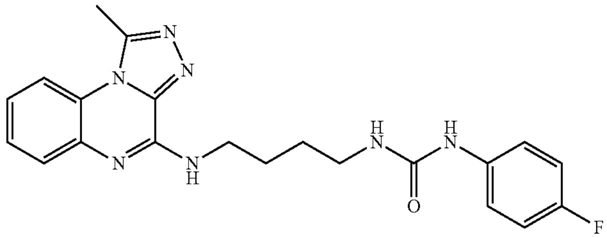 | 1-(4-fluoro-phenyl)-3-[4-(1-methyl-[1,2,4]triazolo[4,3-a]quinoxaline-4-ylamino)-butyl]-urea | Mass (M + H$^+$): 476.1; $^1$H NMR (500 MHz, DMSO-d6): δ1.47 (m, 2H), 1.65 (m, 2H), 2.98 (s, 3H), 3.08 (q, 2H), 3.51 (q, 2H), 6.05 (t, 1H), 6.98 (t, 2H), 7.31 (m, 2H), 7.73 (s, 1H), 8.10 (s, 1H), 8.35 (s, 1H), 8.49 (t, 1H). |
| Example 24 | 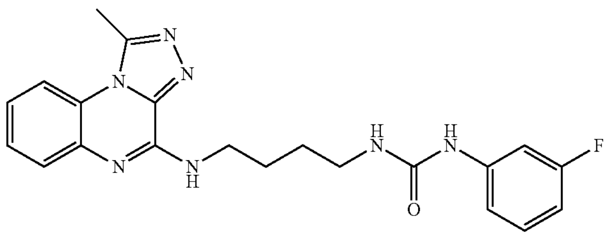 [SMILES: Cc1nnc2c(NCCCCNC(=O)Nc3cccc(F)c3)nc3ccccc3n12] | 1-(3-fluoro-phenyl)-3-[4-(1-methyl-[1,2,4]triazolo[4,3-a]quinoxaline-4-ylamino)-butyl]-urea | Mass (M + H$^+$): 408.1; $^1$H NMR (500 MHz, DMSO-d6): δ1.49 (m, 2H), 1.66 (m, 2H), 2.98 (s, 3H), 3.09 (q, 2H), 3.53 (q, 2H), 6.17 (t, 1H), 6.63 (td, 1H), 6.95 (d, 1H), 7.18 (dd, 1H), 7.27 (t, 1H), 7.39 (m, 2H), 7.56 (d, 1H), 8.05 (dd, 1H), 8.11 (t, 1H), 8.58 (s, 1H). |
| Example 25 | 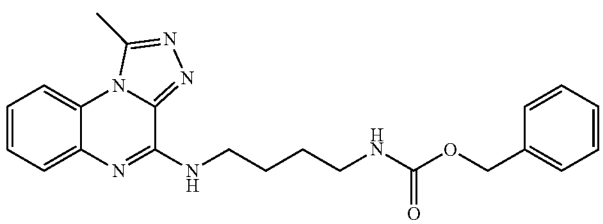 [SMILES: Cc1nnc2c(NCCCCNC(=O)OCc3ccccc3)nc3ccccc3n12] | [4-(1-methyl-[1,2,4]triazolo[4,3-a]quinoxaline-4-ylamino)-butyl]-carbamic acid benzylester | Mass (M + H$^+$): 405.2; $^1$H NMR (300 MHz, DMSO-d6): δ1.46-1.56 (m, 2H), 1.64-1.73 (m, 2H), 3.04 (s, 3H), 3.07-3.09 (m, 2H), 3.54-3.60 (m, 2H), 5.00 (s, 2H), 7.26-7.37 (m, 7H), 7.47 (t, J = 7.41 Hz, 1H), 7.65 (d, J = 8.34 Hz, 1H), 8.11 (d, J = 7.86 Hz, 1H), 8.55 (brs, 1H). |

<Preparative Example 2> Preparation of 4,7,8-trichloro-1-methyl-[1,2,4]triazolo[4,3-a]quinoxaline

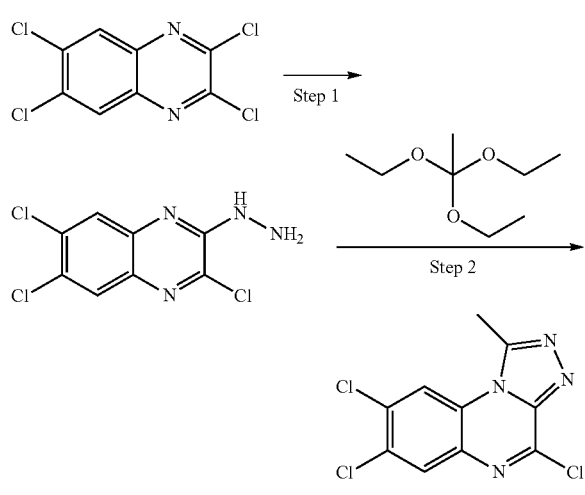

Step 1: Preparation of 2,6,7-trichloro-3-hydrazinylquinoxaline 9.23 g of a target compound was obtained (94% yield) by the same manner as described in step 1 of Preparative Example 1, except that 2,3,6,7-tetrachloroquinoxaline (10.0 g, 37.3 mmol) was used.

Mass (M+H$^+$): 264.0

Step 2: Preparation of 4,7,8-trichloro-1-methyl-[1,2,4]triazolo[4,3-a]quinoxaline 7.9 g of a target compound was obtained (79% yield) by the same manner as described in step 2 of Preparative Example 1, except that 2,6,7-trichloro-3-hydrazinylquinoxaline (9.2 g, 34.9 mmol) prepared in step 1 of Preparative Example 2 was used.

Mass (M+H$^+$): 288.1

$^1$H NMR (500 MHz, DMSO-d6): δ3.09 (s, 3H), 7.20 (s, 1H), 8.35 (s, 1H), 7.41 (s, 1H).

<Example 26> Preparation of [4-(7,8-dichloro-1-methyl-[1,2,4]triazolo[4,3-a]quinoxaline-4-ylamino)-butyl]-carbamic acid-tert-butylester

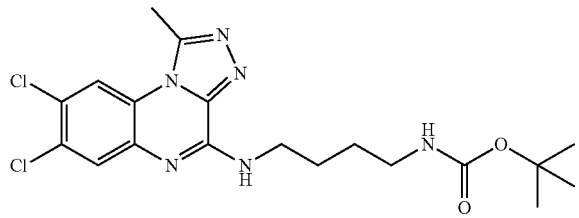 [SMILES: Cc1nnc2c(NCCCCNC(=O)OC(C)(C)C)nc3cc(Cl)c(Cl)cc3n12]

4.5 g of a target compound was obtained (98% yield) by the same manner as described in Example 1 except that 4,7,8-trichloro-1-methyl-[1,2,4]triazolo[4,3-a]quinoxaline prepared in step 2 of Preparative Example 2 was used as a starting material.

Mass (M+H$^+$): 439.1

$^1$H NMR (500 MHz, DMSO-d6) δ1.32 (s, 9H), 1.41 (m, 2H), 1.59 (m, 2H), 2.91 (q, 2H), 3.27 (s, 3H), 3.49 (q, 2H), 6.74 (t, 1H), 7.74 (s, 1H), 8.11 (s, 1H), 8.46 (t, 1H)

<Example 27> Preparation of N$^1$-(7,8-dichloro-1-methyl-[1,2,4]triazolo[4,3-a]quinoxaline-4-yl)butane-1,4-diamine ditrifluoroacetic acid

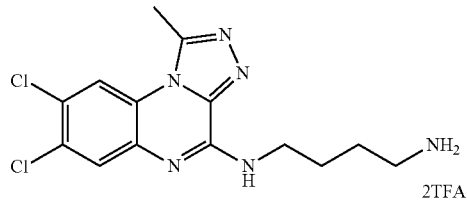 [SMILES: Cc1nnc2c(NCCCCN)nc3cc(Cl)c(Cl)cc3n12]

[4-(7,8-Dichloro-1-methyl-[1,2,4]triazolo[4,3-a]quinoxaline-4-ylamino)-butyl]-carbamic acid-tert-butylester (4 g, 9.1 mmol) prepared in Example 26 was dissolved in 100 ml of dichloromethane, to which trifluoroacetic acid (17 ml, 228 mmol) was added, followed by stirring at room temperature for 4 hours. The reaction mixture was concentrated under reduced pressure, followed by recrystallization in methanol and ether. The resulting compound was dried under reduced pressure and as a result 3.2 g of a target compound was obtained (78% yield) in the state of TFA salt.

Mass (M+H$^+$): 339.1

$^1$H NMR (500 MHz, DMSO-d6): δ1.58 (m, 2H), 1.68 (m, 2H), 2.18 (q, 2H), 3.00 (s, 3H), 3.52 (q, 2H), 7.60 (brm, 2H), 7.72 (s, 1H), 8.13 (s, 1H), 8.52 (t, 1H).

<Example 28> Preparation of N-[4-(7,8-dichloro-1-methyl-[1,2,4]triazolo[4,3-a]quinoxaline-4-ylamino)-butyl]-2,2-dimethyl-propionamide

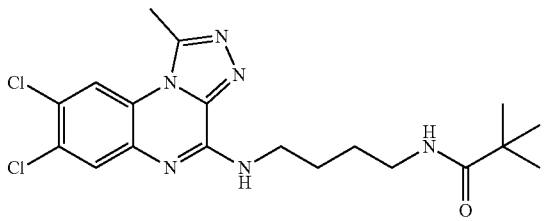 [SMILES: Cc1nnc2c(NCCCCNC(=O)C(C)(C)C)nc3cc(Cl)c(Cl)cc3n12]

190 mg of a target compound was obtained (82% yield) by the same manner as described in Example 3, except that N$^1$-(7,8-dichloro-1-methyl-[1,2,4]triazolo[4,3-a]quinoxaline-4-yl)butane-1,4-diamine ditrifluoroacetic acid (250 mg, 0.55 mmol) prepared in Example 27 was used.

Mass (M+H$^+$): 423.1

$^1$H NMR (250 MHz, DMSO-d6): δ1.02 (s, 9H), 1.44 (m, 2H) 1.60 (m, 2H), 2.98 (s, 3H), 3.05 (q, 2H), 3.49 (m, 2H), 7.36 (t, 1H), 7.72 (s, 1H), 8.11 (s, 1H).

The compounds shown in Table 2 below were prepared by the same manner as described in Example 28.

TABLE 2

| Example | Structure | Name | Data |
|---|---|---|---|
| Example 29 | 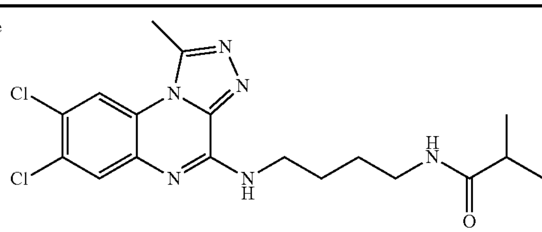 | N-[4-(7,8-dichloro-1-methyl-[,2,4]triazolo[4,3-a]quinoxaline-4-ylamino)-butyl]-isobutyramide | Mass (M + H$^+$): 409.1; $^1$H NMR (500 MHz, DMSO-d6): δ0.93 (d, 6H), 1.42 (m, 2H), 1.61 (m, 2H), 2.37 (m, 1H), 2.98 (s, 3H), 3.03 (m, 2H), 3.49 (q, 2H), 7.62 (t, 1H), 7.73 (s, 1H), 8.11 (s, 1H), 8.48 (t, 1H). |
| Example 30 | 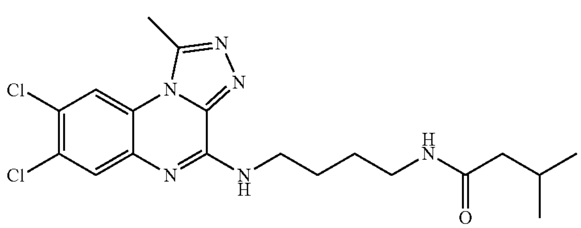 [SMILES: Cc1nnc2c(NCCCCNC(=O)CC(C)C)nc3cc(Cl)c(Cl)cc3n12] | N-[4-(7,8-dichloro-1-methyl-[1,2,4]triazolo[4,3-a]quinoxaline-4-ylamino)-butyl]-3-methyl-butyramide | Mass (M + H$^+$): 424.1; $^1$H NMR (500 MHz, DMSO-d6): δ0.80 (d, 6H), 1.44 (m, 2H), 1.61 (m, 2H), 1.86 (m, 2H), 1.88 (m, 1H), 2.99 (s, 3H), 3.48 (q, 2H), 3.50 (q, 2H), 3.80 (s, 3H), 7.70 (t, 1H), 7.73 (s, 1H), 8.11 (s, 1H), 8.48 (t, 1H). |

TABLE 2-continued

| Example | Structure | Name | Data |
|---|---|---|---|
| Example 31 | 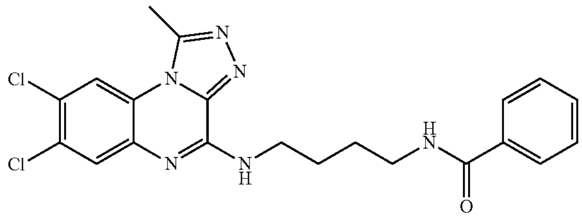 [SMILES: Cc1nnc2c(NCCCCNC(=O)c3ccccc3)nc3cc(Cl)c(Cl)cc3n12] | N-[4-(7,8-dichloro-1-methyl-[1,2,4]triazolo[4,3-a]quinoxaline-4-ylamino)-butyl]-benzamide | Mass (M + H$^+$): 443.1; $^1$H NMR (500 MHz, DMSO-d6): δ1.57 (m, 2H), 1.68 (m, 2H), 2.98 (s, 3H), 3.28 (m, 2H), 3.54 (q, 2H), 7.38 (m, 2H), 7.46 (t, 1H), 7.70 (s, 1H), 7.77 (d, 1H), 8.10 (s, 1H), 8.39 (t, 1H), 8.48 (t, 1H). |
| Example 32 | 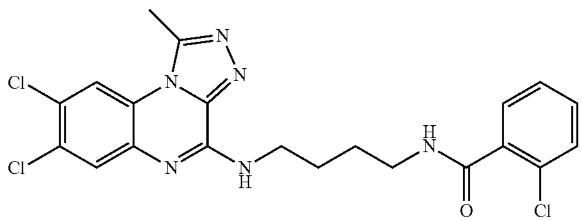 [SMILES: Cc1nnc2c(NCCCCNC(=O)c3ccccc3Cl)nc3cc(Cl)c(Cl)cc3n12] | 2-chloro-N-[4-(7,8-dichloro-1-methyl-[1,2,4]triazolo[4,3-a]quinoxaline-4-ylamino)-butyl]-benzamide | Mass (M + H$^+$): 477.1; $^1$NMR (500 MHz, DMSO-d6): δ1.56 (m, 1H), 1.71 (m, 2H), 2.99 (s, 3H), 3.24 (q, 2H), 3.54 (q, 2H), 7.27~7.40 (m, 3H), 7.42 (d, 1H), 7.73 (s, 1H), 8.12 (s, 1H), 8.35 (t, 1H), 8.50 (t, 1H). |
| Example 33 | 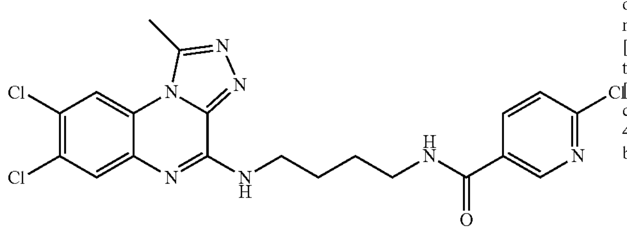 | 6-chloro-N-[4-(7,8-dichloro-1-methyl-[1,2,4]triazolo[4,3-a]quinoxaline-4-ylamino)-butyl]-nicotinamide | Mass (M + H$^+$): 479.1; $^1$H NMR (500 MHz, DMSO-d6): δ1.59 (m, 2H), 1.70 (m, 2H), 2.98 (s, 3H), 3.28 (q, 2H), 3.52 (q, 2H), 7.56 (d, 1H), 7.67 (s, 1H), 8.10 (s, 1H), 8.14 (m, 1H), 8.65 (t, 1H), 8.74 (t, 1H). |

A 7,8-dimethyl[1,2,4]triazolo[4,3-a]quinoxaline compound can be prepared using a 4-chloro-1,7,8-trimethyl-[1,2,4]triazolo[4,3-a]quinoxaline compound by the same manner as described in Preparative Example 2.

<Example 34> Preparation of [4-(1,7,8-trimethyl-[1,2,4]triazolo[4,3-a]quinoxaline-4-ylamino)-butyl]-carbamic acid-tert-butylester

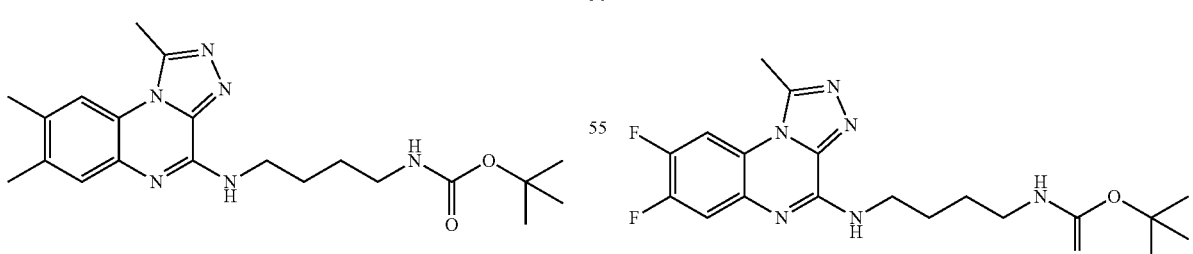

Mass (M+H$^+$): 399.2
$^1$H NMR (300 MHz, CDCl$_3$): δ1.44 (s, 9H), 1.64-1.66 (m, 2H), 1.76-1.80 (m, 2H), 2.36 (s, 3H), 2.39 (s, 3H), 3.09 (s, 3H), 3.21-3.24 (m, 2H), 3.69-3.71 (m, 2H), 4.74 (brs, 1H), 6.17 (brs, 1H), 7.55 (s, 1H), 7.70 (s, 1H).

A 7,8-difluoro[1,2,4]triazolo[4,3-a]quinoxaline compound can be prepared using a 4-chloro-7,8-difluoro-1-methyl-[1,2,4]triazolo[4,3-a]quinoxaline compound by the same manner as described in Preparative Example 2.

<Example 35> Preparation of [4-(7,8-difluoro-1-methyl-[1,2,4]triazolo[4,3-a]quinoxaline-4-ylamino)-butyl]-carbamic acid-tert-butylester Mass (M+H$^+$): 407.3
$^1$H NMR (300 MHz, DMSO-d6): δ1.36 (s, 9H), 1.40-1.50 (m, 2H), 1.56-1.69 (m, 2H), 2.90-2.97 (m, 2H), 3.00 (s, 3H), 3.48-3.55 (m, 2H), 6.78 (brs, 1H), 7.56-7.62 (m, 1H), 8.05-8.11 (m, 1H), 8.32 (t, J=5.67 Hz, 1H).

<Example 36> Preparation of N¹-(7,8-difluoro-1-methyl-[1,2,4]triazolo[4,3-a]quinoxaline-4-yl)-butane-1,4-diamine ditrifluoroacetic acid

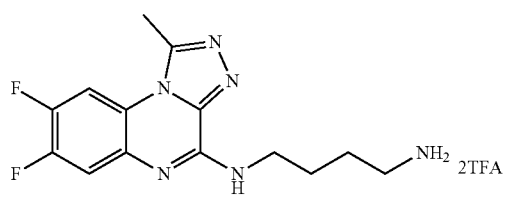 [SMILES: Cc1nnc2c(NCCCCN)nc3cc(F)c(F)cc3n12]

[4-(7,8-Difluoro-1-methyl-1-[1,2,4]triazolo[4,3-a]quinoxaline-4-ylamino)-butyl]-carbamic acid-tert-butylester (1.6 g, 3.96 mmol) prepared in Example 35 was dissolved in 50 ml of dichloromethane, to which trifluoroacetic acid (5.8 ml, 79 mmol) was added, followed by stirring at room temperature for 4 hours. The reaction mixture was concentrated under reduced pressure, followed by recrystallization in methanol and ether. The resulting compound was dried under reduced pressure and as a result 1.73 g of a target compound was obtained (82% yield) in the state of TFA salt.

Mass (M+H⁺): 307.2

<Example 37> Preparation of N-[4-(7,8-difluoro-1-methyl-[1,2,4]triazolo[4,3-a]quinoxaline-4-ylamino)-butyl]-3-methyl-butyramide

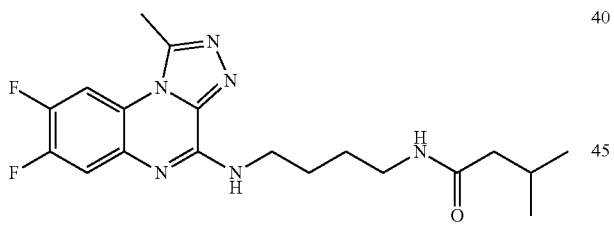

N¹-(7,8-Difluoro-1-methyl-[1,2,4]triazolo[4,3-a]quinoxaline-4-yl)butane-1,4-diamine ditrifluoroacetic acid (200 mg, 0.37 mmol) prepared in Example 36 was dissolved in 5 ml of dichloromethane, to which triethylamine (0.26 ml, 1.87 mmol, 5 eq) and isovalerylchloride (1.15 ml, 0.44 mmol, 1.2 eq) were added at 0~10° C. stepwise. The reaction mixture was stirred at room temperature for 2 hours. Upon completion of the reaction, the reaction was terminated by using methanol, followed by distillation under reduced pressure. The reactant was separated and purified by column chromatography, and as a result 140 mg of a target compound was obtained (97% yield).

Mass (M+H⁺): 391.1

¹H NMR (500 MHz, DMSO-d6): δ0.79 (d, 6H), 1.43 (m, 2H), 1.61 (m, 2H), 1.86 (d, 2H), 1.90 (m, 1H), 2.97 (s, 3H), 3.04 (q, 2H), 3.49 (q, 2H), 7.55 (dd, 1H), 7.69 (t, 1H), 8.06 (dd, 1H), 8.29 (t, 1H).

<Example 38> Preparation of N-[4-(7,8-difluoro-1-methyl-[1,2,4]triazolo[4,3-a]quinoxaline-4-ylamino)-butyl]-2-(R)-hydroxy-3-methyl-butyramide

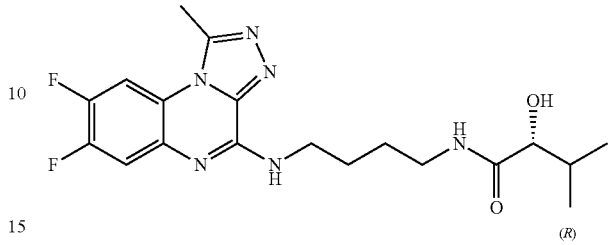

N¹-(7,8-difluoro-1-methyl-[1,2,4]triazolo[4,3-a]quinoxaline-4-yl)butane-1,4-diamine ditrifluoroacetic acid (200 mg, 0.37 mmol) prepared in Example 36 was dissolved in 5 ml of tetrahydrofuran, to which diisopropylethylamine (DIPEA, 0.33 ml, 1.87 mmol, 5 eq), 1-ethyl-3-(3-dimethylaminopropyl)carbodiimide (EDCI, 140 mg, 2 eq), hydroxybenzotriazol (HOBt, 100 mg, 2 eq), and 2-(R)-hydroxy-3-methyl-butyric acid (88 mg, 2 eq) were added stepwise, followed by stirring at room temperature for 3 hours. Upon completion of the reaction, the reactant was extracted with dichloromethane and water. The organic layer was dried over anhydrous magnesium sulfate, and distilled under reduced pressure. The reactant was separated and purified by column chromatography, and as a result 84 mg of a target compound was obtained (55% yield).

Mass (M+H⁺): 407.2

¹H NMR (500 MHz, DMSO-d6) δ0.72 (d, 3H), 0.85 (d, 3H), 1.51 (m, 2H), 1.65 (m, 2H), 1.92 (m, 1H), 2.98 (s, 3H), 3.15 (m, 2H), 3.53 (q, 2H), 3.61 (q, 1H), 5.01 (d, 1H), 7.45 (t, 1H), 7.53 (q, 1H), 8.03 (d, 1H), 8.05 (t, 1H).

<Example 39> Preparation of N-[4-(7,8-difluoro-1-methyl-[1,2,4]triazolo[4,3-a]quinoxaline-4-ylamino)-butyl]-2-(S)-hydroxy-3-methyl-butyramide

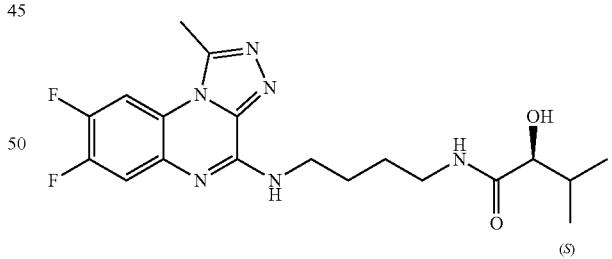

90 mg of a target compound was obtained (59% yield) by the same manner as described in Example 38, except that N¹-(7,8-difluoro-1-methyl-[1,2,4]triazolo[4,3-a]quinoxaline-4-yl)butane-1,4-diamine ditrifluoroacetic acid (200 mg, 0.37 mmol) prepared in Example 36 and 2-(S)-hydroxy-3-methyl-butyric acid (88 mg, 2 eq) were used.

Mass (M+H⁺): 407.2

¹H NMR (500 MHz, DMSO-d6) δ0.72 (d, 3H), 0.85 (d, 3H), 1.51 (m, 2H), 1.65 (m, 2H), 1.92 (m, 1H), 2.98 (s, 3H), 3.15 (m, 2H), 3.53 (q, 2H), 3.61 (q, 1H), 5.01 (d, 1H), 7.45 (t, 1H), 7.53 (q, 1H), 8.03 (d, 1H), 8.05 (t, 1H).

<Preparative Example 3> Preparation of 4-chloro-1,8-dimethyl-[1,2,4]triazolo[4,3-a]quinoxaline

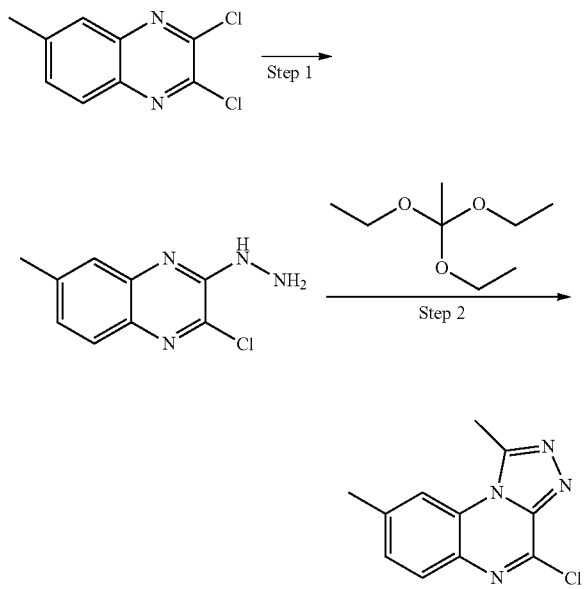

Step 1: Preparation of (3-chloro-7-methyl-quinoxaline-2-yl)-hydrazine

A target compound was obtained (57% yield) by the same manner as described in step 1 of Preparative Example 1, except that 2,3-dichloro-6-methylquinoxaline (1 g, 4.69 mmol) was used.
Mass (M+H$^+$): 209.1

Step 2: Preparation of 4-chloro-1,8-dimethyl-[1,2,4]triazolo[4,3-a]quinoxaline

A target compound was obtained by the same manner as described in step 2 of Preparative Example 1, except that (3-chloro-7-methyl-quinoxaline-2-yl)-hydrazine (0.17 g, 0.82 mmol) prepared in step 1 of Preparative Example 3 was used. The following reaction was carried out without purification.
Mass (M+H$^+$): 233.1

<Example 40> Preparation of [4-(1,8-dimethyl-[1,2,4]triazolo[4,3-a]quinoxaline-4-ylamino)-butyl]-carbamic acid-tert-butylester

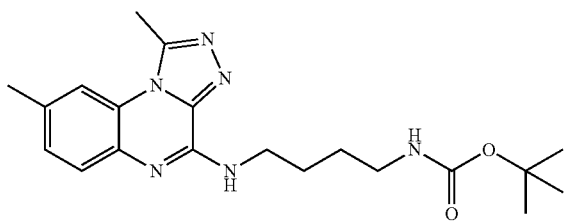 [SMILES: Cc1ccc2nc(NCCCCNC(=O)OC(C)(C)C)c3nnc(C)n3c2c1]

0.22 g of a target compound was obtained (two steps, 71% yield) by the same manner as described in Example 1, except that 4-chloro-1,8-dimethyl-[1,2,4]triazolo[4,3-a]quinoxaline prepared in step 2 of Preparative Example 3 was used.
Mass (M+H$^+$): 385.2
$^1$H NMR (300 MHz, DMSO-d6): δ1.37 (s, 9H), 1.45-1.49 (m, 2H), 1.60-1.66 (m, 2H), 2.46 (s, 3H), 2.95-2.99 (m, 2H), 3.04 (s, 3H), 3.50-3.54 (m, 2H), 6.81 (t, J=5.30 Hz, 1H), 7.27 (d, J=8.20 Hz, 1H), 7.51 (d, J=8.20 Hz, 1H), 7.88 (s, 1H), 7.99 (t, J=5.85 Hz, 1H).

<Example 41> Preparation of [4-(1,8-dimethyl-[1,2,4]triazolo[4,3-a]quinoxaline-4-ylamino)-butane]-1,4-diamine dihydrochloride

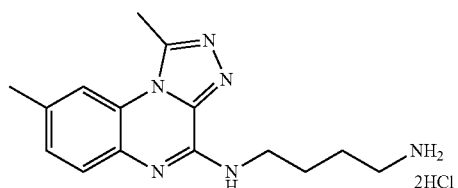

0.60 g of a target compound was obtained (quantitative yield) by the same manner as described in Example 2, except that [4-(1,8-dimethyl-[1,2,4]triazolo[4,3-a]quinoxaline-4-ylamino)-butyl]-carbamic acid-tert-butylester prepared in Example 40 was used.
Mass (M+H$^+$): 285.2

<Example 42> Preparation of N-[4-(1,8-dimethyl-[1,2,4]triazolo[4,3-a]quinoxaline-4-ylamino)-butyl]-2,2-dimethyl-propionamide

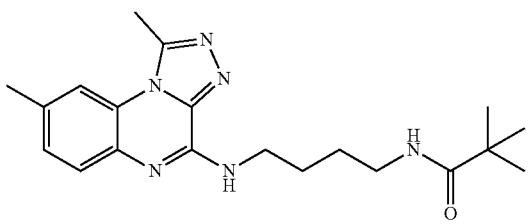 [SMILES: Cc1ccc2nc(NCCCCNC(=O)C(C)(C)C)c3nnc(C)n3c2c1]

0.11 g of a target compound was obtained (59% yield) by the same manner as described in Example 3, except that [4-(1,8-dimethyl-[1,2,4]triazolo[4,3-a]quinoxaline-4-ylamino)-butane]-1,4-diamine dihydrochloride prepared in Example 41 was used.
Mass (M+H$^+$): 368.1
$^1$H NMR (300 MHz, DMSO-d6): δ1.06 (s, 9H), 1.45-1.54 (m, 2H), 1.61-1.70 (m, 2H), 2.46 (s, 3H), 3.05 (s, 3H), 3.08-3.12 (m, 2H), 3.51-3.57 (m, 2H), 7.29 (d, J=8.04 Hz, 1H), 7.43 (t, J=5.37 Hz, 1H), 7.53 (d, J=8.19 Hz, 1H), 7.89 (s, 1H), 8.37 (brs, 1H).

The compounds shown in Table 3 below were prepared by the same manner as described in Example 42.

TABLE 3

| Example | Structure | Name | Data |
|---|---|---|---|
| Example 43 | 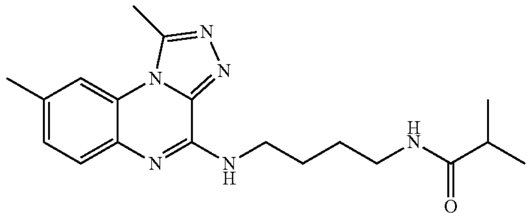 [SMILES: Cc1ccc2nc(NCCCCNC(=O)C(C)C)c3nnc(C)n3c2c1] | N-[4-(1,8-dimethyl-[1,2,4]triazolo[4,3-a]quinoxaline-4-ylamino)-butyl]-isobutyramide | Mass (M + H$^+$): 355.6; $^1$H NMR (300 MHz, DMSO-d6): δ0.97 (d, J = 6.84 Hz, 6H), 1.43-1.53 (m, 2H), 1.61-1.71 (m, 2H), 2.27-2.36 (m, 1H), 3.00 (s, 3H), 2.44 (s, 3H), 3.02-3.10 (m, 2H), 3.49-3.56 (m, 2H), 7.26 (d, J = 9.09 Hz, 1H), 7.49 (d, J = 8.19 Hz, 1H), 7.68 (t, J = 5.28 Hz, 1H), 7.88 (s, 1H), 7.97(t, J = 5.67 Hz, 1H). |
| Example 44 | 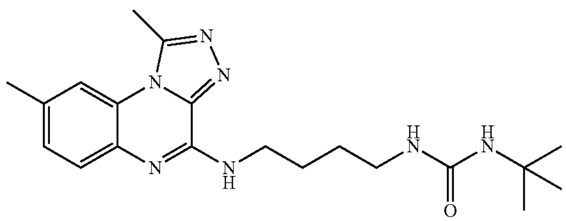 [SMILES: Cc1ccc2nc(NCCCCNC(=O)NC(C)(C)C)c3nnc(C)n3c2c1] | 1-tert--butyl-3-[4-(1,8-dimethyl-[1,2,4]triazolo[4,3-a]quinoxaline-4-ylamino)-butyl]-urea | Mass (M + H$^+$): 384.3; $^1$H NMR (500 MHz, DMSO-d6): δ1.20 (s, 9H), 1.40-1.46 (m, 2H), 1.62-1.68 (m, 2H), 2.46 (s, 3H), 2.97-3.00 (m, 2H), 3.05 (s, 3H), 3.51-3.55 (m, 2H), 5.54 (s, 1H), 5.62 (t, J = 5.50 Hz, 1H), 7.27 (d, J = 8.20 Hz, 1H), 7.51(d, J = 8.20 Hz, 1H), 7.89 (s, 1H), 8.00 (t, J = 5.75 Hz, 1H). |
| Example 45 | 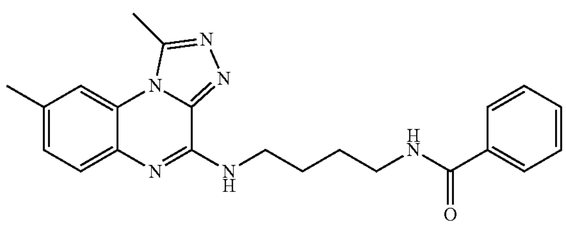 [SMILES: Cc1ccc2nc(NCCCCNC(=O)c3ccccc3)c3nnc(C)n3c2c1] | N-[4-(1,8-dimethyl-[1,2,4]triazolo[4,3-a]quinoxaline-4-ylamino)-butyl]-benzamide | Mass (M +H$^+$): 388.3; $^1$H NMR (300 MHz, DMSO-d6): δ1.61-1.66 (m, 2H), 1.71-1.75 (m, 2H), 2.45 (s, 3H), 3.04 (s, 3H), 3.55-3.59 (m, 2H), 7.26 (d, J = 8.20 Hz, 1H), 7.42-7.52 (m, 4H), 7.82 (d, J = 7.65 Hz, 2H), 7.87 (s, 1H), 8.00 (t, J = 5.60 Hz, 1H), 3.30-3.36 (m, 2H), 8.46 (t, J = 5.40 Hz, 1H). |
| Example 46 | 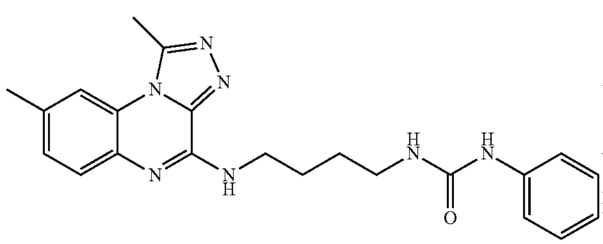 [SMILES: Cc1ccc2nc(NCCCCNC(=O)Nc3ccccc3)c3nnc(C)n3c2c1] | 1-[4-(1,8-dimethyl-[1,2,4]triazolo[4,3-a]quinoxaline-4-ylamino)-butyl]-3-phenyl-urea | Mass (M +H$^+$): 404.2; $^1$H NMR (300 MHz, DMSO-d6): δ1.50-1.56 (m, 2H), 1.67-1.73 (m, 2H), 2.46 (s, 3H), 3.04 (s, 3H), 3.12-3.16 (m, 2H), 3.54-3.58 (m, 2H), 6.13 (t, J = 5.55 Hz, 1H), 6.87 (t, J = 7.30 Hz, 1H), 7.20 (t, J = 7.90 Hz, 2H), 7.27 (d, J = 8.15 Hz, 1H), 7.36 (d, J = 7.95 Hz, 2H), 7.51 (d, J = 8.20 Hz, 1H), 7.89 (s, |

| Example | Structure | Name | Data |
|---|---|---|---|
| | | | 1H), 8.02 (t, J = 5.70 Hz, 1H), 8.37 (s, 1H). |

<Preparative Example 4> Preparation of 4-chloro-8-fluoro-1-methyl-[1,2,4]triazolo[4,3-a]quinoxaline

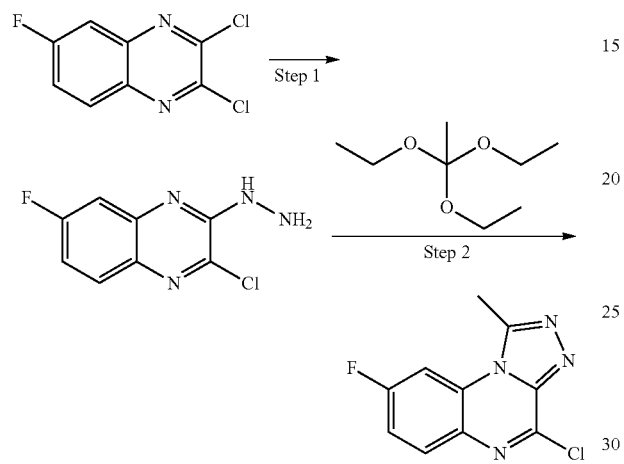

4-Chloro-8-fluoro-1-methyl-[1,2,4]triazolo[4,3-a]quinoxaline was prepared by the same manner as the preparation of 4-chloro-1,8-dimethyl-[1,2,4]triazolo[4,3-a]quinoxaline described in Preparative Example 3.

Step 1: Preparation of (3-chloro-7-fluoro-quinoxaline-2-yl)-hydrazine

Mass (M+H⁺): 209.1

Step 2: Preparation of 4-chloro-8-fluoro-1-methyl-[1,2,4]triazolo[4,3-a]quinoxaline Mass (M+H⁺): 237.0
¹H NMR (300 MHz, DMSO-d6): δ3.11 (s, 3H), 7.60-7.67 (m, 1H), 8.09-8.17 (m, 2H)

<Example 47> Preparation of [4-(8-fluoro-1-methyl-[1,2,4]triazolo[4,3-a]quinoxaline-4-ylamino)-butyl]-carbamic acid-tert-butylester

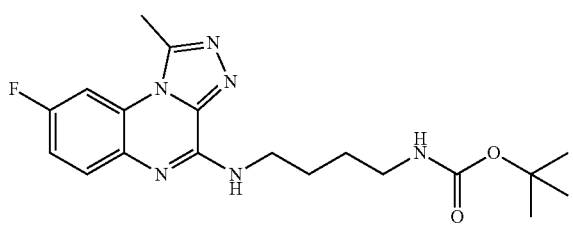 [SMILES: Cc1nnc2c(NCCCCNC(=O)OC(C)(C)C)nc3ccc(F)cc3n12]

0.38 g of a target compound was obtained (82% yield) by the same manner as described in Example 1, except that 4-chloro-8-fluoro-1-methyl-[1,2,4]triazolo[4,3-a]quinoxaline prepared in step 2 of Preparative Example 4 was used.
Mass (M+H⁺): 389.2
¹H NMR (500 MHz, DMSO-d6): δ1.36 (s, 9H), 1.44-1.48 (m, 2H), 1.62-1.68 (m, 2H), 2.95-2.98 (m, 2H), 3.03 (s, 3H), 3.50-3.54 (m, 2H), 6.81 (t, J=5.30 Hz, 1H), 7.31-7.35 (m, 1H), 7.61-7.64 (m, 1H), 7.86-7.88 (m, 1H), 8.12 (t, J=5.60 Hz, 1H), <Example 48> Preparation of [4-(8-fluoro-1-methyl-[1,2,4]triazolo[4,3-a]quinoxaline-4-ylamino)-butyl]-1,4-diamine dihydrochloride

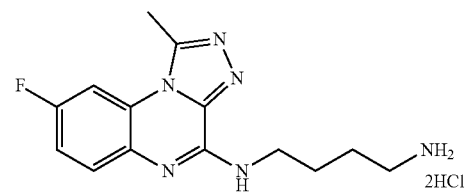 [SMILES: Cc1nnc2c(NCCCCN)nc3ccc(F)cc3n12]

0.36 g of a target compound was obtained (quantitative yield) by the same manner as described in Example 2, except that [4-(8-fluoro-1-methyl-[1,2,4]triazolo[4,3-a]quinoxaline-4-ylamino)-butyl]-carbamic acid-tert-butylester prepared in Example 47 was used.
Mass (M+H⁺): 289.1

<Example 49> Preparation of N-[4-(8-fluoro-1-methyl-[1,2,4]triazolo[4,3-a]quinoxaline-4-ylamino)-butyl]-2,2-dimethyl-propionamide

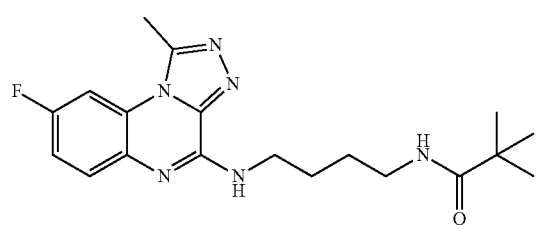 [SMILES: Cc1nnc2c(NCCCCNC(=O)C(C)(C)C)nc3ccc(F)cc3n12]

0.10 g of a target compound was obtained (70% yield) by the same manner as described in Example 3, except that [4-(8-fluoro-1-methyl-[1,2,4]triazolo[4,3-a]quinoxaline-4-ylamino)-butyl]-1,4-diamine dihydrochloride prepared in Example 48 was used.
Mass (M+H⁺): 372.3
¹H NMR (500 MHz, DMSO-d6): δ1.07 (s, 9H), 1.46-1.52 (m, 2H), 1.62-1.68 (m, 2H), 3.03 (s, 3H), 3.06-3.10 (m, 2H), 3.51-3.55 (m, 2H), 7.32-7.36 (m, 1H), 7.43 (t, J=5.45 Hz, 1H), 7.60-7.63 (m, 1H), 7.87-7.89 (m, 1H), 8.13 (t, J=5.70 Hz, 1H).

The compounds shown in Table 4 below were prepared by the same manner as described in Example 49.

TABLE 4

| Example | Structure | Name | Data |
|---------|-----------|------|------|
| Example 50 | 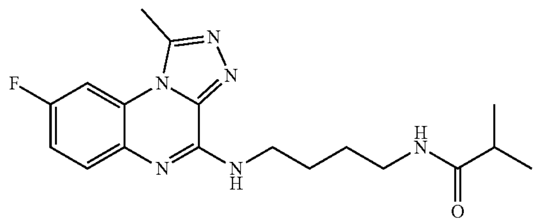 [SMILES: Cc1nnc2c(NCCCCNC(=O)C(C)C)nc3ccc(F)cc3n12] | [4-(8-fluoro-1-methyl-[1,2,4]triazolo[4,3-a]quinoxaline-4-ylamino)-butyl]-isobutyramide | Mass (M + H$^+$): 359.2; $^1$H NMR (300 MHz, DMSO-d$_6$): δ0.97 (d, J = 6.84 Hz, 6H), 1.45-1.52 (m, 2H), 1.61-1.69 (m, 2H), 2.28-2.33 (m, 1H), 3.03-3.09 (m, 2H), 3.02 (s, 3H), 3.50-3.56 (m, 2H), 7.32-7.36 (m, 1H), 7.30-7.37 (m, 1H), 7.59-7.69 (m, 2H), 7.85-7.90 (m, 1H), 8.10 (t, J = 5.70 Hz, 1H). |
| Example 51 | 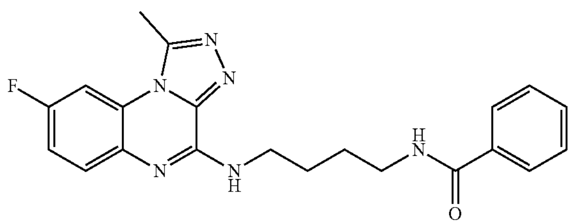 [SMILES: Cc1nnc2c(NCCCCNC(=O)c3ccccc3)nc3ccc(F)cc3n12] | N-[4-(8-fluoro-1-methyl-[1,2,4]triazolo[4,3-a]quinoxaline-4-ylamino)-butyl]-benzamide | Mass (M + H$^+$): 392.4; $^1$H NMR (300 MHz, DMSO-d$_6$): δ1.60-1.69 (m, 2H), 1.71-1.78 (m, 2H), 3.02 (s, 3H), 3.29-3.35 (m, 2H), 3.54-3.62 (m, 2H), 7.29-7.35 (m, 1H), 7.40-7.53 (m, 3H), 7.58-7.63 (m, 1H), 7.80-7.83 (m, 2H), 7.85-7.89 (m, 1H), 8.12 (t, J = 5.67 Hz, 1H), 8.44 (t, J = 5.37 Hz, 1H). |
| Example 52 | 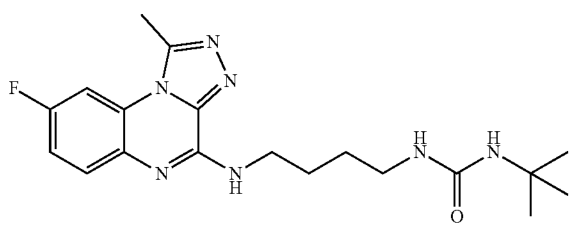 [SMILES: Cc1nnc2c(NCCCCNC(=O)NC(C)(C)C)nc3ccc(F)cc3n12] | 1-tert-butyl-3-[4-(8-fluoro-1-methyl-[1,2,4]triazolo[4,3-a]quinoxaline-4-ylamino)-butyl]-urea | Mass (M + H$^+$): 388.1; $^1$H NMR (500 MHz, DMSO-d$_6$): δ1.20 (s, 9H), 1.40-1.46 (m, 2H), 1.62-1.68 (m, 2H), 2.97-3.01 (m, 2H), 3.03 (s, 3H), 3.51-3.56 (m, 2H), 5.54 (s, 1H), 5.62 (t, J = 5.55 Hz, 1H), 7.32-7.36 (m, 1H), 7.62-7.65 (m, 1H), 7.87-7.90 (m, 1H), 8.14 (t, J = 5.70 Hz, 1H). |
| Example 53 | 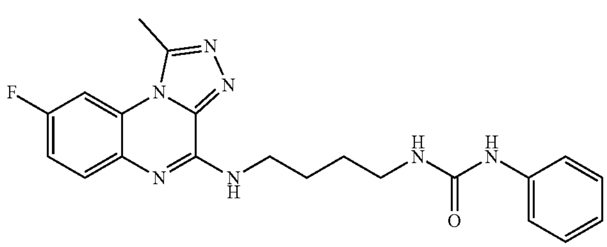 [SMILES: Cc1nnc2c(NCCCCNC(=O)Nc3ccccc3)nc3ccc(F)cc3n12] | 1-[4-(8-fluoro-1-methyl-[1,2,4]triazolo[4,3-a]quinoxaline-4-ylamino)-butyl]-3-phenyl-urea | Mass (M + H$^+$): 408.2; $^1$H NMR (500 MHz, DMSO-d$_6$): δ1.50-1.56 (m, 2H), 1.67-1.73 (m, 2H), 3.03 (s, 3H), 3.12-3.16 (m, 2H), 3.54-3.58 (m, 2H), 6.13 (t, J = 5.60 Hz, 1H), 6.87 (t, J = 7.30 Hz, 1H), 7.20 (t, J = 8.10 Hz, 2H), 7.30-7.34 (m, 1H), 7.36 (d, J = 7.75 Hz, 2H), 7.62-7.64 (m, 1H), 7.87-7.89 (m, 1H), 8.16 (t, J = 5.75 Hz, 1H), 8.37 (s, 1H). |

<Example 54> Preparation of [4-(8-chloro-1-methyl-[1,2,4]triazolo[4,3-a]quinoxaline-4-ylamino)-butyl]-carbamic acid-tert-butylester

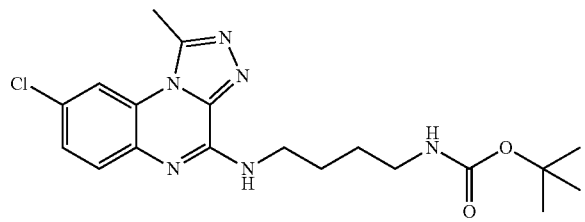 [SMILES: Cc1nnc2c(NCCCCNC(=O)OC(C)(C)C)nc3ccc(Cl)cc3n12]

1.05 g of a target compound was obtained (3 steps, 48% yield) by the same manner as described in Example 1, except that 4,8-dichloro-1-methyl-[1,2,4]triazolo[4,3-a]quinoxaline was used.

Mass (M+H$^+$): 405.2

$^1$H NMR (300 MHz, DMSO-d6): δ1.37 (s, 9H), 1.45-1.49 (m, 2H), 1.62-1.68 (m, 2H), 2.95-2.99 (m, 2H), 3.03 (s, 3H), 3.51-3.55 (m, 2H), 6.80 (t, J=5.45 Hz, 1H), 7.47 (dd, J=8.70 Hz, 2.20 Hz, 1H), 7.59 (d, J=8.70 Hz, 1H), 8.01 (d, J=2.20 Hz, 1H), 8.28 (t, J=5.70 Hz, 1H).

<Example 55> Preparation of N$^1$-(8-chloro-1-methyl-[1,2,4]triazolo[4,3-a]quinoxaline-4-yl)butane-1,4-diamine hydrochloride

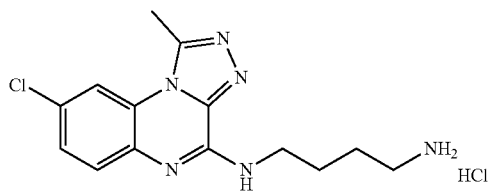 [SMILES: Cc1nnc2c(NCCCCN)nc3ccc(Cl)cc3n12 ; Cl]

A target compound was obtained by the same manner as described in Example 2, except that [4-(8-chloro-1-methyl-[1,2,4]triazolo[4,3-a]quinoxaline-4-ylamino)-butyl]-carbamic acid-tert-butylester prepared in Example 54 was used.

Mass (M+H$^+$): 342.2

<Example 56> Preparation of N-[4-(8-chloro-1-methyl-[1,2,4]triazolo[4,3-a]quinoxaline-4-ylamino)-butyl]-benzamide

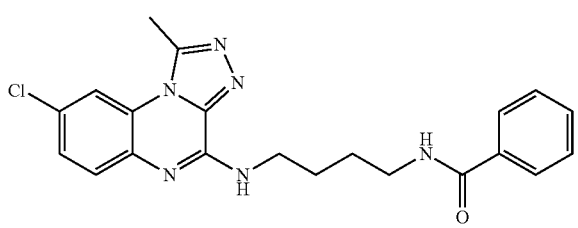 [SMILES: Cc1nnc2c(NCCCCNC(=O)c3ccccc3)nc3ccc(Cl)cc3n12]

A target compound was obtained by the same manner as described in Example 11, except that N$^1$-(8-chloro-1-methyl-[1,2,4]triazolo[4,3-a]quinoxaline-4-yl)butane-1,4-diamine hydrochloride prepared in Example 55 was used.

Mass (M+H$^+$): 408.2

NMR $^1$H NMR (500 MHz, DMSO): δ1.50-1.56 (m, 2H), 1.67-1.73 (m, 2H), 3.03 (s, 3H), 3.12-3.16 (m, 2H), 3.54-3.58 (m, 2H), 6.13 (t, J=5.60 Hz, 1H), 6.87 (t, J=7.30 Hz, 1H), 7.20 (t, J=8.10 Hz, 2H), 7.30-7.34 (m, 1H), 7.36 (d, J=7.75 Hz, 2H), 7.62-7.64 (m, 1H), 7.87-7.89 (m, 1H), 8.16 (t, J=5.75 Hz, 1H), 8.37 (s, 1H).

<Preparative Example 5> Preparation of 4-chloro-7,8-dimethoxy-1-methyl-[1,2,4]triazolo[4,3-a]quinoxaline

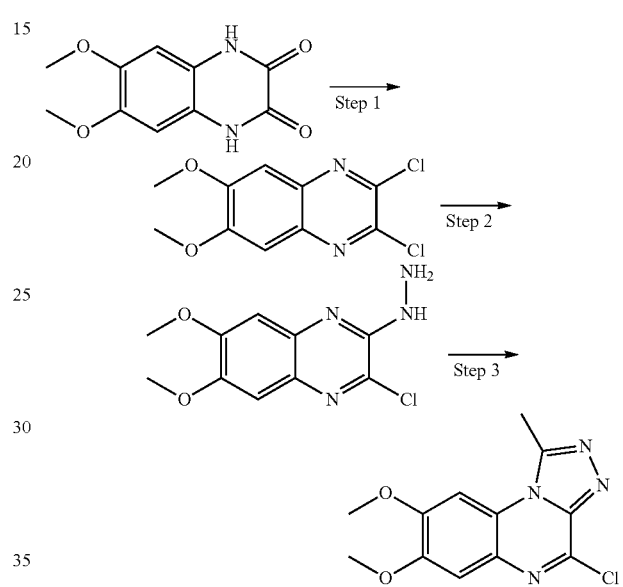

Step 1: Preparation of 2,3-dichloro-6,7-dimethoxy-quinoxaline 6,7-Dimethoxy-1,4-dihydro-quinoxaline-2,3-dione (6.5 g, 29.3 mmol) and triethylamine (6.1 ml, 44.0 mmol) were reflux stirred in 70 ml of POCl$_3$ for 18 hours. The reaction was slowly terminated using methanol:water mixture (1:1) carefully not to induce exothermic reaction. At this time, the resulting solid was filtered and vacuum dried. As a result, 4.9 g of a target compound was obtained (65% yield).

Mass (M+H$^+$): 260.0

$^1$H NMR (500 MHz, DMSO-d6): δ3.94 (s, 6H), 7.42 (s, 2H).

Step 2: Preparation of (3-chloro-6,7-dimethoxy-quinoxaline-2-yl)-hydrazine 2,3-Dichloro-6,7-dimethoxy-quinoxaline (4.9 g, 18.9 mmol) prepared in step 1 of Preparative Example 5, triethylamine (26 ml, 189 mmol) and hydrazine hydrate (1.4 ml, 28.4 mmol) were dissolved in 50 ml of ethanol, followed by stirring at 60-70° C. for 21 hours. Upon completion of the reaction, the temperature was lowered to room temperature and the resulting solid was filtered and dried under reduced pressure. As a result, 4.4 g of a target compound was obtained (91% yield).

Mass (M+H$^+$): 255.1

$^1$H NMR (500 MHz, DMSO-d6): δ3.81 (s, 3H), 3.86 (s, 3H), 4.40 (brs, 2H), 7.06 (s, 1H), 7.16 (s, 1H), 8.34 (s, 1H).

Step 3: Preparation of 4-chloro-7,8-dimethoxy-1-methyl-[1,2,4]triazolo[4,3-a]quinoxaline (3-Chloro-6,7-dimethoxy-quinoxaline-2-yl)-hydrazine (4.39 g, 17.2 mmol) prepared in step 2 of Preparative Example 5 was reflux stirred in 50 ml of triethylorthoacetate for 8 hours. Upon completion of the reaction, the temperature was lowered to room temperature, followed by recrystallization in methanol. The resulting solid was filtered and dried under reduced pressure. As a result, 3.7 g of a target compound was obtained (77% yield).

Mass (M+H$^+$): 279.1

$^1$H NMR (500 MHz, DMSO-d6): δ3.15 (s, 3H), 3.88 (s, 3H), 4.00 (s, 3H), 7.54 (s, 1H), 7.69 (s, 1H).

<Example 57> Preparation of [4-(7,8-dimethoxy-1-methyl-[1,2,4]triazolo[4,3-a]quinoxaline-4-ylamino)-butyl]-carbamic acid-tert-butylester

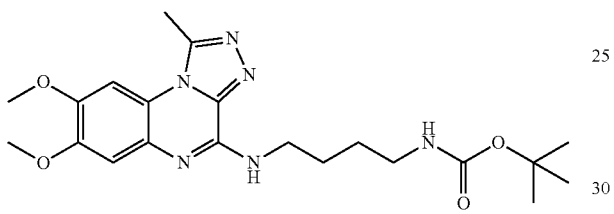

4-Chloro-7,8-dimethoxy-1-methyl-[1,2,4]triazolo[4,3-a]quinoxaline (2 g, 7.18 mmol) prepared in step 3 of Preparative Example 5, diisopropylethylamine (DIPEA, 2.5 ml, 14.4 mmol) and tert-butyl-N-(4-aminobutyl)carbamate (2.75 ml, 14.4 mmol) were reflux stirred in 20 ml of isopropyl alcohol for 18 hours. Upon completion of the reaction, the temperature was lowered to room temperature, followed by recrystallization in methanol. The resulting solid was filtered and dried under reduced pressure. As a result, 2.86 g of a target compound was obtained (93% yield).

Mass (M+H$^+$): 431.2

$^1$H NMR (500 MHz, DMSO-d6): δ1.32 (s, 9H), 1.43 (m, 2H), 1.59 (m, 2H), 2.92 (q, 2H), 3.03 (s, 3H), 3.47 (q, 2H), 3.82 (s, 3H), 3.86 (s, 3H), 6.75 (t, 1H), 7.09 (s, 1H), 7.50 (s, 1H), 7.81 (t, 1H).

<Example 58> Preparation of N$^1$-(7,8-dimethoxy-1-methyl-[1,2,4]triazolo[4,3-a]quinoxaline-4-yl)-butane-1,4-diamine ditrifluoroacetic acid

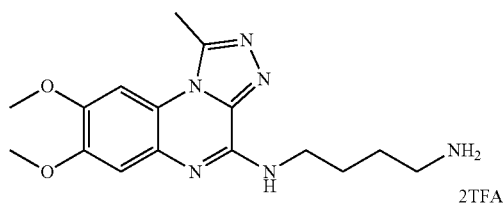 [SMILES: COc1cc2nc(NCCCCN)c3nnc(C)n3c2cc1OC]

[4-(7,8-Dimethoxy-1-methyl-[1,2,4]triazolo[4,3-a]quinoxaline-4-ylamino)-butyl]-carbamic acid-tert-butylester (2.75 g, 5.97 mmol) prepared in Example 57 was diluted in 30 ml of dichloromethane, to which trifluoroacetic acid (9.14 ml, 119 mmol) was added, followed by stirring at room temperature for 2 hours. Upon completion of the reaction, the solvent was eliminated by distillation under reduced pressure, followed by recrystallization in 10 ml of methanol. The resulting solid was filtered and vacuum dried. As a result, 2.95 g of a target compound was obtained (88% yield).

Mass (M+H$^+$): 331.2

$^1$H NMR (500 MHz, DMSO-d6): δ1.59 (m, 2H), 1.68 (m, 2H), 2.81 (q, 2H), 3.51 (q, 2H), 3.82 (s, 3H), 3.88 (s, 3H), 7.10 (s, 1H), 7.53 (s, 1H), 7.62 (brs, 3H), 7.98 (brs, 1H).

<Example 59> Preparation of N-[4-(7,8-dimethoxy-1-methyl-[1,2,4]triazolo[4,3-a]quinoxaline-4-ylamino)-butyl]-2,2-dimethyl-propionamide

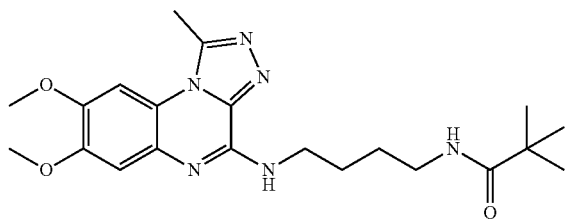 [SMILES: COc1cc2nc(NCCCCNC(=O)C(C)(C)C)c3nnc(C)n3c2cc1OC]

N$^1$-(7,8-dimethoxy-1-methyl-[1,2,4]triazolo[4,3-a]quinoxaline-4-yl)-butane-1,4-diamine ditrifluoroacetic acid (250 mg, 0.45 mmol) prepared in Example 58 and triethylamine (0.31 ml, 2.25 mmol) were dissolved in 5 ml of dichloromethane. The temperature of the mixture was lowered to 0-5° C. and then trimethylacetylchloride (0.07 ml, 0.54 mmol) was slowly added thereto. The reaction mixture was stirred at the same temperature as the above for 2 hours and then the reaction was terminated using methanol. The reactant was distilled under reduced pressure, followed by recrystallization in methanol. The resulting solid was filtered and vacuum dried. As a result, 160 mg of a target compound was obtained (86% yield).

Mass (M+H$^+$): 415.2

$^1$H NMR (500 MHz, DMSO-d6): δ1.02 (s, 9H), 1.46 (m, 2H), 1.60 (m, 2H), 3.03 (s, 3H), 3.05 (q, 2H), 3.47 (q, 2H), 3.82 (s, 3H), 3.87 (s, 3H), 7.09 (s, 1H), 7.37 (t, 1H), 7.51 (s, 1H), 7.81 (t, 1H).

The compounds shown in Table 5 below were prepared by the same manner as described in Example 59.

TABLE 5

| Example | Structure | Name | Data |
|---|---|---|---|
| Example 60 | 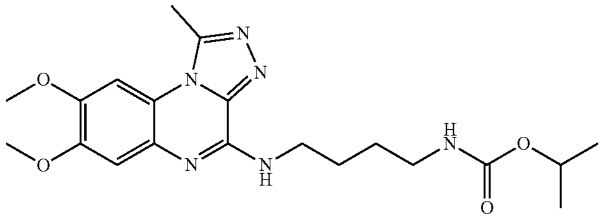 [SMILES: COc1cc2nc(NCCCCNC(=O)OC(C)C)c3nnc(C)n3c2cc1OC] | [4-(7,8-dimethoxy-1-methyl-[1,2,4]triazolo[4,3-a]quinoxaline-4-ylamino)-butyl]-carbamic acid isopropylester | Mass (M + H$^+$): 417.2; $^1$H NMR (500 MHz, DMSO-d$_6$): δ1.10 (d, 6H), 1.45 (m, 2H), 1.60 (m, 2H), 2.96 (q, 2H), 3.03 (s, 3H), 3.47 (q, 2H), 3.82 (s, 3H), 3.86 (s, 3H), 4.68 (m, 1H), 6.94 (t, 1H), 7.09 (s, 1H), 7.50 (s, 1H), 7.80 (t, 1H). |
| Example 61 | 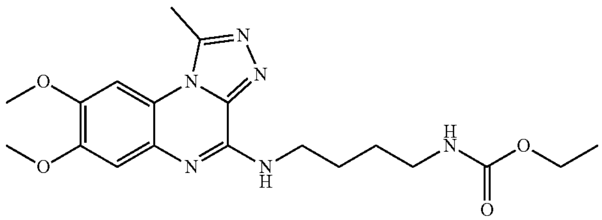 [SMILES: CCOC(=O)NCCCCNc1nc2cc(OC)c(OC)cc2n2c(C)nnc12] | [4-(7,8-dimethoxy-1-methyl-[1,2,4]triazolo[4,3-a]quinoxaline-4-ylamino)-butyl]-carbamic acid ethylester | Mass (M + H$^+$): 403.2; $^1$H NMR (500 MHz, CDCl$_3$): δ1.23 (t, 3H), 1.66 (m, 2H), 1.79 (m, 2H), 3.08 (s, 3H), 3.27 (q, 2H), 3.68 (q, 2H), 3.97 (d, 6H), 4.10 (q, 2H), 4.92 (s, 1H), 6.23 (t, 1H), 7.25 (t, 1H), 7.44 (s, 1H). |
| Example 62 | 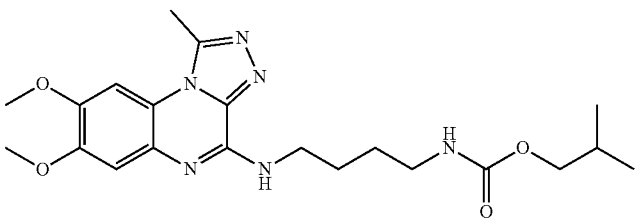 [SMILES: COc1cc2nc(NCCCCNC(=O)OCC(C)C)c3nnc(C)n3c2cc1OC] | [4-(7,8-dimethoxy-1-methyl-[1,2,4]triazolo[4,3-a]quinoxaline-4-ylamino)-butyl]-carbamic acid isobutylester | Mass (M + H$^+$): 431.2; $^1$H NMR (500 MHz, CDCl$_3$): δ0.89 (d, 6H), 1.29 (brs, 1H), 1.66 (m, 2H), 1.77 (m, 2H), 1.78 (m, 2H), 1.85 (m, 1H), 3.10 (s, 3H), 3.26 (q, 2H), 3.63 (q, 2H), 3.82 (d, 2H), 3.97 (d, 6H), 4.88 (brs, 1H), 6.21 (brs, 1H), 7.45 (s, 1H). |
| Example 63 | 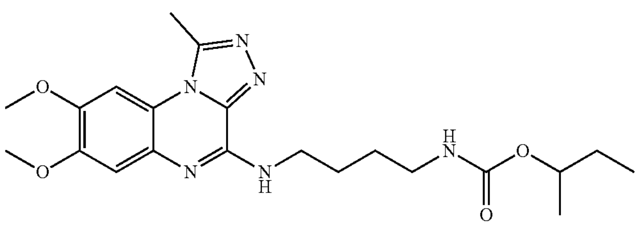 [SMILES: CCC(C)OC(=O)NCCCCNc1nc2cc(OC)c(OC)cc2n2c(C)nnc12] | [4-(7,8-dimethoxy-1-methyl-[1,2,4]triazolo[4,3-a]quinoxaline-4-ylamino)-butyl]-carbamic acid-sec-butylester | Mass (M + H$^+$): 431.2; $^1$H NMR (500 MHz, CDCl$_3$): δ0.79 (t, 3H), 1.07 (d, 3H), 1.42 (m, 4H), 1.60 (m, 2H), 2.97 (q, 2H), 3.03 (s, 3H), 3.47 (q, 2H), 3.82 (s, 3H), 3.87 (s, 3H), 4.53 (m, 1H), 6.96 (t, 1H), 7.10 (s, 1H), 7.52 (s, 1H), 7.82 (t, 1H). |
| Example 64 | 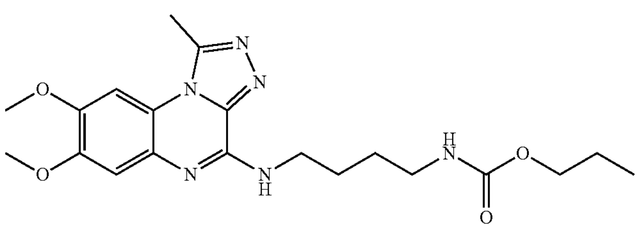 [SMILES: CCCOC(=O)NCCCCNc1nc2cc(OC)c(OC)cc2n2c(C)nnc12] | [4-(7,8-dimethoxy-1-methyl-[1,2,4]triazolo[4,3-a]quinoxaline-4-ylamino)-butyl]-carbamic acid propylester | Mass (M + H$^+$): 417.2; $^1$H NMR (500 MHz, DMSO-d$_6$): δ0.83 (t, 3H), 1.45 (m, 2H), 1.49 (m, 2H), 1.50 (m, 2H), 2.97 (q, 2H), 3.04 (s, 3H), 3.50 (q, 2H), 3.82 (t, 2H), 3.83 (s, 3H), 3.87 (s, 3H), 7.02 (t, 1H), 7.10 (s, 1H), 7.52 (s, 1H), 7.81 (t, 1H). |
| Example 65 | 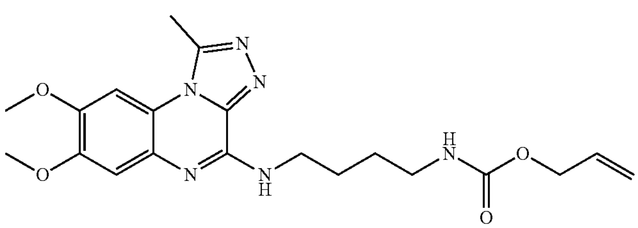 [SMILES: C=CCOC(=O)NCCCCNc1nc2cc(OC)c(OC)cc2n2c(C)nnc12] | [4-(7,8-dimethoxy-1-methyl-[1,2,4]triazolo[4,3-a]quinoxaline-4-ylamino)-butyl]-carbamic acid allylester | Mass (M + H$^+$): 415.2; $^1$H NMR (500 MHz, CDCl$_3$): δ0.87 (m, 1H), 1.68 (m, 1H), 1.79 (m, 2H), 3.10 (s, 1H), 3.29 (q, 2H), 3.70 (q, 2H), 4.10 (d, 6H), 4.55 (d, 2H), 5.01 (brs, 1H), 5.19 (d, 1H), 5.29 (d, 1H), 5.90 (m, 1H), 6.20 (brs, 1H), 7.46 (s, 1H) |

TABLE 5-continued

| Example | Structure | Name | Data |
| --- | --- | --- | --- |
| Example 66 | 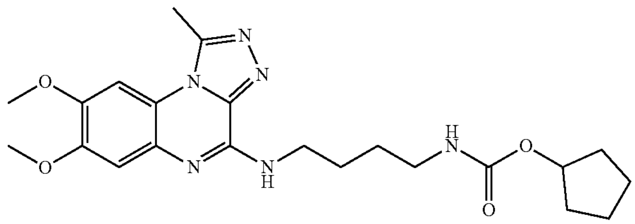 [SMILES: COc1cc2nc(NCCCCNC(=O)OC3CCCC3)c3nnc(C)n3c2cc1OC] | [4-(7,8-dimethoxy-1-methyl-[1,2,4]triazolo[4,3-a]quinoxaline-4-ylamino)-butyl]-carbamic acid cyclopentyl-ester | Mass (M + H$^+$): 443.2; $^1$H NMR (500 MHz, CDCl$_3$): δ1.55 (brs, 2H), 1.65 (m, 6H), 1.78 (m, 4H), 3.08 (s, 3H), 3.25 (q, 2H), 3.69 (q, 2H), 3.97 (d, 6H), 4.79 (brs, 1H), 5.07 (brs, 1H), 6.22 (brs, 1H), 7.22 (s, 1H), 7.44 (s, 1H). |
| Example 67 | 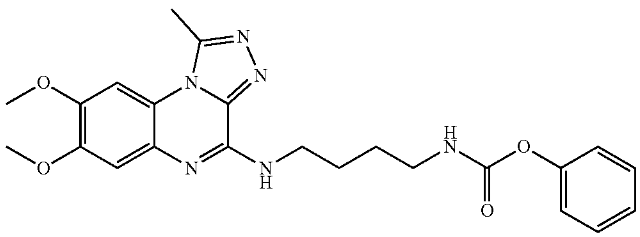 [SMILES: COc1cc2nc(NCCCCNC(=O)Oc3ccccc3)c3nnc(C)n3c2cc1OC] | [4-(7,8-dimethoxy-1-methyl-[1,2,4]triazolo[4,3-a]quinoxaline-4-ylamino)-butyl]-carbamic acid phenylester | Mass (M + H$^+$): 451.2; $^1$H NMR (500 MHz, DMSO-d$_6$): δ1.55 (m, 2H), 1.68 (m, 2H), 3.04 (s, 3H), 3.09 (q, 2H), 3.52 (q, 2H), 3.80 (s, 3H), 3.87 (s, 3H), 7.02 (d, 2H), 7.14 (m, 2H), 7.31 (m, 2H), 7.52 (s, 1H), 7.70 (t, 1H), 7.90 (brs, 1H). |
| Example 68 | 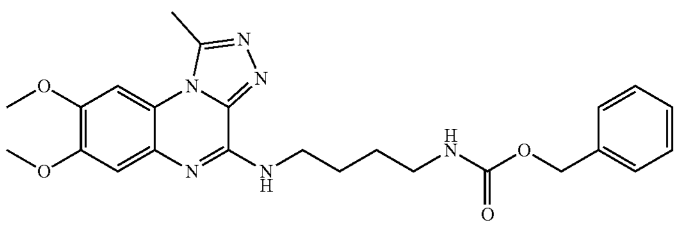 [SMILES: COc1cc2nc(NCCCCNC(=O)OCc3ccccc3)c3nnc(C)n3c2cc1OC] | [4-(7,8-dimethoxy-1-methyl-[1,2,4]triazolo[4,3-a]quinoxaline-4-ylamino)-butyl]-carbamic acid benzylester | Mass (M + H$^+$): 465.2; $^1$H NMR (500 MHz, DMSO-d$_6$): δ1.46 (m, 2H), 1.64 (m, 2H), 3.00 (q, 2H), 3.02 (s, 3H), 3.48 (q, 2H), 3.82 (s, 3H), 3.87 (s, 3H), 4.95 (s, 2H), 7.09 (s, 1H), 7.29 (m, 4H), 7.52 (s, 1H), 9.36 (t, 1H). |
| Example 69 | 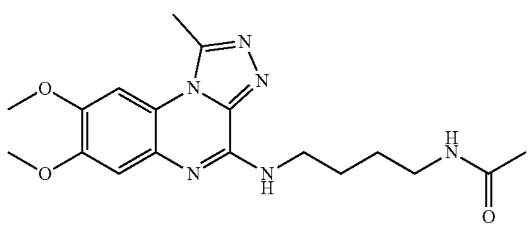 [SMILES: COc1cc2nc(NCCCCNC(C)=O)c3nnc(C)n3c2cc1OC] | N-[4-(7,8-dimethoxy-1-methyl-[1,2,4]triazolo[4,3-a]quinoxaline-4-ylamino)-butyl]-acetamide | Mass (M + H$^+$): 373.2; $^1$H NMR (500 MHz, DMSO-d$_6$): δ1.45 (m, 2H), 1.63 (m, 2H), 1.73 (s, 3H), 3.02 (q, 2H), 3.04 (s, 3H), 3.48 (q, 2H), 3.82 (s, 3H), 3.87 (s, 3H), 7.10 (s, 1H), 7.52 (s, 1H), 7.75 (t, 1H), 7.81 (t, 1H). |
| Example 70 | 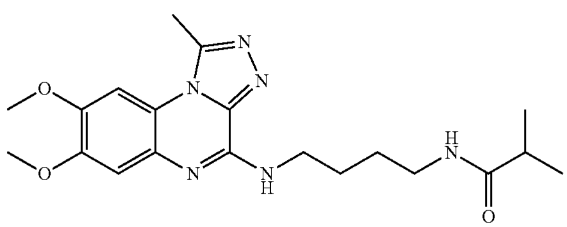 [SMILES: COc1cc2nc(NCCCCNC(=O)C(C)C)c3nnc(C)n3c2cc1OC] | N-[4-(7,8-dimethoxy-1-methyl-[1,2,4]triazolo[4,3-a]quinoxaline-4-ylamino)-butyl]-isobutyramide | Mass (M + H$^+$): 400.47; $^1$H NMR (500 MHz, DMSO-d$_6$): δ0.93 (d, 6H), 1.45 (m, 2H), 1.61 (m, 2H), 2.27 (m, 1H), 3.02 (s, 3H), 3.03 (q, 2H), 3.48 (q, 2H), 3.82 (s, 3H), 3.87 (s, 3H), 7.09 (s, 1H), 7.51 (s, 1H), 7.63 (t, 1H), 7.81 (t, 1H). |
| Example 71 | 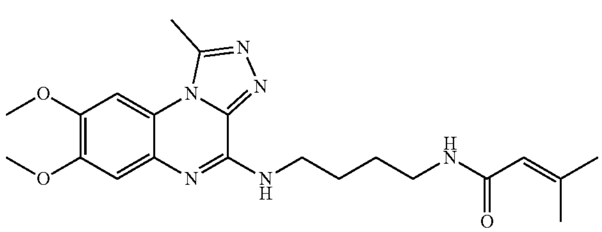 [SMILES: COc1cc2nc(NCCCCNC(=O)C=C(C)C)c3nnc(C)n3c2cc1OC] | 3-methyl-butene-2-oic acid-[4-(7,8-dimethoxy-1-methyl-[1,2,4]triazolo[4,3-a]quinoxaline-4-ylamino)-butyl]-amide | Mass (M + H$^+$): 413.2; $^1$H NMR (500 MHz, DMSO-d$_6$): δ1.45 (m, 2H), 1.62 (m, 2H), 2.01 (s, 2H), 2.39 (s, 6H), 3.03 (q, 2H), 3.05 (s, 3H), 3.47 (q, 2H), 3.81 (s, 3H), 3.87 (s, 3H), 7.10 (s, 1H), 7.52 (s, 1H), 7.65 (t, 1H), 7.81 (t, 1H). |

TABLE 5-continued

| Example | Structure | Name | Data |
|---|---|---|---|
| Example 72 | 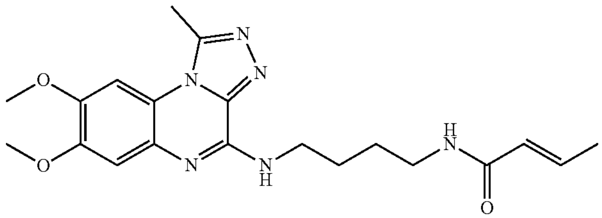 [SMILES: C/C=C/C(=O)NCCCCNc1nc2cc(OC)c(OC)cc2n2c(C)nnc12] | butene-2-oic acid-[4-(7,8-dimethoxy-1-methyl-[1,2,4]triazolo[4,3-a]quinoxaline-4-ylamino)-butyl]-amide | Mass (M + H$^+$): 399.2; $^1$H NMR (500 MHz, DMSO-d$_6$): δ1.44 (m, 2H), 1.62 (m, 2H), 2.46 (d, 3H), 2.82 (d, 1H), 3.04 (q, 2H), 3.05 (s, 3H), 3.48 (q, 2H), 3.82 (s, 3H), 3.87 (s, 3H), 5.04 (m, 1H), 7.10 (s, 1H), 7.52 (s, 1H), 7.77 (t, 1H), 7.81 (t, 1H). |
| Example 73 | 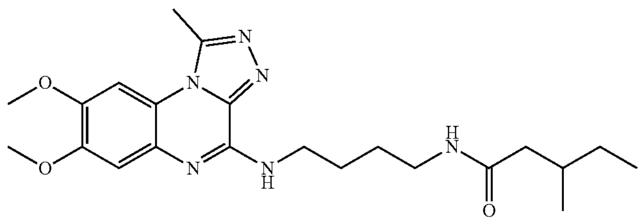 [SMILES: CCC(C)CC(=O)NCCCCNc1nc2cc(OC)c(OC)cc2n2c(C)nnc12] | 3-methyl-pentanoic acid-[4-(7,8-dimethoxy-1-methyl-[1,2,4]triazolo[4,3-a]quinoxaline-4-ylamino)-butyl]-amide | Mass (M + H$^+$): 429.2; $^1$H NMR (500 MHz, DMSO-d$_6$): δ0.7 6 (m, 6H), 1.06 (m, 1H), 1.23 (m, 1H), 1.43 (m, 2H), 1.62 (m, 2H), 1.76 (m, 1H), 1.79 (m, 1H), 1.97 (m, H), 3.04 (q, 2H), 3.06 (s, 3H), 3.48 (q, 2H), 3.82 (s, 3H), 3.87 (s, 3H), 7.10 (s, 1H), 7.52 (s, 1H), 7.08 (t, 1H), 7.81 (t, 1H). |
| Example 74 | 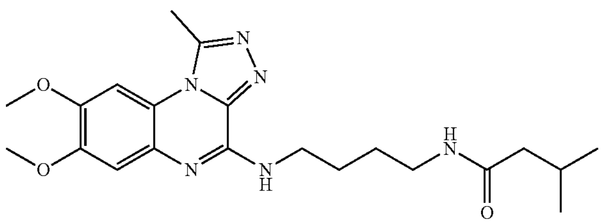 [SMILES: COc1cc2nc(NCCCCNC(=O)CC(C)C)c3nnc(C)n3c2cc1OC] | N-[4-(7,8-dimethoxy-1-methyl-[1,2,4]triazolo[4,3-a]quinoxaline-4-ylamino)-butyl]-3-methyl-butyramide | Mass (M + H$^+$): 415.3; $^1$H NMR (500 MHz, CDCl$_3$): δ0.93 (d, 6H), 1.58 (d, 2H), 1.66 (m, 2H), 1.80 (m, 2H), 2.09 (q, 2H), 2.10 (m, 1H), 3.11 (s, 3H), 3.36 (q, 2H), 3.71 (d, 1H), 3.99 (s, 6H), 5.50 (t, 1H), 6.15 (t, 1H), 7.47 (s, 1H). |
| Example 75 | 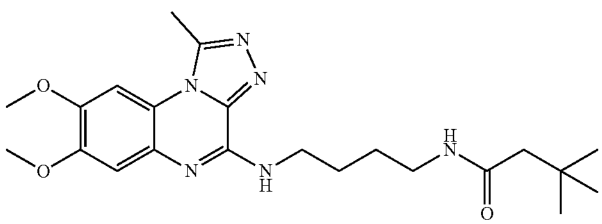 [SMILES: COc1cc2nc(NCCCCNC(=O)CC(C)(C)C)c3nnc(C)n3c2cc1OC] | N-[4-(7,8-dimethoxy-1-methyl-[1,2,4]triazolo[4,3-a]quinoxaline-4-ylamino)-butyl]-3,3-dimethyl-butyramide | Mass (M + H'): 429.3; $^1$H NMR (500 MHz, DMSO-d$_6$): δ0.88 (s, 9H), 1.44 (m, 2H), 1.62 (m, 2H), 1.88 (s, 2H), 3.02 (s, 3H), 3.05 (q, 2H), 3.48 (q, 2H), 3.82 (s, 3H), 3.87 (s, 3H), 7.09 (s, 1H), 7.51 (s, 1H), 7.64 (t, 1H), 7.81 (t, 1H). |
| Example 76 | 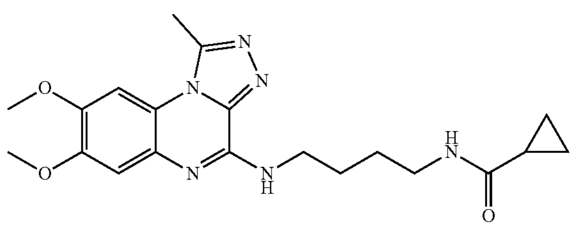 [SMILES: COc1cc2nc(NCCCCNC(=O)C3CC3)c3nnc(C)n3c2cc1OC] | cyclopropane-carboxylic acid-[4-(7,8-dimethoxy-1-methyl-[1,2,4]triazolo[4,3-a]quinoxaline-4-ylamino)-butyl]-amide | Mass (M + H$^+$): 399.0; $^1$H NMR (500 MHz, DMSO-d$_6$): δ0.55 (t, 2H), 0.60 (t, 2H), 1.45 (m, 1H), 1.46 (m, 2H), 1.65 (m, 2H), 3.03 (s, 3H), 3.06 (q, 2H), 3.49 (q, 3H), 3.82 (s, 3H), 3.87 (s, 3H), 7.10 (s, 1H), 7.52 (s, 1H), 7.81 (t, 1H), 7.97 (t, 1H). |
| Example 77 | 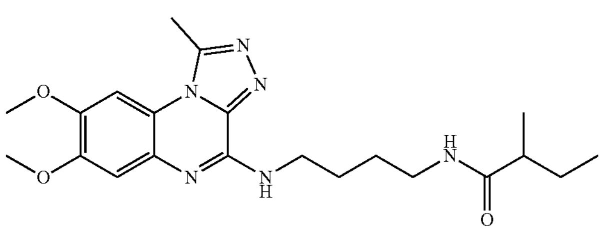 [SMILES: CCC(C)C(=O)NCCCCNc1nc2cc(OC)c(OC)cc2n2c(C)nnc12] | N-[4-(7,8-dimethoxy-1-methyl-[1,2,4]triazolo[4,3-a]quinoxaline-4-ylamino)-butyl]-2-methyl-butyramide | Mass (M + H$^+$): 415.2; $^1$H NMR (500 MHz, CDCl$_3$): δ0.88 (t, 3H), 1.11 (d, 3H), 1.40 (m, 1H), 1.66 (m, 3H), 1.78 (m, 2H), 2.07 (m, 1H), 3.09 (s, 3H), 3.35 (q, 2H), 3.62 (brs, 2H), 3.97 (d, 2H), 5.64 (brs, 1H), 6.25 (brs, 1H), 7.25 (s, 1H), 7.44 (s, 1H). |

TABLE 5-continued

| Example | Structure | Name | Data |
|---|---|---|---|
| Example 78 | 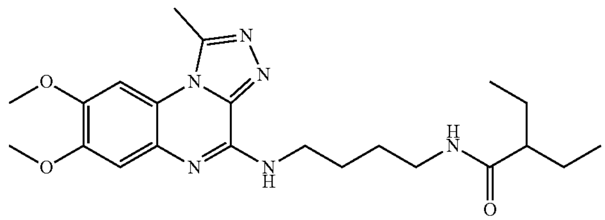 [SMILES: CCC(CC)C(=O)NCCCCNc1nc2cc(OC)c(OC)cc2n2c(C)nnc12] | N-[4-(7,8-dimethoxy-1-methyl-[1,2,4]triazolo[4,3-a]quinoxaline-4-ylamino)-butyl]-2-ethyl-butyramide | Mass (M + H⁺): 429.2; ¹H NMR (500 MHz, CDCl₃): δ0.88 (m, 6H), 1.45 (m, 2H), 1.79 (m, 2H), 3.08 (s, 3H), 3.36 (q, 2H), 3.69 (d, 2H), 3.97 (d, 6H), 5.65 (brs, 1H), 6.25 (brs, 1H), 7.22 (s, 1H), 7.52 (s, 1H). |
| Example 79 | 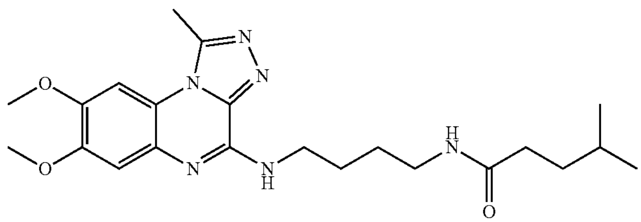 | 4-methyl-pentanoic acid [4-(7,8-dimethoxy-1-methyl-[1,2,4]triazolo[4,3-a]quinoxaline-4-ylamino)-butyl]-amide | Mass (M + H⁺): 429.2; ¹H NMR (500 MHz, DMSO-d₆): δ0.79 (d, 6H), 1.32 (m, 2H), 1.40 (m, 3H), 1.75 (m, 2H), 1.99 (m, 2H), 3.03 (q, 2H), 3.08 (s, 3H), 3.47 (q, 2H), 3.82 (s, 3H), 3.87 (s, 3H), 7.10 (s, 1H), 7.52 (s, 1H), 7.71 (t, 1H), 7.82 (t, 1H). |
| Example 80 | 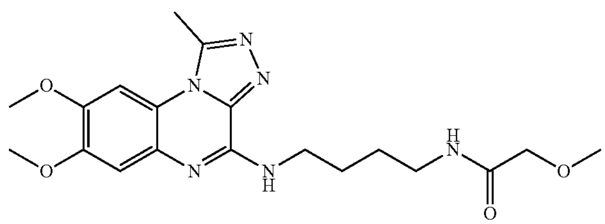 | N-[4-(7,8-dimethoxy-1-methyl-[1,2,4]triazolo[4,3-a]quinoxaline-4-ylamino)-butyl]-2-methoxy-acetamide | Mass (M + H⁺): 403.2; ¹H NMR (500 MHz, CDCl₃): δ1.69 (brs, 2H), 1.70 (m, 2H), 1.80 (m, 2H), 3.10 (s, 3H), 3.36 (q, 2H), 3.93 (s, 3H), 3.71 (brs, 1H), 3.88 (s, 2H), 3.99 (d, 6H), 6.60 (brs, 1H), 6.60 (brs, 1H), 7.47 (s, 1H). |
| Example 81 | 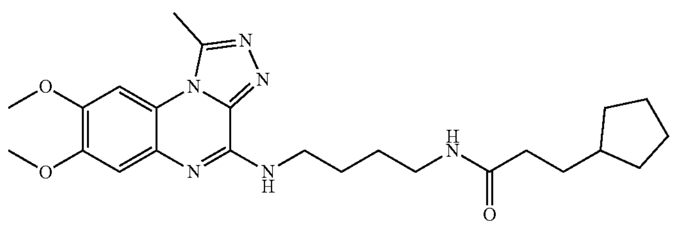 [SMILES: COc1cc2nc(NCCCCNC(=O)CCC3CCCC3)c3nnc(C)n3c2cc1OC] | 3-cyclopentyl-N-[4-(7,8-dimethoxy-1-methyl-[1,2,4]triazolo[4,3-a]quinoxaline-4-ylamino)-butyl]-propionamide | Mass (M + H1): 455.3; ¹H NMR (500 MHz, DMSO-d₆): δ1.03 (m, 2H), 1.42 (m, 2H), 1.45 (m, 8H), 1.63 (m, 2H), 2.01 (m, 2H), 2.20 (m, 1H), 3.03 (q, 2H), 3.05 (s, 3H), 3.48 (q, 2H), 3.82 (s, 3H), 3.87 (s, 3H), 7.10 (s, 1H), 7.51 (s, 1H), 7.69 (t, 1H), 7.81 (t, 1H). |
| Example 82 | 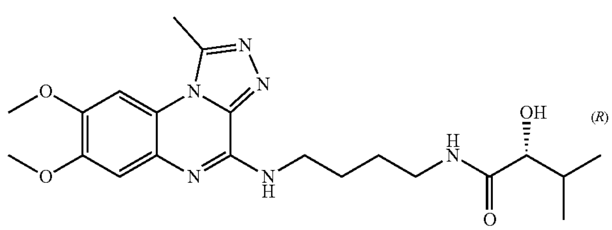 | N-[4-(7,8-dimethoxy-1-methyl-[1,2,4]triazolo[4,3-a]quinoxaline-4-ylamino)-butyl]-2-(R)-hydroxy-3-methyl-butyramide | Mass (M + H⁺): 431.2; NMR (500 MHz, DMSO-d₆): δ0.69 (d, 3H), 0.82 (d, 3H), 1.23 (m, 1H), 1.48 (m, 2H), 1.61 (m, 2H), 1.90 (m, 1H), 3.03 (s, 3H), 3.13 (q, 2H), 3.48 (q, 2H), 3.60 (s, 1H), 3.82 (s, 3H), 3.90 (s, 3H), 5.23 (brs, 1H), 7.10 (s, 1H), 7.51 (s, 1H), 7.65 (t, 1H), 7.83 (t, 1H). |
| Example 83 | 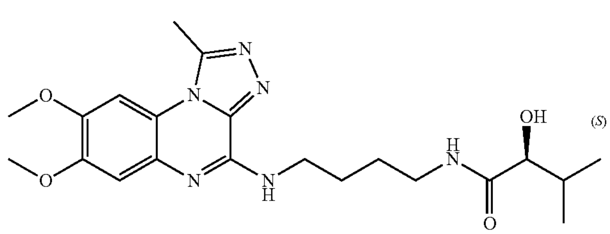 | N-[4-(7,8-dimethoxy-1-methyl-[1,2,4]triazolo[4,3-a]quinoxaline-4-ylamino)-butyl]-2-(S)-hydroxy-3-methyl-butyramide | Mass (M + H⁺): 431.2; ¹H NMR (500 MHz, DMSO-d₆): δ0.69 (d, 3H), 0.82 (d, 3H), 1.23 (m, 1H), 1.48 (m, 2H), 1.61 (m, 2H), 1.90 (m, 1H), 3.03 (s, 3H), 3.13 (q, 2H), 3.48 (q, 2H), 3.60 (s, 1H), 3.82 (s, 3H), 3.90 (s, 3H), 5.23 (brs, 1H), 7.10 (s, 1H), 7.51 (s, 1H), 7.65 (t, 1H), 7.83 (t, 1H). |

TABLE 5-continued

| Example | Structure | Name | Data |
|---|---|---|---|
| Example 84 | 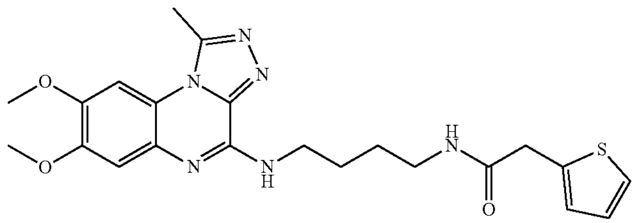 | N-[4-(7,8-dimethoxy-1-methyl-[1,2,4]triazolo[4,3-a]quinoxaline-4-ylamino)-butyl]-2-thiophene-2-yl-acetamide | Mass (M + H$^+$): 455.2; $^1$H NMR (500 MHz, CDCl$_3$): δ1.61 (m, 2H), 1.80 (m, 2H), 3.10 (s, 3H), 3.30 (m, 2H), 3.70 (brs, 2H), 3.77 (s, 2H), 4.01 (d, 6H), 5.76 (brs, 1H), 6.20 (brs, 2H), 6.95 (s, 1H), 6.95 (d, 1H), 7.20 (d, 1H), 7.47 (s, 1H), 7.69 (t, 1H), 7.81 (t, 1H). |
| Example 85 | 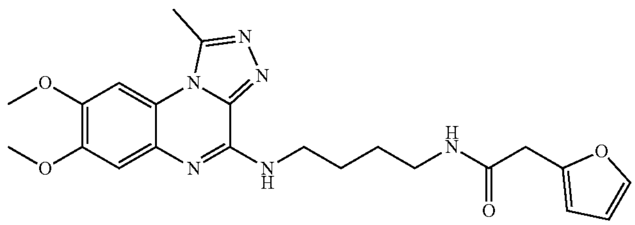 | N-[4-(7,8-dimethoxy-1-methyl-[1,2,4]triazolo[4,3-a]quinoxaline-4-ylamino)-butyl]-2-furan-2-yl-acetamide | Mass (M + H$^+$): 439.2; $^1$H NMR (500 MHz, DMSO-d$_6$): δ1.4 8 (m, 2H), 1.63 (m, 2H), 3.04 (s, 3H), 3.08 (m, 2H), 3.41 (s, 2H), 3.48 (q, 2H), 3.82 (s, 3H), 3.87 (s, 3H), 6.11 (d, 1H), 6.29 (s, 1H), 7.10 (s, 1H), 7.46 (d, 1H), 7.52 (s, 1H), 7.83 (t, 1H), 7.95 (t, 1H). |
| Example 86 | 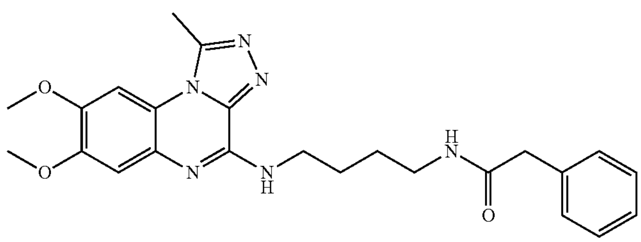 | N-[4-(7,8-dimethoxy-1-methyl-[1,2,4]triazolo[4,3-a]quinoxaline-4-ylamino)-butyl]-2-phenyl-acetamide | Mass (M + H$^+$): 449.2; $^1$H NMR (500 MHz, DMSO-d$_6$): δ1.47 (m, 2H), 1.62 (m, 2H), 3.04 (g, 2H), 3.06 (s, 3H), 3.27 (s, 2H), 3.47 (q, 2H), 3.81 (s, 3H), 3.87 (s, 3H), 7.10 (s, 1H), 7.20 (m, 5H), 7.52 (s, 1H), 7.81 (t, 1H), 7.98 (t, 1H). |
| Example 87 | 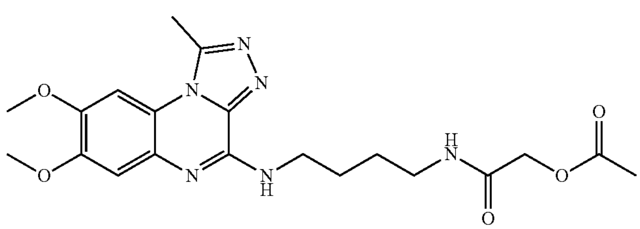 [SMILES: COc1cc2nc(NCCCCNC(=O)COC(C)=O)c3nnc(C)n3c2cc1OC] | acetic acid-[4-(7,8-dimethoxy-1-methyl-[1,2,4]triazolo[4,3-a]quinoxaline-4-ylamino)-butyl]-carbamoyl]-methylester | Mass (M + H$^+$): 431.2; $^1$H NMR (500 MHz, DMSO-d$_6$): δ1.70 (m, 2H), 1.77 (m, 2H), 2.14 (s, 3H), 3.06 (s, 3H), 3.39 (q, 2H), 3.67 (q, 2H), 3.95 (d, 6H), 4.53 (s, 2H), 6.31 (brs, 1H), 6.45 (brs, 1H), 7.19 (s, 1H), 7.38 (s, 1H). |
| Example 88 | 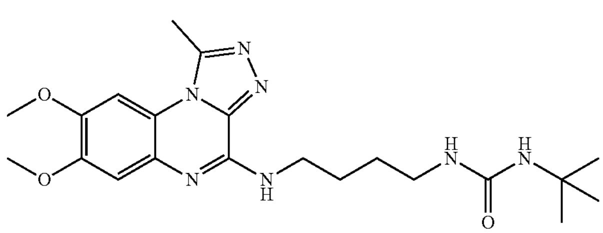 [SMILES: COc1cc2nc(NCCCCNC(=O)NC(C)(C)C)c3nnc(C)n3c2cc1OC] | 1-tert-butyl-3-[4-(7,8-dimethoxy-1-methyl-[1,2,4]triazolo[4,3-a]quinoxaline-4-ylamino)-butyl]-urea | Mass (M + H$^+$): 430.2; $^1$H NMR (500 MHz, DMSO-d$_6$): δ1.15 (s, 9H), 1.40 (m, 2H), 1.60 (m, 2H), 2.95 (q, 2H), 3.03 (s, 3H), 3.48 (q, 2H), 3.82 (s, 3H), 3.87 (s, 3H), 5.48 (s, 1H), 5.57 (t, 1H), 7.10 (s, 1H), 7.52 (s, 1H), 7.82 (t, 1H). |

TABLE 5-continued

| Example | Structure | Name | Data |
|---|---|---|---|
| Example 89 | 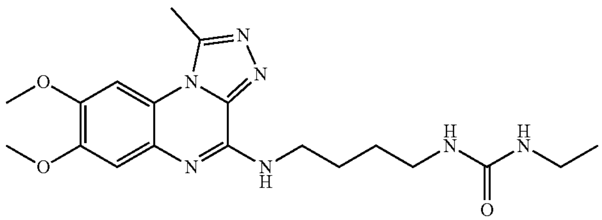 [SMILES: CCNC(=O)NCCCCNc1nc2cc(OC)c(OC)cc2n2c(C)nnc12] | 1-[4-(7,8-dimethoxy-1-methyl-[1,2,4]triazolo[4,3-a]quinoxaline-4-ylamino)-butyl]-3-ethyl-urea | Mass (M + H$^+$): 402.2; $^1$H NMR (500 MHz, DMSO-d$_6$): δ0.93 (t, 3H), 1.42 (m, 2H), 1.60 (m, 2H), 2.93 (q, 2H), 2.94 (q, 2H), 3.03 (s, 3H), 3.48 (q, 2H), 3.82 (s, 3H), 3.87 (s, 3H), 5.65 (t, 1H), 5.73 (t, 1H), 7.10 (s, 1H), 7.52 (s, 1H), 7.81 (t, 1H). |
| Example 90 | 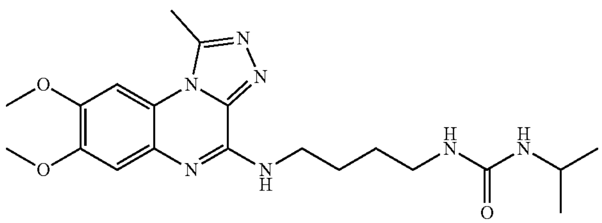 [SMILES: COc1cc2nc(NCCCCNC(=O)NC(C)C)c3nnc(C)n3c2cc1OC] | 1-[4-(7,8-dimethoxy-1-methyl-[1,2,4]triazolo[4,3-a]quinoxaline-4-ylamino)-3-isopropylurea | Mass (M + H$^+$): 416.2; $^1$H NMR (500 MHz, DMSO-d$_6$): δ0.96 (d, 6H), 1.40 (m, 2H), 1.60 (m, 2H), 2.98 (q, 2H), 3.03 (s, 3H), 3.48 (q, 2H), 3.58 (m, 1H), 3.82 (s, 3H), 3.87 (s, 3H), 5.51 (d, 1H), 5.62 (t, 1H), 7.11 (s, 1H), 7.52 (s, 1H), 7.81 (t, 1H). |
| Example 91 | 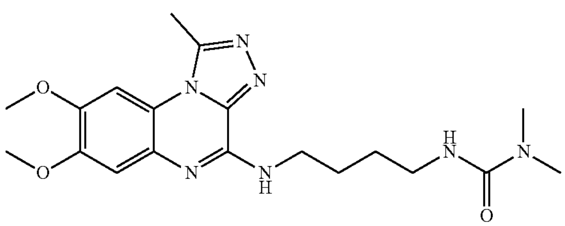 | 3-[4-(7,8-dimethoxy-1-methyl-[1,2,4]triazolo[4,3-a]quinoxaline-4-ylamino)-butyl]-1,1-dimethyl-urea | Mass (M + H$^+$): 402.2; $^1$H NMR (500 MHz, DMSO-d$_6$): δ1.45 (m, 2H), 1.60 (m, 2H), 2.71 (s, 6H), 2.99 (q, 2H), 3.03 (s, 3H), 3.48 (q, 2H), 3.82 (s, 3H), 3.86 (s, 3H), 6.18 (t, 1H), 7.10 (s, 1H), 7.51 (s, 1H), 7.79 (t, 1H). |
| Example 92 | 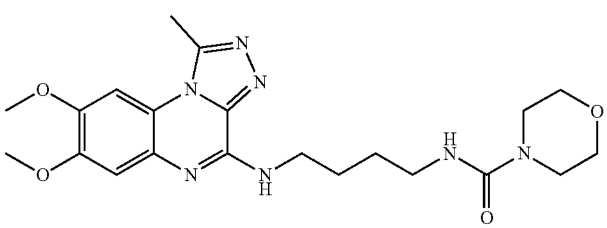 [SMILES: COc1cc2nc(NCCCCNC(=O)N3CCOCC3)c3nnc(C)n3c2cc1OC] | morpholine-4-carboxylic acid-[4-(7,8-dimethoxy-1-methyl-[1,2,4]triazolo[4,3-a]quinoxaline-4-ylamino)-butyl]-amide | Mass (M + H$^+$): 444.2; $^1$H NMR (500 MHz, DMSO-d$_6$): δ1.46 (m, 2H), 1.61 (m, 2H), 3.03 (q, 2H), 3.09 (s, 3H), 3.27 (m, 4H), 3.46 (m, 4H), 3.47 (q, 2H), 3.82 (s, 3H), 3.87 (s, 3H), 6.45 (t, 1H), 7.10 (s, 1H), 7.52 (s, 1H), 7.79 (t, 1H). |
| Example 93 | 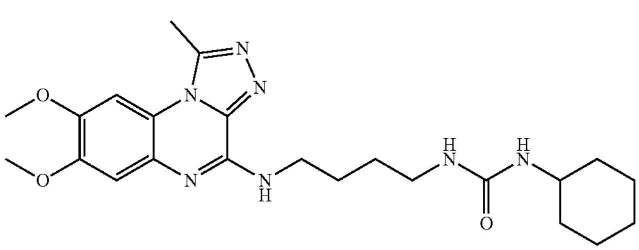 [SMILES: COc1cc2nc(NCCCCNC(=O)NC3CCCCC3)c3nnc(C)n3c2cc1OC] | 1-cyclohexyl-3-[4-(7,8-dimethoxy-1-methyl-[1,2,4]triazolo[4,3-a]quinoxaline-4-ylamino)-butyl]-urea | Mass (M + H$^+$): 456.3; $^1$H NMR (500 MHz, DMSO-d$_6$): δ1.01 (m, 3H), 1.25 (m, 2H), 1.41 (m, 2H), 1.45 (m, 1H), 1.60 (m, 5H), 1.66 (m, 2H), 2.97 (q, 2H), 3.03 (s, 3H), 3.48 (q, 2H), 3.82 (s, 3H), 3.87 (s, 3H), 5.57 (d, 1H), 5.63 (t, 1H) 7.10 (s, 1H), 7.51 (s, 1H), 7.82 (t, 1H). |

TABLE 5-continued

| Example | Name | Data |
|---|---|---|
| Example 94 | 1-4-7,8-dimethoxy-1-methyl-[1,2,4]triazolo[4,3-a]quinoxaline-4-ylamino)-butyl]-3-phenyl-urea | Mass (M + H$^+$): 450.2; $^1$H NMR (500 MHz, DMSO-d$_6$): δ1.50 (m, 2H), 1.66 (m, 2H), 3.03 (s, 3H), 3.10 (q, 2H), 3.51 (q, 2H), 3.81 (s, 3H), 3.87 (s, 3H), 6.08 (t, 1H), 6.84 (m, 1H), 7.10 (s, 1H), 7.15 (m, 2H), 7.31 (m, 2H), 7.52 (s, 1H) 7.85 (t, 1H), 8.32 (s, 1H). |
| Example 95 | N-[4-(7,8-dimethoxy-1-methyl-[1,2,4]triazolo[4,3-a]quinoxaline-4-ylamino)-butyl]-benzamide | Mass (M + H$^+$): 435.2; $^1$H NMR (500 MHz, DMSO-d$_6$): δ1.56 (m, 2H), 1.64 (m, 2H), 3.03 (s, 3H), 3.20 (q, 2H), 3.49 (q, 2H), 3.82 (s, 3H), 3.87 (s, 3H), 7.09 (s, 1H), 7.46 (s, 1H), 7.52 (m, 1H), 7.64 (m, 2H), 7.72 (t, 1H), 7.90 (m, 2H), 9.37 (t, 1H). |
| Example 96 | 4-tert-butyl-N-[4-(7,8-dimethoxy-1-methyl-[1,2,4]triazolo[4,3-a]quinoxaline-4-ylamino)-butyl]-benzamide | Mass (M + H$^+$): 435.2; $^1$H NMR (500 MHz, DMSO-d$_6$): δ1.56 (m, 2H), 1.64 (m, 2H), 3.03 (s, 3H), 3.20 (q, 2H), 3.49 (q-2H), 3.82 is, 3H), 3.87 (s, 3H), 7.09 (s, 1H), 7.46 (s, 1H), 7.52 (m, 1H), 7.64 (m, 2H), 7.72 (t, 1H), 7.90 (m, 2H), 9.37 (t, 1H). |
| Example 97 | N-[4-(7,8-dimethoxy-1-methyl-[1,2,4]triazolo[4,3-a]quinoxaline-4-ylamino)-butyl]-2-methoxy-benzamide | Mass (M + H$^+$): 491.3; $^1$H NMR (500 MHz, DMSO-d$_6$): δ1.23 (s, 9H), 1.57 (m, 2H), 1.67 (m, 2H), 3.02 (s, 3H), 3.26 (q, 2H), 3.50 (q, 2H), 3.79 (s, 3H), 3.86 (s, 3H), 7.08 (s, 1H), 7.39 (q, 2H), 7.50 (s, 1H), 7.70 (q, 2H), 7.82 (t, 1H), 8.31 (t, 1H). |
| Example 98 | N-[4-(7,8-dimethoxy-1-methyl-[1,2,4]triazolo[4,3-a]quinoxaline-4-ylamino)-butyl]-4-fluoro-benzamide | Mass (M + H$^+$): 453.2; $^1$H NMR (500 MHz, DMSO-d$_6$): δ1.59 (m, 2H), 1.68 (m, 2H), 3.03 (s, 3H), 3.26 (q, 2H), 3.51 (q, 2H), 3.80 (s, 3H), 3.86 (s, 3H), 7.08 (s, 1H), 7.23 (m, 2H), 7.51 (s, 1H), 7.84 (m, 3H), 8.43 (t, 1H). |

TABLE 5-continued

| Example | Name | Data |
|---|---|---|
| Example 99 | 2-chloro-N-[4-(7,8-dimethoxy-1-methyl-[1,2,4]triazolo[4,3-a]quinoxaline-4-ylamino)-butyl]-benzamide | Mass (M + H$^+$): 469.2; $^1$H NMR (DMSO-d$_6$): δ1.58 (m, 2H), 1.73 (m, 2H), 3.04 (s, 3H), 3.23 (q, 2H), 3.52 (q, 2H), 3.81 (s, 3H), 3.87 (s, 3H), 7.11 (s, 1H), 7.38 (m, 4H), 7.52 (s, 1H), 7.85 (t, 1H), 8.36 (t, 3H). |
| Example 100 | 4-chloro-N-[4-(7,8-dimethoxy-1-methyl-[1,2,4]triazolo[4,3-a]quinoxaline-4-ylamino)-butyl]-benzamide | Mass (M + H$^+$): 469.2; $^1$H NMR (500 MHz, DMSO-d$_6$): δ1.58 (m, 2H), 1.68 (m, 2H), 3.03 (s, 3H), 3.27 (q, 2H), 3.51 (q, 2H), 3.80 (s, 3H), 3.87 (s, 3H), 7.08 (s, 1H), 7.45 (m, 2H), 7.47 (s, 1H), 7.78 (m, 2H), 7.80 (t, 1H), 8.48 (t, 1H). |
| Example 101 | N-[4-(7,8-dimethoxy-1-methyl-[1,2,4]triazolo[4,3-a]quinoxaline-4-ylamino)-butyl]-4-nitro-benzamide | Mass (M + H$^+$): 480.2; $^1$H NMR (500 MHz, DMSO-d$_6$): δ1.62 (m, 2H), 1.70 (m, 2H), 3.03 (s, 3H), 3.31 (q, 2H), 3.55 (q, 2H), 3.80 (s, 3H), 3.86 (s, 3H), 7.08 (s, 1H), 7.52 (s, 1H), 7.80 (t, 1H), 8.00 (q, 2H), 8.24 (q, 2H), 8.74 (t, 1H). |
| Example 102 | 2,3-dichloro-N-[4-(7,8-dimethoxy-1-methyl-[1,2,4]triazolo[4,3-a]quinoxaline-4-ylamino)-butyl]-benzamide | Mass (M + H$^+$): 504.1; $^1$H NMR (500 MHz, DMSO-d$_6$): δ1.57 (m, 2H), 1.72 (m, 2H), 3.04 (s, 3H), 3.24 (q, 2H), 3.52 (q, 2H), 3.81 (s, 3H), 3.87 (s, 3H), 7.10 (d, 1H), 7.33 (m, 2H), 7.52 (s, 1H), 7.62 (d, 1H), 7.86 (t, 1H), 8.46 (t, 1H). |
| Example 103 | N-[4-(7,8-dimethoxy-1-methyl-[1,2,4]triazolo[4,3-a]quinoxaline-4-ylamino)-butyl]-isonicotinamide | Mass (M + H$^+$): 436.2; $^1$H NMR (500 MHz, CDCl$_3$): δ1.81 (m, 2H), 1.85 (m, 2H), 3.06 (s, 3H), 3.58 (q, 2H), 3.71 (q, 2H), 3.90 (s, 3H), 3.95 (s, 3H), 6.24 (t, 1H), 6.83 (m, 1H), 7.14 (s, 1H), 7.40 (s, 1H), 7.60 (d, 1H), 8.67 (d, 1H). |
| Example 104 | N-[4-(7,8-dimethoxy-1-methyl-[1,2,4]triazolo[4,3-a]quinoxaline-4-ylamino)-butyl]-nicotinamide | Mass (M + H$^+$): 436.2; $^1$H NMR (500 MHz, DMSO-d$_6$): δ1.61 (m, 2H), 1.70 (m, 2H), 3.04 (s, 3H), 3.29 (q, 2H), 3.51 (q, 2H), 3.81 (s, 3H), 3.87 (s, 3H), 7.09 (s, 1H), 7.44 (m, 1H), 7.52 (s, 1H), |

TABLE 5-continued

| Example | Structure | Name | Data |
|---|---|---|---|
| | | | 7.86 (t, 1H), 8.12 (d, 1H), 8.63 (t, 1H), 8.64 (d, 1H), 8.93 (s, 1H). |
| Example 105 | 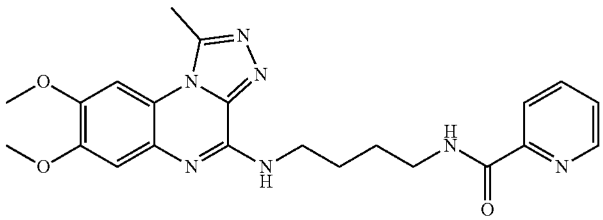 [SMILES: COc1cc2nc(NCCCCNC(=O)c3ccccn3)c3nnc(C)n3c2cc1OC] | pyridine-2-carboxylic acid-[4-(7,8-dimethoxy-1-methyl-[1,2,4]triazolo[4,3-a]quinoxaline-4-ylamino)-butyl]-amide | Mass (M + H$^+$): 436.2; $^1$H NMR (500 MHz, DMSO-d$_6$): δ1.59 (m, 2H), 1.65 (m, 2H), 3.03 (s, 3H), 3.31 (q, 2H), 3.50 (q, 2H), 3.80 (s, 3H), 3.87 (s, 3H), 7.09 (s, 1H), 7.51 (s, 1H), 7.52 (m, 1H), 7.85 (t, 1H), 7.96 (m, 2H), 8.56 (d, 1H), 8.75 (t, 1H). |
| Example 106 | 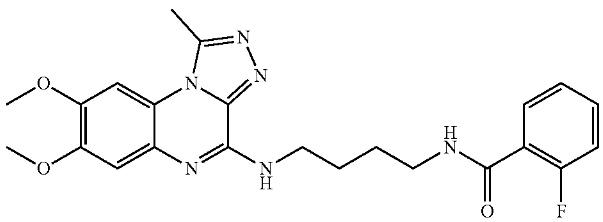 [SMILES: COc1cc2nc(NCCCCNC(=O)c3ccccc3F)c3nnc(C)n3c2cc1OC] | N-[4-(7,8-dimethoxy-1-methyl-[1,2,4]triazolo[4,3-a]quinoxaline-4-ylamino)-butyl]-2-fluoro-benzamide | Mass (M + H$^+$): 453.2, $^1$H NMR (500 MHz, DMSO-d$_6$): δ1.58 (m, 2H), 1.69 (m, 2H), 3.04 (s, 3H), 3.31 (q, 2H), 3.81 (s, 3H), 3.87 (s, 3H), 4.17 (m, 2H), 7.10 (s, 1H), 7.19 (m, 1H), 7.21 (s, 1H), 7.45 (m, 1H), 7.52 (d, 1H), 7.63 (m, 1H), 7.85 (t, 1H), 8.25 (t, 1H). |
| Example 107 | 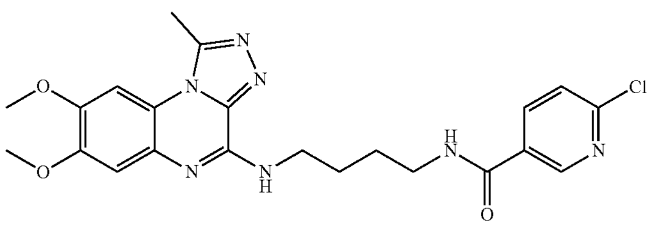 [SMILES: COc1cc2nc(NCCCCNC(=O)c3ccc(Cl)nc3)c3nnc(C)n3c2cc1OC] | 6-chloro-N-[4-(7,8-dimethoxy-1-methyl-[1,2,4]triazolo[4,3-a]quinoxaline-4-ylamino)-butyl]-nicotinamide | Mass (M + H$^+$): 470.0; $^1$H NMR (500 MHz, DMSO-d$_6$): δ1.60 (m, 2H), 1.70 (m, 2H), 3.03 (s, 3H), 3.30 (q, 2H), 3.52 (q, 2H), 3.81 (s, 3H), 3.87 (s, 3H), 7.07 (s, 1H), 7.51 (s, 1H), 7.57 (d, 1H), 7.82 (t, 1H), 8.15 (d, 1H), 8.66 (t, 1H), 8.76 (s, 1H). |
| Example 108 | 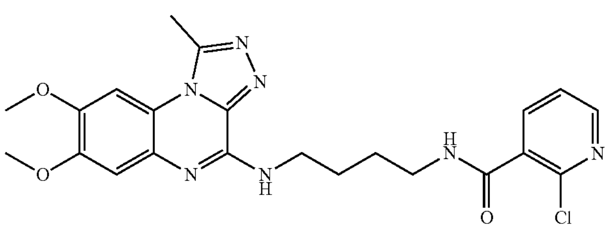 | 2-chloro-N-[4-(7,8-dimethoxy-1-methyl-[1,2,4]triazolo[4,3-a]quinoxaline-4-ylamino)-butyl]-6-methyl-nicotinamide | Mass (M + H$^+$): 484.2; $^1$H NMR (500 MHz, DMSO-d$_6$): δ1.58 (m, 2H), 1.71 (m, 2H), 2.46 (s, 3H), 3.04 (s, 3H), 3.28 (q, 2H), 3.81 (s, 3H), 3.87 (s, 3H), 7.10 (s, 1H), 7.25 (d, 1H), 7.52 (s, 1H), 7.69 (d, 1H), 7.85 (t, 1H), 8.44 (t, 1H). |
| Example 109 | 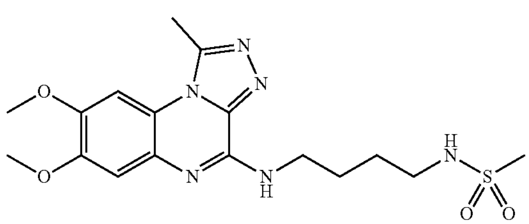 | N-[4-(7,8-dimethoxy-1-methyl-[1,2,4]triazolo[4,3-a]quinoxaline-4-ylamino)-butyl]-methanesulfonamide | Mass (M + H$^+$): 409.2; $^1$H NMR (500 MHz, DMSO-d$_6$): δ1.53 (m, 2H), 1.66 (m, 2H), 2.84 (s, 3H), 2.96 (q, 2H), 3.02 (s, 3H), 3.48 (q, 2H), 3.82 (s, 3H), 3.86 (s, 3H), 6.91 (t, 1H), 7.48 (s, 1H), 7.82 (t, 1H). |

TABLE 5-continued

| Example | Structure | Name | Data |
|---|---|---|---|
| Example 110 | 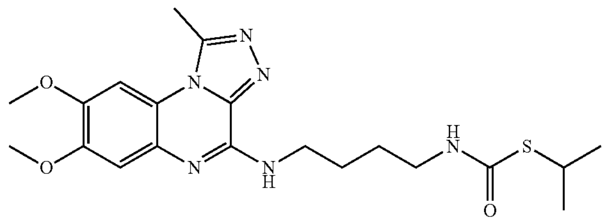 [SMILES: COc1cc2nc(NCCCCNC(=O)SC(C)C)c3nnc(C)n3c2cc1OC] | [4-(7,8-dimethoxy-1-methyl-[1,2,4]triazolo[4,3-a]quinoxaline-4-ylamino)-butyl]-thiocarbamic acid-S-isopropylester | Mass (M + H⁺): 433.2; ¹H NMR (500 MHz, DMSO-d₆): δ1.19 (d, 6H), 1.46 (m, 2H), 1.60 (m, 2H), 3.02 (s, 3H), 3.10 (q, 2H), 3.35 (m, 1H), 3.50 (q, 2H), 3.82 (s, 3H), 3.86 (s, 3H), 7.09 (s, 1H), 7.50 (s, 1H), 7.79 (t, 1H), 7.95 (t, 1H). |

<Preparative Example 6> Preparation of 4-chloro-8-fluoro-1-methyl-6-trifluoromethyl-[1,2,4]triazolo[4,3-a]quinoxaline

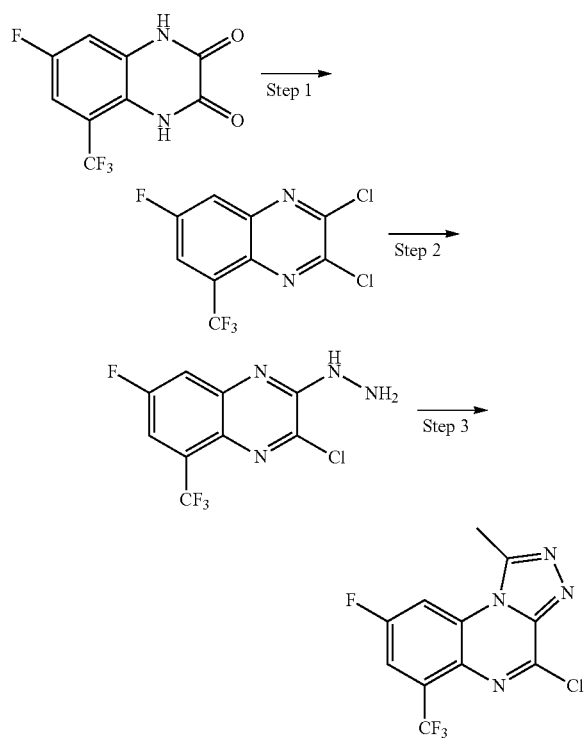

Step 1: Preparation of 2,3-dichloro-7-fluoro-5-trifluoromethyl-quinoxaline

A 7-fluoro-5-trifluoromethyl-1,4-dihydro-quinoxaline-2,3-dione compound (5.1 g, 20.3 mmol) was dissolved in 110 ml of chloroform, to which 5 ml of dimethylformamide and thionylchloride (5 ml, 61.7 mmol) were added stepwise, followed by reflux-stirring for 3 hours. The reaction was terminated by adding water at room temperature. The precipitate was filtered, washed with water, and dried under reduced pressure. As a result, 5.62 g of a target compound was obtained (96% yield).

¹H NMR (500 MHz, DMSO-d6): δ8.27 (d, 1H), 8.36 (d, 1H).

Step 2: Preparation of (3-chloro-7-fluoro-5-trifluoromethyl-quinoxaline-2-yl)-hydrazine 4.5 g of a target compound was obtained (84% yield) by the same manner as described in step 2 of Preparative Example 5, except that 2,3-dichloro-7-fluoro-5-trifluoromethyl-quinoxaline (5.39 g, 18.9 mmol) prepared in step 1 of Preparative Example 6 was used.

Mass (M+H⁺): 281.0

¹H NMR (500 MHz, DMSO-d6): δ7.20 (s, 1H), 7.36 (s, 1H).

Step 3: Preparation of 4-chloro-8-fluoro-1-methyl-6-trifluoromethyl-[1,2,4]triazolo[4,3-a]quinoxaline 1.4 g of a target compound was obtained (30% yield) by the same manner as described in step 3 of Preparative Example 5, except that (3-chloro-7-fluoro-5-trifluoromethyl-quinoxaline-2-yl)-hydrazine (4.45 g, 15.6 mmol) prepared in step 2 of Preparative Example 6 was used.

Mass (M+H⁺): 305.0

¹H NMR (500 MHz, DMSO-d6) δ3.10 (s, 3H), 8.07 (d, 1H), 8.09 (d, 1H).

<Example 111> Preparation of [4-(8-fluoro-1-methyl-6-trifluoromethyl-[1,2,4]triazolo[4,3-a]quinoxaline-4-ylamino)-butyl]-carbamic acid-tert-butylester

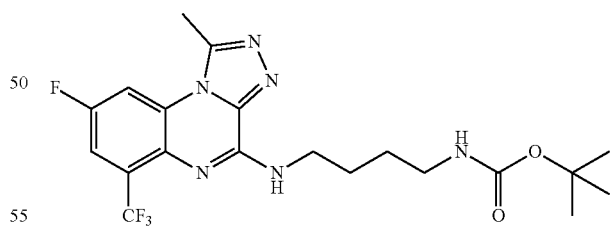

1.55 g of a target compound was obtained (82% yield) by the same manner as described in Example 1, except that 4-chloro-8-fluoro-1-methyl-6-trifluoromethyl-[1,2,4]triazolo[4,3-a]quinoxaline (1.44 g, 4.72 mmol) prepared in step 3 of Preparative Example 6 was used.

Mass (M+H⁺): 457.2

¹H NMR (500 MHz, DMSO-d6): δ1.31 (s, 9H), 1.42 (m, 2H), 1.61 (m, 2H), 2.93 (m, 2H), 2.97 (s, 3H), 3.51 (m, 2H), 3.87 (s, 3H), 6.74 (d, 1H), 7.05 (m, 1H), 7.20 (q, 1H), 7.67 (t, 1H), 7.97 (d, 1H).

<Example 112> Preparation of N¹-(8-fluoro-1-methyl-6-trifluoromethyl-[1,2,4]triazolo[4,3-a]quinoxaline-4-yl)-butane-1,4-diamine dihydrochloride

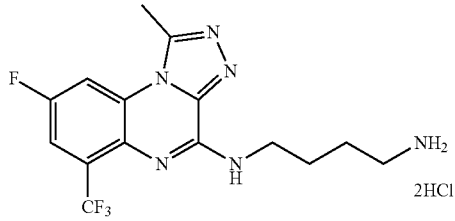 [SMILES: Cc1nnc2c(NCCCCN)nc3c(C(F)(F)F)cc(F)cc3n12]

1.16 g of a target compound was obtained (76% yield) by the same manner as described in Example 2, except that [4-(8-fluoro-1-methyl-6-trifluoromethyl-[1,2,4]triazolo[4,3-a]quinoxaline-4-ylamino)-butyl]-carbamic acid-tert-butylester (1.42 g, 3.54 mmol) prepared in Example 111 was used.

Mass (M+H⁺): 357.1

¹H NMR (500 MHz, DMSO-d6): δ1.60 (m, 2H), 1.70 (m, 2H), 2.73 (m, 2H), 3.01 (s, 3H), 3.52 (m, 2H), 6.04 (brs, 2H), 7.41 (d, 1H), 7.73 (s, 2H), 8.13 (d, 1H), 8.63 (t, 1H).

<Example 113> Preparation of N-[4-(8-fluoro-1-methyl-6-trifluoromethyl-[1,2,4]triazolo[4,3-a]quinoxaline-4-ylamino)-butyl]-2,2-dimethyl-propionamide

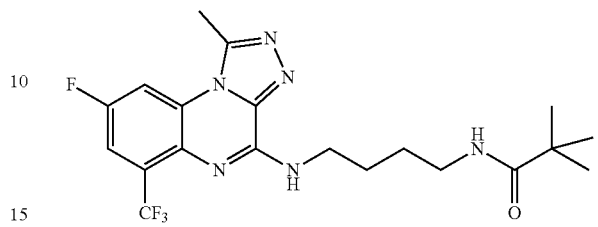

56 mg of a target compound was obtained (80% yield) by the same manner as described in Example 3, except that N¹-(8-fluoro-1-methyl-6-trifluoromethyl-[1,2,4]triazolo[4,3-a]quinoxaline-4-yl)-butane-1,4-diamine dihydrochloride (60 mg, 0.16 mmol) prepared in Example 112 was used.

Mass (M+H⁺): 441.2

¹H NMR (500 MHz, DMSO-d6) δ1.01 (s, 9H), 1.43 (s, 2H), 1.60 (s, 2H), 2.99 (s, 5H), 3.49 (s, 2H), 7.36 (s, 1H), 7.68 (d, 1H), 8.10 (d, 1H), 8.59 (s, 1H).

The compounds shown in Table 6 below were prepared by the same manner as described in Example 113.

TABLE 6

| Example | Structure | Name | Data |
|---|---|---|---|
| Example 114 | 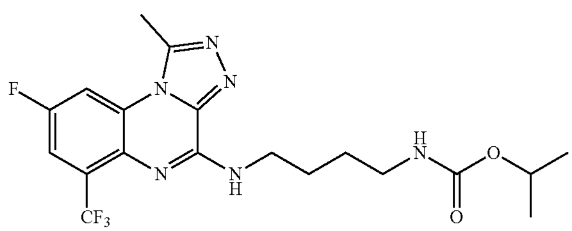 | [4-(8-fluoro-1-methyl-6-trifluoromethyl-[1,2,4]triazolo[4,3-a]quinoxaline-4-ylamino)-butyl]-carbamic acid isopropylester | Mass (M + H⁺): 143.2; ¹H NMR (500 MHz, DMSO-d₆): δ1.09 (s, 6H), 1.43 (m, 2H), 1.62 (m, 2H), 2.94 (m, 2H), 3.00 (s, 3H), 3.51 (m, 2H), 4.68 (s, 1H), 6.92 (t, 1H), 7.72 (d, 1H), 8.13 (d, 1H), 8.60 (t, 1H) |
| Example 115 | 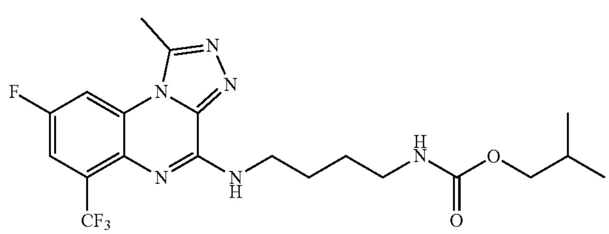 | [4-(8-fluoro-1-methyl-6-trifluoromethyl-[1,2,4]triazolo[4,3-a]quinoxaline-4-ylamino)-butyl]-carbamic acid isobutylester | Mass (M + H⁺): 157.2; ¹H NMR (500 MHz, DMSO-d₆): δ0.87 (s, 9H), 1.40 (m, 2H), 1.62 (m, 2H), 1.86 (s, 2H), 3.00 (s, 5H), 3.28 (s, 1H), 3.51 (m, 2H), 7.63 (s, 1H), 7.69 (d, 1H), 8.10 (d, 1H), 8.59 (m, 1H) |
| Example 116 | 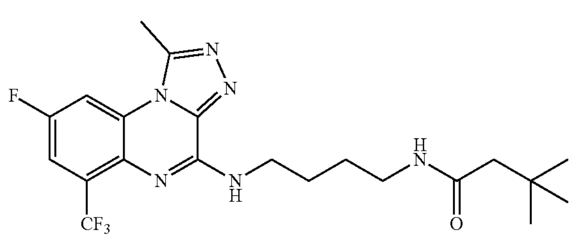 [SMILES: Cc1nnc2c(NCCCCNC(=O)CC(C)(C)C)nc3c(C(F)(F)F)cc(F)cc3n12] | N-[4-(8-fluoro-1-methyl-6-trifluoromethyl-[1,2,4]triazolo[4,3-a]quinoxaline-4-ylamino)-butyl]-3,3-dimethyl-butyramide | Mass (M + H⁺): 455.2; ¹H NMR (500 MHz, DMSO-d₆): δ0.80 (d, 6H), 1.42 (m, 2H), 1.61 (m, 2H), 1.75 (m, 1H), 2.94 (m, 2H), 2.99 (s, 3H), 3.40 (m, 2H), 3.64 (m, 2H), 6.99 (m, 1H), 7.70 (d, 1H), 8.11 (d, 1H), 8.58 (m, 1H) |

<Preparative Example 7> Preparation of 4-chloro-6-methoxy-1-methyl-[1,2,4]triazolo[4,3-a]quinoxaline

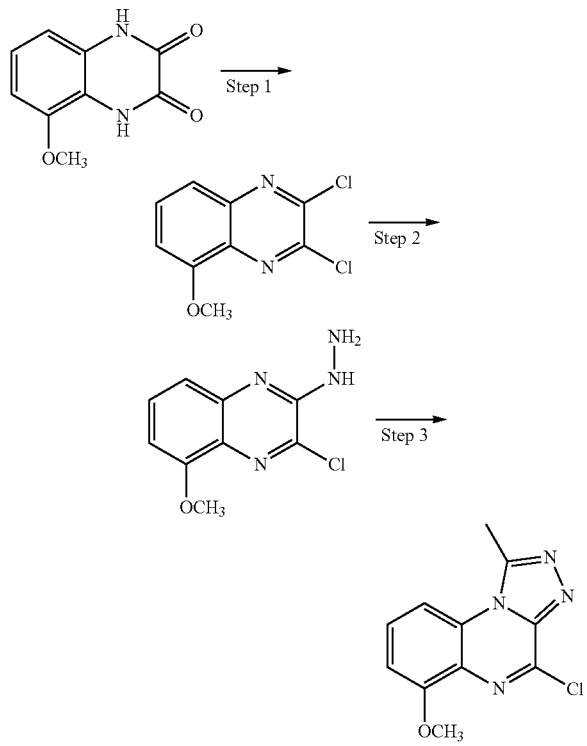

Step 1: Preparation of 2,3-dichloro-5-methoxy-quinoxaline 1.85 g of a target compound was obtained (89% yield) by the same manner as described in step 1 of Preparative Example 5, except that 5-methoxy-1,4-dihydro-quinoxaline-2,3-dione (1.75 g, 9.1 mmol) was used.

Mass (M+H$^+$): 229.0

$^1$H NMR (500 MHz, DMSO-d6) δ3.98 (s, 3H), 7.36 (d, 1H), 7.54 (d, 1H), 7.80 (m, 1H).

Step 2: Preparation of (3-chloro-5-methoxy-quinoxaline-2-yl)-hydrazine 270 mg of a target compound was obtained (33% yield) by the same manner as described in step 2 of Preparative Example 5, except that 2,3-dichloro-5-methoxy-quinoxaline (830 mg, 3.62 mmol) prepared in step 1 of Preparative Example 7 was used.

Mass (M+H$^+$): 225.0

$^1$H NMR (500 MHz, DMSO-d6): δ3.87 (s, 3H), 6.85 (d, 1H), 7.17 (d, 1H), 7.47 (t, 1H), 8.77 (s, 1H).

Step 3: Preparation of 4-chloro-6-methoxy-1-methyl-[1,2,4]triazolo[4,3-a]quinoxaline 260 mg of a target compound was obtained (87% yield) by the same manner as described in step 3 of Preparative Example 5, except that (3-chloro-5-methoxy-quinoxaline-2-yl)-hydrazine (270 mg, 1.2 mmol) prepared in step 2 of Preparative Example 7 was used.

Mass (M+H$^+$): 249.0

$^1$H NMR (500 MHz, DMSO-d6): δ3.05 (s, 3H), 3.96 (s, 3H), 7.28 (d, 1H), 7.69 (t, 1H), 7.87 (d, 1H).

<Example 117> Preparation of [4-(6-methoxy-1-methyl-[1,2,4]triazolo[4,3-a]quinoxaline-4-ylamino)-butyl]-carbamic acid-tert-butylester

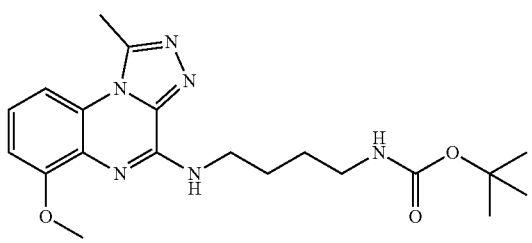 [SMILES: COc1cccc2c1nc(NCCCCNC(=O)OC(C)(C)C)c1nnc(C)n12]

350 mg of a target compound was obtained (89% yield) by the same manner as described in Example 1, except that 4-chloro-6-methoxy-1-methyl-[1,2,4]triazolo[4,3-a]quinoxaline (242 mg, 0.97 mmol) prepared in step 3 of Preparative Example 7 was used.

Mass (M+H$^+$): 401.2

$^1$H NMR (500 MHz, DMSO-d6) δ1.31 (s, 9H), 1.42 (m, 2H), 1.61 (m, 2H), 2.93 (m, 2H), 2.97 (s, 3H), 2.99 (m, 2H), 3.50 (m, 2H), 3.88 (s, 3H), 6.73 (m, 1H), 7.02 (m, 1H), 7.19 (m, 1H), 7.65 (m, 1H), 7.97 (d, 1H).

<Example 118> Preparation of N$^1$-(6-methoxy-1-methyl-[1,2,4]triazolo[4,3-a]quinoxaline-4-yl)-butane-1,4-diamine dihydrochloride

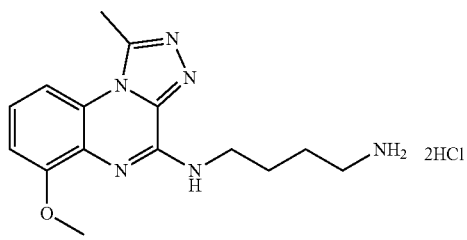 [SMILES: COc1cccc2c1nc(NCCCCN)c1nnc(C)n12]

240 mg of a target compound was obtained (74% yield) by the same manner as described in Example 2, except that [4-(6-methoxy-1-methyl-[1,2,4]triazolo[4,3-a]quinoxaline-4-ylamino)-butyl]-carbamic acid-tert-butylester (350 mg, 0.87 mmol) prepared in Example 117 was used.

Mass (M+H$^+$): 301.2

$^1$H NMR (500 MHz, DMSO-d6): δ1.63 (s, 2H), 1.72 (s, 2H), 2.94 (m, 2H), 3.00 (s, 3H), 3.57 (s, 2H), 3.91 (s, 3H), 5.88 (brs, 2H), 7.10 (s, 1H), 7.25 (s, 1H), 7.70 (d, 1H), 7.92 (s, 2H), 8.26 (s, 1H).

<Example 119> Preparation of N-[4-(6-methoxy-1-methyl-[1,2,4]triazolo[4,3-a]quinoxaline-4-ylamino)-butyl]-2,2-dimethyl-propionamide

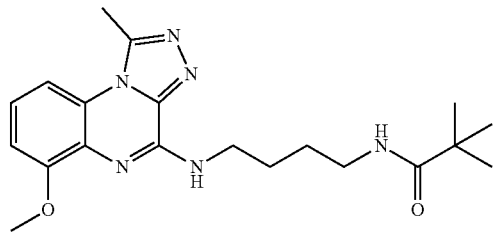 [SMILES: COc1cccc2c1nc(NCCCCNC(=O)C(C)(C)C)c1nnc(C)n12]

59 mg of a target compound was obtained (80% yield) by the same manner as described in Example 59, except that N¹-(6-methoxy-1-methyl-[1,2,4]triazolo[4,3-a]quinoxaline-4-yl)-butane-1,4-diamine dihydrochloride (60 mg, 0.16 mmol) prepared in Example 118 was used.

Mass (M+H⁺): 385.2

¹H NMR (500 MHz, DMSO-d6): δ1.14 (s, 9H), 1.65 (m, 2H), 1.75 (m, 2H), 3.04 (s, 3H), 3.33 (q, 2H), 3.75 (q, 2H), 3.98 (s, 3H), 5.94 (s, 1H), 4.60 (m, 1H), 6.94 (d, 1H), 7.17 (m, 1H), 7.55 (m, 1H)

<Example 120> Preparation of N-[4-(6-methoxy-1-methyl-[1,2,4]triazolo[4,3-a]quinoxaline-4-ylamino)-butyl]-carbamic acid isobutylester

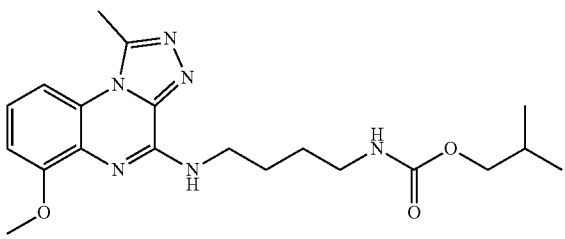 [SMILES: COc1cccc2c1nc(NCCCCNC(=O)OCC(C)C)c1nnc(C)n12]

46 mg of a target compound was obtained (75% yield) by the same manner as described in Example 53, except that N¹-(6-methoxy-1-methyl-[1,2,4]triazolo[4,3-a]quinoxaline-4-yl)-butane-1,4-diamine dihydrochloride (60 mg, 0.16 mmol) prepared in Example 118 was used.

Mass (M+H⁺): 401.2

¹H NMR (500 MHz, DMSO-d6) δ0.80 (d, 6H), 1.45 (m, 2H), 1.75 (m, 2H), 1.96 (m, 1H), 2.97 (s, 3H), 2.99 (m, 2H), 3.53 (m, 2H), 3.65 (m, 2H), 3.87 (s, 3H), 7.04 (m, 1H), 7.06 (m, 1H), 7.19 (m, 1H), 7.67 (d, 1H), 7.98 (m, 1H).

<Preparative Example 8> Preparation of 4-chloro-8-methoxy-1-methyl-[1,2,4]triazolo[4,3-a]quinoxaline

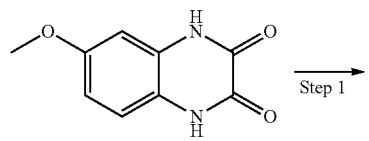

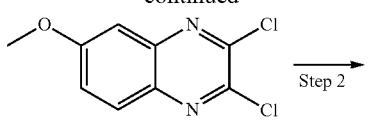

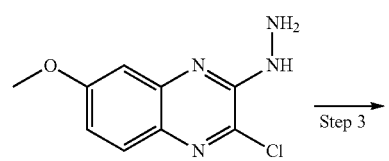

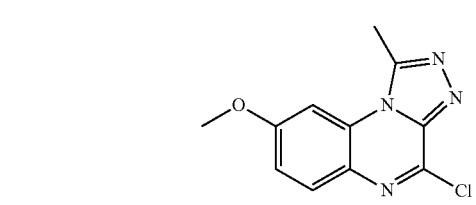

Step 1: Preparation of 2,3-dichloro-6-methoxy-quinoxaline

6-Methoxy-1,4-dihydro-quinoxaline-2,3-dione (15.5 g, 81 mmol) was dissolved in 75 ml of phosphorusoxychloride, followed by reflux stirring for 24 hours. The reaction was terminated using water and methanol (1:1 solution) at 0~5° C. The resulting precipitate was filtered and dried under reduced pressure. As a result, 17.2 g of a target compound was obtained (93% yield).

Mass (M+H⁺): 229.2

¹H NMR (500 MHz, DMSO-d6): δ3.93 (s, 3H), 7.46 (s, 1H), 7.54 (d, 1H), 7.96 (d, 1H).

Step 2: Preparation of 2-chloro-6-methoxy-3-hydrazinylquinoxaline

A target compound was obtained (quantitative yield) by the same manner as described in step 2 of Preparative Example 5, except that 2,3-dichloro-6-methoxy-quinoxaline (750 mg, 3.00 mmol) prepared in step 1 of Preparative Example 8 was used.

Mass (M+H⁺): 225.2

Step 3: Preparation of 4-chloro-8-methoxy-1-methyl-[1,2,4]triazolo[4,3-a]quinoxaline 756 mg of a target compound was obtained (88% yield) by the same manner as described in step 3 of Preparative Example 5, except that 2-chloro-6-methoxy-3-hydrazinylquinoxaline (780 mg, 3.47 mmol) prepared in step 2 of Preparative Example 8 was used.

Mass (M+H⁺): 249.0

¹H NMR (500 MHz, DMSO-d6): δ3.11 (s, 3H), 3.96 (s, 3H), 7.30 (s, 1H), 7.66 (d, 1H), 7.92 (d, 1H).

<Example 121> Preparation of [4-(8-methoxy-1-methyl-[1,2,4]triazolo[4,3-a]quinoxaline-4-ylamino)-butyl]-carbamic acid-tert-butylester

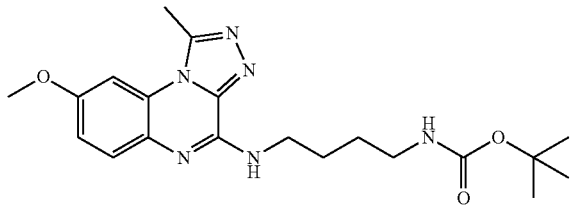 [SMILES: COc1ccc2nc(NCCCCNC(=O)OC(C)(C)C)c3nnc(C)n3c2c1]

3.9 g of a target compound was obtained (82% yield) by the same manner as described in Example 57, except that 4-chloro-8-methoxy-1-methyl-[1,2,4]triazolo[4,3-a]quinoxaline (3 g, 12 mmol) prepared in step 3 of Preparative Example 8 was used.
Mass (M+H$^+$): 401.2
$^1$H NMR (500 MHz, DMSO-d6) δ1.32 (s, 9H), 1.43 (m, 2H), 1.60 (m, 2H), 2.92 (q, 2H), 3.02 (s, 3H), 3.46 (q, 2H), 3.84 (s, 3H), 6.74 (t, 1H), 7.07 (d, 1H), 7.78 (t, 1H)

<Example 122> Preparation of N$^1$-(8-methoxy-1-methyl-[1,2,4]triazolo[4,3-a]quinoxaline-4-yl)-butane-1,4-diamine ditrifluoroacetic acid

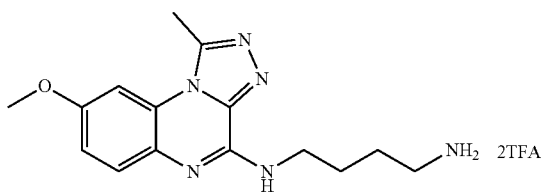 [SMILES: COc1ccc2nc(NCCCCN)c3nnc(C)n3c2c1]

2 g of a target compound was obtained (76% yield) by the same manner as described in Example 58, except that [4-(8-methoxy-1-methyl-[1,2,4]triazolo[4,3-a]quinoxaline-4-ylamino)-butyl]-carbamic acid-tert-butylester (3 g, 7.5 mmol) prepared in Example 121 was used.
Mass (M+H$^+$): 301.2
$^1$H NMR (500 MHz, DMSO-d6): δ1.59 (m, H), 1.68 (m, 2H), 2.80 (q, 2H), 3.03 (s, 3H), 3.51 (s, 3H), 3.51 (q, 2H), 3.85 (s, 3H), 7.08 (d, 1H), 7.50 (m, 2H), 7.52 (brs, 2H), 7.90 (brs, 1H).

<Example 123> Preparation of N-[4-(8-methoxy-1-methyl-[1,2,4]triazolo[4,3-a]quinoxaline-4-ylamino)-butyl]-2,2-dimethyl-propionamide

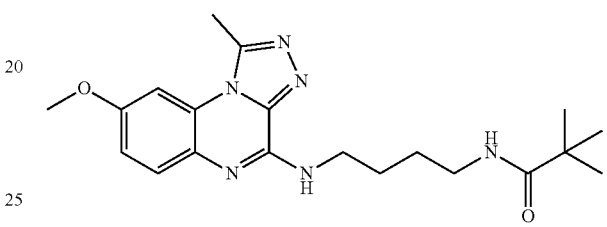

175 mg of a target compound was obtained (90% yield) by the same manner as described in Example 59, except that N$^1$-(8-methoxy-1-methyl-[1,2,4]triazolo[4,3-a]quinoxaline-4-yl)-butane-1,4-diamine ditrifluoroacetic acid (250 mg, 0.83 mmol) prepared in Example 122 was used.
Mass (M+H$^+$): 385.2
$^1$H NMR (500 MHz, DMSO-d6): δ1.02 (s, 9H), 1.46 (m, 2H), 1.60 (m, 2H), 1.60 (m, 2H), 3.02 (s, 3H), 3.04 (q, 2H), 3.45 (q, 2H), 3.84 (s, 3H), 7.07 (d, 1H), 7.36 (t, 1H), 7.49 (s, 1H), 7.51 (d, 1H), 7.78 (t, 1H).

The compounds shown in Table 7 below were prepared by the same manner as described in Example 123.

TABLE 7

| Example | Structure | Name | Data |
|---|---|---|---|
| Example 124 | 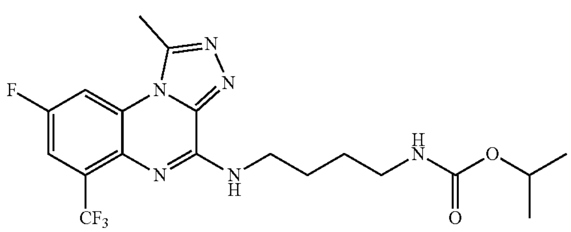 | [4-(8-methoxy-1-methyl-[1,2,4]triazolo[4,3-a]quinoxaline-4-ylamino)-butyl]-3,3-dimethyl-butyramide | Mass (M + H$^+$): 399.2; $^1$H NMR (500 MHz, DMSO-d$_6$): δ0.88 (s, 9H), 1.45 (m, 2H), 1.63 (m, 2H), 1.87 (s, 2H), 3.00 (s, 3H), 3.03 (q, 2H), 3.47 (q, 2H), 3.84 (s, 3H), 7.07 (d, 1H), 7.50 (s, 1H), 7.51 (d, 1H), 7.62 (t, 1H), 7.79 (t, 1H). |
| Example 125 | 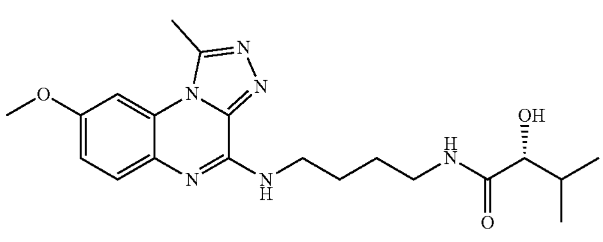 | 2-(R)-hydroxy-N-[4-(8-methoxy-1-methyl-[1,2,4]triazolo[4,3-a]quinoxaline-4-ylamino)-butyl]-3-methyl-butyramide | Mass (M + H$^+$): 401.2; $^1$H NMR (500 MHz, DMSO-d$_6$): δ0.69 (d, 3H), 0.83 (d, 3H), 1.48 (m, 2H), 1.61 (m, 2H), 1.91 (m, 1H), 3.02 (s, 3H), 3.12 (m, 2H), 3.47 (m, 2H), 3.57 (m, 1H), 3.84 (s, 3H), 5.22 (d, 1H), 7.07 |

TABLE 7-continued

| Example | Structure | Name | Data |
|---|---|---|---|
| | | | (d, 1H), 7.50 (d, 1H), 7.51 (s, 1H), 7.62 (t, 1H), 7.80 (t, 1H). |
| Example 126 | 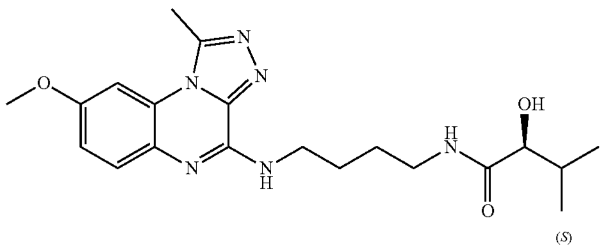 | 2-(S)-hydroxy-N-[4-(8-methoxy-1-methyl-[1,2,4]triazolo[4,3-a]quinoxaline-4-ylamino)-butyl]-3-methyl-butyramide | Mass (M + H$^+$): 401.2; $^1$H NMR (500 MHz, DMSO-d$_6$): δ0.68 (d, 3H), 0.83 (d, 3H), 1.48 (m, 2H), 1.61 (m, 2H), 1.91 (m, 1H), 3.02 (s, 3H), 3.10 (m, 2H), 3.47 (m, 2H), 3.59 (m, 1H), 3.93 (s, 1H), 3.93 (s, 3H), 5.22 (d, 1H), 7.07 (d, 1H), 7.50 (d, 1H), 7.51 (s, 1H), 7.63 (t, 1H), 7.80 (t, 1H). |
| Example 127 | 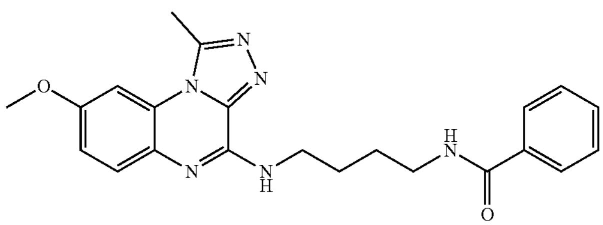 [SMILES: COc1ccc2nc(NCCCCNC(=O)c3ccccc3)c3nnc(C)n3c2c1] | N-[4-(8-methoxy-1-methyl-[1,2,4]triazolo[4,3-a]quinoxaline-4-ylamino)-butyl]-benzamide | Mass (M + H$^+$): 405.2; $^1$H NMR (500 MHz, DMSO-d$_6$): δ1.57 (m, 2H), 1.69 (m, 2H), 3.01 (s, 3H), 3.26 (q, 2H), 3.52 (q, 2H), 3.83 (s, 3H), 7.06 (d, 1H), 7.38 (m, 2H), 7.40 (m, 1H), 7.48 (m, 2H), 7.76 (m, 2H), 7.78 (t, 1H), 8.39 (t, 1H). |
| Example 128 | 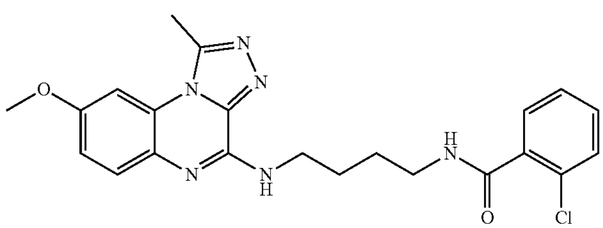 [SMILES: COc1ccc2nc(NCCCCNC(=O)c3ccccc3Cl)c3nnc(C)n3c2c1] | 2-chloro-N-[4-(8-methoxy-1-methyl-[1,2,4]triazolo[4,3-a]quinoxaline-4-ylamino)-butyl]-benzamide | Mass (M + H$^+$): 439.0; $^1$H NMR (500 MHz, DMSO-d$_6$): δ1.58 (m, 2H), 1.71 (m, 2H), 3.02 (s, 3H), 3.27 (q, 2H), 3.51 (q, 2H), 3.85 (s, 3H), 7.08 (d, 1H), 7.34 (m, 4H), 7.53 (m, 2H), 7.82 (t, 1H), 8.36 (t, 1H). |
| Example 129 | 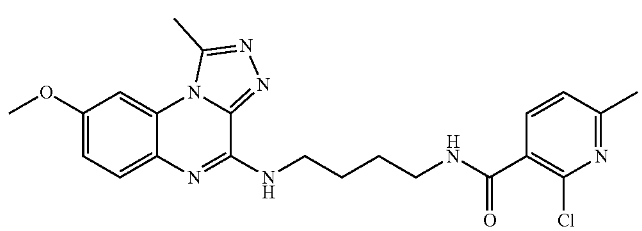 | 2-chloro-N-[4-(8-methoxy-1-methyl-[1,2,4]triazolo[4,3-a]quinoxaline-4-ylamino)-6-methyl-nicotinamide | Mass (M + H$^+$): 454.2; $^1$H NMR (500 MHz, DMSO-d$_6$): δ1.57 (m, 2H), 1.70 (m, 2H), 2.40 (s, 3H), 3.02 (s, 3H), 3.23 (q, 2H), 3.50 (q, 2H), 3.84 (s, 3H), 7.07 (d, 1H), 7.25 (d, 1H), 7.51 (m, 2H), 7.68 (d, 1H) 7.82 (t, 1H), 8.43 (t, 1H). |

<Preparative Example 9> Preparation of 6-methoxy-1,7-dimethyl-[1,2,4]triazolo[4,3-a]quinoxaline

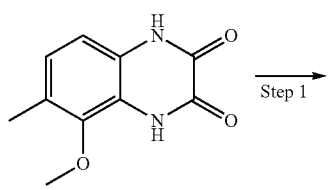

Step 1

-continued

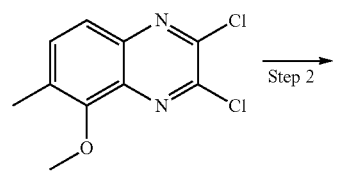

Step 2

-continued

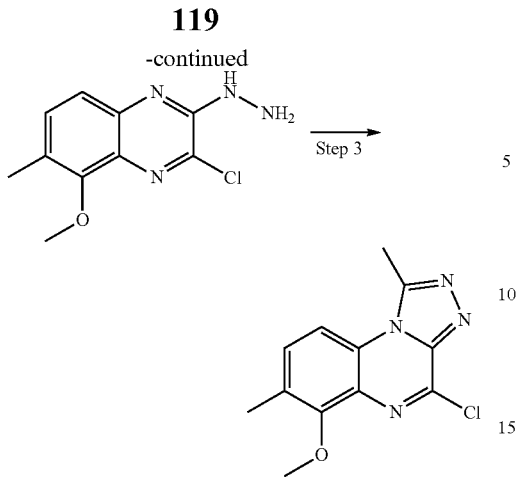

6-Methoxy-1,7-dimethyl-[1,2,4]triazolo[4,3-a]quinoxaline was obtained by the same manner as described in Preparative Example 5, except that 5-methoxy-6-methyl-1,4-dihydro-quinoxaline-2,3-dione was used.

Step 1: Preparation of 2,3-dichloro-5-methoxy-6-methyl-quinoxaline

Mass (M+H$^+$): 243.0

$^1$H NMR (500 MHz, DMSO-d6) δ2.41 (s, 3H), 3.98 (s, 3H), 7.71 (d, 1H), 7.77 (d, 1H).

Step 2: Preparation of 3-chloro-5-methoxy-6-methyl-quinoxaline-2-ylhydrazine

Mass (M+H$^+$): 239.1

Step 3: Preparation of 4-chloro-6-methoxy-1,7-dimethyl-[1,2,4]triazolo[4,3-a]quinoxaline Mass (M+H$^+$): 263.0

$^1$H NMR (500 MHz, DMSO-d6): δ2.35 (s, 3H), 3.03 (s, 3H), 3.96 (s, 3H), 7.60 (d, 1H), 7.96 (d, 1H)

<Example 130> Preparation of {4-[6-methoxy-1,7-dimethyl-[1,2,4]triazolo[4,3-a]quinoxaline-4-ylamino]-butyl}-carbamic acid-tert-butylester

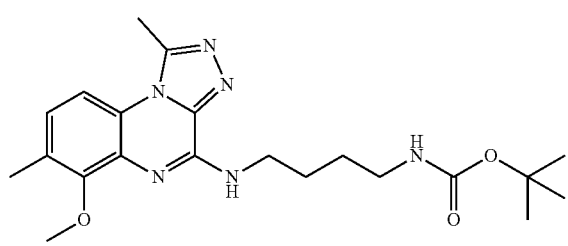 [SMILES: COc1c(C)ccc2c1nc(NCCCCNC(=O)OC(C)(C)C)c1nnc(C)n12]

1.52 g of a target compound was obtained (92% yield) by the same manner as described in Example 57, except that 4-chloro-6-methoxy-1,7-dimethyl-[1,2,4]triazolo[4,3-a]quinoxaline (1.05 g, 4.00 mmol) prepared in step 3 of Preparative Example 9 was used.

Mass (M+H$^+$): 415.2

$^1$H NMR (500 MHz, DMSO-d6) δ1.31 (s, 9H), 1.44 (q, 2H), 1.63 (q, 2H), 2.26 (s, 3H), 2.92 (q, 2H), 2.94 (s, 3H), 3.53 (q, 2H), 3.94 (s, 3H), 6.73 (t, 1H), 7.08 (d, 1H), 7.71 (d, 1H), 8.12 (t, 1H).

<Example 131> Preparation of N$^1$-(6-methoxy-1,7-dimethyl-[1,2,4]triazolo[4,3-a]quinoxaline-4-yl)-butane-1,4-diamine ditrifluoroacetic acid

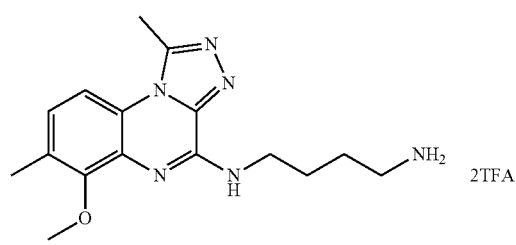 [SMILES: COc1c(C)ccc2c1nc(NCCCCN)c1nnc(C)n12]

1.4 g of a target compound was obtained (71% yield) by the same manner as described in Example 58, except that [4-(6-methoxy-1,7-dimethyl-[1,2,4]triazolo[4,3-a]quinoxaline-4-ylamino)-butyl]-carbamic acid-tert-butylester (1.5 g, 3.62 mmol) prepared in Example 130 was used.

Mass (M+H$^+$): 315.2

$^1$H NMR (500 MHz, DMSO-d6) δ1.61 (m, 2H), 1.71 (m, 2H), 2.27 (s, 3H), 2.81 (m, 2H), 2.96 (s, 3H), 3.58 (q, 2H), 3.95 (s, 3H), 7.10 (d, 1H), 7.61 (brm, 2H), 7.73 (d, 1H), 8.19 (t, 1H).

<Example 132> Preparation of [4-(6-methoxy-1,7-dimethyl-[1,2,4]triazolo[4,3-a]quinoxaline-4-ylamino)-butyl]-2,2-dimethyl-propionamide

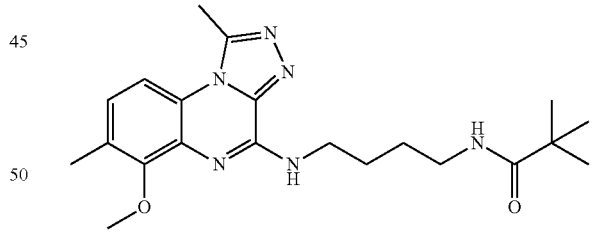

52 mg of a target compound was obtained (60% yield) by the same manner as described in Example 59, except that N$^1$-(6-methoxy-1,7-dimethyl-[1,2,4]triazolo[4,3-a]quinoxaline-4-yl)-butane-1,4-diamine ditrifluoroacetic acid (120 mg, 0.22 mmol) prepared in Example 131 was used.

Mass (M+H$^+$): 399.1

$^1$H NMR (500 MHz, DMSO-d6) δ1.01 (s, 9H), 1.46 (q, 2H), 1.63 (m, 2H), 2.26 (s, 3H), 2.95 (s, 3H), 3.04 (q, 2H), 3.54 (q, 2H), 3.94 (s, 3H), 7.08 (d, 1H), 7.36 (t, 1H), 7.71 (d, 1H), 8.13 (t, 1H).

The compounds shown in Table 8 below were prepared by the same manner as described in Example 132.

TABLE 8

| Example | Name | Data |
|---|---|---|
| Example 133 | [4-(6-methoxy-1,7-dimethyl-[1,2,4]triazolo[4,3-a]quinoxaline-4-ylamino)-butyl]-carbamic acid isopropylester | Mass (M + H+): 401.1; 1H NMR (500 MHz, DMSO-d6): δ1.09 (d, 6H), 1.46 (m, 2H), 1.64 (m, 2H), 2.27 (s, 3H), 2.95 (s, 3H), 2.96 (m, 2H), 3.53 (q, 2H), 3.94 (s, 3H), 4.67 (m, 1H), 6.93 (t, 1H), 7.08 (d, 1H), 7.72 (d, 1H), 8.13 (t, 1H). |
| Example 134 | [4-(6-methoxy-1,7-dimethyl-[1,2,4]triazolo[4,3-a]quinoxaline-4-ylamino)-butyl]-carbamic acid isobutylester | Mass (M + H+): 415.2; 1H NMR (500 MHz, DMSO-d6): δ0.81 (d, 6H), 1.46 (m, 2H), 1.64 (m, 2H), 1.75 (m, 1H), 2.26 (s, 3H), 2.94 (s, 3H), 2.99 (q, 2H), 3.53 (q, 2H), 3.65 (d, 2H), 3.94 (s, 3H). 7.02 (t, 1H), 7.08 (d, 1H), 7.70 (d, 1H), 8.13 (t, 1H). |
| Example 135 | N-[4-(6-methoxy-1,7-dimethyl-[1,2,4]triazolo[4,3-a]quinoxaline-4-ylamino)-butyl]-3-methyl-butyramide | Mass (M + H+): 399.2; 1H NMR (500 MHz, DMSO-d6): δ0.78 (d, 6H), 1.44 (m, 2H), 1.64 (m, 2H), 1.85 (d, 2H), 1.89 (m, 1H), 2.26 (s, 3H), 2.95 (s, 3H), 3.04 (m, 2H), 3.53 (m, 2H), 3.94, (s, 3H), 7.08 (d, 1H), 7.69 (m + d, 2H), 8.13 (t, 1H). |
| Example 136 | 2-(R)-hydroxy-N-[4-(6-methoxy-1,7-dimethyl-[1,2,4]triazolo[4,3-a]quinoxaline-4-ylamino)-butyl]-3-methyl-butyramide | Mass (M + H+): 415.2; 1H NMR (500 MHz, DMSO-d6): δ0.72 (d, 3H), 0.85 (d, 3H), 1.54 (m, 2H), 1.68 (m, 2H), 1.92 (m, 1H), 2.28 (s, 3H), 2.95 (s, 3H), 3.12 (m, 2H), 3.59 (m, 3H), 3.97 (s, 3H), 4.98 (d, 1H), 7.08 (d, 1H), 7.46 (t, 1H), 7.70 (d, 1H), 7.88 (t, 1H). |
| Example 137 | 2-(S)-hydroxy-N-[4-(6-methoxy-1,7-dimethyl-[1,2,4]triazolo[4,3-a]quinoxaline-4-ylamino)-butyl]-3-methyl-butyramide | Mass (M + H+): 415.2; 1H NMR (500 MHz, DMSO-d6): δ0.72 (d, 3H), 0.85 (d, 3H), 1.54 (m, 2H), 1.68 (m, 2H), 1.92 (m, 1H), 2.28 (s, 3H), 2.95 (s, 3H), 3.12 (m, 2H), 3.59 (m, 3H), 3.97 (s, 3H), 4.98 (d, 1H), 7.08 (d, 1H), 7.46 (t, 1H), 7.70 (d, 1H), 7.88 (t, 1H). |

123

124

TABLE 8-continued

| Example | Structure | Name | Data |
|---|---|---|---|
| Example 138 | 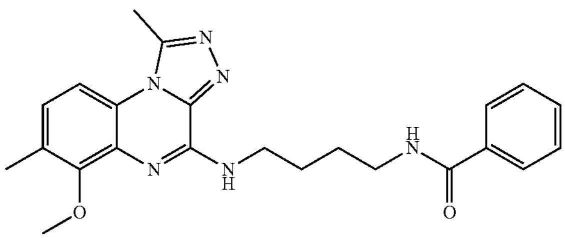 [SMILES: COc1c(C)ccc2c1nc(NCCCCNC(=O)c1ccccc1)c1nnc(C)n12] | N-[4-(6-methoxy-1,7-dimethyl-[1,2,4]triazolo[4,3-a]quinoxaline-4-ylamino)-butyl]-benzamide | Mass (M + H$^+$): 419.1; $^1$H NMR (500 MHz, DMSO-d6): δ1.60 (m, 2H), 1.70 (m, 2H), 2.25 (s, 3H), 2.94 (s, 3H), 3.27 (q, 2H), 3.57 (q, 2H), 3.91 (s, 3H), 7.07 (d, 1H), 7.38 (t, 2H), 7.44 (d, 1H), 7.69 (d, 1H), 7.76 (d, 2H), 8.15 (t, 1H), 8.39 (t, 1H). |
| Example 139 | 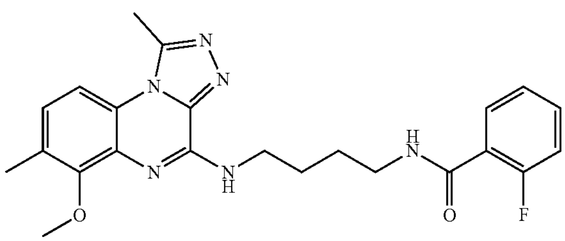 [SMILES: COc1c(C)ccc2c1nc(NCCCCNC(=O)c1ccccc1F)c1nnc(C)n12] | 2-fluoro-N-[4-(6-methoxy-1,7-dimethyl-[1,2,4]triazolo[4,3-a]quinoxaline-4-ylamino)-butyl]-benzamide | Mass (M + H$^+$): 437.2; $^1$H NMR (500 MHz, DMSO-d6): δ1.58 (m, 2H), 1.72 (m, 2H), 2.26 (s, 3H), 2.95 (s, 3H), 3.26 (m, 2H), 3.58 (m, 2H), 3.93 (s, 3H), 7.08 (d, 1H), 7.19 (m, 2H), 7.44 (m, 1H), 7.52 (t, 1H), 7.71 (d, 1H), 8.16 (t, 1H). |
| Example 140 | 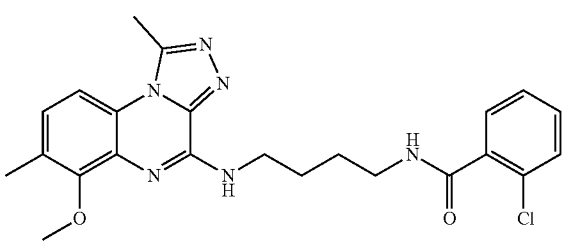 [SMILES: COc1c(C)ccc2c1nc(NCCCCNC(=O)c1ccccc1Cl)c1nnc(C)n12] | 2-chloro-N-[4-(6-methoxy-1,7-dimethyl-[1,2,4]triazolo[4,3-a]quinoxaline-4-ylamino)-butyl]-benzamide | Mass (M + H$^+$): 453.2; $^1$H NMR (500 MHz, DMSO-d6): δ1.59 (m, 2H) 1.74 (m, 2H), 2.27 (s, 3H), 2.95 (s, 1H), 3.24 (q, 2H), 3.59 (q, 2H), 3.95 (s, 3H), 7.09 (d, 1H), 7.29 (t, 1H), 7.32 (m, 1H), 7.35 (m, 1H), 7.38 (m, 1H), 7.42 (d, 1H), 7.71 (d, 1H), 8.16 (t, 1H), 8.35 (t, 1H). |
| Example 141 | 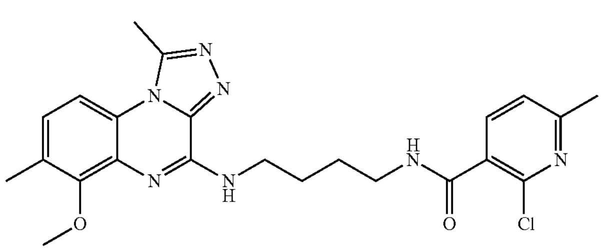 | 2-chloro-N-[4-(6-methoxy-1,7-dimethyl-[1,2,4]triazolo[4,3-a]quinoxaline-4-ylamino)-butyl]-6-methyl-nicotinamide | Mass (M + H$^+$): 468.1; $^1$H NMR (500 MHz, DMSO-d6): δ1.59 (m, 2H), 1.74 (m, 2H), 2.26 (s, 3H), 2.42 (s, 3H), 2.95 (s, 3H), 3.23 (q, 2H), 3.58 (q, 2H), 3.95 (s, 3H), 7.09 (d, 1H), 7.24 (d, 1H), 7.68 (d, 1H), 7.71 (d, 1H), 8.16 (t, 1H), 8.43 (t, 1H). |

<Preparative Example 10> Preparation of 4-chloro-6-methoxy-1-methyl-8-trifluoromethyl-[1,2,4]triazolo[4,3-a]quinoxaline

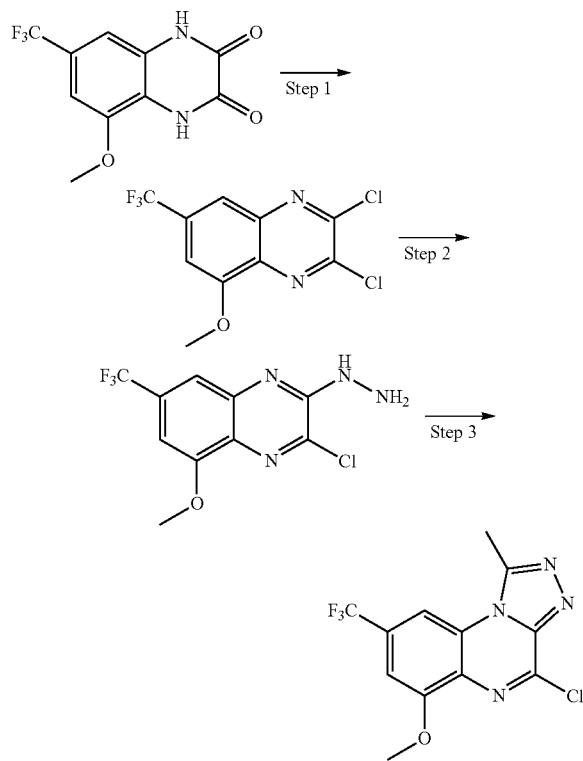

4-Chloro-6-methoxy-1-methyl-8-trifluoromethyl-[1,2,4]triazolo[4,3-a]quinoxaline was obtained by the same manner as described in Preparative Example 5, except that 5-methoxy-7-trifluoromethyl-1,4-dihydro-quinoxaline-2,3-dione was used.

Step 1: Preparation of 2,3-dichloro-5-methoxy-7-trifluoromethyl-quinoxaline $^1$H NMR (500 MHz, DMSO-d6): δ4.07 (s, 3H), 7.53 (s, 1H), 7.96 (s, 1H).

Step 2: Preparation of (3-chloro-5-methoxy-7-trifluoromethyl-quinoxaline-2-yl)-hydrazine Mass (M+H$^+$): 293.0

Step 3: Preparation of 4-chloro-6-methoxy-1-methyl-8-trifluoromethyl-[1,2,4]triazolo[4,3-a]quinoxaline Mass (M+H$^+$): 317.0

$^1$H NMR (500 MHz, DMSO-d6) δ3.10 (s, 3H), 4.06 (s, 3H), 7.57 (s, 1H), 8.01 (s, 1H).

The compounds shown in Table 9 below were prepared by using 4-chloro-6-methoxy-1-methyl-8-trifluoromethyl-[1,2,4]triazolo[4,3-a]quinoxaline prepared by the same manner as described in Preparative Example 10 as an intermediate.

TABLE 9

| Example | Structure | Name | Data |
|---|---|---|---|
| Example 142 | 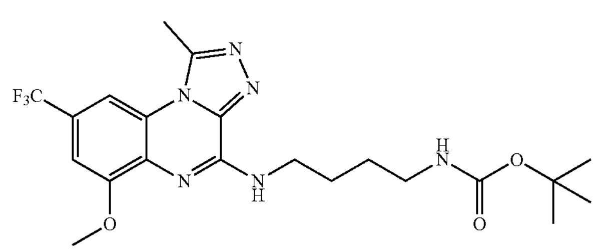 | [4-(6-methoxy-1-methyl-8-trifluoromethyl-[1,2,4]triazolo[4,3-a]quinoxaline-4-ylamino)-butyl]-carbamic acid-tert-butylester | Mass (M + H$^+$): 496.2; $^1$H NMR (500 MHz, DMSO-d6): δ1.31 (s, 9H), 1.43 (m, 2H), 1.62 (m, 2H), 2.92 (m, 2H), 3.01 (s, 3H), 3.54 (m, 2H), 3.95 (s, 3H), 6.73 (t, 1H), 7.28 (s, 1H), 7.85 (s, 1H), 8.44 (t, 1H). |
| Example 143 | 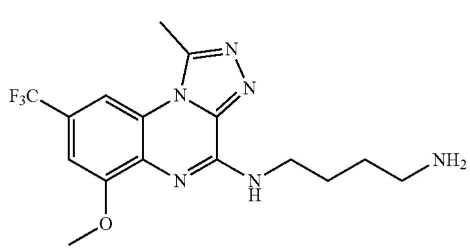 | N$^1$-(6-methoxy-1-methyl-8-trifluoromethyl-[1,2,4]triazolo[4,3-a]quinoxaline-4-yl)-butane-1,4-diamine ditrifluoroacetic acid | Mass (M + H$^+$): 369.1; $^1$H NMR (500 MHz, DMSO-d6): δ1.59 (m, 2H), 1.70 (m, 2H), 2.85 (m, 2H), 3.02 (s, 3H), 3.59 (m, 2H), 3.96 (s, 3H), 7.29 (s, 1H), 7.62 (brm, 2H), 7.86 (s, 1H), 8.51 (t, 1H). |

TABLE 9-continued

| Example | Structure | Name | Data |
|---|---|---|---|
| Example 144 | 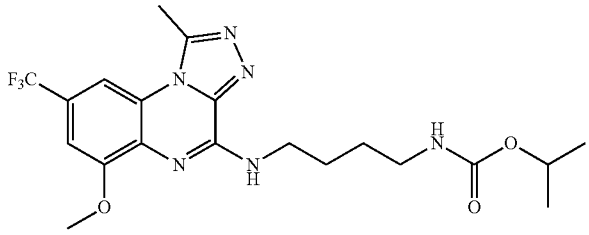 [SMILES: COc1cc(C(F)(F)F)cc2c1nc(NCCCCNC(=O)OC(C)C)c1nnc(C)n12] | [4-(6-methoxy-1-methyl-8-trifluoromethyl-[1,2,4]triazolo[4,3-a]quinoxaline-4-ylamino)-butyl]-carbamic acid isopropylester | Mass (M + H$^+$): 455.2; $^1$H NMR (500 MHz, DMSO-d6): δ1.09 (d, 6H), 1.43 (m, 2H), 1.63 (m, 2H), 2.97 (q, 2H), 3.01 (s, 3H), 3.55 (q, 2H), 3.95 (s, 3H), 4.68 (m, 1H), 6.93 (t, 1H), 7.28 (s, 1H). 7.85 (s, 1H), 8.44 (t, 1H). |
| Example 145 | 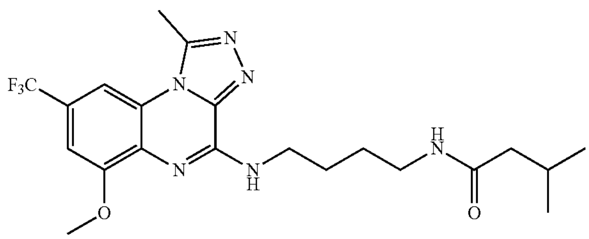 [SMILES: COc1cc(C(F)(F)F)cc2c1nc(NCCCCNC(=O)CC(C)C)c1nnc(C)n12] | N-[4-(6-methoxy-1-methyl-8-trifluoromethyl-[1,2,4]triazolo[4,3-a]quinoxaline-4-ylamino)-butyl]-3-methyl-butyramide | Mass (M + H$^+$): 453.2; $^1$H NMR (500 MHz, DMSO-d6): δ0.79 (d, 6H), 1.44 (m, 2H), 1.64 (m, 2H), 1.87 (m, 1H), 1.87 (d, 2H), 3.01 (s, 3H), 3.05 (q, 2H), 3.55 (m, 2H), 3.95 (s, 3H), 7.28 (s, 1H), 7.68 (t, 1H), 7.85 (s, 1H), 8.45 (t, 1H). |

<Preparative Example 11> Preparation of 4-chloro-8-methoxy-1,7-dimethyl-[1,2,4]triazolo[4,3-a]quinoxaline

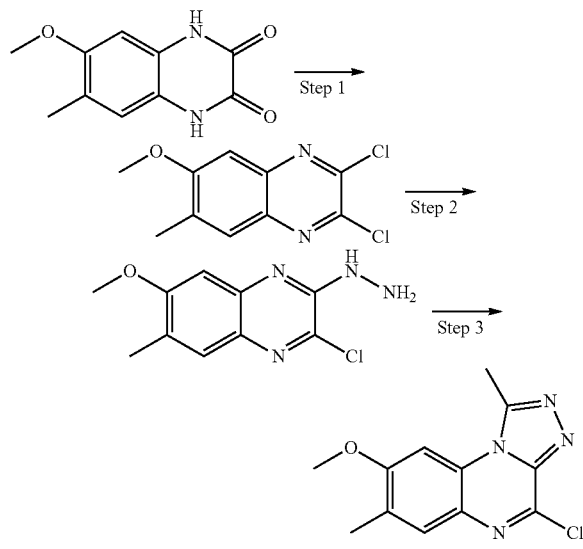

4-Chloro-8-methoxy-1,7-dimethyl-[1,2,4]triazolo[4,3-a]quinoxaline was obtained by the same manner as described in Preparative Example 5, except that 6-methoxy-7-methyl-1,4-dihydro-quinoxaline-2,3-dione was used.

Step 1: Preparation of 2,3-dichloro-6-methoxy-7-methyl-quinoxaline

Mass (M+H$^+$): 243.0

$^1$H NMR (500 MHz, DMSO-d6) δ2.35 (s, 3H), 3.96 (s, 3H), 7.41 (s, 1H), 7.83 (s, 1H).

Step 2: Preparation of (3-chloro-7-methoxy-6-methyl-quinoxaline-2-yl)-hydrazine

Mass (M+H$^+$): 239.1

$^1$H NMR (500 MHz, DMSO-d6) δ2.21 (s, 3H), 3.87 (s, 3H), 4.48 (brs, 2H), 7.02 (s, 1H), 7.47 (s, 1H), 8.55 (s, 1H).

Step 3: Preparation of 4-chloro-8-methoxy-1,7-dimethyl-[1,2,4]triazolo[4,3-a]quinoxaline Mass (M+H$^+$): 263.0

$^1$H NMR (500 MHz, DMSO-d6): δ2.27 (s, 3H), 3.15 (s, 3H), 4.02 (s, 3H), 7.63 (s, 1H), 7.79 (s, 1H)

<Example 146> Preparation of [4-(8-methoxy-1,7-dimethyl-[1,2,4]triazolo[4,3-a]quinoxaline-4-ylamino)-butyl]-carbamic acid-tert-butylester

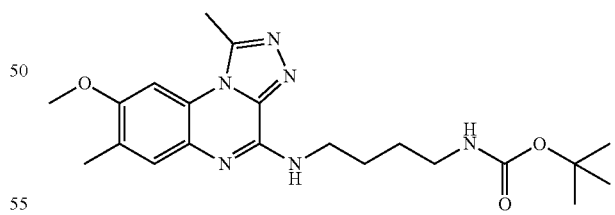

1.80 g of a target compound was obtained (84% yield) by the same manner as described in Example 57, except that 4-chloro-8-methoxy-1,7-dimethyl-[1,2,4]triazolo[4,3-a]quinoxaline (1.35 g, 5.14 mmol) prepared in step 3 of Preparative Example 11 was used.

Mass (M+H$^+$): 415.2

$^1$H NMR (500 MHz, DMSO-d6) δ1.32 (s, 9H), 1.42 (q, 2H), 1.59 (m, 2H), 2.19 (s, 3H), 2.92 (q, 2H), 3.04 (s, 3H), 3.44 (q, 2H), 3.89 (s, 3H), 6.75 (t, 1H), 7.38 (s, 1H), 7.44 (s, 1H), 7.73 (t, 1H).

<Example 147> Preparation of N¹-(8-methoxy-1,7-dimethyl-[1,2,4]triazolo[4,3-a]quinoxaline-4-yl)-butane-1,4-diamine ditrifluoroacetic acid

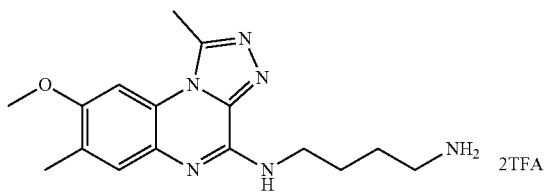 [SMILES: COc1cc2c(cc1C)nc(NCCCCN)c1nnc(C)n12]

1.4 g of a target compound was obtained (71% yield) by the same manner as described in Example 58, except that [4-(8-methoxy-1,7-dimethyl-[1,2,4]triazolo[4,3-a]quinoxaline-4-ylamino)-butyl]-carbamic acid-tert-butylester (1.5 g, 3.62 mmol) prepared in Example 146 was used.

Mass (M+H⁺): 315.1

¹H NMR (500 MHz, DMSO-d6) δ1.58 (m, 2H), 1.67 (m, 2H), 2.21 (s, 3H), 2.80 (m, 2H), 3.07 (s, 3H), 3.50 (q, 2H), 3.90 (s, 3H), 7.39 (s, 1H), 7.48 (s, 1H), 7.60 (brs, 2H), 7.86 (brs, 1H).

<Example 148> Preparation of N-[4-(8-methoxy-1,7-dimethyl-[1,2,4]triazolo[4,3-a]quinoxaline-4-ylamino)-butyl]-2,2-dimethyl-propionamide

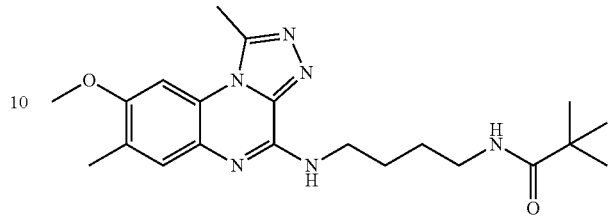

52 mg of a target compound was obtained (60% yield) by the same manner as described in Example 59, except that N¹-(8-methoxy-1,7-dimethyl-[1,2,4]triazolo[4,3-a]quinoxaline-4-yl)-butane-1,4-diamine ditrifluoroacetic acid (120 mg, 0.22 mmol) prepared in Example 147 was used.

Mass (M+H⁺): 399.1

¹H NMR (500 MHz, DMSO-d6) δ1.01 (s, 9H), 1.46 (q, 2H), 1.63 (m, 2H), 2.26 (s, 3H), 2.95 (s, 3H), 3.04 (q, 2H), 3.54 (q, 2H), 3.94 (s, 3H), 7.08 (d, 1H), 7.36 (t, 1H), 7.71 (d, 1H), 8.13 (t, 1H).

The compounds shown in Table 10 below were prepared by the same manner as described in Example 148.

TABLE 10

| Example | Structure | Name | Data |
|---|---|---|---|
| Example 149 | 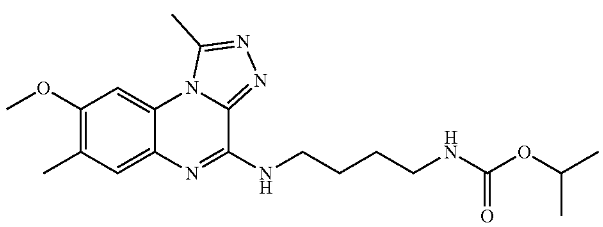 [SMILES: COc1cc2c(cc1C)nc(NCCCCNC(=O)OC(C)C)c1nnc(C)n12] | [4-(8-methoxy-1,7-dimethyl-[1,2,4]triazolo[4,3-a]quinoxaline-4-ylamino)-butyl]-carbamic acid isopropylester | Mass (M + H⁺): 401.1; ¹H NMR (500 MHz, DMSO-d6): δ1.09 (d, 6H), 1.44 (m, 2H), 1.59 (m, 2H), 2.19 (s, 3H), 2.95 (q, 2H), 3.05 (s, 3H), 3.45 (q, 2H), 3.89 (s, 3H), 4.68 (m, 1H), 6.94 (t, 1H), 7.39 (s, 1H), 7.46 (s, 1H), 7.74 (t, 1H). |
| Example 150 | 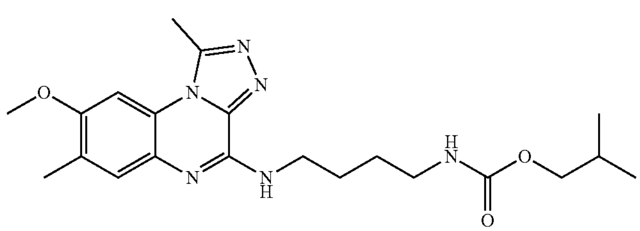 [SMILES: COc1cc2c(cc1C)nc(NCCCCNC(=O)OCC(C)C)c1nnc(C)n12] | [4-(8-methoxy-1,7-dimethyl-[1,2,4]triazolo[4,3-a]quinoxaline-4-ylamino)-butyl]-carbamic acid isobutylester | Mass (M + H⁺): 415.2; ¹H NMR (500 MHz, DMSO-d6): δ0.81 (d, 6H), 1.43 (m, 2H), 1.60 (m, 2H), 1.76 (m, 1H), 2.20 (s, 3H), 2.97 (q, 2H), 3.05 (s, 3H), 3.45 (q, 2H), 3.66 (d, 1H), 3.89 (s, 3H), 7.03 (t, 1H), 7.40 (s, 1H), 7.47 (s, 1H), 7.75 (t, 1H). |
| Example 151 | 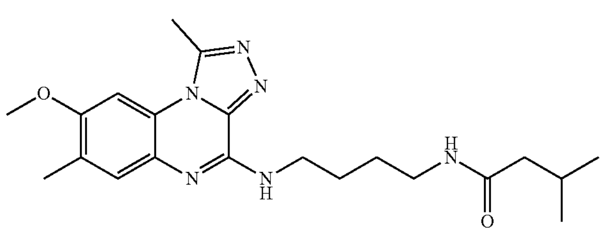 [SMILES: COc1cc2c(cc1C)nc(NCCCCNC(=O)CC(C)C)c1nnc(C)n12] | N-[4-(8-methoxy-1,7-dimethyl-[1,2,4]triazolo[4,3-a]quinoxaline-4-ylamino)-butyl]-3-methyl-butyramide | Mass (M + H⁺): 399.2; ¹H NMR (500 MHz, DMSO-d6): δ0.79 (d, 6H), 1.44 (m, 2H), 1.60 (m, 2H), 1.86 (m, 2H), 1.91 (m, 1H), 2.20 (s, 3H), 3.03 (q, 2H), 3.05 (s, 3H), 3.90 (s, 3H), 7.39 (s, 1H), 7.47 (s, 1H), 7.69 (t, 1H), 7.75 (t, 1H). |

TABLE 10-continued

| Example | Structure | Name | Data |
|---|---|---|---|
| Example 152 | 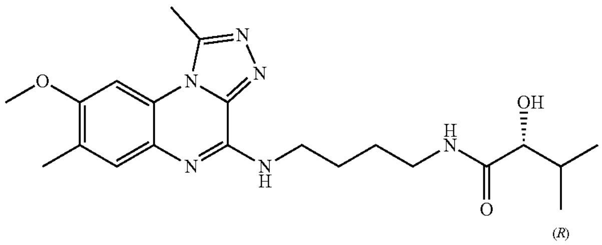 | 2-(R)-hydroxy-N-[4-(8-methoxy-1,7-dimethyl-[1,2,4]triazolo[4,3-a]quinoxaline-4-ylamino)-butyl]-3-methyl-butyramide | Mass (M + H$^+$): 415.2; $^1$H NMR (500 MHz, DMSO-d6): δ0.68 (d, 3H), 0.83 (d, 3H), 1.46 (m, 2H), 1.60 (m, 2H), 1.91 (m, 1H), 2.21 (s, 3H), 3.03 (s, 3H), 3.15 (q, 2H), 3.45 (q, 2H), 3.60 (d, 1H), 5.23 (d, 1H), 7.36 (s, 1H), 7.41 (s, 1H), 7.75 (t, 1H), 7.94 (t, 1H). |
| Example 153 | 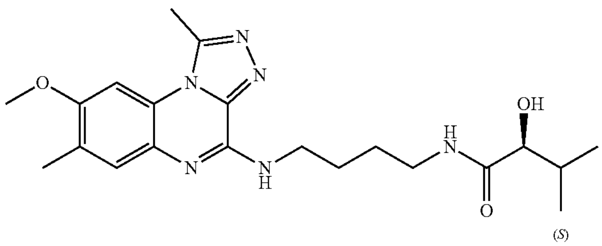 | 2-(S)-hydroxy-N-[4-(8-methoxy-1,7-dimethyl-[1,2,4]triazolo[4,3-a]quinoxaline-4-ylamino)-butyl]-3-methyl-butyramide | Mass (M + H$^+$): 415.2; $^1$H NMR (500 MHz, DMSO-d6): δ0.68 (d, 3H), 0.83 (d, 3H), 1.46 (m, 2H), 1.60 (m, 2H), 1.91 (m, 1H), 2.21 (s, 3H), 3.03 (s, 3H), 3.15 (q, 2H), 3.45 (q, 2H), 3.60 (d, 1H), 5.23 (d, 1H), 7.36 (s, 1H), 7.41 (s, 1H), 7.75 (t, 1H), 7.94 (t, 1H). |
| Example 154 | 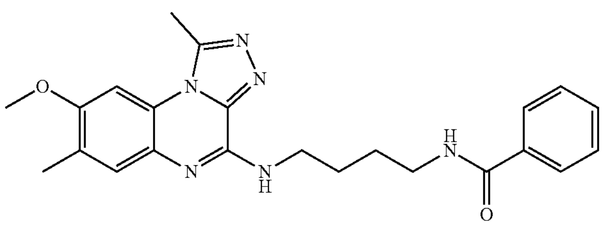 [SMILES: COc1cc2c(cc1C)nc(NCCCCNC(=O)c1ccccc1)c1nnc(C)n12] | N-[4-(8-methoxy-1,7-dimethyl-[1,2,4]triazolo[4,3-a]quinoxaline-4-ylamino)-butyl]-benzamide | Mass (M + H$^+$): 419.2; $^1$H NMR (500 MHz, DMSO-d6): δ1.57 (m, 2H), 1.68 (m, 2H), 2.18 (s, 3H), 3.05 (s, 3H), 3.27 (m, 2H), 3.49 (q, 2H), 3.89 (s, 3H), 7.39 (m, 3H), 7.46 (m, 2H), 7.77 (m, 3H), 8.40 (t, 1H). |
| Example 155 | 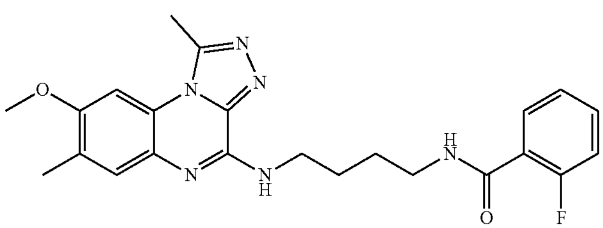 [SMILES: COc1cc2c(cc1C)nc(NCCCCNC(=O)c1ccccc1F)c1nnc(C)n12] | 2-fluoro-N-[4-(8-methoxy-1,7-dimethyl-[1,2,4]triazolo[4,3-a]quinoxaline-4-ylamino)-butyl]-benzamide | Mass (M + H$^+$): 437.2; $^1$H NMR (500 MHz, DMSO-d6): δ1.57 (m, 2H), 1.69 (m, 2H), 2.19 (s, 3H), 3.05 (s, 3H), 3.24 (m, 2H), 3.50 (q, 2H), 3.89 (s, 3H), 7.19 (m, 1H), 7.22 (d, 1H), 7.39 (s, 1H), 7.34 (m, 1H), 7.47 (s, 1H), 7.53 (t, 1H), 7.77 (t, 1H), 8.25 (t, 1H). |
| Example 156 | 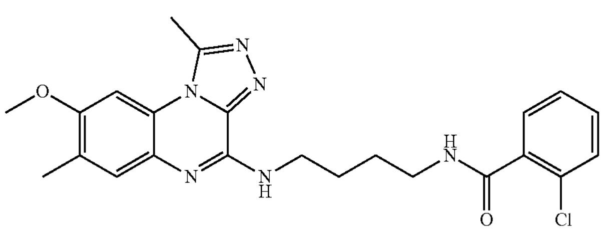 [SMILES: COc1cc2c(cc1C)nc(NCCCCNC(=O)c1ccccc1Cl)c1nnc(C)n12] | 2-chloro-N-[4-(8-methoxy-1,7-dimethyl-[1,2,4]triazolo[4,3-a]quinoxaline-4-ylamino)-butyl]-benzamide | Mass (M + H$^+$): 453.1; $^1$H NMR (500 MHz, DMSO-d6): δ1.56 (m, 2H), 1.70 (m, 2H), 2.19 (s, 3H), 3.05 (s, 3H), 3.23 (m, 2H), 3.49 (m, 2H), 3.89 (s, 3H), 7.28 (m, 1H), 7.33 (m, 1H), 7.34 (m, 1H), 7.40 (m, 2H), 7.46 (m, 1H), 7.78 (t, 1H), 8.35 (t, 1H). |

TABLE 10-continued

| Example | Structure | Name | Data |
|---|---|---|---|
| Example 157 | 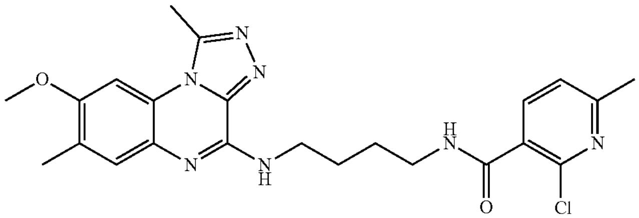 | 2-chloro-N-[4-(8-methoxy-1,7-dimethyl-[1,2,4]triazolo[4,3-a]quinoxaline-4-ylamino)-butyl]-6-methyl nicotinamide | Mass (M + H$^+$): 468.2; $^1$H NMR (500 MHz, DMSO-d6): δ1.57 (m, 2H), 1.70 (m, 2H), 2.20 (s, 3H), 2.41 (s, 3H), 3.06 (s, 3H), 3.24 (q, 2H), 3.49 (q, 2H), 3.90 (s, 3H), 7.24 (d, 1H), 7.39 (s, 1H), 7.47 (s, 1H), 7.68 (d, 1H), 7.79 (t, 1H), 8.43 (t, 1H). |

<Preparative Example 12> Preparation of 4-chloro-8-methoxy-1,6-dimethyl-[1,2,4]triazolo[4,3-a]quinoxaline 4-Chloro-8-methoxy-1,6-dimethyl-[1,2,4]triazolo[4,3-a]quinoxaline was obtained by the same manner as described in Preparative Example 5, except that 6-methoxy-8-methyl-1,4-dihydro-quinoxaline-2,3-dione was used.

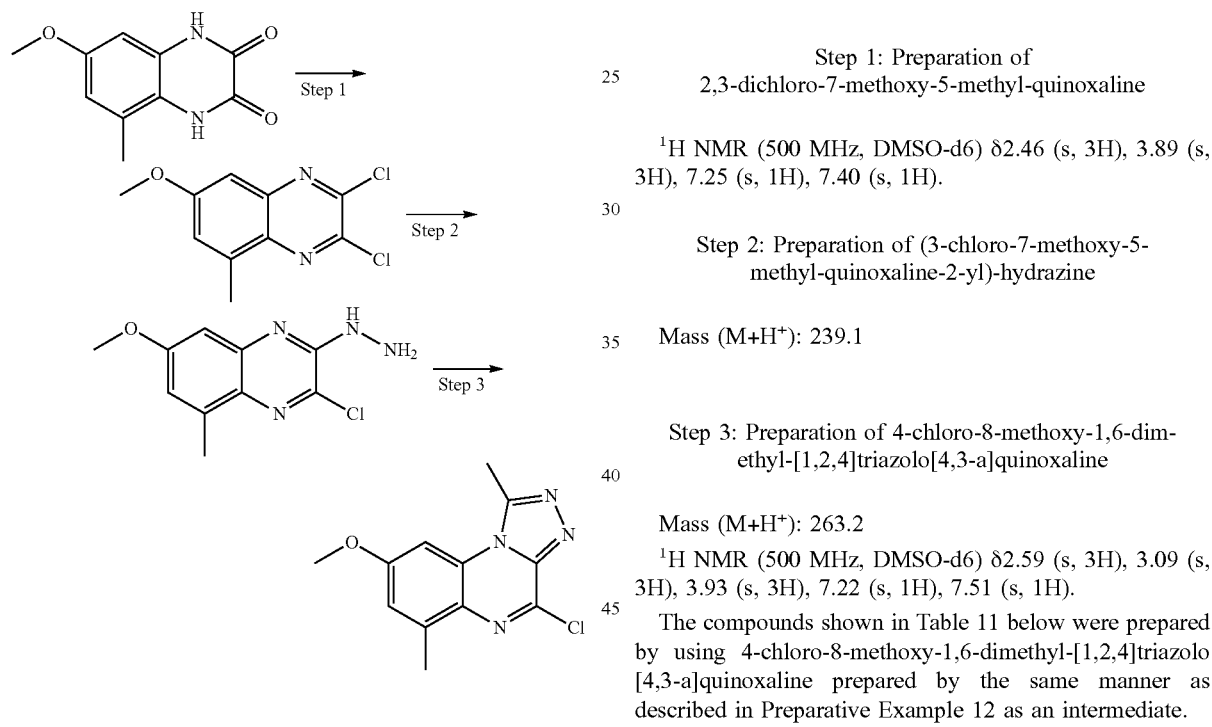

Step 1: Preparation of 2,3-dichloro-7-methoxy-5-methyl-quinoxaline $^1$H NMR (500 MHz, DMSO-d6) δ2.46 (s, 3H), 3.89 (s, 3H), 7.25 (s, 1H), 7.40 (s, 1H).

Step 2: Preparation of (3-chloro-7-methoxy-5-methyl-quinoxaline-2-yl)-hydrazine Mass (M+H$^+$): 239.1

Step 3: Preparation of 4-chloro-8-methoxy-1,6-dimethyl-[1,2,4]triazolo[4,3-a]quinoxaline Mass (M+H$^+$): 263.2

$^1$H NMR (500 MHz, DMSO-d6) δ2.59 (s, 3H), 3.09 (s, 3H), 3.93 (s, 3H), 7.22 (s, 1H), 7.51 (s, 1H).

The compounds shown in Table 11 below were prepared by using 4-chloro-8-methoxy-1,6-dimethyl-[1,2,4]triazolo[4,3-a]quinoxaline prepared by the same manner as described in Preparative Example 12 as an intermediate.

TABLE 11

| Example | Structure | Name | Data |
|---|---|---|---|
| Example 158 | 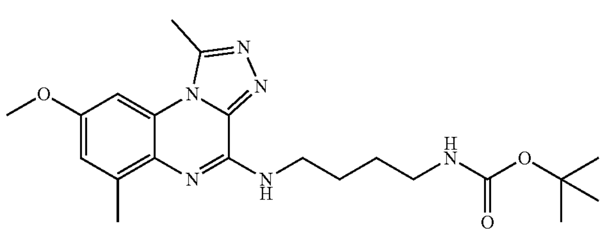 [SMILES: COc1cc(C)c2nc(NCCCCNC(=O)OC(C)(C)C)c3nnc(C)n3c2c1] | [4-(8-methoxy-1,6-dimethyl-[1,2,4]triazolo[4,3-a]quinoxaline-4-ylamino)-butyl]-carbamic acid-tert-butylester | Mass (M + H$^+$): 415.2; $^1$H NMR (500 MHz, DMSO-d6): δ1.31 (s, 9H), 1.44 (m, 2H), 1.63 (m, 2H), 2.47 (s, 3H), 2.92 (q, 2H), 3.00 (s, 3H), 3.49 (q, 2H), 3.82 (s, 3H), 6.73 (t, 1H), 7.00 (s, 1H), 7.37 (s, 1H), 7.80 (t, 1H). |

TABLE 11-continued

| Example | Structure | Name | Data |
|---|---|---|---|
| Example 159 | 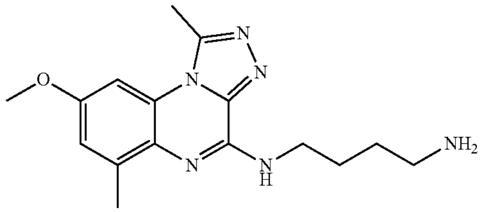 | $N^1$-(8-methoxy-1,6-dimethyl-[1,2,4]triazolo[4,3-a]quinoxaline-4-yl)-butane-1,4-diamine ditrifluoroacetic acid | Mass (M + H$^+$): 315.2; $^1$H NMR (500 MHz, DMSO-d6): δ1.61 (m, 2H), 1.71 (m, 2H), 2.50 (s, 3H), 2.80 (m, 2H), 3.02 (s, 3H), 3.54 (q, 2H), 3.81 (s, 3H), 7.01 (s, 1H), 7.37 (s, 1H), 7.67 (brs, 2H), 7.87 (t, 1H). |
| Example 160 | 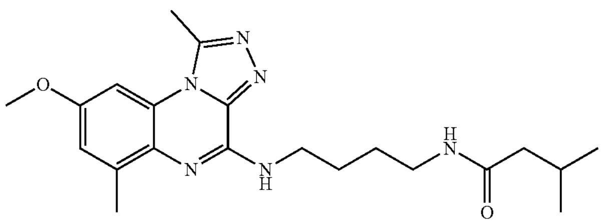 [SMILES: COc1cc(C)c2nc(NCCCCNC(=O)CC(C)C)c3nnc(C)n3c2c1] | N-[4-(8-methoxy-1,6-dimethyl-[1,2,4]triazolo[4,3-a]quinoxaline-4-ylamino)-butyl]-3-methyl-butyramide | Mass (M + H$^+$): 399.2; $^1$H NMR (500 MHz, DMSO-d6): δ0.79 (d, 6H), 1.45 (m, 2H), 1.66 (m, 2H), 1.85 (d, 2H), 1.85 (m, 1H), 2.58 (s, 3H), 3.02 (s, 2H), 3.04 (q, 2H), 3.38 (s, 3H), 7.00 (s, 1H), 7.37 (s, 1H), 7.68 (t, 1H), 7.80 (t, 1H). |
| Example 161 | 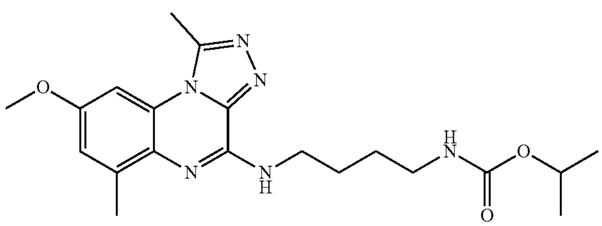 [SMILES: COc1cc(C)c2nc(NCCCCNC(=O)OC(C)C)c3nnc(C)n3c2c1] | [4-(8-methoxy-1,6-dimethyl-[1,2,4]triazolo[4,3-a]quinoxaline-4-ylamino)-butyl]-carbamic acid isopropylester | Mass (M + H$^+$): 399.2; $^1$H NMR (500 MHz, DMSO-d6): δ0.79 (d, 6H), 1.45 (m, 2H), 1.66 (m, 2H), 1.85 (d, 2H), 1.85 (m, 1H), 2.58 (s, 3H), 3.02 (s, 2H), 3.04 (q, 2H), 3.38 (s, 3H), 7.00 (s, 1H), 7.37 (s, 1H), 7.68 (t, 1H), 7.80 (t, 1H). |

<Preparative Example 13> Preparation of 4-chloro-7,8-bis-(2-methoxy-ethoxy)-1-methyl-[1,2,4]triazolo[4,3-a]quinoxaline

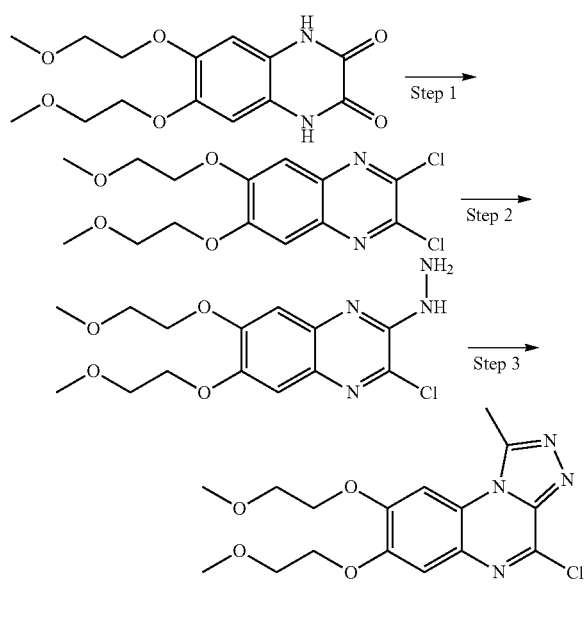

4-Chloro-7,8-bis-(2-methoxy-ethoxy)-1-methyl-[1,2,4]triazolo[4,3-a]quinoxaline was obtained by the same manner as described in Preparative Example 5, except that 6,7-bis-(2-methoxy-ethoxy)-1,4-dihydro-quinoxaline-2,3-dione was used.

Step 1: Preparation of 2,3-dichloro-6,7-bis-(2-methoxy-ethoxy)-quinoxaline

Mass (M+H$^+$): 347.0

$^1$H NMR (500 MHz, DMSO-d6): δ3.31 (s, 6H), 3.72 (t, 4H), 4.29 (t, 4H), 7.45 (s, 2H).

Step 2: Preparation of [3-chloro-6,7-bis-(2-methoxy-ethoxy)-quinoxaline-2-yl]-hydrazine Mass (M+H$^+$): 343.1

$^1$H NMR (500 MHz, DMSO-d6): δ3.30 (s, 6H), 3.68 (m, 4H), 4.15 (t, 2H), 4.20 (t, 2H), 4.43 (brs, 2H), 7.08 (s, 1H), 7.19 (s, 1H), 8.36 (s, 1H).

Step 3: Preparation of 4-chloro-7,8-bis-(2-methoxy-ethoxy)-1-methyl-[1,2,4]triazolo[4,3-a]quinoxaline Mass (M+H$^+$): 367.1

$^1$H NMR (500 MHz, DMSO-d6): δ3.07 (s, 3H), 3.30 (s, 3H), 3.32 (s, 3H), 3.69 (t, 2H), 3.74 (t, 2H), 4.24 (t, 2H), 4.38 (t, 2H), 7.56 (s, 1H), 7.75 (s, 1H).

<Example 162> Preparation of {4-[7,8-bis-(2-methoxy-ethoxy)-1-methyl-[1,2,4]triazolo[4,3-a]quinoxaline-4-ylamino]-butyl}-carbamic acid-tert-butylester

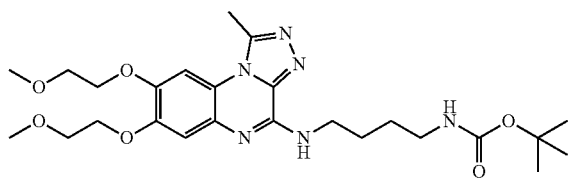 [SMILES: COCCOc1cc2nc(NCCCCNC(=O)OC(C)(C)C)c3nnc(C)n3c2cc1OCCOC]

1.14 g of a target compound was obtained (70% yield) by the same manner as described in Example 57, except that 4-chloro-7,8-bis-(2-methoxy-ethoxy)-1-methyl-[1,2,4]triazolo[4,3-a]quinoxaline (1.15 g, 3.14 mmol) prepared in step 3 of Preparative Example 13 was used.
Mass (M+H$^+$): 519.3
$^1$H NMR (500 MHz, DMSO-d6): δ1.32 (s, 9H), 1.43 (m, 2H), 1.59 (m, 2H), 2.91 (m, 2H), 3.00 (s, 3H), 3.27 (s, 3H), 3.31 (s, 3H), 3.46 (m, 2H), 3.67 (m, 4H), 4.16 (m, 2H), 4.21 (m, 2H), 6.75 (t, 1H), 7.11 (s, 1H), 7.57 (s, 1H), 7.81 (t, 1H).

<Example 163> Preparation of N$^1$-[7,8-bis-(2-methoxy-ethoxy)-1-methyl-[1,2,4]triazolo[4,3-a]quinoxaline-4-yl]-butane-1,4-diamine ditrifluoroacetic acid

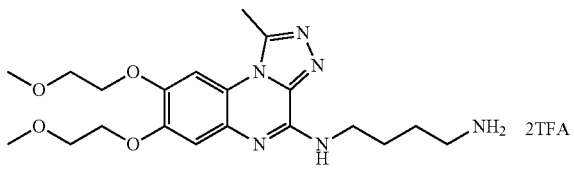 [SMILES: COCCOc1cc2nc(NCCCCN)c3nnc(C)n3c2cc1OCCOC]

1.22 g of a target compound was obtained (88% yield) by the same manner as described in Example 58, except that {4-[7,8-bis-(2-methoxy-ethoxy)-1-methyl-[1,2,4]triazolo[4,3-a]quinoxaline-4-ylamino]-butyl}-carbamic acid-tert-butylester (1.1 g, 2.1 mmol) prepared in Example 162 was used.
Mass (M+H$^+$): 419.2
$^1$H NMR (500 MHz, DMSO-d6): δ1.59 (m, 2H), 1.68 (m, 2H), 2.82 (m, 2H), 3.01 (s, 3H), 3.31 (s, 6H), 3.53 (q, 2H), 3.68 (m, 4H), 4.16 (t, 2H), 4.22 (t, 2H), 7.11 (s, 1H), 7.59 (s, brm, 2H), 7.93 (t, 1H).

<Example 164> Preparation of N-{4-[7,8-bis-(2-methoxy-ethoxy)-1-methyl-[1,2,4]triazolo[4,3-a]quinoxaline-4-ylamino]-butyl}-2,2-dimethyl-propionamide

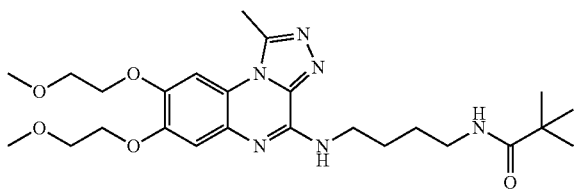 [SMILES: COCCOc1cc2nc(NCCCCNC(=O)C(C)(C)C)c3nnc(C)n3c2cc1OCCOC]

111 mg of a target compound was obtained (100% yield) by the same manner as described in Example 59, except that N$^1$-{4-[7,8-bis-(2-methoxy-ethoxy)-1-methyl-[1,2,4]triazolo[4,3-a]quinoxaline-4-yl]-butane-1,4-diamine ditrifluoroacetic acid (120 mg, 0.19 mmol) prepared in Example 163 was used.
Mass (M+H$^+$): 503.3
$^1$H NMR (500 MHz, DMSO-d6) δ1.02 (s, 9H), 1.45 (m, 2H), 1.60 (m, 2H), 3.00 (s, 3H), 3.04 (q, 2H), 3.30 (s, 3H), 3.31 (s, 3H), 3.47 (q, 2H), 3.67 (m, 4H), 4.16 (t, 2H), 4.22 (t, 2H), 7.11 (s, 1H), 7.37 (t, 1H), 7.58 (s, 1H), 7.81 (t, 1H).

The compounds shown in Table 12 below were prepared by the same manner as described in Example 164.

TABLE 12

| Example | Structure | Name | Data |
|---|---|---|---|
| Example 165 | 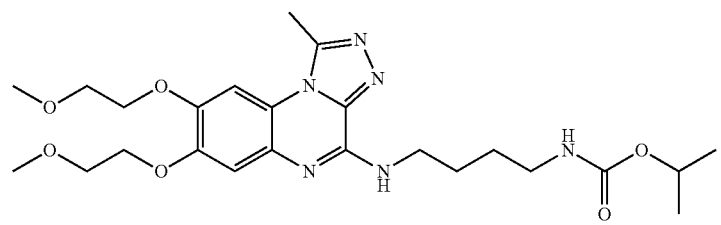 [SMILES: COCCOc1cc2nc(NCCCCNC(=O)OC(C)C)c3nnc(C)n3c2cc1OCCOC] | {4-[7,8-bis-(2-methoxy-ethoxy)-1-methyl-[1,2,4]triazolo[4,3-a]quinoxaline-4-ylamino]-butyl}-carbamic acid isopropylester | Mass (M + H$^+$): 505.2; $^1$H NMR (500 MHz, DMSO-d6): δ1.09 (d, 6H), 1.44 (m, 2H), 1.60 (m, 2H), 2.96 (q, 2H), 3.00 (s, 3H), 3.30 (s, 3H), 3.31 (s, 3H), 3.47 (q, 2H), 3.67 (m, 4H), 4.18 (t, 2H), 4.21 (t, 2H), 4.68 (m, 1H), 6.94 (t, 1H), 7.12 (s, 1H), 7.58 (s, 1H), 7.82 (t, 1H). |
| Example 166 | 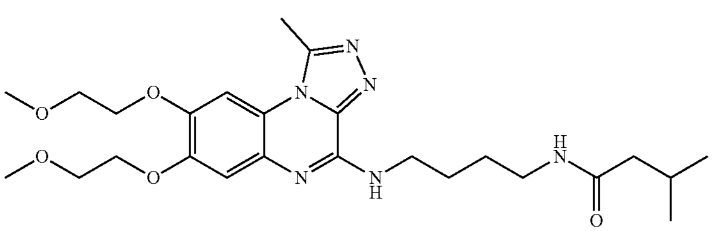 [SMILES: COCCOc1cc2nc(NCCCCNC(=O)CC(C)C)c3nnc(C)n3c2cc1OCCOC] | N-{4-[7,8-bis-(2-methoxy-ethoxy)-1-methyl-[1,2,4]triazolo[4,3-a]quinoxaline-4-ylamino]-butyl}-3-methyl-butyramide | Mass (M + H$^+$): 503.3; $^1$H NMR (500 MHz, DMSO-d6): δ0.80 (d, 6H), 1.44 (t, 2H), 1.61 (t, 2H), 1.86 (t, 2H), 1.91 (m, 1H), 3.00 (s, 3H), 3.04 (q, 2H), 3.30 (s, 3H), 3.33 (s, 3H), 3.48 (q, 2H), 3.67 (m, 4H), 4.16 (t, 2H), 4.22 (t, 2H), 7.11 (s, 1H), 7.58 (s, 1H), 7.89 (t, 1H), 7.82 (t, 1H). |

TABLE 12-continued

| Example | Structure | Name | Data |
|---|---|---|---|
| Example 167 | 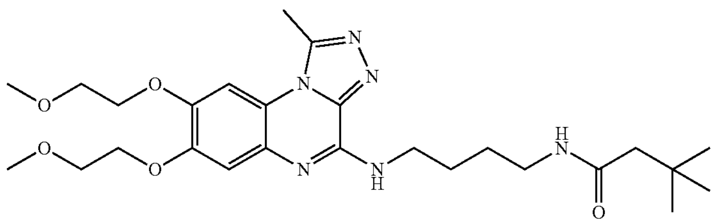 [SMILES: COCCOc1cc2nc(NCCCCNC(=O)CC(C)(C)C)c3nnc(C)n3c2cc1OCCOC] | N-{4-[7,8-bis-(2-methoxy-ethoxy)-1-methyl-[1,2,4]triazolo[4,3-a]quinoxaline-4-ylamino]-butyl}-3,3-dimethyl-butyramide | Mass (M + H$^+$): 517.1; $^1$H NMR (500 MHz, DMSO-d6): δ0.88 (s, 9H), 1.43 (m, 2H), 1.62 (m, 2H), 1.87 (s, 2H), 3.00 (s, 3H), 3.03 (m, 2H), 3.30 (s, 3H), 3.31 (s, 3H), 3.48 (q, 2H), 3.67 (m, 4H), 4.16 (t, 2H), 4.22 (t, 2H), 7.11 (s, 1H), 7.58 (s, 1H), 7.64 (t, 1H), 7.83 (t, 1H). |
| Example 168 | 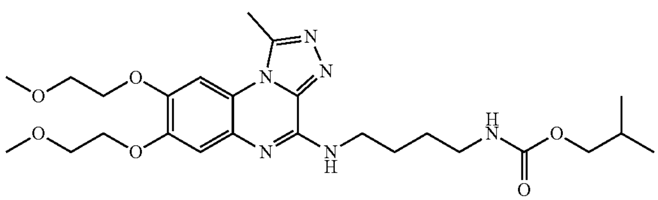 [SMILES: COCCOc1cc2nc(NCCCCNC(=O)OCC(C)C)c3nnc(C)n3c2cc1OCCOC] | {4-[7,8-bis-(2-methoxy-ethoxy)-1-methyl-[1,2,4]triazolo[4,3-a]quinoxaline-4-ylamino]-butyl}-carbamic acid isobutylester | Mass (M + H$^+$): 519.3; $^1$H NMR (500 MHz, DMSO-d6): δ0.81 (d, 6H), 1.44 (m, 2H), 1.61 (m, 2H), 1.76 (m, 1H), 2.97 (m, 2H), 3.00 (s, 3H), 3.48 (q, 2H), 3.67 (m, 6H), 4.17 (t, 2H), 4.22 (t, 2H), 7.03 (t, 1H), 7.12 (s, 1H), 7.58 (s, 1H), 7.82 (t, 1H). |
| Example 169 | 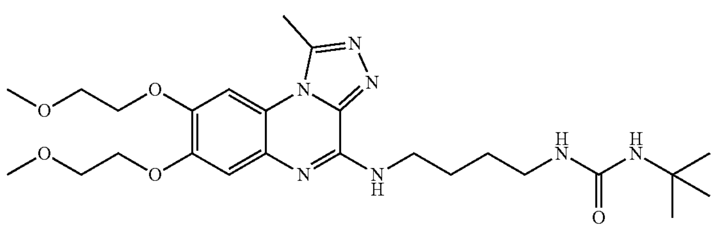 [SMILES: COCCOc1cc2nc(NCCCCNC(=O)NC(C)(C)C)c3nnc(C)n3c2cc1OCCOC] | 1-{4-[7,8-bis-(2-methoxy-ethoxy)-1-methyl-[1,2,4]triazolo[4,3-a]quinoxaline-4-ylamino]-butyl}-3-tert-butyl-urea | Mass (M + H$^+$): 518.2; $^1$H NMR (500 MHz, DMSO-d6): δ1.15 (s, 9H), 1.39 (m, 2H), 1.60 (m, 2H), 2.93 (q, 2H), 3.00 (s, 3H), 3.30 (s, 3H), 3.31 (s, 3H), 3.48 (q, 2H), 3.67 (m, 4H), 4.17 (t, 2H), 4.22 (t, 2H), 5.49 (s, 1H), 5.57 (t, 1H), 7.12 (s, 1H), 7.58 (s, 1H), 7.83 (t, 1H). |
| Example 170 | 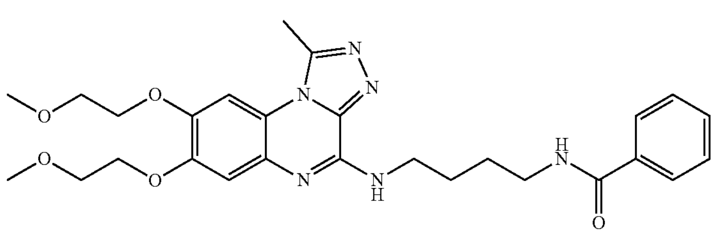 [SMILES: COCCOc1cc2nc(NCCCCNC(=O)c3ccccc3)c3nnc(C)n3c2cc1OCCOC] | N-{4-[7,8-bis-(2-methoxy-ethoxy)-1-methyl-[1,2,4]triazolo[4,3-a]quinoxaline-4-ylamino]-butyl}-benzamide | Mass (M + H$^+$): 523.3; $^1$H NMR (500 MHz, DMSO-d6): δ1.59 (m, 2H), 1.67 (m, 2H), 3.00 (s, 3H), 3.27 (s, 3H), 3.29 (s, 3H), 3.51 (m, 2H), 3.67 (m, 4H), 4.14 (t, 2H), 4.21 (t, 2H), 7.11 (s, 1H), 7.39 (dd, 2H), 7.46 (m, 1H), 7.58 (s, 1H), 7.78 (d, 2H), 7.85 (t, 1H), 8.04 (t, 1H). |

141

TABLE 12-continued

| Example | Structure | Name | Data |
|---|---|---|---|
| Example 171 | 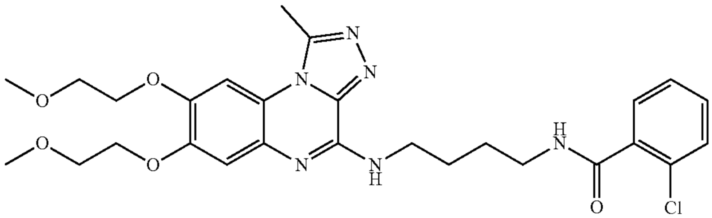 [SMILES: COCCOc1cc2nc(NCCCCNC(=O)c3ccccc3Cl)c3nnc(C)n3c2cc1OCCOC] | N-{4-[7,8-bis-(2-methoxy-ethoxy)-1-methyl-[1,2,4]triazolo[4,3-a]quinoxaline-4-ylamino]-butyl}-2-chloro-benzamide | Mass (M + H⁺): 557.1; ¹H NMR (500 MHz, DMSO-d6): δ1.56 (m, 2H), 1.71 (m, 2H), 3.01 (s, 3H), 3.23 (q, 2H), 3.29 (s, 3H), 3.31 (s, 3H), 3.52 (q, 2H), 3.68 (m, 4H), 4.15 (t, 2H), 4.22 (t, 2H), 7.12 (s, 1H), 7.20 (m, 1H), 7.33 (t, 1H), 7.36 (t, 1H), 7.42 (d, 1H), 7.58 (s, 1H), 7.85 (t, 1H), 8.36 (t, 1H). |
| Example 172 | 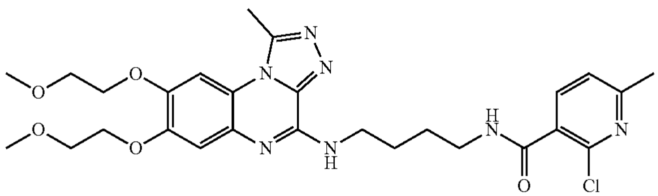 | N-{4-[7,8-bis-(2-methoxy-ethoxy)-1-methyl-[1,2,4]triazolo[4,3-a]quinoxaline-4-ylamino]-butyl}-2-chloro-6-methyl-nicotinamide | Mass (M + H⁺): 572.2; ¹H NMR (500 MHz, DMSO-d6): δ1.57 (m, 2H), 1.71 (m, 2H), 2.41 (s, 3H), 3.01 (s, 3H), 3.22 (q, 2H), 3.30 (s, 3H), 3.31 (s, 3H), 3.49 (q, 2H), 3.68 (m, 4H), 4.15 (t, 2H), 4.22 (t, 2H), 7.12 (s, 1H), 7.24 (d, 1H), 7.58 (s, 1H), 7.68 (d, 1H), 7.86 (t, 1H), 8.44 (t, 1H). |

<Preparative Example 14> Preparation of 4-chloro-7,8-diethoxy-1-methyl-[1,2,4]triazolo[4,3-a]quinoxaline

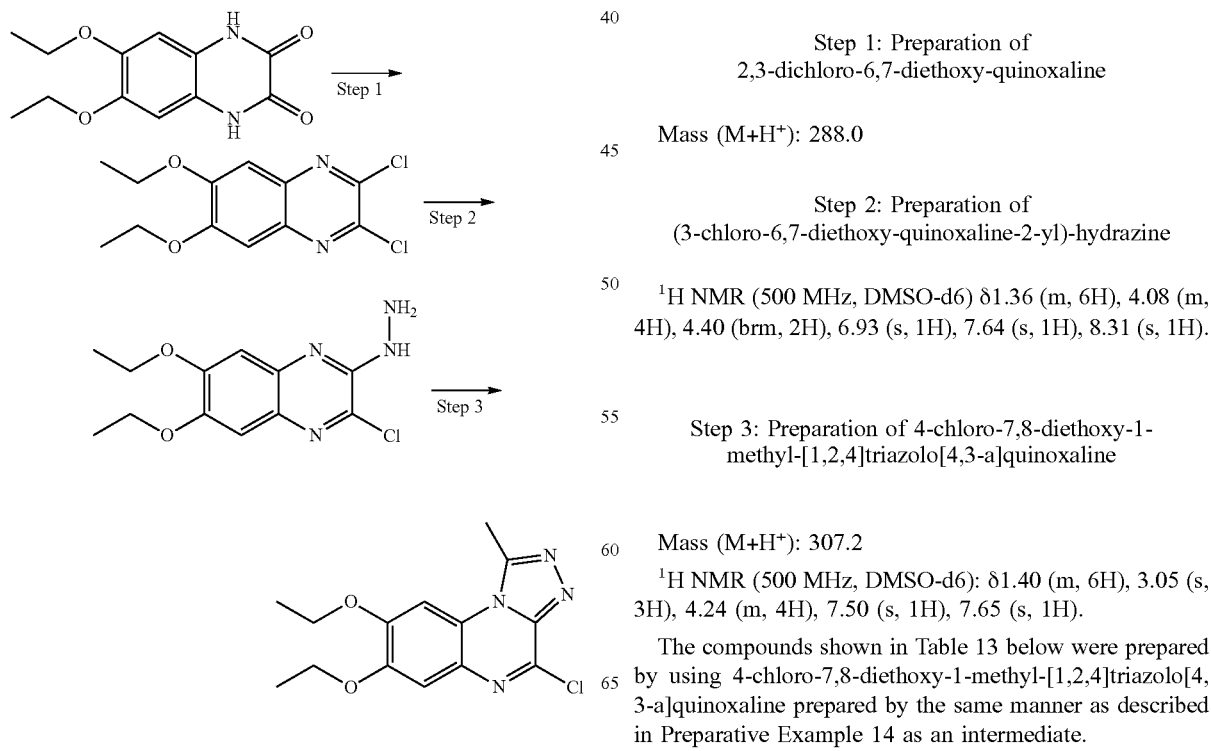

4-Chloro-7,8-diethoxy-1-methyl-[1,2,4]triazolo[4,3-a]quinoxaline was obtained by the same manner as described in Preparative Example 5, except that 6,7-diethoxy-1,4-dihydro-quinoxaline-2,3-dione was used.

Step 1: Preparation of 2,3-dichloro-6,7-diethoxy-quinoxaline

Mass (M+H⁺): 288.0

Step 2: Preparation of (3-chloro-6,7-diethoxy-quinoxaline-2-yl)-hydrazine

¹H NMR (500 MHz, DMSO-d6) δ1.36 (m, 6H), 4.08 (m, 4H), 4.40 (brm, 2H), 6.93 (s, 1H), 7.64 (s, 1H), 8.31 (s, 1H).

Step 3: Preparation of 4-chloro-7,8-diethoxy-1-methyl-[1,2,4]triazolo[4,3-a]quinoxaline Mass (M+H⁺): 307.2

¹H NMR (500 MHz, DMSO-d6): δ1.40 (m, 6H), 3.05 (s, 3H), 4.24 (m, 4H), 7.50 (s, 1H), 7.65 (s, 1H).

The compounds shown in Table 13 below were prepared by using 4-chloro-7,8-diethoxy-1-methyl-[1,2,4]triazolo[4,3-a]quinoxaline prepared by the same manner as described in Preparative Example 14 as an intermediate.

TABLE 13

| Example | Structure | Name | Data |
|---|---|---|---|
| Example 173 | 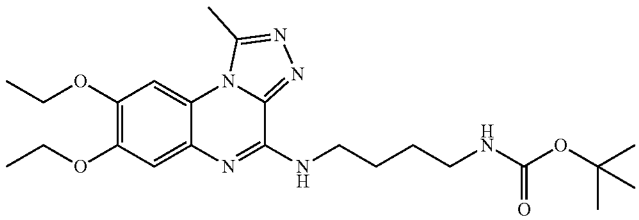 [SMILES: CCOc1cc2nc(NCCCCNC(=O)OC(C)(C)C)c3nnc(C)n3c2cc1OCC] | [4-(7,8-diethoxy-1-methyl-[1,2,4]triazolo[4,3-a]quinoxaline-4-ylamino)-butyl-carbamic acid-tert-butylester | Mass (M + H$^+$): 459.3; $^1$H NMR (500 MHz, DMSO-d6): δ1.32 (s, 9H), 1.34 (m, 6H), 1.42 (m, 2H), 1.65 (m, 2H), 2.92 (q, 2H), 3.00 (s, 1H), 3.46 (q, 2H), 4.12 (m, 4H), 6.75 (t, 1H), 7.08 (s, 1H), 7.50 (s, 1H), 7.79 (t, 1H). |
| Example 174 | 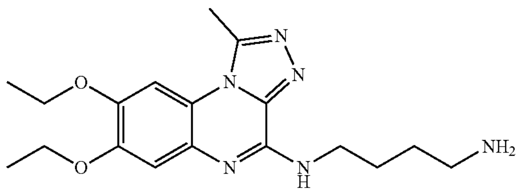 | N$^1$-(7,8-diethoxy-1-methyl-[1,2,4]triazolo[4,3-a]quinoxaline-4-yl)-butane-1,4-diamine ditrifluoroacetic acid | Mass (M + H$^+$): 359.2; $^1$H NMR (500 MHz, DMSO-d6): δ1.34 (m, 6H), 1.59 (m, 2H), 1.68 (m, 2H), 2.81 (q, 2H), 3.01 (s, 3H), 3.51 (q, 2H), 4.09 (m, 2H), 4.14 (m, 2H), 7.09 (s, 1H), 7.51 (s, 1H), 7.67 (brs, 2H), 8.08 (brs, 1H). |
| Example 175 | 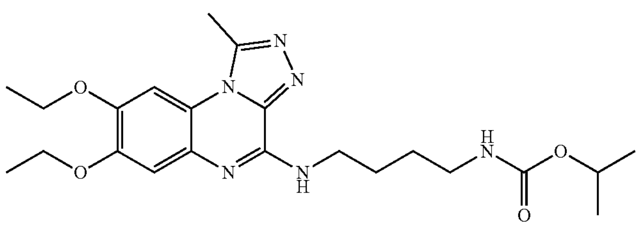 [SMILES: CCOc1cc2nc(NCCCCNC(=O)OC(C)C)c3nnc(C)n3c2cc1OCC] | [4-(7,8-diethoxy-1-methyl-[1,2,4]triazolo[4,3-a]quinoxaline-4-ylamino)-butyl]-carbamic acid isopropylester | Mass (M + H$^+$): 445.2; $^1$H NMR (500 MHz, DMSO-d6): δ1.10 (d, 6H), 1.16 (m, 6H), 1.36 (m, 2H), 1.60 (m, 2H), 3.00 (q, 2H), 3.05 (s, 3H), 3.47 (q, 2H), 4.12 (m, 4H), 4.68 (m, 1H), 6.94 (t, 1H), 7.09 (s, 1H), 7.50 (s, 1H), 7.80 (t, 1H). |
| Example 176 | 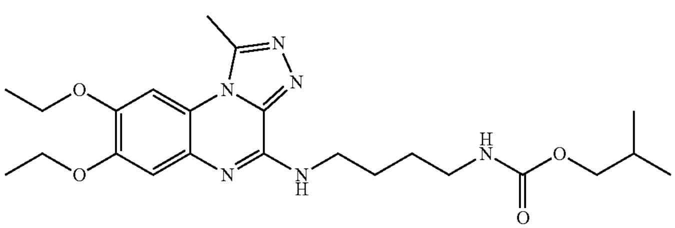 [SMILES: CCOc1cc2nc(NCCCCNC(=O)OCC(C)C)c3nnc(C)n3c2cc1OCC] | [4-(7,8-diethoxy-1-methyl-[1,2,4]triazolo[4,3-a]quinoxaline-4-ylamino)-butyl]-carbamic acid isobutylester | Mass (M + H$^+$): 459.3; $^1$H NMR (500 MHz, DMSO-d6): δ0.82 (d, 6H), 1.13 (d, 2H), 1.32 (m, 6H), 1.44 (m, 2H), 1.61 (m, 2H), 1.76 (m, 1H), 3.00 (s, 3H), 3.47 (q, 2H), 3.66 (q, 2H), 4.12 (m, 4H), 7.03 (t, 1H), 7.08 (s, 1H), 7.50 (s, 1H), 7.78 (t, 1H). |
| Example 177 | 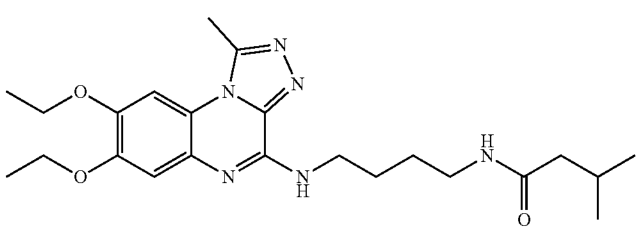 [SMILES: CCOc1cc2nc(NCCCCNC(=O)CC(C)C)c3nnc(C)n3c2cc1OCC] | N-[4-(7,8-diethoxy-1-methyl-[1,2,4]triazolo[4,3-a]quinoxaline-4-ylamino)-butyl-3-methyl-butyramide | Mass (M + H$^+$): 443.2; $^1$H NMR (500 MHz, DMSO-d6): 0.80 (d, 6H), 1.33 (m, 6H), 1.41 (m, 2H), 1.70 (m, 2H), 1.86 (m, 1H), 1.87 (m, 2H), 3.00 (s, 3H), 3.04 (q, 2H), 3.47 (q, 2H), 4.12 (m, 4H), 7.08 (s, 1H), 7.51 (s, 1H), 7.69 (t, 1H), 7.79 (t, 1H). |

<Preparative Example 15> Preparation of 4-chloro-1-methyl-8,9-dihydro-7,10-dioxy-2,3,5,11b-tetraaza-cyclopenta[a]anthracene

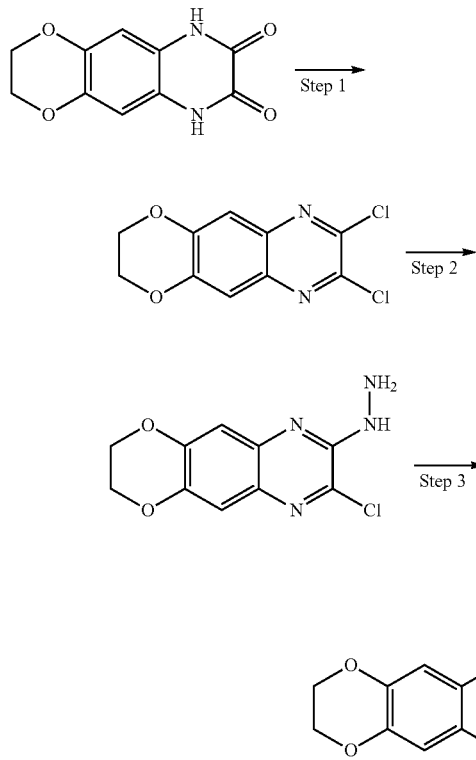

4-Chloro-1-methyl-8,9-dihydro-7,10-dioxy-2,3,5,11b-tetraaza-cyclopenta[a]anthracene was obtained by the same manner as described in Preparative Example 5, except that 2,3,5,8-tetrahydro-1,4-dioxa-5,8-diaza anthracene-6,7-dione was used.

Step 1: Preparation of 6,7-dichloro-2,3-dihydro-1,4-dioxa-5,8-diaza-anthracene Mass (M+H$^+$): 257.0
$^1$H NMR (500 MHz, DMSO-d6): δ4.41 (s, 4H), 7.45 (s, 2H).

Step 2: Preparation of (7-dichloro-2,3-dihydro-1,4-dioxa-5,8-diaza-anthracene-6-yl)-hydrazine Mass (M+H$^+$): 253.0

Step 3: Preparation of 4-chloro-1-methyl-8,9-dihydro-7,10-dioxa-2,3,5,11b-tetraaza-cyclopenta[a]anthracene Mass (M+H$^+$): 277.0
$^1$H NMR (500 MHz, DMSO-d6) δ3.02 (s, 3H), 4.36 (t, 2H), 4.39 (t, 2H), 7.49 (s, 1H), 7.70 (s, 1H).

<Example 178> Preparation of [4-(1-methyl-8,9-dihydro-7,10-dioxa-2,3,5,11b-tetraaza-cyclopenta[a]anthracene-4-ylamino)-butyl]-carbamic acid-tert-butylester

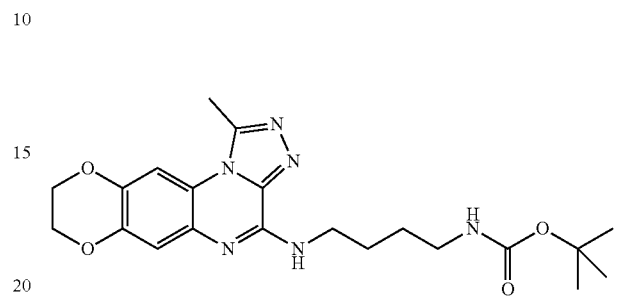

2 g of a target compound was obtained (82% yield) by the same manner as described in Example 57, except that 4-chloro-1-methyl-8,9-dihydro-7,10-dioxa-2,3,5,11b-tetraaza-cyclopenta[a]anthracene (1.58 g, 5.71 mmol) prepared in step 3 of Preparative Example 15 was used.

Mass (M+H$^+$): 429.2
$^1$H NMR (500 MHz, DMSO-d6): δ1.32 (s, 9H), 1.41 (m, 2H), 1.58 (m, 2H), 2.90 (m, 2H), 2.92 (s, 3H), 3.44 (q, 2H), 4.27 (s, 4H), 6.74 (t, 1H), 7.01 (s, 1H), 7.47 (s, 1H), 7.82 (t, 1H).

<Example 179> Preparation of N$^1$-(1-methyl-8,9-dihydro-7,10-dioxa-2,3,5,11b-tetraaza-cyclopenta[a]anthracene-4-yl)-butane-1,4-diamine ditrifluoroacetic acid

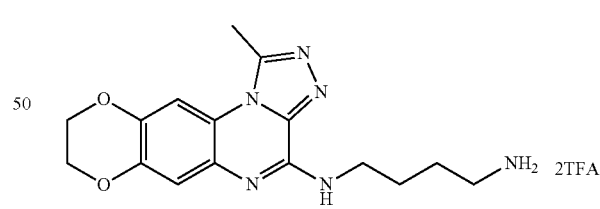

2.2 g of a target compound was obtained (89% yield) by the same manner as described in Example 58, except that [4-(1-methyl-8,9-dihydro-7,10-dioxa-2,3,5,11b-tetraaza-cyclopenta[a]anthracene-4-ylamino)-butyl]-carbamic acid-tert-butylester (1.9 g, 4.43 mmol) prepared in Example 178 was used.

Mass (M+H$^+$): 329.2
$^1$H NMR (500 MHz, DMSO-d6): δ1.58 (m, 2H), 1.66 (m, 2H), 2.82 (m, 2H), 2.94 (s, 3H), 3.48 (q, 2H), 4.28 (s, 4H), 7.01 (s, 1H), 7.49 (s, 1H), 7.60 (brs, 2H), 7.94 (brm, 1H).

<Example 180> Preparation of 2,2-dimethyl-N-[4-(1-methyl-8,9-dihydro-7,10-dioxa-2,3,5,11b-tetraaza-cyclopenta[a]anthracene-4-ylamino)-butyl]-propionamide

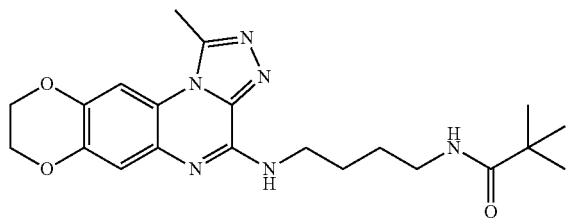

52 mg of a target compound was obtained (60% yield) by the same manner as described in Example 59, except that $N^1$-(1-methyl-8,9-dihydro-7,10-dioxa-2,3,5,11b-tetraaza-cyclopenta[a]anthracene-4-yl)-butane-1,4-diamine ditrifluoroacetic acid (120 mg, 0.22 mmol) prepared in Example 179 was used.

Mass (M+H$^+$): 413.2

$^1$H NMR (500 MHz, DMSO-d6): δ1.02 (s, 9H), 1.43 (m, 2H), 1.58 (m, 2H), 2.93 (s, 3H), 3.03 (q, 2H), 3.44 (q, 2H), 4.27 (s, 4H), 6.99 (s, 1H), 7.36 (t, 1H), 7.47 (s, 1H), 7.81 (t, 1H).

The compounds shown in Table 14 below were prepared by the same manner as described in Example 180.

TABLE 14

| Example | Structure | Name | Data |
|---|---|---|---|
| Example 181 | 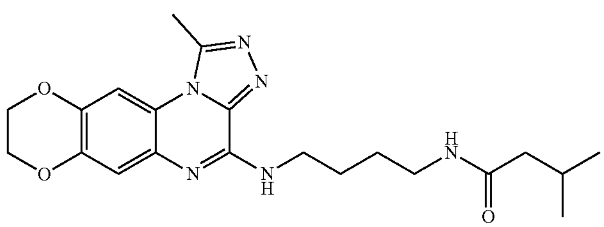 [SMILES: Cc1nnc2c(NCCCCNC(=O)CC(C)C)nc3cc4c(cc3n12)OCCO4] | 3-methyl-N-[4-(1-methyl-8,9-dihydro-7,10-dioxa-2,3,5,11b-tetraaza-cyclopenta[a]anthracene-4-ylamino)-butyl]-butyramide | Mass (M + H$^+$): 413.2; $^1$H NMR (500 MHz, DMSO-d6): δ0.79 (d, 6H), 1.42 (m, 2H), 1.60 (m, 2H), 1.87 (d, 2H), 1.89 (m, 1H), 2.93 (s, 3H), 3.02 (q, 2H), 3.45 (q, 2H), 4.27 (s, 4H), 7.00 (s, 1H), 7.47 (s, 1H), 7.68 (t, 1H), 7.82 (t, 1H). |
| Example 182 | 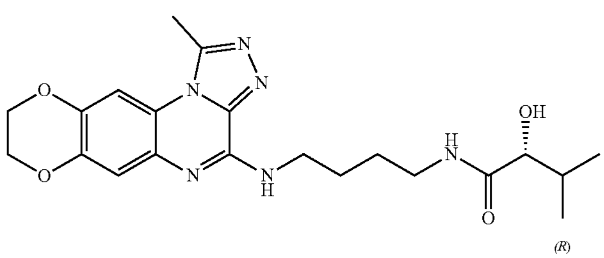 | 2-(R)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide | Mass (M + H$^+$): 429.2; $^1$H NMR (500 MHz, DMSO-d6): δ0.68 (d, 3H), 0.82 (d, 3H), 1.46 (m, 2H), 1.59 (m, 2H), 1.91 (m, 1H), 2.92 (s, 3H), 3.05 (m, 1H), 3.11 (m, 1H), 3.44 (q, 2H), 3.60 (t, 1H), 4.27 (s, 4H), 5.23 (d, 1H), 6.99 (s, 1H), 7.46 (m, 1H), 7.65 (t, 1H), 7.82 (t, 1H). |
| Example 183 | 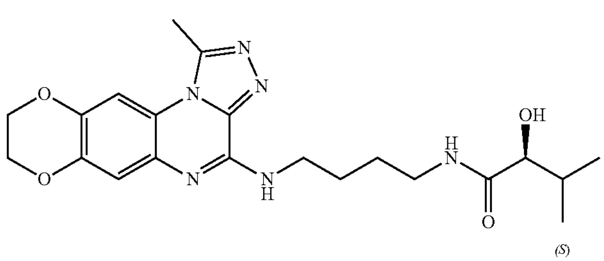 | 2-(S)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide | Mass (M + H$^+$): 429.2; $^1$H NMR (500 MHz, DMSO-d6): δ0.68 (d, 3H), 0.83 (d, 3H), 1.45 (m, 2H), 1.59 (m, 2H), 1.91 (m, 1H), 2.92 (s, 3H), 3.05 (m, 1H), 3.12 (m, 1H), 3.45 (q, 2H), 3.59 (t, 1H), 4.27 (s, 4H), 5.22 (d, 1H), 6.99 (s, 1H), 7.47 (m, 1H), 7.64 (t, 1H), 7.82 (t, 1H). |

TABLE 14-continued

| Example | Structure | Name | Data |
|---|---|---|---|
| Example 184 | 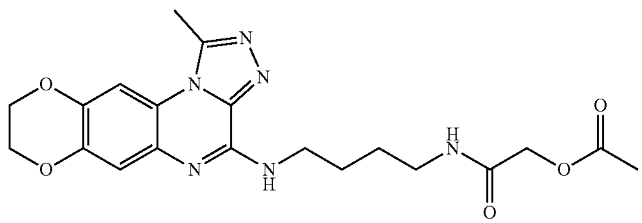 [SMILES: CC(=O)OCC(=O)NCCCCNc1nc2cc3c(cc2n2c(C)nnc12)OCCO3] | acetic acid-[4-(1-methyl-8,9-dihydro-7,10-dioxa-2,3,5,11b-tetraaza-cyclopenta[a]anthracene-4-ylamino)-butyl]-carbamoyl]-methylester | Mass (M + H+): 429.2; 1H NMR (500 MHz, DMSO-d6): δ1.45 (m, 2H), 1.59 (m, 2H), 2.03 (s, 3H), 2.93 (s, 3H), 3.08 (q, 2H), 3.45 (q, 2H), 4.27 (s, 4H), 4.36 (s, 2H), 7.00 (s, 1H), 7.47 (s, 1H), 7.80 (t, 1H), 7.93 (t, 1H). |
| Example 185 | 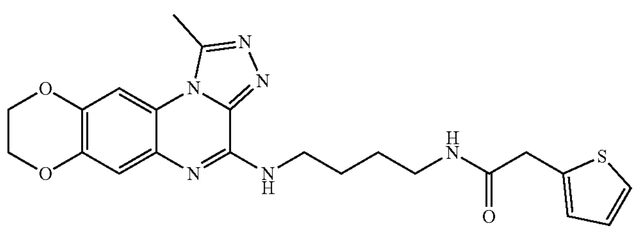 [SMILES: Cc1nnc2c(NCCCCNC(=O)Cc3cccs3)nc3cc4c(cc3n12)OCCO4] | N-[4-(1-methyl-8,9-dihydro-7,10-dioxa-2,3,5,11b-tetraaza-cyclopenta[a]anthracene-4-ylamino)-butyl]-2-thiophene-2-yl-acetamide | Mass (M + H+): 453.1; 1H NMR (500 MHz, DMSO-d6): δ1.46 (m, 2H), 1.61 (m, 2H), 2.923 (s, 3H), 3.06 (q, 2H), 3.46 (q, 2H), 3.56 (s, 2H), 4.27 (s, 4H), 6.83 (d, 1H), 6.87 (q, 1H), 7.01 (s, 1H), 7.26 (d, 1H), 7.48 (s, 1H), 7.83 (t, 1H), 8.01 (t, 1H). |
| Example 186 | 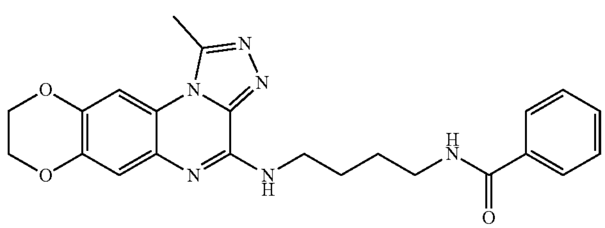 [SMILES: Cc1nnc2c(NCCCCNC(=O)c3ccccc3)nc3cc4c(cc3n12)OCCO4] | N-[4-(1-methyl-8,9-dihydro-7,10-dioxa-2,3,5,11b-tetraaza-cyclopenta[a]anthracene-4-ylamino)-butyl]-benzamide | Mass (M + H+): 433.2; 1H NMR (500 MHz, DMSO-d6): δ1.57 (m, 2H), 1.67 (m, 2H), 2.92 (s, 3H), 3.27 (m, 2H), 3.49 (q, 2H), 4.27 (s, 4H), 7.00 (s, 1H), 7.39 (t, 2H), 7.45 (t, 1H), 7.47 (s, 1H), 7.77 (dd, 2H), 7.83 (t, 1H), 8.39 (t, 1H). |
| Example 187 | 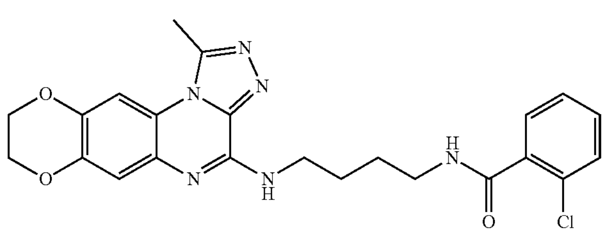 [SMILES: Cc1nnc2c(NCCCCNC(=O)c3ccccc3Cl)nc3cc4c(cc3n12)OCCO4] | 2-chloro-N-[4-(1-methyl-8,9-dihydro-7,10-dioxa-2,3,5,11b-tetraaza-cyclopenta[a]anthracene-4-ylamino)-butyl]-benzamide | Mass (M + H+): 467.1; 1H NMR (500 MHz, DMSO-d6): δ1.55 (m, 2H), 1.70 (m, 2H), 2.93 (s, 3H), 3.22 (q, 2H), 3.48 (q, 2H), 7.01 (s, 1H), 7.30 (t, 1H), 7.33 (m, 1H), 7.38 (t, 1H), 7.42 (d, 1H), 7.48 (s, 1H), 7.85 (t, 1H), 8.35 (t, 1H). |
| Example 188 | 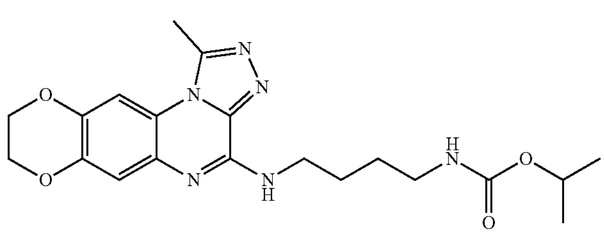 [SMILES: Cc1nnc2c(NCCCCNC(=O)OC(C)C)nc3cc4c(cc3n12)OCCO4] | [4-(1-methyl-8,9-dihydro-7,10-dioxa-2,3,5,11b-tetraaza-cyclopenta[a]anthracene-4-ylamino)-butyl]-carbamic acid isopropylester | Mass (M + H+): 415.2; 1H NMR (500 MHz, DMSO-d6): δ1.09 (d, 6H), 1.42 (m, 2H), 1.59 (m, 2H), 2.93 (s, 3H), 2.96 (q, 2H), 3.45 (q, 2H), 4.27 (s, 4H), 4.68 (m, 1H), 6.93 (t, 1H), 7.01 (s, 1H), 7.47 (s, 1H), 7.81 (t, 1H). |

TABLE 14-continued

| Example | Structure | Name | Data |
|---|---|---|---|
| Example 189 | 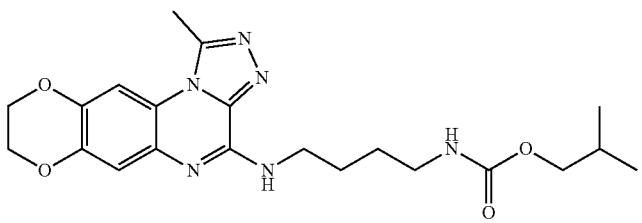 [SMILES: Cc1nnc2c(NCCCCNC(=O)OCC(C)C)nc3cc4c(cc3n12)OCCO4] | [4-(1-methyl-8,9-dihydro-7,10-dioxa-2,3,5,11b-tetraaza-cyclopenta[a]anthracene-4-ylamino)-butyl]-carbamic acid isobutylester | Mass (M + H⁺): 429.2; ¹H NMR (500 MHz, DMSO-d6): δ0.81 (d, 6H), 1.43 (m, 2H), 1.59 (m, 2H), 1.76 (m, 1H), 2.93 (s, 3H), 2.97 (q, 2H), 3.66 (d, 2H), 4.27 (s, 4H), 7.00 (s, 1H), 7.03 (t, 1H), 8.83 (t, 1H). |
| Example 190 | 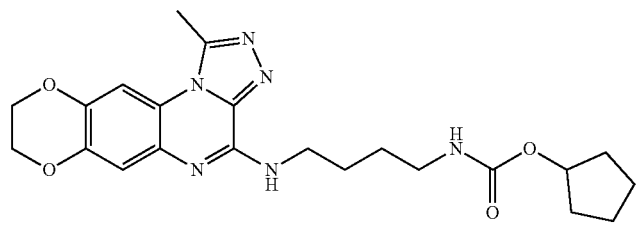 [SMILES: Cc1nnc2c(NCCCCNC(=O)OC3CCCC3)nc3cc4c(cc3n12)OCCO4] | [4-(1-methyl-8,9-dihydro-7,10-dioxa-2,3,5,11b-tetraaza-cyclopenta[a]anthracene-4-ylamino)-butyl]-carbamic acid cyclopentylester | Mass (M + H⁺): 441.2; ¹H NMR (500 MHz, DMSO-d6): 1.38~1.60 (m, 10H), 1.73 (m, 2H), 2.93 (s, 3H), 2.96 (m, 2H), 3.45 (q, 2H), 4.27 (s, 4H), 4.88 (m, 1H), 6.93 (t, 1H), 7.01 (s, 1H), 7.47 (s, 1H), 7.81 (t, 1H). |
| Example 191 | 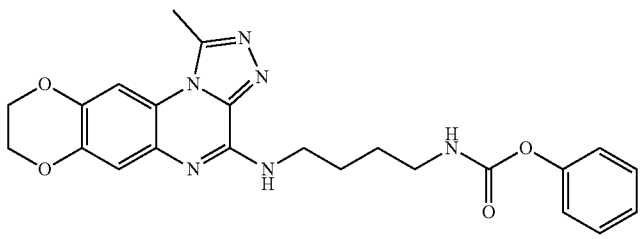 [SMILES: Cc1nnc2c(NCCCCNC(=O)Oc3ccccc3)nc3cc4c(cc3n12)OCCO4] | [4-(1-methyl-8,9-dihydro-7,10-dioxa-2,3,5,11b-tetraaza-cyclopenta[a]anthracene-4-ylamino)-butyl]-carbamic acid phenylester | Mass (M + H⁺): 449.2; ¹H NMR (500 MHz, DMSO-d6): δ1.52 (m, 2H), 1.66 (m, 2H), 2.93 (s, 3H), 3.07 (q, 2H), 3.48 (m, 2H), 4.27 (s, 4H), 7.02 (s, 2H), 7.04 (m, 1H), 7.14 (t, 1H), 7.32 (t, 2H), 7.49 (s, 1H), 7.70 (t, 1H), 7.88 (t, 1H). |
| Example 192 | 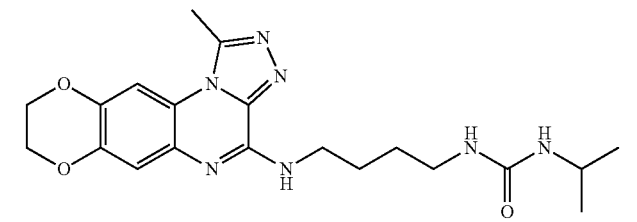 [SMILES: Cc1nnc2c(NCCCCNC(=O)NC(C)C)nc3cc4c(cc3n12)OCCO4] | 1-isopropyl-3-[4-(1-methyl-8,9-dihydro-7,10-dioxa-2,3,5,11b-tetraaza-cyclopenta[a]anthracene-4-ylamino)-butyl]-urea | Mass (M + H⁺): 414.2; ¹H NMR (500 MHz, DMSO-d6): δ0.95 (d, 6H), 1.39 (m, 2H), 1.58 (m, 2H), 2.93 (s, 3H), 2.97 (q, 2H), 3.45 (q, 2H), 3.59 (m, 1H), 4.27 (s, 4H), 5.52 (d, 1H), 5.61 (t, 1H), 7.01 (s, 1H), 7.47 (s, 1H), 7.82 (t, 1H). |

<Preparative Example 16> Preparation of 4-chloro-6,7,8-trimethoxy-1-methyl-[1,2,4]triazolo[4,3-a]quinoxaline

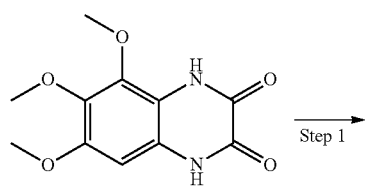

Step 1

-continued

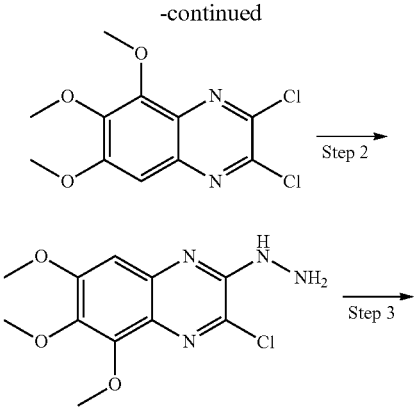

-continued

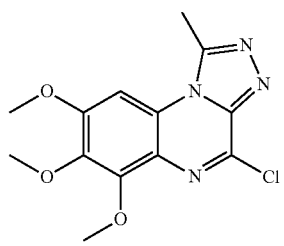

4-Chloro-6,7,8-trimethoxy-1-methyl-[1,2,4]triazolo[4,3-a]quinoxaline was obtained by the same manner as described in Preparative Example 5 was used.

Step 1: Preparation of 2,3-chloro-5,6,7-trimethoxy-quinoxaline

Mass (M+H$^+$): 289.0

$^1$H NMR (500 MHz, DMSO-d6): δ3.91 (s, 3H), 3.96 (s, 3H), 4.01 (s, 3H), 7.31 (s, 1H).

Step 2: Preparation of [3-chloro-5,6,7-trimethoxy)-quinoxaline-2-yl]hydrazine

Mass (M+H$^+$): 283.1

Step 3: Preparation of 4-chloro-6,7,8-trimethoxy-1-methyl-[1,2,4]triazolo[4,3-a]quinoxaline Mass (M+H$^+$): 309.0

$^1$H NMR (500 MHz, DMSO-d6) δ3.13 (s, 3H), 3.78 (s, 3H), 3.99 (s, 3H), 4.03 (s, 3H), 7.49 (s, 1H)

<Example 193> Preparation of [4-(6,7,8-trimethoxy-1-methyl-[1,2,4]triazolo[4,3-a]quinoxaline-4-ylamino)-butyl]-carbamic acid-tert-butylester

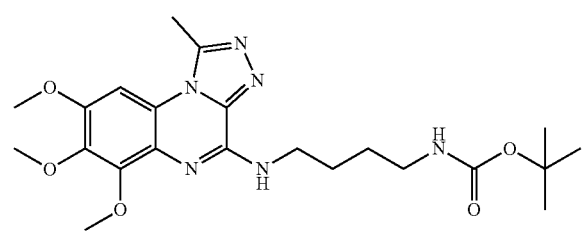 [SMILES: COc1cc2c(nc(NCCCCNC(=O)OC(C)(C)C)c3nnc(C)n32)c(OC)c1OC]

0.35 g of a target compound was obtained (61% yield) by the same manner as described in Example 57, except that 4-chloro-1-methyl-6,7,8-trimethoxy-[1,2,4]triazolo[4,3-a]quinoxaline prepared in step 3 of Preparative Example 16 was used.

Mass (M+H$^+$): 461.2

$^1$H NMR (500 MHz, DMSO-d6): δ1.32 (s, 9H), 1.43 (m, 2H), 1.62 (m, 2H), 2.92 (m, 2H), 3.03 (s, 3H), 3.50 (q, 2H), 3.76 (s, 3H), 3.89 (s, 3H), 3.97 (s, 3H), 6.73 (t, 1H), 7.35 (s, 1H), 7.93 (t, 1H).

<Example 194> Preparation of N$^1$-(6,7,8-trimethoxy-1-methyl-[1,2,4]triazolo[4,3-a]quinoxaline-4-yl)-butane-1,4-diamine ditrifluoroacetic acid

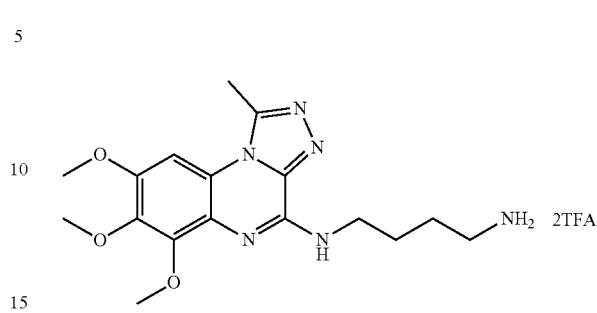

0.29 g of a target compound was obtained (67% yield) by the same manner as described in Example 58, except that [4-(6,7,8-trimethoxy-1-methyl-[1,2,4]triazolo[4,3-a]quinoxaline-4-ylamino)-butyl]-carbamic acid-tert-butylester prepared in Example 193 was used.

Mass (M+H$^+$): 361.2

<Example 195> Preparation of 3-methyl-N-[4-(6,7,8-trimethoxy-1-methyl-[1,2,4]triazolo[4,3-a]quinoxaline-4-ylamino)-butyl]-butyramide

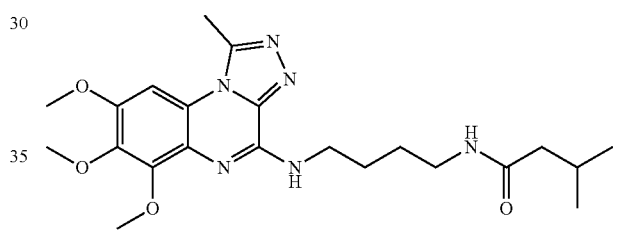

0.06 g of a target compound was obtained (51% yield) by the same manner as described in Example 37, except that N$^1$-(6,7,8-trimethoxy-1-methyl-[1,2,4]triazolo[4,3-a]quinoxaline-4-yl)-butane-1,4-diamine ditrifluoroacetic acid prepared in Example 194 was used.

Mass (M+H$^+$): 445.1

$^1$H NMR (500 MHz, DMSO-d6): δ0.79 (d, 6H), 1.45 (m, 2H), 1.63 (m, 2H), 1.85 (m, 2H), 1.87 (m, 1H), 3.03 (q, 2H), 3.04 (s, 3H), 3.51 (m, 2H), 3.76 (s, 3H), 3.89 (s, 3H), 3.96 (s, 3H), 7.36 (s, 1H), 7.68 (t, 1H), 7.94 (t, 1H)

<Example 196> Preparation of 3-methyl-pentanoic acid-[4-(6,7,8-trimethoxy-1-methyl-[1,2,4]triazolo[4,3-a]quinoxaline-4-ylamino)-butyl]-amide

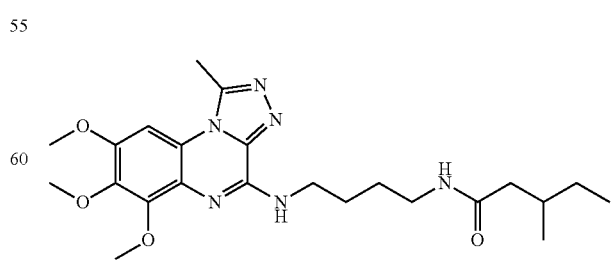

0.03 g of a target compound was obtained (30% yield) by the same manner as described in Example 73, except that N¹-(6,7,8-trimethoxy-1-methyl-[1,2,4]triazolo[4,3-a]quinoxaline-4-yl)-butane-1,4-diamine ditrifluoroacetic acid prepared in Example 194 was used.

Mass (M+H⁺): 459.2

¹H NMR (500 MHz, DMSO-d6): δ0.76 (m, 6H), 1.06-1.23 (brm, 2H), 1.44 (m, 2H), 1.63 (m, 2H), 1.78 (m, 2H), 1.97 (m, 1H), 3.04 (q, 2H), 3.05 (s, 3H), 3.50 (q, 2H), 3.77 (s, 3H), 3.89 (s, 3H), 3.95 (s, 3H), 7.36 (s, 1H), 7.68 (t, 1H), 7.94 (t, 1H).

<Preparative Example 17> Preparation of methyl-3-chloro-2-hydrazinylquinoxaline-6-carboxylate

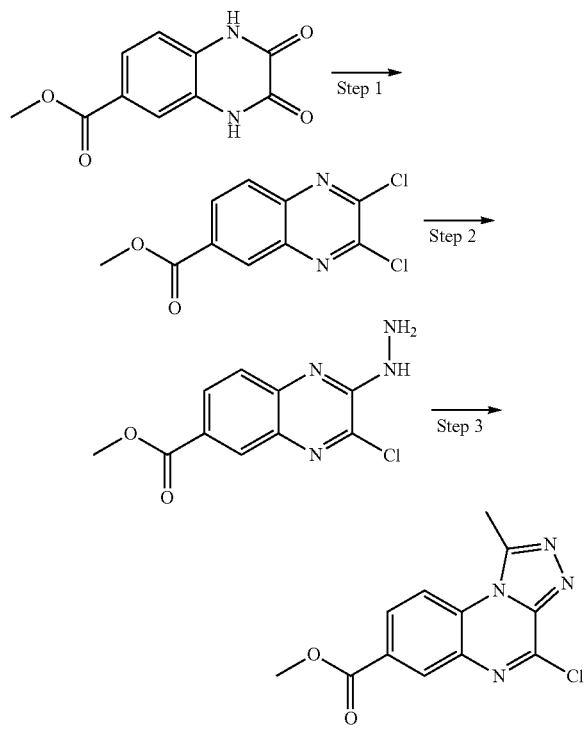

Step 1: Preparation of methyl-2,3-dichloroquinoxaline-6-carboxylate

A target compound was obtained (72% yield) by the same manner as described in step 1 of Preparative Example 5, except that methyl-2,3-dioxo-1,2,3,4-tetrahydroquinoxaline-6-carboxylate (7 g, 31.8 mmol) was used.

Mass (M+H⁺): 257.1

¹H NMR (300 MHz, DMSO-d6): δ3.96 (s, 3H), 7.12 (d, J=8.65 Hz, 1H), 7.28 (d, J=8.65 Hz, 1H), 8.45 (s, 1H).

Step 2: Preparation of methyl-3-chloro-2-hydrazinylquinoxaline-6-carboxylate

A target compound was obtained (91% yield) by the same manner as described in step 2 of Preparative Example 5, except that methyl-2,3-dichloroquinoxaline-6-carboxylate (5.42 g, 21.1 mmol) prepared in step 1 of Preparative Example 17 was used.

Mass (M+H⁺): 253.0

Step 3: Preparation of methyl-4-chloro-1-methyl-[1,2,4]triazolo[4,3-a]quinoxaline-7-carboxylate A target compound was obtained (86% yield) by the same manner as described in step 3 of Preparative Example 5, except that methyl-3-chloro-2-hydrazinylquinoxaline-6-carboxylate (5.50 g, 21.8 mmol) prepared in step 2 of Preparative Example 17 was used.

Mass (M+H⁺): 277.0

¹H NMR (500 MHz, DMSO-d6) δ3.13 (s, 3H), 3.95 (s, 3H), 8.27 (dd, J=8.75, 1.50 Hz, 1H), 7.48 (d, J=8.75 Hz, 1H), 8.45 (d, J=1.50 Hz, 1H).

<Example 197> Preparation of 4-(4-tert-butoxycarbamoylamino-butylamino)-1-methyl-[1,2,4]triazolo[4,3-a]quinoxaline-7-carboxylic acid methylester

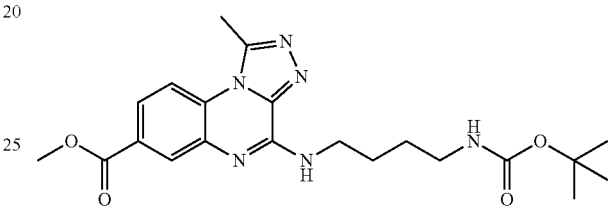

A target compound was obtained (79% yield) by the same manner as described in Example 57, except that methyl-4-chloro-1-methyl-[1,2,4]triazolo[4,3-a]quinoxaline-7-carboxylate (2 g, 7.23 mmol) prepared in step 3 of Preparative Example 16 was used.

Mass (M+H⁺): 429.2

¹H NMR (500 MHz, DMSO-d6): δ1.44-1.50 (m, 2H), 1.64-1.70 (m, 2H), 2.95-2.99 (m, 2H), 3.04 (s, 3H), 3.53-3.57 (m, 2H), 3.91 (s, 3H), 6.81 (t, J=5.40 Hz, 1H), 8.10 (d, J=1.95 Hz, 1H), 8.20 (d, J=8.70 Hz, 1H), 8.37 (t, J=5.70 Hz, 1H), 8.82 (dd, J=8.70 Hz, 1.95 Hz, 1H).

<Example 198> Preparation of 4-(4-amino-butylamino)-1-methyl-[1,2,4]triazolo[4,3-a]quinoxaline-7-carboxylic acid methylester ditrifluoroacetic acid

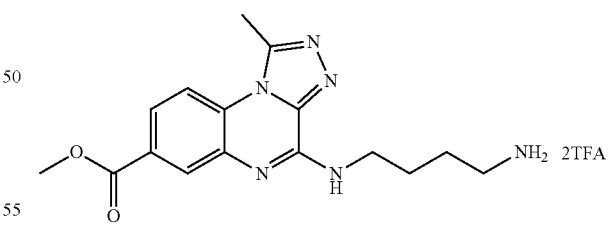

2 g of a target compound was obtained (77% yield) by the same manner as described in Example 58, except that 4-(4-tert-butoxycarbamoylamino-butylamino)-1-methyl-[1,2,4]triazolo[4,3-a]quinoxaline-7-carboxylic acid methylester (2 g, 4.67 mmol) prepared in Example 197 was used.

Mass (M+H⁺): 329.1

¹H NMR (500 MHz, DMSO-d6): δ1.60 (m, 2H), 1.70 (m, 2H), 2.81 (m, 2H), 3.01 (s, 3H), 3.56 (m, 2H), 3.87 (s, 3H), 7.61 (brs, 1H), 7.81 (d, 1H). 8.08 (s, 1H), 8.19 (d, 1H), 8.39 (t, 1H).

<Example 199> Preparation of 1-methyl-4-[4-(3-methyl-butyrylamino)-butylamino]-[1,2,4]triazolo[4,3-a]quinoxaline-7-carboxylic acid methylester

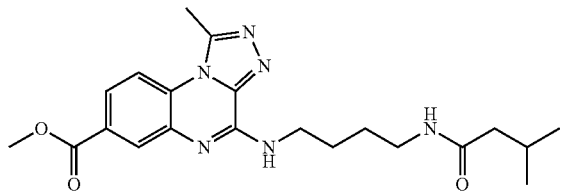 [SMILES: COC(=O)c1ccc2c(c1)nc(NCCCCNC(=O)CC(C)C)c1nnc(C)n12]

0.71 g of a target compound was obtained (95% yield) by the same manner as described in Example 37, except that 4-(4-amino-butylamino)-1-methyl-[1,2,4]triazolo[4,3-a]quinoxaline-7-carboxylic acid methylester ditrifluoroacetic acid (1 g, 1.8 mmol) prepared in Example 198 was used.

Mass (M+H$^+$): 413.2

$^1$H NMR (500 MHz, DMSO-d6) δ0.78 (d, 6H), 1.45 (m, 2H), 1.63 (m, 2H), 1.86 (d, 2H), 1.88 (m, 1H), 2.99 (s, 3H), 3.05 (q, 2H), 3.51 (q, 2H), 3.86 (s, 3H), 7.69 (t, 1H), 7.78 (d, 1H), 8.05 (s, 1H), 8.15 (d, 1H), 8.31 (t, 1H).

<Example 200> Preparation of 4-[(4-tert-butoxycarbamoylamino)-butylamino]-1-methyl-[1,2,4]triazolo[4,3-a]quinoxaline-7-carboxylic acid

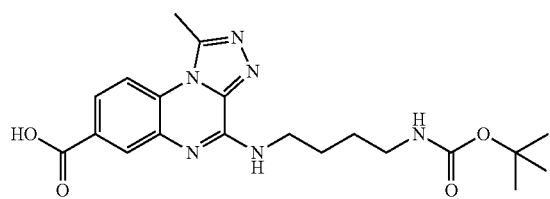 [SMILES: Cc1nnc2c(NCCCCNC(=O)OC(C)(C)C)nc3cc(C(=O)O)ccc3n12]

4-(4-tert-butoxycarbamoylamino-butylamino)-1-methyl-[1,2,4]triazolo[4,3-a]quinoxaline-7-carboxylic acid methylester (2 g, 4.67 mmol) prepared in Example 197 was dissolved in tetrahydrofuran, to which water containing sodium hydroxide (0.56 g, 14 mmol) dissolved therein was added dropwise, followed by stirring at room temperature for 17 hours. Upon completion of the reaction, tetrahydrofuran solvent was eliminated by distillation under reduce pressure, and pH was adjusted to 2-3 with 1 N hydrochloric acid aqueous solution. The resulting solid was filtered and vacuum dried. As a result, a target compound was obtained (86% yield).

Mass (M+H$^+$): 415.2

$^1$H NMR (300 MHz, DMSO-d6): δ1.35 (s, 9H), 1.45-1.49 (m, 2H), 1.65-1.67 (m, 2H), 2.96-2.98 (m, 2H), 3.04 (s, 3H), 3.57-3.58 (m, 2H), 6.80 (s, 1H), 8.83 (d, J=8.52 Hz, 1H), 8.15 (s, 1H), 8.20 (d, J=8.70 Hz, 1H), 8.51 (brs, 1H), 13.14 (brs, 1H).

<Example 201> Preparation of 1-methyl-4-[4-(3-methyl-butyrylamino)-butylamino]-[1,2,4]triazolo[4,3-a]quinoxaline-7-carboxylic acid

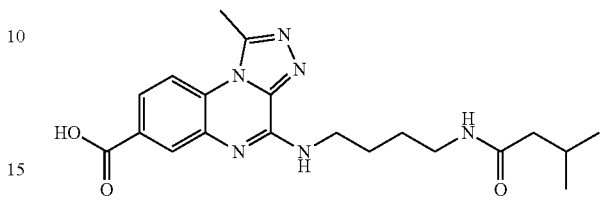

3.9 g of a target compound was obtained (100% yield) by the same manner as described in Example 200, except that 1-methyl-4-[4-(3-methyl-butyrylamino)-butylamino]-[1,2,4]triazolo[4,3-a]quinoxaline-7-carboxylic acid methylester (4 g, 9.7 mmol) prepared in Example 199 was used.

Mass (M+H$^+$): 399.2

$^1$H NMR (500 MHz, DMSO-d6) δ0.78 (d, 6H), 1.46 (m, 2H), 1.64 (m, 2H), 1.86 (s, 2H), 1.88 (m, 1H), 3.00 (s, 3H), 3.04 (q, 2H), 3.52 (m, 2H), 7.68 (t, 1H), 7.78 (d, 1H), 8.04 (s, 1H), 8.14 (d, 1H), 8.28 (t, 1H), 13.05 (s, 1H)

<Example 202> [Preparation of 4-(7-isopropylcarbamoyl-1-methyl-[1,2,4]triazolo[4,3-a]quinoxaline-4-ylamino)-butyl]-carbamic acid-tert-butylester

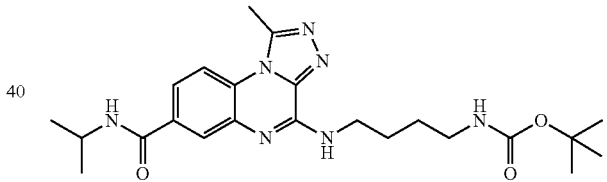

4-(4-Tert-butoxycarbamoylamino-butylamino)-1-methyl-[1,2,4]triazolo[4,3-a]quinoxaline-7-carboxylic acid (0.50 g, 1.21 mmol) prepared in Example 200, isopropylamine (0.09 g, 1.45 mmol), HCTU (0.60 g, 1.45 mmol) and diisopropylethylamine (0.85 mL, 4.84 mmol) were dissolved in dimethylformamide, followed by stirring at room temperature for 2 hours. Upon completion of the reaction, the reactant was extracted with ethylacetate and sodium bicarbonate solutions 3 times, followed by washing the organic layer with sodium bicarbonate solution. The organic layer was dried over magnesium sulfate, filtered, distilled under reduced pressure, and purified by MPLC. As a result, a target compound was obtained (82% yield).

Mass (M+H$^+$): 455.8

$^1$H NMR (300 MHz, DMSO-d6): δ1.19 (d, J=6.30 Hz, 6H), 1.36 (s, 9H), 1.42-1.49 (m, 2H), 1.64-1.69 (m, 2H), 2.95-2.97 (m, 2H), 3.04 (s, 3H), 3.54-3.56 (m, 2H), 4.08-4.17 (m, 1H), 6.80 (brs, 1H), 7.76 (d, J=8.55 Hz, 1H), 8.12-8.15 (m, 2H), 8.26 (brs, 1H), 8.43 (d, J=7.38 Hz, 1H).

The compounds shown in Table 15 below were prepared by the same manners as described in Example 197 Example

TABLE 15

| Example | Structure | Name | Data |
| --- | --- | --- | --- |
| Example 203 | 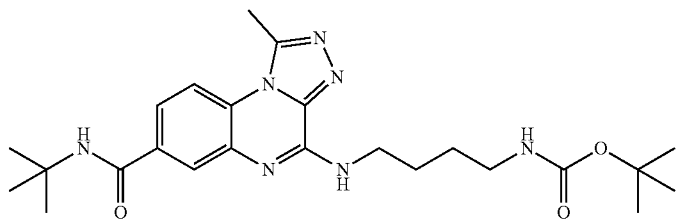 [SMILES: Cc1nnc2c(NCCCCNC(=O)OC(C)(C)C)nc3cc(C(=O)NC(C)(C)C)ccc3n12] | [4-(7-tert-butylcarbamoyl-1-methyl-[1,2,4]triazolo[4,3-a]quinoxaline-4-ylamino)-butyl]-carbamic acid-tert-butylester | Mass (M + H$^+$): 469.5; $^1$H NMR (500 MHz, DMSO-d6): δ1.36 (s, 9H), 1.41 (s, 9H), 1.43-1.49 (m, 2H), 1.65-1.71 (m, 2H), 2.92-2.99 (m, 2H), 3.04 (s, 3H), 3.54-3.56 (m, 2H), 6.80 (brs, 1H), 7.71 (d, J = 8.49 Hz, 1H), 8.06 (s, 1H), 8.11 (d, J = 8.49 Hz, 1H), 8.23 (brs, 1H). |
| Example 204 | 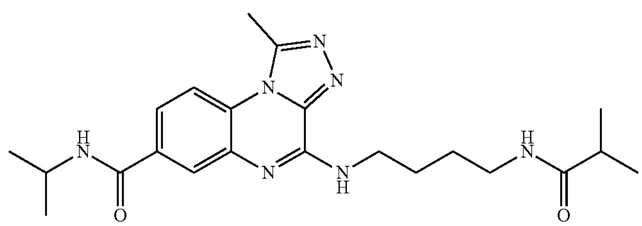 [SMILES: Cc1nnc2c(NCCCCNC(=O)C(C)C)nc3cc(C(=O)NC(C)C)ccc3n12] | 4-(4-isobutylamino-butylamino)-1-methyl-[1,2,4]triazolo[4,3-a]quinoxaline-7-carboxylic acid isopropylamide | Mass (M + H$^+$): 426.3; $^1$H NMR (300 MHz, DMSO-d6): δ0.97 (d, J = 6.81 Hz, 6H), 1.19 (d, J = 6.60 Hz, 6H), 1.44-1.53 (m, 2H), 1.63-1.73 (m, 2H), 2.27-2.36 (m, 1H), 3.04 (s, 3H), 3.05-3.11 (m, 2H), 3.53-3.59 (m, 2H), 4.09-4.20 (m, 1H), 7.68 (t, J = 5.28 Hz, 1H), 7.77 (dd, J = 8.64 Hz, 1.95 Hz, 1H), 8.12-8.16 (m, 2H), 8.30 (brs, 1H), 8.44 (d, J = 7.77 Hz, 1H). |
| Example 205 | 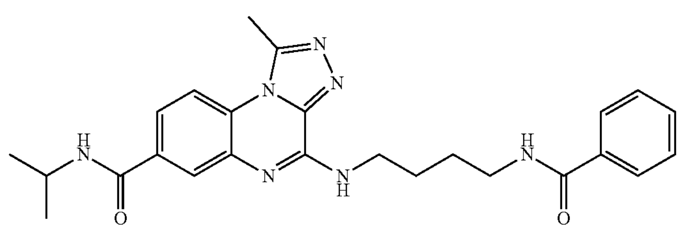 [SMILES: Cc1nnc2c(NCCCCNC(=O)c3ccccc3)nc3cc(C(=O)NC(C)C)ccc3n12] | 4-(4-benzoylamino-butylamino)-1-methyl-[1,2,4]triazolo[4,3-a]quinoxaline-7-carboxylic acid isopropylamide | Mass (M + H$^+$): 460.2; $^1$H NMR (300 MHz, DMSO-d6): δ1.19 (d, J = 6.57 Hz, 6H), 1.59-1.68 (m, 2H), 1.71-1.79 (m, 2H), 3.04 (s, 3H), 3.28-3.34 (m, 2H), 3.57-3.62 (m, 2H), 4.06-4.18 (m, 1H), 7.40-7.50 (m, 3H), 7.75-7.83 (m, 3H), 8.13-8.16 (m, 2H), 8.27 (t, J = 5.79 Hz, 1H), 8.42-8.47 (m, 2H). |
| Example 206 | 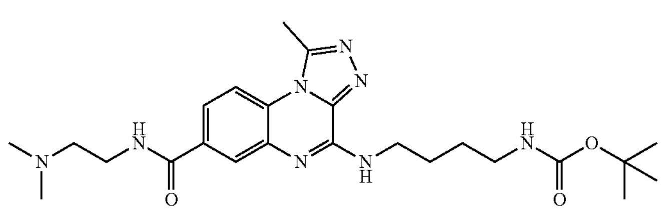 [SMILES: Cc1nnc2c(NCCCCNC(=O)OC(C)(C)C)nc3cc(C(=O)NCCN(C)C)ccc3n12] | {4-[7-(2-dimethylamino-ethylcarbamoyl)-1-methyl-[1,2,4]triazolo[4,3-a]quinoxaline-4-ylamino]-butyl}-carbamic acid-tert-butylester | Mass (M + H$^+$): 385.3; $^1$H NMR (300 MHz, DMSO-d6): δ1.36 (s, 9H), 1.40-1.52 (m, 2H), 1.62-1.69 (m, 2H), 2.90 (s, 6H), 2.93-3.00 (m, 2H), 3.05 (s, 3H), 3.18-3.22 (m, 2H), 3.52-3.64 (m, 4H), 6.81 (brs, 1H), 7.77 (dd, J = 8.64 Hz, 1.89 Hz, 1H), 8.14 (d, J = 1.77 Hz, 1H), 8.18 (d, J = 8.70 Hz, 1H), 8.31 (t, J = 5.67 Hz, 1H), 8.80 (t, J = 5.40 Hz, 1H). |

TABLE 15-continued

| Example | Structure | Name | Data |
|---|---|---|---|
| Example 207 | 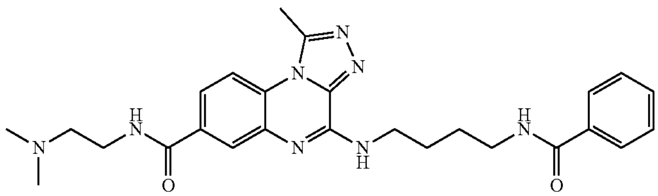 [SMILES: Cc1nnc2c(NCCCCNC(=O)c3ccccc3)nc3cc(C(=O)NCCN(C)C)ccc3n12] | 4-(4-benzoylamino-butylamino)-1-methyl-[1,2,4]triazolo[4,3-a]quinoxaline-7-carboxylic acid-(2-dimethylamino-ethyl)-amide | Mass (M + H⁺): 488.6 |
| Example 208 | 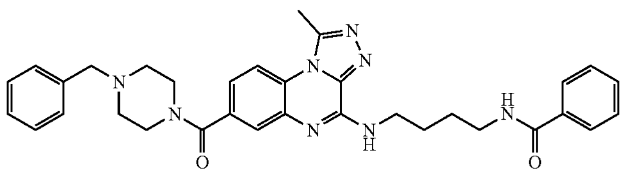 [SMILES: Cc1nnc2c(NCCCCNC(=O)c3ccccc3)nc3cc(C(=O)N4CCN(Cc5ccccc5)CC4)ccc3n12] | N-{4-[7-(4-benzyl-piperazine-1-carbonyl)-1-methyl-[1,2,4]triazolo[4,3-a]quinoxaline-4-ylamino]-butyl}-benzamide | Mass (M + H⁺): 576.5; ¹H NMR (300 MHz, DMSO-d6): δ1.60-1.64 (m, 2H), 1.66-1.72 (m, 2H), 3.05 (s, 3H), 3.14-3.18 (m, 3H), 3.20-3.35 (m, 4H), 3.55-3.65 (m, 6H), 4.34 (brs, 2H), 7.40-7.44 (m, 6H), 7.46-7.55 (m, 2H), 7.66-7.74 (m, 3H), 7.82-7.85 (m, 2H), 8.07 (d, J = 1.23 Hz, 1H), 8.53-8.56 (m, 1H). |
| Example 209 | 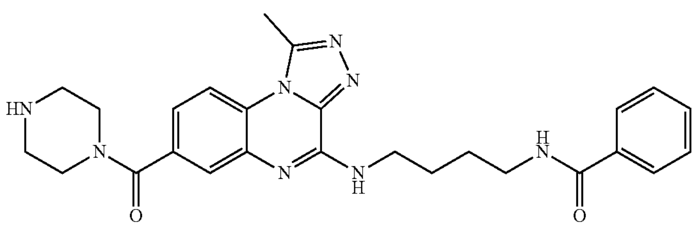 [SMILES: Cc1nnc2c(NCCCCNC(=O)c3ccccc3)nc3cc(C(=O)N4CCNCC4)ccc3n12] | N-{4-[1-methyl-7-(piperazine-1-carbonyl)-[1,2,4]triazolo[4,3-a]quinoxaline-4-ylamino]-butyl}-benzamide | Mass (M + H⁺): 486.7 |
| Example 210 | 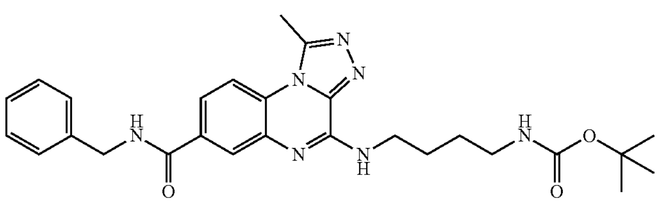 [SMILES: Cc1nnc2c(NCCCCNC(=O)OC(C)(C)C)nc3cc(C(=O)NCc4ccccc4)ccc3n12] | [4-(7-benzylcarbamoyl-1-methyl-[1,2,4]triazolo[4,3-a]quinoxaline-4-ylamino)-butyl]-carbamic acid-tert-butylester | Mass (M + H⁺): 503.7; ¹H NMR (300 MHz, DMSO-d6): δ1.35 (s, 9H), 1.41-1.52 (m, 2H), 1.64-1.72 (m, 2H), 2.92-3.00 (m, 2H), 3.04 (s, 3H), 3.52-3.59 (m, 2H), 4.50 (d, J = 5.34 Hz, 2H), 6.80 (brs, 1H), 7.24-7.82 (m, 5H), 8.17 (brs, 2H), 8.27 (brs, 1H), 9.25 (t, J = 5.85 Hz, 1H). |
| Example 211 | 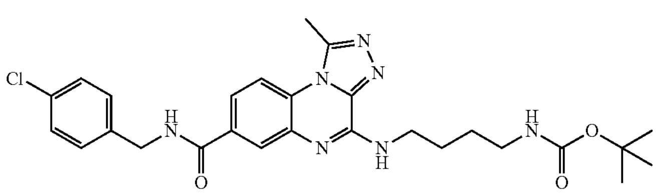 [SMILES: Cc1nnc2c(NCCCCNC(=O)OC(C)(C)C)nc3cc(C(=O)NCc4ccc(Cl)cc4)ccc3n12] | {4-[7-(4-chloro-benzylcarbamoyl)-1-methyl-[1,2,4]triazolo[4,3-a]quinoxaline-4-ylamino]-butyl}-carbamic acid-tert-butylester | Mass (M + H⁺): 537.8; ¹H NMR (300 MHz, DMSO-d6): δ1.35 (s, 9H), 1.40-1.48 (m, 2H), 1.60-1.72 (m, 2H), 2.92-3.00 (m, 2H), 3.04 (s, 3H), 3.49-3.57 (m, 2H), 4.48 (d, J = 5.40 Hz, 2H), 6.80 (brs, 1H), 7.35-7.42 (m, 5H), 7.79 (d, J = 8.46 Hz, 1H), 8.16-8.18 (m, 2H), 8.29 (brs, 1H), 9.27 (brs, 1H). |

TABLE 15-continued

| Example | Name | Data |
|---|---|---|
| Example 212 | [4-(1-methyl-7-phenylcarbamoyl-[1,2,4]triazolo[4,3-a]quinoxaline-4-ylamino)-butyl]-carbamic acid-tert-butylester | Mass (M + H$^+$): 489.8; $^1$H NMR (300 MHz, DMSO-d6): δ1.35 (s, 9H), 1.45-1.50 (m, 2H), 1.66-1.71 (m, 2H), 2.92-3.00 (m, 2H), 3.06 (s, 3H), 3.54-3.61 (m, 2H), 6.80 (brs, 1H), 6.81 (brs, 1H), 7.12 (t, J = 7.29 Hz, 1H), 7.37 (t, J = 8.10 Hz, 2H), 7.82-7.88 (m, 3H), 8.21-8.27 (m, 2H), 8.31 (t, J = 5.55 Hz, 1H). |
| Example 213 | {4-[7-(2-amino-phenylcarbamoyl)-1-methyl-[1,2,4]triazolo[4,3-a]quinoxaline-4-ylamino]-butyl}-carbamic acid-tert-butylester | Mass (M − H$^+$): 503.3; $^1$H NMR (500 MHz, DMSO-d6): δ1.31 (s, 9H), 1.44 (m, 2H), 1.64 (m, 2H), 2.92 (q, 2H), 3.02 (s, 3H), 3.53 (m, 2H), 4.90 (brs, 2H), 6.57 (t, 1H), 6.76 (d, 1H), 6.94 (t, 1H), 7.16 (d, 1H), 7.85 (d, 1H), 8.15 (m, 1H), 8.23 (s, 1H), 8.26 (m, 1H), 9.84 (s, 1H). |
| Example 214 | {4-[7-(2-amino-4-methyl-phenylcarbamoyl)-1-methyl-[1,2,4]triazolo[4,3-a]quinoxaline-4-ylamino]-butyl}-carbamic acid-tert-butylester | Mass (M + H$^+$): 519.30; $^1$H NMR (500 MHz, DMSO-d6): δ1.28 (s, 9H), 1.44 (m, 2H), 1.62 (m, 2H), 2.16 (s, 3H), 2.92 (m, 2H), 3.02 (s, 3H), 3.52 (m, 2H), 6.38 (d, 1H), 6.57 (s, 1H), 6.76 (d, 1H), 7.02 (d, 1H), 7.82 (d, 1H), 8.13 (m, 1H), 8.22 (m, 2H), 9.74 (s, 1H). |
| Example 215 | 1-methyl-4-[4-(3-methyl-butyrylamino)-butylamino]-[1,2,4]triazolo[4,3-a]quinoxaline-7-carboxylic acid-(2-amino-phenyl)-amide | Mass (M + H$^+$): 489.3; $^1$H NMR (500 MHz, DMSO-d6): δ0.79 (d, 6H), 1.45 (m, 2H), 1.65 (m, 2H), 1.86 (s, 2H), 1.89 (m, 1H), 3.03 (s, 3H), 3.06 (m, 2H), 3.27 (brs, 2H), 3.53 (q, 2H), 6.61 (t, 1H), 6.77 (d, 1H), 6.95 (t, 1H), 7.16 (d, 1H), 7.71 (t, 1H), 7.83 (d, 1H), 8.16 (d, 1H), 8.23 (s, 1H), 8.28 (t, 1H), 9.82 (s, 1H). |

TABLE 15-continued

| Example | Structure | Name | Data |
|---|---|---|---|
| Example 216 | 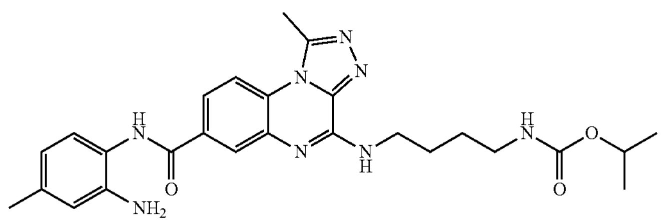 [SMILES: Cc1ccc(NC(=O)c2ccc3c(c2)nc(NCCCCNC(=O)OC(C)C)c2nnc(C)n23)c(N)c1] | 1-methyl-4-[4-(3-methyl-butyrylamino)-butylamino]-[1,2,4]triazolo[4,3-a]quinoxaline-7-carboxylic acid-(2-amino-4-methyl-phenyl)-amide | Mass (M + H$^+$): 503.3 |
| Example 217 | 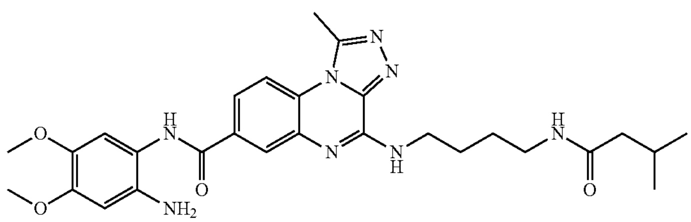 [SMILES: COc1cc(N)c(NC(=O)c2ccc3c(c2)nc(NCCCCNC(=O)CC(C)C)c2nnc(C)n23)cc1OC] | 1-methyl-4-[4-(3-methyl-butyrylamino)-butylamino]-[1,2,4]triazolo[4,3-a]quinoxaline-7-carboxylic acid-(2-amino-4,5-dimethoxy-phenyl)-amide | Mass (M + H$^+$): 549.3; $^1$H NMR (500 MHz, DMSO-d6): δ 0.79 (d, dH), 1.46 (m, 2H), 1.65 (m, 2H), 1.87 (d, 2H), 1.91 (m, 1H), 3.02 (s, 3H), 3.05 (q, 2H), 3.54 (q, 2H), 3.61 (s, 3H), 3.68 (s, 3H), 4.54 (s, 2H), 6.45 (s, 1H), 6.81 (s, 1H), 7.70 (t, 1H), 7.83 (dd, 1H), 8.15 (d, 1H), 8.22 (s, 1H), 8.28 (t, 1H), 9.76 (s, 1H). |

<Example 218> Preparation of {4-[7-(1H-benzoimidazole-2-yl)-1-methyl-[1,2,4]triazolo[4,3-a]quinoxaline-4-ylamino]-butyl}-carbamic acid-tert-butylester <Example 219> Preparation of {4-[1-methyl-7-(5-methyl-1H-benzoimidazole-2-yl)-[1,2,4]triazolo[4,3-a]quinoxaline-4-ylamino]-butyl}-carbamic acid-tert-butylester

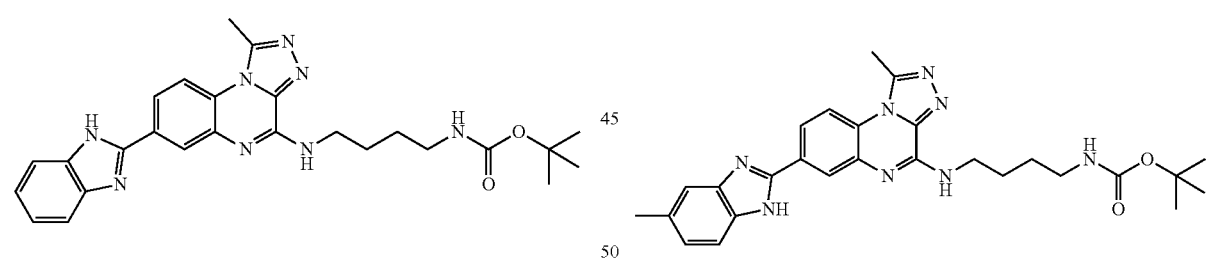

{4-[7-(2-Amino-phenylcarbamoyl)-1-methyl-[1,2,4]triazolo[4,3-a]quinoxaline-4-ylamino]-butyl}-carbamic acid-tert-butylester (0.70 g, 1.39 mmol) prepared in Example 213 was dissolved in 5 ml of acetic acid, followed by stirring at 50° C. for 4 hours. Upon completion of the reaction, 5 ml of methanol was added thereto at room temperature. Distilled water was slowly added thereto dropwise to solidify the product. The resulting solid was filtered, washed with water, and dried under reduced pressure. As a result, 0.54 g of a target compound was obtained (80% yield).

Mass (M+H$^+$): 487.3

$^1$H NMR (500 MHz, DMSO-d6): δ1.32 (s, 9H), 1.45 (m, 2H), 1.64 (m, 2H), 2.95 (q, 2H), 3.04 (s, 3H), 3.55 (q, 2H) 6.78 (t, 1H), 7.20 (m, 2H), 7.58 (m, 2H), 8.08 (d, 1H), 8.21 (d, 1H), 8.29 (t, 1H), 8.38 (s, 1H).

34 mg of a target compound was obtained (33% yield) by the same manner as described in Example 218, except that {4-[7-(2-amino-4-methyl-phenylcarbamoyl)-1-methyl-[1,2,4]triazolo[4,3-a]quinoxaline-4-ylamino]-butyl}-carbamic acid-tert-butylester (110 mg, 0.21 mmol) prepared in Example 214 was used.

Mass (M+H$^+$): 501.1

$^1$H NMR (500 MHz, DMSO-d6): δ1.32 (s, 9H), 1.45 (m, 2H), 1.65 (m, 2H), 2.40 (s, 3H), 2.93 (q, 2H), 3.03 (s, 3H), 3.53 (q, 2H), 6.78 (t, 1H), 7.00 (d, 1H), 7.34 (brm, 1H) 7.47 (brm, 1H), 8.07 (d, 1H), 8.19 (d, 1H), 8.24 (t, 1H), 8.34 (s, 1H), 12.86 (brs, 1H).

<Example 220> Preparation of {4-[1-methyl-7-(1-methyl-1H-benzoimidazole-2-yl)-[1,2,4]triazolo[4,3-a]quinoxaline-4-ylamino]-butyl}-carbamic acid-tert-butylester

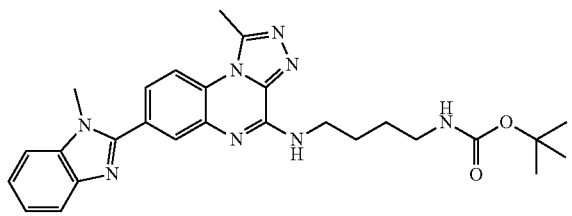 [SMILES: Cc1nnc2c(NCCCCNC(=O)OC(C)(C)C)nc3cc(-c4nc5ccccc5n4C)ccc3n12]

{4-[7-(1H-benzoimidazole-2-yl)-1-methyl-[1,2,4]triazolo[4,3-a]quinoxaline-4-ylamino]-butyl}-carbamic acid-tert-butylester (1.25 g, 2.6 mmol) prepared in Example 218 was dissolved in 15 ml of dimethylformamide, to which potassium carbonate (0.71 g, 5.14 mmol) was added. Iodomethane (0.19 ml, 3.1 mmol) was slowly added thereto, followed by stirring at room temperature for 18 hours. Upon completion of the reaction, water was slowly added thereto for recrystallization. The resulting solid was filtered, washed with water, and dried under reduced pressure. As a result, 1.13 g of a target compound was obtained (85% yield).

Mass (M+H$^+$): 487.3

$^1$H NMR (500 MHz, DMSO-d6) δ1.32 (s, 9H), 1.45 (m, 2H), 1.64 (m, 2H), 2.95 (q, 2H), 3.04 (s, 3H), 3.55 (q, 2H) 6.78 (t, 1H), 7.20 (m, 2H), 7.58 (m, 2H), 8.08 (d, 1H), 8.21 (d, 1H), 8.29 (t, 1H), 8.38 (s, 1H)

<Example 221> Preparation of N$^1$-[1-methyl-7-(1-methyl-1H-benzoimidazole-2-yl)-[1,2,4]triazolo[4,3-a]quinoxaline-4-yl]-butane-1,4-diamine ditrifluoroacetic acid

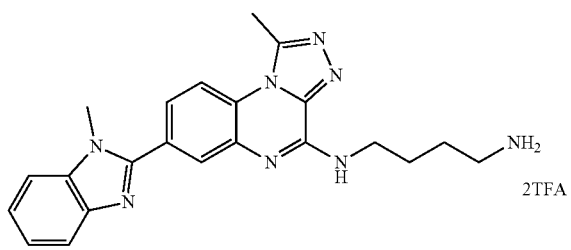 [SMILES: Cc1nnc2c(NCCCCN)nc3cc(-c4nc5ccccc5n4C)ccc3n12]

2.6 g of a target compound was obtained (99% yield) by the same manner as described in Example 58, except that {4-[1-methyl-7-(1l-methyl-1H-benzoimidazole-2-yl)-[1,2,4]triazolo[4,3-a]quinoxaline-4-ylamino]-butyl}-carbamic acid-tert-butylester (2.1 g, 4.2 mmol) prepared in Example 220 was used.

Mass (M+H$^+$): 401.2

$^1$H NMR (500 MHz, DMSO-d6) δ1.61 (m, 2H), 1.71 (m, 2H), 2.83 (m, 2H), 3.06 (s, 3H), 3.58 (m, 2H), 3.97 (s, 3H), 7.41 (m, 2H), 7.65 (brs, 3H), 7.78 (m, 3H), 8.04 (s, 1H), 8.30 (d, 1H), 8.43 (t, 1H).

<Example 222> Preparation of 3-methyl-N-{4-[1-methyl-7-(1-methyl-1H-benzoimidazole-2-yl)-[1,2,4]triazolo[4,3-a]quinoxaline-4-ylamino]-butyl}-butyramide

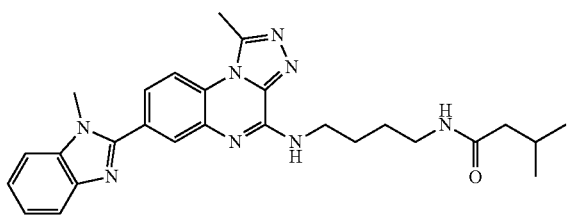 [SMILES: Cc1nnc2c(NCCCCNC(=O)CC(C)C)nc3cc(-c4nc5ccccc5n4C)ccc3n12]

A target compound was obtained (89% yield) by the same manner as described in Example 37, except that N$^1$-[1-methyl-7-(1-methyl-1H-benzoimidazole-2-yl)-[1,2,4]triazolo[4,3-a]quinoxaline-4-yl]-butane-1,4-diamine ditrifluoroacetic acid prepared in Example 221 was used.

Mass (M+H$^+$): 485.3

$^1$H NMR (500 MHz, DMSO-d6): δ0.77 (d, 6H), 1.46 (m, H), 1.66 (m, 2H), 1.86 (d, 2H), 1.89 (m, 1H), 3.05 (s, 3H), 3.07 (m, 2H), 3.55 (q, 2H), 3.92 (s, 3H), 7.23 (t, 1H), 7.28 (t, 1H), 7.60 (d, 1H), 7.67 (d, 1H), 7.70 (t, 1H), 7.74 (dd, 1H), 7.99 (d, 1H), 8.23 (d, 1H), 8.27 (t, 1H).

The compounds shown in Table 16 below were prepared by the same manner as described in Examples 220~222.

TABLE 16

| Example | Structure | Name | Data |
|---|---|---|---|
| Example 223 | 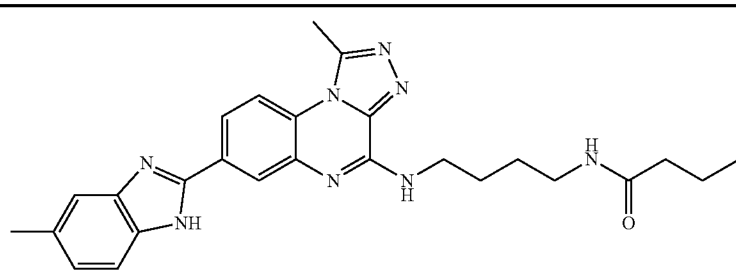 | 3-methyl-N-{4-[1-methyl-7-(5-methyl-1H-benzoimidazole-2-yl)-[1,2,4]triazolo[4,3-a]quinoxaline-4-ylamino]-butyl}-butyramide | Mass (M + H$^+$): 485.3; $^1$H NMR (500 MHz, DMSO-d6): δ0.78 (d, 6H), 1.48 (m, 2H), 1.67 (m, 2H), 1.87 (d, 2H), 1.89 (m, 1H), 2.40 (s, 3H), 3.03 (s, 3H), 3.07 (q, 2H), 3.55 (m, 2H), 7.00 (d, 1H), 7.34 |

TABLE 16-continued

| Example | Structure | Name | Data |
|---|---|---|---|
| | | | (brs, 1H), 7.45 (brs, 1H), 7.72 (t, 1H), 8.08 (d, 1H), 8.18 (d, 1H), 8.26 (t, 1H), 8.34 (s, 1H), 12.88 (brs, 1H). |
| Example 224 | 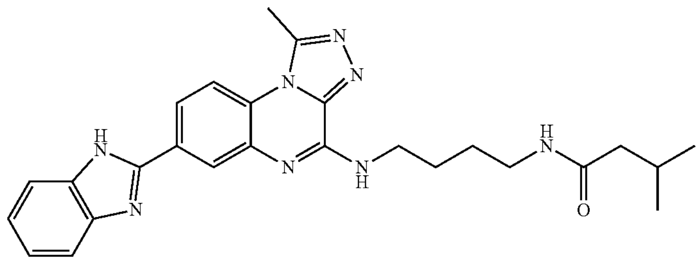 [SMILES: Cc1nnc2c(NCCCCNC(=O)CC(C)C)nc3cc(-c4nc5ccccc5[nH]4)ccc3n12] | N-{4-[7-(1H-benzo-imidazole-2-yl)-1-methyl-[1,2,4]tri-azolo[4,3-a]quinoxaline-4-ylamino]-butyl}-3-methyl-butyramide | Mass (M + H$^+$): 471.3; $^1$H NMR (500 MHz, DMSO-d6): δ0.79 (d, 6H), 1.47 (m, 2H), 1.67 (m, 2H), 1.87 (m, 2H), 1.89 (d, 2H), 3.04 (m, 1H), 3.06 (s, 3H), 3.54 (q, 2H), 7.20 (q, 2H), 7.58 (t, 2H), 7.72 (d, 2H), 8.08 (t, 1H), 8.21 (d, 1H), 8.29 (d, 1H), 8.38 (t, 1H), 13.02 (s, 1H) (s, 1H). |
| Example 225 | 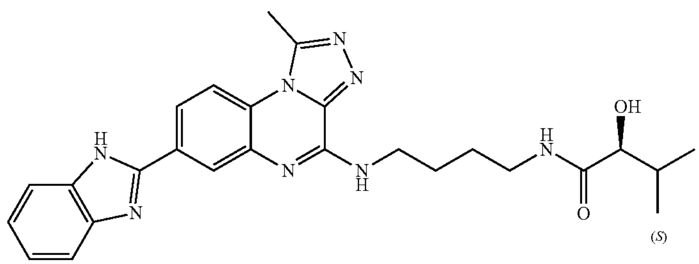 | N-{4-[7-(1H-benzo-imidazole-2-yl)-1-methyl-[1,2,4]tri-azolo[4,3-a]quinoxaline-4-ylamino]-butyl}-2-(S)-hydroxy-3-methyl-butyramide | Mass (M + H$^+$): 487.2; $^1$H NMR (500 MHz, DMSO-d6): δ0.67 (d, 3H), 0.83 (d, 3H), 1.23 (m, 1H), 1.50 (m, 2H), 1.66 (m, 2H), 1.93 (m, 1H), 3.05 (s, 3H), 3.09 (m, 1H), 3.15 (m, 1H), 3.55 (q, 2H), 3.61 (s, 1H), 7.34 (d, 2H), 7.69 (m, 3H), 8.10 (d, 1H), 8.27 (d, 1H), 8.42 (brm, 2H). |
| Example 226 | 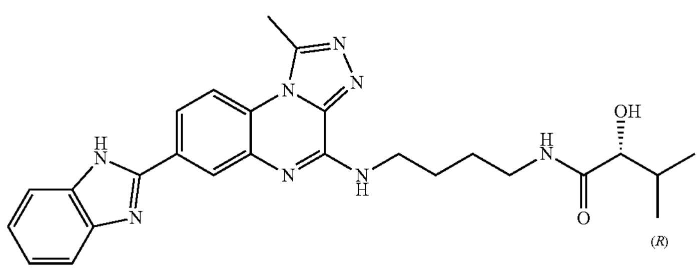 | N-{4-[7-(1H-benzo-imidazole-2-yl)-1-methyl-[1,2,4]tri-azolo[4,3-a]quinoxaline-4-ylamino]-butyl}-2-(R)-hydroxy-3-methyl-butyramide | Mass (M + H$^+$): 487.2; $^1$H NMR (500 MHz, DMSO-d6): δ0.67 (d, 3H), 0.83 (d, 3H), 1.23 (m, 1H), 1.50 (m, 2H), 1.66 (m, 2H), 1.93 (m, 1H), 3.05 (s, 3H), 3.09 (m, 1H), 3.15 (m, 1H), 3.55 (q, 2H), 3.61 (s, 1H), 7.34 (d, 2H), 7.69 (m, 3H), 8.10 (d, 1H), 8.27 (d, 1H), 8.42 (brm, 2H). |

TABLE 16-continued

| Example | Name | Data |
|---|---|---|
| Example 227 | N-{4-[7-(5,6-dimethoxy-1H-benzo-imidazol-2-yl)-1-methyl-[1,2,4]tri-azolo[4,3-a]quinoxaline-4-ylamino]-butyl}-3-methyl-butyramide | Mass (M + H$^+$): 531.3; $^1$H NMR (500 MHz, DMSO-d6): δ0.77 (d, 6H), 1.47 (m, H), 1.67 (m, 2H), 1.87 (d, 2H), 1.90 (m, 1H), 3.03 (s, 3H), 3.06 (q, 2H), 3.54 (q, 2H), 3.79 (s, 6H), 6.95 (m, 1H), 7.20 (m, 1H), 7.72 (t, 1H), 8.03 (d, 1H), 8.15 (d, 1H), 8.24 (t, 1H), 8.28 (d, 1H), 12.75 (s, 1H). |
| Example 228 | {4-[1-methyl-7-(1-methyl-1H-benzo-imidazol-2-yl)-[1,2,4]tri-azolo[4,3-a]quinoxaline-4-ylamino]-butyl}-carbamic acid propylester | Mass (M + H$^+$): 487.2; $^1$H NMR (500 MHz, DMSO-d6): δ0.80 (t, 3H), 1.48 (m, 4H), 1.69 (m, 2H), 3.02 (q, 2H), 3.05 (s, 3H), 3.59 (s, 3H), 3.83 (q, 2H), 3.92 (t, 3H), (s, 3H), 6.78 (brm, 1H), 7.23 (t, 1H), 7.28 (t, 1H), 7.58 (d, 1H), 7.67 (d, 1H), 7.74 (d, 1H), 8.01 (s, 2H), 8.23 (d, 1H). |
| Example 229 | {4-[1-methyl-7-(1-methyl-1H-benzo-imidazol-2-yl)-[1,2,4]tri-azolo[4,3-a]quinoxaline-4-ylamino]-butyl}-carbamic acid cyclopent-ylester | Mass (M + H$^+$): 513.3; $^1$H NMR (500 MHz, DMSO-d6): δ1.44~1.52 (m, 8H), 1.64 (m, 4H), 2.98 (q, 2H), 3.04 (s, 3H), 3.54 (q, 2H), 3.92 (s, 3H), 4.85 (m, 1H), 6.94 (t, 1H), 7.23 (t, 1H), 7.28 (t, 1H), 7.60 (d, 1H), 7.67 (d, 1H), 7.75 (d, 1H), 8.00 (s, 1H), 8.22 (d, 1H), 8.27 (t, 1H). |

TABLE 16-continued

| Example | Structure | Name | Data |
|---|---|---|---|
| Example 230 | 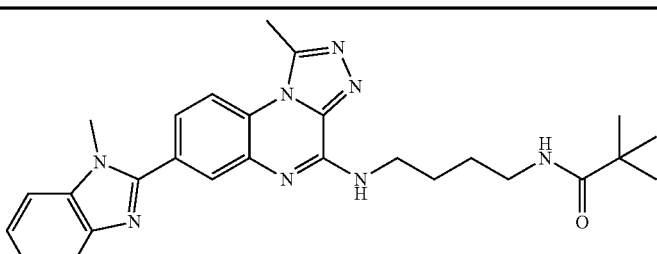 | 2,2-dimethyl-N-{4-[1-methyl-7-(1-methyl-1H-benzoimid-azole-2-yl)-[1,2,4]tri-azolo[4,3-a]quinoxaline-4-ylamino]-butyl}-propionamide | Mass (M + H$^+$): 485.3; $^1$H NMR (500 MHz, DMSO-d6): δ1.01 (s, 9H), 1.48 (m, 2H), 1.62 (m, 2H), 3.04 (s, 3H), 3.06 (q, 2H), 3.54 (q, 2H), 3.92 (s, 3H), 7.23 (t, 1H), 7.28 (t, 1H), 7.39 (t, 1H), 7.60 (d, 1H), 7.67 (d, 1H), 7.72 (d, 1H), 7.99 (s, 1H), 8.22 (d, 1H), 8.28 (t, 1H). |
| Example 231 | 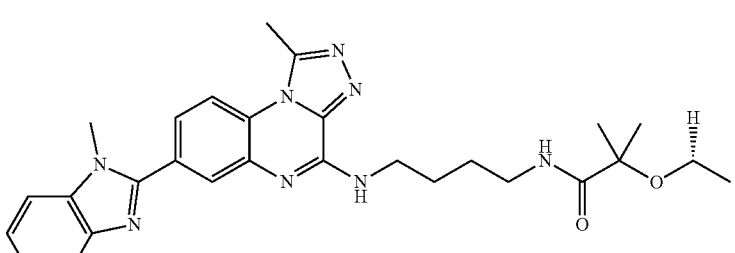 | acetic acid-1-{4-[7-(1-methyl-1H-benzoimid-azole-2-yl)-1-methyl-[1,2,4]tri-azolo[4,3-a]quinoxaline-4-ylamino]-butylcarbamo-yl}-1-methyl-ethylester | Mass (M + H$^+$): 529.3; $^1$H NMR (500 MHz, DMSO-d6): δ1.38 (s, 6H), 1.47 (m, 2H), 1.64 (m, 2H), 1.92 (m, 2H), 3.04 (s, 3H), 3.07 (s, 3H), 3.55 (q, 2H), 3.92 (q, 2H), 7.23 (d, 3H), 7.28 (t, 1H), 7.60 (t, 1H), 7.66 (d, 1H), 7.75 (m, 2H), 8.00 (d, 1H), 8.22 (s, 1H), 8.27 (d, 1H), (t, 1H). |
| Example 232 | 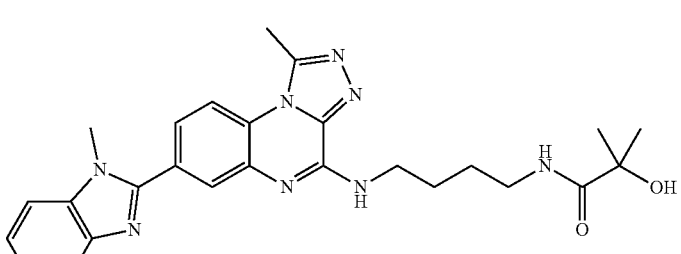 | 2-hydroxy-N-{4-(7-(1-methyl-1H-benzoimid-azole-2-yl)-1-methyl-[1,2,4]tri-azolo[4,3-a]quinoxaline-4-ylamino)-butyl}-2-methyl-propionamide | Mass (M + H$^+$): 487.3; $^1$H NMR (500 MHz, DMSO-d6): δ1.17 (s, 6H), 1.50 (m, 2H), 1.64 (m, 2H), 3.03 (m, 2H), 3.09 (s, 3H), 3.55 (q, 2H), 3.92 (q, 2H), 5.26 (s, 3H), 7.22 (s, 1H), 7.26 (t, 2H), 7.59 (t, 2H), 7.66 (m, 2H), 7.73 (d, 1H), 7.99 (d, 1H), 8.20 (s, 1H), 8.28 (d, 1H), (t, 1H). |
| Example 233 | 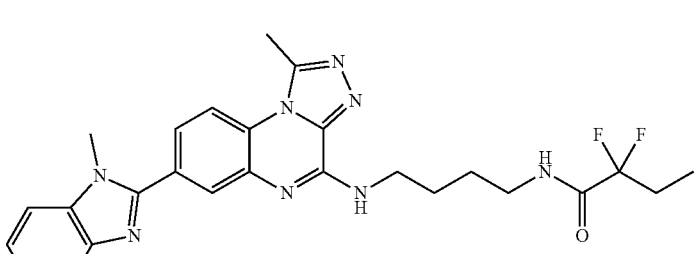 | 2,2-difluoro-N-{4-[1-methyl-7-(1-methyl-1H-benzoimid-azole-2-yl)-[1,2,4]tri-azolo[4,3-a]quinoxaline-4-ylamino]-butyl}-butyramide | Mass (M + H$^+$): 507.2; $^1$H NMR (500 MHz, DMSO-d6): δ0.82 (t, 3H), 1.53 (m, 2H), 1.65 (m, 2H), 1.95 (m, 2H), 3.04 (s, 3H), 3.16 (q, 2H), 3.56 (q, 2H), 3.92 |

TABLE 16-continued

| Example | Structure | Name | Data |
|---|---|---|---|
| | | | (s, 3H), 7.23 (t, 1H), 7.28 (t, 1H), 7.60 (d, 1H), 7.67 (d, 1H), 7.77 (d, 1H), 7.99 (s, 1H), 8.22 (d, 1H), 8.29 (t, 1H), 8.64 (t, 1H). |
| Example 234 | 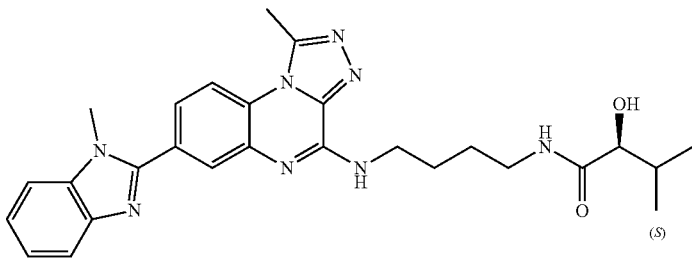 | 2-(S)-hydroxy-3-methyl-N-{4-[1-methyl-7-(1-methyl-1H-benzoimid-azole-2-yl)-[1,2,4]tri-azolo[4,3-a]quinoxaline-4-ylamino]-butyl}-butyramide | Mass (M + H⁺): 501.3; ¹H NMR (500 MHz, DMSO-d6): δ0.66 (d, 3H), 0.81 (d, 3H), 1.20 (m, 1H), 1.49 (m, 2H), 1.65 (m, 2H), 1.89 (m, 1H), 3.04 (s, 3H), 3.08 (m, 1H), 3.14 (m, 1H), 3.56 (m, 2H), 3.92 (s, 3H), 5.24 (d, 1H), 7.23 (t, 1H), 7.28 (t, 1H), 7.60 (d, 1H), 7.61 (m, 2H), 7.74 (d, 1H), 8.00 (s, 1H), 8.23 (d, 1H), 8.30 (t, 1H). |
| Example 235 | 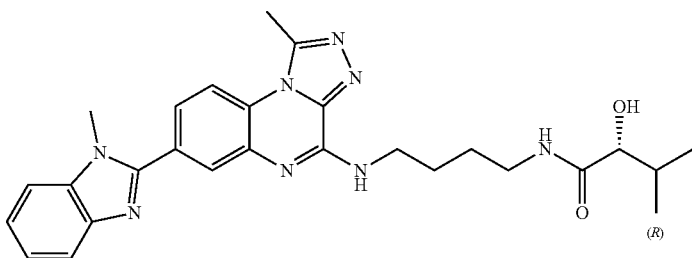 | 2-(R)-hydroxy-3-methyl-N-{4-[1-methyl-7-(1-methyl-1H-benzoimid-azole-2-yl)-[1,2,4]tri-azolo[4,3-a]quinoxaline-4-ylamino]-butyl}-butyramide | Mass (M + H⁺): 501.3; ¹H NMR (500 MHz, DMSO-d6): δ0.66 (d, 3H), 0.80 (d, 3H), 1.20 (m, 1H), 1.65 (m, 2H), 1.89 (m, 1H), 3.04 (s, 3H), 3.08 (m, 1H), 3.14 (m, 1H), 3.56 (m, 2H), 3.92 (s, 3H), 5.25 (d, 1H), 7.23 (t, 1H), 7.28 (t, 1H), 7.60 (d, 1H), 7.65 (m, 2H), 7.74 (d, 1H), 7.99 (s, 1H), 8.21 (d, 1H), 8.29 (t, 1H), 7.74 (d, 1H), 7.99 (s, 1H), 8.21 (d, 1H), 8.29 (t, 1H). |
| Example 236 | 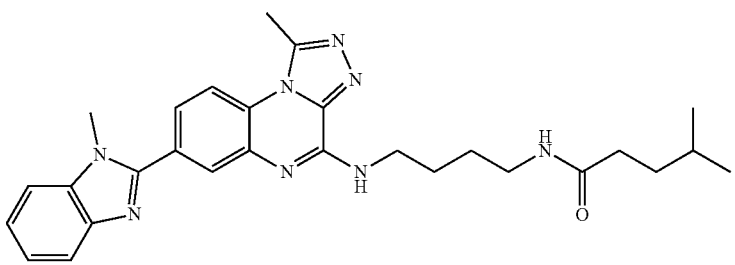 [SMILES: Cc1nnc2c(NCCCCNC(=O)CCC(C)C)nc3cc(-c4nc5ccccc5n4C)ccc3n12] | 4-methyl-pentanoic acid-{4-[1-methyl-7-(1-methyl-1H-benzoimid-azole-2-yl)-[1,2,4]tri-azolo[4,3-a]quinoxaline-4-ylamino]-butyl}-amide | Mass (M + H⁺): 499.3; ¹H NMR (500 MHz, DMSO-d6): δ0.74 (d, 6H), 1.36 (m, 2H), 1.38 (m, 1H), 1.45 (m, 2H), 1.65 (m, 2H), 1.98 (t, 2H), 3.04 (s, 3H), 3.05 |

TABLE 16-continued

| Example | Structure | Name | Data |
|---|---|---|---|
| | | | (m, 2H), 3.56 (q, 2H), 3.92 (s, 3H), 7.23 (t, 1H), 7.28 (t, 1H), 7.60 (d, 1H), 7.67 (d, 1H), 7.71 (m, 2H), 7.09 (s, 1H), 8.22 (d, 1H), 8.28 (t, 1H). |
| Example 237 | 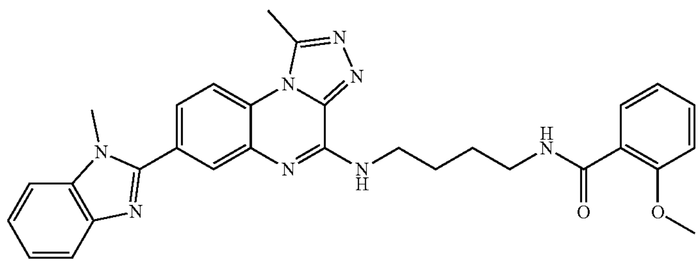 [SMILES: COc1ccccc1C(=O)NCCCCNc1nc2cc(-c3nc4ccccc4n3C)ccc2n2c(C)nnc12] | 2-methoxy-N-{4-[1-methyl-7-(1-methyl-1H-benzo-imidazole-2-yl)-[1,2,4]tri-azolo[4,3-a]quinoxaline-4-ylamino]-butyl}-benzamide | Mass (M + H$^+$): 535.3; $^1$H NMR (500 MHz, DMSO-d6): δ1.59 (m, 2H), 1.73 (m, 2H), 3.04 (s, 3H), 3.31 (m, 2H), 3.59 (q, 2H), 3.77 (s, 3H), 3.90 (s, 3H), 6.90 (t, 1H), 7.01 (d, 1H), 7.23 (t, 1H), 7.28 (t, 1H), 7.36 (t, 1H), 7.61 (m, 2H), 7.67 (d, 1H), 7.73 (d, 1H), 7.97 (s, 1H), 8.11 (t, 1H), 8.21 (d, 1H), 8.31 (t, 1H). |
| Example 238 | 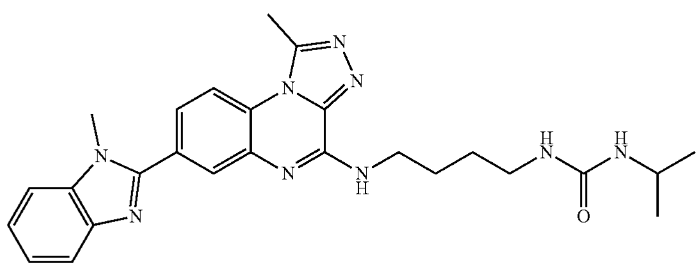 [SMILES: Cc1nnc2c(NCCCCNC(=O)NC(C)C)nc3cc(-c4nc5ccccc5n4C)ccc3n12] | 1-isopropyl-3-{4-[1-methyl-7-(1-methyl-1H-benzoimid-azole-2-yl)-[1,2,4]tri-azolo[4,3-a]quinoxaline-4-ylamino]-butyl}-urea | Mass (M + H$^+$): 486.3; $^1$H NMR (500 MHz, DMSO-d6): δ0.93 (d, 6H), 1.43 (m, 2H), 1.63 (m, 2H), 2.99 (q/ 2H), 3.04 (s, 3H), 3.56 (m, 2H), 3.61 (m, 1H), 3.92 (s, 3H), 5.52 (d, 1H), 5.63 (t, 1H), 7.23 (t, 1H), 7.28 (t, 1H), 7.60 (d, 1H), 7.67 (d, 1H), 7.74 (d, 1H), 8.00 (s, 1H), 8.22 (d, 1H), 8.29 (t, 1H). |
| Example 239 | 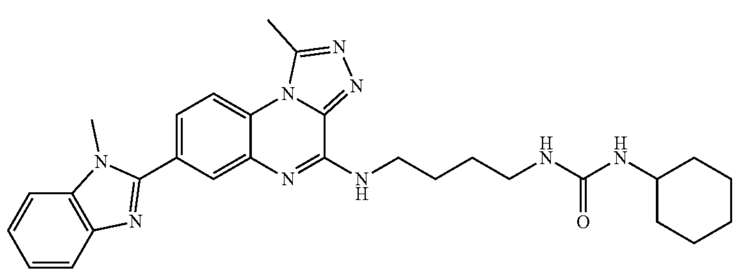 [SMILES: Cc1nnc2c(NCCCCNC(=O)NC3CCCCC3)nc3cc(-c4nc5ccccc5n4C)ccc3n12] | 1-cyclohexyl-3-{4-[1-methyl-7-(1-methyl-1H-benzoimid-azole-2-yl)-[1,2,4]tri-azolo[4,3-a]quinoxaline-4-ylamino]-butyl}-urea | Mass (M + H$^+$): 526.3; $^1$H NMR (500 MHz, DMSO-d6): δ0.98 (m, 3H), 1.17 (m, 3H), 1.42 (m, 3H), 1.52 (m, 2H), 1.64 (m, 4H), 3.00 (q, 2H), 3.04 (s, 3H), 3.55 (s, 3H), 3.58 (q, 2H), 3.92 (s, 3H), 5.64 (d, 1H), 7.23 (t, 1H), 7.28 (t, 1H) |

TABLE 16-continued

| Example | Structure | Name | Data |
|---|---|---|---|
| | | | (t, 1H), 7.60 (d, 1H), 7.67 (d, 1H), 7.75 (d, 1H), 8.00 (s, 1H), 8.22 (d, 1H), 8.31 (t, 1H). |
| Example 240 | 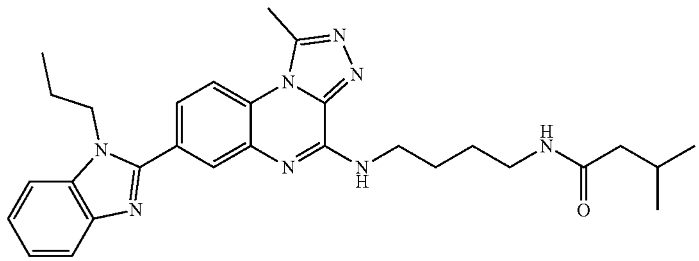 [SMILES: CCCn1c(-c2ccc3c(c2)nc(NCCCCNC(=O)CC(C)C)c2nnc(C)n23)nc2ccccc21] | 3-methyl-N-{4-[1-methyl-7-(1-propyl-1H-benzoimid-azole-2-yl)-[1,2,4]tri-azolo[4,3-a]quinoxaline-4-ylamino]-butyl}-butyramide | Mass (M + H⁺): 513.3; ¹H NMR (500 MHz, DMSO-d6): δ0.71 (t, 3H) 0.77 (d, 6H) 1.45 (m, 2H), 1.68 (m, 4H), 1.86 (d, 2H), 1.88 (m, 1H), 3.04 (s, 3H), 3.06 (m, 2H), 3.54 (m, 2H), 4.30 (m, 2H), 7.15~7.29 (m, 3H), 7.63~7.71 (m, 3H), 7.90 (d, 1H), 8.24 (d, 1H), 8.28 (t, 1H). |
| Example 241 | 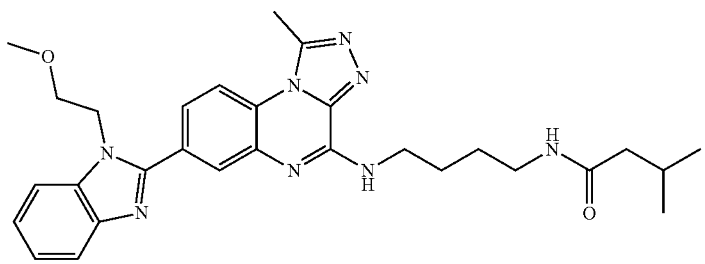 [SMILES: COCCn1c(-c2ccc3c(c2)nc(NCCCCNC(=O)CC(C)C)c2nnc(C)n23)nc2ccccc21] | N-(4-{7-[1-(2-methoxy-ethyl)-1H-benzoimid-azole-2-yl]-1-methyl-[1,2,4]tri-azolo[4,3-a]quinoxaline-4-ylamino}-butyl)-3-methyl-butyramide | Mass (M + H⁺): 529.3; ¹H NMR (500 MHz, DMSO-d6): δ0.77 (d, 6H), 1.46 (m, 2H), 1.65 (m, 2H), 1.85 (d, 2H), 1.89 (m, 1H), 3.04 (s, 3H), 3.06 (q, 2H), 3.10 (s, 3H), 3.54 (q, 2H), 3.68 (t, 2H), 4.49 (t, 2H), 7.25 (m, 2H), 7.67 (dd, 2H), 7.71 (t, 2H), 8.00 (s, 1H), 8.22 (d, 1H), 8.28 (t, 1H). |

<Preparative Example 18> Preparation of 4-chloro-1-methyl-7-nitro[1,2,4]triazolo[4,3-a]quinoxaline

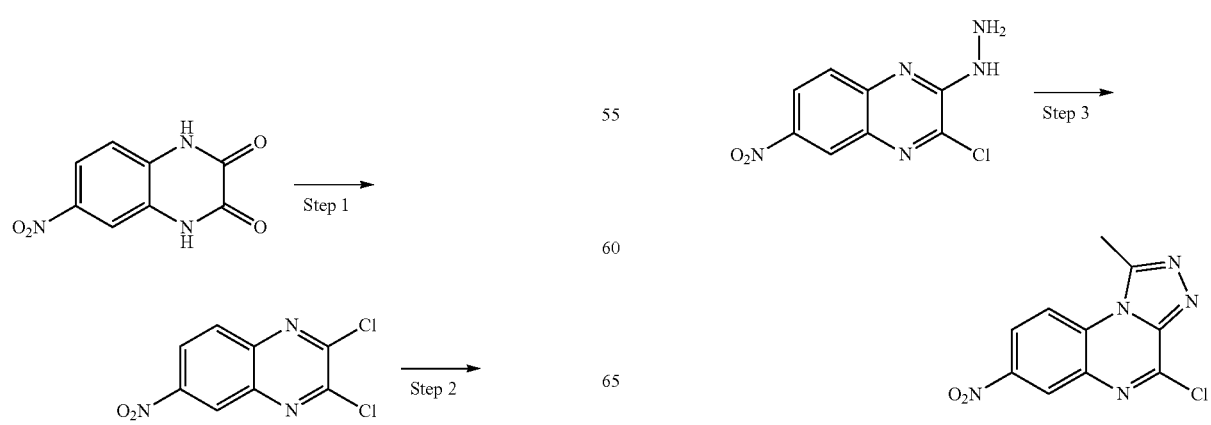

Step 1: Preparation of 2,3-dichloro-6-nitroquinoxaline

6-Nitroquinoxaline-2,3-(1H,4H)-dione (12 g, 59.0 mmol), thionylchloride (28.1 g, 236 mmol) and catalytic amount of dimethylformamide (0.86 g, 11.8 mmol) were dissolved in dichloroethane solvent, followed by reflux stirring for 2 hours. Upon completion of the reaction, the solvent was eliminated. The temperature was lowered to 0~5° C. to solidify the product. The resulting solid was filtered, and dried under reduced pressure. As a result, 12.3 g of a target compound was obtained (87% yield).

Mass (M+H$^+$): 244.1

$^1$H NMR (300 MHz, DMSO-d6): δ8.31 (d, J=9.15 Hz, 1H), 8.60 (d, J=9.15 Hz, 1H), 8.88 (s, 1H).

Step 2: Preparation of 3-chloro-6-nitroquinoxaline-2-ylhydrazine 2.3 g of a target compound was obtained (92% yield) by the same manner as described in step 2 of Preparative Example 2, except that 2,3-dichloro-6-nitroquinoxaline (2.55 g, 10.5 mmol) prepared in step 1 of Preparative Example 18 was used.

Mass (M+H$^+$): 240.1

Step 3: 4-chloro-1-methyl-7-nitro[1,2,4]triazolo[4,3-a]quinoxaline 1.2 g of a target compound was obtained (44% yield) by the same manner as described in step 3 of Preparative Example 5, except that 3-chloro-6-nitroquinoxaline-2-ylhydrazine (2.5 g, 10.4 mmol) prepared in step 2 of Preparative Example 18 was used.

Mass (M+H$^+$): 264.0

<Example 242> Preparation of [4-(1-methyl-7-nitro-[1,2,4]triazolo[4,3-a]quinoxaline-4-ylamino)-butyl]-carbamic acid-tert-butylester

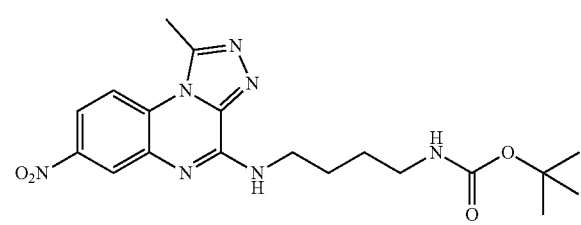 [SMILES: Cc1nnc2c(NCCCCNC(=O)OC(C)(C)C)nc3cc([N+](=O)[O-])ccc3n12]

1.3 g of a target compound was obtained (83% yield) by the same manner as described in Example 57, except that 4-chloro-1-methyl-7-nitro-[1,2,4]triazolo[4,3-a]quinoxaline (1.03 g, 3.91 mmol) prepared in step 3 of Preparative Example 18 was used.

Mass (M+H$^+$): 416.2

$^1$H NMR (500 MHz, DMSO-d6): δ1.36 (s, 9H), 1.45-1.51 (m, 2H), 1.64-1.70 (m, 2H), 2.96-3.00 (m, 2H), 3.03 (s, 3H), 3.53-3.57 (m, 2H), 6.81 (t, J=5.05 Hz, 1H), 8.02 (dd, J=9.05 Hz, 2.40 Hz, 1H), 8.20 (d, J=2.00 Hz, 1H), 8.23 (d, J=9.10 Hz, 1H), 8.60 (t, J=5.45 Hz, 1H).

<Example 243> Preparation of [4-(7-amino-1-methyl-[1,2,4]triazolo[4,3-a]quinoxaline-4-ylamino)-butyl]-carbamic acid-tert-butylester

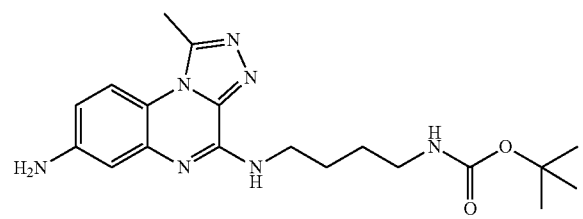

[4-(1-Methyl-7-nitro-[1,2,4]triazolo[4,3-a]quinoxaline-4-ylamino)-butyl]-carbamic acid-tert-butylester prepared in Example 242 and Pd/C (10 W %) were dissolved in ethanol, followed by stirring in the presence of hydrogen gas at 5 bar for 3 hours. As a result, a target compound obtained (quantitative yield).

Mass (M+H$^+$): 386.2

$^1$H NMR (300 MHz, DMSO-d6): δ1.36 (s, 9H), 1.40-1.47 (m, 2H), 1.58-1.65 (m, 2H), 2.93-2.98 (m, 5H), 3.48-3.50 (m, 2H), 5.28 (s, 2H), 6.77 (s, 2H), 7.76 (d, J=8.76 Hz, 1H), 7.85 (t, J=4.53 Hz, 1H).

<Example 244> Preparation of 3-methyl-N-[4-(1-methyl-8-nitro-[1,2,4]triazolo[4,3-a]quinoxaline-4-ylamino)-butyl]-butyramide

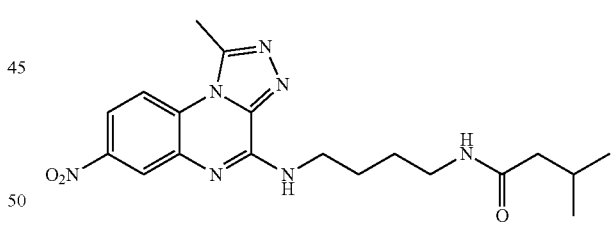

4-Chloro-1-methyl-7-nitro-[1,2,4]triazolo[4,3-a]quinoxaline (1.03 g, 3.91 mmol) prepared in step 3 of Preparative Example 18 was dissolved in 20 ml of isopropylalcohol, to which diisopropylethylamine (0.74 ml, 3.4 mmol) and N-(4-aminobutyl)-3-methyl-butyramide ditrifluoroacetic acid (2.34 g, 5.86 mmol) were added, followed by reflux stirring for 18 hours. Upon completion of the reaction, the resulting solid was filtered and dried under reduced pressure. As a result, 1.3 g of a target compound was obtained (83% yield).

Mass (M+H$^+$): 400.2

$^1$H NMR (500 MHz, DMSO-d6) δ0.79 (d, 6H), 1.46 (m, 2H), 1.65 (m, 2H), 1.86 (d, 2H), 1.87 (m, 1H), 3.01 (s, 3H), 3.05 (q, 2H), 3.54 (q, 2H), 7.781 (t, 1H), 8.05 (d, 1H), 8.22 (s, 1H), 8.26 (d, 1H), 8.59 (t, 1H).

<Example 245> Preparation of N-[4-(7-amino-1-methyl-[1,2,4]triazolo[4,3-a]quinoxaline-4-ylamino)-butyl]-3-methyl-butyramide

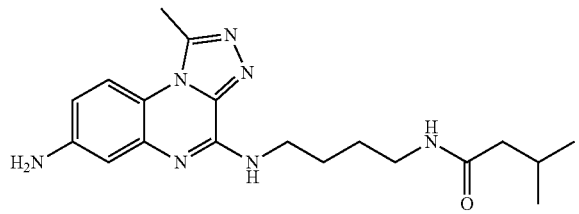 [SMILES: Cc1nnc2c(NCCCCNC(=O)CC(C)C)nc3cc([N+](=O)[O-])ccc3n12]

0.72 g of a target compound was obtained (78% yield) by the same manner as described in Example 243, except that 3-methyl-N-[4-(1-methyl-7-nitro-[1,2,4]triazolo[4,3-a]quinoxaline-4-ylamino)-butyl]-butyramide (1 g, 2.5 mmol) prepared in Example 244 was used.

Mass (M+H$^+$): 370.0

$^1$H NMR (500 MHz, DMSO-d6) δ0.80 (d, 6H), 1.44 (m, 2H), 1.61 (m, 2H), 1.86 (d, 2H), 1.95 (m, 1H), 2.89 (s, 3H), 3.04 (q, 2H), 3.27 (d, 2H), 3.47 (q, 2H), 6.73 (t, 1H), 7.69 (d, 1H), 7.73 (d, 1H), 7.92 (t, 1H), 8.41 (s, 1H).

The compounds shown in Table 17 below were prepared by using the compound prepared by the same manner as described in Examples 243~245 as an intermediate.

TABLE 17

| Example | Structure | Name | Data |
|---|---|---|---|
| Example 246 | 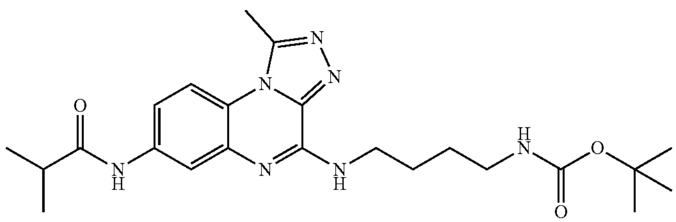 [SMILES: Cc1nnc2c(NCCCCNC(=O)OC(C)(C)C)nc3cc(NC(=O)C(C)C)ccc3n12] | [4-(7-iso-butyramido-1-methyl-[1,2,4]triazolo[4,3-a]quinoxaline-4-ylamino)-butyl]-carbamic acid-tert-butylester | Mass (M + H$^+$): 456.3; $^1$H NMR (500 MHz, DMSO-d6): δ1.13 (d, J = 6.80 Hz, 6H), 1.36 (s, 9H), 1.45-1.48 (m, 2H), 1.62-1.68 (m, 2H), 2.60-2.65 (m, 1H), 2.94-2.98 (m, 2H), 3.00 (s, 3H), 3.52-3.53 (m, 2H), 6.81 (t, J = 5.10 Hz, 1H), 7.47 (dd, J = 9.05 Hz, 1.76 Hz, 1H), 7.99 (d, J = 1.85 Hz, 1H), 8.02 (d, J = 9.00 Hz, 1H), 8.13 (t, J = 5.60 Hz, 1H), 9.98 (s, 1H). |
| Example 247 | 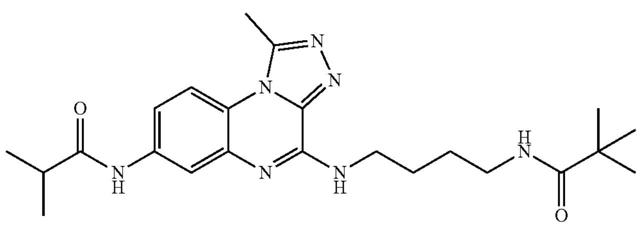 [SMILES: Cc1nnc2c(NCCCCNC(=O)C(C)(C)C)nc3cc(NC(=O)C(C)C)ccc3n12] | N-[4-(7-iso-butyramido-1-methyl-[1,2,4]triazolo[4,3-a]quinoxaline-4-ylamino)-butyl]-2,2-dimethyl-propionamide | Mass (M + H$^+$): 440.6; $^1$H NMR (500 MHz, DMSO-d6): δ1.07 (s, 9H), 1.13 (d, J = 6.75 Hz, 6H), 1.46-1.52 (m, 2H), 1.62-1.68 (m, 2H), 2.60-2.65 (m, 1H), 3.00 (s, 3H), 3.07-3.11 (m, 2H), 3.52-3.56 (m, 2H), 7.43 (t, J = 5.40 Hz, 1H), 7.47 (dd, J = 9.95 Hz, 2.45 Hz, 1H), 7.99 (d, J = 1.55 Hz, 1H), 8.02 (d, J = 9.05 Hz, 1H), 8.13 (brs, 1H), 9.98 (s, 1H). |
| Example 248 | 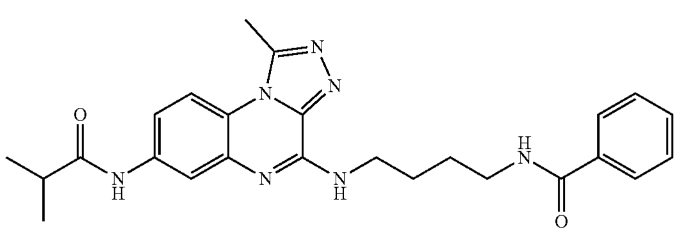 [SMILES: Cc1nnc2c(NCCCCNC(=O)c3ccccc3)nc3cc(NC(=O)C(C)C)ccc3n12] | N-[4-(7-iso-butyramido-1-methyl-[1,2,4]triazolo[4,3-a]quinoxaline-4-ylamino)-butyl]-benzamide | Mass (M + H$^+$): 460.7; $^1$H NMR (500 MHz, DMSO-d6): δ1.13 (d, J = 6.80 Hz, 6H), 1.60-1.66 (m, 2H), 1.71-1.77 (m, 2H), 2.60-2.65 (m, 1H), 3.00 (s, 3H), 3.30-3.33 (m, 2H), 3.56-3.60 (m, 2H), 7.42-7.52 (m, 4H), 7.82 (d, J = 7.40 Hz, 2H), 7.99 (d, J = 2.10 Hz, 1H), 8.02 |

TABLE 17-continued

| Example | Structure | Name | Data |
|---|---|---|---|
| | | | (d, J = 9.05 Hz, 1H), 8.15 (t, J = 5.70 Hz, 1H), 8.46 (t, J = 5.50 Hz, 1H). |
| Example 249 | 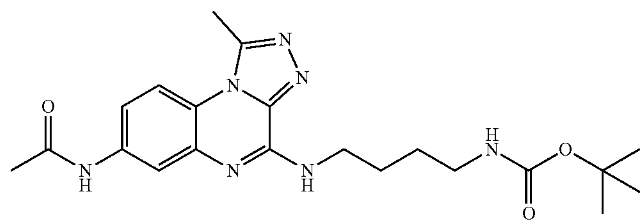 [SMILES: CC(=O)Nc1ccc2c(c1)nc(NCCCCNC(=O)OC(C)(C)C)c1nnc(C)n12] | [4-(7-acetylamino-methyl-[1,2,4]tri-azolo[4,3-a]quinoxaline-4-ylamino)-butyl]-carbamic acid-tert-butylester | Mass (M + H$^+$): 427.7; $^1$H NMR (500 MHz, DMSO-d6): δ1.36 (s, 9H), 1.44-1.48 (m, 2H), 1.62-1.66 (m, 2H), 2.09 (s, 3H), 2.94-2.98 (m, 2H), 3.01 (s, 3H), 3.52-3.54 (m, 2H), 6.81 (brs, 1H), 7.43 (d, J = 8.75 Hz, 1H), 7.98 (s, 1H), 8.01 (d, J = 8.95 Hz, 1H), 8.13 (t, J = 5.40 Hz, 1H), 10.1 (s, 1H). |
| Example 250 | 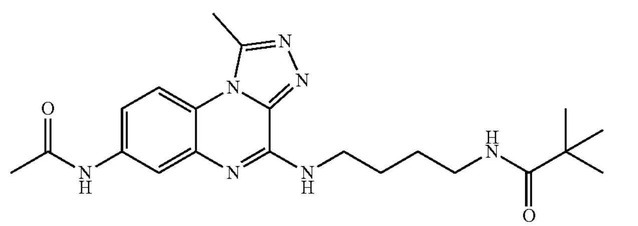 [SMILES: CC(=O)Nc1ccc2c(c1)nc(NCCCCNC(=O)C(C)(C)C)c1nnc(C)n12] | N-[4-(7-acetylamino-methyl-[1,2,4]tri-azolo[4,3-a]quinoxaline-4-ylamino)-butyl]-2,2-dimethyl-propionamide | Mass (M + H$^+$): 411.6; $^1$H NMR (500 MHz, DMSO-d6): δ1.07 (s, 9H), 1.47-1.50 (m, 2H), 1.62-1.68 (m, 2H), 2.09 (s, 3H), 3.00 (s, 3H), 3.07-3.11 (m, 2H), 3.52-3.56 (m, 2H), 7.41-7.44 (m, 2H), 7.98 (d, J = 2.15 Hz, 1H), 8.02 (d, J = 9.05 Hz, 1H), 8.12 (brs, 1H), 10.1 (s, 1H). |
| Example 251 | 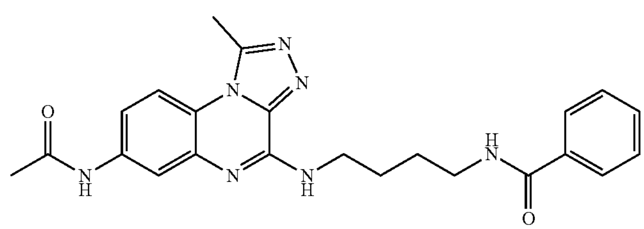 [SMILES: CC(=O)Nc1ccc2c(c1)nc(NCCCCNC(=O)c1ccccc1)c1nnc(C)n12] | N-[4-(7-acetylamino-methyl-[1,2,4]tri-azolo[4,3-a]quinoxaline-4-ylamino)-butyl]-benzamide | Mass (M + H$^+$): 432.3; $^1$H NMR (500 MHz, DMSO-d6): δ1.57-1.71 (m, 4H), 2.09 (s, 3H), 3.00 (s, 3H), 3.30-3.35 (m, 2H), 3.53-3.56 (m, 2H), 7.42-7.45 (m, 2H), 7.49-7.52 (m, 1H), 7.81-7.83 (m, 1H), 7.97-7.99 (m, 1H), 8.03 (dd, J = 9.00 Hz, 2.25 Hz, 1H), 8.14 (t, J = 5.55 Hz, 1H), 8.46 (t, J = 5.70 Hz, 1H), 10.1 (s, 1H). |
| Example 252 | 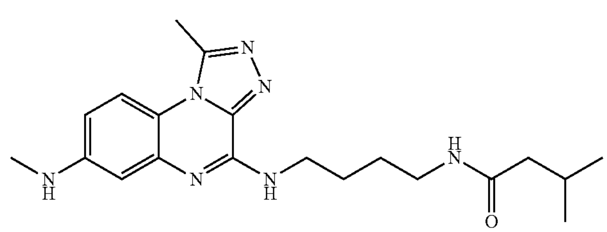 [SMILES: CNc1ccc2c(c1)nc(NCCCCNC(=O)CC(C)C)c1nnc(C)n12] | 3-methyl-N-[4-(1-methyl-7-methylamino-[1,2,4]tri-azolo[4,3-a]quinoxaline-4-ylamino)-butyl]-butyramide | Mass (M + H$^+$): 384.2; $^1$H NMR (500 MHz, DMSO-d6): δ0.79 (d, 6H), 1.48 (m, 2H), 1.66 (m, 2H), 1.86 (d, 2H), 1.87 (m, 1H), 3.09 (s, 3H), 3.07 (q, 2H), 3.57 (q, 2H), 7.70 (m, 3H), 8.11 (s, 1H), 8.34 (d, 1H), 8.54 (t, 1H). |

TABLE 17-continued

| Example | Name | Data |
|---|---|---|
| Example 253 | 3-methyl-N-[4-(1-methyl-7-propylamino-[1,2,4]triazolo[4,3-a]quinoxaline-4-ylamino)-butyl]-butyramide | Mass (M + H⁺): 412.3; ¹H NMR (500 MHz, DMSO-d6): δ0.91 (d, 6H), 1.02 (m, 2H), 1.24 (m, 2H), 1.67 (m, 3H), 1.75 (m, 2H), 2.02 (m, 2H), 3.03 (s, 3H), 3.16 (q, 2H), 3.35 (m, 3H), 3.70 (t, 2H), 5.71 (t, 1H), 6.40 (t, 1H), 6.56 (d, 1H), 6.89 (s, 1H), 7.71 (d, 1H). |
| Example 254 | N-{4-[7-(3-cyano-propylamino)-1-methyl-[1,2,4]triazolo[4,3-a]quinoxaline-4-ylamino]-butyl}-3-methyl-butyramide | Mass (M + H⁺): 437.2; ¹H NMR (500 MHz, DMSO-d6): δ0.80 (d, 6H), 1.44 (m, 2H), 1.61 (m, 2H), 1.83 (m, 2H), 1.86 (d, 2H), 1.87 (m, 1H), 2.58 (q, 2H), 2.90 (s, 3H), 3.03 (q, 2H), 3.13 (m, 2H), 3.48 (m, 2H), 5.91 (t, 1H), 6.57 (d, 1H), 6.66 (s, 1H), 7.69 (t, 1H), 7.79 (d, 1H), 7.86 (t, 1H). |
| Example 255 | N-{4-[7-(3-isopropyl-ureido)-1-methyl-[1,2,4]triazolo[4,3-a]quinoxaline-4-ylamino]-butyl}-3-methyl-butyramide | Mass (M + H⁺): 455.2; ¹H NMR (500 MHz, DMSO-d6): δ0.79 (d, 6H), 1.08 (d, 6H), 1.45 (m, 2H), 1.62 (m, 2H), 1.86 (d, 2H), 1.87 (m, 1H), 2.93 (s, 3H), 3.10 (q, 2H), 3.48 (q, 2H), 3.75 (m, 1H), 7.17 (t, 1H), 7.50 (d, 1H), 7.72 (d, 1H), 7.88 (s, 1H), 7.94 (t, 1H), 8.00 (d, 1H), 8.45 (s, 1H). |
| Example 256 | N-{4-[7-(3-isopropyl-thioureido)-1-methyl-[1,2,4]triazolo[4,3-a]quinoxaline-4-ylamino]-butyl}-3-methyl-butyramide | Mass (M + H⁺): 471.0; ¹H NMR (500 MHz, DMSO-d6): δ0.80 (d, 6H), 1.14 (d, 6H), 1.43 (m, 2H), 1.62 (m, 2H), 1.87 (d, 2H), 1.90 (m, 1H), 2.96 (s, 3H), 3.04 (q, 2H), 3.50 (q, 2H), 4.37 (t, 1H), 7.34 (d, 1H), 7.71 (m, 3H), 7.98 (d, 1H), 8.07 (s, 1H), 9.43 (s, 1H). |

TABLE 17-continued

| Example | Structure | Name | Data |
|---|---|---|---|
| Example 257 | 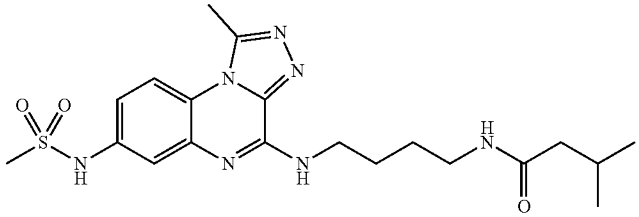 [SMILES: Cc1nnc2c(NCCCCNC(=O)CC(C)C)nc3cc(NS(C)(=O)=O)ccc3n12] | N-[4-(7-methanesulfonylamino-1-methyl-[1,2,4]triazolo[4,3-a]quinoxaline-4-ylamino)-butyl]-3-methyl-butyramide | Mass (M + H⁺): 448.2; ¹H NMR (500 MHz, DMSO-d6): δ0.79 (d, 6H), 1.45 2H) 1.63 (m, 2H) 1.86 (d, 2H) 1.87 (m, 1H), 2.69 (q, 2H) 2.85 (s, 3H) 2.97 (q, 2H) 3.02 (s, 3H) 7.51 (d, 1H) 7.69 (t, 1H), 7.91 (s, 1H), 8.09 (d, 1H), 8.30 (t, 1H), 11.34 (s, 1H). |
| Example 258 | 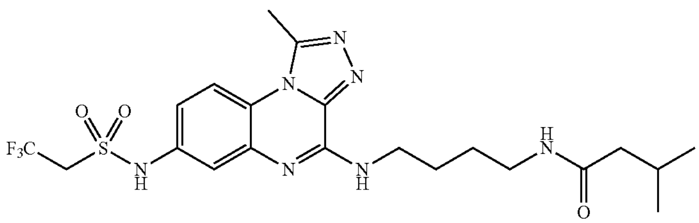 [SMILES: Cc1nnc2c(NCCCCNC(=O)CC(C)C)nc3cc(NS(=O)(=O)CC(F)(F)F)ccc3n12] | 3-methyl-N-{4-[1-methyl-7-2,2,2-trifluoro-ethanesulfonylamino)-[1,2,4]triazolo[4,3-a]quinoxaline-4-ylamino]-butyl}-butyramide | Mass (M − H⁺): 514.2; ¹H NMR (500 MHz, DMSO-d6): δ0.70 (d, 6H), 1.44 (m, 2H), 1.61 (m, 2H), 1.86 (d, 2H), 1.87 (m, 1H), 2.90 (s, 2H), 2.97 (q, 2H), 3.32 (s, 3H), 3.51 (q, 2H), 6.96 (t, 1H), 7.13 (t, 1H), 7.46 (d, 1H), 7.53 (s, 1H), 7.70 (d, 1H), 8.04 (t, 1H). |
| Example 259 | 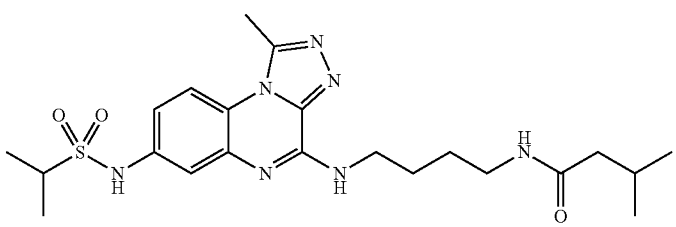 [SMILES: Cc1nnc2c(NCCCCNC(=O)CC(C)C)nc3cc(NS(=O)(=O)C(C)C)ccc3n12] | 3-methyl-N-{4-[1-methyl-7-(propane-2-sulfonylamino)-[1,2,4]triazolo[4,3-a]quinoxaline-4-ylamino]-butyl}-butyramide | Mass (M + H⁺): 476.2; ¹H NMR (500 MHz, DMSO-d6): δ0.79 (d, 6H), 1.44 (m, 2H), 1.63 (m, 2H), 1.86 (d, 2H), 1.88 (m, 1H), 2.69 (s, 3H), 2.85 (d, 3H), 2.94 (q, 2H), 2.98 (q, 2H), 3.51 (m, 1H), 3.70 (q, 2H), 7.51 (d, 1H), 7.70 (t, 1H), 8.08 (t, 1H), 8.10 (d, 1H), 11.36 (s, 1H). |

<Example 260> Preparation of [4-(7-benzoyl-1-methyl-[1,2,4]triazolo[4,3-a]quinoxaline-4-ylamino)-butyl]-carbamic acid-tert-butylester

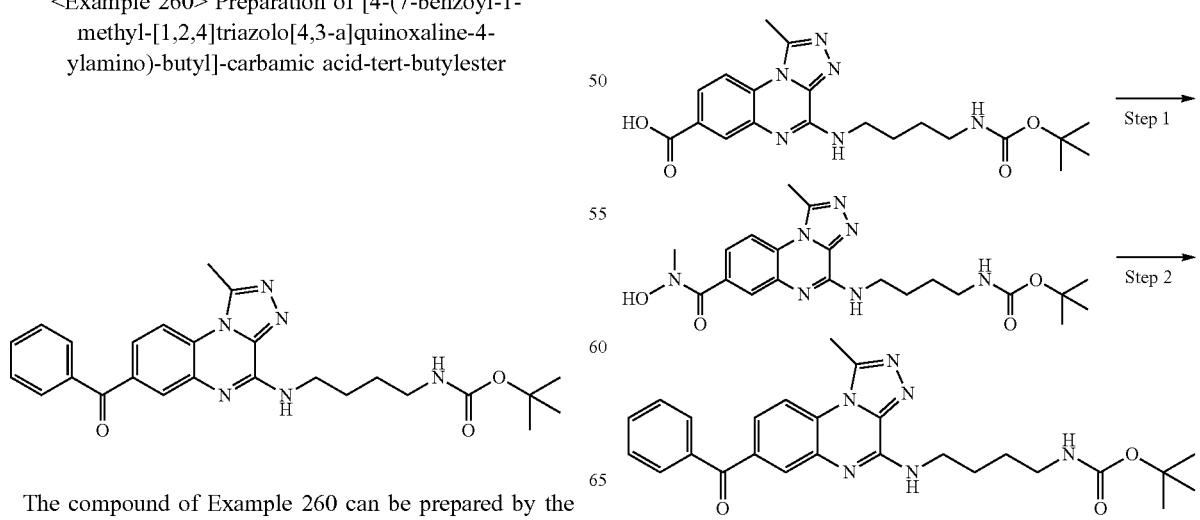

The compound of Example 260 can be prepared by the following two-step reaction.

Step 1: Preparation of tert-butyl-(4-{[7-(methoxymethyl)carbamoyl]-1-methyl-[1,2,4]triazolo[4,3-a]quinoxaline-4-ylamino}-butyl)-carbamate 4-[(4-Tert-butoxycarbamoylamino)-butylamino]-1-methyl-[1,2,4]triazolo[4,3-a]quinoxaline-7-carboxylic acid (0.30 g, 0.72 mmol) prepared in Example 200, methoxylmethylamine hydrochloride (0.08 g, 0.86 mmol), HCTU (0.36 g, 0.86 mmol) and DIPEA (0.38 mL, 2.16 mmol) were dissolved in dimethylformamide, followed by stirring at room temperature for 3 hours. Upon completion of the reaction, the reactant was extracted with ethylacetate and sodium bicarbonate aqueous solution. The organic layer was washed with 1 N aqueous hydrochloric acid solution and brine. The reactant was purified by MPLC (isopropyl alcohol/dichloromethane). As a result, a target compound was obtained (quantitative yield).

Mass (M+H$^+$): 444.1

Step 2: Preparation of {4-[7-(4-benzoyl)-1-methyl-[1,2,4]triazolo[4,3-a]quinoxaline-4-ylamino]-butyl}-carbamic acid-tert-butylester Tert-butyl-(4-{[7-(methoxymethyl)carbamoyl]-1-methyl-[1,2,4]triazolo[4,3-a]quinoxaline-4-ylamino}-butyl)-carbamate (0.10 g, 0.22 mmol) prepared in step 1 was dissolved in anhydrous tetrahydrofuran, to which excessive amount of 4-methoxyphenylmagnesiumbromide was added in the presence of nitrogen, followed by reflux stirring for 15 minutes. The reaction was terminated by adding 1 N aqueous hydrochloric acid solution at room temperature and the reactant was extracted with ethylacetate. The collected organic layer was washed with brine, dried over magnesium sulfate, and then purified by MPLC (isopropyl alcohol/dichloromethane). As a result, a target compound was obtained (78% yield).

Mass (M+H$^+$): 474.5

$^1$H NMR (300 MHz, DMSO-d6): δ1.36 (s, 9H), 1.45-1.52 (m, 2H), 1.62-1.70 (m, 2H), 2.94-3.00 (m, 2H), 3.08 (s, 3H), 3.53-3.60 (m, 2H), 6.79 (brs, 1H), 7.60-7.76 (m, 3H), 7.79-7.82 (m, 2H), 7.88 (d, J=1.77 Hz, 1H), 8.27 (d, J=8.64 Hz, 1H), 8.26 (brs, 1H), 8.48 (brs, 1H)

The compounds shown in Table 18 below were prepared by the same manner as described in Example 260.

TABLE 18

| Example | Structure | Name | Data |
|---|---|---|---|
| Example 261 | 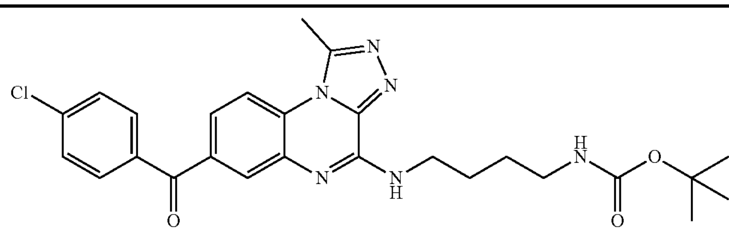 | {4-[7-(4-chlorobenzoyl)-1-methyl-[1,2,4]triazolo[4,3-a]quinoxaline-4-ylamino]-butyl}-carbamic acid-tert-butylester | Mass (M + H$^+$): 508.9; $^1$H NMR (300 MHz, DMSO-d6): δ1.34 (s, 9H), 1.43-1.47 (m, 2H), 1.62-1.69 (m, 2H), 2.94-2.98 (m, 2H), 3.06 (s, 3H), 3.53-3.55 (m, 2H), 6.77 (brs, 1H), 7.63-7.69 (m, 3H), 7.79-7.84 (m, 3H), 8.26 (d, J = 8.49 Hz, 1H), 8.36 (brs, 1H). |
| Example 262 | 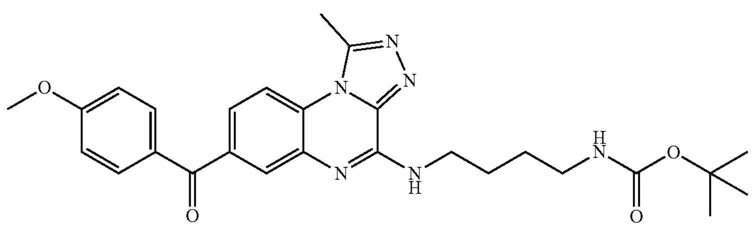 [SMILES: COc1ccc(C(=O)c2ccc3c(c2)nc(NCCCCNC(=O)OC(C)(C)C)c2nnc(C)n23)cc1] | {4-[7-(4-methoxybenzoyl)-1-methyl-[1,2,4]triazolo[4,3-a]quinoxaline-4-ylamino]-butyl}-carbamic acid-tert-butylester | Mass (M + H$^+$): 504.8; $^1$H NMR (300 MHz, CDCl$_3$): δ1.35 (s, 9H), 1.54-1.58 (m, 2H), 1.66-1.76 (m, 2H), 3.06 (s, 3H), 3.09-3.15 (m, 2H), 3.61-3.78 (m, 2H), 3.84 (s, 3H), 4.62 (brs, 1H), 6.42 (brs, 1H), 6.93 (d, J = 8.76 Hz, 2H), 7.65 (dd, J = 8.52 Hz, 1.74 Hz, 1H), 7.80 (d, J = 8.79 Hz, 2H), 7.99 (d, J = 8.61 Hz, 1 H), 8.03 (d, J = 1.74 Hz, 1H). |

<Preparative Example 19> Preparation of 4-chloro-1-methyl-8-trifluoromethoxy-[1,2,4]triazolo[4,3-a]quinoxaline and 4-chloro-1-methyl-7-trifluoromethoxy-[1,2,4]triazolo[4,3-a]quinoxaline

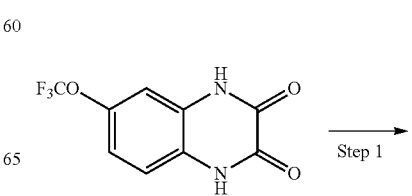

Step 1

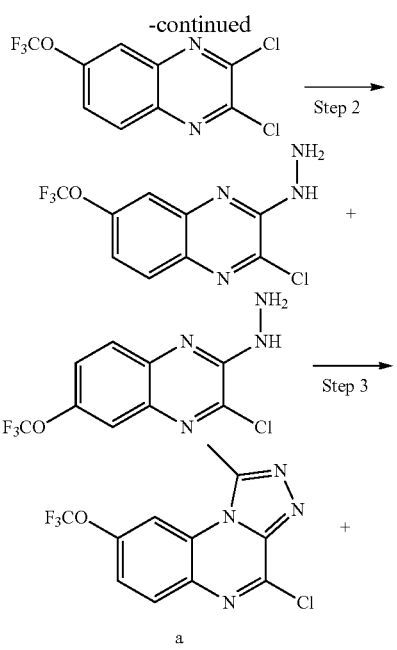

4-Chloro-1-methyl-8-trifluoromethoxy-[1,2,4]triazolo[4,3-a]quinoxaline (a) and 4-chloro-1-methyl-7-trifluoromethoxy-[1,2,4]triazolo[4,3-a]quinoxaline (b) were prepared by the same manner as described in Preparative Example 5.

Step 1: Preparation of 2,3-dichloro-6-trifluoromethoxy-quinoxaline

Mass (M+H⁺): 283.0

Step 2: Preparation of (3-chloro-7-trifluoromethoxy-quinoxaline-2-yl)-hydrazine and (3-chloro-6-trifluoromethoxy-quinoxaline-2-yl)-hydrazine mixture (3-Chloro-7-trifluoromethoxy-quinoxaline-2-yl)-hydrazine and (3-chloro-6-trifluoromethoxy-quinoxaline-2-yl)-hydrazine mixture was prepared by the same manner as described in step 2 of Preparative Example 5, except that 2,3-dichloro-6-trifluoromethoxy-quinoxaline (4.5 g, 16 mmol) prepared in step 1 of Preparative Example 19 was used. The two compounds proceeded to the next reaction in the form of a mixture, followed by separation and purification.
Mass (M+H⁺): 279.0

Step 3: Preparation of 4-chloro-1-methyl-8-trifluoromethoxy-[1,2,4]triazolo[4,3-a]quinoxaline (a) and 4-chloro-1-methyl-7-trifluoromethoxy-[1,2,4]triazolo[4,3-a]quinoxaline (b)

4-Chloro-1-methyl-8-trifluoromethoxy-[1,2,4]triazolo[4,3-a]quinoxaline (a) and 4-chloro-1-methyl-7-trifluoromethoxy-[1,2,4]triazolo[4,3-a]quinoxaline (b) mixture was prepared by the same manner as described in step 3 of Preparative Example 5 except that (3-chloro-7-trifluoromethoxy-quinoxaline-2-yl)-hydrazine and (3-chloro-6-trifluoromethoxy-quinoxaline-2-yl)-hydrazine mixture (4.4 g, 15.7 mmol) prepared in step 2 of Preparative Example 19 was used. The reaction mixture was purified by column chromatography and as a result 2.8 g (58% yield) of a target compound (a) and 1 g (21% yield) of another target compound (b) were obtained.

(a). 4-chloro-1-methyl-8-trifluoromethoxy-[1,2,4]triazolo[4,3-a]quinoxaline

Mass (M+H⁺): 303.1
¹H NMR (500 MHz, DMSO-d6): δ3.08 (s, 3H), 7.73 (d, 1H), 8.14 (s, 1H), 8.19 (d, 1H).

(b). 4-chloro-1-methyl-7-trifluoromethoxy-[1,2,4]triazolo[4,3-a]quinoxaline

Mass (M+H⁺): 303.1

<Example 263> Preparation of [4-(1-methyl-8-trifluoromethoxy-[1,2,4]triazolo[4,3-a]quinoxaline-4-ylamino)-butyl]-carbamic acid-tert-butylester

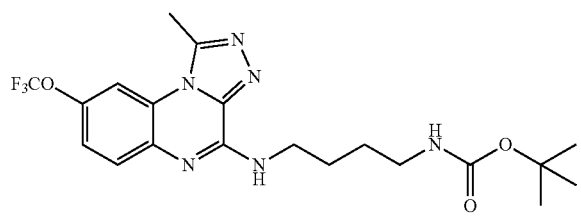 [SMILES: Cc1nnc2c(NCCCCNC(=O)OC(C)(C)C)nc3ccc(OC(F)(F)F)cc3n12]

690 mg of a target compound was obtained (90% yield) by the same manner as described in Example 57, except that 4-chloro-1-methyl-8-trifluoromethoxy-[1,2,4]triazolo[4,3-a]quinoxaline (a) (510 mg, 1.69 mmol) prepared in step 3 of Preparative Example 19 was used as a starting material.
Mass (M+H⁺): 455.3
¹H NMR (500 MHz, DMSO-d6) δ1.31 (s, 9H), 1.43 (m, 1H), 1.61 (m, 1H), 2.92 (q, 2H), 2.98 (s, 3H), 3.49 (q, 1H), 6.74 (t, 1H), 7.41 (d, 1H), 7.64 (d, 1H), 7.92 (s, 1H), 8.27 (t, 1H).

<Example 264> Preparation of N¹-(1-methyl-8-trifluoromethoxy-[1,2,4]triazolo[4,3-a]quinoxaline-4-yl)-butane-1,4-diamine ditrifluoroacetic acid

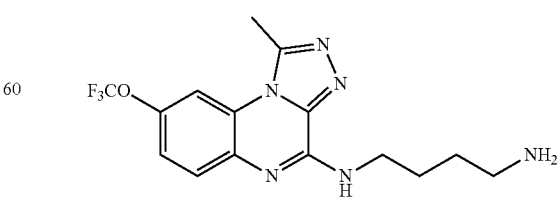

710 mg of a target compound was obtained (81% yield) by the same manner as described in Example 58, except that [4-(1-methyl-8-trifluoromethoxy-[1,2,4]triazolo[4,3-a]quinoxaline-4-ylamino)-butyl]-carbamic acid-tert-butylester (690 mg, 1.52 mmol) prepared in Example 253 was used.

Mass (M+H$^+$): 355.3
$^1$H NMR (500 MHz, DMSO-d6) δ1.60 (m, 2H), 1.68 (m, 2H), 2.79 (m, 2H), 2.99 (s, 3H), 3.54 (q, 2H), 7.45 (t, 1H), 7.65 (d, 1H), 7.79 (brm, 2H), 7.94 (d, 1H), 8.33 (t, 1H).

<Example 265> Preparation of 2,2-dimethyl-N-[4-(1-methyl-8-trifluoromethoxy-[1,2,4]triazolo[4,3-a]quinoxaline-4-ylamino)-butyl]-propionamide 140 mg of a target compound was obtained (74% yield) by the same manner as described in Example 59, except that N$^1$-(1-methyl-8-trifluoromethoxy-[1,2,4]triazolo[4,3-a]quinoxaline-4-yl)-butane-1,4-diamine ditrifluoroacetic acid (250 mg, 0.43 mmol) prepared in Example 264 was used.
Mass (M+H$^+$): 437.2
$^1$H NMR (500 MHz, DMSO-d6) δ1.02 (s, 9H), 1.45 (m, 2H) 1.60 (m, 2H), 2.98 (s, 3H), 3.03 (q, 2H), 3.50 (q, 2H), 7.36 (t, 1H), 7.42 (d, 1H), 7.63 (d, 1H), 7.92 (d, 1H), 8.27 (t, 1H).

The compounds shown in Table 19 below were prepared by the same manner as described in Example 265.

TABLE 19

| Example | Structure | Name | Data |
|---|---|---|---|
| Example 266 | 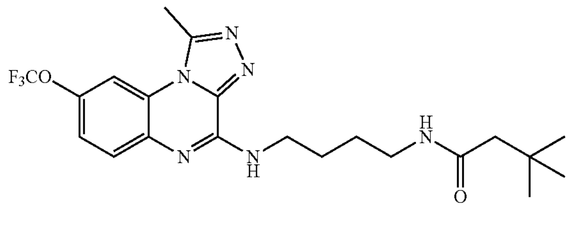 [SMILES: Cc1nnc2c(NCCCCNC(=O)CC(C)(C)C)nc3ccc(OC(F)(F)F)cc3n12] | 3,3-dimethyl-N-[4-(1-methyl-8-trifluoromethoxy-[1,2,4]triazolo[4,3-a]quinoxaline-4-ylamino)-butyl]-butyramide | Mass (M + H$^+$): 453.2; $^1$H NMR (500 MHz, DMSO-d6): δ0.90 (s, 9H), 1.44 (m, 2H), 1.63 (m, 2H), 1.87 (s, 2H), 2.98 (s, 3H), 3.04 (m, 2H), 3.50 (q, 2H), 7.42 (t, 1H), 7.63 (d, 1H), 7.92 (s, 1H), 8.29 (t, 1H). |
| Example 267 | 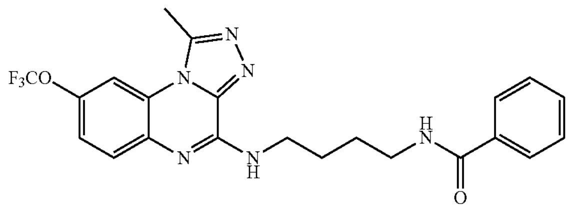 [SMILES: Cc1nnc2c(NCCCCNC(=O)c3ccccc3)nc3ccc(OC(F)(F)F)cc3n12] | N-[4-(1-methyl-8-trifluoromethoxy-[1,2,4]triazolo[4,3-a]quinoxaline-4-ylamino)-butyl]-benzamide | Mass (M + H$^+$): 459.2; $^1$H NMR (500 MHz, DMSO-d6): δ1.59 (m, 2H), 1.69 (m, 2H), 2.98 (s, 3H), 3.28 (q, 2H), 3.55 (q, 2H), 7.37 (m, 3H), 7.40 (m, 1H), 7.48 (m, 1H), 7.62 (d, 1H), 7.77 (t, 2H), 7.92 (s, 1H), 8.29 (t, 1H), 8.39 (t, 1H). |
| Example 268 | 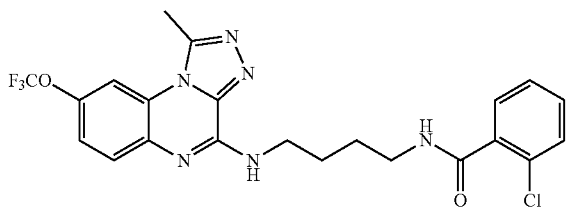 [SMILES: Cc1nnc2c(NCCCCNC(=O)c3ccccc3Cl)nc3ccc(OC(F)(F)F)cc3n12] | 2-chloro-N-[4-(1-methyl-8-trifluoromethoxy-[1,2,4]triazolo[4,3-a]quinoxaline-4-ylamino)-butyl]-benzamide | Mass (M + H$^+$): 493.1; $^1$H NMR (500 MHz, DMSO-d6): δ1.57 (m, 2H), 1.72 (m, 2H), 2.98 (s, 3H), 3.25 (q, 2H), 3.55 (m, 2H), 7.33 (m, 3H), 7.42 (d, 2H), 7.64 (d, 1H), 7.92 (d, 1H), 8.32 (t, 1H), 8.35 (t, 1H). |

<Example 269> Preparation of [4-(1-methyl-7-trifluoromethoxy-[1,2,4]triazolo[4,3-a]quinoxaline-4-ylamino)-butyl]-carbamic acid-tert-butylester

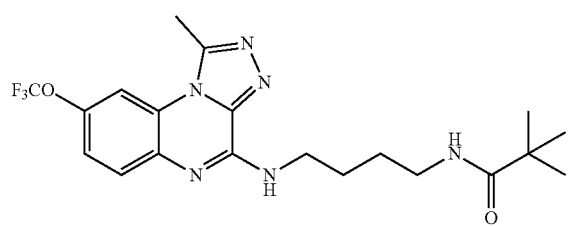

4.5 g of a target compound was obtained (93% yield) by the same manner as described in Example 57, except that 4-chloro-1-methyl-7-trifluoromethoxy-[1,2,4]triazolo[4,3-a]quinoxaline (b) (1 g, 3.3 mmol) prepared in step 3 of Preparative Example 19 was used as a starting material.
Mass (M+H$^+$): 455.3
$^1$H NMR (500 MHz, DMSO-d6) δ1.31 (s, 9H), 1.42 (m, 2H), 1.61 (m, 2H), 2.92 (q, 2H), 2.98 (s, 3H), 3.50 (q, 2H), 7.23 (t, 1H), 7.45 (d, 1H), 7.67 (s, 1H), 8.14 (d, 1H), 8.40 (t, 1H).

<Example 270> Preparation of N¹-(1-methyl-7-trifluoromethoxy-[1,2,4]triazolo[4,3-a]quinoxaline-4-yl)-butane-1,4-diamine ditrifluoroacetic acid

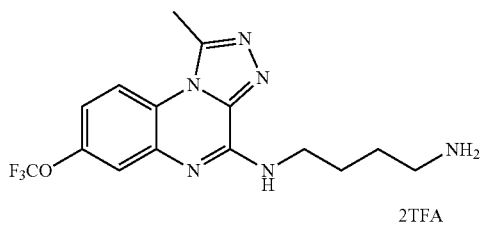 [SMILES: Cc1nnc2c(NCCCCN)nc3cc(OC(F)(F)F)ccc3n12]

1.3 g of a target compound was obtained (71% yield) by the same manner as described in Example 58, except that [4-(1-methyl-7-trifluoromethoxy-[1,2,4]triazolo[4,3-a]quinoxaline-4-ylamino)-butyl]-carbamic acid-tert-butylester (1.2 g, 2.64 mmol) prepared in Example 269 was used.

Mass (M+H⁺): 355.1

¹H NMR (500 MHz, DMSO-d6): δ1.60 (m, 2H), 1.68 (m, 2H), 2.80 (m, 2H), 2.98 (s, 3H), 3.54 (q, 2H), 7.25 (t, 1H), 7.45 (s, 1H), 7.72 (brm, 2H), 8.16 (d, 1H), 8.46 (t, 1H).

<Example 271> Preparation of 2,2-dimethyl-N-[4-(1-methyl-7-trifluoromethoxy-[1,2,4]triazolo[4,3-a]quinoxaline-4-ylamino)-butyl]-propionamide

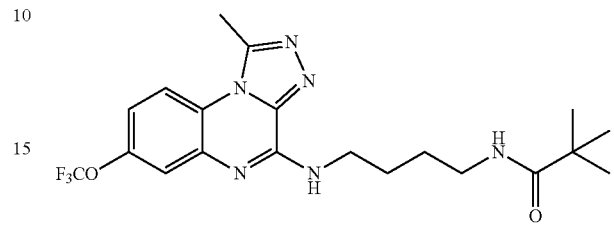

120 mg of a target compound was obtained (63% yield) by the same manner as described in Example 59, except that N¹-(1-methyl-7-trifluoromethoxy-[1,2,4]triazolo[4,3-a]quinoxaline-4-yl)-butane-1,4-diamine ditrifluoroacetic acid (250 mg, 0.43 mmol) prepared in Example 270 was used.

Mass (M+H⁺): 439.2

¹H NMR (500 MHz, DMSO-d6): δ1.02 (s, 9H), 1.45 (m, 2H) 1.61 (m, 2H), 2.98 (s, 3H), 3.05 (q, 2H), 3.50 (q, 2H), 7.23 (d, 1H), 7.36 (t, 1H), 7.43 (s, 1H), 8.14 (d, 1H), 8.40 (t, 1H).

The compounds shown in Table 20 below were prepared by the same manner as described in Example 271.

TABLE 20

| Example | Structure | Name | Data |
| --- | --- | --- | --- |
| Example 272 | ![structure] | 3,3-dimethyl-N-[4-(1-methyl-7-trifluoromethoxy-[1,2,4]triazolo[4,3-a]quinoxaline-4-ylamino)-butyl]-butyramide | Mass (M + H⁺): 453.2; ¹H NMR (500 MHz, DMSO-d6): δ0.87 (s, 9H), 1.43 (m, 2H), 1.63 (m, 2H), 1.87 (s, 2H), 2.98 (s, 3H), 3.03 (m, 2H), 3.51 (q, 2H), 7.22 (d, 1H), 7.43 (s, 1H), 7.64 (t, 1H), 8.15 (d, 1H), 8.40 (t, 1H). |
| Example 273 | ![structure] | N-[4-(1-methyl-7-trifluoromethoxy-[1,2,4]triazolo[4,3-a]quinoxaline-4-ylamino)-butyl]-benzamide | Mass (M + H⁺): 459.2; ¹H NMR (500 MHz, DMSO-d6): δ1.59 (m, 2H), 1.70 (m, 2H), 2.98 (s, 3H), 3.28 (m, 2H), 3.55 (q, 2H), 7.21 (d, 1H), 7.42 (brm, 4H), 7.77 (d, 2H), 8.14 (d, 3H), 8.40 (t, 2H). |
| Example 274 | ![structure] | 2-chloro-N-[4-(1-methyl-7-trifluoromethoxy-[1,2,4]triazolo[4,3-a]quinoxaline-4-ylamino)-butyl]-benzamide | Mass (M + H⁺): 493.1; ¹H NMR (500 MHz, DMSO-d6): δ1.57 (m, 2H), 1.72 (m, 2H), 2.98 (s, 3H), 3.24 (q, 2H), 3.55 (q, 2H), 7.23 (d, 1H), 7.40 (brm, 4H), 7.45 (s, 1H), 8.15 (d, 1H), 8.36 (t, 1H), 8.43 (t, 1H). |

<Preparative Example 20> Preparation of 4-(3-hydrazino-7-methoxy-quinoxaline-2-ylamino)-butyl]-carbamic acid-tert-butylester

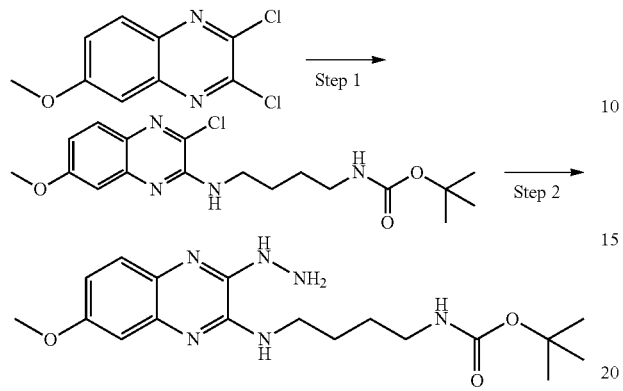

Step 1: Preparation of [4-(3-chloro-7-methoxy-quinoxaline-2-ylamino)-butyl]-carbamic acid-tert-butylester 14.5 g of a target compound was obtained (95% yield) by the same manner as described in Example 57, except that 2,3-dichloro-6-methoxy-quinoxaline (9.2 g, 40.3 mmol) prepared in step 1 of Preparative Example 8 was used.

Mass (M+H$^+$): 381.0

$^1$H NMR (500 MHz, DMSO-d6) δ1.33 (s, 9H), 1.41 (m, 2H), 1.57 (m, 2H), 2.91 (q, 2H), 3.41 (q, 2H), 3.83 (s, 3H), 6.74 (t, 1H), 6.97 (d, 1H), 6.98 (d, 1H), 7.33 (t, 1H), 7.57 (d, 1H).

Step 2: Preparation of [4-(3-hydrazino-7-methoxy-quinoxaline-2-ylamino)-butyl]-carbamic acid-tert-butylester

[4-(3-chloro-7-methoxy-quinoxaline-2-ylamino)-butyl]-carbamic acid-tert-butylester (14.5 g, 38 mmol) prepared in step 1 of Preparative Example 20 and hydrazine hydrate (73 ml, 1.5 mol) were dissolved in 150 ml of ethanol, followed by reflux stirring for 3 hours. Upon completion of the reaction, the solvent was distilled under reduced pressure. The reaction mixture was extracted with ethylacetate and water. The reactant was dried over magnesium sulfate, filtered, distilled and dried under reduced pressure. As a result, 13.5 g of a target compound was obtained (94% yield), which proceeded to the next reaction without purification.

Mass (M+H$^+$): 377.1

<Example 275> Preparation of [4-(7-methoxy-1-methyl-[1,2,4]triazolo[4,3-a]quinoxaline-4-ylamino)-butyl]-carbamic acid-tert-butylester

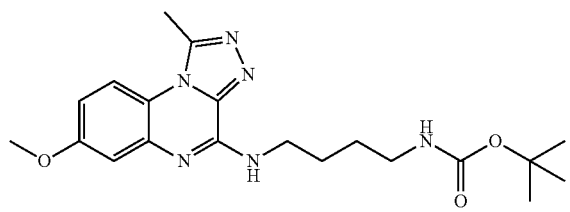

0.65 g of a target compound was obtained (61% yield) by the same manner as described in step 3 of Preparative Example 5, except that [4-(3-hydrazino-7-methoxy-quinoxaline-2-ylamino)-butyl]-carbamic acid-tert-butylester (1 g, 2.7 mmol) prepared in step 2 of Preparative Example 20 was used.

Mass (M+H$^+$): 401.2

$^1$H NMR (500 MHz, DMSO-d6) δ1.32 (s, 9H), 1.43 (m, 2H), 1.60 (m, 2H), 2.90 (q, 2H), 2.94 (s, 3H), 3.50 (q, 2H), 3.80 (s, 3H), 6.75 (t, 1H), 6.85 (d, 1H), 7.06 (s, 1H), 7.95 (d, 1H), 8.08 (t, 1H).

<Example 276> Preparation of N$^1$-(7-methoxy-1-methyl-[1,2,4]triazolo[4,3-a]quinoxaline-4-yl)-butane-1,4-diamine ditrifluoroacetic acid

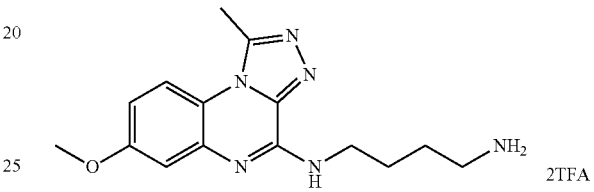

610 mg of a target compound was obtained (71% yield) by the same manner as described in Example 58, except that [4-(7-methoxy-1-methyl-[1,2,4]triazolo[4,3-a]quinoxaline-4-ylamino)-butyl]-carbamic acid-tert-butylester (650 mg, 1.62 mmol) prepared in Example 275 was used.

Mass (M+H$^+$): 301.1

$^1$H NMR (500 MHz, DMSO-d6): δ1.59 (m, 2H), 1.68 (m, 2H), 2.81 (q, 2H), 2.96 (s, 3H), 3.54 (q, 2H), 3.80 (s, 3H), 6.87 (d, 1H), 7.05 (s, 1H), 7.65 (brm, 2H), 7.97 (d, 1H), 8.20 (t, 1H).

<Example 277> Preparation of N-[4-(7-methoxy-1-methyl-[1,2,4]triazolo[4,3-a]quinoxaline-4-ylamino)-butyl]-2,2-dimethyl-propionamide

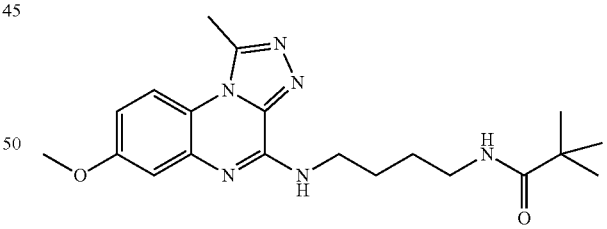

41 mg of a target compound was obtained (31% yield) by the same manner as described in Example 59, except that N$^1$-(7-methoxy-1-methyl-[1,2,4]triazolo[4,3-a]quinoxaline-4-yl)-butane-1,4-diamine ditrifluoroacetic acid (150 mg, 0.28 mmol) prepared in Example 276 was used.

Mass (M+H$^+$): 385.2

$^1$H NMR (500 MHz, DMSO-d6) δ1.02 (s, 9H), 1.45 (m, 2H), 1.60 (m, 2H), 2.95 (s, 3H), 3.05 (q, 2H), 3.49 (q, 2H), 3.80 (s, 3H), 6.85 (d, 1H), 7.05 (s, 1H), 7.37 (t, 1H), 7.95 (s, 1H), 8.08 (t, 1H).

The compounds shown in Table 21 below were prepared by the same manner as described in Example 277.

TABLE 21

| Example | Structure | Name | Data |
|---|---|---|---|
| Example 278 | 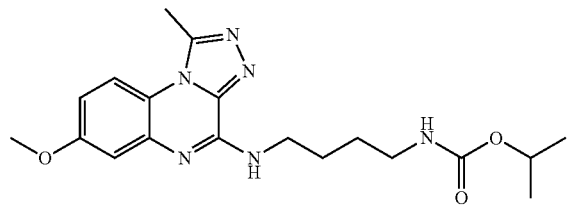 [SMILES: COc1ccc2c(c1)nc(NCCCCNC(=O)OC(C)C)c1nnc(C)n12] | [4-(7-methoxy-1-methyl-[1,2,4]tri-azolo[4,3-a]quinoxaline-4-ylamino)-butyl]-carbamic acid isopropylester | Mass (M + H$^+$): 387.2; $^1$H NMR (500 MHz, DMSO-d6): δ1.10 (d, 6H), 1.45 (m, 2H), 1.62 (m, 2H), 2.95 (s, 3H), 2.99 (m, 2H), 3.50 (q, 2H), 3.80 (s, 3H), 4.68 (m, 1H), 6.85 (d, 1H), 6.95 (t, 1H), 7.06 (s, 1H), 7.95 (s, 1H), 8.08 (t, 1H). |
| Example 279 | 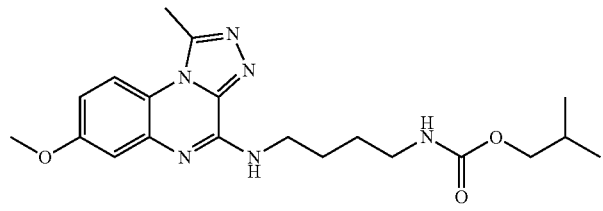 | [4-(7-methoxy-1-methyl-[1,2,4]tri-azolo[4,3-a]quinoxaline-4-ylamino)-butyl]-carbamic acid isobutylester | Mass (M + H$^+$): 401.2; $^1$H NMR (500 MHz, DMSO-d6): δ0.80 (d, 6H), 1.45 (m, 2H), 1.63 (m, 2H), 1.75 (m, 1H), 2.95 (s, 3H), 2.99 (m, 2H), 3.60 (q, 2H), 3.66 (q, 2H), 3.80 (s, 3H), 6.85 (d, 1H), 7.00 (t, 1H), 7.06 (s, 1H), 7.95 (s, 1H), 8.08 (t, 1H). |
| Example 280 | 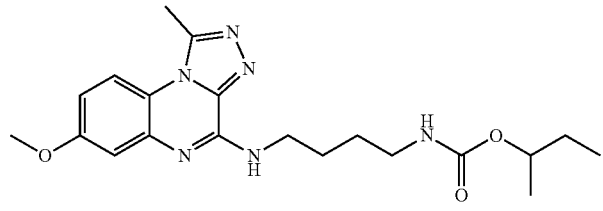 [SMILES: CCC(C)OC(=O)NCCCCNc1nc2cc(OC)ccc2n2c(C)nnc12] | [4-(7-methoxy-1-methyl-[1,2,4]tri-azolo[4,3-a]quinoxaline-4-ylamino)-butyl]-carbamic acid-sec-butylester | Mass (M + H$^+$): 401.2; $^1$H NMR (500 MHz, DMSO-d6): δ0.78 (t, 3H), 1.08 (d, 3H), 1.42 (m, 2H), 1.44 (m, 2H), 1.62 (m, 2H), 2.95 (s, 3H), 2.98 (m, 2H), 3.50 (q, 2H), 3.80 (s, 3H), 4.52 (m, 1H), 6.84 (d, 1H), 6.95 (t, 1H), 7.06 (s, 1H), 7.95 (s, 1H), 8.08 (t, 1H). |
| Example 281 | 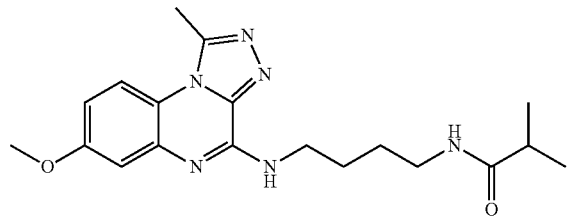 [SMILES: COc1ccc2c(c1)nc(NCCCCNC(=O)C(C)C)c1nnc(C)n12] | N-[4-(7-methoxy-1-methyl-[1,2,4]tri-azolo[4,3-a]quinoxaline-4-ylamino)-butyl]-isobutyramide | Mass (M + H$^+$): 371.2 $^1$H NMR (500 MHz, DMSO-d6): δ0.93 (d, 6H), 1.45 (m, 2H), 1.62 (m, 2H), 2.27 (m, 1H), 2.95 (s, 3H), 3.04 (q, 2H), 3.50 (q, 2H), 3.82 (s, 3H), 6.85 (d, 1H), 7.06 (s, 1H), 7.63 (t, 1H), 7.95 (d, 1H), 8.09 (t, 1H). |
| Example 282 | 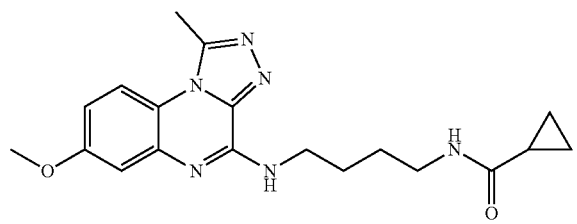 [SMILES: COc1ccc2c(c1)nc(NCCCCNC(=O)C1CC1)c1nnc(C)n12] | cyclopropane; carboxylic acid-[4-(7-methoxy-1-methyl-[1,2,4]tri-azolo[4,3-a]quinoxaline-4-ylamino)-butyl]-amide | Mass (M + H$^+$): 369.2; $^1$H NMR (500 MHz, DMSO-d6): δ0.55 (m, 2H), 0.60 (m, 2H), 1.46 (m, 3H), 1.63 (m, 2H), 2.95 (s, 3H), 3.07 (q, 2H), 3.52 (q, 2H), 3.80 (s, 3H), 6.84 (t, 1H), 7.07 (d, 1H), 7.95 (s, 1H), 7.96 (d, 1H), 8.10 (t, 1H). |
| Example 283 | 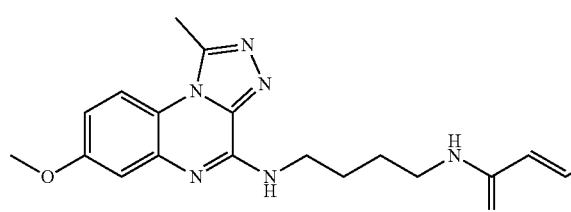 | butene-2-oic acid-[4-(7-methoxy-1-methyl-[1,2,4]tri-azolo[4,3-a]quinoxaline-4-ylamino)-butyl]-amide | Mass (M + H$^+$): 369.2; $^1$H NMR (500 MHz, DMSO-d6): δ1.46 (m, 2H), 1.60 (m, 2H), 1.73 (d, 3H), 2.95 (s, 3H), 3.10 (q, 2H), 3.50 (q, 2H), 3.82 (s, 3H), 5.05 (d, 1H), 5.84 (m, 1H), 6.86 (d, 1H), 7.06 (s, 1H), 7.80 (t, 1H), 7.96 (d, 1H), 8.09 (t, 1H). |

TABLE 21-continued

| Example | Structure | Name | Data |
|---|---|---|---|
| Example 284 | 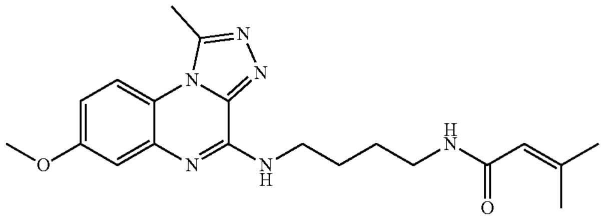 [SMILES: COc1ccc2c(c1)nc(NCCCCNC(=O)C=C(C)C)c1nnc(C)n12] | 3-methyl-butene-2-oic acid-[4-(7-methoxy-1-methyl-[1,2,4]tri-azolo[4,3-a]quinoxaline-4-ylamino)-butyl]-amide | Mass (M + H⁺): 383.2; ¹H NMR (500 MHz, DMSO-d6): δ1.45 (m, 2H), 1.63 (m, 2H), 1.71 (s, 3H), 2.02 (s, 3H), 2.94 (s, 3H), 3.07 (m, 2H), 3.52 (m, 2H), 3.80 (s, 3H), 5.57 (s, 1H), 6.83 (d, 1H), 7.05 (s, 1H), 7.67 (m, 1H), 7.92 (d, 1H), 8.09 (m, 1H). |
| Example 285 | 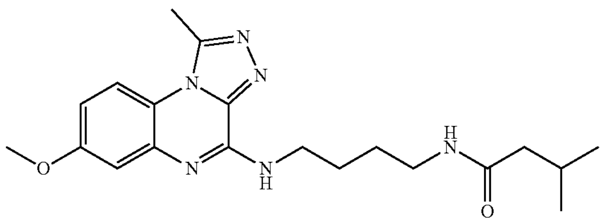 [SMILES: COc1ccc2c(c1)nc(NCCCCNC(=O)CC(C)C)c1nnc(C)n12] | N-[4-(7-methoxy-1-methyl-[1,2,4]tri-azolo[4,3-a]quinoxaline-4-ylamino)-butyl]-3-methyl-butyramide | Mass (M + H⁺): 385.2; ¹H NMR (500 MHz, DMSO-d6): δ0.79 (d, 6H), 1.44 (m, 2H), 1.62 (m, 2H), 1.86 (m, 2H), 1.90 (m, 1H), 2.95 (s, 3H), 3.05 (q, 2H), 3.50 (q, 2H), 3.80 (s, 3H), 6.85 (d, 1H), 7.06 (s, 1H), 7.69 (t, 1H), 7.95 (s, 1H), 8.08 (t, 1H). |
| Example 286 | 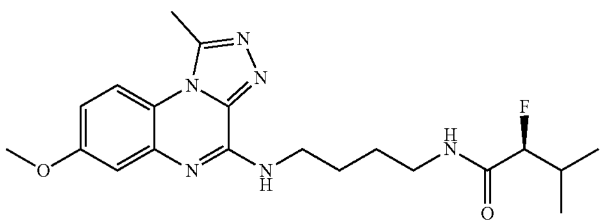 [SMILES: COc1ccc2c(c1)nc(NCCCCNC(=O)[C@@H](F)C(C)C)c1nnc(C)n12] | 2-(S)-fluoro-N-[4-(7-methoxy-1-methyl-[1,2,4]tri-azolo[4,3-a]quinoxaline-4-ylamino)-butyl]-3-methyl-butyramide | Mass (M + H⁺): 403.2; ¹H NMR (500 MHz, DMSO-d6): δ0.79 (d, 3H), 0.90 (d, 3H), 1.49 (m, 2H), 1.63 (m, 2H), 2.06 (m, 1H), 2.94 (s, 3H), 2.94 (m, 2H), 3.50 (m, 2H), 3.80 (s, 3H), 4.56 (d, 1H), 6.82 (d, 1H), 7.03 (s, 1H), 7.91 (d, 1H), 8.09 (m, 1H). |
| Example 287 | 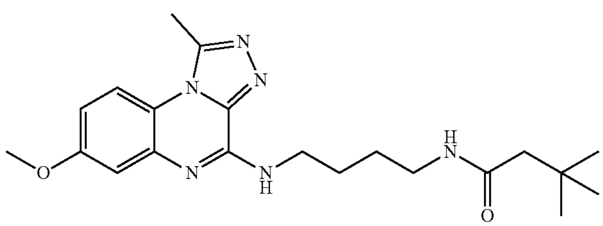 [SMILES: COc1ccc2c(c1)nc(NCCCCNC(=O)CC(C)(C)C)c1nnc(C)n12] | N-[4-(7-methoxy-1-methyl-[1,2,4]tri-azolo[4,3-a]quinoxaline-4-ylamino)-butyl]-3,3-dimethyl-butyramide | Mass (M + H⁺): 399.2; ¹H NMR (500 MHz, DMSO-d6): δ0.86 (s, 3H), 1.45 (m, 2H), 1.63 (m, 2H), 1.88 (s, 2H), 2.95 (s, 3H), 3.04 (q, 2H), 3.50 (q, 2H), 3.80 (s, 3H), 6.85 (d, 1H), 7.06 (s, 1H), 7.64 (t, 1H), 7.96 (d, 1H), 8.09 (t, 1H). |
| Example 288 | 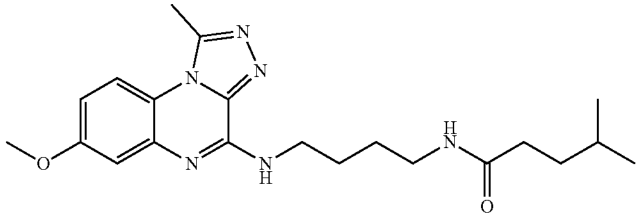 | 4-methyl-pentanoic acid-[4-(7-methoxy-1-methyl-[1,2,4]tri-azolo[4,3-a]quinoxaline-4-ylamino)-butyl]-amide | Mass (M + H⁺): 399.2; ¹H NMR (500 MHz, DMSO-d6): δ0.78 (d, 6H), 1.31 (m, 2H), 1.42 (m, 3H), 1.62 (m, 2H), 1.98 (m, 2H), 2.95 (s, 3H), 3.04 (q, 2H), 3.51 (q, 2H), 3.80 (s, 3H), 6.85 (d, 1H), 7.06 (s, 1H), 7.70 (t, 1H), 7.96 (d, 1H), 8.09 (t, 1H). |

TABLE 21-continued

| Example | Structure | Name | Data |
|---|---|---|---|
| Example 289 | 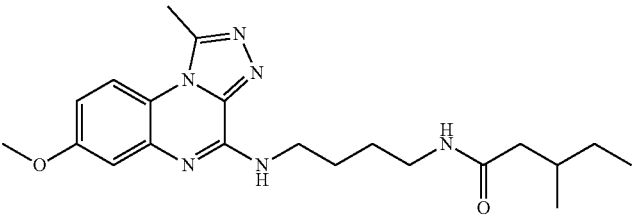 [SMILES: CCC(C)CC(=O)NCCCCNc1nc2cc(OC)ccc2n2c(C)nnc12] | 3-methyl-pentanoic acid-[4-(7-methoxy-1-methyl-[1,2,4]tri-azolo[4,3-a]quinoxaline-4-ylamino)-butyl]-amide | Mass (M + H$^+$): 399.2; $^1$H NMR (500 MHz, DMSO-d6): δ0.76 (m, 6H), 1.06-1.23 (brm, 2H), 1.44 (m, 2H), 1.63 (m, 2H), 1.78 (m, 2H), 1.97 (m, 1H), 2.95 (s, 3H), 3.05 (q, 2H), 3.50 (q, 2H), 3.81 (s, 3H), 6.85 (d, 1H), 7.06 (s, 1H), 7.70 (t, 1H), 7.96 (s, 1H), 8.09 (t, 1H). |
| Example 290 | 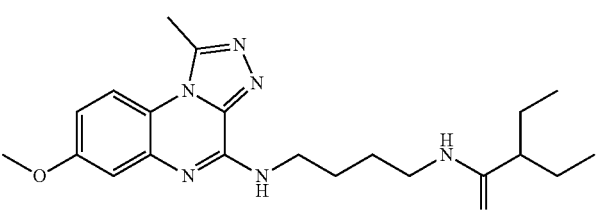 | 2-ethyl-N-[4-(7-methoxy-1-methyl-[1,2,4]tri-azolo[4,3-a]quinoxaline-4-ylamino)-butyl]-butyramide | Mass (M + H$^+$): 399.2; $^1$H NMR (500 MHz, DMSO-d6): δ0.72 (m, 6H), 1.26 (m, 2H), 1.36 (m, 2H), 1.47 (m, 2H), 1.63 (m, 2H), 1.86 (m, 1H), 2.95 (s, 3H), 3.07 (q, 2H), 3.51 (q, 2H), 3.80 (s, 3H), 6.86 (d, 1H), 7.05 (s, 1H), 7.72 (t, 1H), 7.96 (d, 1H), 8.10 (t, 1H), |
| Example 291 | 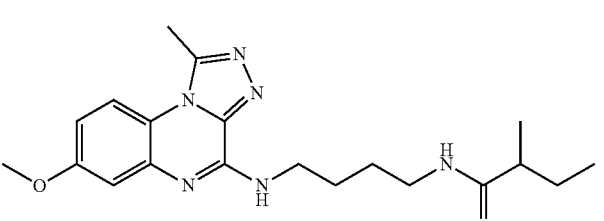 | N-[4-(7-methoxy-1-methyl-[1,2,4]tri-azolo[4,3-a]quinoxaline-4-ylamino)-butyl]-2-methyl-butyramide | Mass (M + H$^+$): 385.2; $^1$H NMR (500 MHz, DMSO-d6): δ0.73 (t, 3H), 0.91 (d, 3H), 1.46 (m, 2H), 2.06 (m, 1H), 2.94 (s, 3H), 3.08 (q, 2H), 3.51 (q, 2H), 3.80 (s, 3H), 6.85 (d, 1H), 7.05 (s, 1H), 7.67 (s, 1H), 7.95 (d, 1H), 8.09 (t, 1H), |
| Example 292 | 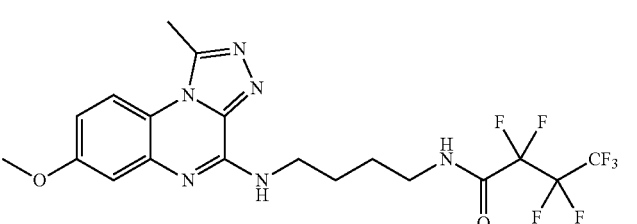 | 2,2,3,3,4,4,4-heptafluoro-N-[4-(7-methoxy-1-methyl-[1,2,4]tri-azolo[4,3-a]quinoxaline-4-ylamino)-butyl]-butyramide | Mass (M + H$^+$): 497.1; $^1$H NMR (500 MHz, DMSO-d6): δ1.54 (m, 2H), 1.67 (m, 2H), 2.95 (s, 3H), 3.21 (m, 2H), 3.53 (m, 2H), 3.80 (s, 3H), 6.84 (d, 1H), 7.10 (s, 1H), 7.94 (d, 1H), 8.23 (s, 1H), 9.38 (s, 1H). |
| Example 293 | 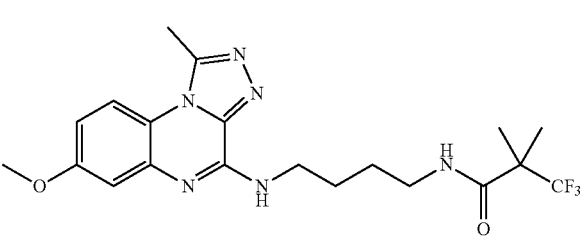 [SMILES: COc1ccc2c(c1)nc(NCCCCNC(=O)C(C)(C)C(F)(F)F)c1nnc(C)n12] | 3,3,3-trifluoro-N-[4-(7-methoxy-1-methyl-[1,2,4]tri-azolo[4,3-a]quinoxaline-4-ylamino)-butyl]-2,2-dimethyl-propaneamide | Mass (M + H$^+$): 439.2; $^1$H NMR (500 MHz, DMSO-d6): δ1.27 (d, 6H), 1.48 (m, 2H), 1.60 (m, 2H), 2.96 (s, 3H), 3.11 (q, 2H), 3.51 (q, 2H), 3.81 (s, 3H), 6.84 (d, 1H), 7.06 (s, 1H), 7.87 (t, 1H), 7.96 (s, 1H), 8.11 (t, 1H). |

TABLE 21-continued

| Example | Name | Data |
|---|---|---|
| Example 294 | 2,2-difluoro-N-[4-(7-methoxy-1-methyl-[1,2,4]triazolo[4,3-a]quinoxaline-4-ylamino)-butyl]-butyramide | Mass (M + H+): 407.1; 1H NMR (500 MHz, DMSO-d6): δ0.84 (m, 3H), 1.44 (m, 2H), 1.63 (m, 2H), 1.96 (m, 2H), 2.95 (s, 3H), 3.15 (q, 2H), 3.51 (q, 2H), 3.81 (s, 3H), 6.85 (d, 1H), 7.06 (s, 1H), 7.95 (d, 1H), 8.12 (t, 1H), 8.64 (t, 1H). |
| Example 295 | 2-(R)-hydroxy-N-[4-(7-methoxy-1-methyl-[1,2,4]triazolo[4,3-a]quinoxaline-4-ylamino)-butyl]-propaneamide | Mass (M + H+): 373.2; 1H NMR (500 MHz, DMSO-d6): δ1.14 (s, 3H), 1.21 (m, 1H), 1.48 (m, 2H), 1.52 (m, 2H), 2.95 (s, 3H), 3.10 (m, 2H), 3.53 (m, 2H), 3.81 (s, 3H), 3.90 (m, 1H), 6.86 (d, 1H), 7.11 (s, 1H), 7.66 (m, 1H), 7.96 (d, 1H), 8.35 (s, 1H) |
| Example 296 | acetic acid-1-[4-(7-methoxy-1-methyl-[1,2,4]triazolo[4,3-a]quinoxaline-4-ylamino)-butylcarbamoyl]-1-methyl-ethylester | Mass (M + H+): 429.2; 1H NMR (500 MHz, DMSO-d6): δ1.39 (s, 6H), 1.45 (m, 2H), 1.60 (m, 2H), 1.94 (s, 3H), 2.94 (s, 3H), 3.04 (q, 2H), 3.49 (q, 2H), 3.80 (s, 3H), 6.84 (dd, 1H), 7.06 (s, 1H), 7.67 (t, 1H), 7.95 (d, 1H), 8.07 (t, 1H). |
| Example 297 | 2-hydroxy-N-[4-(7-methoxy-1-methyl-[1,2,4]triazolo[4,3-a]quinoxaline-4-ylamino)-butyl]-2-methyl-propionamide | Mass (M + H+): 387.2; 1H NMR (500 MHz, DMSO-d6): δ1.18 (s. 6H), 1.47 (m, 2H), 1.61 (m, 2H), 2.94 (s, 3H), 3.08 (q, 2H), 3.50 (q, 2H), 3.80 (s, 3H), 5.24 (s, 1H), 6.83 (dd, 1H), 7.05 (s, 1H), 7.59 (t, 1H), 7.93 (d, 1H), 8.09 (t, 1H). |
| Example 298 | 2-(R)-hydroxy-N-[4-(7-methoxy-1-methyl-[1,2,4]triazolo[4,3-a]quinoxaline-4-ylamino)-butyl]-3-methyl-butyramide | Mass (M + H+): 401.2; 1H NMR (500 MHz, DMSO-d6): δ0.68 (d, 3H), 0.84 (d, 3H), 1.48 (m, 2H), 1.63 (m, 2H), 1.95 (m, 1H), 2.95 (s, 3H), 3.10 (m, 2H), 3.51 (m, 2H), 3.60 (s, 1H), 3.81 (s, 3H), 6.84 (d, 1H), 7.09 (s, 1H), 7.66 (m, 1H), 7.94 (m, 1H). |
| Example 299 | 2-(S)-hydroxy-N-[4-(7-methoxy-1-methyl-[1,2,4]triazolo[4,3-a]quinoxaline-4-ylamino)-butyl]-3- | Mass (M + H+): 401.2; 1H NMR (500 MHz, DMSO-d6): δ0.68 (m, 3H), 0.84 (m, 3H), 1.48 (m, 2H), 1.63 (m, 2H), 1.91 (m, 1H), 2.47 (s, 3H), 2.95 (s, 3H), 3.14 (m, 2H), 3.60 (m, 2H), 3.61 (s, 1H), |

TABLE 21-continued

| Example | Name | Data |
|---|---|---|
| | methyl-butyramide | 3.80 (s, 3H), 6.84 (d, 1H), 7.10 (s, 1H), 7.66 (s, 1H), 7.94 (d, 1H). |
| Example 300 | 2-(R)-methoxy-N-[4-(7-methoxy-1-methyl-[1,2,4]triazolo[4,3-a]quinoxaline-4-ylamino)-butyl]-3-methyl-butyramide | Mass (M + H$^+$): 415.2; $^1$H NMR (500 MHz, DMSO-d6): δ1.45 (m, 2H), 1.63 (m, 2H), 1.71 (s, 3H), 2.02 (d, 3H), 2.94 (s, 3H), 3.07 (m, 2H), 3.29 (s, 4H), 3.50 (m, 2H), 3.80 (s, 3H), 5.57 (s, 1H), 6.83 (d, 1H), 7.05 (s, 1H), 7.67 (m, 1H), 7.92 (d, 1H), 8.09 (m, 1H). |
| Example 301 | 2-(S)-methoxy-N-[4-(7-methoxy-1-methyl-[1,2,4]triazolo[4,3-a]quinoxaline-4-ylamino)-butyl]-3-methyl-butyramide | Mass (M + H$^+$): 415.2; $^1$H NMR (500 MHz, DMSO-d6): δ0.76 (m, 6H), 1.48 (m, 2H), 1.62 (m, 2H), 1.63 (m, 1H), 2.95 (s, 3H), 3.11 (m, 2H), 3.18 (s, 3H), 3.60 (s, 3H), 6.85 (d, 1H), 7.04 (s, 1H), 7.79 (m, 1H), 7.93 (d, 1H), 8.10 (m, 1H). |
| Example 302 | 2-(S)-bromo-N-[4-(7-methoxy-1-methyl-[1,2,4]triazolo[4,3-a]quinoxaline-4-ylamino)-butyl]-3-methyl-butyramide | Mass (M + H$^+$): 463.1; $^1$H NMR (500 MHz, DMSO-d6): δ0.83 (d, 3H), 0.97 (d, 3H), 1.48 (m, 2H),1.63 (m, 2H), 2.03 (m, 1H), 2.95 (s, 3H), 3.10 (m, 2H), 3.50 (m, 2H), 3.81 (s, 3H), 4.03 (d, 1H), 6.84 (d, 1H), 7.10 (d, 1H), 7.94 (d, 1H), 8.11 (m, 1H), 8.17 (m, 1H). |
| Example 303 | acetic acid-[4-(7-methoxy-1-methyl-[1,2,4]triazolo[4,3-a]quinoxaline-4-ylamino)-butylcarbamoyl]-methylester | Mass (M + H$^+$): 400.4; $^1$H NMR (500 MHz, DMSO-d6): δ1.35 (m, 2H), 1.47 (m, 2H), 2.02 (s, 3H), 2.94 (q, 2H), 3.06 (s, 3H), 3.88 (s, 3H), 4.15 (q, 2H), 4.87 (s, 2H), 7.34 (dd, 1H), 7.54 (s, 1H), 7.80 (t, 1H), 7.96 (t, 1H), 8.26 (d, 1H). |
| Example 304 | 2-hydroxy-N-[4-(7-methoxy-1-methyl-[1,2,4]triazolo[4,3-a]quinoxaline-4-ylamino)-butyl]-acetamide | Mass (M + H$^+$): 359.2; $^1$H NMR (500 MHz, DMSO-d6): δ1.19 (br, 1H), 1.47 (m, 2H), 1.62 (m, 2H), 2.94 (s, 3H), 3.12 (q, 2H), 3.51 (q, 2H), 3.74 (d, 2H), 3.84 (s, 3H), 6.85 (d, 1H), 7.06 (s, 1H), 7.69 (t, 1H), 7.96 (d, 1H), 8.09 (t, 1H). |

TABLE 21-continued

| Example | Structure | Name | Data |
|---|---|---|---|
| Example 305 | 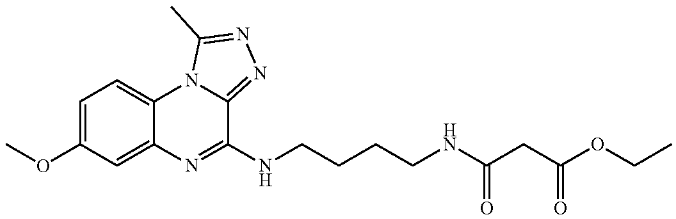 [SMILES: CCOC(=O)CC(=O)NCCCCNc1nc2cc(OC)ccc2n2c(C)nnc12] | N-[4-(7-methoxy-1-methyl-[1,2,4]triazolo[4,3-a]quinoxaline-4-ylamino)-butyl]-malonamic acid ethylester | Mass (M + H$^+$): 415.2; $^1$H NMR (500 MHz, DMSO-d6): δ1.11-1.15 (brm, 5H), 1.46 (m, 2H), 1.65 (m, 2H), 2.95 (s, 3H), 3.11 (q, 2H), 3.51 (q, 2H), 3.81 (s, 3H), 4.06 (q, 2H), 6.85 (d, 1H), 7.07 (s, 1H), 7.96 (d, 1H), 8.03 (t, 1H), 8.09 (t, 1H). |
| Example 306 | 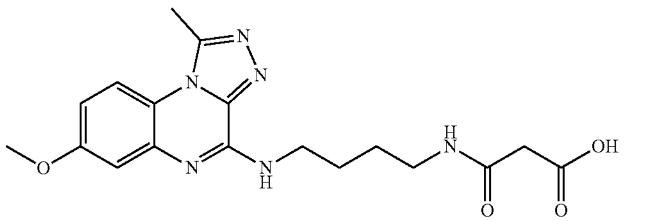 [SMILES: COc1ccc2c(c1)nc(NCCCCNC(=O)CC(=O)O)c1nnc(C)n12] | N-[4-(7-methoxy-1-methyl-[1,2,4]triazolo[4,3-a]quinoxaline-4-ylamino)-butyl]-malonamic acid | Mass (M + H$^+$): 387.1; $^1$H NMR (500 MHz, DMSO-d6): δ1.46 (m, 2H), 1.64 (m, 2H), 2.95 (s, 3H), 3.08 (q, 2H), 3.31 (q, 2H), 3.52 (q, 2H), 3.81 (s, 3H), 6.85 (d, 1H), 7.11 (t, 1H), 7.95 (d, 1H), 8.02 (t, 1H), 8.19 (br, 1H), 12.40 (br, 1H). |
| Example 307 | 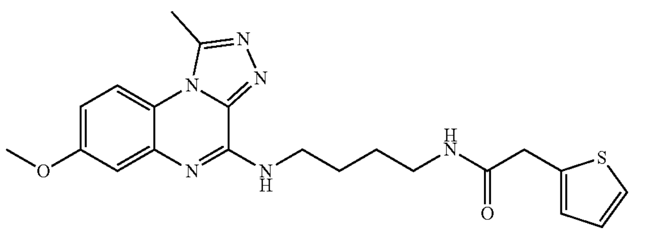 [SMILES: COc1ccc2c(c1)nc(NCCCCNC(=O)Cc1cccs1)c1nnc(C)n12] | N-[4-(7-methoxy-1-methyl-[1,2,4]triazolo[4,3-a]quinoxaline-4-ylamino)-butyl]-2-thiophene-2-yl-acetamide | Mass (M + H$^+$): 425.2; $^1$H NMR (500 MHz, DMSO-d6): δ1.47 (m, 2H), 1.64 (m, 2H), 2.95 (s, 3H), 3.07 (q, 2H), 3.51 (q, 2H), 3.57 (s, 2H), 3.80 (s, 3H), 6.83 (t, 1H), 6.86 (m, 2H), 7.06 (s, 1H), 7.26 (d, 1H), 7.96 (d, 1H), 8.03 (t, 1H), 8.10 (t, 1H). |
| Example 308 | 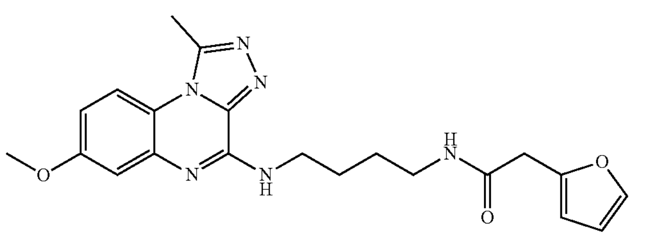 [SMILES: COc1ccc2c(c1)nc(NCCCCNC(=O)Cc1ccco1)c1nnc(C)n12] | 2-furan-2-yl-N-[4-(7-methoxy-1-methyl-[1,2,4]triazolo[4,3-a]quinoxaline-4-ylamino)-butyl]-acetamide | Mass (M + H$^+$): 409.2; $^1$H NMR (500 MHz, DMSO-d6): δ1.47 (m, 2H), 1.63 (m, 2H), 2.95 (s, 3H), 3.08 (q, 2H), 3.41 (s, 2H), 3.50 (q, 2H), 3.80 (s, 3H), 6.12 (d, 1H), 6.30 (d, 1H), 6.85 (dd, 1H), 7.07 (d, 1H), 7.46 (s, 1H), 7.96 (m, 2H), 8.11 (t, 1H). |
| Example 309 | 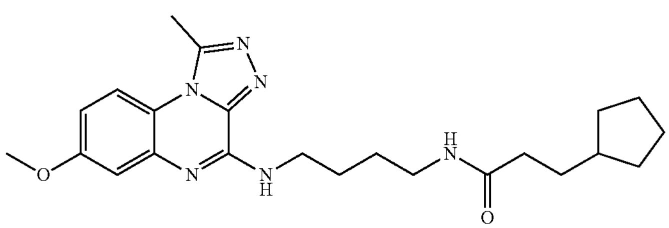 [SMILES: COc1ccc2c(c1)nc(NCCCCNC(=O)CCC1CCCC1)c1nnc(C)n12] | 3-cyclopentyl-N-[4-(7-methoxy-1-methyl-[1,2,4]triazolo[4,3-a]quinoxaline-4-ylamino)-butyl]-propionamide | Mass (M + H$^+$): 423.2; $^1$H NMR (500 MHz, DMSO-d6): δ0.97 (brs, 2H), 1.42 (m, 2H), 4.45 (m, 2H), 1.50 (m, 4H), 1.62 (m, 5H), 2.01 (m, 2H), 2.95 (s, 3H), 3.04 (q, 2H), 3.51 (q, 2H), 3.80 (s, 3H), 6.85 (d, 1H), 7.06 (s, 1H), 7.71 (t, 1H), 7.96 (d, 1H), 8.08 (t, 1H), |

TABLE 21-continued

| Example | Structure | Name | Data |
|---|---|---|---|
| Example 310 | 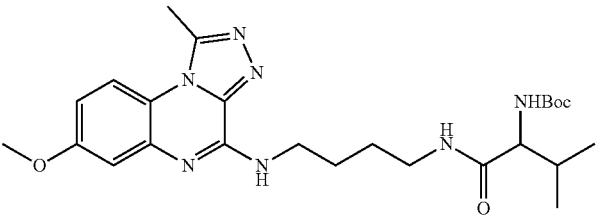 [SMILES: COc1ccc2c(c1)nc(NCCCCNC(=O)C(NC(=O)OC(C)(C)C)C(C)C)c1nnc(C)n12] | {1-[4-(7-methoxy-1-methyl-[1,2,4]triazolo[4,3-a]quinoxaline-4-ylamino)-butylcarbamoyl]-2-methyl-propyl}-carbamic acid-tert-butylester | Mass (M + H⁺): 500.3; ¹H NMR (500 MHz, DMSO-d6): δ0.71 (d, 6H), 1.27 (s, 9H), 1.43 (m, 2H), 1.61 (m, 2H), 1.81 (m, 1H), 2.91 (s, 3H), 3.07 (q, 2H), 3.47 (q, 2H), 3.06 (d, 1H), 3.77 (s, 3H), 6.46 (d, 1H), 6.82 (d, 1H), 7.02 (s, 1H), 7.75 (t, 1H), 7.93 (d, 1H), 8.05 (t, 1H). |
| Example 311 | 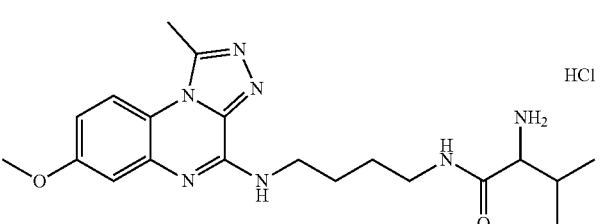 | 2-amino-N-[4-(7-methoxy-1-methyl-[1,2,4]triazolo[4,3-a]quinoxaline-4-ylamino)-butyl]-3-methyl-butyramide | Mass (M + H⁺): 400.2; ¹H NMR (500 MHz, DMSO-d6): δ0.88 (d, 6H), 1.56 (m, 2H), 1.73 (m, 2H) 2.02 (m, 1H), 2.99 (s, 3H), 3.08 (m, 1H), 3.21 (m, 1H) 3.51 (m, 1H), 3.82 (s, 5H), 7.00 (d, 1H), 8.03 (d, 1H), 8.18 (s, 2H), 8.61 (s, 1H). |
| Example 312 | 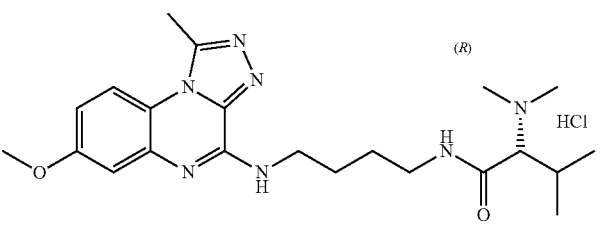 | 2-(R)-dimethylamino-N-[4-(7-methoxy-1-methyl-[1,2,4]triazolo[4,3-a]quinoxaline-4-ylamino)-butyl]-3-methyl-butyramide | Mass (M + H⁺): 428.3; ¹H NMR (500 MHz, DMSO-d6): δ0.69 (d, 3H), 0.82 (d, 3H), 1.47 (m, 2H), 1.67 (m, 2H), 1.95 (m, 1H), 2.11 (s, 6H), 2.36 (s, 1H), 2.95 (s, 3H), 3.10 (m, 2H), 3.80 (s, 3H), 6.84 (d, 1H), 7.05 (s, 1H), 7.724 (s, 1H), 7.96 (d, 1H), 8.11 (m, 1H). |
| Example 313 | 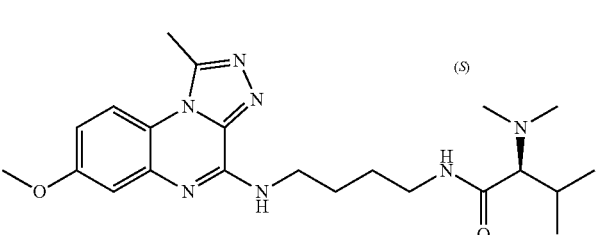 | 2-(S)-dimethylamino-N-[4-(7-methoxy-1-methyl-[1,2,4]triazolo[4,3-a]quinoxaline-4-ylamino)-butyl]-3-methyl-butyramide | Mass (M + H⁺): 428.3; ¹H NMR (500 MHz, DMSO-d6): δ0.70 (d, 3H), 0.83 (d, 3H), 1.46 (m, 2H), 1.65 (m, 2H), 1.95 (m, 1H), 2.15 (s, 6H), 2.95 (s, 3H), 3.10 (m, 2H), 3.50 (m, 2H), 3.80 (s, 3H), 6.84 (d, 1H), 7.05 (s, 1H), 7.94 (s, 1H), 7.96 (d, 1H), 8.12 (m, 1H). |
| Example 314 | 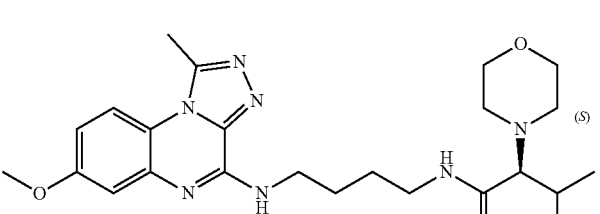 | N-[4-(7-methoxy-1-methyl-[1,2,4]triazolo[4,3-a]quinoxaline-4-ylamino)-butyl]-3-methyl-2-(S)-morpholine-4-yl-butyramide | Mass (M + H⁺): 470.3; ¹H NMR (500 MHz, DMSO-d6): δ0.69 (m, 3H), 0.85 (m, 3H), 1.48 (m, 2H), 1.64 (m, 2H), 1.92 (m, 1H), 2.46 (m, 1H), 2.95 (s, 3H), 3.08 (m, 2H), 3.30 (m, 2H), 3.45 (m, 4H), 3.81 (s, 3H), 6.84 (d, 1H), 7.06 (d, 1H), 7.79 (m, 1H), 7.96 (d, 1H), 8.11 (m, 1H). |

TABLE 21-continued

| Example | Structure | Name | Data |
|---|---|---|---|
| Example 315 | 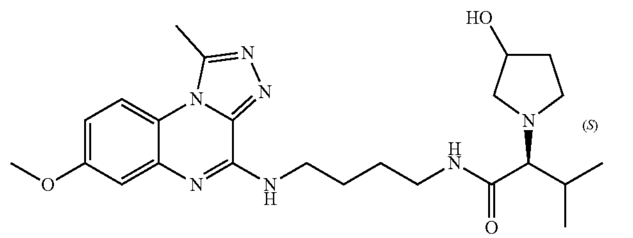 | 2-(S)-(3-hydroxy-pyrrolidine-1-yl)-N-[4-(7-methoxy-1-methyl-[1,2,4]triazolo[4,3-a]quinoxaline-4-ylamino)-butyl]-3-methyl-butyramide | Mass (M + H$^+$): 470.3; $^1$H NMR (500 MHz, DMSO-d6): δ0.74 (m, 3H), 0.83 (m, 3H), 1.46 (m, 3H), 1.65 (m, 2H), 1.90 (m, 2H), 2.46 (m, 2H), 2.55 (m, 2H), 2.70 (m, 1H), 2.94 (s, 3H), 3.08 (m, 2H), 3.50 (m, 2H), 3.80 (s, 3H), 4.04 (s, 1H), 4.56 (s, 1H), 6.83 (d, 1H), 7.03 (d, 1H), 7.71 (s, 1H), 7.91 (d 1H), 8.10 (m, 1H). |
| Example 316 | 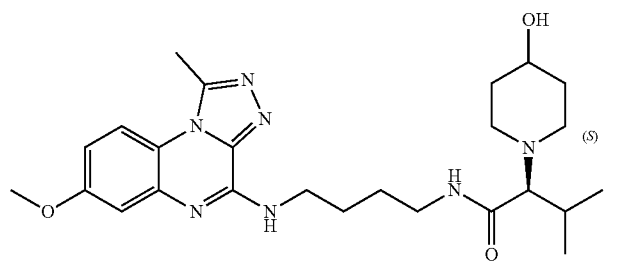 | 2-(S)-(4-hydroxy-piperidine-1-yl)-N-[4-(7-methoxy-1-methyl-[1,2,4]triazolo[4,3-a]quinoxaline-4-ylamino)-butyl]-3-methyl-butyramide | Mass (M + H$^+$): 484.3; $^1$H NMR (500 MHz, DMSO-d6): δ0.69 (m, 3H), 0.82 (m, 3H), 1.16 (m, 2H), 1.45 (m, 2H), 1.63 (m, 4H), 1.90 (m, 1H), 2.15 (m, 2H), 2.46 (m, 1H), 2.48 (m, 2H), 2.95 (s, 3H), 3.10 (m, 2H), 3.25 (m, 1H), 3.52 (s, 1H), 3.80 (s, 3H), 6.85 (d, 1H), 7.05 (d, 1H), 7.71 (s, 1H), 7.94 (d, 1H), 8.11 (m, 1H). |
| Example 317 | 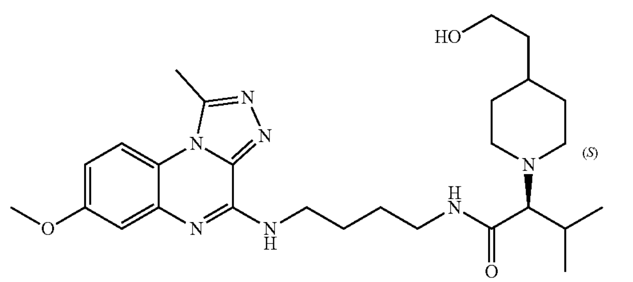 | 2-(S)-[4-(2-hydroxy-ethyl)-piperidine-1-yl]-N-[4-(7-methoxy-1-methyl-[1,2,4]triazolo[4,3-a]quinoxaline-4-ylamino)-butyl]-3-methyl-butyramide | Mass (M + H$^+$): 512.1; $^1$H NMR (500 MHz, DMSO-d6): δ0.68 (m, 3H), 0.80 (m, 3H), 0.90 (m, 1H), 1.05 (m, 2H), 1.15 (m, 1H), 1.22 (m, 2H), 1.45 (m, 4H), 1.55 (m, 2H), 1.90 (m, 1H), 2.02 (m, 2H), 2.40 (d, 1H), 2.64 (m, 2H), 2.95 (s, 3H), 3.00 (m, 2H), 3.50 (m, 2H), 3.80 (s, 3H), 4.21 (m 1H), 6.84 (d, 1H), 7.05 (m, 1H), 7.68 (s, 1H), 7.94 (d, 1H), 7.96 (m, 1H). |
| Example 318 | 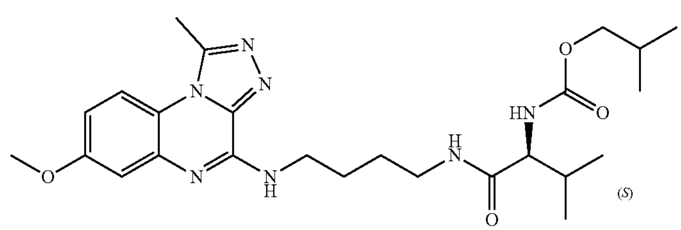 | (S)-{1-[4-(7-methoxy-1-methyl-[1,2,4]triazolo[4,3-a]quinoxaline-4-ylamino)-butylcarbamoyl]-2-methyl-propyl}-carbamic acid isobutylester | Mass (M + H$^+$): 500.3; $^1$H NMR (500 MHz, CDCl$_3$): δ0.85 (m, 6H), 0.93 (m, 6H), 1.67 (m, 2H), 1.77 (m, 2H), 1.79 (m, 1H), 2.10 (s, 1H), 3.03 (s, 3H), 3.34 (m, 2H), 3.75 (s, 2H), 3.80 (m, 1H), 3.89 (s, 3H), 3.95 (m, 1H), 5.47 (s, 1H), 6.41 (s, 1H), 6.57 (s, 1H), 6.57 (s, 1H), 6.84 (d, 1H), 7.19 (s, 1H), 7.79 (d, 1H). |

TABLE 21-continued

| Example | Structure | Name | Data |
| --- | --- | --- | --- |
| Example 319 | 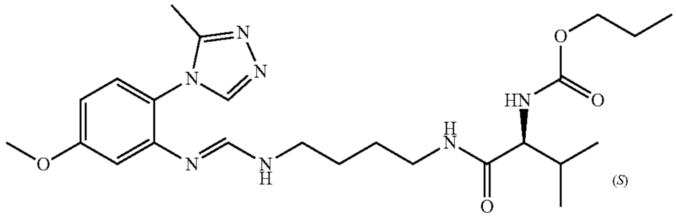 | (S)-{1-[4-(7-methoxy-1-methyl-[1,2,4]triazolo[4,3-a]quinoxaline-4-ylamino)-butylcarbamoyl]-2-methyl-propyl}-carbamic acid propylester | Mass (M + H$^+$): 486.3; $^1$H NMR (500 MHz, CDCl$_3$): δ0.87 (m, 9H), 1.57 (m, 2H), 1.65 (m, 2H), 1.78 (m, 2H), 2.10 (s, 1H), 2.10 (s, 1H), 3.03 (s, 3H), 3.34 (m, 2H), 3.75 (s, 2H), 3.88 (s, 3H), 3.97 (m, 2H), 5.44 (s, 1H), 6.43 (s, 1H), 6.56 (s, 1H), 6.84 (d, 1H), 7.19 (s, 1H), 7.84 (d, 1H). |
| Example 320 | 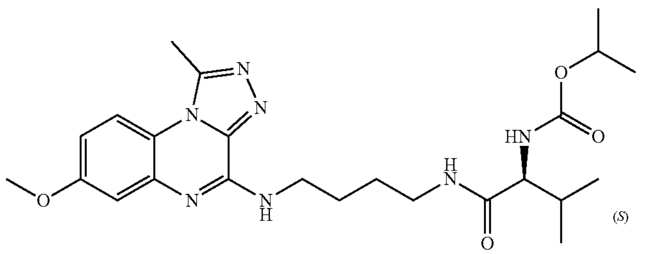 | (S)-{1-[4-(7-methoxy-1-methyl-[1,2,4]triazolo[4,3-a]quinoxaline-4-ylamino)-butylcarbamoyl]-2-methyl-propyl}-carbamic acid isopropylester | Mass (M + H$^+$): 486.3; $^1$H NMR (500 MHz, CDCl$_3$): δ0.89 (m, 6H), 1.19 (m, 6H), 1.67 (m, 2H), 1.78 (m, 2H), 2.11 (s, 1H), 3.04 (s, 3H), 3.34 (m, 2H), 3.89 (s, 2H), 3.89 (s, 3H), 3.96 (m, 1H), 4.85 (s, 1H), 5.28 (s, 1H), 6.34 (m, 1H), 6.85 (d, 1H), 7.25 (s, 1H), 7.80 (d, 1H). |
| Example 321 | 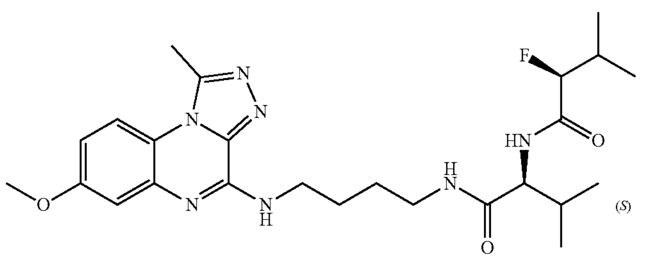 | (S)-2-(S)-fluoro-N-{1-[4-(7-methoxy-1-methyl-[1,2,4]triazolo[4,3-a]quinoxaline-4-ylamino)-butyl carbamoyl]-2-methyl-propyl}-3-methyl-butyramide | Mass (M + H$^+$): 502.3; $^1$H NMR (500 MHz, CDCl$_3$): δ0.89 (m, 9H), 1.05 (m, 3H), 1.71 (m, 2H), 1.82 (m, 2H), 2.10 (m, 1H), 2.25 (m, 1H), 3.02 (s, 3H), 3.34 (m, 2H), 3.76 (s, 2H), 3.87 (s, 3H), 4.30 (m, 1H), 4.74 (d, 1H), 6.85 (m, 2H), 7.00 (m, 1H), 7.35 (m, 1H), 7.72 (m, 2H). |
| Example 322 | 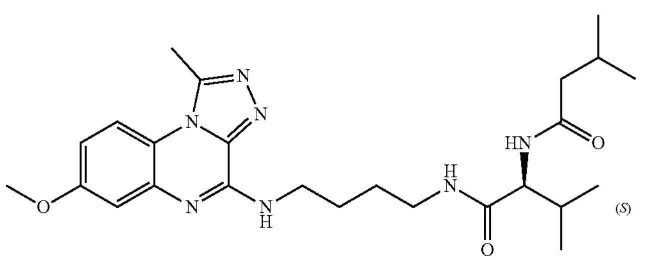 | (S)-N-[4-(7-methoxy-1-methyl-[1,2,4]triazolo[4,3-a]quinoxaline-4-ylamino)-butyl]-3-methyl-2-(3-methyl-butyryl-amino)-butyramide | Mass (M + H$^+$): 484.3; $^1$H NMR (500 MHz, DMSO-d6): δ0.76 (m, 12H), 1.45 (m, 2H), 1.61 (m, 2H), 1.92 (m, 2H), 2.94 (s, 3H), 3.05 (m, 4H), 3.49 (m, 2H), 3.81 (s, 1H), 4.02 (m, 1H), 6.85 (d, 1H), 7.05 (s, 1H), 7.68 (d, 1H), 7.89 (m, 1H), 7.94 (d, 1H), 8.18 (m, 1H). |
| Example 323 | 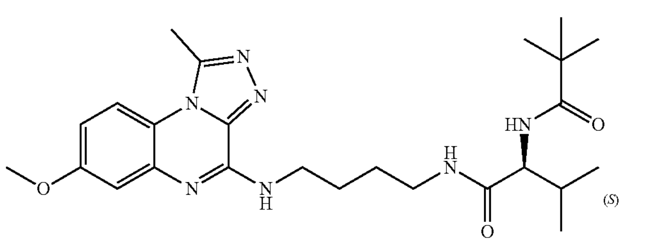 | (S)-2-(2,2-dimethyl-propionylamino)-N-[4-(7-methoxy-1-methyl-[1,2,4]triazolo[4,3-a]quinoxaline-4-ylamino)-butyl]-3-methyl-butyramide | Mass (M + H$^+$): 484.3; $^1$H NMR (500 MHz, DMSO-d6): δ0.74 (m, 6H), 1.05 (s, 9H), 1.45 (m, 2H), 1.63 (m, 2H), 1.90 (m, 2H), 2.94 (s, 3H), 3.05 (m, 2H), 3.49 (m, 2H), 3.80 (s, 3H), 4.04 (m, 1H), 6.84 (d, 1H), 7.00 (d, 1H), 7.10 (s, 1H), 7.85 (m, 1H), 7.99 (d, 1H), 8.10 (s, 1H). |

TABLE 21-continued

| Example | Structure | Name | Data |
|---|---|---|---|
| Example 324 | 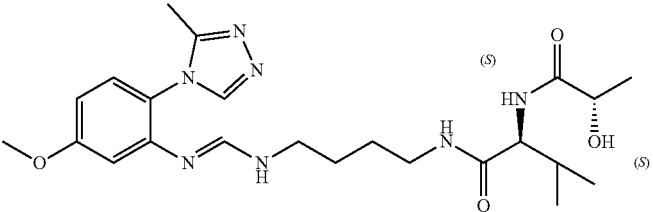 | 2-(S)-(2-(S)-hydroxy-propionylamino)-N-[4-(7-methoxy-1-methyl-[1,2,4]triazolo[4,3-a]quinoxaline-4-ylamino)-butyl]-3-methyl-butyramide | Mass (M + H⁺): 472.3; ¹H NMR (500 MHz, DMSO-d6): δ0.76 (m, 6H), 1.17 (m, 3H), 1.51 (m, 2H), 1.66 (m, 2H), 1.67 (HI, 1H), 2.98 (s, 6H), 3.05 (m, 2H), 3.82 (s, 3H), 3.92 (m, 2H), 4.10 (s, 1H), 6.99 (d, 1H), 7.38 (d, 1H), 7.59 (s, 1H), 8.01 (d, 1H), 8.15 (m, 1H). |
| Example 325 | 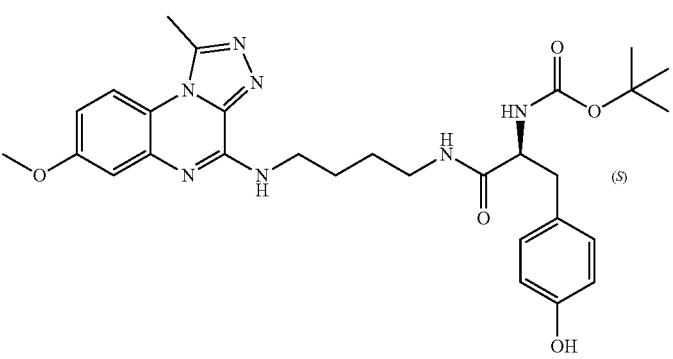 | (S)-{2-(4-hydroxy-phenyl)-1-[4-(7-methoxy-1-methyl-[1,2,4]triazolo[4,3-a]quinoxaline-4-ylamino)-butyl carbamoyl]-ethyl}-carbamic acid-tert-butylester | Mass (M + H⁺): 564.3; ¹H NMR (500 MHz, DMSO-d6): δ1.25 (s, 9H), 1.44 (m, 2H), 1.61 (m, 2H), 2.47 (m, 2H), 2.94 (s, 3H), 3.10 (m, 2H), 3.50 (m, 2H), 3.79 (s, 3H), 3.95 (m, 1H), 6.57 (d, 2H), 6.80 (d, 1H), 6.90 (d, 2H), 7.06 (s, 1H), 7.78 (m, 1H), 7.93 (d, 1H), 8.08 (m, 1H), 9.09 (s, 1H). |
| Example 326 | 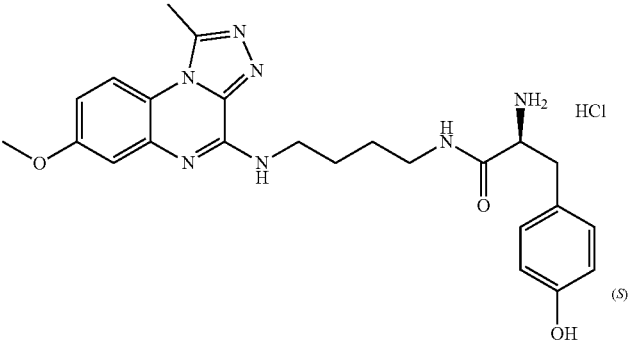 | 2-(S)-amino-3-(4-hydroxy-phenyl)-N-[4-(7-methoxy-1-methyl-[1,2,4]triazolo[4,3-a]quinoxaline-4-ylamino)-butyl]-propionamide | Mass (M + H⁺): 464.2; ¹H NMR (500 MHz, DMSO-d6): δ1.48 (m, 2H), 1.63 (m, 2H), 2.47 (m, 2H), 3.00 (m, 4H), 3.10 (m, 1H), 3.80 (m, 6H), 6.63 (d, 2H), 6.97 (d, 2H), 7.01 (m, 2H), 8.02 (d, 1H), 8.04 (s, 1H), 8.27 (s, 2H), 8.66 (m, 1H). |
| Example 327 | 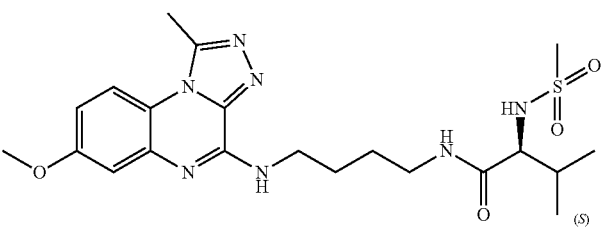 | 2-(S)-methanesulfonylamino-N-[4-(7-methoxy-1-methyl-[1,2,4]triazolo[4,3-a]quinoxaline-4-ylamino)-butyl]-3-methyl-butyramide | Mass (M + H⁺): 478.2; ¹H NMR (500 MHz, DMSO-d6): δ0.79 (m, 6H), 1.48 (m, 2H), 1.63 (m, 2H), 1.85 (m, 1H), 2.74 (s, 3H), 2.95 (s, 3H), 3.10 (m, 1H), 3.46 (s, 3H), 3.81 (s, 3H), 6.85 (d, 1H), 7.05 (d, 1H), 7.10 (d, 1H), 7.95 (d, 1H), 8.05 (d, 1H), 8.10 (d, 1H). |
| Example 328 | 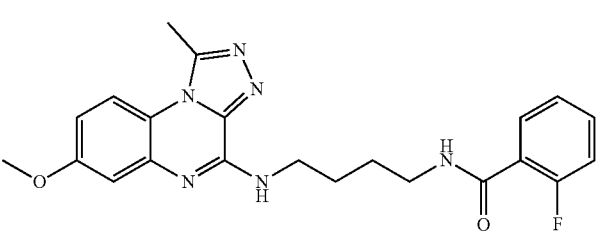 [SMILES: COc1ccc2c(c1)nc(NCCCCNC(=O)c1ccccc1F)c1nnc(C)n12] | 2-fluoro-N-[4-(7-methoxy-1-methyl-[1,2,4]triazolo[4,3-a]quinoxaline-4-ylamino)-butyl]-benzramide | Mass (M + H⁺): 423.2; ¹H NMR (500 MHz, DMSO-d6): δ1.58 (m, 2H), 1.69 (m, 2H), 2.95 (s, 3H), 3.26 (q, 2H), 3.54 (q, 2H), 3.80 (s, 3H) 6.85 (d, 1H), 7.06 (s, 1H), 7.20 (m, 2H), 7.44 (m, 1H), 7.53 (m, 1H), 7.95 (d, 1H), 8.12 (t, 1H), 8.26 (t, 1H). |

TABLE 21-continued

| Example | Structure | Name | Data |
|---|---|---|---|
| Example 329 | 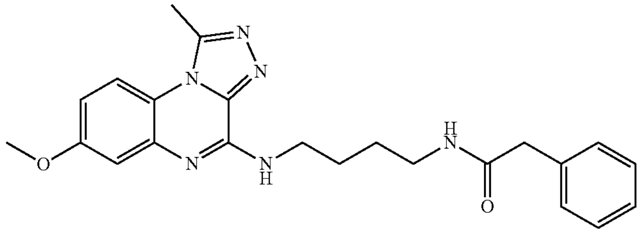 [SMILES: COc1ccc2c(c1)nc(NCCCCNC(=O)Cc1ccccc1)c1nnc(C)n12] | N-[4-(7-methoxy-1-methyl-[1,2,4]triazolo[4,3-a]quinoxaline-4-ylamino)-butyl]-2-phenyl-acetamide | Mass (M + H⁺): 419.2; ¹H NMR (500 MHz, DMSO-d6): δ1.46 (m, 2H), 1.62 (m, 2H), 2.95 (s, 3H), 3.06 (q, 2H), 3.33 (s, 2H), 3.51 (q, 2H), 3.80 (s, 3H), 6.86 (dd, 1H), 7.06 (d, 1H), 7.19 (m, 1H), 7.20 (m, 4H), 7.97 (m, 2H), 8.09 (t, 1H). |
| Example 330 | 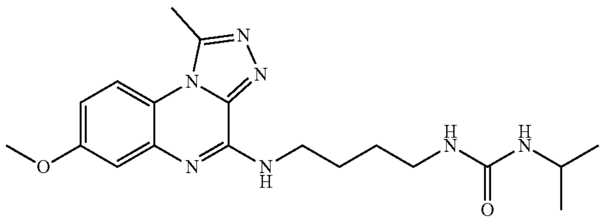 [SMILES: COc1ccc2c(c1)nc(NCCCCNC(=O)NC(C)C)c1nnc(C)n12] | 1-isopropyl-3-[4-(7-methoxy-1-methyl-[1,2,4]triazolo[4,3-a]quinoxaline-4-ylamino)-butyl]-urea | Mass (M + H⁺): 386.2; ¹H NMR (500 MHz, DMSO-d6): δ0.95 (d, 6H), 1.41 (m, 2H), 1.60 (m, 2H), 2.95 (s, 3H), 2.97 (q, 2H), 3.50 (q, 2H), 3.60 (m, 1H), 3.81 (s, 3H), 5.54 (d, 1H), 5.65 (t, 1H), 6.85 (d, 1H), 7.07 (s, 1H), 7.95 (d, 1H), 8.09 (t, 1H). |
| Example 331 | 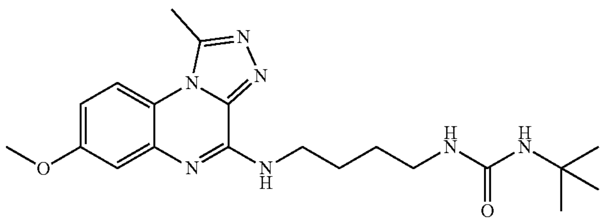 [SMILES: COc1ccc2c(c1)nc(NCCCCNC(=O)NC(C)(C)C)c1nnc(C)n12] | 1-tert-butyl-3-[4-(7-methoxy-1-methyl-[1,2,4]triazolo[4,3-a]quinoxaline-4-ylamino)-butyl]-urea | Mass (M + H⁺): 400.2; ¹H NMR (500 MHz, DMSO-d6): δ1.15 (s, 9H), 1.39 (m, 2H), 1.60 (m, 2H), 2.94 (m, 2H), 2.96 (s, 3H), 3.80 (s, 3H), 5.49 (s, 1H), 5.57 (t, 1H), 6.84 (d, 1H), 7.06 (d, 1H), 7.94 (d, 1H), 8.10 (t, 1H). |
| Example 332 | 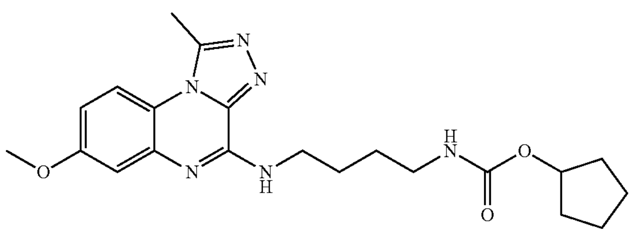 [SMILES: COc1ccc2c(c1)nc(NCCCCNC(=O)OC1CCCC1)c1nnc(C)n12] | [4-(7-methoxy-1-methyl-[1,2,4]triazolo[4,3-a]quinoxaline-4-ylamino)-butyl]-carbamic acid cyclopentylester | Mass (M + H⁺): 413.2; ¹H NMR (500 MHz, DMSO-d6): δ1.44~1.55 (m, 8H), 1.62 (m, 2H), 1.73 (m, 2H), 2.95 (s, 3H), 2.99 (m, 2H), 3.50 (q, 2H), 3.80 (s, 3H), 4.89 (m, 1H), 6.85 (d, 1H), 6.95 (t, 1H), 7.06 (s, 1H), 7.95 (d, 1H), 8.08 (t, 1H). |
| Example 333 | 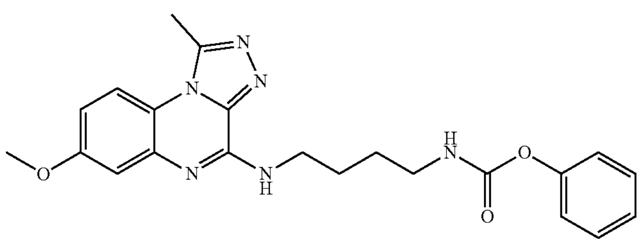 [SMILES: COc1ccc2c(c1)nc(NCCCCNC(=O)Oc1ccccc1)c1nnc(C)n12] | [4-(7-methoxy-1-methyl-[1,2,4]triazolo[4,3-a]quinoxaline-4-ylamino)-butyl]-carbamic acid phenylester | Mass (M + H⁺): 421.2; ¹H NMR (500 MHz, DMSO-d6): δ1.54 (m, 2H), 1.69 (m, 2H), 2.95 (s, 3H), 3.09 (q, 2H), 3.53 (m, 2H), 3.80 (s, 3H), 6.85 (d, 1H), 7.06 (m, 3H), 7.14 (t, 1H), 7.30 (t, 2H), 7.71 (t, 1H), 7.95 (d, 1H), 8.12 (t, 1H). |
| Example 334 | 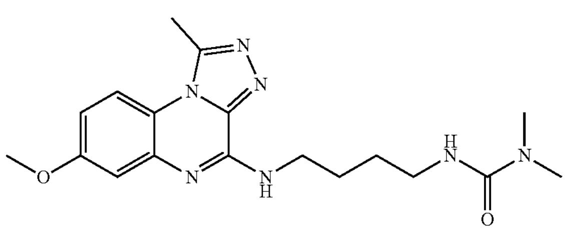 | 3-[4-(7-methoxy-1-methyl-[1,2,4]triazolo[4,3-a]quinoxaline-4-ylamino)-butyl]-1,1-dimethyl-urea | Mass (M + H⁺): 372.2; ¹H NMR (500 MHz, DMSO-d6): δ1.45 (m, 2H), 1.61 (m, 2H), 2.71 (s, 6H), 2.94 (s, 3H), 3.01 (q, 2H), 3.52 (q, 2H), 3.80 (s, 3H), 6.19 (t, 1H), 6.84 (dd, 1H), 7.04 (s, 1H), 7.93 (d, 1H), 8.06 (t, 1H). |

TABLE 21-continued

| Example | Structure | Name | Data |
|---|---|---|---|
| Example 335 | 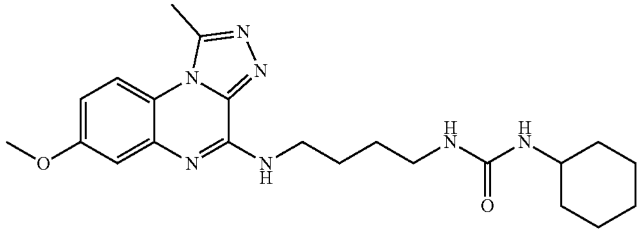 [SMILES: COc1ccc2c(c1)nc(NCCCCNC(=O)NC1CCCCC1)c1nnc(C)n12] | 1-cyclohexyl-3-[4-(7-methoxy-1-methyl-[1,2,4]triazolo[4,3-a]quinoxaline-4-ylamino)-butyl]-urea | Mass (M + H$^+$): 426.3; $^1$H NMR (500 MHz, DMSO-d6): δ0.01 (m, 2H), 1.08 (m, 1H), 1.18 (m, 2H), 1.40 (m, 2H), 1.49 (m, 1H), 1.60 (m, 4H), 1.69 (m, 2H), 2.95 (s, 3H), 2.99 (m, 2H), 3.31 (m, 1H), 3.50 (q, 2H), 3.81 (s, 3H), 5.60 (d, 1H), 5.65 (t, 1H), 6.85 (d, 1H), 7.07 (s, 1H), 7.95 (s, 1H), 8.08 (t, 1H). |
| Example 336 | 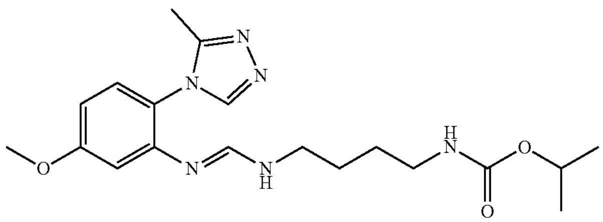 | [4-(7-methoxy-1-methyl-[1,2,4]triazolo[4,3-a]quinoxaline-4-ylamino)-butyl]-thiocarbamic acid-S-isopropyl ester | Mass (M + H$^+$): 403.2; $^1$H NMR (500 MHz, DMSO-d6): δ1.19 (d, 6H), 1.47 (m, 2H), 1.61 (m, 2H), 2.95 (s, 3H), 3.10 (m, 2H), 3.39 (m, 1H), 3.50 (q, 2H), 3.81 (s, 3H), 6.86 (d, 1H), 7.08 (t, 1H), 7.95 (s, 1H), 7.96 (d, 1H), 8.21 (t, 1H). |
| Example 337 | 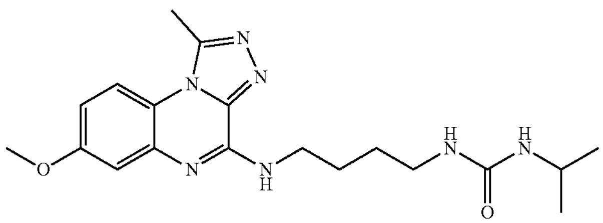 | 1-isopropyl-3-[4-(7-methoxy-1-methyl-[1,2,4]triazolo[4,3-a]quinoxaline-4-ylamino)-butyl]-thiourea | Mass (M + H$^+$): 402.2; $^1$H NMR (500 MHz, DMSO-d6): δ1.04 (d, 6H), 1.53 (m, 2H), 1.63 (m, 2H), 3.02 (s, 3H), 3.45 (br, 2H), 3.52 (q, 2H), 3.80 (s, 3H), 6.85 (dd, 1H), 7.07 (dd, 2H), 7.20 (br, 1H), 7.95 (d, 1H), 8.11 (t, 1H). |
| Example 338 | 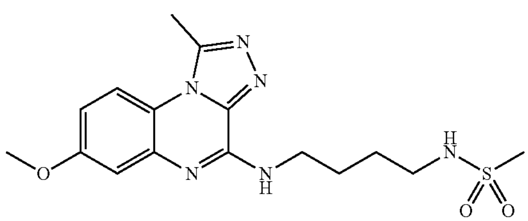 | N-[4-(7-methoxy-1-methyl-[1,2,4]triazolo[4,3-a]quinoxaline-4-ylamino)-butyl]-methanesulfonamide | Mass (M + H$^+$): 379.2; $^1$H NMR (500 MHz, DMSO-d6): δ1.53 (m, 2H), 1.67 (m, 2H), 2.84 (s, 3H), 2.95 (s, 3H), 2.96 (q, 2H), 3.52 (q, 2H), 3.80 (s, 3H), 6.84 (d, 1H), 6.90 (t, 1H), 7.05 (s, 1H), 7.93 (d, 1H), 8.10 (t, 1H). |

<Example 339> Preparation of N-{4-[7-methoxy-1-methyl-8-(4-nitro-benzyl)-[1,2,4]triazolo[4,3-a]quinoxaline-4-ylamino]-butyl}-3-methyl-butyramide

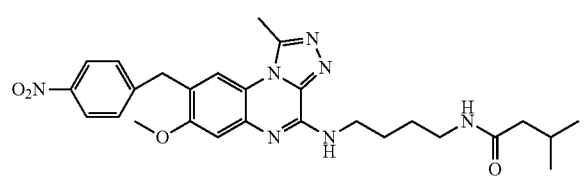 [SMILES: COc1cc2nc(NCCCCNC(=O)CC(C)C)c3nnc(C)n3c2cc1Cc1ccc([N+](=O)[O-])cc1]

N-[4-(7-methoxy-1-methyl-[1,2,4]triazolo[4,3-a]quinoxaline-4-ylamino)-butyl]-3-methyl-butyramide (100 mg, 0.26 mmol) prepared in Example 285 was dissolved in 2 ml of dichloromethane, to which silvertrifluoromethanesulfonate (67 mg, 0.26 mmol) and 4-nitrobenzylbromide were added, followed by reaction at room temperature for 18 hours. Upon completion of the reaction, the precipitate was filtered. The filtrate was distilled under reduced pressure. The concentrate was separated and purified by column chromatography. As a result, 78 mg of a target compound was obtained (58% yield).

Mass (M+H$^+$): 520.0

$^1$H NMR (500 MHz, DMSO-d6) δ0.80 (d, 6H), 1.40 (m, 2H), 1.61 (m, 2H), 1.87 (d, 2H), 1.90 (m, 1H), 3.00 (q, 2H), 3.36 (s, 3H), 3.50 (q, 2H), 3.76 (s, 2H), 3.86 (s, 3H), 6.50 (d, 1H), 7.17 (t, 1H), 7.48 (dd, 2H), 7.68 (d, 1H), 8.19 (t, 1H), 8.23 (dd, 2H).

<Example 340> Preparation of N-[4-(7-hydroxy-1-methyl-[1,2,4]triazolo[4,3-a]quinoxaline-4-ylamino)-butyl]-3-methyl-butyramide

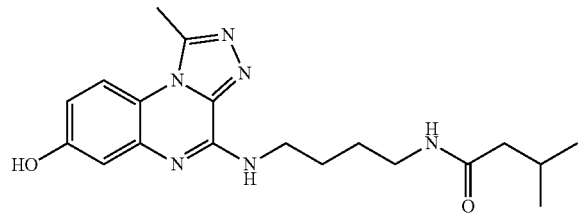 [SMILES: Cc1nnc2c(NCCCCNC(=O)CC(C)C)nc3cc(O)ccc3n12]

N-[4-(7-methoxy-1-methyl-[1,2,4]triazolo[4,3-a]quinoxaline-4-ylamino)-butyl]-3-methyl-butyramide (0.1 g, 0.26 mmol) prepared in Example 285 and aluminum chloride (AlCl₃) were dissolved in toluene solvent, followed by reflux stirring for 3 hours. Upon completion of the reaction, ph of the reactant was adjusted to 8 at room temperature. The reactant was extracted with ethylacetate and water. The extract was dried over magnesium sulfate, and then distilled under reduced pressure. As a result, 0.7 g of a target compound was obtained (73% yield).

Mass (M+H$^+$): 371.2

$^1$H NMR (500 MHz, DMSO-d6) δ0.79 (d, 6H), 1.44 (m, 2H), 1.62 (m, 2H), 1.87 (m, 3H), 2.93 (s, 3H), 3.04 (q, 2H), 3.48 (q, 2H), 6.70 (d, 1H), 6.90 (s, 1H), 7.70 (s, 1H), 7.86 (d, 1H), 7.98 (s, 1H), 9.64 (s, 1H).

<Example 341> Preparation of N-{4-[7-(4-cyanobenzyloxy)-1-methyl-[1,2,4]triazolo[4,3-a]quinoxaline-4-ylamino]-butyl}-3-methyl-butyramide

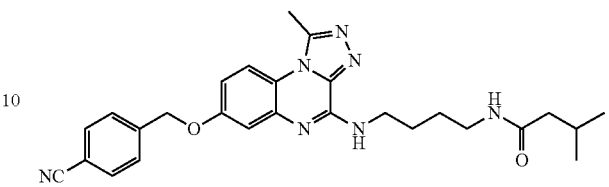

N-[4-(7-hydroxy-1-methyl-[1,2,4]triazolo[4,3-a]quinoxaline-4-ylamino)-butyl]-3-methyl-butyramide (0.3 g, 0.79 mmol) prepared in Example 340, alpha-bromo-P-tolunitrile (0.31 g, 2 eq) and cesiumcarbonate (1.28 g, 5 eq) were dissolved in NMP solvent, followed by reflux stirring at 100° C. for 2 hours. Upon completion of the reaction, the resulting solid was filtered and as a result, 0.11 g of a target compound was obtained (29% yield).

Mass (M+H$^+$): 486.2

$^1$H NMR (500 MHz, DMSO-d6) δ0.78 (d, 6H), 1.44 (m, 2H), 1.61 (m, 2H), 1.87 (m, 3H), 2.95 (s, 3H), 3.04 (q, 2H), 3.50 (q, 2H), 5.30 (d, 2H), 5.86 (s, 1H), 6.93 (d, 1H), 7.15 (s, 1H), 7.63 (d, 2H), 7.70 (m, 1H), 7.84 (d, 2H), 7.85 (d, 1H), 8.20 (s, 1H).

The compounds shown in Table 22 below were prepared by the same manner as described in Example 341.

TABLE 22

| Example | Structure | Name | Data |
|---|---|---|---|
| Example 342 | 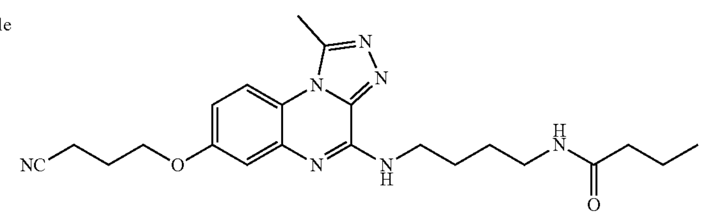 | N-{4-[7-(3-cyano-propoxy)-1-methyl-[1,2,4]triazolo[4,3-a]quinoxaline-4-ylamino]-butyl}-3-methyl-butyramide | Mass (M + H$^+$): 438.3; $^1$H NMR (500 MHz, DMSO-d6): δ0.79 (d, 6H), 1.44 (m, 2H), 1.63 (m, 2H), 1.87 (m, 3H), 2.02 (m, 2H), 2.65 (t, 2H), 2.95 (s, 3H), 3.13 (q, 2H), 3.50 (d, 2H), 4.09 (d, 2H), 6.85 (d, 1H), 7.07 (s, 1H), 7.70 (m, 1H), 7.95 (d, 1H), 8.10 (m, 1H). |
| Example 343 | 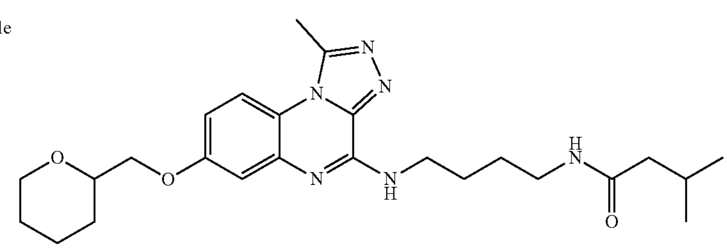 | 3-methyl-N-{4-[1-methyl-7-(tetrahydropyran-2-yl-methoxy)-[1,2,4]triazolo[4,3-a]quinoxaline-4-ylamino]-butyl}-butyramide | Mass (M + H$^+$): 469.3; $^1$H NMR (500 MHz, DMSO-d6): δ0.79 (d, 6H), 1.30 (m, 1H), 1.46 (m, 5H), 1.61 (m, 3H), 1.80 (m, 1H), 1.86 (m, 3H), 2.94 (s, 3H), 3.04 (m, 2H), 3.37 (m, |

TABLE 22-continued

| Example | Structure | Name | Data |
|---|---|---|---|
| | | | 1H), 3.49 (m, 2H), 3.60 (m, 1H), 3.86 (m, 1H), 3.96 (d, 2H), 6.84 (d, 1H), 7.03 (s, 1H), 7.69 (t, 1H), 7.92 (d, 1H), 8.08 (t, 1H). |
| Example 344 | 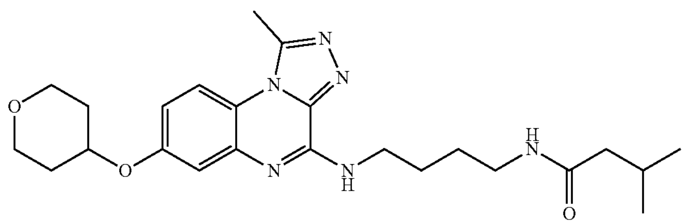 [SMILES: Cc1nnc2c(NCCCCNC(=O)CC(C)C)nc3cc(OC4CCOCC4)ccc3n12] | 3-methyl-N-{4-[1-methyl-7-(tetrahydro-pyran-4-yloxy)-[1,2,4]triaz-olo[4,3-a]quinoxaline-4-ylamino]-butyl}-butyramide | Mass (M + H$^+$): 455.3; $^1$H NMR (500 MHz, DMSO-d6): δ0.79 (d, 6H), 1.44 (s, 2H), 1.62 (m, 4H), 1.87 (s, 3H), 1.97 (d, 2H), 2.94 (s, 3H), 3.04 (s, 2H), 3.47 (m, 4H), 3.84 (d, 2H), 4.69 (s, 1H), 6.87 (d, 1H), 7.11 (s, 1H), 7.71 (s, 1H), 7.94 (d, 1H), 8.01 (s, 1H). |
| Example 345 | 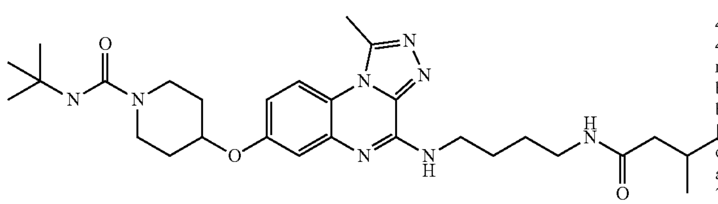 [SMILES: Cc1nnc2c(NCCCCNC(=O)CC(C)C)nc3cc(OC4CCN(C(=O)NC(C)(C)C)CC4)ccc3n12] | 4-{1-methyl-4-[4-(3-methyl-butylamino)-butylamino]-[1,2,4]triaz-olo[4,3-a]quinoxaline-7-yloxy}-piperidine-1-carboxylic acid-tert-butylester | Mass (M + H$^+$): 554.3; $^1$H NMR (500 MHz, DMSO-d6): δ0.78 (d, 9H), 1.36 (s, 6H), 1.44 (m, 4H), 1.45 (m, 2H), 1.60 (m, 2H), 1.87 (m, 7H), 2.93 (s, 3H), 2.95 (s, 2H), 3.63 (m, 2H), 6.88 (s, 1H), 7.11 (s, 1H), 7.69 (s, 1H), 7.92 (t, 1H), 8.11 (s, 1H). |
| Example 346 | 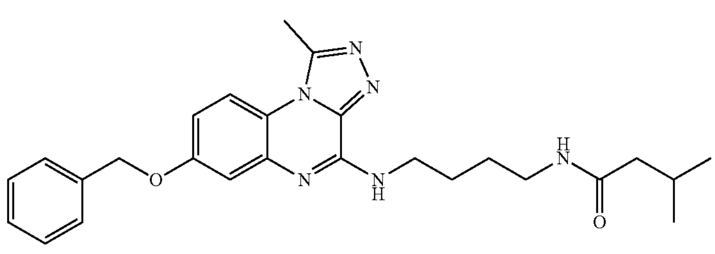 [SMILES: Cc1nnc2c(NCCCCNC(=O)CC(C)C)nc3cc(OCc4ccccc4)ccc3n12] | N-[4-(7-benzyloxy-1-methyl-[1,2,4]triaz-olo[4,3-a]quinoxaline-4-ylamino)-butyl]-3-methyl-butyramide | Mass (M + H$^+$): 461.2; $^1$H NMR (500 MHz, DMSO-d6): δ0.77 (d, 6H), 1.44 (m, 2H), 1.64 (m, 2H), 1.87 (m, 3H), 2.94 (s, 3H), 3.04 (q, 2H), 3.51 (q, 2H), 5.17 (s, 2H), 6.90 (d, 2H), 7.14 (s, 1H), 7.30 (m, 1H), 7.37 (m, 2H), 7.44 (m, 2H), 7.70 (t, 1H), 7.93 (d, 1H), 8.10 (s, 1H). |

<Example 347> Preparation of N-(4-{7-[4-(N-hydroxycarbamimidoyl)-benzoyl]-1-methyl-[1,2,4]triazolo[4,3-a]quinoxaline-4-ylamino}-butyl)-3-methyl-butyramide

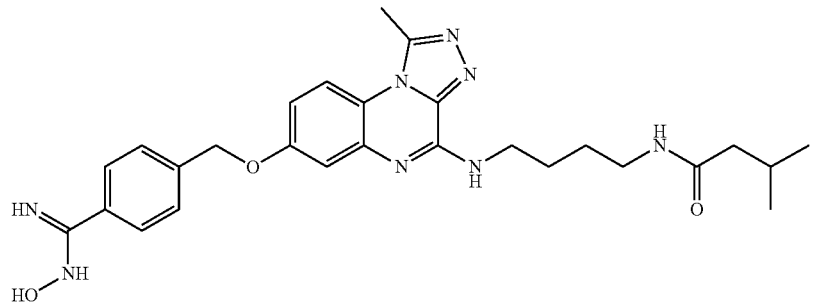 [SMILES: Cc1nnc2c(NCCCCNC(=O)CC(C)C)nc3cc(OCc4ccc(C(=N)NO)cc4)ccc3n12]

N-{4-[7-(4-Cyano-benzyloxy)-1-methyl-[1,2,4]triazolo[4,3-a]quinoxaline-4-ylamino]-butyl}-3-methyl-butyramide (0.04 g, 0.08 mmol) prepared in Example 341, potassium-tert-butoxide (0.03 mg, 3.5 eq) and hydroxylamine hydrochloride (0.03 mg, 4.5 eq) were dissolved in dimethylformamide, followed by stirring at room temperature for 2 days. Upon completion of the reaction, the reaction mixture was extracted with ethylacetate and water. The organic layer was dried over magnesium sulfate to eliminate moisture, followed by distillation and drying under reduced pressure.

As a result, 0.03 g of a target compound was obtained (47% yield).

Mass (M+H$^+$): 519.3

$^1$H NMR (500 MHz, DMSO-d6) δ0.79 (d, 6H), 1.44 (m, 2H), 1.63 (m, 2H), 1.87 (m, 3H), 2.95 (s, 3H), 3.04 (q, 2H), 3.50 (q, 2H), 5.20 (d, 2H), 5.86 (s, 1H), 6.93 (d, 1H), 7.15 (s, 1H), 7.43 (d, 2H), 7.66 (d, 2H), 7.67 (m, 1H), 7.95 (d, 1H), 8.10 (m, 1H), 9.63 (s, 1H).

The compounds shown in Table 23 below were prepared by using the compound prepared by the same manner as described in Example 341 as an intermediate.

TABLE 23

| Example | Structure | Name | Data |
|---|---|---|---|
| Example 348 | 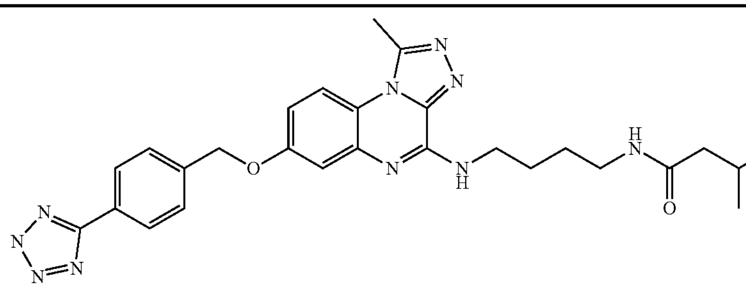 | 3-methyl-N-(4-{1-methyl-7-[4-(2H-tetrazol-5-yl)-benzyloxy]-[1,2,4]triazolo[4,3-a]quinoxaline-4-ylamino}-butyl)-butyramide | Mass (M + H$^+$): 529.3; $^1$H NMR (500 MHz, DMSO-d6): δ0.79 (d, 6H), 1.45 (s, 2H), 1.62 (m, 4H), 1.88 (s, 3H), 2.95 (s, 3H), 3.06 (m, 2H), 3.53 (s, 2H), 5.29 (s, 2H), 6.96 (d, 1H), 7.20 (m, 1H), 7.65 (d, 2H), 7.80 (s, 1H), 7.96 (d, 1H), 8.15 (d, 1H). |
| Example 349 | 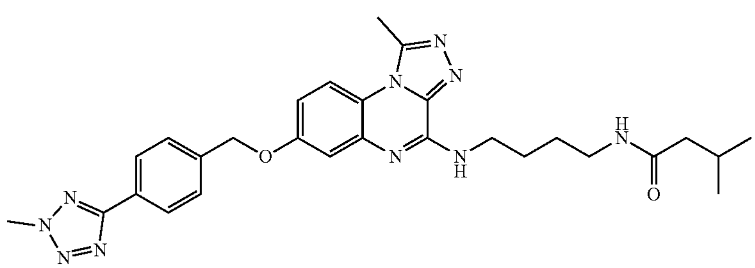 [SMILES: Cc1nnc2c(NCCCCNC(=O)CC(C)C)nc3cc(OCc4ccc(-c5nnn(C)n5)cc4)ccc3n12] | 3-methyl-N-(4-{1-methyl-7-[4-(2-methyl-2H-tetrazolo-5-yl)-benzyloxy]-[1,2,4]triazolo[4,3-a]quinoxaline-4-ylamino}-butyl)-butyramide | Mass (M + H$^+$): 543.3; $^1$H NMR (500 MHz, DMSO-d6): δ0.79 (d, 6H), 1.46 (s, 2H), 1.63 (m, 2H), 1.87 (m, 3H), 2.95 (s, 3H), 3.04 (m, 2H), 3.50 (m, 2H), 4.39 (s, 3H), 5.28 (s, 2H), 6.96 (d, 1H), 7.18 (d, 2H), 7.62 (m, 2H), 7.70 (m, 1H), 7.96 (d, 1H), 8.05 (d, 2H), 8.06 (s, 1H). |

<Example 350> Preparation of benzoic acid 1-methyl-4-[4-(3-methyl-butylamino)-butylamino]-[1,2,4]triazolo[4,3-a]quinoxaline-7-yl ester

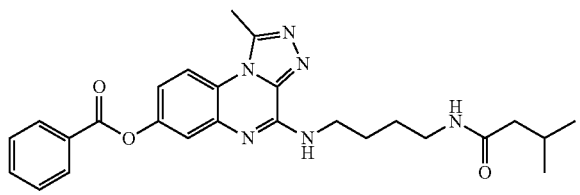 [SMILES: Cc1nnc2c(NCCCCNC(=O)CC(C)C)nc3cc(OC(=O)c4ccccc4)ccc3n12]

N-[4-(7-hydroxy-1-methyl-[1,2,4]triazolo[4,3-a]quinoxaline-4-ylamino)-butyl]-3-methyl-butyramide (0.2 g, 0.54 mmol) prepared in Example 340, triethylamine (0.37 ml, 10 eq) and benzoylchloride (0.14 g, 1.1 eq) were dissolved in dichloromethane, followed by stirring at room temperature for 2 days. The reaction was terminated by adding methanol, followed by distillation under reduced pressure. The reactant was purified by column chromatography. As a result, 0.12 g of a target compound was obtained (93% yield).

Mass (M+H$^+$): 475.2

$^1$H NMR (500 MHz, DMSO-d6): δ0.77 (t, 6H), 1.44 (m, 2H), 1.64 (m, 2H), 1.87 (m, 3H), 3.00 (s, 3H), 3.04 (q, 2H), 3.50 (q, 2H), 7.20 (d, 2H), 7.46 (s, 1H), 7.60 (m, 2H), 7.73 (m, 2H), 8.13 (m, 3H), 8.30 (s, 1H).

The compounds shown in Table 24 below were prepared by the same manner as described in Example 350.

TABLE 24

| Example | Structure | Name | Data |
|---|---|---|---|
| Example 351 | 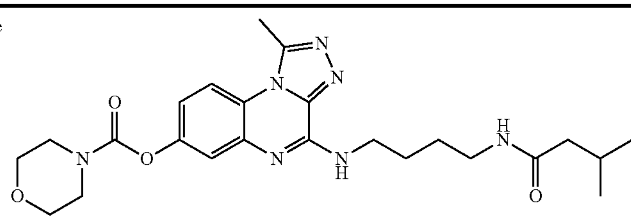 | morpholine-4-carboxylic acid-1-methyl-4-[4-(3-methyl-butylamino)-butylamino]-[1,2,4]triazolo[4,3-a]quinoxaline-7-yl-ester | Mass (M + H$^+$): 484.3; $^1$H NMR (500 MHz, DMSO-d6): δ0.79 (d, 6H), 1.44 (m, 2H), 1.62 (m, 2H), 1.87 (m, 3H), 2.98 (s, 3H), 3.04 (q, 2H), 3.40 (s, 2H), 3.49 (m, 2H), 3.60 (s, 2H), 3.63 (s, 4H), 7.03 (d, 1H), 7.30 (s, 1H), 7.69 (t, 1H), 8.02 (d, 1H), 8.21 (t, 1H). |
| Example 352 | 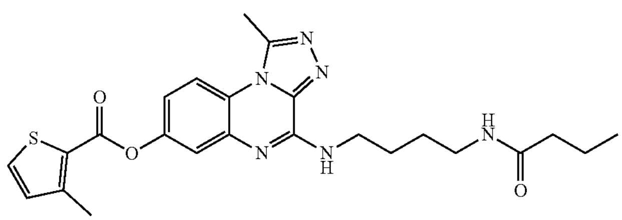 | 3-methyl-thiophene-2-carboxylic acid-1-methyl-4-[4-(3-methyl-butylamino)-butylamino]-[1,2,4]triazolo[4,3-a]quinoxaline-7-yl-ester | Mass (M + H$^+$): 495.2; $^1$H NMR (500 MHz, DMSO-d6): δ0.78 (d, 6H), 1.44 (m, 2H), 1.62 (m, 2H), 1.87 (m, 3H), 2.53 (m, 3H), 3.00 (s, 3H), 3.05 (s, 3H), 3.51 (q, 2H), 7.13 (q, 2H), 7.40 (m, 2H), 7.69 (s, 1H), 7.91 (s, 1H), 8.09 (d, 1H), 8.27 (d, 1H), (t, 1H). |
| Example 353 | 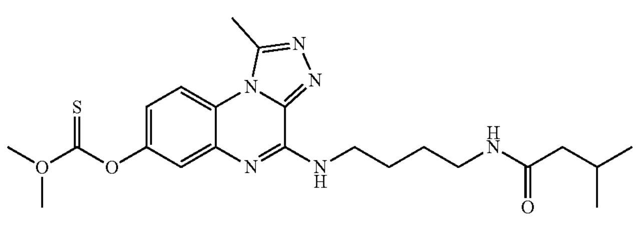 | dimethyl-thiocarbamic acid-O-{1-methyl-4-[4-(3-methyl-butylamino)-butylamino]-[1,2,4]triazolo[4,3-a]quinoxaline-7-yl}-ester | Mass (M + H$^+$): 458.2; $^1$H NMR (500 MHz, DMSO-d6): δ0.79 (d, 6H), 1.44 (m, 2H), 1.62 (m, 2H), 1.87 (m, 2H), 2.99 (m, 3H), 3.05 (s, 3H), 3.32 (m, 2H), 3.35 (s, 3H), 6.97 (s, 3H), 7.20 (d, 1H), 7.69 (s, 1H), 8.04 (s, 1H), 8.26 (d, 1H), (s, 1H). |

<Preparative Example 21> Preparation of [4-(3-hydrazino-7-methylsulfanyl-3,4-dihydro-quinoxaline-2-ylamino)-butyl]-carbamic acid-tert-butylester

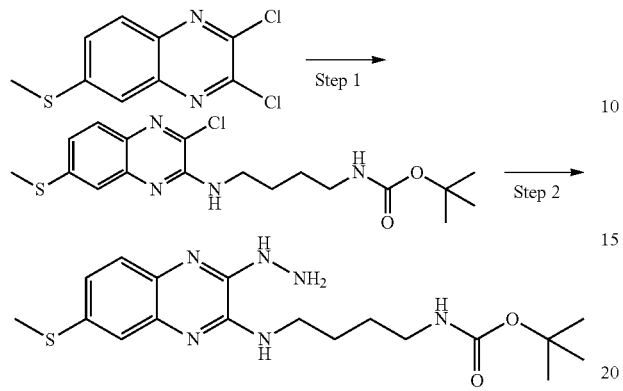

Step 1: Preparation of [4-(3-chloro-7-methylsulfanyl-quinoxaline-2-ylamino)-butyl]-carbamic acid-tert-butylester 1.3 g of a target compound was obtained (89% yield) by the same manner as described in Example 57, except that 2,3-dichloro-6-methylsulfanyl-quinoxaline (0.9 g, 3.67 mmol) was used.

Mass (M+H$^+$): 397.2

$^1$H NMR (500 MHz, DMSO-d6): δ1.32 (s, 9H), 1.42 (m, 2H), 1.57 (m, 2H), 2.54 (s, 3H), 2.92 (m, 2H), 3.42 (q, 2H), 6.73 (t, 1H), 7.18 (dd, 1H), 7.29 (d, 1H), 7.42 (t, 1H), 7.56 (d, 1H).

Step 2: Preparation of [4-(3-hydrazino-7-methylsulfanyl-quinoxaline-2-ylamino)-butyl]-carbamic acid-tert-butylester

[4-(3-Chloro-7-methylsulfanyl-quinoxaline-2-ylamino)-butyl]-carbamic acid-tert-butylester (1.3 g, 3.28 mmol) prepared in step 1 of Preparative Example 21 and hydrazine hydrate (4.77 ml, 98 mmol) were dissolved in 15 ml of dioxane, followed by reflux stirring for 5 hours. Upon completion of the reaction, the reaction mixture was extracted with ethylacetate and water. The extract was dried over magnesium sulfate to eliminate moisture, followed by filtering, distillation and drying under reduced pressure. As a result, 1.29 g of a target compound (100% yield) was obtained, which proceeded to the next reaction without purification.

Mass (M+H$^+$): 393.2

<Example 354> Preparation of [4-(1-methyl-7-methylsulfanyl-[1,2,4]triazolo[4,3-a]quinoxaline-4-ylamino)-butyl]-carbamic acid-tert-butylester

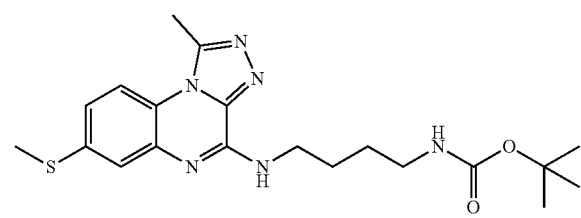

1.1 g of a target compound was obtained (80% yield) by the same manner as described in step 3 of Preparative Example 5, except that [4-(3-hydrazino-7-methylsulfanyl-quinoxaline-2-ylamino)-butyl]-carbamic acid-tert-butylester (1.29 g, 3.29 mmol) prepared in step 2 of Preparative Example 21 was used.

Mass (M+H$^+$): 417.2

$^1$H NMR (500 MHz, DMSO-d6) δ1.32 (s, 9H), 1.43 (m, 2H), 1.61 (m, 2H), 2.52 (s, 3H), 2.93 (q, 2H), 2.96 (s, 3H), 3.49 (q, 2H), 6.75 (t, 1H), 7.13 (d, 1H), 7.36 (s, 1H), 7.96 (d, 1H), 8.15 (t, 1H).

<Example 355> Preparation of N$^1$-(1-methyl-7-methylsulfanyl-[1,2,4]triazolo[4,3-a]quinoxaline-4-yl)-butane-1,4-diamine ditrifluoroacetic acid

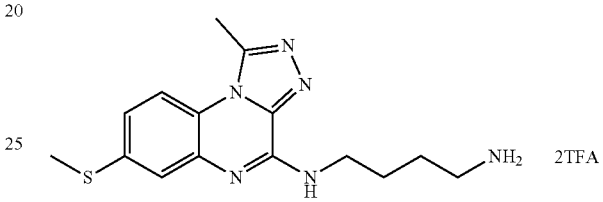

1.13 g of a target compound was obtained (86% yield) by the same manner as described in Example 58, except that [4-(1-methyl-7-methylsulfanyl-[1,2,4]triazolo[4,3-a]quinoxaline-4-ylamino)-butyl]-carbamic acid-tert-butylester (1 g, 2.4 mmol) prepared in Example 354 was used.

Mass (M+H$^+$): 317.2

$^1$H NMR (500 MHz, DMSO-d6) δ1.60 (m, 2H), 1.69 (m, 2H), 2.52 (s, 3H), 2.82 (q, 2H), 2.97 (s, 3H), 3.54 (q, 2H), 7.15 (d, 1H), 7.36 (s, 1H), 7.69 (br, 2H), 7.98 (d, 1H), 8.33 (t, 1H).

<Example 356> Preparation of 3-methyl-N-[4-(1-methyl-7-methylsulfanyl-[1,2,4]triazolo[4,3-a]quinoxaline-4-ylamino)-butyl]-butyramide

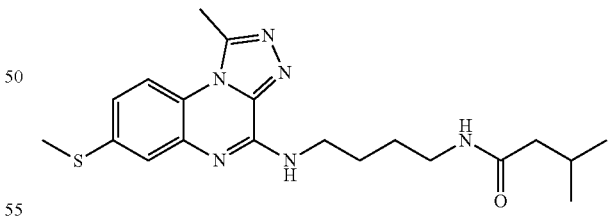

0.35 g of a target compound was obtained (95% yield) by the same manner as described in Example 37, except that N$^1$-(1-methyl-7-methylsulfanyl-[1,2,4]triazolo[4,3-a]quinoxaline-4-yl)-butane-1,4-diamine ditrifluoroacetic acid (0.5 g, 0.92 mmol) prepared in Example 355 was used.

Mass (M+H$^+$): 401.2

$^1$H NMR (500 MHz, DMSO-d6): δ0.79 (d, 6H), 1.45 (m, 2H), 1.62 (m, 2H), 1.87 (m, 2H), 1.90 (m, 1H), 2.46 (s, 3H), 2.96 (s, 3H), 3.03 (q, 2H), 3.50 (q, 2H), 7.14 (d, 1H), 7.35 (s, 1H), 7.70 (t, 1H), 7.96 (s, 1H), 8.16 (t, 1H).

<Example 357> Preparation of 2-(S)-fluoro-3-methyl-N-[4-(1-methyl-7-methylsulfanyl-[1,2,4]triazolo[4,3-a]quinoxaline-4-ylamino)-butyl]-butyramide

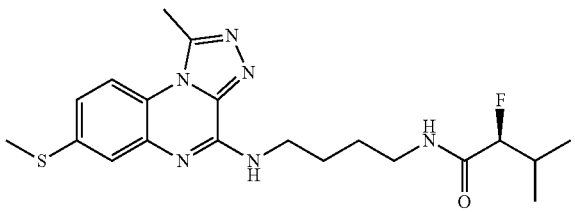

63 mg of a target compound was obtained (42% yield) by the same manner as described in Example 356.
Mass (M+H$^+$): 419.1
$^1$H NMR (500 MHz, DMSO-d6): δ0.79 (d, 3H), 0.89 (d, 3H), 1.49 (m, 2H), 1.62 (m, 2H), 2.10 (m, 1H), 2.52 (s, 3H), 2.96 (s, 3H), 3.16 (m, 2H), 3.50 (q, 2H), 4.61 (d, 1H), 7.13 (d, 1H), 7.35 (s, 1H), 7.96 (d, 1H), 8.07 (t, 1H), 8.18 (t, 1H).

<Example 358> Preparation of 2-(S)-hydroxy-3-methyl-N-[4-(1-methyl-7-methylsulfanyl-[1,2,4]triazolo[4,3-a]quinoxaline-4-ylamino)-butyl]-butyramide

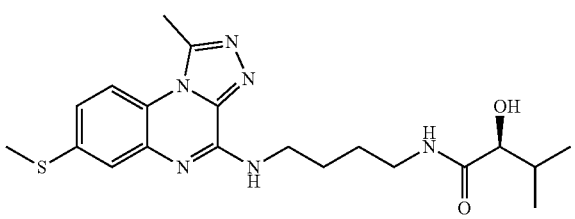 [SMILES: CSc1ccc2c(c1)nc(NCCCCNC(=O)[C@@H](O)C(C)C)c1nnc(C)n12]

70 mg of a target compound was obtained (68% yield) by the same manner as described in Example 39, except that N1-(1-methyl-(7-methylsulfanyl-[1,2,4]triazolo[4,3-a]quinoxaline-4-yl)-butane-1,4-diamine ditrifluoroacetic acid (0.14 g, 0.25 mmol) prepared in Example 355 was used.
Mass (M+H$^+$): 417.2

<Example 359> Preparation of N-[4-(7-methanesulfinyl-1-methyl-[1,2,4]triazolo[4,3-a]quinoxaline-4-ylamino)-butyl]-3-methyl-butyramide

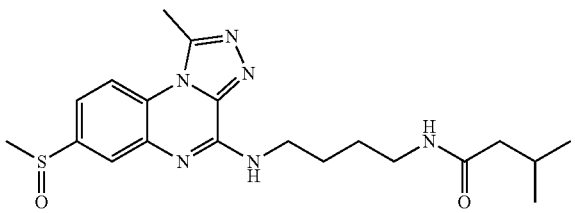 [SMILES: Cc1nnc2c(NCCCCNC(=O)CC(C)C)nc3cc(S(C)=O)ccc3n12]

3-Methyl-N-[4-(1-methyl-7-methylsulfanyl-[1,2,4]triazolo[4,3-a]quinoxaline-4-ylamino)-butyl]-butyramide (100 mg, 0.25 mmol) prepared in Example 356 was dissolved in a mixed solution comprising 5 ml of dichloromethane and 2 ml of methanol, to which m-CPBA (120 mg, 0.5 mmol) was slowly added, followed by reaction at room temperature for 18 hours. Upon completion of the reaction, the solvent was concentrated under reduced pressure, followed by column chromatography for separation and purification. As a result, 70 mg of a target compound (70% yield) was obtained.
Mass (M+H$^+$): 417.2
$^1$H NMR (500 MHz, DMSO-d6): δ0.78 (d, 6H), 1.44 (m, 2H), 1.63 (m, 2H), 1.87 (m, 2H), 1.90 (m, 1H), 2.77 (s, 3H), 3.00 (s, 3H), 3.03 (q, 2H), 3.51 (q, 2H), 7.53 (d, 1H), 7.72 (t, 1H), 7.80 (s, 1H), 8.23 (d, 1H), 8.36 (t, 1H)

<Example 360> Preparation of N-[4-(7-methanesulfonyl-1-methyl-[1,2,4]triazolo[4,3-a]quinoxaline-4-ylamino)-butyl]-3-methyl-butyramide

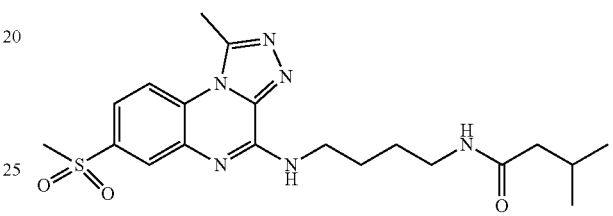

3-Methyl-N-[4-(1-methyl-7-methylsulfanyl-[1,2,4]triazolo[4,3-a]quinoxaline-4-ylamino)-butyl]-butyramide (100 mg, 0.25 mmol) prepared in Example 356 was dissolved in a mixture comprising 5 ml of dichloromethane and 2 ml of methanol, to which m-CPBA (240 mg, 1 mmol) was slowly added, followed by reaction at room temperature for 24 hours. Upon completion of the reaction, the solvent was concentrated under reduced pressure, followed by column chromatography for separation and purification. As a result, 67 mg of a target compound (61% yield) was obtained.
Mass (M+H$^+$): 433.2
$^1$H NMR (500 MHz, DMSO-d6): δ0.79 (d, 6H), 1.44 (m, 2H), 1.63 (m, 2H), 1.87 (m, 2H), 1.90 (m, 1H), 3.01 (s, 3H), 3.06 (q, 2H), 3.26 (s, 3H), 3.53 (q, 2H), 7.72 (m, 2H), 7.99 (s, 1H), 8.27 (d, 1H), 8.49 (t, 1H)

<Preparative Example 22> Preparation of [4-(7-fluoro-3-hydrazino-quinoxaline-2-ylamino)-butyl]-carbamic acid-tert-butylester

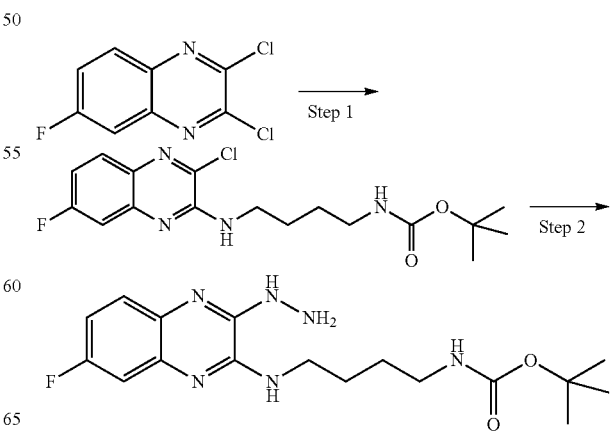

Step 1: Preparation of [4-(3-chloro-7-fluoro-quinoxaline-2-ylamino)-butyl]-carbamic acid-tert-butylester A target compound was obtained (64% yield) by the same manner as described in Example 57, except that 2,3-dichloro-6-fluoroquinoxaline (0.50 g, 2.30 mmol) was used. The following reaction was carried out without purification.
Mass (M+H⁺): 369.1
¹H NMR (300 MHz, CDCl₃): δ1.47 (s, 9H), 1.62-1.67 (m, 2H), 1.74-1.80 (m, 2H), 3.20-3.25 (m, 2H), 3.60-3.65 (m, 2H), 4.80 (brs, 1H), 5.73 (brs, 1H), 7.12-7.16 (m, 1H), 7.35-7.38 (m, 1H), 7.75-7.78 (m, 1H).

Step 2: Preparation of [4-(7-fluoro-3-hydrazino-quinoxaline-2-ylamino)-butyl]-carbamic acid-tert-butylester A target compound was obtained (2 steps, 46% yield) by the same manner as described in step 2 of Preparative Example 20, except that [4-(3-chloro-7-fluoro-quinoxaline-2-ylamino)-butyl]-carbamic acid-tert-butylester (2 g, 9.21 mmol) prepared in step 1 of Preparative Example 22 was used.
Mass (M+H⁺): 365.2

<Example 361> Preparation of [4-(7-fluoro-1-methyl-[1,2,4]triazolo[4,3-a]quinoxaline-4-ylamino)-butyl]-carbamic acid-tert-butylester

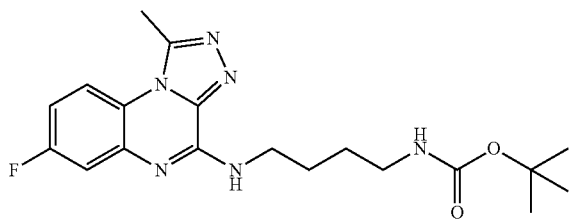 [SMILES: Cc1nnc2c(NCCCCNC(=O)OC(C)(C)C)nc3cc(F)ccc3n12]

A target compound was obtained (2 steps, 54% yield) by the same manner as described in step 3 of Preparative Example 5, except that [4-(7-fluoro-3-hydrazino-quinoxaline-2-ylamino)-butyl]-carbamic acid-tert-butylester prepared in step 2 of Preparative Example 22 was used.
Mass (M+H⁺): 388.4
¹H NMR (300 MHz, DMSO-d6): δ1.36 (s, 9H), 1.36-1.50 (m, 2H), 1.60-1.68 (m, 2H), 2.93-3.00 (m, 2H), 3.02 (s, 3H), 3.50-3.57 (m, 2H), 6.79 (t, J=5.07 Hz, 1H), 7.11-7.17 (m, 1H), 7.33-7.38 (m, 1H), 8.08-8.13 (m, 1H), 8.35 (t, J=5.67 Hz, 1H).

<Example 362> Preparation of 4-(7-chloro-1-methyl-[1,2,4]triazolo[4,3-a]quinoxaline-4-ylamino)-carbamic acid-tert-butylester

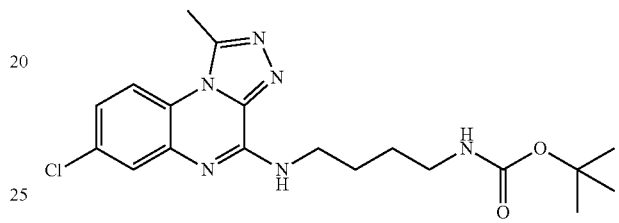

A target compound was obtained by the same manner as described in Example 361, except that 2,3,6-trichloro-quinoxaline was used instead of 2,3-dichloro-6-fluoroquinoxaline.
Mass (M+H⁺): 405.1
¹H NMR (300 MHz, DMSO-d6): δ1.36 (s, 9H), 1.41-1.51 (m, 2H), 1.60-1.68 (m, 2H), 2.93-2.97 (m, 2H), 3.00 (s, 3H), 3.51-3.57 (m, 2H), 6.79 (brs, 1H), 7.30 (dd, J=8.88 Hz, 1H), 7.59 (d, J=2.34 Hz, 1H), 8.08 (d, J=8.88 Hz, 1H), 8.37 (t, J=5.61 Hz, 1H).

<Preparative Example 23> Preparation of {4-[3-hydrazino-7-(2-methoxy-ethoxy)-quinoxaline-2-ylamino]-butyl}-carbamic acid-tert-butylester

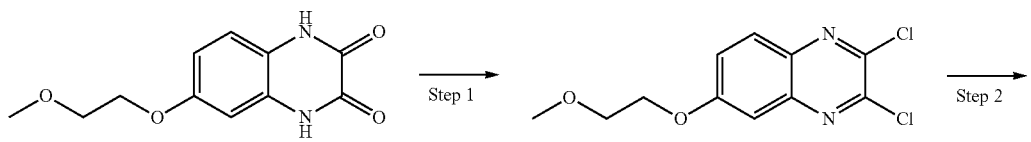

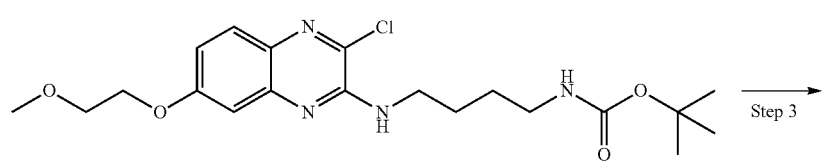

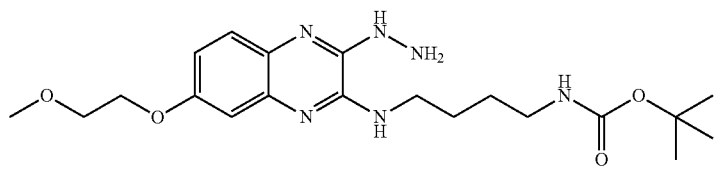

Step 1: Preparation of 2,3-dichloro-6-(2-methoxy-ethoxy)-quinoxaline 1.6 g of a target compound was obtained (73% yield) by the same manner as described in step 1 of Preparative Example 5, except that 6-(2-methoxy-ethoxy)-1,4-dihydro-quinoxaline-2,3-dione (1.9 g, 8.0 mmol) was used.

Mass (M+H$^+$): 273.0

$^1$H NMR (500 MHz, DMSO-d6): δ3.29 (s 3H), 3.70 (t, 2H), 4.28 (t, 2H), 7.47 (s, 1H), 7.56 (dd, 1H), 7.95 (d, 1H)

Step 2: Preparation of {4-[3-chloro-7-(2-methoxy-ethoxy)-quinoxaline-2-ylamino]-butyl}-carbamic acid-tert-butylester 632 mg of a target compound was obtained (81% yield) by the same manner as described in Example 57, except that 2,3-dichloro-6-(2-methoxy-ethoxy)-quinoxaline (500 mg, 1.83 mmol) prepared in step 1 of Preparative Example 23 was used.

Mass (M+H$^+$): 425.1

$^1$H NMR (500 MHz, DMSO-d6): δ1.32 (s, 9H), 1.40 (m, 2H), 1.57 (m, 2H), 2.91 (q, 2H), 3.28 (s, 3H), 3.41 (q, 2H), 3.66 (m, 2H), 4.18 (m, 2H), 6.74 (t, 1H), 6.96 (s, 1H), 6.99 (d, 2H), 7.33 (t, 1H), 7.57 (d, 1H).

Step 3: Preparation of {4-[3-hydrazino-7-(2-methoxy-ethoxy)-quinoxaline-2-ylamino]-butyl}-carbamic acid-tert-butylester 2.3 g of a target compound was obtained (72% yield) by the same manner as described in step 2 of Preparative Example 20, except that {4-[3-chloro-7-(2-methoxy-ethoxy)-quinoxaline-2-ylamino]-butyl}-carbamic acid-tert-butylester (3.3 g, 7.8 mmol) prepared in step 2 of Preparative Example 23 and hydrazine hydrate (7.5 ml, 155 mmol) were used.

Mass (M+H$^+$): 421.2

<Example 363> Preparation of {4-[7-(2-methoxy-ethoxy)-1-methyl-[1,2,4]triazolo[4,3-a]quinoxaline-4-ylamino]-butyl}-carbamic acid-tert-butylester

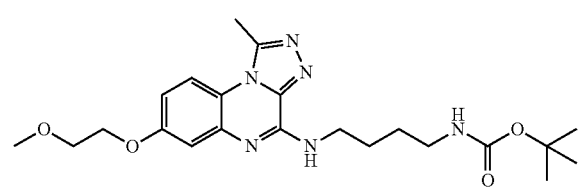 [SMILES: COCCOc1ccc2c(c1)nc(NCCCCNC(=O)OC(C)(C)C)c1nnc(C)n12]

1.05 g of a target compound was obtained (47% yield) by the same manner as described in step 3 of Preparative Example 5, except that {4-[3-hydrazino-7-(2-methoxy-ethoxy)-quinoxaline-2-ylamino]-butyl}-carbamic acid-tert-butylester (2.1 g, 5.0 mmol) prepared in step 3 of Preparative Example 23 was used.

Mass (M+H$^+$): 445.2

$^1$H NMR (500 MHz, DMSO-d6) δ1.32 (s, 9H), 1.43 (m, 2H), 1.60 (m, 2H), 2.92 (q, 2H), 2.94 (s, 3H), 3.29 (s, 3H), 3.50 (m, 2H), 3.65 (t, 2H), 4.15 (t, 2H), 6.76 (t, 1H), 6.84 (dd, 1H), 7.06 (d, 1H), 7.94 (d, 1H), 8.08 (brm, 1H).

<Example 364> Preparation of N$^1$-[7-(2-methoxy-ethoxy)-1-methyl-[1,2,4]triazolo[4,3-a]quinoxaline-4-yl]-butane-1,4-diamine ditrifluoroacetic acid

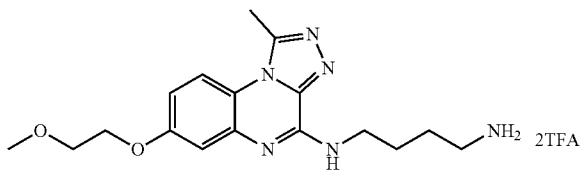 [SMILES: COCCOc1ccc2c(c1)nc(NCCCCN)c1nnc(C)n12]

1 g of a target compound was obtained (86% yield) by the same manner as described in Example 58, except that {4-[7-(2-methoxy-ethoxy)-1-methyl-[1,2,4]triazolo[4,3-a]quinoxaline-4-ylamino]-butyl}-carbamic acid-tert-butylester (0.9 g, 2.02 mmol) prepared in Example 363 was used.

Mass (M+H$^+$): 345.2

$^1$H NMR (500 MHz, DMSO-d6) δ1.59 (m, 2H), 1.68 (m, 2H), 2.83 (m, 2H), 2.96 (s, 3H), 3.29 (s, 3H), 3.53 (m, 2H), 3.66 (t, 2H), 4.15 (t, 2H), 6.89 (dd, 1H), 7.06 (s, 1H), 7.62 (brs, 2H), 7.97 (d, 1H), 8.18 (t, 1H).

<Example 365> Preparation of N-{4-[7-(2-methoxy-ethoxy)-1-methyl-[1,2,4]triazolo[4,3-a]quinoxaline-4-ylamino]-butyl}-3-methyl-butyramide

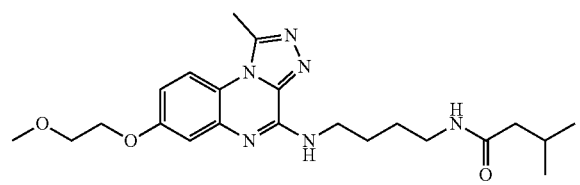 [SMILES: COCCOc1ccc2c(c1)nc(NCCCCNC(=O)CC(C)C)c1nnc(C)n12]

60 mg of a target compound was obtained (67% yield) by the same manner as described in Example 37, except that N$^1$-[7-(2-methoxy-ethoxy)-1-methyl-[1,2,4]triazolo[4,3-a]quinoxaline-4-yl]-butane-1,4-diamine ditrifluoroacetic acid (120 mg, 0.21 mmol) prepared in Example 364 and isovalerylchloride (0.03 ml, 0.23 mmol) were used.

Mass (M+H$^+$): 429.2

$^1$H NMR (500 MHz, DMSO-d6): δ0.79 (d, 6H), 1.45 (m, 2H), 1.62 (m, 2H), 1.86 (d, 2H), 1.88 (m, 1H), 2.95 (s, 3H), 3.04 (q, 2H), 3.27 (s, 3H), 3.50 (q, 2H), 3.65 (t, 1H), 4.15 (t, 2H), 6.86 (dd, 1H), 7.05 (s, 1H), 7.69 (t, 1H), 7.95 (d, 1H), 8.09 (t, 1H).

The compounds shown in Table 25 below were prepared by the same manner as described in Example 365.

TABLE 25

| Example | Structure | Name | Data |
|---|---|---|---|
| Example 366 | 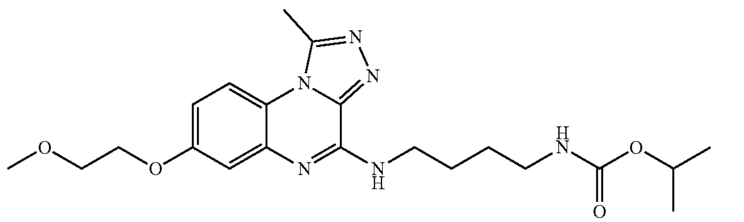 [SMILES: COCCOc1ccc2c(c1)nc(NCCCCNC(=O)OC(C)C)c1nnc(C)n12] | {4-[7-(2-methoxy-ethoxy)-1-methyl-[1,2,4]triazolo[4,3-a]quinoxaline-4-ylamino]-butyl}-carbamic acid isopropylester | Mass (M + H$^+$): 431.2; $^1$H NMR (500 MHz, DMSO-d6): δ1.10 (d, 6H), 1.45 (m, 2H), 1.60 (m, 2H), 2.95 (s, 3H), 2.99 (m, 2H), 3.27 (s, 3H), 3.50 (m, 2H), 3.64 (t, 2H), 4.15 (t, 2H), 4.18 (m, 1H), 6.86 (d, 1H), 6.94 (t, 1H), 7.06 (s, 1H), 7.95 (d, 1H), 8.08 (t, 1H), 7.06 (s, 1H), 7.95 (d, 1H), 8.08 (t, 1H). |
| Example 367 | 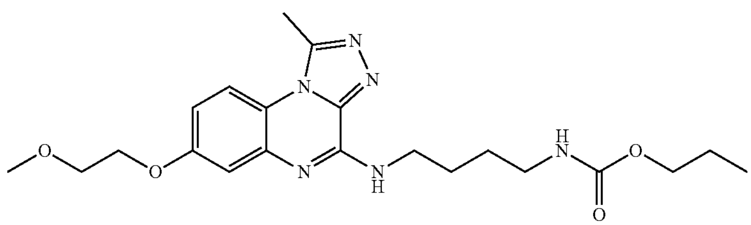 [SMILES: CCCOC(=O)NCCCCNc1nc2cc(OCCOC)ccc2n2c(C)nnc12] | {4-[7-(2-methoxy-ethoxy)-1-methyl-[1,2,4]triazolo[4,3-a]quinoxaline-4-ylamino]-butyl}-carbamic acid propylester | Mass (M + H$^+$): 431.2; $^1$H NMR (500 MHz, DMSO-d6): δ0.83 (t, 3H), 1.50 (m, 4H), 1.66 (m, 2H), 2.95 (s, 3H), 3.02 (q, 2H), 3.31 (s, 3H), 3.53 (q, 2H), 3.67 (t, 2H), 3.85 (t, 2H), 4.17 (t, 2H), 6.79 (brm, 1H), 6.87 (d, 1H), 7.09 (s, 1H), 7.82 (m, 1H), 7.95 (d, 1H). |
| Example 368 | 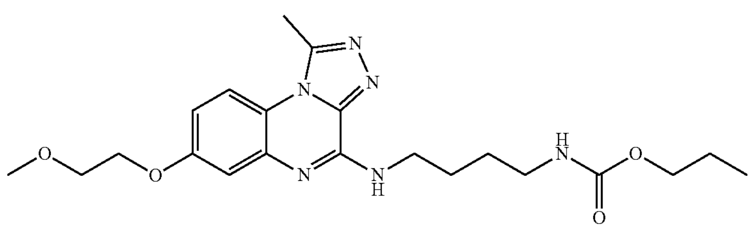 | {4-[7-(2-methoxy-ethoxy)-1-methyl-[1,2,4]triazolo[4,3-a]quinoxaline-4-ylamino]-butyl}-carbamic acid-sec-butylester | Mass (M + H$^+$): 445.2; $^1$H NMR (500 MHz, DMSO-d6): δ.78 (t, 3H), 1.07 (d, 3H), 1.42 (m, 2H), 1.45 (m, 2H), 1.63 (m, 2H), 2.95 (s, 3H), 2.97 (m, 2H), 3.29 (s, 3H), 3.45 (q, 2H), 3.66 (t, 2H), 4.15 (t, 2H), 4.53 (m, 1H), 6.89 (dd, 1H), 6.91 (t, 1H), 6.99 (t, 1H), 7.19 (s, 1H), 7.96 (d, 1H). |
| Example 369 | 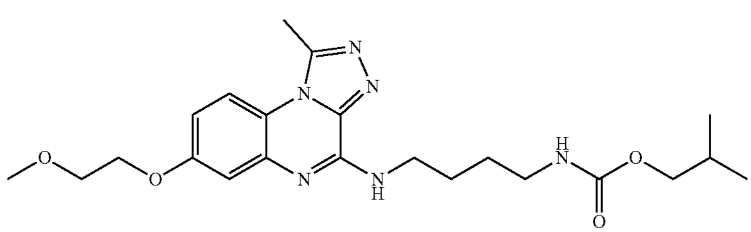 [SMILES: COCCOc1ccc2c(c1)nc(NCCCCNC(=O)OCC(C)C)c1nnc(C)n12] | {4-[7-(2-methoxy-ethoxy)-1-methyl-[1,2,4]triazolo[4,3-a]quinoxaline-4-ylamino]-butyl}-carbamic acid isobutylester | Mass (M + H$^+$): 445.2; $^1$H NMR (500 MHz, DMSO-d6): δ0.81 (d, 1H), 1.45 (m, 2H), 1.62 (m, 2H), 1.76 (m, 1H), 2.95 (s, 3H), 2.99 (q, 2H), 3.28 (s, 3H), 3.59 (q, 2H), 3.66 (m, 4H), 4.15 (t, 2H), 6.86 (dd, 1H), 7.03 (t, 1H), 7.07 (s, 1H), 7.95 (d, 1H), 8.09 (t, 1H). |

TABLE 25-continued

| Example | Structure | Name | Data |
|---|---|---|---|
| Example 370 | 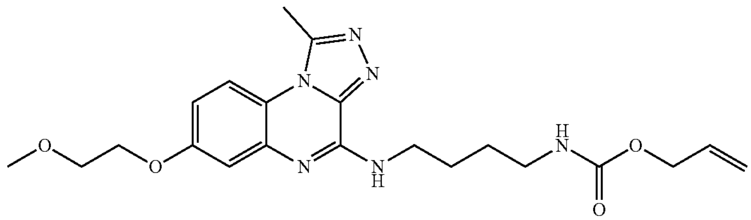 [SMILES: C=CCOC(=O)NCCCCNc1nc2cc(OCCOC)ccc2n2c(C)nnc12] | {4-[7-(2-methoxyethoxy)-1-methyl-[1,2,4]triazolo[4,3-a]quinoxaline-4-ylamino]-butyl}-carbamic acid allylester | Mass (M + H$^+$): 429.2; $^1$H NMR (500 MHz, DMSO-d6): δ1.46 (m, 2H), 1.62 (m, 2H), 2.95 (s, 3H), 3.00 (q, 2H), 3.29 (s, 3H), 3.50 (q, 2H), 3.66 (t, 2H), 4.15 (t, 2H), 4.41 (d, 2H), 5.10 (d, 1H), 5.23 (d, 1H), 5.84 (m, 1H), 6.87 (d, 1H), 7.06 (s, 1H), 7.16 (t, 1H), 7.95 (d, 1H), 8.11 (t, 1H). |
| Example 371 | 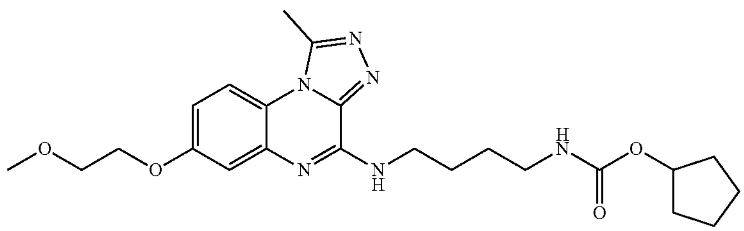 [SMILES: COCCOc1ccc2c(c1)nc(NCCCCNC(=O)OC1CCCC1)c1nnc(C)n12] | {4-[7-(2-methoxyethoxy)-1-methyl-[1,2,4]triazolo[4,3-a]quinoxaline-4-ylamino]-butyl}-carbamic acid cyclopentylester | Mass (M + H$^+$): 457.2; $^1$H NMR (500 MHz, DMSO-d6): δ1.43 (m, 2H), 1.45 (m, 2H), 1.48 (m, 2H), 1.60 (m, 2H), 2.95 (s, 3H), 2.97 (m, 2H), 3.28 (s, 3H), 3.38 (m, 4H), 3.50 (m, 2H), 3.66 (t, 2H), 4.15 (t, 2H), 4.88 (m, 1H), 6.86 (dd, 1H), 6.97 (t, 1H), 7.07 (d, 1H), 7.94 (d, 1H), 8.14 (t, 1H). |
| Example 372 | 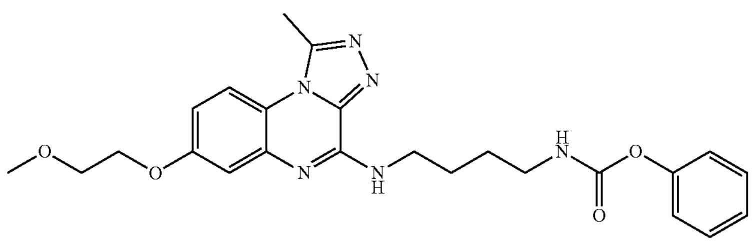 [SMILES: COCCOc1ccc2c(c1)nc(NCCCCNC(=O)Oc1ccccc1)c1nnc(C)n12] | {4-[7-(2-methoxyethoxy)-1-methyl-[1,2,4]triazolo[4,3-a]quinoxaline-4-ylamino]-butyl}-carbamic acid phenylester | Mass (M + H$^+$): 467.2; $^1$H NMR (500 MHz, DMSO-d6): δ1.54 (m, 2H), 1.68 (m, 2H), 2.95 (s, 3H), 3.09 (m, 2H), 3.29 (s, 3H), 3.53 (m, 2H), 3.64 (t, 2H), 4.14 (t, 1H), 6.86 (dd, 1H), 7.03 (m, 2H), 7.07 (d, 1H), 7.15 (t, 1H), 7.32 (m, 2H), 7.72 (t, 1H), 7.93 (d, 1H), 8.12 (t, 1H). |
| Example 373 | 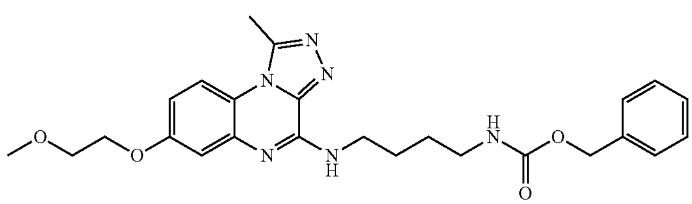 [SMILES: COCCOc1ccc2c(c1)nc(NCCCCNC(=O)OCc1ccccc1)c1nnc(C)n12] | {4-[7-(2-methoxyethoxy)-1-methyl-[1,2,4]triazolo[4,3-a]quinoxaline-4-ylamino]-butyl}-carbamic acid benzylester | Mass (M + H$^+$): 479.2; $^1$H NMR (500 MHz, DMSO-d6): δ1.47 (m, 2H), 1.62 (m, 2H), 2.95 (s, 3H), 3.02 (q, 2H), 3.28, (s, 3H), 3.50 (q, 2H), 3.65 (t, 2H), 4.14 (t, 2H), 4.95 (s, 2H), 6.87 (d, 1H), 7.07 (s, 1H), 7.25 (t, 1H), 7.30 (m, 5H), 7.96 (d, 1H), 8.11 (t, 1H). |

TABLE 25-continued

| Example | Structure | Name | Data |
| --- | --- | --- | --- |
| Example 374 | 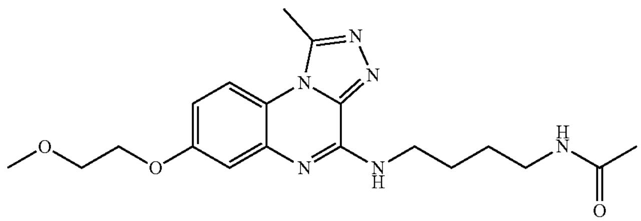 [SMILES: COCCOc1ccc2c(c1)nc(NCCCCNC(C)=O)c1nnc(C)n12] | {4-[7-(2-methoxy-ethoxy)-1-methyl-[1,2,4]tri-azolo[4,3-a]quinoxaline-4-ylamino]-butyl}-acetamide | Mass (M + H$^+$): 387.2; $^1$H NMR (500 MHz, DMSO-d6): δ1.43 (m, 2H), 1.62 (m, 2H), 1.74 (s, 3H), 2.94 (s, 3H), 3.02 (m, 2H), 3.28 (s, 3H), 3.50 (q, 2H), 3.65 (brm, 2H), 4.15 (brm, 2H), 6.86 (d, 1H), 7.06 (s, 1H), 7.76 (brm, 1H), 7.94 (d, 1H), 8.09 (t, 1H). |
| Example 375 | 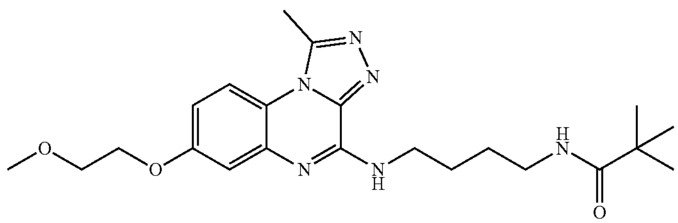 [SMILES: COCCOc1ccc2c(c1)nc(NCCCCNC(=O)C(C)(C)C)c1nnc(C)n12] | {4-[7-(2-methoxy-ethoxy)-1-methyl-[1,2,4]tri-azolo[4,3-a]quinoxaline-4-ylamino]-butyl}-2,2-dimethyl-propionamide | Mass (M + H$^+$): 429.2; $^1$H NMR (500 MHz, DMSO-d6): δ1.03 (s, 9H), 1.46 (q, 2H), 1.60 (q, 2H), 2.95 (s, 3H), 3.05 (m, 2H), 3.29 (s, 3H), 3.49 (q, 2H), 3.65 (t, 2H), 4.15 (t, 2H), 6.86 (d, 1H), 7.06 (s, 1H), 7.38 (t, 1H), 7.95 (d, 1H), 8.10 (t, 1H). |
| Example 376 | 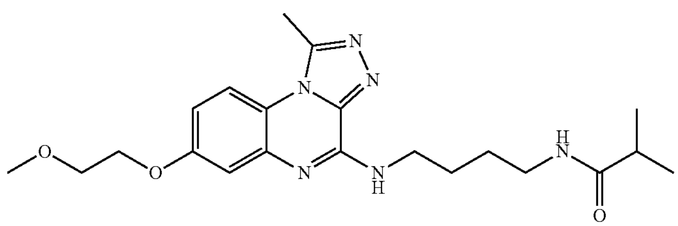 [SMILES: COCCOc1ccc2c(c1)nc(NCCCCNC(=O)C(C)C)c1nnc(C)n12] | {4-[7-(2-methoxy-ethoxy)-1-methyl-[1,2,4]tri-azolo[4,3-a]quinoxaline-4-ylamino]-butyl}-isobutyramide | Mass (M + H$^+$): 415.2; $^1$H NMR (500 MHz, DMSO-d6): δ0.92 (d, 6H), 1.43 (m, 2H), 1.62 (m, 2H), 2.27 (m, 1H), 2.95 (s, 3H), 3.02 (q, 2H), 3.29 (s, 3H), 3.50 (q, 2H), 3.66 (t, 2H), 4.15 (t, 2H), 6.84 (d, 1H), 7.06 (s, 1H), 7.66 (t, 1H), 7.94 (d, 1H), 8.10 (t, 1H). |
| Example 377 | 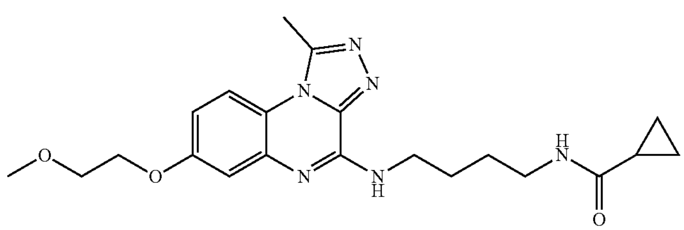 [SMILES: COCCOc1ccc2c(c1)nc(NCCCCNC(=O)C1CC1)c1nnc(C)n12] | cyclopropane carboxylic acid-{4-[7-(2-methoxy-ethoxy)-1-methyl-[1,2,4]tri-azolo[4,3-a]quinoxaline-4-ylamino]-butyl}-amide | Mass (M + H$^+$): 413.2; $^1$H NMR (500 MHz, DMSO-d6): δ0.55 (m, 6H), 0.59 (m, 2H), 1.45 (m, 2H), 1.63 (m, 2H), 2.95 (s, 3H), 3.05 (m, 1H), 3.06 (q, 2H), 3.29 (s, 3H), 3.50 (q, 2H), 3.65 (q, 2H), 4.15 (q, 2H), 6.86 (d, 1H), 7.06 (d, 1H), 7.94 (s, 1H), 7.98 (t, 1H), 8.11 (t, 1H). |
| Example 378 | 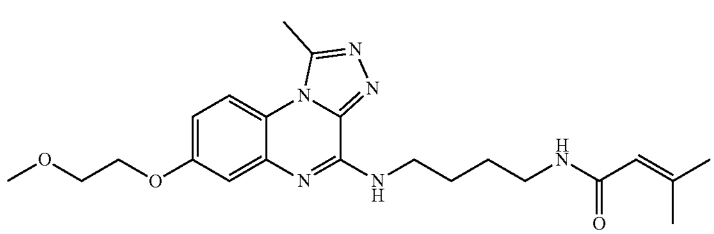 [SMILES: COCCOc1ccc2c(c1)nc(NCCCCNC(=O)C=C(C)C)c1nnc(C)n12] | 3-methyl-butene-2-oic acid-{4-[7-(2-methoxy-ethoxy)-1-methyl-[1,2,4]tri-azolo[4,3-a]quinoxaline-4-ylamino]-butyl}-amide | Mass (M + H$^+$): 427.2; $^1$H NMR (500 MHz, DMSO-d6): δ1.46 (m, 2H), 1.63 (m, 3H), 1.71 (s, 3H), 2.01 (s, 3H), 2.95 (s, 3H), 3.06 (q, 2H), 3.29 (s, 3H), 3.50 (q, 2H), 3.66 (t, 2H), 4.15 (t, |

TABLE 25-continued

| Example | Structure | Name | Data |
|---|---|---|---|
| | | | 2H), 5.57 (s, 1H), 6.87 (d, 1H), 7.06 (s, 1H), 7.66 (t, 1H), 7.96 (d, 1H), 8.10 (t, 1H). |
| Example 379 | 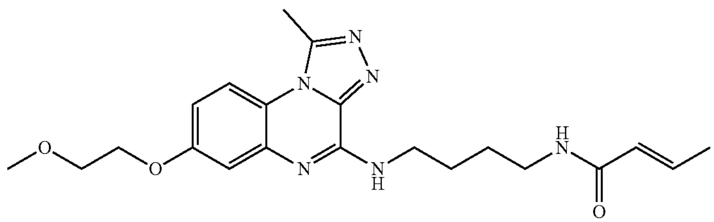 [SMILES: C/C=C/C(=O)NCCCCNc1nc2cc(OCCOC)ccc2n2c(C)nnc12] | butene-2-oic acid{4-[7-(2-methoxy-ethoxy)-1-methyl-[1,2,4]tri-azolo[4,3-a]quinoxaline-4-ylamino]-butyl}-amide | Mass (M + H⁺): 413.2; ¹H NMR (500 MHz, DMSO-d6): δ1.50 (m, 2H), 1.66 (m, 2H), 1.74 (d, 2H), 2.95 (s, 3H), 3.10 (q, 2H), 3.13 (s, 3H), 3.45 (q, 2H), 3.67 (t, 2H), 4.17 (t, 2H), 5.86 (d, 1H), 6.55 (m, 1H), 6.88 (d, 1H), 7.08 (s, 1H), 7.63 (t, 1H), 7.85 (t, 1H), 7.96 (d, 1H). |
| Example 380 | 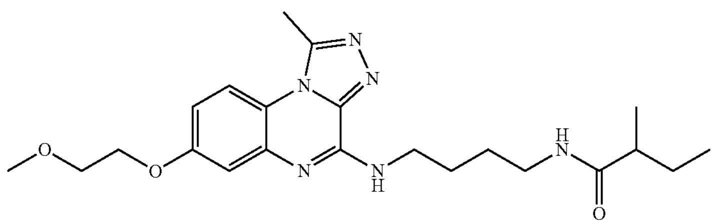 [SMILES: CCC(C)C(=O)NCCCCNc1nc2cc(OCCOC)ccc2n2c(C)nnc12] | N-{4-[7-(2-methoxy-ethoxy)-1-methyl-[1,2,4]tri-azolo[4,3-a]quinoxaline-4-ylamino]-butyl}-2-methyl-butyramide | Mass (M + H⁺): 429.2; ¹H NMR (500 MHz, DMSO-d6): δ0.73 (t, 3H), 1.91 (d, 3H), 1.20 (m, 1H), 1.46 (m, 3H), 1.62, (m, 2H), 2.05 (m, 1H), 2.94 (s, 3H), 3.07 (m, 2H), 3.49, (q, 2H), 3.66 (t, 2H), 4.15 (t, 2H), 6.87 (d, 2H), 7.05 (s, 1H), 7.67 (t, 1H), 7.95 (d, 1H), 8.10 (t, 1H). |
| Example 381 | 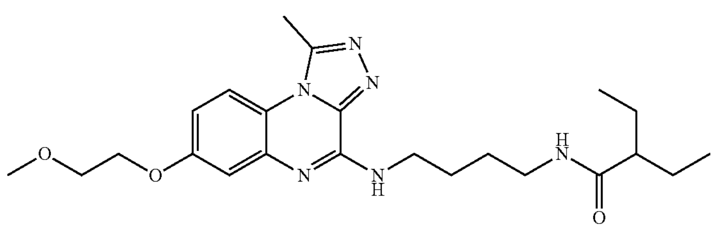 [SMILES: CCC(CC)C(=O)NCCCCNc1nc2cc(OCCOC)ccc2n2c(C)nnc12] | 2-ethyl-N-{4-[7-(2-methoxy-ethoxy)-1-methyl-[1,2,4]tri-azolo[4,3-a]quinoxaline-4-ylamino]-butyl}-butyramide | Mass (M + H⁺): 443.3; ¹H NMR (500 MHz, DMSO-d6): δ0.71 (m, 6H), 1.26 (m, 2H), 1.36 (m, 2H), 1.45 (m, 2H), 1.63 (m, 2H), 1.85 (m, 1H), 2.94 (s, 3H), 3.07 (q, 2H), 3.97 (s, 3H), 3.50 (q, 2H), 3.65 (t, 2H), 4.14 (t, 2H), 6.87 (d, 1H), 7.05 (s, 1H), 7.73 (t, 1H), 7.93 (d, 1H), 8.10 (t, 1H). |
| Example 382 | 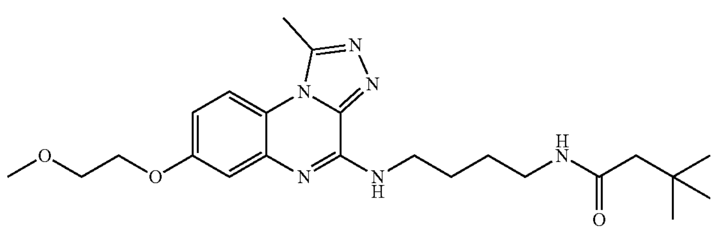 [SMILES: COCCOc1ccc2c(c1)nc(NCCCCNC(=O)CC(C)(C)C)c1nnc(C)n12] | N-{4-[7-(2-methoxy-ethoxy)-1-methyl-[1,2,4]tri-azolo[4,3-a]quinoxaline-4-ylamino]-butyl}-3,3-dimethyl-butyramide | Mass (M + H⁺): 443.2; ¹H NMR (500 MHz, DMSO-d6): δ0.88 (s, 9H), 1.44 (m, 2H), 1.62 (m, 2H), 1.88 (s, 2H), 2.95, (s, 3H), 3.04 (m, 2H), 3.28 (s, 3H), 3.52 (q, 2H), 3.66, (t, 2H), 4.15 (t, 2H), 6.86 (dd, 1H), 7.06 (s, 1H), 7.64 (t, 1H), 7.94 (d, 1H), 8.09 (t, 1H). |

TABLE 25-continued

| Example | Structure | Name | Data |
|---|---|---|---|
| Example 383 | 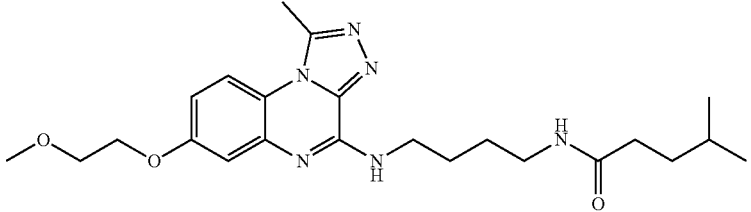 [SMILES: COCCOc1ccc2c(c1)nc(NCCCCNC(=O)CCC(C)C)c1nnc(C)n12] | 4-methyl-pentanoic acid{4-[7-(2-methoxy-ethoxy)-1-methyl-[1,2,4]tri-azolo[4,3-a]quinoxaline-4-ylamino]-butyl}-amide | Mass (M + H⁺): 443.2; ¹H NMR (500 MHz, DMSO-d6): δ0.78 (d, 6H), 1.31 (m, 2H), 1.42 (m, 3H), 1.65 (m, 2H), 1.99 (m, 2H), 2.95 (s, 3H), 3.04 (q, 2H), 3.27 (s, 3H), 3.50 (q, 2H), 3.65 (t, 2H), 4.15 (t, 2H), 6.87 (d, 1H), 7.06 (s, 1H), 7.71 (t, 1H), 7.96 (d, 1H), 8.09 (t, 1H). |
| Example 384 | 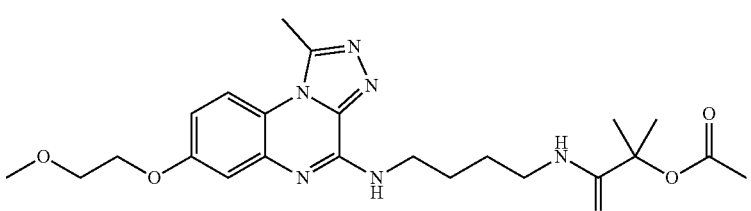 | acetic acid-1-{4-[7-(2-methoxy-ethoxy)-1-methyl-[1,2,4]tri-azolo[4,3-a]quinoxaline-4-ylamino]-butylcarbamo-yl}-1-methyl-ethylester | Mass (M + H⁺): 473.2; ¹H NMR (500 MHz, DMSO-d6): δ1.39 (s, 6H), 1.44 (m, 2H), 1.60 (m, 2H), 1.94 (s, 3H), 2.94 (s, 3H), 3.05 (q, 2H), 3.29 (s, 3H), 3.48 (q, 2H), 3.65 (t, 2H), 4.14 (t, 2H), 6.85 (dd, 1H), 7.05 (s, 1H), 7.66 (t, 1H), 7.94 (d, 1H), 8.06 (t, 1H). |
| Example 385 | 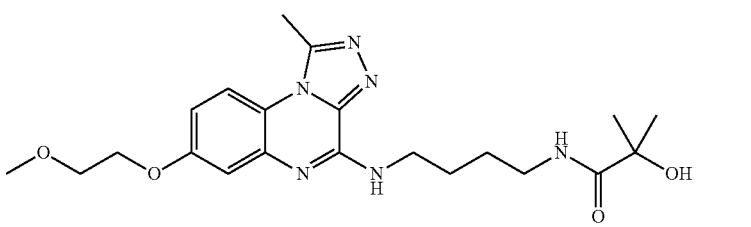 [SMILES: COCCOc1ccc2c(c1)nc(NCCCCNC(=O)C(C)(C)O)c1nnc(C)n12] | 2-hydroxy-N-{4-(7-(2-methoxy-ethoxy)-1-methyl-[1,2,4]tri-azolo[4,3-a]quinoxaline-4-ylamino)-butyl}-2-methyl-propionamide | Mass (M + H⁺): 431.2; ¹H NMR (500 MHz, DMSO-d6): δ1.18 (s, 6H), 1.47 (m, 2H), 1.61 (m, 2H), 2.94 (s, 3H), 3.07 (q, 2H), 3.29 (s, 3H), 3.50 (q, 2H), 3.65 (t, 2H), 4.15 (t, 2H), 5.24 (s, 1H), 6.85 (dd, 1H), 7.05 (s, 1H), 7.60 (t, 1H), 7.94 (dd, 1H), 8.09 (t, 1H). |
| Example 386 | 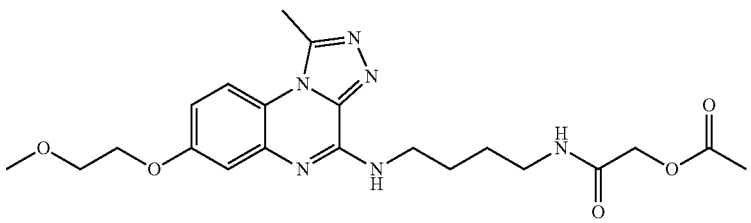 [SMILES: COCCOc1ccc2c(c1)nc(NCCCCNC(=O)COC(C)=O)c1nnc(C)n12] | acetic acid-{4-[7-(2-methoxy-ethoxy)-1-methyl-[1,2,4]tri-azolo[4,3-a]quinoxaline-4-ylamino]-butylcarbamo-yl}-methylester | Mass (M + H⁺): 445.2; ¹H NMR (500 MHz, DMSO-d6): δ1.45 (m, 2H), 1.62 (m, 2H), 2.03 (s, 3H), 2.95 (s, 3H), 3.10 (m, 2H), 3.29 (s, 3H), 3.51 (m, 2H), 3.65 (m, 2H), 4.15 (m, 2H), 4.37 (s, 2H), 6.87 (d, 1H), 7.07 (s, 1H), 7.94 (s, 1H), 7.96 (d, 1H), 8.10 (t, 1H). |

TABLE 25-continued

| Example | Name | Data |
|---|---|---|
| Example 387 | 2-hydroxy-N-{4-[7-(2-methoxy-ethoxy)-1-methyl-[1,2,4]triazolo[4,3-a]quinoxaline-4-ylamino]-butyl}-acetamide | Mass (M + H⁺): 403.2; ¹H NMR (500 MHz, DMSO-d6): δ1.49 (m, 2H), 1.62 (m, 2H), 2.94 (s, 3H), 3.12 (m, 2H), 3.29 (s, 3H), 3.51 (m, 2H), 3.65 (m, 2H), 3.73 (m, 2H), 4.15 (d, 2H), 5.39 (t, 1H), 6.85 (d, 1H), 7.06 (s, 1H), 7.69 (t, 1H), 7.93 (d, 1H), 8.08 (t, 1H). |
| Example 388 | 2-(R)-hydroxy-N-{4-[7-(2-methoxy-ethoxy)-1-methyl-[1,2,4]triazolo[4,3-a]quinoxaline-4-ylamino]-butyl}-3-methyl-butyramide | Mass (M + H⁺): 445.2; ¹H NMR (500 MHz, DMSO-d6): δ0.68 (d, 3H), 0.83 (d, 3H), 1.47 (m, 2H), 1.62 (m, 2H), 1.91 (m, 1H), 2.95 (s, 3H), 3.10 (m, 2H), 3.29 (s, 3H), 3.51 (m, 2H), 3.61 (m, 1H), 3.66 (m, 2H), 4.15 (m, 2H), 5.24 (d, 1H), 6.86 (d, 1H), 7.06 (s, 1H), 7.66 (t, 1H), 7.94 (s, 1H), 8.09 (t, 1H). |
| Example 389 | 2-(S)-hydroxy-N-{4-[7-(2-methoxy-ethoxy)-1-methyl-[1,2,4]triazolo[4,3-a]quinoxaline-4-ylamino]-butyl}-3-methyl-butyramide | Mass (M + H⁺): 445.2; ¹H NMR (500 MHz, DMSO-d6): δ0.69 (d, 3H), 0.83 (d, 3H), 1.48 (m, 2H), 1.61 (m, 2H), 1.91 (m, 1H), 2.94 (s, 3H), 3.13 (q, 2H), 3.50 (q, 2H), 3.60 (d, 1H), 3.66 (t, 2H), 4.15 (t, 2H), 5.23 (d, 1H), 6.86 (d, 1H), 7.06 (s, 1H), 7.65 (t, 1H), 7.93 (d, 1H), 8.10 (t, 1H). |
| Example 390 | 2-(R)-methoxy-N-{4-[7-(2-methoxy-ethoxy)-1-methyl-[1,2,4]triazolo[4,3-a]quinoxaline-4-ylamino]-butyl}-3-methyl-butyramide | Mass (M + H⁺): 449.2; ¹H NMR (500 MHz, DMSO-d6): δ0.79 (m, 6H), 1.48 (m, 2H), 1.62 (m, 2H), 1.80 (m, 1H), 2.95 (s, 3H), 3.15 (q, 2H), 3.17 (s, 3H), 3.29 (d, 2H), 3.50 (q, 2H), 3.66 (t, 2H), 4.15 (t, 2H), 6.87 (d, 1H), 7.05 (s, 1H), 7.79 (t, 1H), 7.95 (d, 1H), 8.10 (t, 1H). |

TABLE 25-continued

| Example | Name | Data |
|---|---|---|
| Example 391 | 2,2-difluoro-N-{4-[7-(2-methoxy-ethoxy)-1-methyl-[1,2,4]triazolo[4,3-a]quinoxaline-4-ylamino]-butyl}-butyramide | Mass (M + H$^+$): 451.2; $^1$H NMR (500 MHz, DMSO-d6): δ0.83 (t, 3H), 1.52 (m, 2H), 1.60 (m, 2H), 1.97 (m, 2H), 2.94 (s, 3H), 3.15 (q, 2H), 3.28 (s, 3H), 3.52 (q, 2H), 3.65 (t, 2H), 4.14 (t, 2H), 6.86 (dd, 1H), 7.05 (s, 1H), 7.94 (d, 1H), 8.10 (t, 1H), 8.64 (t, 1H). |
| Example 392 | 3,3,3-trifluoro-N-{4-[7-(2-methoxy-ethoxy)-1-methyl-[1,2,4]triazolo[4,3-a]quinoxaline-4-ylamino]-butyl}-2,2-dimethyl-propionamide | Mass (M + H$^+$): 483.2; $^1$H NMR (500 MHz, DMSO-d6): δ1.27 (s, 6H), 1.49 (m, 2H), 1.61 (m, 2H), 2.95 (s, 3H), 3.11 (q, 2H), 3.29 (s, 3H), 3.49 (q, 2H), 3.66 (t, 2H), 4.14 (t, 2H), 6.87 (d, 1H), 7.06 (s, 1H), 7.86 (t, 1H), 7.96 (d, 1H), 8.10 (t, 1H). |
| Example 393 | 3-cyclopentyl-N-{4-[7-(2-methoxy-ethoxy)-1-methyl-[1,2,4]triazolo[4,3-a]quinoxaline-4-ylamino]-butyl}-propionamide | Mass (M + H$^+$): 469.2; $^1$H NMR (500 MHz, DMSO-d6): δ0.97 (m, 2H), 1.32 (m, 2H), 1.44 (m, 4H), 1.51 (m, 2H), 1.62 (m, 5H), 2.00 (m, 2H), 2.95 (s, 3H), 3.04 (m, 2H), 3.29 (s, 3H), 3.52 (q, 2H), 3.66 (t, 2H), 4.15 (t, 2H), 6.86 (dd, 1H), 7.06 (s, 1H), 7.69 (t, 1H), 7.94 (d, 1H), 8.09 (t, 1H). |
| Example 394 | N-{4-[7-(2-methoxy-ethoxy)-1-methyl-[1,2,4]triazolo[4,3-a]quinoxaline-4-ylamino]-butyl}-malonamic acid ethylester | Mass (M + H$^+$): 459.2; $^1$H NMR (500 MHz, DMSO-d6): δ1.10 (t, 3H), 1.13 (q, 2H), 1.47 (m, 2H), 1.64 (m, 2H), 2.95 (s, 3H), 3.06 (m, 2H), 3.14 (s, 2H), 3.29 (s, 3H), 3.52 (q, 2H), 3.66 (t, 2H), 4.15 (t, 2H), 6.86 (dd, 1H), 7.06 (s, 1H), 7.95 (d, 1H), 8.03 (t, 1H), 8.10 (t, 1H). |

TABLE 25-continued

| Example | Structure | Name | Data |
|---------|-----------|------|------|
| Example 395 | 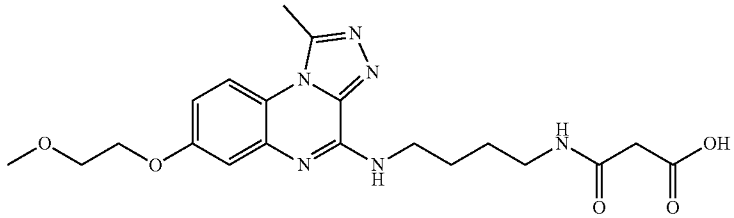 [SMILES: COCCOc1ccc2c(c1)nc(NCCCCNC(=O)CC(=O)O)c1nnc(C)n12] | N-{4-[7-(2-methoxy-ethoxy)-1-methyl-[1,2,4]tri-azolo[4,3-a]quinoxaline-4-ylamino]-butyl}-malonamic acid | Mass (M + H⁺): 429.2; ¹H NMR (500 MHz, DMSO-d6): δ1.64 (m, 2H), 1.71 (m, 2H), 2.76 (m, 2H), 2.95 (s, 3H), 3.14 (m, 2H), 3.30 (s, 3H), 3.55 (m, 2H), 3.66 (t, 2H), 4.17 (t, 2H), 6.86 (dd, 1H), 7.07 (s, 1H), 7.80 (t, 1H), 7.88 (br, 1H), 7.95 (d, 1H), 8.95 (t, 1H). |
| Example 396 | 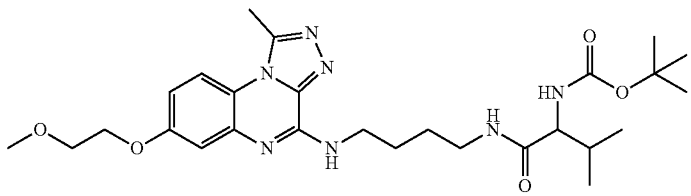 [SMILES: COCCOc1ccc2c(c1)nc(NCCCCNC(=O)C(NC(=O)OC(C)(C)C)C(C)C)c1nnc(C)n12] | (1-{4-[7-(2-methoxy-ethoxy)-1-methyl-[1,2,4]tri-azolo[4,3-a]quinoxaline-4-ylamino]-butylcarbamo-yl}-2-methyl-propyl)-carbamic acid-tert-butylester | Mass (M + H⁺): 544.2; ¹H NMR (500 MHz, DMSO-d6): δ0.75 (m, 6H), 1.32 (s, 9H), 1.45 (q, 2H), 1.63 (q, 2H), 1.82 (m, 1H), 2.95 (s, 3H), 3.12 (m, 2H), 3.28 (s, 3H), 3.52 (q, 2H), 3.65 (t, 2H), 3.66 (m, 1H), 4.15 (t, 2H), 6.50 (d, 1H), 6.86 (dd, 1H), 7.06 (s, 1H), 7.79 (t, 1H), 7.94 (d, 1H), 8.09 (t, 1H). |
| Example 397 | 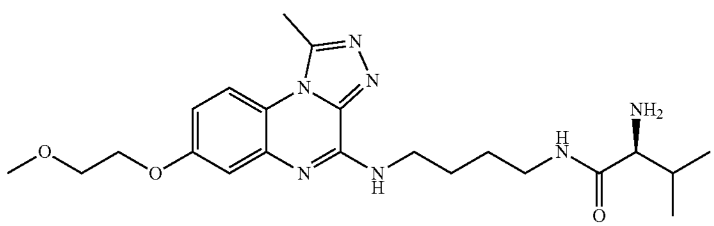 [SMILES: COCCOc1ccc2c(c1)nc(NCCCCNC(=O)[C@@H](N)C(C)C)c1nnc(C)n12] | 2-amino-N-{4-[7-(2-methoxy-ethoxy)-1-methyl-[1,2,4]tri-azolo[4,3-a]quinoxaline-4-ylamino]-butyl}-3-methyl-butyramide | Mass (M + H⁺): 444.2; ¹H NMR (500 MHz, DMSO-d6): δ0.71 (d, 3H), 0.79 (d, 3H), 1.46 (q, 2H), 1.63 (q, 2H), 1.80 (m, 1H), 1.98 (br, 2H), 2.85 (m, 1H), 2.95 (s, 3H), 3.09 (m, 2H), 3.29 (s, 3H), 3.52 (q, 2H), 3.65 (t, 2H), 4.15 (t, 2H), 6.86 (dd, 1H), 7.05 (s, 1H), 7.79 (t, 1H), 7.94 (d, 1H), 8.09 (t, 1H). |
| Example 398 | 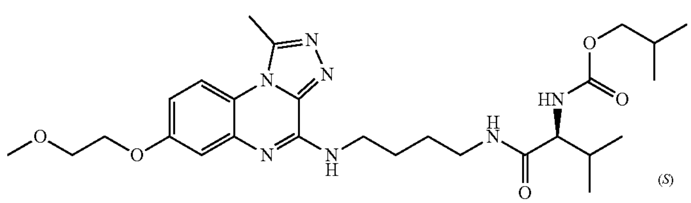 | (S)-(1-{4-[7-(2-methoxy-ethoxy)-1-methyl-[1,2,4]tri-azolo[4,3-a]quinoxaline-4-ylamino]-butylcarbamo-yl}-2-methyl-propyl)-carbamic acid isobutylester | Mass (M + H⁺): 544.2; ¹H NMR (500 MHz, DMSO-d6): δ0.77 (m, 6H), 0.82 (m, 6H), 1.44 (q, 2H), 1.63 (q, 2H), 1.78 (m, 1H), 1.86 (m, 1H), 2.95 (s, 3H), 3.05 (m, 2H), 3.29 (s, 3H), 3.49 (q, 2H), 3.65 (t, 2H), 3.66 (m, 1H), 4.15 (t, 2H), 6.85 (dd, 1H), 6.97 (d, 1H), 7.05 (s, 1H), 7.85 (t, 1H), 7.94 (d, 1H), 8.09 (t, 1H). |

TABLE 25-continued

| Example | Structure | Name | Data |
|---|---|---|---|
| Example 399 | 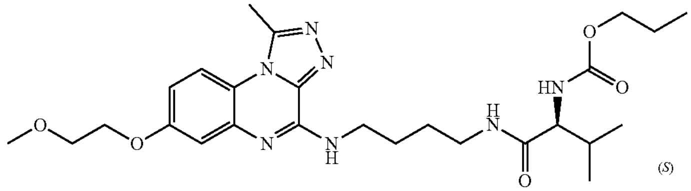 | (S)-(1-{4-[7-(2-methoxy-ethoxy)-1-methyl-[1,2,4]tri-azolo[4,3-a]quinoxaline-4-ylamino]-butylcarbamo-yl}-2-methyl-propyl)-carbamic acid propylester | Mass (M + H⁺): 530.2; ¹H NMR (500 MHz, DMSO-d6): δ0.76 (m, 3H), 1.47 (m, 4H), 1.65 (q, 2H), 1.85 (m, 1H), 2.95 (s, 3H), 3.04 (m, 2H), 3.29 (s, 3H), 3.50 (q, 2H), 3.65 (t, 2H), 3.66 (m, 1H), 3.83 (q, 2H), 4.15 (t, 2H), 6.85 (dd, 1H), 6.89 (d, 1H), 7.05 (s, 1H), 7.84 (t, 1H), 7.94 (d, 1H), 8.08 (t, 1H). |
| Example 400 | 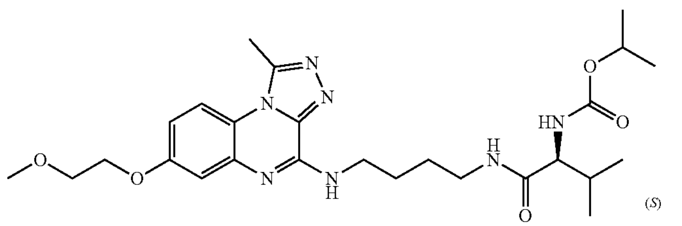 | (S)-(1-{4-[7-(2-methoxy-ethoxy)-1-methyl-[1,2,4]tri-azolo[4,3-a]quinoxaline-4-ylamino]-butylcarbamo-yl}-2-methyl-propyl)-carbamic acid isopropylester | Mass (M + H⁺): 530.2; ¹H NMR (500 MHz, DMSO-d6): δ0.76 (m, 6H), 1.10 (m, 6H), 1.45 (q, 2H), 1.63 (q, 2H), 1.84 (m, 1H), 2.95 (s, 3H), 3.04 (m, 2H), 3.29 (s, 3H), 3.49 (q, 2H), 3.65 (t, 2H), 3.66 (m, 1H), 4.15 (t, 2H), 4.67 (m, 1H), 6.78 (d, 1H), 6.85 (dd, 1H), 7.06 (s, 1H), 7.83 (t, 1H), 7.94 (d, 1H), 8.10 (t, 1H). |
| Example 401 | 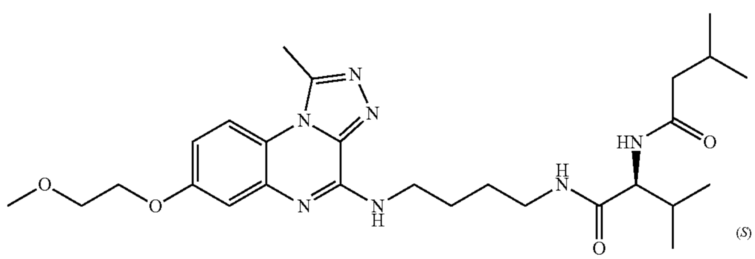 | (S)-N-{4-[7-(2-methoxy-ethoxy)-1-methyl-[1,2,4]tri-azolo[4,3-a]quinoxaline-4-ylamino]-butyl}-3-methyl-2-(3-methyl-butyryl-amino)-butyramide | Mass (M + H⁺): 528.2; ¹H NMR (500 MHz, DMSO-d6): δ0.77 (d, 6H), 0.81 (d, 6H), 1.45 (q, 2H), 1.63 (q, 2H), 1.82 (m, 1H), 1.88 (m, 1H), 1.98 (m, 2H), 2.95 (s, 3H), 3.05 (m, 2H), 3.29 (s, 3H), 3.49 (q, 2H), 3.65 (t, 2H), 4.04 (m, 1H), 4.15 (t, 2H), 6.85 (dd, 1H), 7.05 (s, 1H), 7.69 (d, 1H), 7.88 (t, 1H), 7.93 (d, 1H), 8.08 (t, 1H). |
| Example 402 | 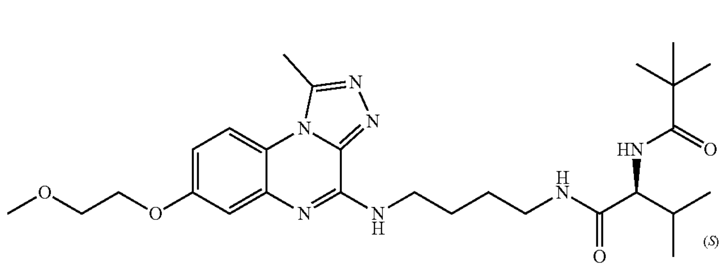 | (S)-2-(2,2-dimethyl-propionyl-amino)-N-{4-[7-(2-methoxy-ethoxy)-1-methyl-[1,2,4]tri-azolo[4,3-a]quinoxaline-4-ylamino]-butyl}-3-methyl-butyramide | Mass (M + H⁺): 528.2; ¹H NMR (500 MHz, DMSO-d6): δ0.75 (m, 6H), 1.05 (s, 9H), 1.46 (q, 2H), 1.63 (q, 2H), 1.90 (m, 1H), 2.95 (s, 3H), 3.04 (m, 2H), 3.29 (s, 3H), 3.51 (q, 2H), 3.66 (t, 2H), 4.02 (m, 1H), 4.15 (t, 2H), 6.87 (dd, 1H), 6.97 (d, 1H) 7.10 (s, 1H), 7.88 (t, 1H), 7.95 (d, 1H), 8.18 (t, 1H). |

TABLE 25-continued

| Example | Structure | Name | Data |
| --- | --- | --- | --- |
| Example 403 | 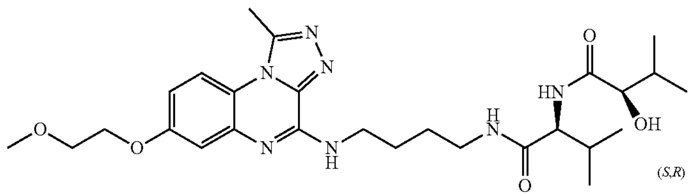 | 2-(S,R)-hydroxy-N-(1-{4-[7-(2-methoxy-ethoxy)-1-methyl-[1,2,4]tri-azolo[4,3-a]quinoxaline-4-ylamino]-butylcarbamo-yl}-2-methyl-propyl)-3-methyl-butyramide | Mass (M + H⁺): 544.2; ¹H NMR (500 MHz, DMSO-d6): δ0.77 (t, 6H), 0.79 (d, 3H), 0.88 (d, 3H), 1.50 (q, 2H), 1.66 (q, 2H), 1.89 (m, 1H), 1.97 (m, 1H), 2.96 (s, 3H), 3.11 (m, 2H), 3.31 (s, 3H), 3.54 (q, 2H), 3.67 (m, 3H), 4.13 (m, 1H), 4.17 (t, 2H), 5.35 (d, 1H), 6.87 (d, 1H), 7.08 (s, 1H), 7.37 (d, 1H), 7.86 (t, 1H), 7.88 (t, 1H), 7.96 (d, 1H). |
| Example 404 | 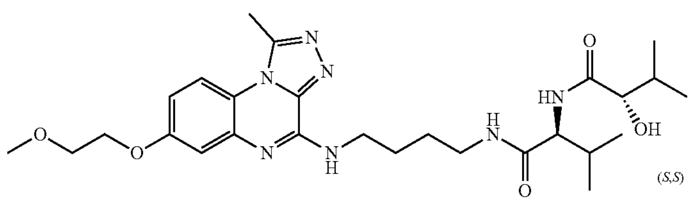 | 2-(S,S)-hydroxy-N-(1-{4-[7-(2-methoxy-ethoxy)-1-methyl-[1,2,4]tri-azolo[4,3-a]quinoxaline-4-ylamino]-butylcarbamo-yl}-2-methyl-propyl)-3-methyl-butyramide | Mass (M + H⁺): 544.2; ¹H NMR (500 MHz, DMSO-d6): δ0.65 (d, 3H), 0.77 (t, 6H), 0.84 (d, 3H), 1.45 (q, 2H), 1.63 (q, 2H), 1.84 (m, 1H), 1.86 (m, 1H), 2.95 (s, 3H), 3.05 (m, 2H), 3.29 (s, 3H), 3.49 (q, 2H), 3.66 (t, 2H), 3.68 (m, 1H), 4.08 (m, 1H), 4.15 (t, 2H), 5.35 (d, 1H), 6.86 (dd, 1H), 7.06 (d, 1H), 7.41 (d, 1H), 7.74 (d, 1H), 7.99 (t, 1H), 8.09 (t, 1H). |
| Example 405 | 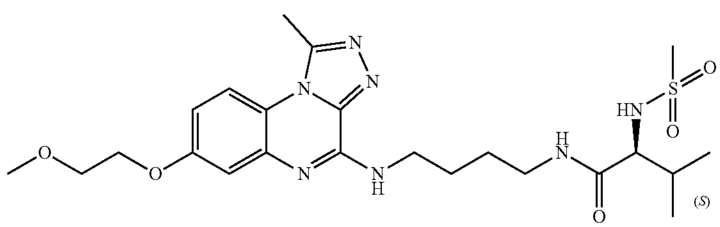 | 2-(S)-methanesul-fonylamino-{4-[7-(2-methoxy-ethoxy)-1-methyl-[1,2,4]tri-azolo[4,3-a]quinoxaline-4-ylamino]-butyl}-3-methyl-butyramide | Mass (M + H⁺): 522.2; ¹H NMR (500 MHz, DMSO-d6): δ0.79 (m, 6H), 1.48 (q, 2H), 1.65 (q, 2H), 1.82 (m, 1H), 2.74 (s, 3H), 2.95 (s, 3H), 3.11 (m, 2H), 3.29 (s, 3H), 3.47 (m, 1H), 3.52 (q, 2H), 3.66 (t, 2H), 4.15 (t, 2H), 6.86 (dd, 1H), 7.05 (s, 1H), 7.12 (d, 1H), 7.94 (d, 1H), 8.05 (t, 1H), 8.13 (t, 1H). |
| Example 406 | 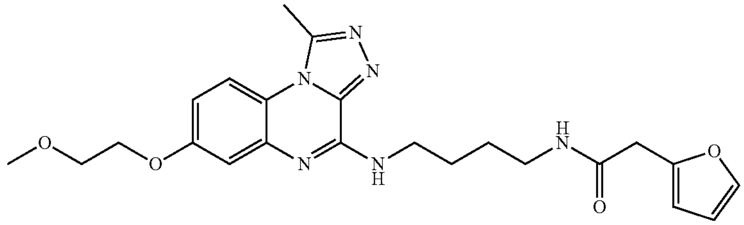 | N-{4-[7-(2-methoxy-ethoxy)-1-methyl-[1,2,4]tri-azolo[4,3-a]quinoxaline-4-ylamino]-butyl}-2-thiophene-2-yl-acetamide | Mass (M + H⁺): 469.2; ¹H NMR (500 MHz, DMSO-d6): δ1.46 (m, 2H), 1.63 (m, 2H), 2.95 (s, 3H), 3.07 (q, 2H), 3.29 (s, 3H), 3.49 (q, 2H), 3.56 (s, 2H), 3.65 (t, 2H), 4.15 (t, 2H), 6.83 (s, 1H), 6.87 (m, 2H), 7.06 (s, 1H), 7.29 (d, 1H), 7.95 (d, 1H), 8.02 (t, 2H), 8.09 (t, 2H). |

TABLE 25-continued

| Example | Name | Data |
|---|---|---|
| Example 407 | 2-furan-2-yl-N-{4-[7-(2-methoxy-ethoxy)-1-methyl-[1,2,4]tri-azolo[4,3-a]quinoxaline-4-ylamino]-butyl}-acetamide | Mass (M + H⁺): 453.2; ¹H NMR (500 MHz, DMSO-d6): δ1.47 (m, 2H), 1.63 (m, 2H), 2.95 (s, 3H), 3.08 (q, 2H), 3.27 (s, 3H), 3.41 (s, 2H), 3.50 (q, 2H), 3.66 (t, 2H), 4.15 (t, 2H), 6.11 (s, 1H), 6.29 (s, 1H), 6.87 (d, 1H), 7.07 (s, 1H), 7.45 (s, 1H), 7.96 (d, 2H), 8.10 (t, 1H). |
| Example 408 | N-{4-[7-(2-methoxy-ethoxy)-1-methyl-[1,2,4]tri-azolo[4,3-a]quinoxaline-4-ylamino]-butyl}-benzamide | Mass (M + H⁺): 449.2; ¹H NMR (500 MHz, DMSO-d6): δ1.60 (m, 2H), 1.69 (m, 2H), 2.94 (s, 3H), 3.28 (s, 3H), 3.29 (m, 2H), 3.55 (q, 2H), 3.65 (t, 2H), 4.13 (t, 2H), 6.48 (d, 1H), 7.04 (s, 1H), 7.39 (t, 2H), 7.46 (t, 1H), 7.77 (dd, 2H), 7.94 (d, 1H), 8.12 (t, 1H), 8.41 (t, 1H). |
| Example 409 | 2-fluoro-N-{4-[7-(2-methoxy-ethoxy)-1-methyl-[1,2,4]tri-azolo[4,3-a]quinoxaline-4-ylamino]-butyl}-benzamide | Mass (M + H⁺): 467.2; ¹H NMR (500 MHz, DMSO-d6): δ1.59 (m, 2H), 1.70 (m, 2H), 2.96 (s, 3H), 3.28 (m, 2H), 3.29 (s, 3H), 3.57 (q, 2H), 3.65 (t, 2H), 4.14 (t, 2H), 6.89 (dd, 1H), 7.15 (t, 1H), 7.20 (t, 1H), 7.22 (m, 2H), 7.45 (t, 1H), 7.53 (t, 1H), 7.96 (d, 1H), 8.28 (t, 1H). |
| Example 410 | 3-fluoro-N-{4-[7-(2-methoxy-ethoxy)-1-methyl-[1,2,4]tri-azolo[4,3-a]quinoxaline-4-ylamino]-butyl}-benzamide | Mass (M + H⁺): 467.2; ¹H NMR (500 MHz, DMSO-d6): δ1.58 (m, 2H), 1.69 (m, 2H), 2.94 (s, 3H), 3.26 (m, 2H), 3.28 (s, 3H), 3.52 (q, 1 2H), 3.64 (t, 2H), 4.13 (t, 2H), 6.87 (d, 1H), 7.04 (s, 1H), 7.22 (dd, 2H), 7.85 (dd, 2H), 7.94 (d, 1H), 8.12 (t, 1H), 8.43 (t, 1H). |

TABLE 25-continued

| Example | Structure | Name | Data |
|---|---|---|---|
| Example 411 | 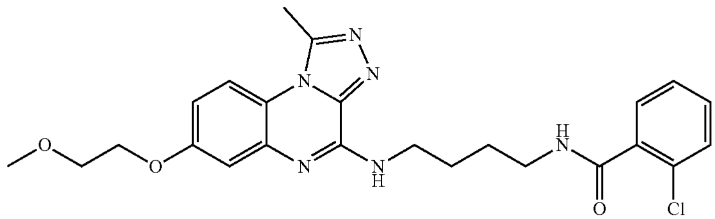 [SMILES: COCCOc1ccc2c(c1)nc(NCCCCNC(=O)c1ccccc1Cl)c1nnc(C)n12] | 2-chloro-N-{4-[7-(2-methoxy-ethoxy)-1-methyl-[1,2,4]triazolo[4,3-a]quinoxaline-4-ylamino]-butyl}-benzamide | Mass (M + H⁺): 483.2; ¹H NMR (500 MHz, DMSO-d6): δ1.58 (m, 2H), 1.72 (m, 2H), 2.95 (s, 3H), 3.24 (m, 2H), 3.29 (s, 3H), 3.53 (q, 2H), 3.65 (t, 2H), 4.14 (t, 2H), 6.86 (dd, 1H), 7.07 (d, 1H), 7.29 (t, 1H), 7.34 (dd, 1H), 7.38 (dd, 1H), 7.41 (d, 1H), 7.95 (d, 1H), 8.12 (t, 1H), 7.36 (t, 1H). |
| Example 412 | 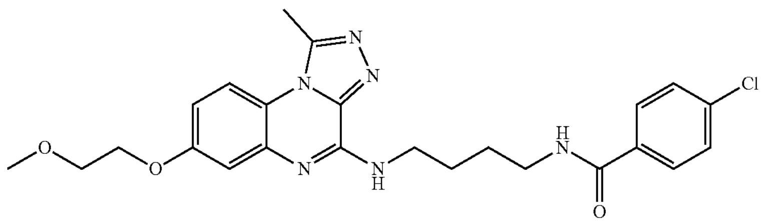 [SMILES: COCCOc1ccc2c(c1)nc(NCCCCNC(=O)c1ccc(Cl)cc1)c1nnc(C)n12] | 2-chloro-N-{4-[7-(2-methoxy-ethoxy)-1-methyl-[1,2,4]triazolo[4,3-a]quinoxaline-4-ylamino]-butyl}-benzamide | Mass (M + H⁺): 483.2; ¹H NMR (500 MHz, DMSO-d6): δ1.58 (m, 2H), 1.69 (m, 2H), 2.94 (s, 3H), 3.20 (q, 2H), 3.29 (s, 3H), 3.50 (q, 2H), 3.66 (t, 2H), 4.13 (t, 2H), 6.87 (d, 1H), 7.04 (d, 1H), 7.47 (d, 2H), 7.80 (d, 2H), 7.95 (d, 1H), 8.10 (t, 1H), 8.49 (t, 1H). |
| Example 413 | 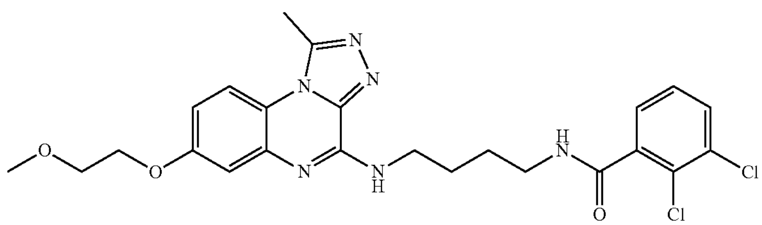 [SMILES: COCCOc1ccc2c(c1)nc(NCCCCNC(=O)c1cccc(Cl)c1Cl)c1nnc(C)n12] | 2,3-dichloro-N-{4-[7-(2-methoxy-ethoxy)-1-methyl-[1,2,4]triazolo[4,3-a]quinoxaline-4-ylamino]-butyl}-benzamide | Mass (M + H⁺): 518.2; ¹H NMR (500 MHz, DMSO-d6): δ1.58 (m, 2H), 1.72 (m, 2H), 2.95 (s, 3H), 3.25 (q, 2H), 3.28 (s, 3H), 3.50 (q, 2H), 3.66 (t, 2H), 4.14 (t, 2H), 6.87 (d, 1H), 7.07 (s, 1H), 7.31 (m, 2H), 7.62 (d, 1H), 7.96 (d, 1H), 8.13 (t, 1H), 8.47 (t, 1H). |
| Example 414 | 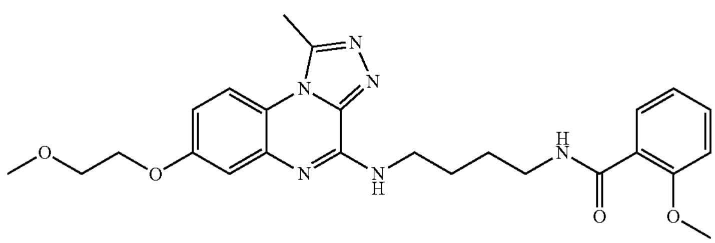 | 2-methoxy-N-{4-[7-(2-methoxy-ethoxy)-1-methyl-[1,2,4]triazolo[4,3-a]quinoxaline-4-ylamino]-butyl}-benzamide | Mass (M + H⁺): 479.2; ¹H NMR (500 MHz, DMSO-d6): δ1.57 (m, 2H), 1.70 (m, 2H), 2.94 (s, 3H), 3.28 (s, 3H), 3.31 (m, 2H), 3.54 (q, 2H), 3.64 (t, 2H), 3.78 (s, 3H), 4.12 (t, 2H), 6.85 (dd, 1H), 6.95 (t, 1H), 7.05 (t, 2H), 7.39 (t, 1H), 7.65 (d, 1H), 7.94 (d, 1H), 8.12 (m, 2H). |
| Example 415 | 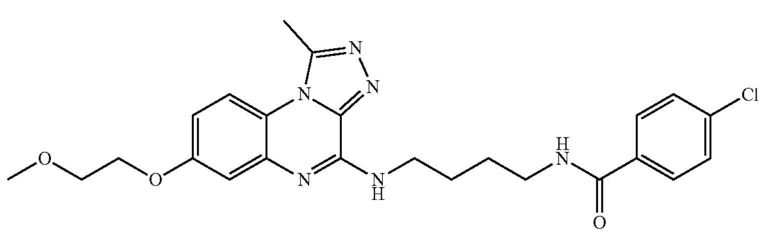 | N-{4-[7-(2-methoxy-ethoxy)-1-methyl-[1,2,4]triazolo[4,3-a]quinoxaline-4-ylamino]-butyl}-4-nitro-butyramide | Mass (M + H⁺): 494.2; ¹H NMR (500 MHz, DMSO-d6): δ1.61 (m, 2H), 1.71 (m, 2H), 2.94 (s, 3H), 3.27 (s, 3H), 3.28 (q, 2H), 3.55 (q, 2H), 3.65 (t, 2H), 4.12 (t, 2H), 6.86 |

TABLE 25-continued

| Example | Structure | Name | Data |
|---|---|---|---|
| | | | (d, 1H), 7.03 (s, 1H), 7.93 (d, 2H), 7.62 (d, 1H), 7.96 (d, 1H), 8.00 (d, 2H), 8.10 (t, 1H), 8.24 (d, 2H), 8.74 (t, 1H). |
| Example 416 | 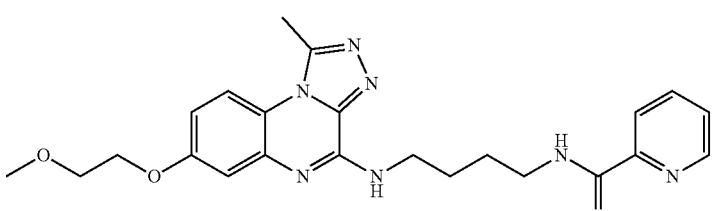 | pyridine-2-carboxylic acid-{4-[7-(2-methoxy-ethoxy)-1-methyl-[1,2,4]tri-azolo[4,3-a]quinoxaline-4-ylamino]-butyl}-amide | Mass (M + H<sup>+</sup>): 450.2; <sup>1</sup>H NMR (500 MHz, DMSO-d6): δ1.61 (m, 2H), 1.69 (m, 2H), 2.95 (s, 3H), 3.29 (s, 3H), 3.33 (m, 2H), 3.53 (m, 2H), 3.66 (t, 2H), 4.15 (t, 2H), 6.88 (dd, 1H), 7.05 (s, 1H), 7.54 (m, 1H), 7.93 (m, 1H), 7.97 (m, 2H), 8.11 (t, 1H), 8.56 (d, 1H), 8.75 (t, 1H). |
| Example 417 | 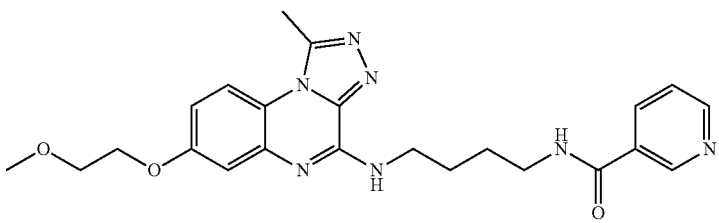 [SMILES: COCCOc1ccc2c(c1)nc(NCCCCNC(=O)c1cccnc1)c1nnc(C)n12] | N-{4-[7-(2-methoxy-ethoxy)-1-methyl-[1,2,4]tri-azolo[4,3-a]quinoxaline-4-ylamino]-butyl}-nicotinamide | Mass (M + H<sup>+</sup>): 450.2; <sup>1</sup>H NMR (500 MHz, DMSO-d6): δ1.63 (m, 2H), 1.73 (m, 2H), 2.95 (s, 3H), 3.31 (s, 3H), 3.33 (m, 2H), 3.53 (m, 2H), 3.66 (t, 2H), 4.15 (t, 2H), 6.88 (dd, 1H), 7.07 (s, 1H), 7.42 (m, 1H), 7.94 (m, 1H), 7.96 (d, 1H), 8.10 (d, 1H), 8.49 (t, 1H), 8.64 (t, 1H), 8.95 (s, 1H). |
| Example 418 | 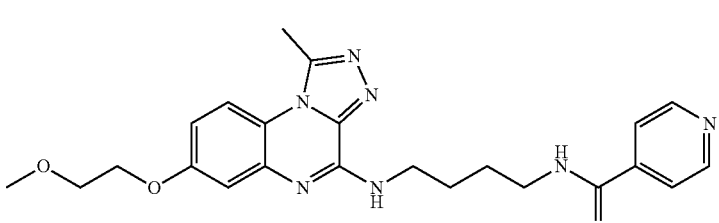 | N-{4-[7-(2-methoxy-ethoxy)-1-methyl-[1,2,4]tri-azolo[4,3-a]quinoxaline-4-ylamino]-butyl}-iso-nicotinamide | Mass (M + H<sup>+</sup>): 450.2; <sup>1</sup>H NMR (500 MHz, DMSO-d6): δ1.60 (m, 2H), 1.70 (m, 2H), 2.95 (s, 3H), 3.28 (s, 3H), 3.31 (m, 2H), 3.53 (m, 2H), 3.65 (t, 2H), 4.13 (t, 2H), 6.86 (dd, 1H), 7.05 (s, 1H), 7.68 (m, 2H), 7.95 (d, 1H), 8.12 (t, 1H), 8.65 (m, 2H), 8.71 (t, 1H). |
| Example 419 | 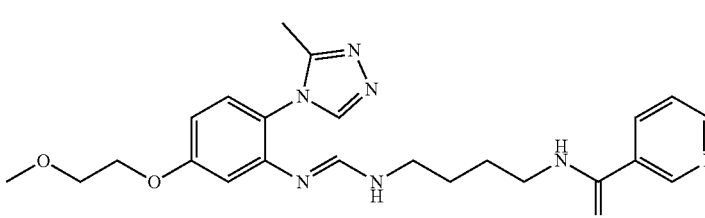 | 6-chloro-N-{4-[7-(2-methoxy-ethoxy)-1-methyl-[1,2,4]tri-azolo[4,3-a]quinoxaline-4-ylamino]-butyl}-nicotinamide | Mass (M + H<sup>+</sup>): 483.95; <sup>1</sup>H NMR (500 MHz, DMSO-d6): δ1.61 (m, 2H), 1.70 (m, 2H), 2.94 (s, 3H), 3.28 (s, 3H), 3.30 (q, 2H), 3.52 (q, 2H), 3.66 (t, 2H), 4.14 (t, 2H), 6.86 (d, 1H), 7.04 (s, 1H), 7.57 (d, 1H), 7.95 (d, 1H), 8.11 (t, 1H), 8.15 (d, 1H), 8.76 (s, 1H). |

TABLE 25-continued

| Example | Structure | Name | Data |
|---|---|---|---|
| Example 420 | 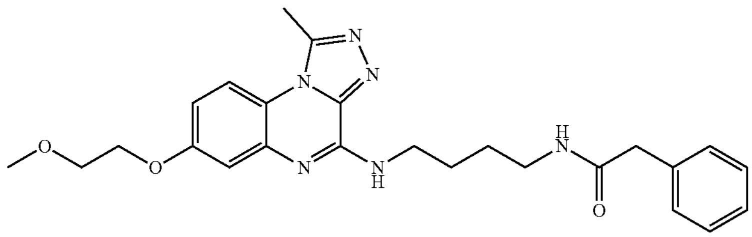 [SMILES: COCCOc1ccc2c(c1)nc(NCCCCNC(=O)Cc1ccccc1)c1nnc(C)n12] | N-{4-[7-(2-methoxy-ethoxy)-1-methyl-[1,2,4]tri-azolo[4,3-a]quinoxaline-4-ylamino]-butyl}-2-phenyl-acetamide | Mass (M + H⁺): 463.2; ¹H NMR (500 MHz, DMSO-d6): δ1.46 (m, 2H), 1.62 (m, 2H), 2.95 (s, 3H), 3.05 (q, 2H), 3.25 (s, 3H), 3.28 (s, 2H), 3.50 (q, 2H), 3.64 (t, 2H), 4.13 (t, 2H), 6.86 (d, 2H), 7.06 (s, 1H), 7.15 (t, 1H), 7.20 (m, 1H), 7.22 (m, 3H), 7.95 (d, 1H), 7.98 (t, 1H), 8.09 (t, 1H). |
| Example 421 | 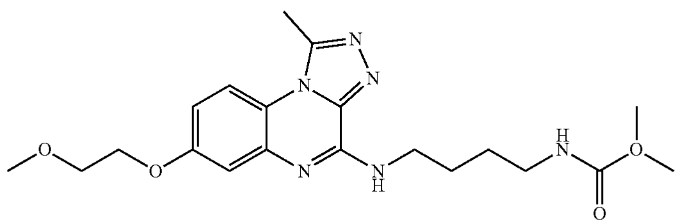 | 3-{4-[7-(2-methoxy-ethoxy)-1-methyl-[1,2,4]tri-azolo[4,3-a]quinoxaline-4-ylamino]-butyl}-1,1-dimethyl-urea | Mass (M + H⁺): 416.2; ¹H NMR (500 MHz, DMSO-d6): δ1.45 (m, 2H), 1.61 (m, 2H), 2.95 (s, 3H), 3.01 (q, 2H), 3.29 (s, 3H), 3.50 (q, 2H), 3.66 (t, 2H), 4.16 (t, 2H), 6.19 (t, 1H), 6.87 (d, 1H), 7.06 (s, 1H), 7.95 (d, 1H), 8.07 (t, 1H). |
| Example 422 | 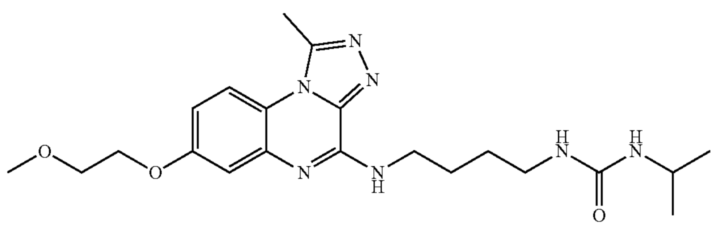 [SMILES: COCCOc1ccc2c(c1)nc(NCCCCNC(=O)NC(C)C)c1nnc(C)n12] | 1-isopropyl-3-{4-[7-(2-methoxy-ethoxy)-1-methyl-[1,2,4]tri-azolo[4,3-a]quinoxaline-4-ylamino]-butyl}-urea | Mass (M + H⁺): 430.2; ¹H NMR (500 MHz, DMSO-d6): δ0.95 (d, 6H), 1.41 (m, 2H), 1.61 (m, 2H), 2.94 (s, 3H), 2.98 (q, 2H), 3.29 (s, 3H), 3.50 (q, 2H), 3.60 (m, 1H), 3.66 (q, 2H), 4.15 (t, 2H), 5.53 (d, 1H), 5.63 (t, 1H), 6.86 (d, 1H), 7.06 (s, 1H), 7.94 (d, 1H), 8.10 (t, 1H). |
| Example 423 | 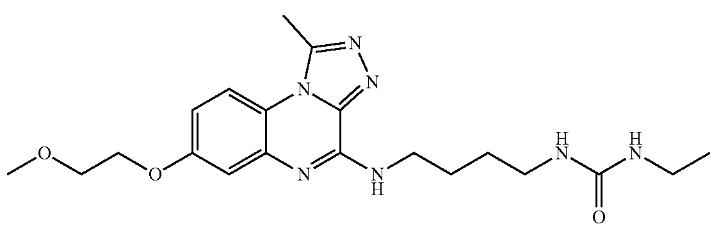 [SMILES: CCNC(=O)NCCCCNc1nc2cc(OCCOC)ccc2n2c(C)nnc12] | 1-ethyl-3-{4-[7-(2-methoxy-ethoxy)-1-methyl-[1,2,4]tri-azolo[4,3-a]quinoxaline-4-ylamino]-butyl}-urea | Mass (M + H⁺): 416.2; ¹H NMR (500 MHz, DMSO-d6): δ0.92 (t, 3H), 1.41 (m, 2H), 1.60 (m, 2H), 2.94 (q, 2H), 2.94 (s, 3H), 2.95 (q, 2H), 3.29 (s, 3H), 3.52 (q, 2H), 3.65 (t, 2H), 4.15 (t, 2H), 5.66 (t, 1H), 5.74 (t, 1H), 6.87 (dd, 1H), 7.07 (s, 1H), 7.94 (d, 1H), 8.09 (t, 1H). |
| Example 424 | 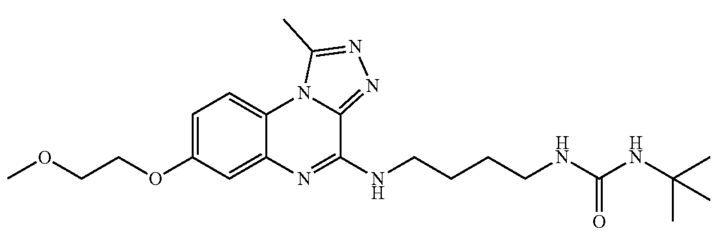 [SMILES: COCCOc1ccc2c(c1)nc(NCCCCNC(=O)NC(C)(C)C)c1nnc(C)n12] | 1-tert-butyl-3-{4-[7-(2-methoxy-ethoxy)-1-methyl-[1,2,4]tri-azolo[4,3-a]quinoxaline-4-ylamino]-butyl}-urea | Mass (M + H⁺): 444.2; ¹H NMR (500 MHz, DMSO-d6): δ1.16 (s, 9H), 1.39 (m, 2H), 1.60 (m, 2H), 2.94 (q, 2H), 2.95 (s, 3H), 3.28 (s, 3H), 3.52 (q, 2H), 3.66 (t, 2H), 4.15 |

TABLE 25-continued

| Example | Structure | Name | Data |
|---|---|---|---|
| | | | (t, 2H), 5.49 (t, 1H), 5.57 (t, 1H), 6.87 (dd, 1H), 7.07 (s, 1H), 7.95 (d, 1H), 8.10 (t, 1H). |
| Example 425 | 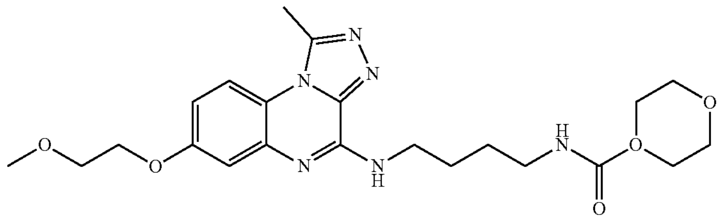 | morpholine-4-carboxylic acid-{4-[7-(2-methoxy-ethoxy)-1-methyl-[1,2,4]tri-azolo[4,3-a]quinoxaline-4-ylamino]-butyl}-amide | Mass (M + H$^+$): 458.3; $^1$H NMR (500 MHz, DMSO-d6): δ1.47 (m, 2H), 1.62 (m, 2H), 2.94 (s, 3H), 3.05 (q, 2H), 3.17 (m, 4H), 3.29 (s, 3H), 3.45 (q, 2H), 3.47 (m, 4H), 3.65 (q, 2H), 4.15 (q, 2H), 6.46 (t, 1H), 6.86 (d, 1H), 7.05 (s, 1H), 7.92 (d, 1H), 8.08 (t, 1H). |
| Example 426 | 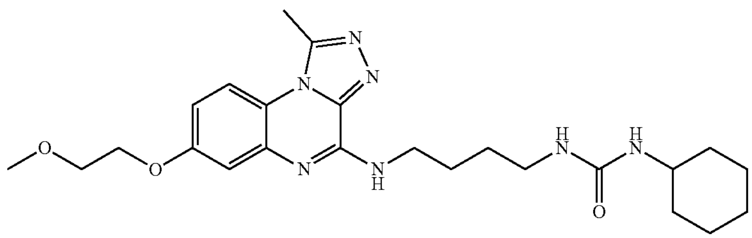 [SMILES: COCCOc1ccc2c(c1)nc(NCCCCNC(=O)NC1CCCCC1)c1nnc(C)n12] | 1-cyclohexyl-3-{4-[7-(2-methoxy-ethoxy)-1-methyl-[1,2,4]tri-azolo[4,3-a]quinoxaline-4-ylamino]-butyl}-urea | Mass (M + H$^+$): 470.3; $^1$H NMR (500 MHz, DMSO-d6): δ0.99 (m, 2H), 1.09 (m, 1H), 1.18 (m, 2H), 1.40 (t, 2H), 1.46 (m, 1H), 1.58 (m, 2H), 1.61 (m, 2H), 1.69 (m, 2H), 2.95 (s, 3H), 2.97 (t, 2H), 3.28 (m, 1H), 3.29 (s, 1H), 3.49 (q, 2H), 3.65 (t, 2H), 4.15 (t, 2H), 5.57 (d, 1H), 5.63 (t, 1H), 6.86 (d, 1H), 7.06 (s, 1H), 7.95 (d, 1H), 8.09 (t, 1H). |
| Example 427 | 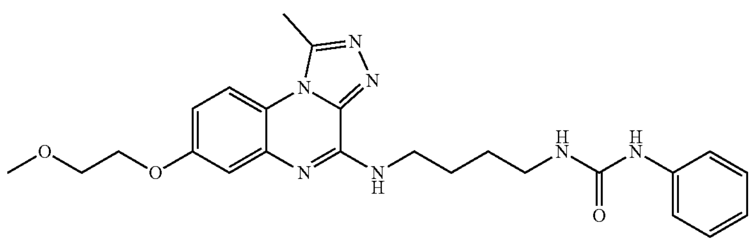 [SMILES: COCCOc1ccc2c(c1)nc(NCCCCNC(=O)Nc1ccccc1)c1nnc(C)n12] | 3-{4-[7-(2-methoxy-ethoxy)-1-methyl-[1,2,4]tri-azolo[4,3-a]quinoxaline-4-ylamino]-butyl}-1-phenyl-urea | Mass (M + H$^+$): 464.2; $^1$H NMR (500 MHz, DMSO-d6): δ1.49 (m, 2H), 1.66 (m, 2H), 2.95 (s, 3H), 3.10 (m, 2H), 3.28 (s, 3H), 3.53 (m, 2H), 3.64 (t, 2H), 4.14 (t, 2H), 6.09 (t, 1H), 6.83 (t, 1H), 6.85 (dd, 1H), 7.07 (s, 1H), 7.16 (m, 2H), 7.32 (m, 2H), 7.74 (d, 1H), 8.13 (t, 1H), 8.33 (t, 1H). |
| Example 428 | 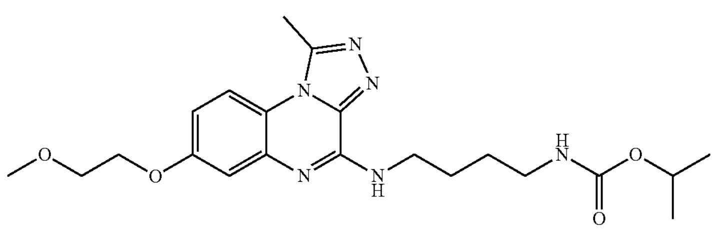 | {4-[7-(2-methoxy-ethoxy)-1-methyl-[1,2,4]tri-azolo[4,3-a]quinoxaline-4-ylamino]-butyl}-thiocarbamic acid-S-isopropylester | Mass (M + H$^+$): 447.2; $^1$H NMR (500 MHz, DMSO-d6): δ1.19 (d, 6H), 1.47 (m, 2H), 1.61 (m, 2H), 2.95 (s, 3H), 3.10 (m, 2H), 3.26 (s, 3H), 3.39 (m, 1H), 3.51 (m, 2H), 3.66 (m, 2H), 4.15 (m, 2H), 6.87 (d, 1H), 7.07 (s, 1H), 7.94 (s, 1H), 7.96 (d, 1H), 8.10 (t, 1H). |

TABLE 25-continued

| Example | Structure | Name | Data |
|---|---|---|---|
| Example 429 | 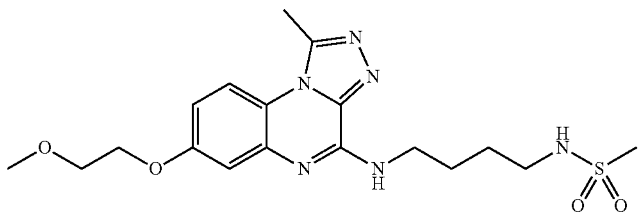 | N-{4-[7-(2-methoxy-ethoxy)-1-methyl-[1,2,4]tri-azolo[4,3-a]quinoxaline-4-ylamino]-butyl}-methanesulfon-amide | Mass (M + H⁺): 416.2; ¹H NMR (500 MHz, DMSO-d6): δ1.53 (m, 2H), 1.67 (m, 2H), 2.83 (s, 3H), 2.96 (s, 3H), 3.01 (q, 2H), 3.29 (s, 3H), 3.51 (q 2H), 3.65 (t, 2H), 4.14 (t, 2H), 6.86 (d, 1H), 6.91 (t, 1H), 7.06 (s, 1H), 7.92 (d, 1H), 8.11 (t, 1H). |

<Preparative Example 24> Preparation of {4-[3-hydrazino-7-(2-morpholine-4-yl-ethoxy)-quinoxaline-2-ylamino]-butyl}-carbamic acid-tert-butylester

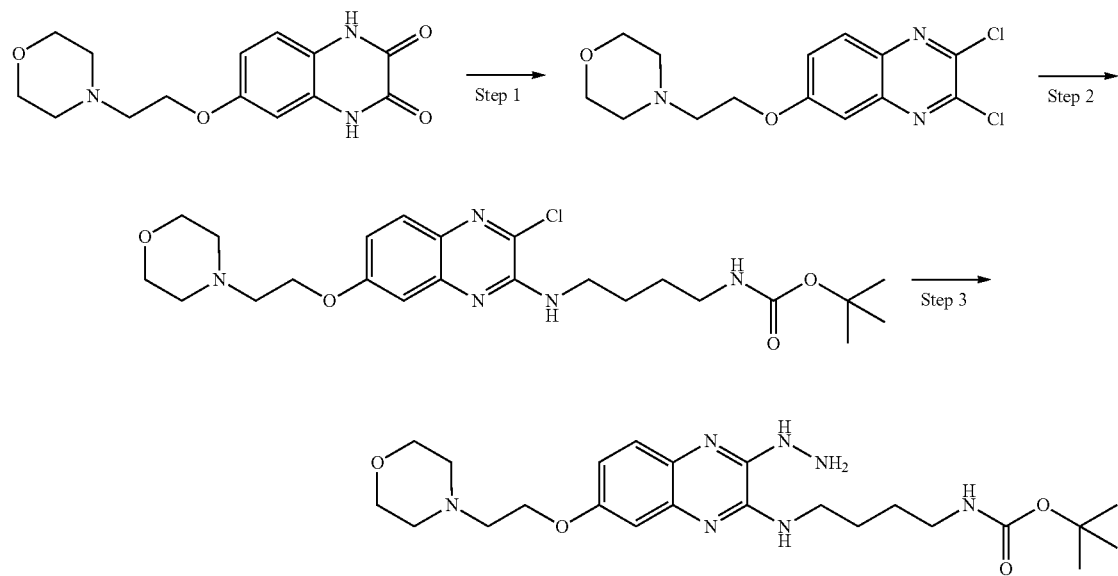

{4-[3-hydrazino-7-(2-morpholine-4-yl-ethoxy)-quinoxaline-2-ylamino]-butyl}-carbamic acid-tert-butylester, a target compound of Preparative Example 24 was obtained by the same manner as described in Preparative Example 20.

Step 1: Preparation of 2,3-dichloro-6-(2-morpholine-4-yl-ethoxy)-quinoxaline

Mass (M+H⁺): 328.0
¹H NMR (500 MHz, DMSO-d6): δ2.62 (brm, 2H), 2.90 (brm, 2H), 3.76 (brm, 4H), 4.27 (brm, 2H), 7.29 (s, 1H), 7.44 (d, 1H), 7.89 (d, 1H).

Step 2: Preparation of {4-[3-chloro-7-(2-morpholine-4-yl-ethoxy)-quinoxaline-2-ylamino]-butyl}-carbamic acid-tert-butylester Mass (M+H⁺): 500.1
¹H NMR (500 MHz, DMSO-d6) δ1.32 (s, 9H), 1.40 (m, 2H), 1.57 (m, 2H), 2.46 (brm, 4H), 2.69 (t, 2H), 2.91 (m, 2H), 3.40 (q, 2H), 3.54 (t, 4H), 4.16 (t, 2H), 6.74 (t, 1H), 6.98 (dd, 1H), 7.01 (s, 1H), 7.34 (t, 1H), 7.56 (d, 1H)

Step 3: Preparation of {4-[3-hydrazino-7-(2-morpholine-4-yl-ethoxy)-quinoxaline-2-ylamino]-butyl}-carbamic acid-tert-butylester Mass (M+H⁺): 476.3

Examples of the compounds synthesized using {4-[3-hydrazino-7-(2-morpholine-4-yl-ethoxy)-quinoxaline-2-ylamino]-butyl}-carbamic acid-tert-butyl ester prepared in Preparative Example 24 are shown in Table 26 below.

TABLE 26

| Example | Structure | Name | Data |
|---|---|---|---|
| Example 430 | 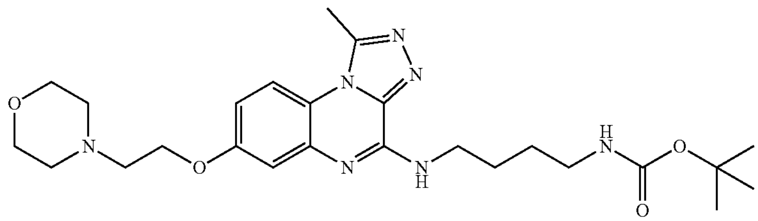 [SMILES: Cc1nnc2c(NCCCCNC(=O)OC(C)(C)C)nc3cc(OCCN4CCOCC4)ccc3n12] | {4-[1-methyl-7-(2-morpholine-4-yl-ethoxy)-[1,2,4]triazolo[4,3-a]quinoxaline-4-ylamino]-butyl}-carbamic acid-tert-butylester | Mass (M + H⁺): 500.3; ¹H NMR (500 MHz, DMSO-d6): δ1.32 (s, 9H), 1.43 (m, 2H), 1.61 (m, 2H), 2.68 (t, 2H), 2.92 (m, 2H), 2.94 (t, 4H), 3.27 (s, 3H), 3.48 (m, 2H), 3.55 (t, 4H), 4.14 (t, 2H), 6.74 (t, 1H), 6.85 (dd, 1H), 7.08 (s, 1H), 7.93 (d, 1H), 8.08 (t, 1H). |
| Example 431 | 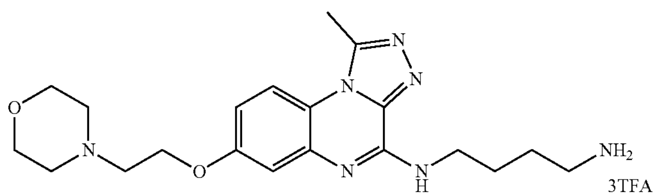 [SMILES: Cc1nnc2c(NCCCCN)nc3cc(OCCN4CCOCC4)ccc3n12 ; "3TFA"] | N¹-{4-[1-methyl-7-(2-morpholine-4-yl-ethoxy)-[1,2,4]triazolo[4,3-a]quinoxaline-4-yl]-butane-1,4-diamine trifluoroacetic acid | Mass (M + H⁺): 400.2; ¹H NMR (500 MHz, DMSO-d6): δ1.61 (m, 2H), 1.69 (m, 2H), 2.81 (m, 2H), 2.96 (m, 2H), 3.26 (s, 3H), 3.53 (brm, 2H), 3.58 (brm, 4H), 3.72 (m, 2H), 3.95 (brm, 2H), 4.43 (brm, 2H), 6.93 (t, 2H), 7.17 (dd, 1H), 7.76 (d, 1H), 8.00 (brm, 2H), 8.29 (d, 1H), (t, 1H). |
| Example 432 | 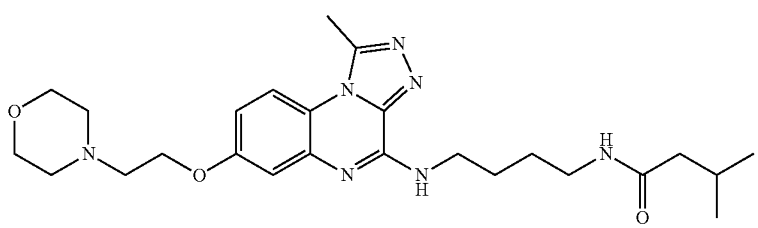 | 3-methyl-N-{4-[1-methyl-7-(2-morpholine-4-yl-ethoxy)-[1,2,4]triazolo[4,3-a]quinoxaline-4-ylamino]-butyl}-butyramide | Mass (M + H⁺): 484.3; ¹H NMR (500 MHz, DMSO-d6): δ0.80 (d, 6H), 1.43 (m, 2H), 1.62 (m, 2H), 1.86 (m, 2H), 1.92 (m, 1H), 2.46 (m, 4H), 2.69 (t, 2H), 2.94 (s, 3H), 3.04 (q, 2H), 3.49 (m, 2H), 3.55 (m, 4H), 4.14 (t, 2H), 6.85 (dd, H), 7.07 (s, 1H), 7.69 (t, 1H), 7.94 (d, 1H), 8.10 (t, 1H). |

TABLE 26-continued

| Example | Name | Data |
|---|---|---|
| Example 433 | 2,2-dimethyl-N-{4-[1-methyl-7-(2-morpholine-4-yl-ethoxy)-[1,2,4]triazolo[4,3-a]quinoxaline-4-ylamino]-butyl}-propionamide | Mass (M + H⁺): 484.3; ¹H NMR (500 MHz, DMSO-d6): δ1.02 (s, 9H), 1.45 (m, 2H), 1.60 (m, 2H), 2.46 (brm, 4H), 2.68 (t, 2H), 2.94 (s, 3H), 3.04 (q, 2H), 3.49 (q, 2H), 3.55 (t, 4H), 4.14 (t, 2H), 6.85 (dd, 1H), 7.06 (s, 1H), 7.37 (t, 1H), 7.93 (d, 1H), 8.08 (t, 1H) |
| Example 434 | 2-(R)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide | Mass (M + H⁺): 500.3; ¹H NMR (500 MHz, DMSO-d6): δ0.68 (d, 3H), 0.83 (d, 3H), 1.46 (m, 1H), 1.61 (m, 1H), 1.90 (m, 1H), 2.68 (t, 2H), 2.94 (s, 3H), 3.06 (m, 1H), 3.13 (m, 1H), 3.49 (m, 2H), 3.55 (t, 4H), 3.61 (t, 1H), 4.14 (t, 2H), 5.23 (d, 1H), 6.84 (d, 1H), 7.07 (s, 1H), 7.65 (t, 1H), 7.93 (d, 1H), 8.10 (t, 1H). |
| Example 435 | 2-(S)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide | Mass (M + H⁺): 500.3; ¹H NMR (500 MHz, DMSO-d6): δ0.68 (d, 3H), 0.83 (d, 3H), 1.46 (m, 1H), 1.61 (m, 1H), 1.90 (m, 1H), 2.68 (t, 2H), 2.94 (s, 3H), 3.06 (m, 1H), 3.13 (m, 1H), 3.49 (m, 2H), 3.55 (t, 4H), 3.61 (t, 1H), 4.14 (t, 2H), 5.23 (d, 1H), 6.84 (d, 1H), 7.07 (s, 1H), 7.65 (t, 1H), 7.93 (d, 1H), 8.10 (t, 1H). |

TABLE 26-continued

| Example | Structure | Name | Data |
|---|---|---|---|
| Example 436 | 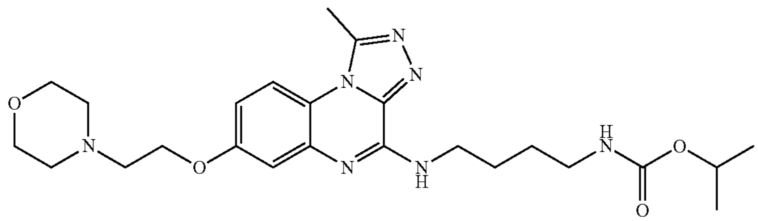 [SMILES: Cc1nnc2c(NCCCCNC(=O)OC(C)C)nc3cc(OCCN4CCOCC4)ccc3n12] | {4-[1-methyl-7-(2-morpholine-4-yl-ethoxy)-[1,2,4]triazolo[4,3-a]quinoxaline-4-ylamino]-butyl}-carbamic acid isopropylester | Mass (M + H$^+$): 486.3; $^1$H NMR (500 MHz, DMSO-d6): δ1.10 (d, 6H), 1.43 (m, 2H), 1.61 (m, 2H), 2.46 (m, 4H), 2.68 (t, 2H), 2.94 (m, 2H), 2.96 (s, 3H), 3.49 (q, 2H), 3.55 (t, 4H), 4.14 (t, 2H), 4.68 (m, 1H), 6.85 (dd, 1H), 6.95 (t, 1H), 7.08 (s, 1H), 7.94 (d, 1H), 8.08 (t, 1H). |
| Example 437 | 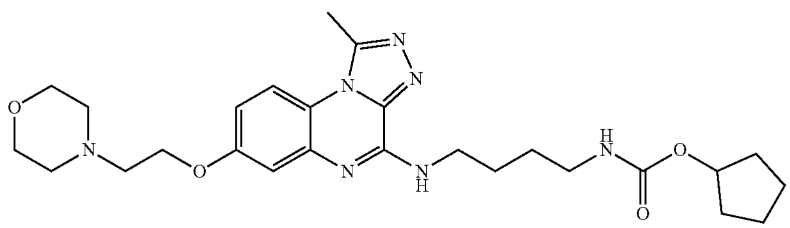 [SMILES: Cc1nnc2c(NCCCCNC(=O)OC3CCCC3)nc3cc(OCCN4CCOCC4)ccc3n12] | {4-[1-methyl-7-(2-morpholine-4-yl-ethoxy)-[1,2,4]triazolo[4,3-a]quinoxaline-4-ylamino]-butyl}-carbamic acid cyclopentylester | Mass (M + H$^+$): 512.3; $^1$H NMR (500 MHz, DMSO-d6): δ1.40~1.64 (m, 10H), 1.71 (m, 2H), 2.46 (m, 4H), 2.68 (t, 2H), 2.94 (s, 3H), 2.99 (m, 2H), 3.49 (q, 2H), 3.55 (t, 4H), 4.14 (t, 2H), 4.88 (m, 1H), 6.86 (dd, 1H), 6.94 (t, 1H), 7.08 (s, 1H), 7.94 (d, 1H), 8.07 (t, 1H). |
| Example 438 | 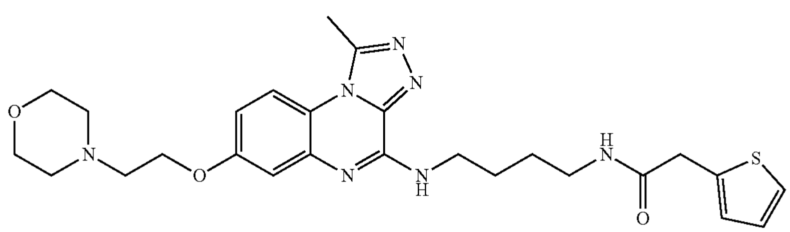 [SMILES: Cc1nnc2c(NCCCCNC(=O)Cc3cccs3)nc3cc(OCCN4CCOCC4)ccc3n12] | N-{4-[1-methyl-7-(2-morpholine-4-yl-ethoxy)-[1,2,4]triazolo[4,3-a]quinoxaline-4-ylamino]-butyl}-2-thiophene-2-yl-acetamide | Mass (M + H$^+$): 524.1; $^1$H NMR (500 MHz, DMSO-d6): δ1.47 (m, 2H), 1.63 (m, 2H), 2.46 (m, 4H), 2.69 (m, 2H), 2.95 (s, 3H), 3.08 (q, 2H), 3.52 (q, 2H), 3.55 (m, 4H), 3.56 (s, 2H), 4.14 (t, 2H), 6.83 (t, 1H), 6.86 (m, 2H), 7.08 (s, 1H), 7.29 (d, 1H), 7.94 (d, 1H), 8.02 (t, 1H), 8.09 (t, 1H). |

TABLE 26-continued

| Example | Structure | Name | Data |
|---|---|---|---|
| Example 439 | 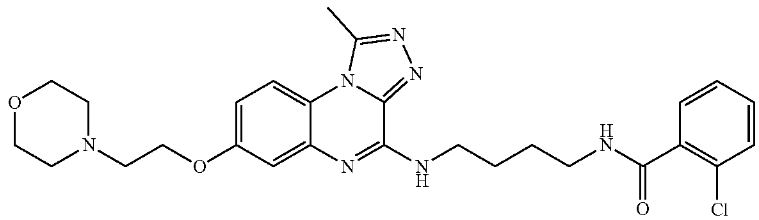 [SMILES: Cc1nnc2c(NCCCCNC(=O)c3ccccc3Cl)nc3cc(OCCN4CCOCC4)ccc3n12] | 2-chloro-N-{4-[1-methyl-7-(2-morpholine-4-yl-ethoxy)-[1,2,4]triazolo[4,3-a]quinoxaline-4-ylamino]-butyl}-benzamide | Mass (M + H⁺): 538.2; ¹H NMR (500 MHz, DMSO-d6): δ1.57 (m, 2H), 1.72 (m, 2H), 2.46 (m, 4H), 2.68 (t, 2H), 2.95 (s, 3H), 3.24 (t, 2H), 3.52 (m, 2H), 3.54 (t, 4H), 4.13 (t, 2H), 6.85 (dd, 1H), 7.09 (d, 1H), 7.29 (td, 1H), 7.33 (td, 1H), 7.37 (t, 1H), 7.41 (d, 1H), 7.94 (d, 1H), 8.12 (t, 1H), 8.36 (t, 1H). |

<Preparative Example 25> Preparation of [4-(3-hydrazino-7-ethoxy-quinoxaline-2-ylamino)-butyl]-carbamic acid-tert-butylester

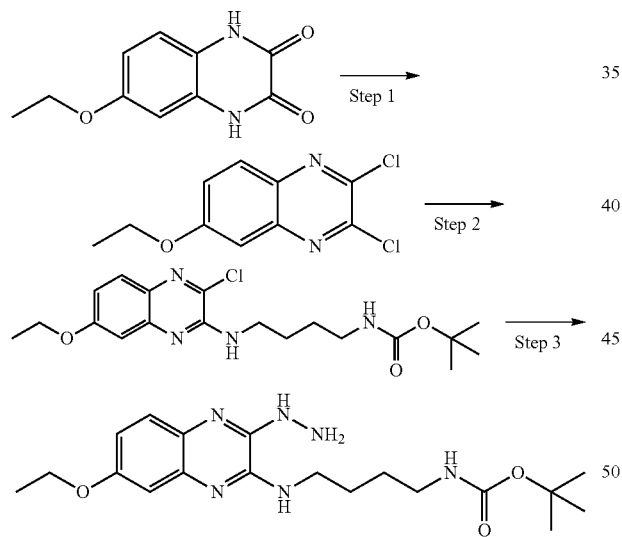

[4-(3-hydrazino-7-ethoxy-quinoxaline-2-ylamino)-butyl]-carbamic acid-tert-butylester, a target compound of Preparative Example 25, was obtained by the same manner as described in Preparative Example 20.

Step 1: Preparation of 2,3-dichloro-6-ethoxy-quinoxaline

Mass (M+H⁺): 243.0

¹H NMR (500 MHz, DMSO-d6): δ1.36 (t, 3H), 4.18 (q, 2H), 7.41 (d, 1H), 7.51 (d, 1H), 7.92 (d, 1H).

Step 2: Preparation of [4-(3-chloro-7-ethoxy-quinoxaline-2-ylamino)-butyl]-carbamic acid-tert-butylester Mass (M+H⁺): 395.1

¹H NMR (500 MHz, DMSO-d6): δ1.42 (m, 9H), 1.60 (m, 2H), 1.70 (m, 2H), 3.20 (s, 2H), 3.56 (q, 2H), 4.11 (m, 2H), 6.97 (m, 1H), 6.99 (m, 1H), 7.62 (d, 1H).

Step 3: Preparation of [4-(7-ethoxy-3-hydrazino-quinoxaline-2-ylamino)-butyl]-carbamic acid-tert-butylester Mass (M+H⁺): 391.2

<Example 440> Preparation of [4-(7-ethoxy-1-methyl-[1,2,4]triazolo[4,3-a]quinoxaline-4-ylamino)-butyl]-carbamic acid-tert-butylester

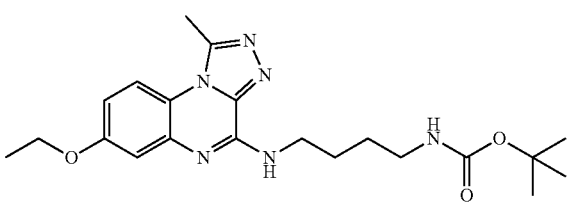 [SMILES: CCOc1ccc2c(c1)nc(NCCCCNC(=O)OC(C)(C)C)c1nnc(C)n12]

0.64 g a target compound was obtained (47% yield) by the same manner as described in step 3 of Preparative Example 5, except that [4-(7-ethoxy-3-hydrazino-quinoxaline-2-ylamino)-butyl]-carbamic acid-tert-butylester (1.28 g, 3.27 mmol) prepared in step 3 of Preparative Example 25 was used.

Mass (M+H⁺): 415.0

¹H NMR (500 MHz, CDCl₃): δ1.43 (m, 9H), 1.64 (m, 2H), 1.78 (m, 2H), 3.04 (s, 3H), 3.18 (m, 2H), 3.71 (m, 2H), 4.12 (m, 2H), 4.76 (s, 1H), 6.42 (s, 1H), 6.86 (d, 1H), 7.23 (s, 1H), 7.81 (d, 1H).

<Example 441> Preparation of N¹-(7-ethoxy-1-methyl-[1,2,4]triazolo[4,3-a]quinoxaline-4-yl)-butane-1,4-diamine dihydrochloride

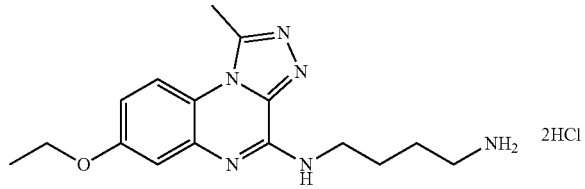 [SMILES: CCOc1ccc2c(c1)nc(NCCCCN)c1nnc(C)n12]

510 mg of a target compound was obtained (86% yield) by the same manner as described in Example 2, except that [4-(7-ethoxy-1-methyl-[1,2,4]triazolo[4,3-a]quinoxaline-4-ylamino)-butyl]-carbamic acid-tert-butylester (640 mg, 1.54 mmol) prepared in Example 440 was used.

¹H NMR (500 MHz, DMSO-d6) δ1.33 (t, 3H), 1.67 (m, 2H), 1.74 (m, 2H), 2.79 (m, 2H), 2.98 (s, 3H), 4.05 (m, 2H), 4.09 (m, 2H), 6.97 (t, 1H), 7.99 (m, 3H).

<Example 442> Preparation of N-[4-(7-ethoxy-1-methyl-[1,2,4]triazolo[4,3-a]quinoxaline-4-ylamino)-butyl]-3-methyl-butyramide

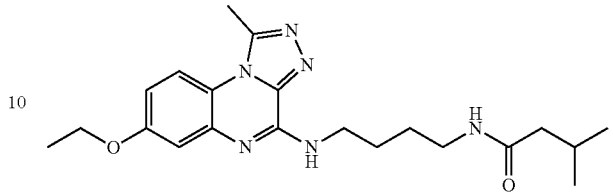

17 mg of a target compound was obtained (13% yield) by the same manner as described in Example 37, except that N¹-(7-ethoxy-1-methyl-[1,2,4]triazolo[4,3-a]quinoxaline-4-yl)-butane-1,4-diamine dihydrochloride (130 mg, 0.33 mmol) prepared in Example 441 was used.

Mass (M+H⁺): 399.2

¹H NMR (500 MHz, DMSO-d6): δ0.78 (d, 6H), 1.31 (m, 3H), 1.45 (m, 2H), 1.60 (m, 2H), 1.87 (m, 4H), 2.94 (s, 3H), 3.04 (m, 2H), 3.49 (m, 2H), 4.07 (m, 2H), 6.82 (d, 1H), 2.02 (s, 1H), 7.73 (m, 1H), 7.94 (d, 1H), 8.07 (m, 1H).

The compounds shown in Table 27 below were prepared by the same manner as described in Example 442.

TABLE 27

| Example | Structure | Name | Data |
| --- | --- | --- | --- |
| Example 443 | 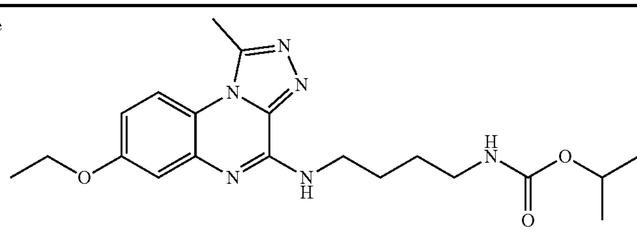 | [4-(7-ethoxy-1-methyl-[1,2,4]triazolo[4,3-a]quinoxaline-4-ylamino)-butyl]-carbamic acid isopropylester | Mass (M + H⁺): 401.2; ¹H NMR (500 MHz, DMSO-d6): δ1.09 (t, 6H), 1.31 (m, 3H), 1.59 (m, 2H), 1.60 (m, 2H), 2.94 (s, 3H), 2.98 (m, 2H), 3.49 (m, 2H), 4.05 (m, 2H), 4.67 (m, 1H), 6.81 (d, 1H), 6.94 (s, 1H), 7.03 (s, 1H), 7.91 (d, 1H), 8.06 (m, 1H). |
| Example 444 | 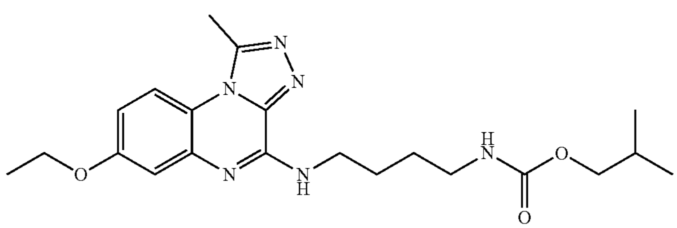 [SMILES: CCOc1ccc2c(c1)nc(NCCCCNC(=O)OCC(C)C)c1nnc(C)n12] | [4-(7-ethoxy-1-methyl-[1,2,4]triazolo[4,3-a]quinoxaline-4-ylamino)-butyl]-carbamic acid isobutylester | Mass (M + H⁺): 415.2; ¹H NMR (500 MHz, DMSO-d6): δ0.80 (d, 6H), 1.31 (t, 3H), 1.45 (m, 2H), 1.62 (m, 2H), 1.76 (m, 1H), 2.94 (s, 3H), 2.98 (m, 2H), 3.50 (m, 2H), 3.66 (m, 2H), 4.06 (m, 2H), 6.83 (d, 1H), 7.02 (s, 2H), 7.91 (s, 1H), 8.07 (m, 1H). |
| Example 445 | 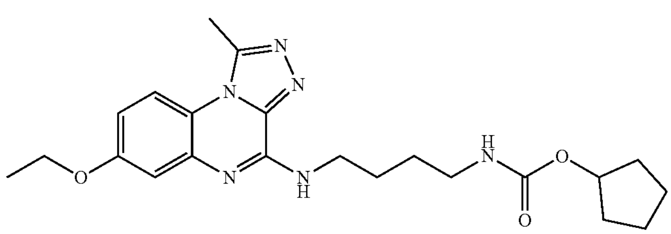 [SMILES: CCOc1ccc2c(c1)nc(NCCCCNC(=O)OC1CCCC1)c1nnc(C)n12] | [4-(7-ethoxy-1-methyl-[1,2,4]triazolo[4,3-a]quinoxaline-4-ylamino)-butyl]-carbamic acid cyclopentylester | Mass (M + H⁺): 427.2; ¹H NMR (500 MHz, DMSO-d6): δ1.31 (m, 3H), 1.31 (t, 3H), 1.44 (m, 8H), 1.60 (m, 2H), 1.70 (m, 2H), 2.94 (s, 3H), 2.97 (m, 2H), 3.49 (m, 2H), 4.06 (m, 2H), 4.87 (m, 1H), 6.82 (d, 1H), 6.90 (s, 1H), 7.02 (s, 1H), 7.91 (d, 1H), 8.06 (m, 1H). |

TABLE 27-continued

| Example | Structure | Name | Data |
|---|---|---|---|
| Example 446 | 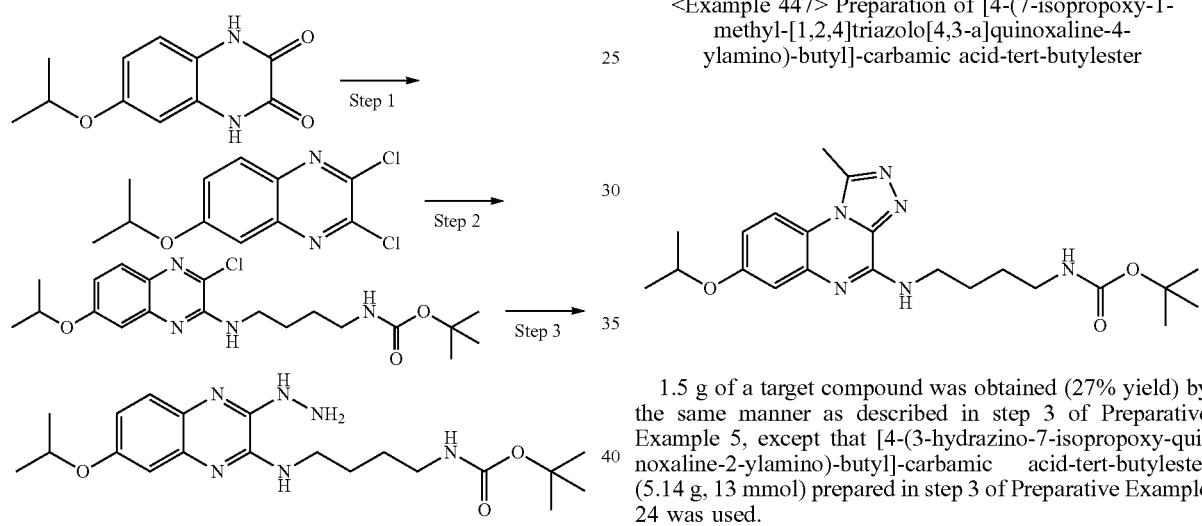 | N-[4-(7-ethoxy-1-methyl-[1,2,4]triazolo[4,3-a]quinoxaline-4-ylamino)-butyl]-2-thiophene-2-yl-acetamide | Mass (M + H$^+$): 439.2; $^1$H NMR (500 MHz, DMSO-d6): δ1.36 (t, 3H), 1.46 (m, 2H), 1.64 (m, 2H), 2.94 (s, 3H), 3.06 (m, 2H), 3.49 (m, 2H), 3.56 (m, 2H), 4.04 (q, 2H), 6.83 (m, 2H), 6.84 (m, 2H), 7.02 (s, 1H), 7.25 (s, 1H), 7.92 (d, 1H), 8.04 (m, 1H), 8.09 (m, 1H). |

<Preparative Example 26> Preparation of [4-(3-hydrazino-7-isopropoxy-quinoxaline-2-ylamino)-butyl]-carbamic acid-tert-butylester

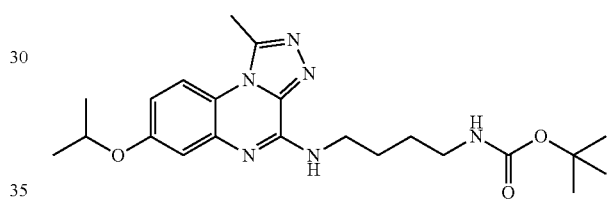

[4-(3-hydrazino-7-isopropoxy-quinoxaline-2-ylamino)-butyl]-carbamic acid-tert-butylester, a target compound of Preparative Example 26, was obtained by the same manner as described in Preparative Example 20.

Step 1: Preparation of 2,3-dichloro-6-isopropoxy-quinoxaline

Mass (M+H$^+$): 257.0

$^1$H NMR (500 MHz, DMSO-d6): δ1.33 (d, 6H), 4.86 (m, 1H), 7.44 (s, 1H), 7.49 (dd, 1H), 7.93 (d, 1H).

Step 2: Preparation of [4-(3-chloro-7-isopropoxy-quinoxaline-2-ylamino)-butyl]-carbamic acid-tert-butylester Mass (M+H$^+$): 409.2

$^1$H NMR (500 MHz, DMSO-d6): δ1.28 (d, 6H), 1.32 (s, 9H), 1.40 (m, 2H), 1.58 (m, 2H), 2.92 (m, 2H), 3.42 (m, 2H), 4.74 (m, 1H), 6.82 (t, 1H), 6.92 (d, 1H), 6.96 (s, 1H), 7.31 (t, 1H), 7.56 (d, 1H).

Step 3: Preparation of [4-(3-hydrazino-7-isopropoxy-quinoxaline-2-ylamino)-butyl]-carbamic acid-tert-butylester Mass (M+H$^+$): 405.1

<Example 447> Preparation of [4-(7-isopropoxy-1-methyl-[1,2,4]triazolo[4,3-a]quinoxaline-4-ylamino)-butyl]-carbamic acid-tert-butylester

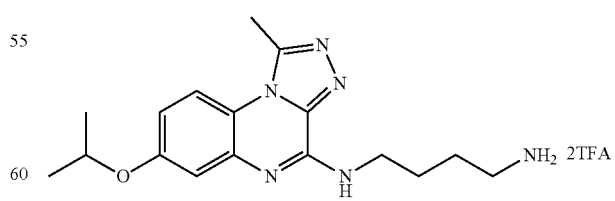

1.5 g of a target compound was obtained (27% yield) by the same manner as described in step 3 of Preparative Example 5, except that [4-(3-hydrazino-7-isopropoxy-quinoxaline-2-ylamino)-butyl]-carbamic acid-tert-butylester (5.14 g, 13 mmol) prepared in step 3 of Preparative Example 24 was used.

Mass (M+H$^+$): 429.0

$^1$H NMR (500 MHz, DMSO-d6): δ1.25 (s, 9H), 1.32 (d, 6H), 1.42 (m, 2H), 1.61 (m, 2H), 2.91 (q, 2H), 2.94 (s, 3H), 3.50 (q, 2H), 4.69 (m, 1H), 6.80 (t, 1H), 6.82 (d, 1H), 7.03 (s, 1H), 7.93 (d, 1H), 8.05 (t, 1H)

<Example 448> Preparation of N$^1$-(7-isopropoxy-1-methyl-[1,2,4]triazolo[4,3-a]quinoxaline-4-yl)-butane-1,4-diamine ditrifluoroacetic acid 1.3 g of a target compound was obtained (82% yield) by the same manner as described in Example 58, except that [4-(7-isopropoxy-1-methyl-[1,2,4]triazolo[4,3-a]quinoxaline-4-ylamino)-butyl]-carbamic acid-tert-butylester (1.3 g, 3.0 mmol) prepared in Example 447 was used.

Mass (M+H⁺): 329.2

¹H NMR (500 MHz, DMSO-d6): δ1.27 (d, 6H), 1.59 (m, 2H), 1.69 (m, 2H), 2.83 (q, 2H), 2.05 (s, 3H), 3.53 (q, 2H), 4.69 (m, 2H), 6.84 (d, 1H), 7.03 (s, 1H), 7.61 (brs, 2H), 7.36 (d, 1H), 8.19 (brs, 1H).

<Example 449> Preparation of N-[-(7-isopropoxy-1-methyl-[1,2,4]triazolo[4,3-a]quinoxaline-4-ylamino)-butyl]-3-methyl-butyramide

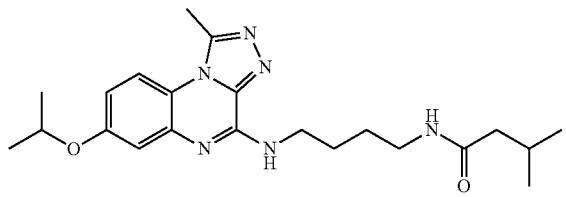

67 mg of a target compound was obtained (57% yield) by the same manner as described in Example 37, except that N¹-(7-isopropoxy-1-methyl-[1,2,4]triazolo[4,3-a]quinoxaline-4-yl)-butane-1,4-diamine ditrifluoroacetic acid (150 mg, 0.3 mmol) prepared in Example 448 was used.

Mass (M+H⁺): 413.2

¹H NMR (500 MHz, DMSO-d6) δ0.80 (d, 6H), 1.27 (d, 6H), 1.45 (m, 2H), 1.62 (m, 2H), 1.87 (d, 2H), 1.89 (m, 1H), 2.94 (s, 3H), 3.05 (q, 2H), 3.50 (q, 2H), 4.70 (m, 1H), 6.83 (d, 1H), 7.03 (s, 1H), 7.69 (t, 1H), 7.94 (d, 1H), 8.06 (t, 1H).

The compounds shown in Table 28 below were prepared by the same manner as described in Example 449.

TABLE 28

| Example | Structure | Name | Data |
|---|---|---|---|
| Example 450 | 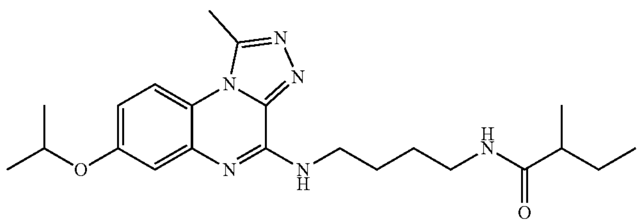 [SMILES: CCC(C)C(=O)NCCCCNc1nc2cc(OC(C)C)ccc2n2c(C)nnc12] | N-[4-(7-isopropoxy-1-methyl-[1,2,4]triazolo[4,3-a]quinoxaline-4-ylamino)-butyl]-2-methyl-butyramide | Mass (M + H⁺): 413.3; ¹H NMR (500 MHz, DMSO-d6): δ0.73 (t, 3H), 0.91 (d, 3H), 1.27 (m, 2H), 1.30 (d, 6H), 1.44 (m, 2H), 1.62 (m, 2H), 2.06 (m, 1H), 2.94 (s, 3H), 3.03 (q, 2H), 3.50 (q, 2H), 4.69 (m, 2H), 6.83 (d, 1H), 7.03 (s, 1H), 7.67 (t, 1H), 7.94 (d, 1H), 8.06 (t, 1H). |
| Example 451 | 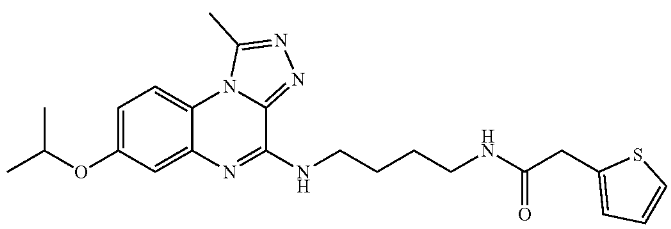 [SMILES: Cc1nnc2c(NCCCCNC(=O)Cc3cccs3)nc3cc(OC(C)C)ccc3n12] | N-[4-(7-isopropoxy-1-methyl-[1,2,4]triazolo[4,3-a]quinoxaline-4-ylamino)-butyl]-2-thiophene-2-yl-acetamide | Mass (M + H⁺): 453.2; ¹H NMR (500 MHz, DMSO-d6): δ1.26 (d, 6H), 1.47 (m, 2H), 1.63 (m, 2H), 2.94 (s, 3H), 3.06 (q, 2H), 3.31 (q, 2H), 3.56 (s, 2H), 4.69 (m, 1H), 6.83 (m, 1H), 6.87 (m, 2H), 7.04 (s, 1H), 7.26 (d, 1H), 7.94 (d, 1H), 8.02 (t, 1H), 8.06 (t, 1H). |
| Example 452 | 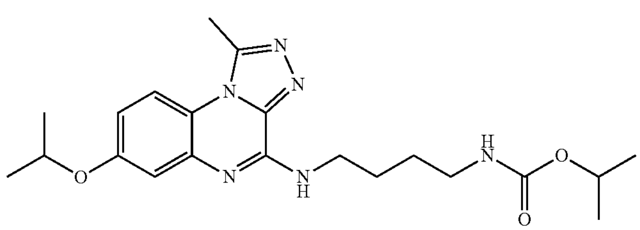 [SMILES: Cc1nnc2c(NCCCCNC(=O)OC(C)C)nc3cc(OC(C)C)ccc3n12] | [4-(7-isopropoxy-1-methyl-[1,2,4]triazolo[4,3-a]quinoxaline-4-ylamino)-butyl]-carbamic acid isopropylester | Mass (M + H⁺): 415.2; ¹H NMR (500 MHz, DMSO-d6): δ1.09 (d, 6H), 1.27 (d, 6H), 1.43 (m, 2H), 1.65 (m, 2H), 2.94 (s, 3H), 3.05 (q, 2H), 3.50 (q, 2H), 4.70 (m, 2H), 6.83 (d, 1H), 6.95 (t, 1H), 7.04 (s, 1H), 7.94 (d, 1H), 8.05 (t, 1H). |

TABLE 28-continued

| Example | Structure | Name | Data |
|---|---|---|---|
| Example 453 | 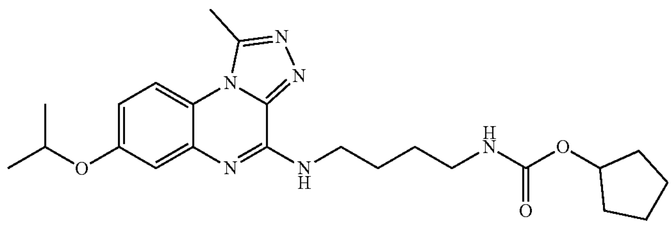 [SMILES: Cc1nnc2c(NCCCCNC(=O)OC3CCCC3)nc3cc(OC(C)C)ccc3n12] | [4-(7-isopropoxy-1-methyl-[1,2,4]triazolo[4,3-a]quinoxaline-4-ylamino)-butyl]-carbamic acid cyclopentyl ester | Mass (M + H$^+$): 441.2; $^1$H NMR (500 MHz, DMSO-d6): δ1.38 (m, 6H), 1.53 (m, 2H), 1.65 (m, 6H), 1.79 (m, 4H), 3.03 (s, 3H), 3.24 (s, 3H), 3.72 (q, 2H), 4.64 (m, 1H), 4.89 (m, 1H), 5.07 (t, 1H), 6.52 (t, 1H), 6.84 (d, 1H), 7.25 (s, 1H) 7.82 (d, 2H). |
| Example 454 | 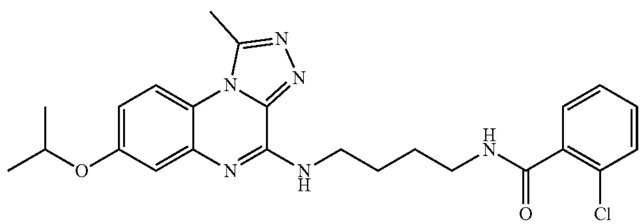 [SMILES: Cc1nnc2c(NCCCCNC(=O)c3ccccc3Cl)nc3cc(OC(C)C)ccc3n12] | 2-chloro-N-[4-(7-isopropoxy-1-methyl-[1,2,4]triazolo[4,3-a]quinoxaline-4-ylamino)-butyl]-benzamide | Mass (M + H$^+$): 467.2; $^1$H NMR (500 MHz, DMSO-d6): δ1.26 (d, 6H), 1.58 (m, 2H), 1.72 (m, 2H), 2.94 (s, 3H), 3.27 (q, 2H), 3.54 (q, 2H), 4.68 (m, 1H), 6.83 (d, 1H), 7.04 (s, 1H), 7.41 (m, 4H), 7.94 (d, 1H), 8.09 (t, 1H), 8.37 (t, 1H). |

<Preparative Example 27> Preparation of [4-(3-hydrazino-7-methoxy-5-methyl-quinoxaline-2-ylamino)-butyl]-carbamic acid-tert-butylester

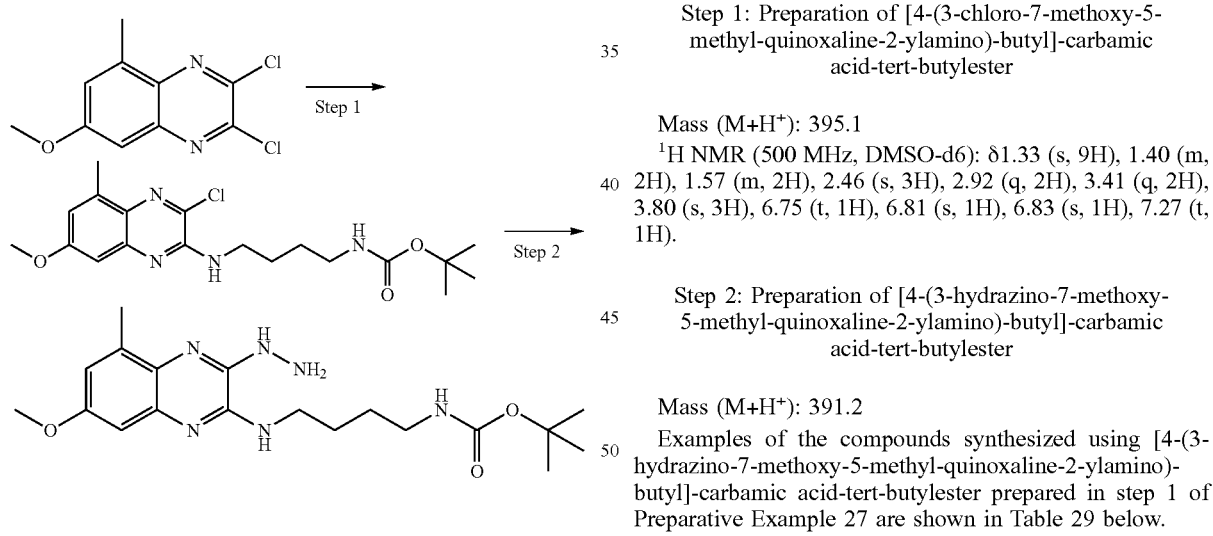

[4-(3-hydrazino-7-methoxy-5-methyl-quinoxaline-2-ylamino)-butyl]-carbamic acid-tert-butylester, a target compound of Preparative Example 27, was obtained by the same manner as described in Preparative Example 20.

Step 1: Preparation of [4-(3-chloro-7-methoxy-5-methyl-quinoxaline-2-ylamino)-butyl]-carbamic acid-tert-butylester Mass (M+H$^+$): 395.1
$^1$H NMR (500 MHz, DMSO-d6): δ1.33 (s, 9H), 1.40 (m, 2H), 1.57 (m, 2H), 2.46 (s, 3H), 2.92 (q, 2H), 3.41 (q, 2H), 3.80 (s, 3H), 6.75 (t, 1H), 6.81 (s, 1H), 6.83 (s, 1H), 7.27 (t, 1H).

Step 2: Preparation of [4-(3-hydrazino-7-methoxy-5-methyl-quinoxaline-2-ylamino)-butyl]-carbamic acid-tert-butylester Mass (M+H$^+$): 391.2

Examples of the compounds synthesized using [4-(3-hydrazino-7-methoxy-5-methyl-quinoxaline-2-ylamino)-butyl]-carbamic acid-tert-butylester prepared in step 1 of Preparative Example 27 are shown in Table 29 below.

TABLE 29

| Example | Structure | Name | Data |
|---|---|---|---|
| Example 455 | 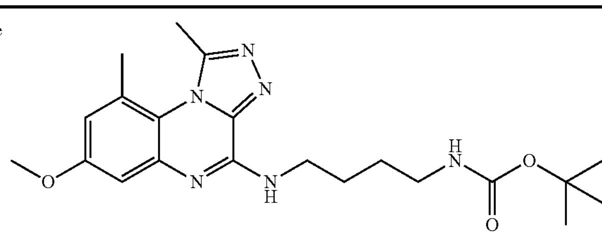 | [4-(7-methoxy-1,9-dimethyl-[1,2,4]triazolo[4,3-a]quinoxaline-4-ylamino)-butyl]-carbamic acid-tert-butylester | Mass (M + H$^+$): 415.2; $^1$H NMR (500 MHz, DMSO-d6): δ1.31 (s, 9H), 1.42 (m, 2H), 1.59 (m, 2H), 2.50 (s, 3H), 2.74 (s, 3H), 2.92 (q, 2H), 3.48 (q, 2H), 3.82 (s, 3H), 6.67 |

TABLE 29-continued

| Example | Structure | Name | Data |
|---|---|---|---|
| | | | (s, 1H), 6.75 (t, 1H), 6.88 (s, 1H), 8.05 (t, 1H). |
| Example 456 | 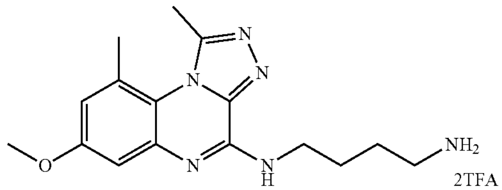 [SMILES: COc1cc(C)c2c(c1)nc(NCCCCN)c1nnc(C)n12 ; "2TFA"] | N¹-(7-methoxy-1,9-dimethyl-[1,2,4]triazolo[4,3-a]quinoxaline-4-yl)-butane-1,4-diamine ditrifluoroacetic acid | Mass (M + H⁺): 315.2; ¹H NMR (500 MHz, DMSO-d6): δ1.58 (m, 2H), 1.67 (m, 2H), 2.46 (s, 3H), 2.75 (s, 3H), 2.80 (m, 2H), 3.52 (q, 2H), 3.78 (s, 3H), 6.72 (s, 1H), 6.89 (s, 1H), 7.63 (brm, 2H), 8.25 (brm, 1H). |
| Example 457 | 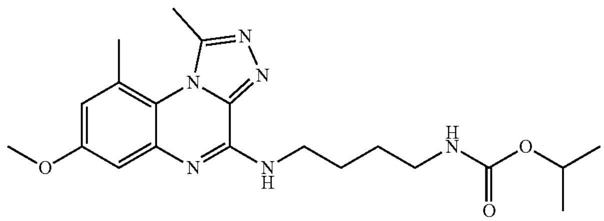 [SMILES: COc1cc(C)c2c(c1)nc(NCCCCNC(=O)OC(C)C)c1nnc(C)n12] | [4-(7-methoxy-1,9-dimethyl-[1,2,4]triazolo[4,3-a]quinoxaline-4-ylamino)-butyl]-carbamic acid-isopropylester | Mass (M + H⁺): 400.47; ¹H NMR (500 MHz, DMSO-d6): δ1.10 (d, 6H), 1.43 (m, 2H), 1.59 (m, 2H), 2.50 (s, 3H), 2.74 (s, 3H), 2.95 (q, 2H), 3.47 (q, 2H), 3.77 (s, 3H), 4.68 (m, 1H), 6.68 (s, 1H), 6.88 (s, 1H), 6.94 (t, 1H), 8.05 (t, 1H). |
| Example 458 | 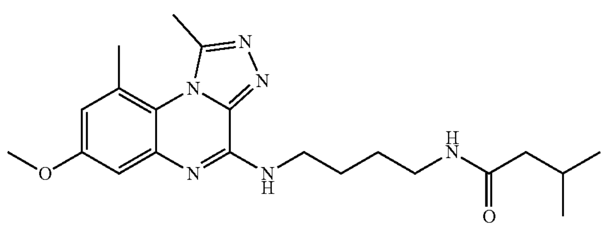 [SMILES: COc1cc(C)c2c(c1)nc(NCCCCNC(=O)CC(C)C)c1nnc(C)n12] | [4-(7-methoxy-1,9-dimethyl-[1,2,4]triazolo[4,3-a]quinoxaline-4-ylamino)-butyl]-3-methyl-butyramide | Mass (M + H⁺): 399.2; ¹H NMR (500 MHz, DMSO-d6): δ0.81 (d, 6H), 1.44 (m, 2H), 1.60 (m, 2H), 1.86 (d, 2H), 1.87 (m, 1H), 2.48 (s, 3H), 2.74 (s, 3H), 3.04 (q, 2H), 3.47 (q, 2H), 3.82 (s, 3H), 6.68 (s, 1H), 6.87 (s, 1H), 7.69 (t, 1H), 8.06 (t, 1H). |

<Preparative Example 28> Preparation of [4-(8-chloro-3-hydrazino-7-methoxy-quinoxaline-2-ylamino)-butyl]-carbamic acid-tert-butylester

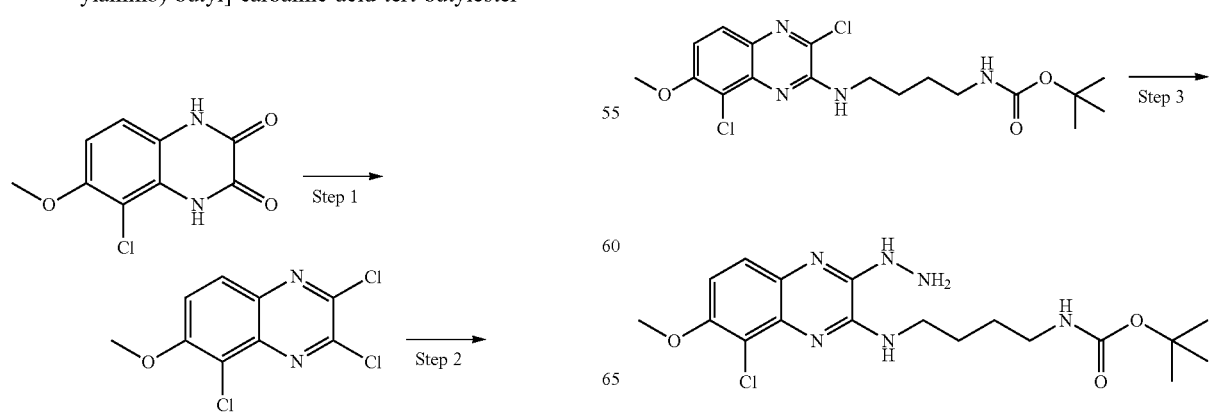

[4-(8-chloro-3-hydrazino-7-methoxy-quinoxaline-2-ylamino)-butyl]-carbamic acid-tert-butylester, a target compound of Preparative Example 28, was obtained by the same manner as described in Preparative Example 20.

Step 1: Preparation of 2,3,5-trichloro-6-methoxy-quinoxaline (M+H$^+$): 262.9

$^1$H NMR (500 MHz, DMSO-d6) δ4.06 (s, 3H), 7.92 (d, 1H), 8.04 (d, 1H).

Step 2: Preparation of [4-(3,8-dichloro-7-methoxy-quinoxaline-2-ylamino)-butyl]-carbamic acid-tert-butylester (M+H$^+$): 415.1
$^1$H NMR (500 MHz, DMSO-d6): δ1.42 (s, 3H), 1.62 (m, 2H), 1.76 (m, 2H), 3.19 (m, 2H), 3.65 (m, 2H), 4.01 (s, 3H), 4.65 (s, 1H), 5.76 (s, 1H), 7.10 (d, 1H), 7.65 (d, 1H).

Step 3: Preparation of [4-(8-chloro-3-hydrazino-7-methoxy-quinoxaline-2-ylamino)-butyl]-carbamic acid-tert-butylester (M+H$^+$): 411.2

Examples of the compounds synthesized using [4-(8-chloro-3-hydrazino-7-methoxy-quinoxaline-2-ylamino)-butyl]-carbamic acid-tert-butylester prepared in step 3 of Preparative Example 28 are shown in Table 30 below.

TABLE 30

| Example | Structure | Name | Data |
| --- | --- | --- | --- |
| Example 459 | 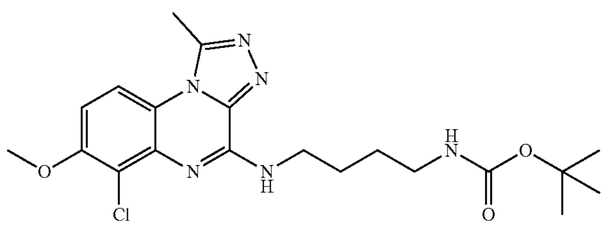 [SMILES: COc1ccc2c(nc(NCCCCNC(=O)OC(C)(C)C)c3nnc(C)n32)c1Cl] | [4-(6-chloro-7-methoxy-1-methyl-[1,2,4]triazolo[4,3-a]quinoxaline-4-ylamino)-butyl]-carbamic acid-tert-butylester | Mass (M + H$^+$): 435.2; $^1$HNMR (500 MHz, DMSO-d6): δ1.30 (m, 9H), 1.43 (m, 2H), 1.65 (m, 2H), 2.93 (m, 5H), 3.54 (m, 2H), 3.88 (s, 3H), 6.72 (s, 1H), 7.01 (d, 1H), 7.93 (d, 1H), 8.38 (s, 1H) |
| Example 460 | 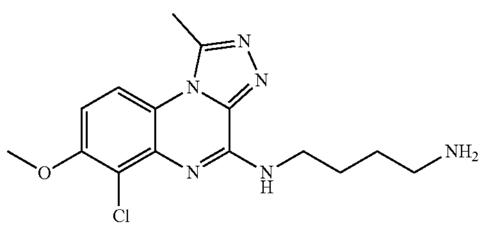 [SMILES: COc1ccc2c(nc(NCCCCN)c3nnc(C)n32)c1Cl] | [4-(6-chloro-7-methoxy-1-methyl-[1,2,4]triazolo[4,3-a]quinoxaline-4-yl)-butane-1,4-diamine dihydrochloride | Mass (M + H$^+$): 335.1; $^1$HNMR (500 MHz, DMSO-d6): δ1.62 (m, 2H), 1.72 (m, 2H), 2.82 (m, 2H), 2.97 (s, 3H), 3.58 (d, 2H), 3.89 (s, 3H), 7.05 (d, 1H), 7.95 (m, 4H), 8.48 (s, 1H) |
| Example 461 | 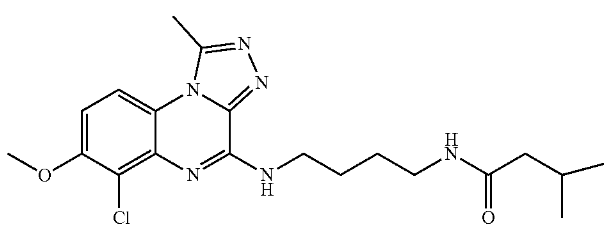 [SMILES: COc1ccc2c(nc(NCCCCNC(=O)CC(C)C)c3nnc(C)n32)c1Cl] | [4-(6-chloro-7-methoxy-1-methyl-[1,2,4]triazolo[4,3-a]quinoxaline-4-ylamino)-butyl]-3-methyl-butyramide | Mass (M + H$^+$): 419.2; $^1$HNMR (500 MHz, DMSO-d6): δ0.78 (m, 6H), 1.44 (m, 2H), 1.65 (m, 2H), 1.86 (m, 3H), 2.96 (s, 3H), 3.28 (m, 2H), 3.56 (m, 2H), 3.89 (s, 3H), 7.04 (d, 1H), 7.67 (s, 1H), 7.95 (d, 1H), 8.39 (t, 1H) |
| Example 462 | 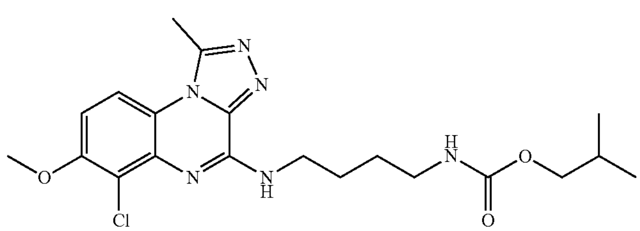 | [4-(6-chloro-7-methoxy-1-methyl-[1,2,4]triazolo[4,3-a]quinoxaline-4-ylamino)-butyl]-carbamic acid isobutylester | Mass (M + H$^+$): 459.1; $^1$HNMR (500 MHz, DMSO-d6): δ1.46 (m, 2H), 1.66 (m, 2H), 2.95 (s, 3H), 3.07 (m, 2H), 3.55 (m, 4H), 3.89 (m, 3H), 6.82 (s, 1H), 6.83 (m, 1H), 7.05 (d, 1H), 8.40 (t, 1H) |

TABLE 30-continued

| Example | Structure | Name | Data |
|---|---|---|---|
| Example 463 | 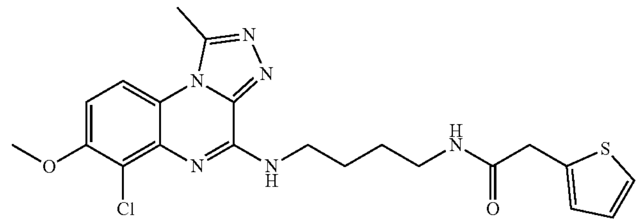 | N-[4-(6-chloro-7-methoxy-1-methyl-[1,2,4]triazolo[4,3-a]quinoxaline-4-ylamino)-butyl]-2-thiophene-2-yl-acetamide | Mass (M + H⁺): 435.2; ¹HNMR (500 MHz, DMSO-d6): δ0.80 (m, 6H), 1.45 (m, 2H), 1.65 (m, 2H), 1.67 (m, 1H), 2.95 (m, 5H), 3.57 (m, 2H), 3.65 (m, 2H), 3.88 (s, 3H), 7.01 (m, 2H), 7.92 (d, 1H), 8.40 (t, 1H) |

<Preparative Example 29>[Preparation of 4-(3-hydrazino-7-methoxy-6-methyl-quinoxaline-2-ylamino)-butyl]-carbamic acid-tert-butylester

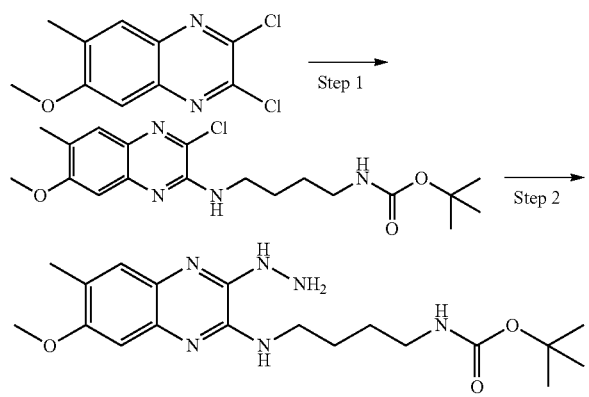

[4-(3-Hydrazino-7-methoxy-6-methyl-quinoxaline-2-ylamino)-butyl]-carbamic acid-tert-butylester, a target compound of Preparative Example 20, was obtained by the same manner as described in Preparative Example 20 using 2,3-dichloro-6-methoxy-7-methyl-quinoxaline prepared in step 1 of Preparative Example 11.

Step 1: Preparation of [4-(3-chloro-7-methoxy-6-methyl-quinoxaline-2-ylamino)-butyl]-carbamic acid-tert-butylester Mass (M+H⁺): 395.1
¹H NMR (500 MHz, DMSO-d6) δ1.33 (s, 9H), 1.40 (m, 2H), 1.55 (m, 2H), 2.21 (s, 3H), 2.92 (q, 2H), 3.39 (q, 2H), 3.87 (s, 3H), 6.74 (t, 1H), 6.96 (s, 1H), 7.19 (t, 1H), 7.44 (s, 1H).

Step 2: Preparation of [4-(3-hydrazino-7-methoxy-6-methyl-quinoxaline-2-ylamino)-butyl]-carbamic acid-tert-butylester Mass (M+H⁺): 391.2

<Example 464> Preparation of [4-(7-methoxy-1,8-dimethyl-[1,2,4]triazolo[4,3-a]quinoxaline-4-ylamino)-butyl]-carbamic acid-tert-butylester

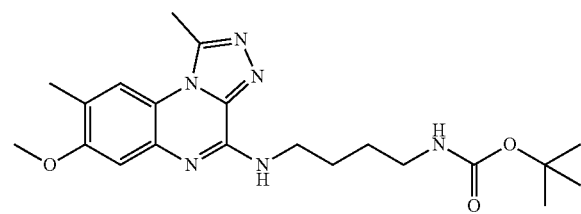 [SMILES: COc1cc2nc(NCCCCNC(=O)OC(C)(C)C)c3nnc(C)n3c2cc1C]

1.1 g of a target compound was obtained (86% yield) by the same manner as described in step 2 of Preparative Example 1, except that [4-(3-hydrazino-7-methoxy-6-methyl-quinoxaline-2-ylamino)-butyl]-carbamic acid-tert-butylester (1.2 g, 3.1 mmol) prepared in step 2 of Preparative Example 29 was used.

Mass (M+H⁺): 415.2
¹H NMR (500 MHz, DMSO-d6) δ1.32 (s, 9H), 1.43 (m, 2H), 1.60 (m, 2H), 2.24 (s, 3H), 2.90 (q, 2H), 2.96 (s, 3H), 3.48 (q, 2H), 3.84 (s, 3H), 6.75 (t, 1H), 7.05 (s, 1H), 7.80 (s, 1H), 7.90 (t, 1H).

<Example 465> Preparation of N¹-(7-methoxy-1,8-dimethyl-[1,2,4]triazolo[4,3-a]quinoxaline-4-yl)-butane-1,4-diamine ditrifluoroacetic acid

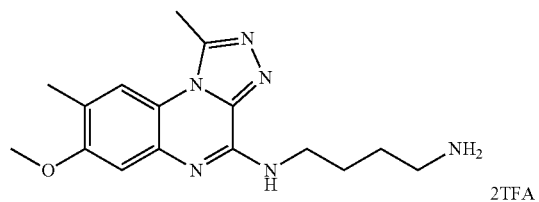 [SMILES: COc1cc2nc(NCCCCN)c3nnc(C)n3c2cc1C]

0.91 g of a target compound was obtained (70% yield) by the same manner as described in Example 58, except that [4-(7-methoxy-1,8-dimethyl-[1,2,4]triazolo[4,3-a]quinoxaline-4-ylamino)-butyl]-carbamic acid-tert-butylester (1.0 g, 2.4 mmol) prepared in Example 464 was used.

Mass (M+H⁺): 315.1
¹H NMR (500 MHz, DMSO-d6): δ1.60 (m, 2H), 1.69 (m, 2H), 2.25 (s, 3H), 2.82 (m, 2H), 2.98 (s, 3H), 3.53 (q, 2H), 3.84 (s, 3H), 7.04 (s, 1H), 7.63 (brm, 3H), 7.83 (s, 1H), 8.07 (brm, 1H).

<Example 466> Preparation of N-[4-(7-methoxy-1,8-dimethyl-[-[1,2,4]triazolo[4,3-a]quinoxaline-4-ylamino)-butyl]-2,2-dimethyl-propionamide

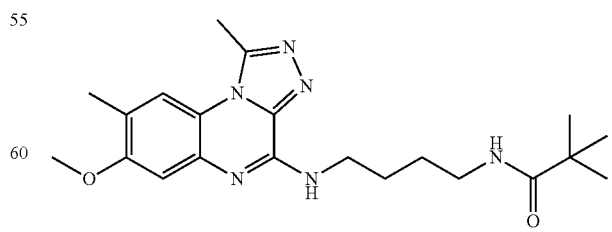

62 mg of a target compound was obtained (70% yield) by the same manner as described in Example 59, except that N¹-(7-methoxy-1,8-dimethyl-[1,2,4]triazolo[4,3-a]quinoxaline-4-yl)-butane-1,4-diamine ditrifluoroacetic acid (120 mg, 0.22 mmol) prepared in Example 465 was used.

Mass (M+H⁺): 399.2

¹H NMR (500 MHz, DMSO-d6) δ1.02 (s, 9H), 1.45 (m, 2H), 1.60 (m, 2H), 2.24 (s, 3H), 2.97 (s, 3H), 3.04 (q, 2H), 3.49 (q, 2H), 3.84 (s, 3H), 7.04 (s, 1H), 7.37 (t, 1H), 7.81 (s, 1H), 7.94 (t, 1H).

The compounds shown in Table 31 below were prepared by the same manner as described in Example 466.

TABLE 31

| Example | Structure | Name | Data |
|---------|-----------|------|------|
| Example 467 | 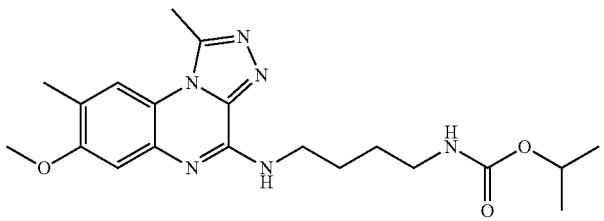 [SMILES: COc1cc2nc(NCCCCNC(=O)OC(C)C)c3nnc(C)n3c2cc1C] | [4-(7-methoxy-1,8-dimethyl-[1,2,4]triazolo[4,3-a]quinoxaline-4-ylamino)-butyl]-carbamic acid isopropylester | Mass (M + H⁺): 401.1; ¹HNMR (500 MHz, DMSO-d6): δ1.09 (d, 6H), 1.45 (m, 2H), 1.61 (m, 2H), 2.24 (s, 3H), 2.96 (s, 3H + m, 2H), 3.49 (q, 2H), 3.84 (s, 3H), 4.68 (m, 1H), 6.95 (t, 1H), 7.05 (s, 1H), 7.80 (s, 1H), 7.94 (t, 1H). |
| Example 468 | 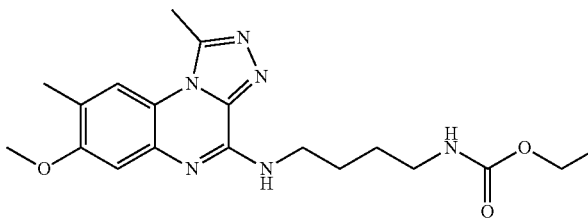 | [4-(7-methoxy-1,8-dimethyl-[1,2,4]triazolo[4,3-a]quinoxaline-4-ylamino)-butyl]-carbamic acid isobutylester | Mass (M + H⁺): 415.1; ¹HNMR (500 MHz, DMSO-d6): δ0.81 (d, 6H), 1.44 (m, 2H), 1.61 (m, 2H), 1.76 (m, 1H), 2.97 (s, 3H), 2.98 (m, 2H), 3.48 (q, 2H), 3.66 (q, 2H), 3.84 (s, 3H), 7.04 (s + t, 2H), 7.81 (s, 1H), 7.94 (t, 1H). |
| Example 469 | 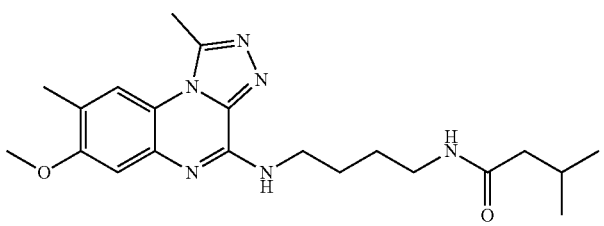 [SMILES: COc1cc2nc(NCCCCNC(=O)CC(C)C)c3nnc(C)n3c2cc1C] | N-[4-(7-methoxy-1,8-dimethyl-[1,2,4]triazolo[4,3-a]quinoxaline-4-ylamino)-butyl]-3-methyl-butyramide | Mass (M + H⁺): 399.2; ¹HNMR (500 MHz, DMSO-d6): δ0.80 (d, 6H), 1.44 (m, 2H), 1.61 (m, 2H), 1.87 (d, 2H), 1.90 (m, 1H), 2.24 (s, 3H), 2.96 (s, 3H), 3.04 (q, 2H), 3.48 (q, 2H), 3.84 (s, 3H), 7.04 (s, 1H), 7.70 (t, 1H), 7.80 (s, 1H), 7.94 (t, 1H). |
| Example 470 | 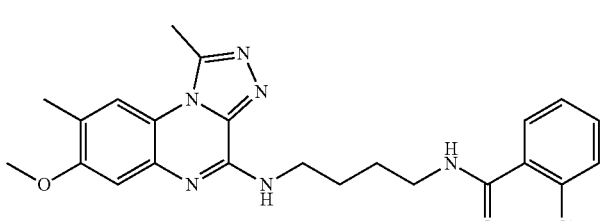 | 2-chloro-N-[4-(7-methoxy-(1,8-dimethyl-[1,2,4]triazolo[4,3-a]quinoxaline-4-ylamino)-butyl]-benzamide | Mass (M + H⁺): 453.2; ¹HNMR (500 MHz, DMSO-d6): δ1.57 (brm, 2H), 1.72 (brm, 2H), 2.24 (s, 3H), 2.97 (s, 3H), 3.26 (q, 2H), 3.52 (m, 2H), 3.83 (s, 3H), 7.05 (s, 1H), 7.32 (m, 3H), 7.41 (m, 1H), 7.80 (s, 1H), 7.97 (t, 1H), 8.36 (t, 1H). |

<Preparative Example 30> Preparation of [4-(3-hydrazino-7-methoxy-6-trifluoromethyl-quinoxaline-2-ylamino)-butyl]-carbamic acid-tert-butylester

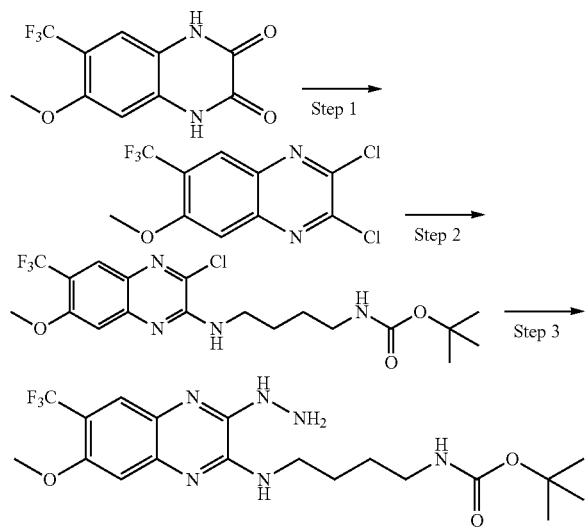

[4-(3-Hydrazino-7-methoxy-6-trifluoromethyl-quinoxaline-2-ylamino)-butyl]-carbamic acid-tert-butylester, a target compound of Preparative Example 30, was obtained by the same manner as described in Preparative Example 20.

Step 1: Preparation of 2,3-dichloro-6-methoxy-7-trifluoromethyl-quinoxaline $^1$H NMR (500 MHz, DMSO-d6): δ4.04 (s, 3H), 7.75 (s, 1H), 8.37 (s, 1H).

Step 2: Preparation of [4-(3-chloro-7-methoxy-6-trifluoromethyl-quinoxaline-2-ylamino)-butyl]-carbamic acid tert-butylester Mass (M+H$^+$): 449.1
$^1$H NMR (500 MHz, DMSO-d6) δ1.31 (s, 9H), 1.40 (m, 2H), 1.58 (m, 2H), 2.91 (q, 2H), 3.44 (m, 2H), 3.95 (s, 3H), 6.74 (t, 1H), 7.17 (s, 1H), 7.79 (t, 1H), 7.90 (s, 1H)

Step 3: Preparation of [4-(3-hydrazino-7-methoxy-6-trifluoromethyl-quinoxaline-2-ylamino)-butyl]-carbamic acid-tert-butylester Mass (M+H$^+$): 445.1

Examples of the compounds synthesized using [4-(3-hydrazino-7-methoxy-6-trifluoromethyl-quinoxaline-2-ylamino)-butyl]-carbamic acid-tert-butylester prepared in step 3 of Preparative Example 30 are shown in Table 32 below.

TABLE 32

| Example | Structure | Name | Data |
|---|---|---|---|
| Example 471 | 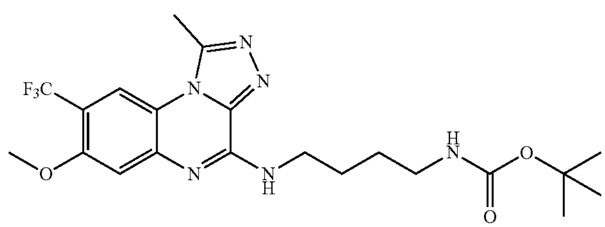 [SMILES: COc1cc2nc(NCCCCNC(=O)OC(C)(C)C)c3nnc(C)n3c2cc1C(F)(F)F] | [4-(7-methoxy-1-methyl-8-trifluoromethyl-[1,2,4]triazolo[4,3-a]quinoxaline-4-ylamino)-butyl]-carbamic acid-tert-butylester | Mass (M + H$^+$): 469.2; $^1$H NMR (500 MHz, DMSO-d6): δ1.32 (s, 9H), 1.44 (m, 2H), 1.62 (m, 2H), 2.92 (q, 2H), 2.98 (s, 3H), 3.53 (q, 2H), 3.93 (s, 3H), 6.75 (t, 1H), 7.26 (s, 1H), 8.09 (s, 1H), 8.56 (t, 1H). |
| Example 472 | 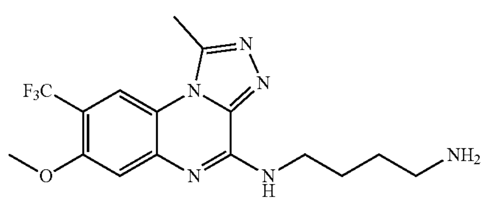 | N$^1$-(7-methoxy-1-methyl-8-trifluoromethyl-[1,2,4]triazolo[4,3-a]quinoxaline-4-yl)-butane-1,4-diamine ditrifluoro acetic acid | Mass (M + H$^+$): 369.1; $^1$H NMR (500 MHz, DMSO-d6): δ1.59 (m, 2H), 1.70 (m, 2H), 2.82 (m, 2H), 2.99 (s, 3H), 3.57 (q, 2H), 3.93 (s, 3H), 7.24 (s, 1H), 7.61 (brm, 2H), 8.11 (s, 1H), 8.61 (t, 1H). |
| Example 473 | 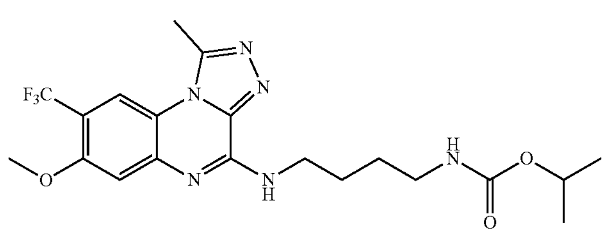 [SMILES: COc1cc2nc(NCCCCNC(=O)OC(C)C)c3nnc(C)n3c2cc1C(F)(F)F] | [4-(7-methoxy-1-methyl-8-trifluoromethyl-[1,2,4]triazolo[4,3-a]quinoxaline-4-ylamino)-butyl]-carbamic acid isopropylester | Mass (M + H$^+$): 455.2; $^1$H NMR (500 MHz, DMSO-d6): δ1.10 (d, 6H), 1.45 (m, 2H), 1.62 (m, 2H), 2.96 (m, 2H), 2.99 (s, 3H), 3.54 (q, 2H), 3.93 (s, 3H), 4.68 (m, 1H), 6.96 (t, 1H), 7.26 (s, 1H), 8.09 (s, 1H), 8.56 (t, 1H). |

TABLE 32-continued

| Example | Name | Data |
|---|---|---|
| Example 474 | [4-(7-methoxy-1-methyl-8-trifluoromethyl-[1,2,4]triazolo[4,3-a]quinoxaline-4-ylamino)-butyl]-carbamic acid isobutylester | Mass (M + H⁺): 469.2; ¹H NMR (500 MHz, DMSO-d6): δ0.81 (d, 6H), 1.45 (m, 2H), 1.63 (m, 2H), 1.76 (m, 1H), 2.97 (m, 2H), 2.99 (s, 3H), 3.53 (q, 2H), 3.65 (d, 2H), 3.93 (s, 3H), 7.03 (t, 1H), 7.26 (s, 1H), 8.09 (s, 1H), 8.56 (t, 1H). |
| Example 475 | [4-(7-methoxy-1-methyl-8-trifluoromethyl-[1,2,4]triazolo[4,3-a]quinoxaline-4-ylamino)-butyl]-carbamic acid cyclopentyl ester | Mass (M + H⁺): 481.2; ¹H NMR (500 MHz, DMSO-d6): δ1.38~1.55 (m, 8H), 1.62 (m, 2H), 1.73 (m, 2H), 2.95 (m, 2H), 2.98 (s, 1H), 3.53 (q, 2H), 3.93 (s, 3H), 4.68 (m, 2H), 6.94 (t, 1H), 7.25 (s, 1H), 8.08 (s, 1H), 8.56 (t, 1H). |
| Example 476 | N-[4-(7-methoxy-1-methyl-8-trifluoromethyl-[1,2,4]triazolo[4,3-a]quinoxaline-4-ylamino)-butyl]-3-methyl-butyramide | Mass (M + H⁺): 453.3; ¹H NMR (500 MHz, DMSO-d6): δ0.79 (d, 6H), 1.44 (m, 2H), 1.64 (m, 2H), 1.87 (d, 2H), 1.89 (m, 1H), 2.98 (s, 3H), 3.05 (q, 2H), 3.53 (q, 2H), 3.93 (s, 3H), 7.26 (s, 1H), 7.70 (t, 1H), 8.09 (s, 1H), 8.57 (t, 1H). |
| Example 477 | N-[4-(7-methoxy-1-methyl-8-trifluoromethyl-[1,2,4]triazolo[4,3-a]quinoxaline-4-ylamino)-butyl]-2,2-dimethyl-propionamide | Mass (M + H⁺): 453.2; ¹H NMR (500 MHz, DMSO-d6): δ1.02 (s, 9H), 1.45 (m, 2H), 1.62 (m, 2H), 2.98 (s, 3H), 3.04 (q, 2H), 3.53 (q, 2H), 3.93 (s, 3H), 7.25 (s, 1H), 7.38 (t, 1H), 8.09 (s, 1H), 8.56 (t, 1H). |
| Example 478 | 2-(R)-hydroxy-N-[4-(7-methoxy-1-methyl-8-trifluoromethyl-[1,2,4]triazolo[4,3-a]quinoxaline-4-ylamino)-butyl]-3-methyl-butyramide | Mass (M + H⁺): 469.2; ¹H NMR (500 MHz, DMSO-d6): δ0.68 (d, 3H), 0.83 (d, 3H), 1.47 (m, 2H), 1.63 (m, 2H), 1.91 (m, 1H), 2.97 (s, 3H), 3.06 (m, 1H), 3.13 (m, 1H), 3.53 (q, 2H), 3.60 (t, 1H), 3.93 (s, 3H), 5.24 (d, 1H), 7.25 (s, 1H), 7.65 (t, 1H), 8.58 (t, 1H). |

TABLE 32-continued

| Example | Structure | Name | Data |
|---|---|---|---|
| Example 479 | 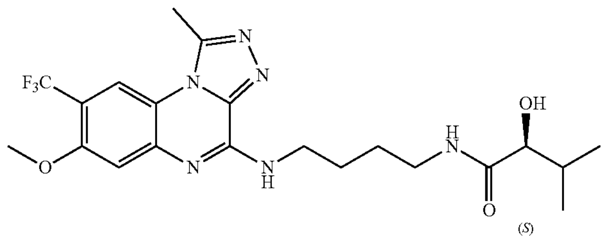 | 2-(S)-hydroxy-N-[4-(7-methoxy-1-methyl-8-trifluoromethyl-[1,2,4]triazolo[4,3-a]quinoxaline-4-ylamino)-butyl]-3-methyl-butyramide | Mass (M + H⁺): 469.2; ¹H NMR (500 MHz, DMSO-d6): δ0.68 (d, 3H), 0.83 (d, 3H), 1.47 (m, 2H), 1.63 (m, 2H), 1.91 (m, 1H), 2.97 (s, 3H), 3.06 (m, 1H), 3.13 (m, 1H), 3.53 (q, 2H), 3.60 (t, 1H), 3.93 (s, 3H), 5.24 (d, 1H), 7.25 (s, 1H), 7.65 (t, 1H), 8.58 (t, 1H). |
| Example 480 | 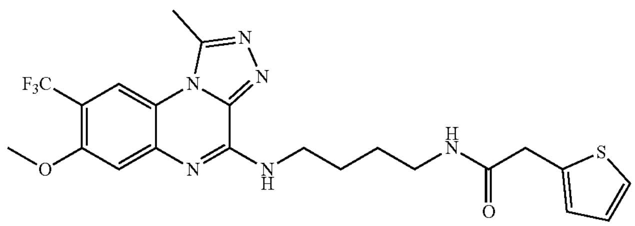 | N-[4-(7-methoxy-1-methyl-8-trifluoromethyl-[1,2,4]triazolo[4,3-a]quinoxaline-4-ylamino)-butyl]-2-thiophene-2-yl-acetamide | Mass (M + H⁺): 493.1; ¹H NMR (500 MHz, DMSO-d6): δ1.47 (m, 2H), 1.64 (m, 2H), 2.98 (s, 3H), 3.08 (q, 2H), 3.54 (q, 2H), 3.56 (s, 2H), 3.92 (s, 3H), 6.83 (s, 1H), 6.87 (d, 1H), 7.26 (s + d, 2H), 8.02 (t, 1H), 8.90 (s, 1H), 8.57 (t, 1H). |
| Example 481 | 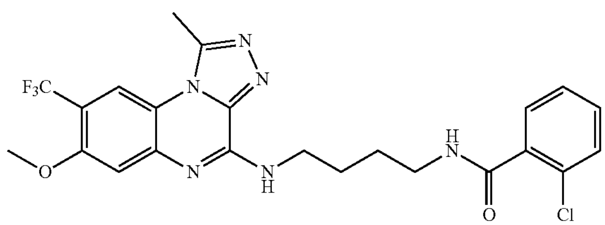 [SMILES: COc1cc2nc(NCCCCNC(=O)c3ccccc3Cl)c3nnc(C)n3c2cc1C(F)(F)F] | 2-chloro-N-[4-(7-methoxy-1-methyl-8-trifluoromethyl-[1,2,4]triazolo[4,3-a]quinoxaline-4-ylamino)-butyl]-benzamide | Mass (M + H⁺): 507.1; ¹H NMR (500 MHz, DMSO-d6): δ1.57 (m, 2H), 1.73 (m, 2H), 2.98 (s, 3H), 3.23 (q, 2H), 3.25 (s, 3H), 3.58 (q, 2H), 3.92 (s, 3H), 7.27 (s, 1H), 7.29~7.42 (m, 4H), 8.10 (s, 2H), 8.36 (t, 1H), 8.60 (t, 1H). |
| Example 482 | 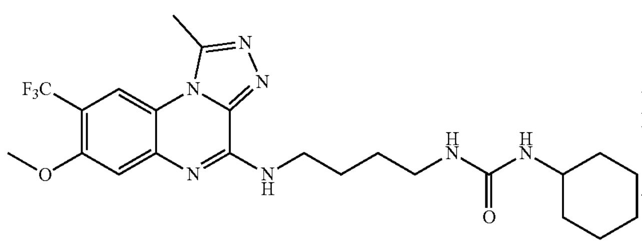 | 1-cyclohexyl-3-[4-(7-methoxy-1-methyl-8-trifluoromethyl-[1,2,4]triazolo[4,3-a]quinoxaline-4-ylamino)-butyl]-urea | Mass (M + H⁺): 494.2; ¹H NMR (500 MHz, DMSO-d6): δ0.98 (m, 2H), 1.04 (m, 1H), 1.18 (m, 2H), 1.40 (m, 2H), 1.49 (m, 2H), 1.54 (m, 2H), 1.62 (m, 2H), 1.69 (m, 2H), 2.96 (m, 2H), 2.98 (s, 3H), 3.54 (q, 2H), 3.93 (s, 3H), 5.59 (d, 1H), 5.64 (t, 1H), 7.27 (s, 1H), 8.09 (s, 1H), 8.57 (t, 1H). |

<Preparative Example 31> Preparation of 4-chloro-7-methoxy-8-(2-methoxy-ethoxy)-1-methyl-[1,2,4]triazolo[4,3-a]quinoxaline

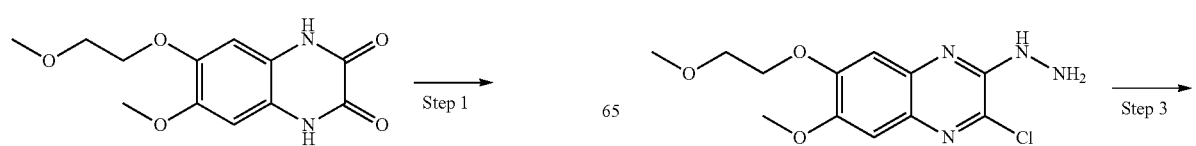

303
-continued

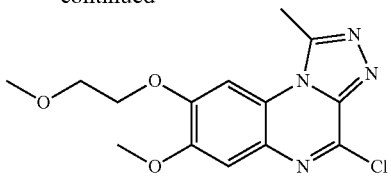

4-Chloro-8-methoxy-7-(2-methoxy-ethoxy)-1-methyl-[1,2,4]triazolo[4,3-a]quinoxaline, a target compound of Preparative Example 31, was obtained by the same manner as described in Preparative Example 5.

Step 1: Preparation of 2,3-chloro-6-methoxy-7-(2-methoxy-ethoxy)-quinoxaline Mass (M+H$^+$): 267.0
$^1$H NMR (500 MHz, DMSO-d6) δ3.27 (s, 3H), 3.61 (t, 2H), 3.69 (s, 3H), 3.95 (t, 2H), 6.69 (s, 2H), 11.66 (s, 1H), 11.67 (s, 1H).

Step 2: Preparation of [3-chloro-6-methoxy-7-(2-methoxy-ethoxy)-quinoxaline-2-yl]-hydrazine Mass (M+H$^+$): 303.0
$^1$H NMR (500 MHz, DMSO-d6) δ3.30 (s, 3H), 3.71 (t, 2H), 3.95 (s, 3H), 4.28 (t, 2H), 7.42 (s, 1H), 7.44 (s, 1H).

Step 3: Preparation of 4-chloro-7-methoxy-8-(2-methoxy-ethoxy)-1-methyl-[1,2,4]triazolo[4,3-a]quinoxaline Mass (M+H$^+$): 323.1
$^1$H NMR (500 MHz, DMSO-d6): δ3.13 (s, 3H), 3.28 (s, 3H), 3.68 (t, 2H), 4.00 (s, 3H), 4.21 (t, 2H), 7.50 (s, 1H), 7.64 (s, 1H).

<Example 483> Preparation of {4-[7-methoxy-8-(2-methoxy-ethoxy)-1-methyl-[1,2,4]triazolo[4,3-a]quinoxaline-4-ylamino]-butyl}-carbamic acid-tert-butylester

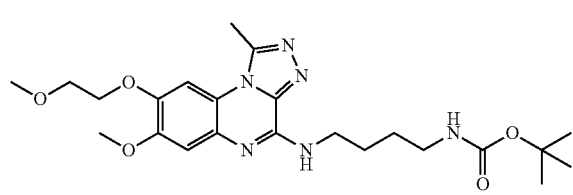 [SMILES: COCCOc1cc2c(cc1OC)nc(NCCCCNC(=O)OC(C)(C)C)c1nnc(C)n12]

0.17 g of a target compound was obtained (26% yield) by the same manner as described in Example 57, except that 4-chloro-7-methoxy-8-(2-methoxy-ethoxy)-1-methyl-[1,2,4]triazolo[4,3-a]quinoxaline prepared in step 3 of Preparative Example 31 was used.

Mass (M+H$^+$): 475.2
$^1$H NMR (500 MHz, DMSO-d6) δ1.32 (s, 9H), 1.42 (m, 2H), 1.60 (m, 2H), 2.92 (q, 2H), 3.01 (s, 3H), 3.31 (s, 3H), 3.47 (q, 2H), 3.68 (t, 2H), 3.83 (s, 3H), 4.20 (t, 2H), 6.75 (t, 1H), 7.09 (s, 1H), 7.54 (s, 1H), 7.80 (t, 1H)

304

<Example 484> Preparation of N$^1$-[7-methoxy-8-(2-methoxy-ethoxy)-1-methyl-[1,2,4]triazolo[4,3-a]quinoxaline-4-yl]-butane-1,4-diamine ditrifluoroacetic acid

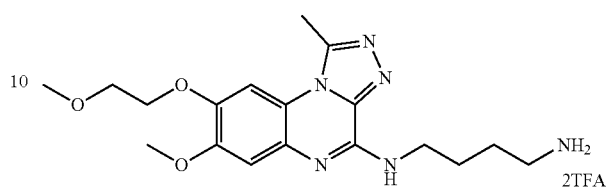

0.13 g of a target compound was obtained (84% yield) by the same manner as described in Example 58, except that {4-[7-methoxy-8-(2-methoxy-ethoxy)-1-methyl-[1,2,4]triazolo[4,3-a]quinoxaline-4-ylamino]-butyl}-carbamic acid-tert-butylester prepared in Example 483 was used.

Mass (M+H$^+$): 375.0
$^1$H NMR (500 MHz, DMSO-d6): δ1.59 (m, 2H), 1.68 (m, 2H), 2.82 (m, 2H), 3.31 (s, 3H), 3.52 (q, 2H), 3.69 (t, 2H), 3.83 (s, 3H), 4.21 (t, 2H), 7.09 (s, 1H), 7.57 (s, 1H), 7.63 (brm, 2H), 7.94 (brs, 1H)

<Example 485> Preparation of N-{4-[7-methoxy-8-(2-methoxy-ethoxy)-1-methyl-[1,2,4]triazolo[4,3-a]quinoxaline-4-ylamino]-butyl}-3-methyl-butyramide

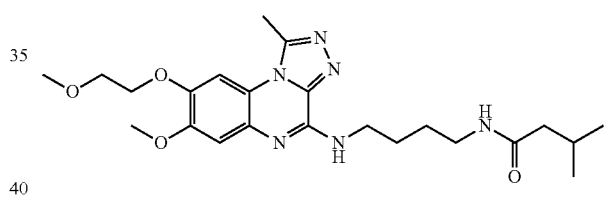

0.05 g of a target compound was obtained (81% yield) by the same manner as described in Example 65, except that N$^1$-[7-methoxy-8-(2-methoxy-ethoxy)-1-methyl-[1,2,4]triazolo[4,3-a]quinoxaline-4-yl]-butane-1,4-diamine ditrifluoroacetic acid prepared in Example 484 was used.

Mass (M+H$^+$): 459.2
$^1$H NMR (500 MHz, DMSO-d6) δ0.79 (d, 6H), 1.45 (m, 2H), 1.62 (m, 2H), 1.86 (m, 2H), 1.91 (m, 1H), 3.01 (s, 3H), 3.04 (m, 2H), 3.31 (s, 3H), 3.47 (q, 2H), 3.68 (t, 2H), 3.83 (s, 3H), 4.21 (t, 2H), 7.10 (s, 1H), 7.56 (s, 1H), 7.70 (t, 1H), 7.82 (t, 1H).

<Preparative Example 32> Preparation of [4-(3-hydrazino-5,6,7-trimethoxy-quinoxaline-2-ylamino)butyl]-carbamic acid-tert-butyl ester

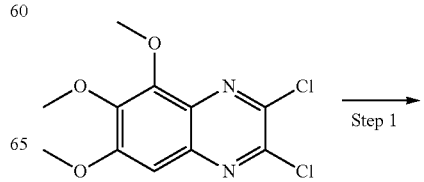

-continued

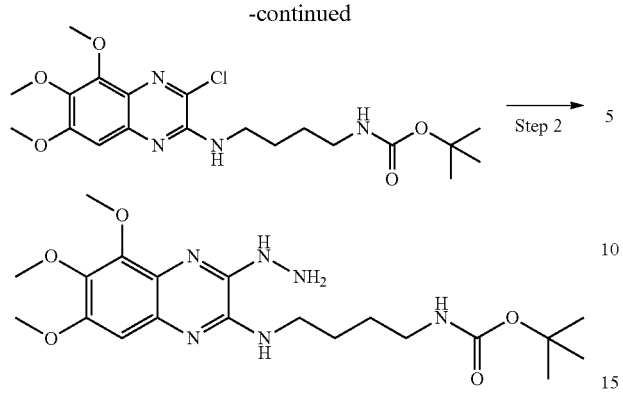

[4-(3-Hydrazino-5,6,7-trimethoxy-quinoxaline-2-ylamino)butyl]-carbamic acid-tert-butyl ester, a target compound of Preparative Example 32, was obtained by the same manner as described in Preparative Example 20.

Step 1: Preparation of [4-(3-chloro-5,6,7-trimethoxy-quinoxaline-2-ylamino)-butyl]carbamic acid-tert-butylester Mass (M+H$^+$): 441.1
$^1$H NMR (500 MHz, DMSO-d6): δ1.31 (s, 9H), 1.40 (m, 2H), 1.56 (m, 2H), 2.91 (m, 2H), 3.40 (m, 2H), 3.75 (s, 3H), 3.87 (s, 3H), 3.94 (s, 3H), 6.73 (t, 1H), 6.82 (s, 1H), 7.23 (t, 1H).

Step 2: Preparation of {4-[(3-hydrazino-7,8,9-trimethoxy)-quinoxaline-2-ylamino]butyl]carbamic acid-tert-butylester Mass (M+H$^+$): 437.1

<Example 486> Preparation of [4-(7,8,9-trimethoxy-1-methyl-[1,2,4]triazolo[4,3-a]quinoxaline-4-ylamino)-butyl]-carbamic acid-tert-butylester

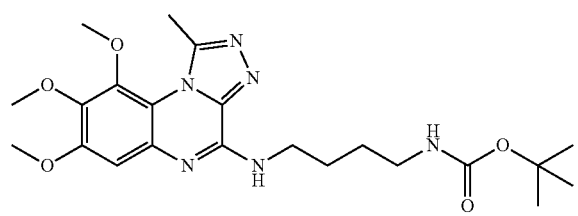 [SMILES: COc1cc2nc(NCCCCNC(=O)OC(C)(C)C)c3nnc(C)n3c2c(OC)c1OC]

0.32 g of a target compound was obtained (94% yield) by the same manner as described in step 3 of Preparative Example 5, except that {4-[(3-hydrazino-7,8,9-trimethoxy)-quinoxaline-2-ylamino]butyl}carbamic acid-tert-butylester prepared in step 2 of Preparative Example 32 was used.
Mass (M+H$^+$): 461.2
$^1$H NMR (500 MHz, DMSO-d6) δ1.32 (s, 9H), 1.43 (m, 2H), 1.59 (m, 2H), 2.83 (s, 3H), 2.93 (m, 2H), 3.47 (m, 2H), 3.79 (s, 3H), 3.82 (s, 3H), 3.86 (s, 3H), 6.74 (t, 1H), 6.91 (s, 1H), 7.95 (t, 1H).

<Example 487> Preparation of N$^1$-(7,8,9-trimethoxy-1-methyl-[1,2,4]triazolo[4,3-a]quinoxaline-4-yl)-butane-1,4-diamine ditrifluoroacetic acid

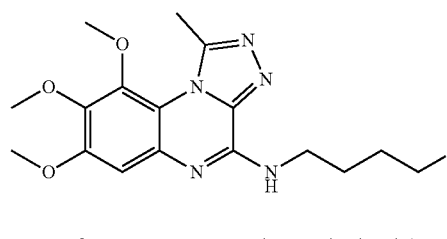

0.35 g of a target compound was obtained (97% yield) by the same manner as described in Example 58, except that [4-(7,8,9-trimethoxy-1-methyl-[1,2,4]triazolo[4,3-a]quinoxaline-4-ylamino)-butyl]-carbamic acid-tert-butylester prepared in Example 486 was used.
Mass (M+H$^+$): 361.2

<Example 488> Preparation of 3-methyl-N-[4-(7,8,9-trimethoxy-1-methyl-[1,2,4]triazolo[4,3-a]quinoxaline-4-ylamino)-butyl]-butyramide

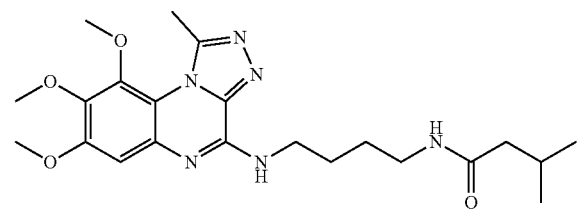 [SMILES: COc1cc2nc(NCCCCNC(=O)CC(C)C)c3nnc(C)n3c2c(OC)c1OC]

0.08 g of a target compound was obtained (52% yield) by the same manner as described in Example 37, except that N$^1$-(7,8,9-trimethoxy-1-methyl-[1,2,4]triazolo[4,3-a]quinoxaline-4-yl)-butane-1,4-diamine ditrifluoroacetic acid prepared in Example 487 was used.
Mass (M+H$^+$): 445.2
$^1$H NMR (500 MHz, DMSO-d6): δ0.79 (d, 6H), 1.45 (m, 2H), 1.63 (m, 2H), 1.85 (m, 2H), 1.87 (m, 1H), 2.83 (s, 3H), 2.92 (q, 2H), 3.47 (m, 2H), 3.79 (s, 3H), 3.82 (s, 3H), 3.85 (s, 3H), 6.74 (t, 1H), 6.91 (s, 1H), 7.94 (t, 1H)

<Example 489> 3-methyl-pentanoic acid-[4-(6,8,9-trimethoxy-1-methyl-[1,2,4]triazolo[4,3-a]quinoxaline-4-ylamino)-butyl]-amide 의 제조

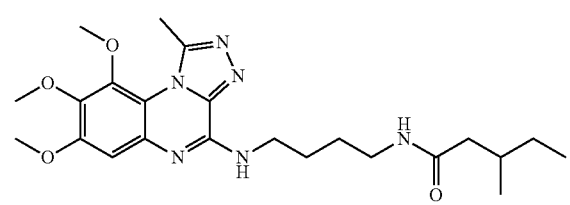 [SMILES: CCC(C)CC(=O)NCCCCNc1nc2cc(OC)c(OC)c(OC)c2n2c(C)nnc12]

0.11 g of a target compound was obtained (68% yield) by the same manner as described in Example 73, except that N$^1$-(7,8,9-trimethoxy-1-methyl-[1,2,4]triazolo[4,3-a]quinoxaline-4-yl)-butane-1,4-diamine ditrifluoroacetic acid prepared in Example 487 was used.

Mass (M+H$^+$): 459.2

$^1$H NMR (500 MHz, DMSO-d6): δ0.76 (m, 6H), 1.08-1.20 (brm, 2H), 1.45 (m, 2H), 1.62 (m, 2H), 1.78 (m, 2H), 1.98 (m, 1H), 2.83 (s, 3H), 2.92 (q, 2H), 3.47 (m, 2H), 3.78 (s, 3H), 3.82 (s, 3H), 3.85 (s, 3H), 6.74 (t, 1H), 6.91 (s, 1H), 7.94 (t, 1H).

<Preparative Example 33> Preparation of [4-(3-hydrazino-7-imidazole-1-yl-quinoxaline-2-ylamino)-butyl]-carbamic acid-tert-butylester

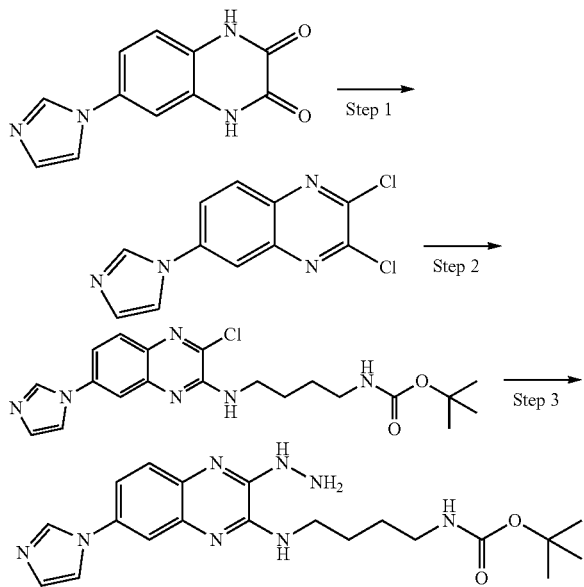

[4-(3-Hydrazino-7-imidazole-1-yl-quinoxaline-2-ylamino)-butyl]-carbamic acid-tert-butylester, a target compound of Preparative Example 33, was obtained by the same manner as described in Preparative Example 20.

Step 1: Preparation of 2,3-dichloro-6-imidazole-1-yl-quinoxaline

Mass (M+H$^+$): 265.1

$^1$H NMR (500 MHz, DMSO-d6) δ7.16 (s, 1H), 8.02 (s, 1H), 8.16 (d, 1H), 8.30 (d, 1H), 8.39 (d, 1H), 8.55 (s, 1H).

Step 2: Preparation of [4-(3-chloro-7-imidazole-1-yl-quinoxaline-2-ylamino)-butyl]-carbamic acid-tert-butylester Mass (M+H$^+$): 417.1

$^1$H NMR (500 MHz, DMSO-d6) δ1.31 (s, 9H), 1.42 (m, 2H), 1.60 (m, 2H), 2.91 (m, 2H), 3.43 (m, 2H), 6.75 (s, 1H), 7.10 (s, 1H), 7.76 (m, 1H), 7.77 (m, 1H), 7.80 (m, 2H), 7.92 (m, 1H), 8.42 (s, 1H).

Step 3: Preparation of [4-(3-hydrazino-7-imidazole-1-yl-quinoxaline-2-ylamino)-butyl]-carbamic acid-tert-butylester Mass (M+H$^+$): 413.2 Examples of the compounds synthesized using [4-(3-hydrazino-7-imidazole-1-yl-quinoxaline-2-ylamino)-butyl]-carbamic acid-tert-butylester prepared in step 3 of Preparative Example 33 are shown in Table 33 below.

TABLE 33

| Example | Structure | Name | Data |
|---|---|---|---|
| Example 490 | 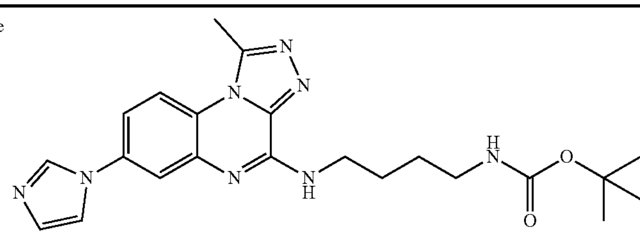 | [4-(7-imidazole-1-yl-1-methyl-[1,2,4]triazolo[4,3-a]quinoxaline-4-ylamino)-butyl]-carbamic acid-tert-butylester | Mass (M + H$^+$): 437.2; $^1$H NMR (500 MHz, DMSO-d6): δ1.31 (m, 9H), 1.44 (m, 2H), 1.63 (m, 2H), 2.93 (m, 2H), 3.00 (s, 3H) 3.52 (m, 2H), 6.80 (s, 1H), 7.10 (s, 1H), 7.54 (d, 1H), 7.80 (s, 1H), 7.86 (s, 1H), 8.11 (d, 1H), 8.32 (m, 1H), 8.36 (s, 1H). |
| Example 491 | 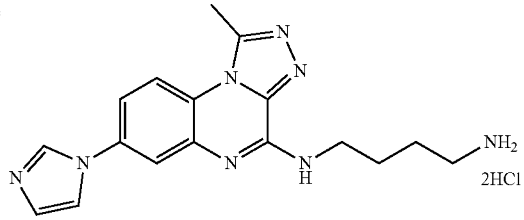 [SMILES: Cc1nnc2c(NCCCCN)nc3cc(-n4ccnc4)ccc3n12 ; "2HCl"] | N$^1$-(7-imidazole-1-yl-1-methyl-[1,2,4]triazolo[4,3-a]quinoxaline-4-yl)-butane-1,4-diamine dihydrochloride | Mass (M + H$^+$): 337.1; $^1$H NMR (500 MHz, DMSO-d6): δ1.65 (m, 2H), 1.72 (m, 2H), 2.80 (m, 2H), 3.04 (s, 3H), 3.59 (m, 2H), 7.70 (d, 1H), 7.93 (s, 1H), 8.05 (s, 2H), 8.10 (s, 3H), 8.23 (d, 1H), 8.42 (s, |

TABLE 33-continued

| Example | Structure | Name | Data |
|---|---|---|---|
| | | | 1H), 8.72 (s, 1H), 9.90 (s, 1H) |
| Example 492 | 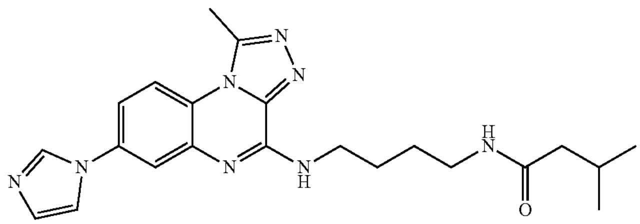 [SMILES: Cc1nnc2c(NCCCCNC(=O)CC(C)C)nc3cc(-n4ccnc4)ccc3n12] | N-[4-(7-imidazole-1-yl-1-methyl-[1,2,4]triazolo[4,3-a]quinoxaline-4-ylamino)-butyl]-3-methyl-butyramide | Mass (M + H⁺): 421.2; ¹H NMR (500 MHz, DMSO-d6): δ0.78 (m, 6H), 1.46 (m, 2H), 1.63 (m, 2H), 1.87 (m, 3H), 3.01 (s, 3H), 3.04 (m, 2H), 3.53 (m, 2H), 7.12 (s, 1H), 7.56 (d, 1H), 7.72 (s, 1H), 7.81 (s, 1H), 7.88 (s, 1H), 8.12 (d, 1H), 8.32 (s, 1H), 8.41 (s, 1H). |
| Example 493 | 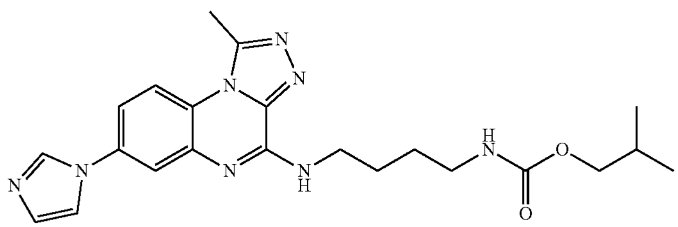 [SMILES: Cc1nnc2c(NCCCCNC(=O)OCC(C)C)nc3cc(-n4ccnc4)ccc3n12] | 4-(7-imidazole-1-yl-1-methyl-[1,2,4]triazolo[4,3-a]quinoxaline-4-ylamino)-butyl]-carbamic acid isobutylester | Mass (M + H⁺): 437.2; ¹H NMR (500 MHz, DMSO-d6): δ0.79 (t, 6H), 1.46 (m, 2H), 1.63 (m, 2H), 1.75 (m, 1H), 2.98 (m, 5H), 3.53 (m, 2H), 3.66 (m, 2H), 7.03 (s, 1H), 7.11 (s, 1H), 7.54 (d, 1H), 7.80 (s, 1H), 7.87 (s, 1H), 8.11 (d, 1H), 8.13 (s, 1H), 8.38 (s, 1H). |
| Example 494 | 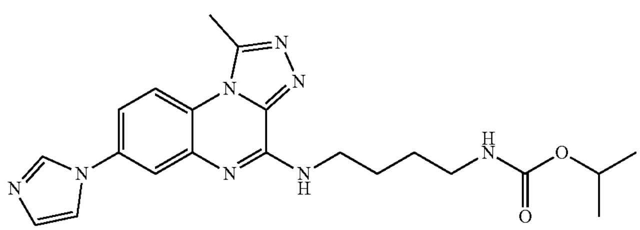 [SMILES: Cc1nnc2c(NCCCCNC(=O)OC(C)C)nc3cc(-n4ccnc4)ccc3n12] | [4-(7-imidazole-1-yl-1-methyl-[1,2,4]triazolo[4,3-a]quinoxaline-4-ylamino)-butyl]-carbamic acid isopropylester | Mass (M + H⁺): 423.2; ¹H NMR (500 MHz, DMSO-d6): δ1.08 (t, 6H), 1.45 (m, 2H), 1.64 (m, 2H), 2.97 (m, 2H), 3.01 (s, 3H), 3.55 (m, 2H), 6.95 (s, 2H), 7.23 (s, 1H), 7.55 (d, 1H), 7.84 (s, 1H), 7.95 (s, 1H), 8.14 (d, 1H), 8.34 (s, 1H), 8.60 (s, 1H). |
| Example 495 | 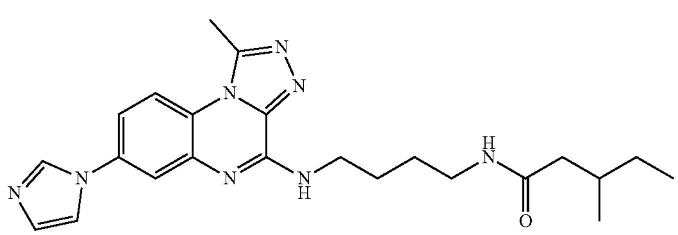 [SMILES: CCC(C)CC(=O)NCCCCNc1nc2cc(-n3ccnc3)ccc2n2c(C)nnc12] | 3-methyl-pentanoic acid-[4-(7-imidazole-1-yl-1-methyl-[1,2,4]triazolo[4,3-a]quinoxaline-4-ylamino)-butyl]-amide | Mass (M + H⁺): 435.2; ¹H NMR (500 MHz, DMSO-d6): δ0.74 (m, 6H), 1.05 (m, 1H), 1.22 (m, 1H), 1.45 (m, 2H), 1.63 (m, 3H), 1.79 (m, 1H), 3.01 (s, 3H), 3.05 (m, 2H), 3.52 (m, 2H), 7.10 (s, 1H), 7.55 (d, 1H), 7.72 (s, 1H), 7.81 (s, 1H), 7.87 (s, |

TABLE 33-continued

| Example | Structure | Name | Data |
|---|---|---|---|
| | | | 1H), 8.12 (d, 1H), 8.32 (s, 1H), 8.37 (s, 1H). |
| Example 496 | 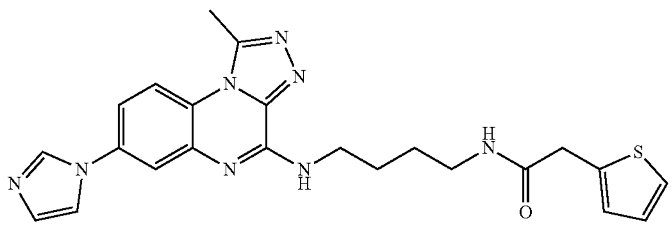 [SMILES: Cc1nnc2c(NCCCCNC(=O)Cc3cccs3)nc3cc(-n4ccnc4)ccc3n12] | N-[4-(7-imidazole-1-yl-1-methyl-[1,2,4]triazolo[4,3-a]quinoxaline-4-ylamino)-butyl]-2-thiophene-2-yl-acetamide | Mass (M + H$^+$): 461.2; $^1$H NMR (500 MHz, DMSO-d6): δ1.47 (m, 2H), 1.64 (m, 2H), 3.00 (s, 3H), 3.08 (m, 2H), 3.53 (m, 2H), 3.56 (s, 2H), 6.83 (m, 2H), 7.20 (s, 1H), 7.24 (d, 1H), 7.25 (d, 1H), 7.81 (d, 1H), 7.92 (s, 1H), 8.05 (m, 1H), 8.12 (d, 1H), 8.30 (m, 1H), 8.53 (s, 1H). |

<Preparative Example 34> Preparation of [4-(3-hydrazino-7-morpholine-4-yl-quinoxaline-2-ylamino)-butyl]-carbamic acid-tert-butylester

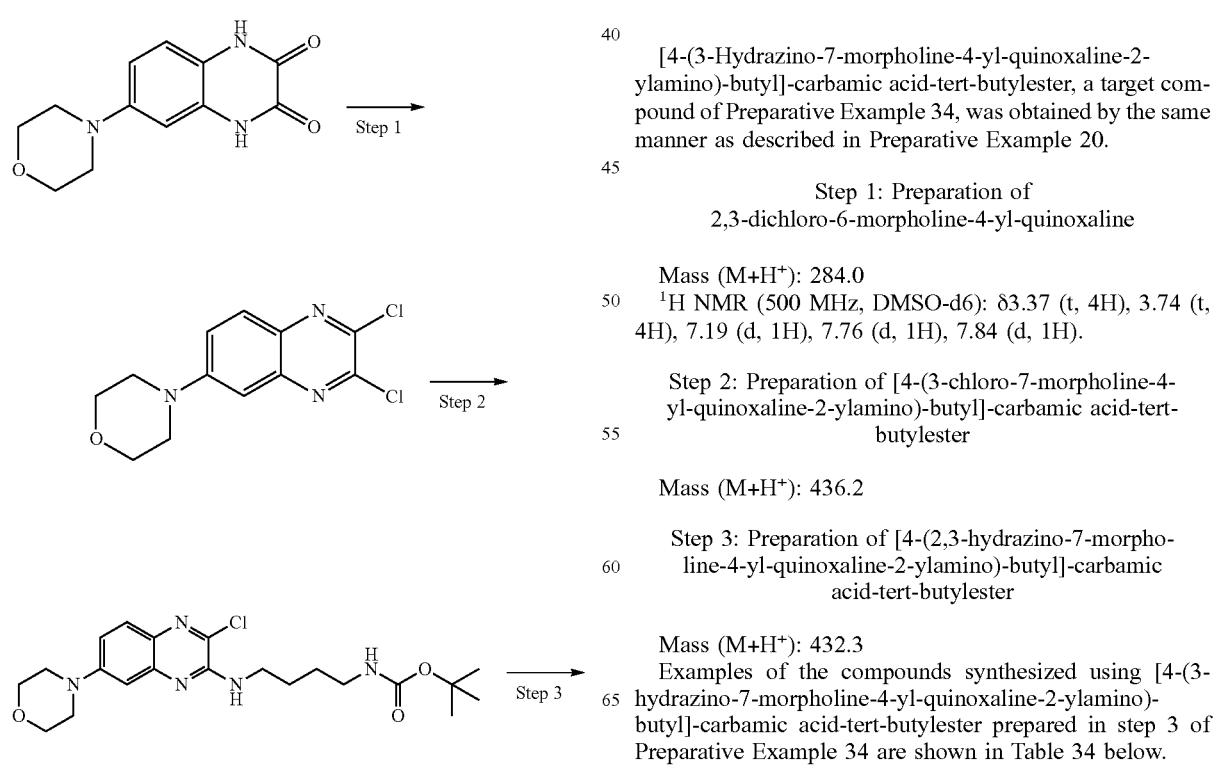

[4-(3-Hydrazino-7-morpholine-4-yl-quinoxaline-2-ylamino)-butyl]-carbamic acid-tert-butylester, a target compound of Preparative Example 34, was obtained by the same manner as described in Preparative Example 20.

Step 1: Preparation of 2,3-dichloro-6-morpholine-4-yl-quinoxaline

Mass (M+H$^+$): 284.0
$^1$H NMR (500 MHz, DMSO-d6): δ3.37 (t, 4H), 3.74 (t, 4H), 7.19 (d, 1H), 7.76 (d, 1H), 7.84 (d, 1H).

Step 2: Preparation of [4-(3-chloro-7-morpholine-4-yl-quinoxaline-2-ylamino)-butyl]-carbamic acid-tert-butylester Mass (M+H$^+$): 436.2

Step 3: Preparation of [4-(2,3-hydrazino-7-morpholine-4-yl-quinoxaline-2-ylamino)-butyl]-carbamic acid-tert-butylester Mass (M+H$^+$): 432.3

Examples of the compounds synthesized using [4-(3-hydrazino-7-morpholine-4-yl-quinoxaline-2-ylamino)-butyl]-carbamic acid-tert-butylester prepared in step 3 of Preparative Example 34 are shown in Table 34 below.

TABLE 34

| Example | Structure | Name | Data |
|---|---|---|---|
| Example 497 | 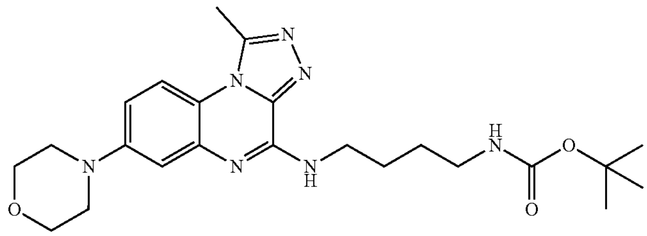 [SMILES: Cc1nnc2c(NCCCCNC(=O)OC(C)(C)C)nc3cc(N4CCOCC4)ccc3n12] | [4-(1-methyl-7-morpholine-4-yl-[1,2,4]triazolo[4,3-a]quinoxaline-4-ylamino)-butyl]-carbamic acid-tert-butylester | Mass (M + H⁺): 456.3; ¹H NMR (500 Hz, DMSO-d6): δ1.32 (s, 9H), 1.42 (m, 2H), 1.61 (m, 2H), 2.93 (m, 5H), 3.14 (t, 4H), 3.50 (m, 2H), 3.72 (t, 4H), 6.75 (s, 1H), 6.91 (d, 1H), 7.00 (d, 1H), 7.87 (d, 1H), 7.97 (s, 1H). |
| Example 498 | 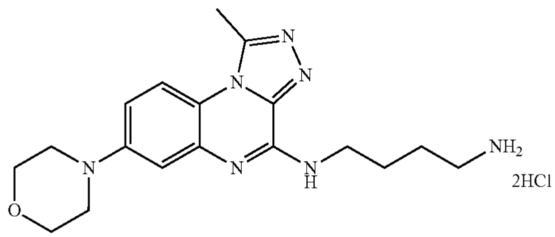 [SMILES: Cc1nnc2c(NCCCCN)nc3cc(N4CCOCC4)ccc3n12 ; "2HCl"] | N¹-(1-methyl-7-morpholine-4-yl-[1,2,4]triazolo[4,3-a]quinoxaline-4-yl)-butane-1,4-diamine dihydrochloride | Mass (M + H⁺): 356.2; ¹H NMR (500 MHz, DMSO-d6): δ1.70 (m, 2H), 1.75 (m, 2H), 2.81 (m, 2H), 2.99 (s, 3H), 3.16 (m, 4H), 3.75 (m, 4H), 3.88 (m, 2H), 4.20 (s, 2H), 7.06 (d, 1H), 7.94 (d, 1H), 8.05 (s, 4H) |
| Example 499 | 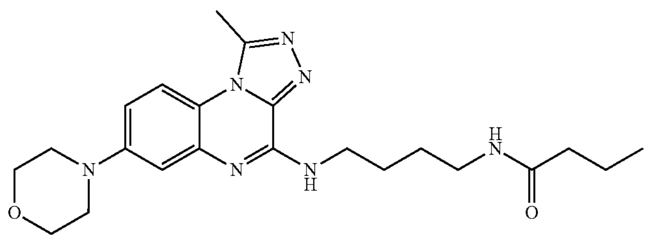 | 3-methyl-N-[4-(1-methyl-7-morpholine-4-yl-[1,2,4]triazolo[4,3-a]quinoxaline-4-ylamino)-butyl]-butyramide | Mass (M + H⁺): 440.2; ¹H NMR (500 MHz, DMSO-d6): δ0.80 (d, 6H), 1.43 (m, 2H), 1.61 (m, 2H), 1.88 (m, 3H), 2.93 (s, 3H), 3.04 (m, 2H), 3.14 (s, 4H), 3.49 (m, 2H), 3.73 (d, 4H), 6.90 (d, 2H), 7.00 (s, 1H), 7.86 (d, 1H), 8.00 (s, 1H) |
| Example 500 | 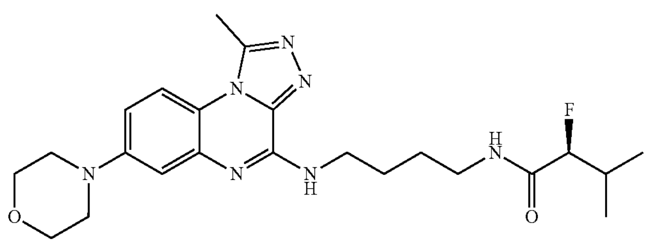 [SMILES: Cc1nnc2c(NCCCCNC(=O)[C@@H](F)C(C)C)nc3cc(N4CCOCC4)ccc3n12] | 2-(S)-fluoro-3-methyl-N-[4-(1-methyl-7-morpholine-4-yl-[1,2,4]triazolo[4,3-a]quinoxaline-4-ylamino)-butyl]-butyramide | Mass (M + H⁺): 458.2; ¹H NMR (500 MHz, DMSO-d6): δ0.78 (m, 3H), 0.90 (m, 3H), 1.49 (m, 2H), 1.61 (m, 2H), 2.10 (m, 1H), 2.90 (s 3H), 3.10 (m, 6H), 3.49 (m, 2H), 3.73 (s, 4H), 4.56 (d, 1H), 6.90 (d, 1H), 7.00 (s, 1H), 7.86 (d, 1H), 8.08 (s, 1H). |
| Example 501 | 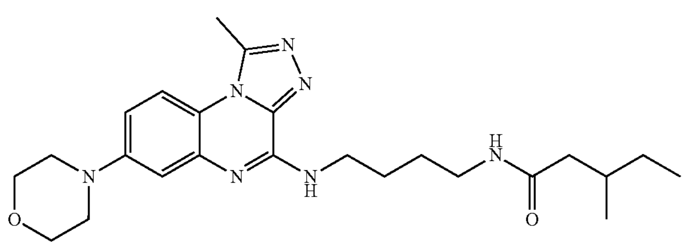 [SMILES: CCC(C)CC(=O)NCCCCNc1nc2cc(N3CCOCC3)ccc2n2c(C)nnc12] | 3-methyl-pentanoic acid-[4-(1-methyl-7-morpholine-4-yl-[1,2,4]triazolo[4,3-a]quinoxaline-4-ylamino)-butyl]-amide | Mass (M + H⁺): 454.3; ¹H NMR (500 MHz, DMSO-d6): δ0.75 (m, 6H), 1.05 (m, 1H), 1.25 (m, 1H), 1.45 (m, 2H), 1.63 (m, 2H), 1.75 (m, 1H), 1.81 (m, 1H), 1.97 (m, 1H), 2.94 (s, 3H), 3.00 (m, 2H), 3.19 (m, 4H), 3.49 (m, 2H), 3.72 (m, 4H), 6.93 (d, 1H), 7.01 (s, 1H), 7.70 (m, 1H), 7.88 (d, 1H), 8.00 (s, 1H) |

TABLE 34-continued

| Example | Structure | Name | Data |
|---|---|---|---|
| Example 502 | 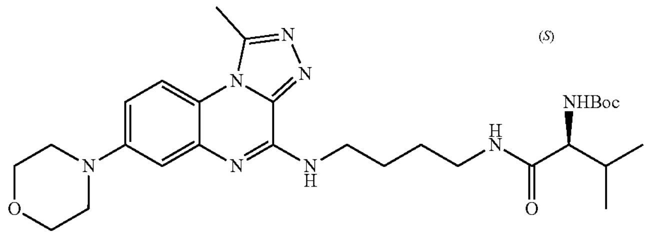 [SMILES: Cc1nnc2c(NCCCCNC(=O)[C@@H](NC(=O)OC(C)(C)C)C(C)C)nc3cc(N4CCOCC4)ccc3n12 ; "(S)"] | (S)-{2-methyl-1-[4-(1-methyl-7-morpholine-4-yl-[1,2,4]triazolo[4,3-a]quinoxaline-4-ylamino)-butylcarbamoyl]-propyl}-carbamic acid-tert-butylester | Mass (M + H⁺): 555.4; ¹H NMR (500 MHz, DMSO-d6): δ0.73 (m, 6H), 1.32 (m, 9H), 1.44 (m, 2H), 1.63 (m, 2H), 1.80 (m, 1H), 2.94 (s, 3H), 3.12 (m, 1H), 3.15 (m, 5H), 3.49 (m, 2H), 3.67 (m, 1H), 3.73 (m, 4H), 6.48 (d, 1H), 6.91 (d, 1H), 7.01 (s, 1H), 7.79 (s, 1H), 7.88 (d, 1H), 8.00 (s, 1H). |
| Example 503 | 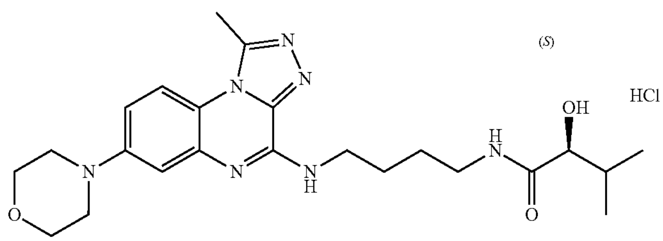 [SMILES: Cc1nnc2c(NCCCCNC(=O)[C@@H](O)C(C)C)nc3cc(N4CCOCC4)ccc3n12 ; "(S)" ; Cl] | 2-(S)-amino-3-methyl-N-[4-(1-methyl-7-morpholine-4-yl-[1,2,4]triazolo[4,3-a]quinoxaline-4-ylamino)-butyl]-butyramide hydrochloride | Mass (M + H⁺): 455.3; ¹H NMR (500 MHz, DMSO-d6): δ0.86 (m, 6H), 1.57 (m, 2H), 1.72 (m, 2H), 2.03 (m, 1H), 3.00 (s, 3H), 3.16 (m, 6H), 3.15 (m, 5H), 3.55 (m, 1H), 3.75 (m, 4H), 3.85 (s, 2H), 7.08 (d, 1H), 6.95 (d, 1H), 8.21 (s, 3H), 8.67 (s, 1H). |
| Example 504 | 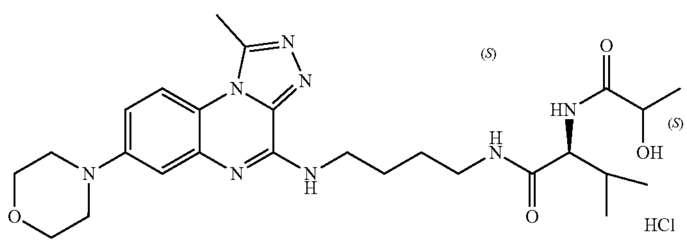 | (S)-2-(2-(S)-hydroxy-propionylamino)-3-methyl-N-[4-(1-methyl-7-morpholine-4-yl-[1,2,4]triazolo[4,3-a]quinoxaline-4-ylamino)-butyl]-butyramide hydrochloride | Mass (M + H⁺): 527.3; ¹H NMR (500 MHz, DMSO-d6): δ0.77 (m, 6H), 1.17 (s, 3H), 1.49 (m, 2H), 1.66 (m, 2H), 1.95 (m, 1H), 3.00 (s, 3H), 3.15 (m, 6H), 3.55 (m, 2H), 3.75 (m, 4H), 3.90 (s, 1H), 4.10 (d, 1H), 7.00 (d, 1H), 7.35 (d, 1H), 7.60 (s, 1H), 7.90 (d, 1H), 8.15 (m, 1H). |
| Example 505 | 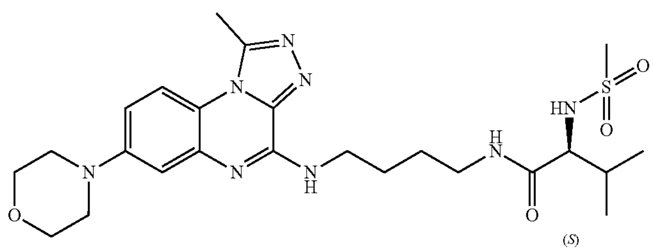 | 2-(S)-methanesulfonylamino-3-methyl-N-[4-(1-methyl-7-morphonyl-4-yl-[1,2,4]triazolo[4,3-a]quinoxaline-4-ylamino)-butyl]-butyramide | Mass (M + H⁺): 533.3; ¹H NMR (500 MHz, DMSO-d6): δ0.79 (m, 6H), 1.47 (m, 2H), 1.63 (m, 2H), 1.81 (m, 1H), 2.74 (s, 3H), 2.94 (s, 3H), 3.15 (m, 6H), 3.55 (m, 3H), 3.72 (m, 4H), 6.90 (d, 1H), 7.00 (d, 1H), 7.10 (d, 1H), 7.89 (d, 1H), 8.00 (m, 2H). |

TABLE 34-continued

| Example | Structure | Name | Data |
|---|---|---|---|
| Example 506 | 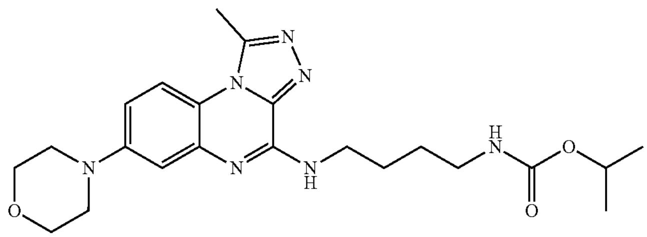 [SMILES: Cc1nnc2c(NCCCCNC(=O)OC(C)C)nc3cc(N4CCOCC4)ccc3n12] | [4-(1-methyl-7-morpholine-4-yl-[1,2,4]triazolo[4,3-a]quinoxaline-4-ylamino)-butyl]-carbamic acid isopropylester | Mass (M + H⁺): 442.2; ¹H NMR (500 MHz, DMSO-d6): δ1.10 (d, 6H), 1.43 (m, 2H), 1.60 (m, 2H), 2.93 (s, 3H), 2.98 (m, 2H), 3.15 (s, 4H), 3.47 (m, 2H), 3.73 (s, 4H), 4.67 (m, 1H), 6.89 (d, 1H), 6.91 (s, 1H), 7.00 (s, 1H), 7.86 (d, 1H), 7.97 (s, 1H) |
| Example 507 | 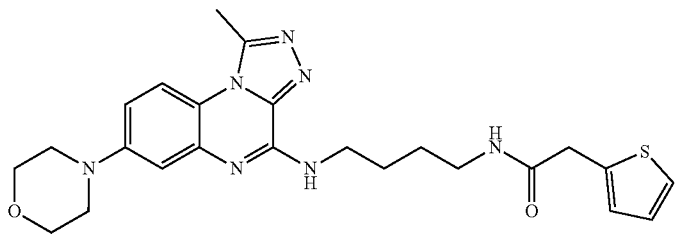 [SMILES: Cc1nnc2c(NCCCCNC(=O)Cc3cccs3)nc3cc(N4CCOCC4)ccc3n12] | N-[4-(1-methyl-7-morpholine-4-yl-[1,2,4]triazolo[4,3-a]quinoxaline-4-ylamino)-butyl]-2-thiophene-2-yl-acetamide | Mass (M + H⁺): 480.2; ¹H NMR (500 MHz, DMSO-d6): δ1.46 (m, 2H), 1.62 (m, 2H), 1.88 (m, 3H), 2.94 (s, 3H), 3.13 (m, 2H), 3.15 (m, 4H), 3.50 (m, 2H), 3.57 (s, 2H), 3.73 (t, 4H), 6.84 (m, 4H), 7.00 (s, 1H), 7.25 (s, 1H), 7.87 (d, 1H), 7.98 (m, 1H), 8.05 (m, 1H) |

<Preparative Example 35> Preparation of {4-[3-hydrazino-7-(2,6-dimethyl-morpholine-4-yl)-quinoxaline-2-ylamino]-butyl}-carbamic acid-tert-butylester

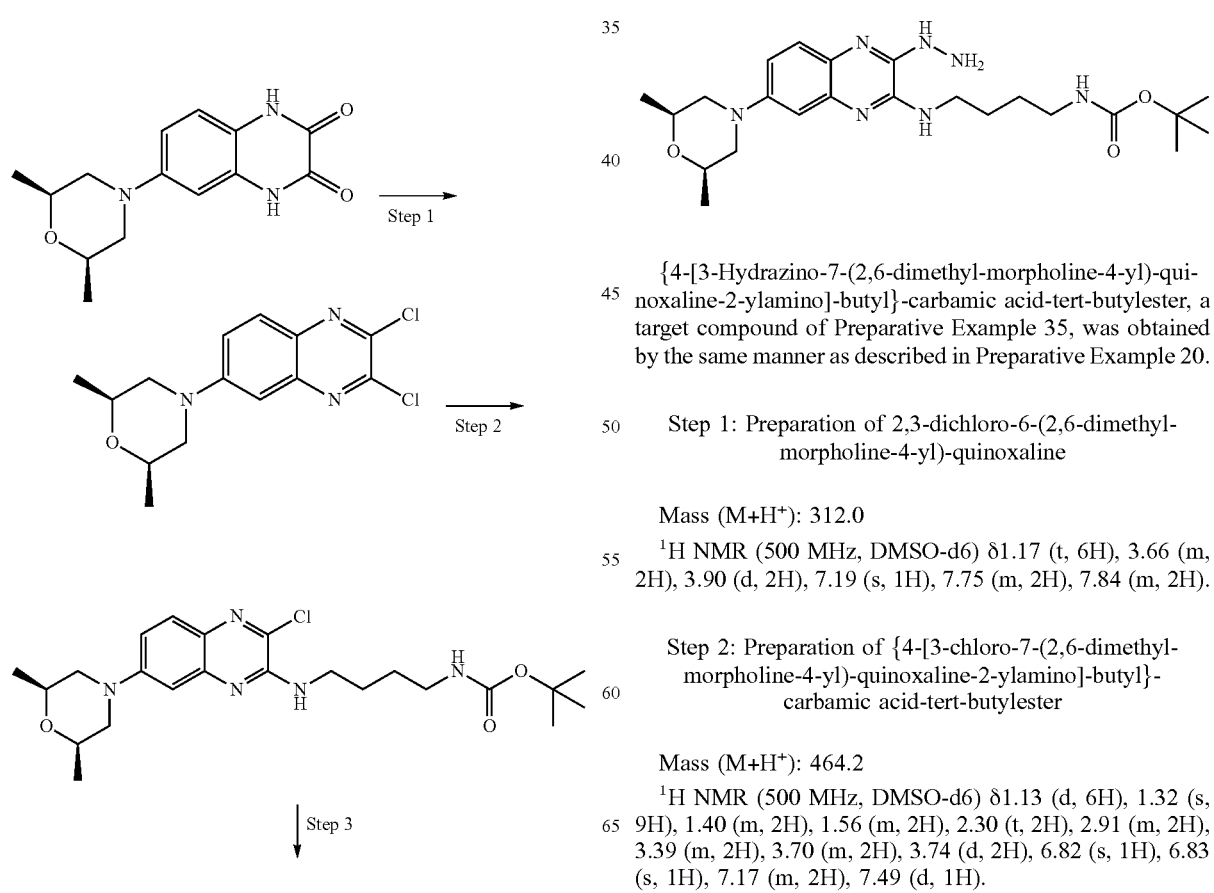

{4-[3-Hydrazino-7-(2,6-dimethyl-morpholine-4-yl)-quinoxaline-2-ylamino]-butyl}-carbamic acid-tert-butylester, a target compound of Preparative Example 35, was obtained by the same manner as described in Preparative Example 20.

Step 1: Preparation of 2,3-dichloro-6-(2,6-dimethyl-morpholine-4-yl)-quinoxaline Mass (M+H⁺): 312.0

¹H NMR (500 MHz, DMSO-d6) δ1.17 (t, 6H), 3.66 (m, 2H), 3.90 (d, 2H), 7.19 (s, 1H), 7.75 (m, 2H), 7.84 (m, 2H).

Step 2: Preparation of {4-[3-chloro-7-(2,6-dimethyl-morpholine-4-yl)-quinoxaline-2-ylamino]-butyl}-carbamic acid-tert-butylester Mass (M+H⁺): 464.2

¹H NMR (500 MHz, DMSO-d6) δ1.13 (d, 6H), 1.32 (s, 9H), 1.40 (m, 2H), 1.56 (m, 2H), 2.30 (t, 2H), 2.91 (m, 2H), 3.39 (m, 2H), 3.70 (m, 2H), 3.74 (d, 2H), 6.82 (s, 1H), 6.83 (s, 1H), 7.17 (m, 2H), 7.49 (d, 1H).

Step 3: Preparation of {4-[3-hydrazino-7-(2,6-dimethyl-morpholine-4-yl)-quinoxaline-2-ylamino]-butyl}-carbamic acid-tert-butylester Mass (M+H⁺): 484.3

Examples of the compounds synthesized using {4-[3-hydrazino-7-(2,6-dimethyl-morpholine-4-yl)-quinoxaline-2-ylamino]-butyl}-carbamic acid-tert-butylester prepared in step 3 of Preparative Example 35 are shown in Table 35 below.

TABLE 35

| Example | Structure | Name | Data |
|---|---|---|---|
| Example 508 | 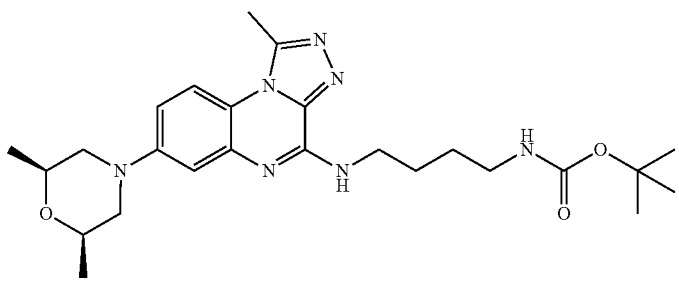 [SMILES: Cc1nnc2c(NCCCCNC(=O)OC(C)(C)C)nc3cc(N4C[C@@H](C)O[C@@H](C)C4)ccc3n12] | {4-[7-(2,6-dimethyl-morphonyl-4-yl)-1-methyl-[1,2,4]triazolo[4,3-a]quinoxaline-4-ylamino]-butyl}-carbamic acid-tert-butylester | Mass (M + H⁺): 484.3; ¹H NMR (500 MHz, DMSO-d6): δ1.14 (m, 6H), 1.32 (s, 9H), 1.43 (m, 2H), 1.61 (m, 2H), 2.23 (m, 2H), 2.94 (m, 5H), 3.47 (m, 2H), 3.65 (m, 4H), 6.80 (s, 1H), 6.90 (d, 1H), 7.00 (s, 1H), 7.84 (d, 1H), 8.00 (m, 1H). |
| Example 509 | 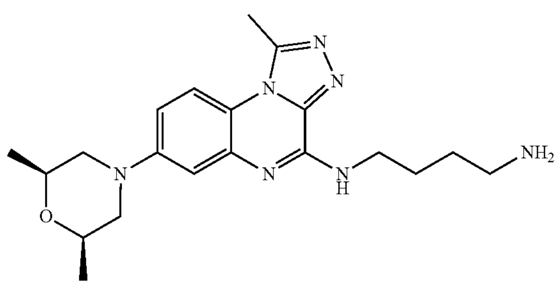 | N¹-[7-(2,6-dimethyl-morphonyl-4-yl)-1-methyl-[1,2,4]triazolo[4,3-a]quinoxaline-4-yl]-butane-1,4-diamine ditrifluoroacetic acid | Mass (M + H⁺): 384.2; ¹H NMR (500 MHz, DMSO-d6): δ1.14 (m, 6H), 1.60 (m, 2H), 1.69 (m, 2H), 2.25 (m, 2H), 2.80 (m, 2H), 2.95 (s, 3H), 3.53 (m, 2H), 3.65 (m, 4H), 6.95 (d, 1H), 7.03 (s, 1H), 7.67 (d, 3H), 7.89 (d, 1H), 8.22 (s, 1H). |
| Example 510 | 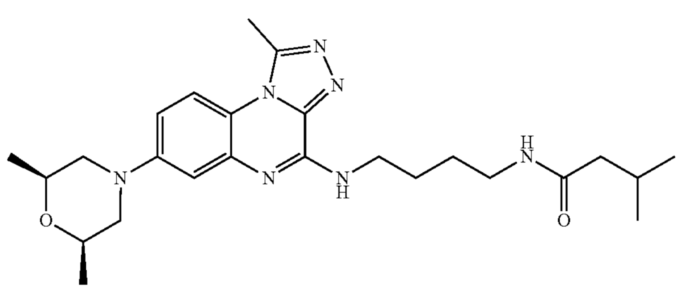 [SMILES: Cc1nnc2c(NCCCCNC(=O)CC(C)C)nc3cc(N4C[C@@H](C)O[C@@H](C)C4)ccc3n12] | N-{4-[7-(2,6-dimethyl-morpholine-4-yl)-1-methyl-[1,2,4]triazolo[4,3-a]quinoxaline-4-ylamino]-butyl}-3-methyl-butyramide | Mass (M + H⁺): 468.3; ¹H NMR (500 MHz, DMSO-d6): δ0.79 (m, 6H), 1.14 (m, 6H), 1.44 (m, 2H), 1.62 (m, 2H), 1.87 (m, 3H), 2.24 (t, 2H), 2.93 (s, 3H), 3.04 (m, 2H), 3.48 (m, 2H), 3.63 (m, 4H), 6.93 (d, 1H), 7.00 (d, 1H), 7.70 (m, 1H), 7.86 (d, 1H), 7.97 (d, 1H). |

TABLE 35-continued

| Example | Structure | Name | Data |
|---------|-----------|------|------|
| Example 511 | 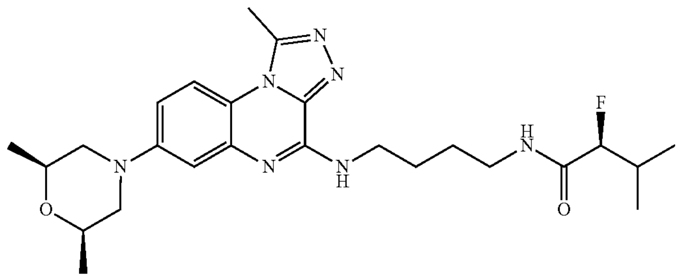 [SMILES: Cc1nnc2c(NCCCCNC(=O)[C@@H](F)C(C)C)nc3cc(N4C[C@@H](C)O[C@@H](C)C4)ccc3n12] | N-{4-[7-(2,6-dimethyl-morphonyl-4-yl)-1-methyl-[1,2,4]triazolo[4,3-a]quinoxaline-4-ylamino]-butyl}-2-(S)-fluoro-3-methyl-butyramide | Mass (M + H$^+$): 486.3; $^1$H NMR (500 MHz, DMSO-d6): δ 0.90 (m, 3H), 0.92 (m, 3H), 1.14 (m, 6H), 1.55 (m, 2H), 1.68 (m, 2H), 2.05 (m, 1H), 2.35 (t, 2H), 2.98 (s, 3H), 3.11 (m, 2H), 3.62 (m, 2H), 3.71 (m, 4H), 4.57 (m, 1H), 7.08 (d, 1H), 7.72 (s, 1H), 7.93 (d, 1H), 8.16 (m, 1H), 9.47 (s, 1H). |
| Example 512 | 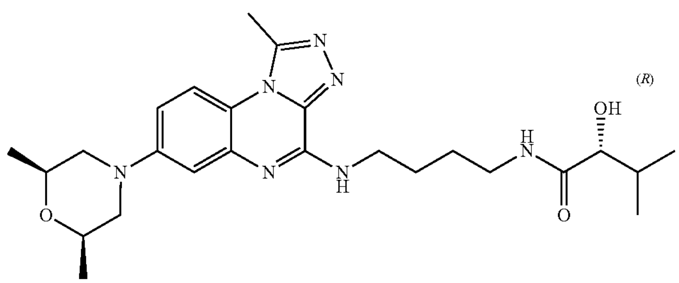 | N-{4-[7-(2,6-dimethyl-morpholine-4-yl)-1-methyl-[1,2,4]triazolo[4,3-a]quinoxaline-4-ylamino]-butyl}-2-(R)-hydroxy-3-methyl-butyramide | Mass (M + H$^+$): 484.3; $^1$H NMR (500 MHz, DMSO-d6): δ 0.68 (m, 3H), 0.84 (m, 3H), 1.14 (s, 6H), 1.47 (m, 2H), 1.62 (m, 2H), 1.92 (m, 1H), 2.24 (t, 2H), 2.93 (s, 3H), 3.04 (m, 2H), 3.28 (m, 2H), 3.68 (m, 6H), 5.23 (d, 1H), 6.93 (d, 1H), 7.01 (s, 1H), 7.65 (m, 1H), 7.85 (d, 1H), 7.98 (s, 1H). |
| Example 513 | 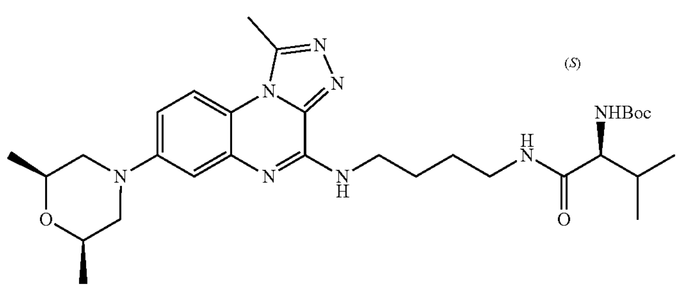 [SMILES: Cc1nnc2c(NCCCCNC(=O)[C@@H](NC(=O)OC(C)(C)C)C(C)C)nc3cc(N4C[C@@H](C)O[C@@H](C)C4)ccc3n12 ; "(S)"] | (S)-{2-methyl-1-[4-(1-methyl-7-(2,6-dimethyl-morpholine-4-yl)-[1,2,4]triazolo[4,3-a]quinoxaline-4-ylamino)-butylcarbamoyl]-propyl}-carbamic acid-tert-butylester | Mass (M + H$^+$): 583.4; $^1$H NMR (500 MHz, DMSO-d6): δ 0.77 (m, 6H), 1.14 (m, 6H), 1.32 (s, 9H), 1.45 (m, 2H), 1.63 (m, 2H), 1.84 (m, 1H), 2.26 (t, 2H), 2.93 (s, 3H), 3.04 (m, 2H), 3.50 (m, 2H), 3.68 (m, 5H), 6.48 (d, 1H), 6.93 (d, 1H), 7.01 (d, 1H), 7.79 (m, 1H), 7.86 (d, 1H), 7.97 (m, 1H). |

TABLE 35-continued

| Example | Structure | Name | Data |
|---|---|---|---|
| Example 514 | 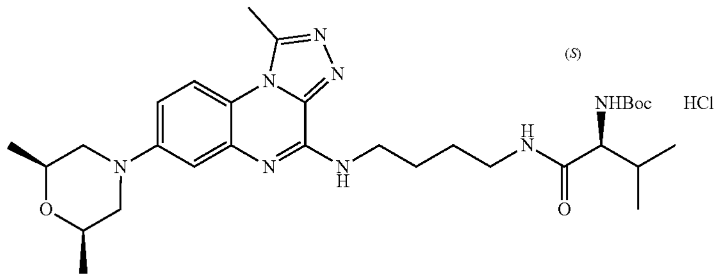 [SMILES: Cc1nnc2c(NCCCCNC(=O)[C@@H](NC(=O)OC(C)(C)C)C(C)C)nc3cc(N4C[C@@H](C)O[C@@H](C)C4)ccc3n12 ; "(S)" ; Cl] | 2-(S)-amino-N-{4-[7-(2,6-dimethyl-morpholine-4-yl)-1-methyl-[1,2,4]triazolo[4,3-a]quinoxaline-4-ylamino]-butyl}-3-methyl-butyramide hydrochloride | Mass (M + H⁺): 483.3; ¹H NMR (500 MHz, DMSO-d6): δ 0.87 (m, 6H), 1.14 (m, 6H), 1.57 (m, 2H), 1.71 (m, 2H), 2.03 (m, 1H), 2.33 (t, 2H), 2.98 (s, 3H), 3.08 (m, 1H), 3.22 (m, 1H), 3.55 (m, 2H), 3.64 (m, 6H), 7.07 (d, 1H), 7.95 (s, 1H), 8.19 (s, 3H), 8.62 (s, 1H). |
| Example 515 | 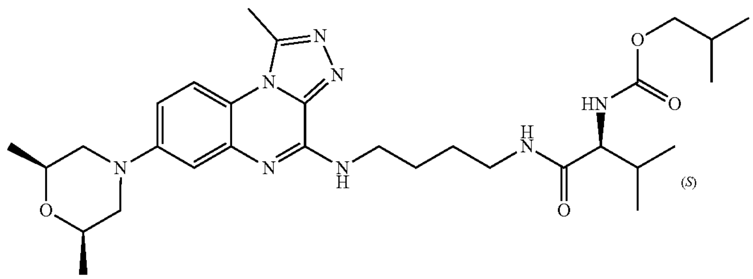 | (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isobutylester | Mass (M + H⁺): 584.4; ¹H NMR (500 MHz, DMSO-d6): δ 0.77 (m, 12H), 1.14 (m, 6H), 1.45 (m, 2H), 1.63 (m, 2H), 1.84 (m, 2H), 2.26 (t, 2H), 2.93 (s, 3H), 3.08 (m, 2H), 3.55 (m, 2H), 3.69 (m, 7H), 6.92 (m, 2H), 7.01 (s, 1H), 7.84 (d, 2H), 7.88 (s, 1H). |
| Example 516 | 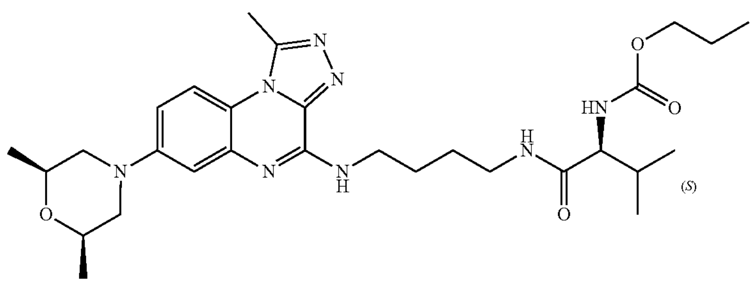 | (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid propylester | Mass (M + H⁺): 570.4; ¹H NMR (500 MHz, DMSO-d6): δ 0.77 (m, 9H), 1.14 (m, 6H), 1.45 (m, 4H), 1.63 (m, 2H), 1.84 (m, 1H), 2.26 (m, 2H), 2.93 (s, 3H), 3.10 (m, 2H), 3.49 (m, 2H), 3.63 (m, 5H), 3.80 (s, 2H), 6.91 (m, 2H), 7.01 (s, 1H), 7.84 (m, 2H), 8.00 (s, 1H). |
| Example 517 | 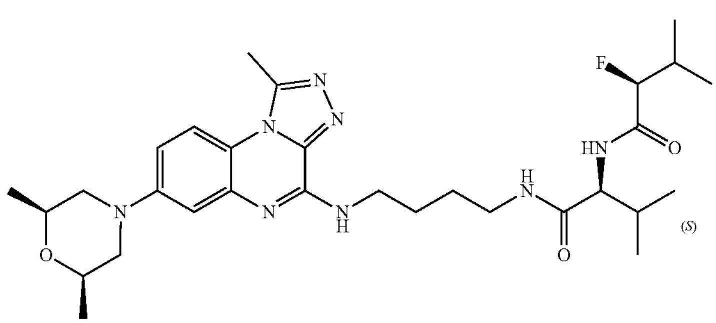 | (S)-N-(1-{4-[7-(2,6-dimethyl-morpholine-methyl-[1,2,4]triazolo[4,3-a]quinoxaline-4-ylamino]-butylcarbamoyl}-2-methyl-propyl)-2-(S)-fluoro-3-methyl-butyramide | Mass (M + H⁺): 585.4; ¹H NMR (500 MHz, DMSO-d6): δ 0.77 (m, 12H), 1.15 (m, 6H), 1.46 (m, 2H), 1.63 (m, 2H), 2.00 (m, 3H), 2.24 (t, 2H), 2.93 (s, 3H), 3.08 (m, 2H), 3.48 (m, 2H), 3.65 (m, 4H), 4.12 (m, 1H), 4.65 (d, 1H), 6.93 (d, 2H), 7.00 (s, 1H), 7.62 (d, 1H), |

TABLE 35-continued

| Example | Structure | Name | Data |
|---|---|---|---|
| | | | 7.86 (d, 1H), 7.87 (m, 1H), 8.04 (m, 1H). |
| Example 518 | 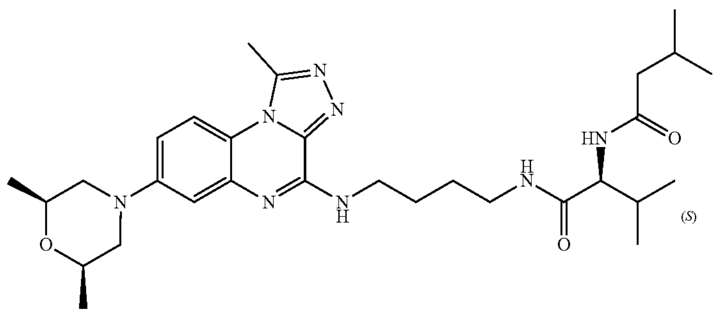 | (S)-N-{4-[7-(2,6-dimethyl-morpholine-4-yl)-1-methyl-[1,2,4]triazolo[4,3-a]quinoxaline-4-ylamino]-butyl}-3-methyl-2-(3-methyl-butyrylamino)-butyramide | Mass (M + H⁺): 567.4; ¹H NMR (500 MHz, DMSO-d6): δ0.79 (m, 12H), 1.15 (m, 6H), 1.45 (m, 2H), 1.63 (m, 2H), 1.98 (m, 4H), 2.25 (t, 2H), 2.94 (s, 3H), 3.08 (m, 2H), 3.49 (m, 2H), 3.66 (m, 4H), 4.04 (m, 1H), 6.93 (d, 1H), 7.01 (s, 1H), 7.67 (d, 1H), 7.86 (d, 1H), 7.88 (m, 1H) |
| Example 519 | 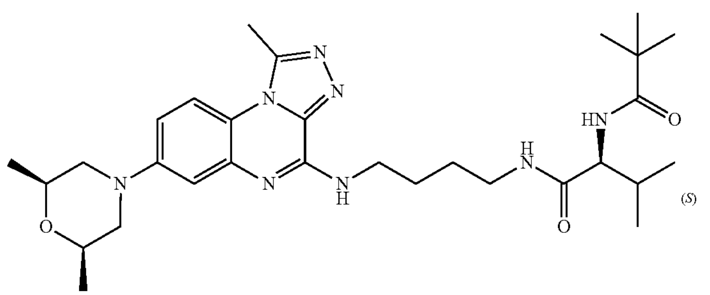 | (S)-N-{4-[7-(2,6-dimethyl-morpholine-methyl-[1,2,4]triazolo[4,3-a]quinoxaline-4-ylamino]-butyl}-2-(2,2-dimethyl-propionylamino)-3-methyl-butyramide | Mass (M + H⁺): 567.4; ¹H NMR (500 MHz, DMSO-d6): δ0.75 (m, 6H), 1.05 (m, 9H), 1.14 (s, 6H), 1.45 (m, 2H), 1.63 (m, 2H), 1.90 (m, 1H), 2.26 (t, 2H), 2.93 (s, 3H), 3.00 (m, 1H), 3.15 (m, 1H), 3.48 (m, 2H), 3.66 (m, 4H), 4.04 (t, 3H), 6.95 (m, 2H), 7.00 (s, 1H), 7.86 (d, 2H), 7.97 (m, 1H). |
| Example 520 | 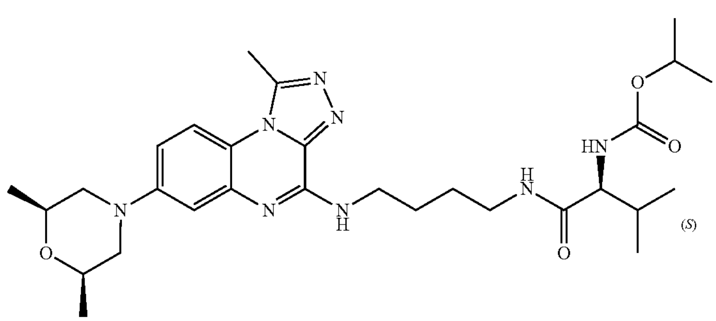 | (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isopropylester | Mass (M + H⁺): 569.3; ¹H NMR (500 MHz, DMSO-d6): δ0.77 (m, 6H), 1.14 (m, 12H), 1.45 (m, 2H), 1.63 (m, 2H), 1.84 (m, 2H), 2.26 (t, 2H), 2.93 (s, 3H), 3.08 (m, 2H), 3.55 (m, 2H), 3.69 (m, 5H), 4.66 (m, 1H), 6.91 (d, 1H), 6.90 (d, 1H), 7.00 (s, 1H), 7.86 (s, 1H), 7.88 (d, 1H), 7.97 (m, 1H). |

<Preparative Example 36> Preparation of [4-(3-hydrazino-7-thiomorpholine-4-yl-quinoxaline-2-ylamino)-butyl]-carbamic acid-tert-butylester

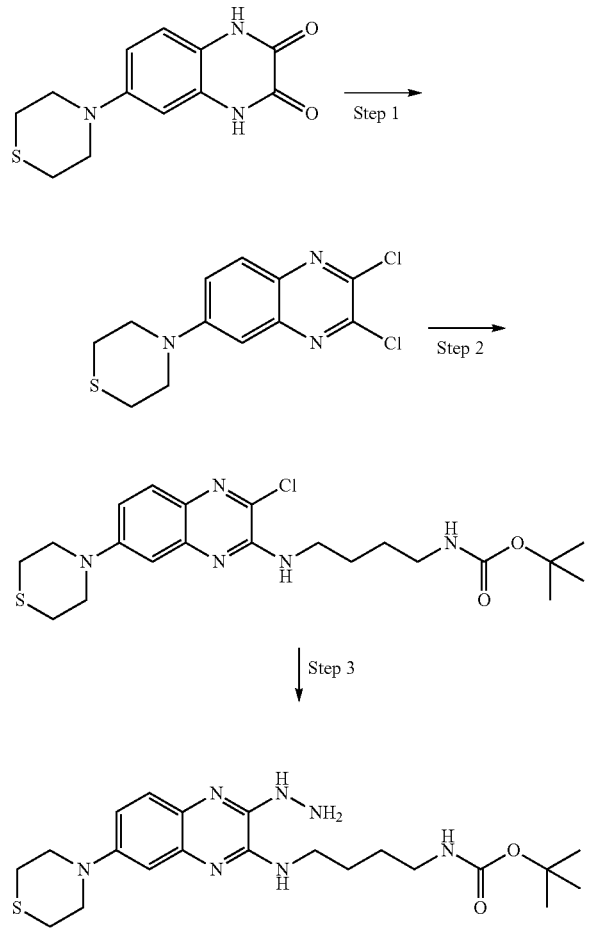

[4-(3-thiomorpholine-4-yl-quinoxalineinoxaline-2-ylamino)-butyl]-carbamic acid-tert-butylester, a target compound of Preparative Example 36, was obtained by the same manner as described in Preparative Example 20.

Step 1: Preparation of 2,3-dichloro-6-thiomorpholine-4-yl-quinoxaline

Mass (M+H⁺): 301.0
¹H NMR (500 MHz, DMSO-d6): δ2.60 (m, 4H), 3.40 (m, 4H), 6.63 (s, 1H), 6.71 (d, 1H), 6.99 (d, 1H)

Step 2: Preparation of [4-(3-chloro-7-thiomorpholine-4-yl-quinoxaline-2-ylamino)-butyl]-carbamic acid-tert-butylester Mass (M−H⁺): 451.0
¹H NMR (500 MHz, DMSO-d6): δ1.31 (s, 9H), 1.39 (m, 4H), 1.65 (m, 4H), 2.91 (m, 4H), 3.41 (m, 4H), 6.75 (t, 1H), 7.02 (s, 1H), 7.30 (t, 1H), 7.51 (d, 1H), 7.60 (d, 1H).

Step 3: Preparation of [4-(3-hydrazino-7-thiomorpholine-4-yl-quinoxaline-2-ylamino)-butyl]-carbamic acid-tert-butylester Mass (M+H⁺): 448.3

<Example 521> Preparation of {[4-(1-methyl-7-thiomorpholine-4-yl)-[1,2,4]triazolo[4,3-a]quinoxaline-4-ylamino]-butyl}-carbamic acid-tert-butylester

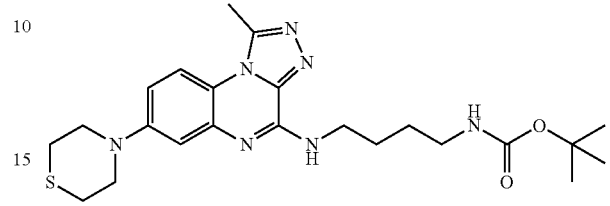

0.14 g of a target compound was obtained (10% yield) by the same manner as described in step 3 of Preparative Example 5, except that [4-(3-hydrazino-7-thiomorpholine-4-yl-quinoxaline-2-ylamino)-butyl]-carbamic acid-tert-butylester (1.3 g, 2.88 mmol) prepared in step 3 of Preparative Example 36 was used.

Mass (M+H⁺): 472.2
¹H NMR (500 MHz, DMSO-d6): δ1.32 (s, 9H), 1.43 (m, 2H), 1.60 (m, 2H), 2.65 (m, 4H), 2.95 (q, 2H), 2.93 (s, 3H), 3.40 (q, 2H), 3.58 (m, 4H), 6.75 (t, 1H), 6.89 (d, 1H), 6.99 (s, 1H), 7.87 (d, 1H), 7.96 (t, 1H).

<Example 522> Preparation of N¹-(1-methyl-7-thiomorphonyl-4-yl-[1,2,4]triazolo[4,3-a]quinoxaline-4-yl)-butane-1,4-diamine ditrifluoroacetic acid

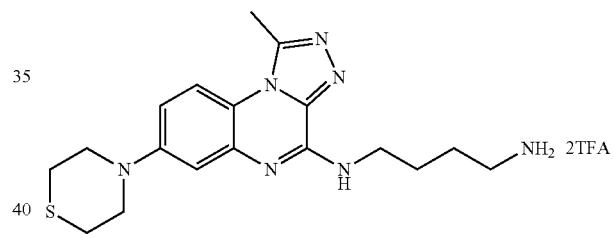

0.13 g of a target compound was obtained (76% yield) by the same manner as described in Example 58, except that {[4-(1-methyl-7-thiomorpholine-4-yl)-[1,2,4]triazolo[4,3-a]quinoxaline-4-ylamino]-butyl}-carbamic acid-tert-butylester (0.14 g, 0.3 mmol) prepared in Example 521 was used.

Mass (M+H⁺): 372.2
¹H NMR (500 MHz, DMSO-d6): δ1.59 (m, 2H), 1.69 (m, 2H), 2.66 (m, 4H), 2.82 (q, 2H), 2.98 (s, 3H), 3.50 (q, 2H), 3.60 (m, 4H), 6.93 (d, 1H), 7.00 (d, 1H), 7.66 (brs, 3H), 7.90 (d, 1H), 8.21 (br, 1H).

<Example 523> Preparation of 3-methyl-N-[4-(1-methyl-7-thiomorpholine-4-yl-[1,2,4]triazolo[4,3-a]quinoxaline-4-ylamino)-butyl]-butyramide

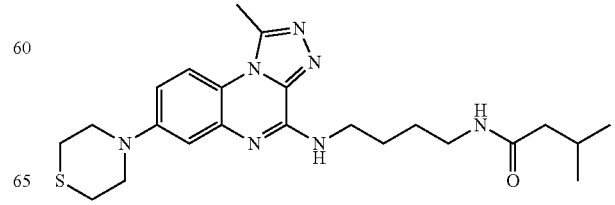

35 mg of a target compound was obtained (64% yield) by the same manner as described in Example 37, except that N$^1$-(1-methyl-7-thiomorphonyl-4-yl-[1,2,4]triazolo[4,3-a]quinoxaline-4-yl)-butane-1,4-diamine ditrifluoroacetic acid (70 mg, 0.12 mmol) prepared in Example 522 was used.

Mass (M+H$^+$): 456.2

$^1$H NMR (500 MHz, DMSO-d6) δ0.80 (d, 6H), 1.43 (m, 2H), 1.62 (m, 2H), 1.86 (d, 2H), 1.87 (m, 1H), 2.66 (m, 4H), 2.93 (s, 3H), 3.05 (q, 2H), 3.38 (q, 2H), 3.58 (m, 4H), 6.88 (d, 1H), 6.99 (s, 1H), 7.69 (t, 1H), 7.88 (d, 1H), 7.98 (t, 1H).

The compounds shown in Table 36 below were prepared by the same manner as described in Example 38, except that N$^1$-(1-methyl-7-thiomorphonyl-4-yl-[1,2,4]triazolo[4,3-a]quinoxaline-4-yl)-butane-1,4-diamine ditrifluoroacetic acid prepared in Example 522 was used.

TABLE 36

| Example | Structure | Name | Data |
| --- | --- | --- | --- |
| Example 524 | 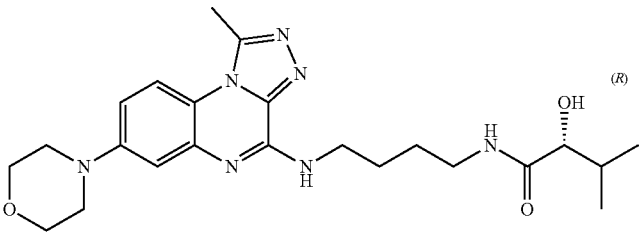 | N-[4-(7-thiomorphonyl-4-yl-1-methyl-[1,2,4]triazolo[4,3-a]quinoxaline-4-ylamino)-butyl]-2-(R)-hydroxy-3-methyl-butyramide | Mass (M + H$^+$): 472.2; $^1$H NMR (500 MHz, DMSO-d6): δ0.69 (d, 3H), 0.83 (d, 3H), 1.46 (m, 2H), 1.61 (m, 2H), 1.91 (m, 1H), 2.66 (m, 4H), 2.93 (s, 3H), 3.12 (m, 2H), 3.40 (q, 2H), 3.59 (q, 1H), 3.60 (m, 4H), 5.22 (d, 1H), 6.90 (d, 1H), 6.99 (s, 1H), 7.65 (t, 1H), 7.89 (d, 1H), 7.98 (t, 1H). |
| Example 525 | 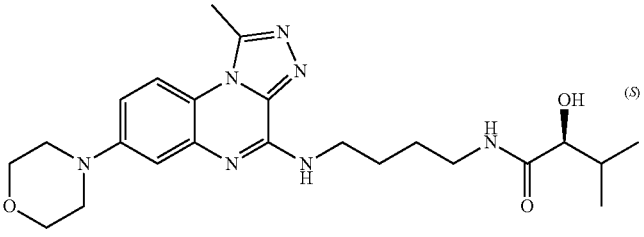 | N-[4-(7-thiomorphonyl-4-yl-1-methyl-[1,2,4]triazolo[4,3-a]quinoxaline-4-ylamino)-butyl]-2-(S)-hydroxy-3-methyl-butyramide | Mass (M + H$^+$): 472.2; $^1$H NMR (500 MHz, DMSO-d6): δ0.69 (d, 3H), 0.83 (d, 3H), 1.46 (m, 2H), 1.61 (m, 2H), 1.91 (m, 1H), 2.66 (m, 1H), 2.93 (m, 4H), 3.12 (s, 3H), 3.40 (m, 2H), 3.59 (q, 2H), 3.60 (q, 1H), 5.22 (m, 4H), 6.90 (d, 1H), 6.99 (d, 1H), 7.65 (s, 1H), 7.89 (t, 1H), 7.98 (d, 1H), (t, 1H). |

331

<Preparative Example 37> Preparation of {4-[3-hydrazino-7-(6,7-dihydro-4H-thiano[3,2-c]pyridine-5-yl)-quinoxaline-2-ylamino]-butyl}-carbamic acid-tert-butylester

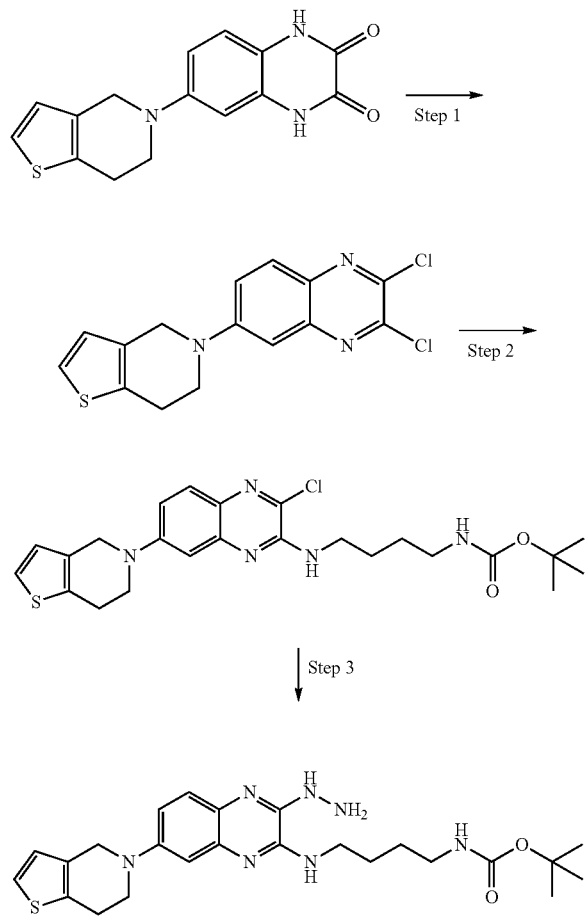

{4-[3-Hydrazino-7-(6,7-dihydro-4H-thiano[3,2-c]pyridine-5-yl)-quinoxaline-2-ylamino]-butyl}-carbamic acid-tert-butylester, a target compound of Preparative Example 37, was obtained by the same manner as described in Preparative Example 20.

Step 1: Preparation of 2,3-dichloro-6-(6,7-dihydro-4H-thiano[3,2-c]pyridine-5-yl)-quinoxaline Mass (M+H$^+$): 337.1
$^1$H NMR (500 MHz, DMSO-d6): δ2.93 (t, 2H), 3.86 (t, 2H), 4.53 (s, 2H), 6.91 (d, 1H), 7.23 (s, 1H), 7.32 (d, 1H), 7.83 (m, 2H).

Step 2: Preparation of {4-[3-chloro-7-(6,7-dihydro-4H-thiano[3,2-c]pyridine-5-yl)-quinoxaline-2-ylamino]-butyl}-carbamic acid-tert-butylester Mass (M+H$^+$): 488.2
$^1$H NMR (500 MHz, DMSO-d6): δ1.33 (s, 9H), 1.41 (m, 2H), 1.56 (m, 2H), 2.91 (m, 4H), 3.40 (q, 2H), 3.72 (t, 2H), 4.41 (s, 2H), 6.78 (t, 1H), 6.89 (d, 1H), 6.93 (d, 1H), 7.18 (t, 1H), 7.25 (dd, 1H), 7.31 (d, 1H), 7.51 (d, 1H).

332

Step 3: Preparation of {4-[3-hydrazino-7-(6,7-dihydro-4H-thiano[3,2-c]pyridine-5-yl)-quinoxaline-2-ylamino]-butyl}-carbamic acid-tert-butylester Mass (M+H$^+$): 484.1

<Example 526> Preparation of {4-[7-(6,7-dihydro-4H-thiano[3,2-c]pyridine-5-yl)-1-methyl-[1,2,4]triazolo[4,3-a]quinoxaline-4-ylamino]-butyl}-carbamic acid-tert-butylester

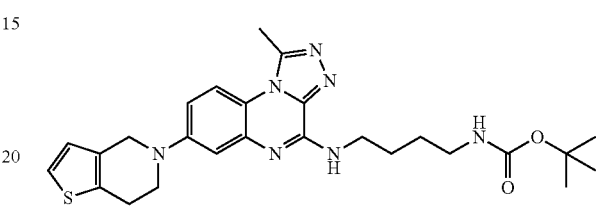

0.6 g of a target compound was obtained (77% yield) by the same manner as described in step 3 of Preparative Example 5, except that {4-[3-hydrazino-7-(6,7-dihydro-4H-thiano[3,2-c]pyridine-5-yl)-quinoxaline-2-ylamino]-butyl}-carbamic acid-tert-butylester (0.74 g, 1.53 mmol) prepared in step 3 of Preparative Example 37 was used.

Mass (M+H$^+$): 508.1
$^1$H NMR (500 MHz, DMSO-d6): δ1.32 (s, 9H), 1.43 (m, 2H), 1.60 (m, 2H), 2.90 (q, 2H), 2.92 (m, 2H), 2.94 (s, 3H), 3.49 (q, 2H), 3.65 (q, 2H), 4.34 (s, 2H), 6.78 (t, 1H), 6.93 (d, 1H), 6.99 (d, 1H), 7.07 (s, 1H), 7.29 (s, 1H), 7.88 (d, 1H), 7.96 (t, 1H).

<Example 527> Preparation of N$^1$-[7-(6,7-dihydro-4H-thiano[3,2-c]pyridine-5-yl)-1-methyl-[1,2,4]triazolo[4,3-a]quinoxaline-4-yl]-butane-1,4-diamine ditrifluoroacetic acid

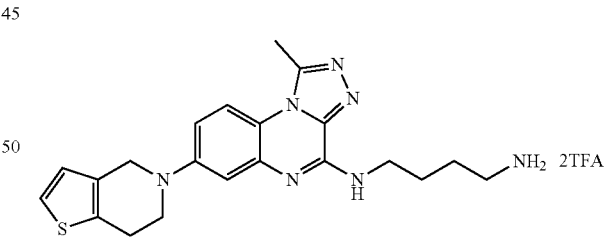

0.35 g of a target compound was obtained (88% yield) by the same manner as described in Example 58, except that {4-[7-(6,7-dihydro-4H-thiano[3,2-c]pyridine-5-yl)-1-methyl-[1,2,4]triazolo[4,3-a]quinoxaline-4-ylamino]-butyl}-carbamic acid-tert-butylester (0.32 g, 0.63 mmol) prepared in Example 526 was used.

Mass (M+H$^+$): 408.1
$^1$H NMR (500 MHz, DMSO-d6): δ1.61 (m, 2H), 1.69 (m, 2H), 2.82 (m, 2H), 2.91 (q, 2H), 2.95 (s, 3H), 3.54 (q, 2H), 3.66 (q, 2H), 4.35 (s, 2H), 6.93 (d, 1H), 7.05 (dd, 1H), 7.10 (d, 1H), 7.31 (d, 1H), 7.65 (br, 3H), 7.91 (d, 1H).

<Example 528> Preparation of N-{4-[7-(6,7-dihydro-4H-thiano[3,2-c]pyridine-5-yl)-1-methyl-[1,2,4]triazolo[4,3-a]quinoxaline-4-ylamino]-butyl}-3-methyl-butyramide

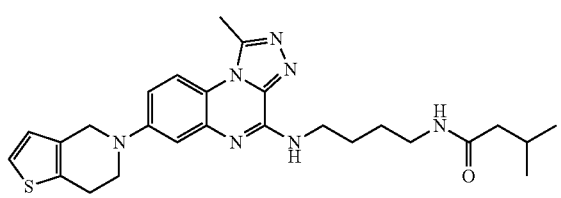 [SMILES: Cc1nnc2c(NCCCCNC(=O)CC(C)C)nc3cc(N4CCc5sccc5C4)ccc3n12]

105 mg of a target compound was obtained (88% yield) by the same manner as described in Example 37, except that N¹-[7-(6,7-dihydro-4H-thiano[3,2-c]pyridine-5-yl)-1-methyl-[1,2,4]triazolo[4,3-a]quinoxaline-4-yl]-butane-1,4-diamine ditrifluoroacetic acid (150 mg, 0.24 mmol) prepared in Example 527 was used.

Mass (M+H⁺): 492.1

$^1$H NMR (500 MHz, DMSO-d6) δ0.80 (d, 6H), 1.45 (m, 2H), 1.63 (m, 2H), 1.87 (m, 2H), 1.90 (m, 1H), 2.90 (q, 2H), 2.94 (s, 3H), 3.04 (q, 2H), 3.50 (q, 2H), 3.66 (q, 2H), 4.34 (s, 2H), 6.93 (t, 1H), 7.02 (d, 1H), 7.07 (s, 1H), 7.30 (d, 1H), 7.71 (t, 1H), 7.89 (d, 1H), 7.96 (t, 1H)

<Example 529> Preparation of N-{4-[7-(6,7-dihydro-4H-thiano[3,2-c]pyridine-5-yl)-1-methyl-[1,2,4]triazolo[4,3-a]quinoxaline-4-ylamino]-butyl}-2-(S)-fluoro-3-methyl-butyramide

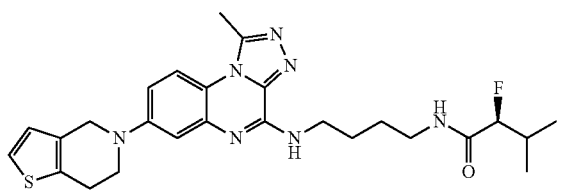 [SMILES: Cc1nnc2c(NCCCCNC(=O)[C@@H](F)C(C)C)nc3cc(N4CCc5sccc5C4)ccc3n12]

N¹-[7-(6,7-dihydro-4H-thiano[3,2-c]pyridine-5-yl)-1-methyl-[1,2,4]triazolo[4,3-a]quinoxaline-4-yl]-butane-1,4-diamine ditrifluoroacetic acid (150 mg, 0.24 mmol) prepared in Example 527 was dissolved in 5 ml of dichloromethane, to which DCC (97 mg, 0.47 ml), DMAP (12 mg, 0.47 mmol) and 2-(S)-fluoroisovaleric acid (57 mg, 0.47 mmol) were added, followed by stirring at 0~5° C. for 5 hours. Upon completion of the reaction, the reaction mixture was concentrated under reduced pressure, followed by column chromatography for separation and purification. As a result, 40 mg of a target compound was obtained (33% yield).

Mass (M+H⁺): 510.2

$^1$H NMR (500 MHz, DMSO-d6): δ0.79 (d, 3H), 0.89 (d, 3H), 1.50 (m, 2H), 1.62 (m, 2H), 2.10 (m, 1H), 2.90 (q, 2H), 2.94 (s, 3H), 3.13 (m, 2H), 3.49 (q, 2H), 3.66 (q, 2H), 4.34 (s, 2H), 4.60 (d, 1H), 6.92 (t, 1H), 7.01 (d, 1H), 7.07 (s, 1H), 7.31 (d, 1H), 7.88 (d, 1H), 7.98 (t, 1H), 8.09 (t, 1H).

<Preparative Example 38> Preparation of methyl-2-({4-[(tert-butoxycarbonyl)amino]-butyl}-amino)-3-hydrazinylquinoxaline-6-carboxylate

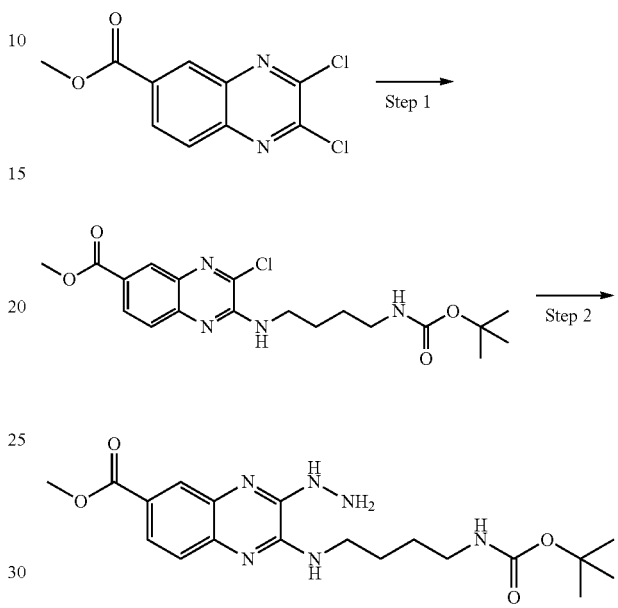

Step 1: Preparation of methyl-2-{4-[(tert-butoxycarbonylamino)-butyl]-amino}-3-chloroquinoxaline-6-carboxylate 2,3-Dichloro-quinoxaline-6-carboxylic acid methylester (2 g, 7.78 mmol) and tert-butyl(4-aminobutyl)carbamate (1.61 g, 8.56 mmol) were stirred at room temperature for 17 hours. Upon completion of the reaction, the reaction mixture was distilled under reduced pressure, followed by purification by MPLC (dichloromethane/ethylacetate). As a result, a target compound was obtained (79% yield).

Mass (M+H⁺): 409.2

$^1$H NMR (300 MHz, DMSO-d6): δ1.36 (s, 9H), 1.40-1.58 (m, 2H), 1.56-1.65 (m, 2H), 2.93-3.00 (m, 2H), 3.46-3.52 (m, 2H), 3.89 (s, 3H), 6.78 (t, J=5.37 Hz, 1H), 7.67 (d, J=8.70 Hz, 1H), 7.92 (t, J=5.70 Hz, 1H), 8.06 (dd, J=8.76 Hz, 2.04 Hz, 1H), 8.25 (d, J=1.92 Hz, 1H).

Step 2: Preparation of methyl-2-{4-[(tert-butoxycarbonylamino)-butyl]-amino}-3-hydrazinylquinoxaline-6-carboxylate Methyl-2-{4-[(tert-butoxycarbonylamino)-butyl]-amino}-3-chloroquinoxaline-6-carboxylate (3.11 g, 7.61 mmol) prepared in step 1 of Preparative Example 31, hydrazine hydrate (1.52 g, 30.4 mmol) and diisopropylethylamine (DIPEA, 3.98 ml, 22.8 mmol) were dissolved in isopropyl alcohol at room temperature, followed by stirring at 40° C. for 18 hours. Upon completion of the reaction, the reaction mixture was distilled under reduced pressure, which was proceeded to the next reaction.

Mass (M+H⁺): 405.2

<Example 530> Preparation of 4-(4-tert-butoxycarbonylamino-butylamino)-1-methyl-[1,2,4]triazolo[4,3-a]quinoxaline-8-carboxylic acid methylester

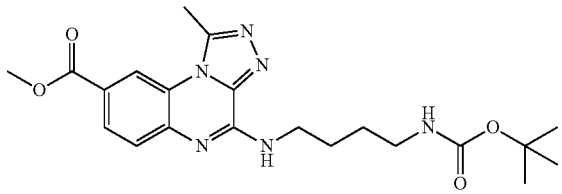 [SMILES: COC(=O)c1ccc2nc(NCCCCNC(=O)OC(C)(C)C)c3nnc(C)n3c2c1]

A target compound was obtained (74% yield) by the same manner as described in step 2 of Preparative Example 20, except that methyl-2-{4-[(tert-butoxycarbonylamino)-butyl]-amino}-3-hydrazinylquinoxaline-6-carboxylate prepared in step 2 of Preparative Example 38 was used.

Mass (M+H$^+$): 429.2

$^1$H NMR (300 MHz, CDCl$_3$): δ1.35 (s, 9H), 1.54-1.58 (m, 2H), 1.66-1.76 (m, 2H), 3.06 (s, 3H), 3.09-3.15 (m, 2H), 3.61-3.78 (m, 2H), 3.84 (s, 3H), 4.62 (brs, 1H), 6.42 (brs, 1H), 6.93 (d, J=8.76 Hz, 2H), 7.65 (dd, J=8.52 Hz, 1.74 Hz, 1H), 7.80 (d, J=8.79 Hz, 2H), 7.99 (d, J=8.61 Hz, 1H), 8.03 (d, J=1.74 Hz, 1H).

<Example 531> Preparation of 4-(4-tert-butoxycarbonylamino-butylamino)-1-methyl-[1,2,4]triazolo[4,3-a]quinoxaline-8-carboxylic acid

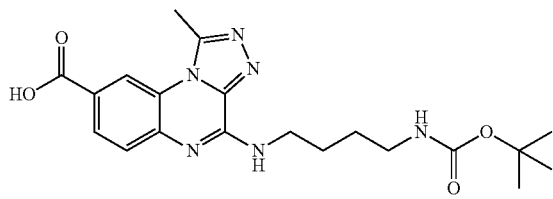 [SMILES: Cc1nnc2c(NCCCCNC(=O)OC(C)(C)C)nc3ccc(C(=O)O)cc3n12]

4-(4-tert-butoxycarbonylamino-butylamino)-1-methyl-[1,2,4]triazolo[4,3-a]quinoxaline-8-carboxylic acid methylester (2 g, 4.67 mmol) prepared in Example 530 was dissolved in tetrahydrofuran, to which sodium hydroxide (0.56 g, 14 mmol) dissolved in water was added at room temperature, followed by stirring at the same temperature for 18 hours. Upon completion of the reaction, the solvent was eliminated by distillation under reduced pressure. The pH was adjusted to 1 with 1 N aqueous hydrochloric acid solution to form a solid. The resulting solid was filtered and dried under reduced pressure. As a result, a target compound was obtained (98% yield).

Mass (M+H$^+$): 414.7

$^1$H NMR (300 MHz, DMSO-d6): δ1.36 (s, 9H), 1.42-1.51 (m, 2H), 1.62-1.70 (m, 2H), 2.93-3.00 (m, 2H), 3.05 (s, 3H), 3.54-3.60 (m, 2H), 6.79 (t, J=5.28 Hz, 1H), 7.64 (d, J=8.46 Hz, 1H), 7.96 (dd, J=8.46 Hz, 1.59 Hz, 1H), 8.57 (d, J=1.56 Hz, 1H), 8.60 (brs, 1H), 13.1 (brs, 1H).

<Example 532> Preparation of [4-(8-isopropylcarbamoyl-1-methyl-[1,2,4]triazolo[4,3-a]quinoxaline-4-ylamino)-butyl]-carbamic acid-tert-butylester

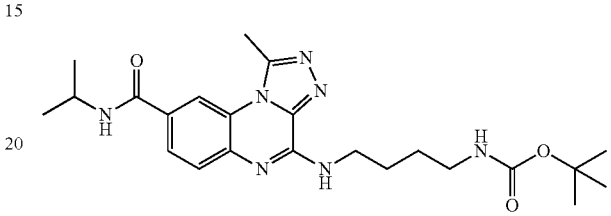

4-(4-tert-butoxycarbonylamino-butylamino)-1-methyl-[1,2,4]triazolo[4,3-a]quinoxaline-8-carboxylic acid (0.30 g, 0.72 mmol) prepared in Example 531, isopropylamine (0.05 g, 0.86 mmol), HCTU (0.36 g, 0.86 mmol) and DIPEA (0.19 ml, 1.08 mmol) were dissolved in dimethylformamide, followed by stirring at room temperature for 3 hours. Upon completion of the reaction, the reaction mixture was extracted with sodium bicarbonate aqueous solution and ethylacetate. The organic layer was washed with brine and 1 N aqueous hydrochloric acid solution. The reactant was dried over magnesium sulfate, filtered, and purified by MPLC (isopropyl alcohol/dichloromethane). As a result, a target compound was obtained (79% yield).

Mass (M+H$^+$): 456.2

$^1$H NMR (300 MHz, DMSO-d6): δ1.20 (d, J=6.63 Hz, 6H), 1.36 (s, 9H), 1.42-1.51 (m, 2H), 1.61-1.70 (m, 2H), 2.93-3.01 (m, 2H), 3.09 (s, 3H), 3.52-3.59 (m, 2H), 4.08-4.20 (m, 1H), 6.80 (t, J=5.31 Hz, 1H), 7.62 (d, J=8.49 Hz, 1H), 7.94 (dd, J=8.55 Hz, 1.65 Hz, 1H), 8.34 (t, J=6.81 Hz, 1H), 8.41 (t, J=5.73 Hz, 1H), 8.46 (d, J=1.50 Hz, 1H).

The compound prepared in Example 532 was obtained in the form of the primary amine by removal of the protecting group by trifluoroacetic acid. The compound was obtained in quantitative yield and can be used in the next reaction to produce various amide compounds.

Examples of the compounds prepared by the same manner as described in Examples 530~532 are shown in Table 37 below.

TABLE 37

| Example | Structure | Name | Data |
|---|---|---|---|
| Example 533 | ![structure] | [4-(8-carbamoyl-1-methyl-[1,2,4]triazolo[4,3-a]quinoxaline-4-ylamino)-butyl]-carbamic acid-tert-butylester | Mass (M + H$^+$): 414.2; $^1$H NMR (300 MHz, DMSO-d6): δ1.36 (s, 9H), 1.44-1.49 (m, 2H), 1.63-1.68 (m, 2H), 2.93-3.00 (m, 2H), 3.08 (s, 3H), 3.55-3.57 (m, 2H), 6.80 (brs, 1H), 7.46 (s, 1H), 7.61 (d, J = 8.46 Hz, |

| Example | Structure | Name | Data |
|---|---|---|---|
| | | | 1H), 7.94 (d, J = 7.23 Hz, 1H), 8.41 (t, J = 8.85 Hz, 1 H), 8.12 (s, 1H), 8.48 (s, 1H). |
| Example 534 | 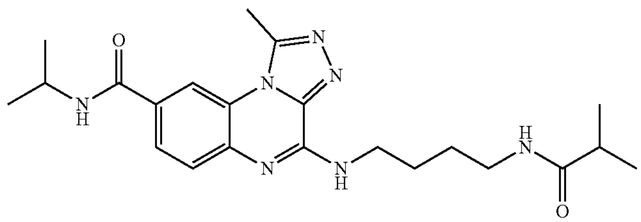 [SMILES: Cc1nnc2c(NCCCCNC(=O)C(C)C)nc3ccc(C(=O)NC(C)C)cc3n12] | 4-(4-isobutylamino-butylamino)-1-methyl-[1,2,4]tria-zolo[4,3-a]quinoxaline-8-carboxylic acid isopropylamide | Mass (M + H⁺): 426.2; ¹H NMR (500 MHz, DMSO-d6): δ0.97 (d, J = 6.85 Hz, 6H), 1.21 (d, J = 6.55 Hz, 6H), 1.60-1.71 (m, 2H), 2.29-2.38 (m, 1H), 3.06-3.10 (m, 5H), 3.55-3.63 (m, 2H), 4.11-4.18 (m, 1H), 7.62 (d, J = 8.45 Hz, 1H), 7.70 (t, J = 5.40 Hz, 1H), 7.95 (dd, J = 8.55 Hz, 1.65 Hz, 1H), 8.36 (d, J = 7.65 Hz, 1H), 8.43 (t, J = 5.70 Hz, 1H), 8.48 (d, J = 1.60 Hz, 1H, 1.46-1.52 (m, 2H). |
| Example 535 | 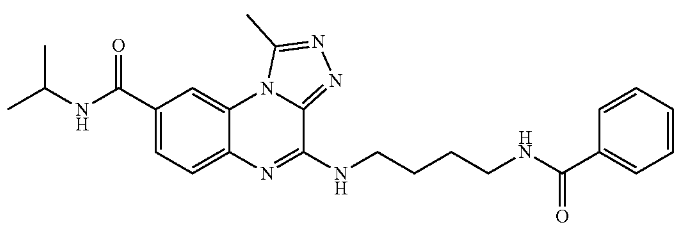 [SMILES: Cc1nnc2c(NCCCCNC(=O)c3ccccc3)nc3ccc(C(=O)NC(C)C)cc3n12] | 4-(4-benzylamino-butylamino)-1-methyl-[1,2,4]tria-zolo[4,3-a]quinoxaline-8-carboxylic acid isopropylamide | Mass (M + H⁺): 460.2; ¹H NMR (500 MHz, DMSO-d6): δ1.21 (d, J = 6.60 Hz, 6H), 1.60-1.67 (m, 2H), 1.72-1.78 (m, 2H), 3.07 (s, 3H), 3.31-3.35 (m, 2H), 3.59-3.62 (m, 2H), 4.11-4.19 (m, 1H), 7.44 (t, J = 7.25 Hz, 2H), 7.51 (t, J = 7.35 Hz, 1H), 7.61 (d, J = 8.45 Hz, 1H), 7.82-7.84 (m, 2H), 7.94 (dd, J = 8.55 Hz, 1.55 Hz, 1H), 8.36 (d, J = Hz, 1H), 8.43-8.47 (m, 3H). |
| Example 536 | 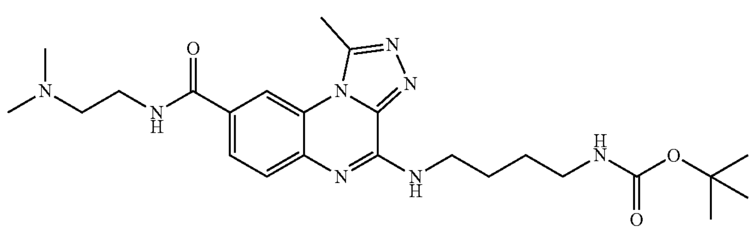 [SMILES: Cc1nnc2c(NCCCCNC(=O)OC(C)(C)C)nc3ccc(C(=O)NCCN(C)C)cc3n12] | {4-[8-(2-dimethylamino-ethylcar-bamoyl)-1-methyl-[1,2,4]tria-zolo[4,3-a]quinoxaline-4-ylamino]-butyl}-carbamic acid-tert-butylester | Mass (M + H⁺): 485.3; ¹H NMR (300 MHz, DMSO-d6): δ1.36 (s, 9H), 1.42-1.52 (m, 2H), 1.62-1.69 (m, 2H), 2.20 (s, 6H), 2.42-2.46 (m, 2H), 2.94-3.00 (m, 2H), 3.09 (s, 3H), 3.37-3.43 (m, 2H), 3.53-3.59 (m, 2H), 6.79 (t, J = 4.89 Hz, 1H), 7.62 (d, J = 8.49 Hz, 1H), 7.90 (dd, J = 8.55 Hz, 1.47 Hz, 1H), 8.40 (t, J = 5.64 Hz, 1H), 8.45 (d, J = 1.23 Hz, 1H), 8.53 (t, J = 5.58 Hz, 1H). |

TABLE 37-continued

| Example | Name | Data |
|---|---|---|
| Example 537 | 4-(4-benzoylamino)-1-methyl-[1,2,4]triazolo[4,3-a]quinoxaline-8-carboxylic acid-(2-dimethylaminoethyl)-amide | Mass (M + H⁺): 488.9 |
| Example 538 | [4-(1-methyl-8-phenylcarbamoyl-[1,2,4]triazolo[4,3-a]quinoxaline-4-ylamino)-butyl]-carbamic acid-tert-butylester | Mass (M + H⁺): 490.2; ¹H NMR (300 MHz, DMSO-d6): δ1.36 (s, 9H), 1.45-1.52 (m, 2H), 1.63-1.70 (m, 2H), 2.94-3.00 (m, 2H), 3.12 (s, 3H), 3.55-3.61 (m, 2H), 6.78-6.82 (m, 1H), 7.12 (t, J = 7.38 Hz, 1H), 7.38 (t, J = 8.04 Hz, 2H), 7.70 (d, J = 8.49 Hz, 1H), 7.80 (d, J = 7.77 Hz, 2H), 8.12 (dd, J = 8.55 Hz, 1.62 Hz, 1H), 8.49 (t, J = 5.67 Hz, 1H), 8.57(d, J = 1.53 Hz, 1H), 10.40 (s, 1H). |
| Example 539 | N-{4-[8-(4-benzyl-piperazine-1-carbonyl)-1-methyl-[1,2,4]triazolo[4,3-a]quinoxaline-4-ylamino]-butyl}-benzamide | Mass (M + H⁺): 576.5; ¹H NMR (300 MHz, DMSO-d6): δ1.60-1.64 (m, 2H), 1.66-1.72 (m, 2H), 3.05 (s, 3H), 3.14-3.18 (m, 3H), 3.20-3.35 (m, 4H), 3.55-3.65 (m, 6H), 4.34 (brs, 2H), 7.40-7.44 (m, 6H), 7.46-7.55 (m, 2H), 7.66-7.74 (m, 3H), 7.82-7.85 (m, 2H), 8.07 (d, J = 1.23 Hz, 1H), 8.53-8.56 (m, 1H). |
| Example 540 | N-{4-[1-methyl-8-(piperazine-1-carbonyl)-[1,2,4]triazolo[4,3-a]quinoxaline-4-ylamino]-butyl}-benzamide | Mass (M + H⁺): 486.5 |

<Preparative Example 39> Preparation of tert-butyl-[4-(3-hydrazinyl-6-nitroquinoxaline-2-ylamino)-butyl]-carbamate

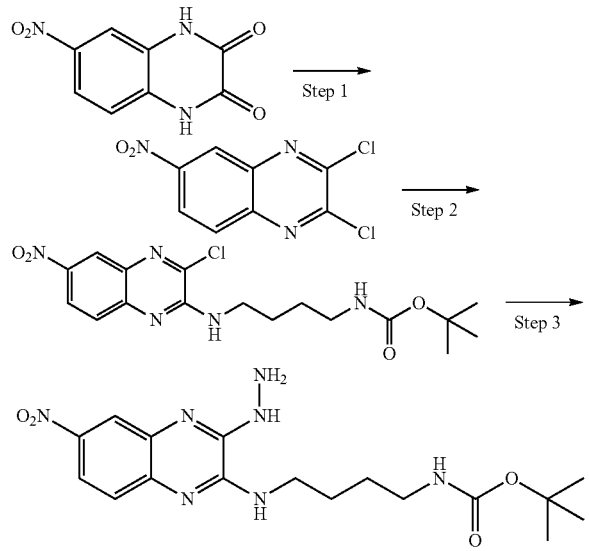

Step 1: Preparation of 2,3-dichloro-6-nitroquinoxaline

6-Nitroquinoxaline-2,3-(1H,4H)-dione (12 g, 59.0 mmol), thionylchloride (28.1 g, 236 mmol), and catalytic amount of dimethylformamide (0.86 g, 11.8 mmol) were reflux stirred in dichloroethane for 2 hours. Upon completion of the reaction, the solvent was eliminated and the temperature was lowered to 0-5° C. to form a solid. The resulting solid was filtered and dried under reduced pressure. As a result, 12.3 g of a target compound was obtained (87% yield).

Mass (M+H$^+$): 244.1
$^1$H NMR (300 MHz, DMSO-d6) δ8.31 (d, J=9.15 Hz, 1H), 8.60 (d, J=9.15 Hz, 1H), 8.88 (s, 1H).

Step 2: Preparation of tert-butyl-[4-(3-chloro-6-nitroquinoxaline-2-ylamino)-butyl]-carbamate 2.2 g of a target compound was obtained (92% yield) by the same manner as described in step 1 of Preparative Example 20, except that 2,3-dichloro-6-nitroquinoxaline (2.55 g, 10.5 mmol) prepared in step 1 of Preparative Example 39 was used.

Mass (M+H$^+$): 396.2
$^1$H NMR (500 MHz, DMSO-d6): δ1.36 (s, 9H), 1.43-1.49 (m, 2H), 1.63-1.67 (m, 2H), 2.95-3.00 (m, 2H), 3.50-3.54 (m, 2H), 6.79 (t, J=5.20 Hz, 1H), 7.73 (d, J=9.20 Hz, 1H), 8.24 (t, J=5.70 Hz, 1H), 8.33 (dd, J=9.25 Hz, 2.65 Hz, 1H), δ8.55 (d, J=2.60 Hz, 1H)

Step 3: Preparation of tert-butyl-[4-(3-hydrazinyl-6-nitroquinoxaline-2-ylamino)-butyl]-carbamate A target compound was obtained (quantitative yield) by the same manner as described in step 2 of Preparative Example 39, except that tert-butyl-[4-(3-chloro-6-nitroquinoxaline-2-ylamino)-butyl]-carbamate (2.30 g, 5.81 mmol) prepared in step 2 of Preparative Example 39 was used. The following reaction was carried out without purification.

Mass (M+H$^+$): 392.2

<Example 541> Preparation of [4-(1-methyl-8-nitro-[1,2,4]triazolo[4,3-a]quinoxaline-4-ylamino)-butyl]-carbamic acid-tert-butylester

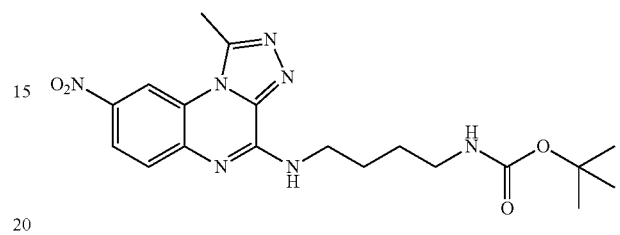

A target compound was obtained (76% yield) by the same manner as described in step 3 of Preparative Example 5, except that tert-butyl-[4-(3-hydrazinyl-6-nitroquinoxaline-2-ylamino)-butyl]-carbamate prepared in step 3 of Preparative Example 39 was used.

Mass (M+H$^+$): 416.2
$^1$H NMR (500 MHz, DMSO-d6): δ1.37 (s, 9H), 1.44-1.50 (m, 2H), 1.64-1.70 (m, 2H), 2.95-3.00 (m, 2H), 3.09 (s, 3H), 3.58-3.62 (m, 2H), 6.81 (t, J=5.10 Hz, 1H), 7.70 (d, J=8.95 Hz, 1H), 8.27 (dd, J=8.85 Hz, 1.70 Hz, 1H), 8.78 (d, J=1.35 Hz, 1H), δ9.00 (t, J=5.65 Hz, 1H)

<Example 542> Preparation of [4-(8-amino-1-methyl-[1,2,4]triazolo[4,3-a]quinoxaline-4-ylamino)-butyl]-carbamic acid-tert-butylester

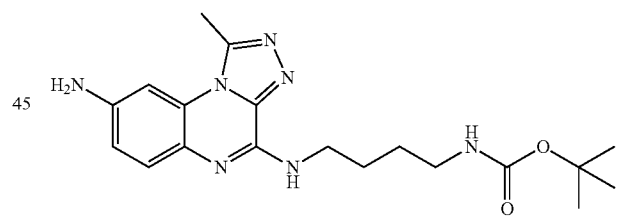

[4-(1-Methyl-8-nitro-[1,2,4]triazolo[4,3-a]quinoxaline-4-ylamino)-butyl]-carbamic acid-tert-butylester (1.50 g, 3.61 mmol) prepared in Example 541 and Pd/C (10 W %) were loaded in ethanol, followed by stirring at room temperature at 5 bar of hydrogen for 4 hours. Upon completion of the reaction, paladium catalyst was filtered and eliminated. The filtrate was distilled under reduced pressure, followed by recrystallization in methanol. As a result, a target compound was obtained (92% yield).

Mass (M+H$^+$): 386.3
$^1$H NMR (500 MHz, DMSO-d6): δ1.37 (s, 9H), 1.43-1.49 (m, 2H), 1.60-1.66 (m, 2H), 2.94-2.97 (m, 2H), 2.99 (s, 3H), 3.46-3.50 (m, 2H), 5.83 (brs, 2H), 6.78 (dd, J=8.70 Hz, 2.20 Hz, 1H), 6.81 (t, J=5.60 Hz, 1H), 7.38 (d, J=8.90 Hz, 1H), 7.40 (d, J=2.10 Hz, 1H), 7.66 (brs, 1H).

<Example 543> Preparation of [4-(8-isobutylamino-1-methyl-[1,2,4]triazolo[4,3-a]quinoxaline-4-ylamino)-butyl]-carbamic acid-tert-butylester

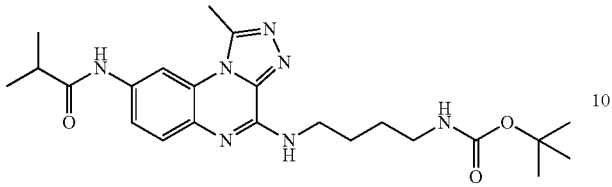

A target compound was obtained (69% yield) by the same manner as described in Example 70, except that [4-(8-amino-1-methyl-[1,2,4]triazolo[4,3-a]quinoxaline-4-ylamino)-butyl]-carbamic acid-tert-butylester (0.50 g, 1.30 mmol) prepared in Example 542 was used.

Mass (M+H$^+$): 455.5

$^1$H NMR (500 MHz, DMSO-d6): δ1.15 (d, J=6.80 Hz, 6H), 1.37 (s, 9H), 1.44-1.49 (m, 2H), 1.62-1.69 (m, 2H), 2.61-2.66 (m, 1H), 2.95-3.00 (m, 2H), 3.02 (s, 3H), 3.49-3.53 (m, 2H), 6.81 (t, J=5.40 Hz, 1H), 7.53 (d, J=8.80 Hz, 1H), 7.58 (dd, J=8.80 Hz, 2.00 Hz, 1H), 7.95 (t, J=5.75 Hz, 1H), 8.80 (d, J=1.85 Hz, 1H), 10.1 (s, 1H).

<Example 544> Preparation of N-[4-(4-aminobutylamino)-1-methyl-[1,2,4]triazolo[4,3-a]quinoxaline-8-yl]-isobutyramide ditrifluoroacetic acid

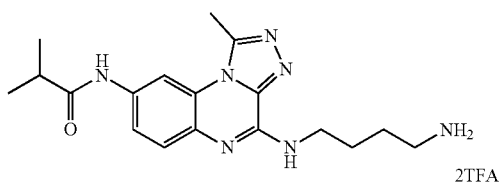 [SMILES: Cc1nnc2c(NCCCCN)nc3ccc(NC(=O)C(C)C)cc3n12]

A target compound was obtained by the same manner as described in Example 58, except that [4-(8-isobutylamino-1-methyl-[1,2,4]triazolo[4,3-a]quinoxaline-4-ylamino)-butyl]-carbamic acid-tert-butylester (0.15 g, 0.33 mmol) prepared in Example 543 was used.

Mass (M+H$^+$): 356.3

<Example 545> Preparation of N-[4-(8-isobutylamino-1-methyl-[1,2,4]triazolo[4,3-a]quinoxaline-4-ylamino)-butyl]-2,2-dimethyl-propionamide A target compound was obtained (64% yield) by the same manner as described in Example 59, except that N-[4-(4-aminobutylamino)-1-methyl-[1,2,4]triazolo[4,3-a]quinoxaline-8-yl]-isobutyramide ditrifluoroacetic acid prepared in Example 544 was used.

Mass (M+H$^+$): 439.4

$^1$H NMR (500 MHz, DMSO-d6): δ1.07 (s, 9H), 1.15 (d, J=6.80 Hz, 6H), 1.46-1.52 (m, 2H), 1.62-1.67 (m, 2H), 2.61-2.66 (m, 1H), 3.02 (s, 3H), 3.07-3.12 (m, 2H), 3.50-3.54 (m, 2H), 7.43 (t, J=5.65 Hz, 1H), 7.52 (d, J=8.75 Hz, 1H), 7.58 (dd, J=8.90 Hz, 2.10 Hz, 1H), 7.95 (t, J=5.75 Hz, 1H), 8.80 (s, 1H), 10.1 (s, 1H).

Examples of the compounds prepared by the same manner as described in Examples 543 and 544 are shown in Table 38 below.

TABLE 38

| Example | Structure | Name | Data |
|---|---|---|---|
| Example 546 | 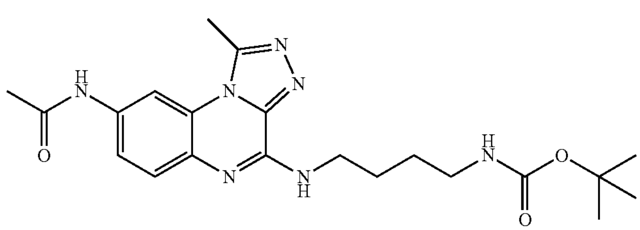 [SMILES: CC(=O)Nc1ccc2nc(NCCCCNC(=O)OC(C)(C)C)c3nnc(C)n3c2c1] | [4-(8-acetamino-1-methyl-[1,2,4]triazolo[4,3-a]quinoxaline-4-ylamino)-butyl]-carbamic acid-tert-butylester | Mass (M + H$^+$): 427.6; $^1$H NMR (500 MHz, DMSO-d6): δ1.37 (s, 9H), 1.45-1.49 (m, 2H), 1.62-1.66 (m, 2H), 2.10 (s, 3H), 2.95-2.99 (m, 2H), 3.00 (s, 3H), 3.49-3.53 (m, 2H), 6.80 (t, J = 5.35 Hz, 1H), 7.52-7.57 (m, 2H), 7.95 (t, J = 5.70 Hz, 1H), 8.69 (d, J = 1.70 Hz, 1H), 10.2 (s, 1H). |

TABLE 38-continued

| Example | Structure | Name | Data |
|---|---|---|---|
| Example 547 | 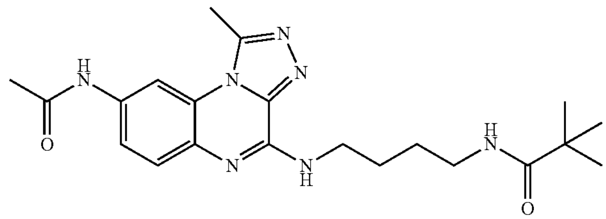 [SMILES: CC(=O)Nc1ccc2nc(NCCCCNC(=O)C(C)(C)C)c3nnc(C)n3c2c1] | N-[4-(8-acetamino-1-methyl-[1,2,4]triazolo[4,3-a]quinoxaline-4-ylamino)-butyl]-2,2-dimethyl-propionamide | Mass (M + H$^+$): 411.6; $^1$H NMR (500 MHz, DMSO-d6): δ1.07 (s, 9H), 1.46-1.52 (m, 2H), 1.61-1.67 (m, 2H), 2.10 (s, 3H), 3.00 (s, 3H), 3.06-3.10 (m, 2H), 3.50-3.54 (m, 2H), 7.43 (t, J = 5.65 Hz, 1H), 7.52-7.53 (m, 1H), 7.55-7.57 (m, 1H), 7.95 (t, J = 5.55 Hz, 1H), 8.69 (d, J = 1.95 Hz, 1H), 10.2 (s, 1H). |
| Example 548 | 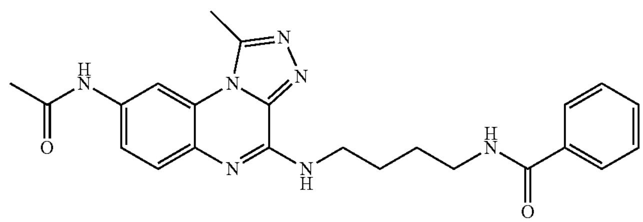 [SMILES: CC(=O)Nc1ccc2nc(NCCCCNC(=O)c3ccccc3)c3nnc(C)n3c2c1] | N-[4-(8-acetamino-1-methyl-[1,2,4]triazolo[4,3-a]quinoxaline-4-ylamino)-butyl]-benzamide | Mass (M + H$^+$): 431.9; $^1$H NMR (500 MHz, DMSO-d6): δ1.60-1.65 (m, 2H), 1.70-1.76 (m, 2H), 2.10 (s, 3H), 3.00 (s, 3H), 3.30-3.34 (m, 2H), 3.54-3.58 (m, 2H), 7.44 (t, J = 7.20 Hz, 2H), 7.49-7.56 (m, 3H), 7.82-7.83 (m, 2H), 7.98 (t, J = 5.80 Hz, 1H), 8.46 (t, J = 5.50 Hz, 1H), 8.69 (d, J = 1.90 Hz, 1H), 10.2 (s, 1H). |
| Example 549 | 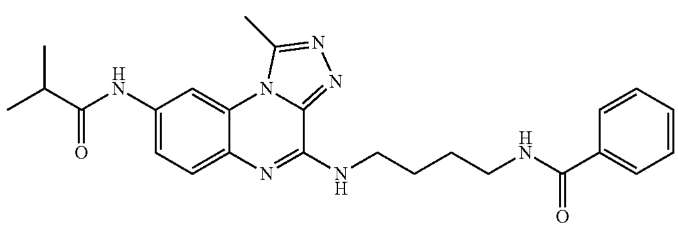 [SMILES: Cc1nnc2c(NCCCCNC(=O)c3ccccc3)nc3ccc(NC(=O)C(C)C)cc3n12] | N-[4-(8-isobutylamino-1-methyl-[1,2,4]triazolo[4,3-a]quinoxaline 4-ylamino)-butyl]-benzamide | Mass (M + H$^+$): 459.5; $^1$H NMR (500 MHz, DMSO-d6): δ1.15 (d, J = 6.85 Hz, 6H), 1.61-1.67 (m, 2H), 1.70-1.76 (m, 2H), 2.61-2.65 (m, 1H), 3.01 (s, 3H), 3.30-3.36 (m, 2H), 3.54-3.59 (m, 2H), 7.44 (t, J = 7.35 Hz, 2H), 7.49-7.53 (m, 2H), 7.57 (dd, J = 8.70 Hz, 1.75 Hz, 1H), 7.83 (d, J = 7.65 Hz, 2H), 7.98 (t, J = 5.70 Hz, 1H), 8.46 (t, J = 5.40 Hz, 1H), 8.80 (s, 1H), 10.1 (s, 1H). |

<Preparative Example 40> Preparation of N-[4-(3-hydrazino-6-nitroquinoxaline-2-ylamino)butyl]-3-methyl-butyramide

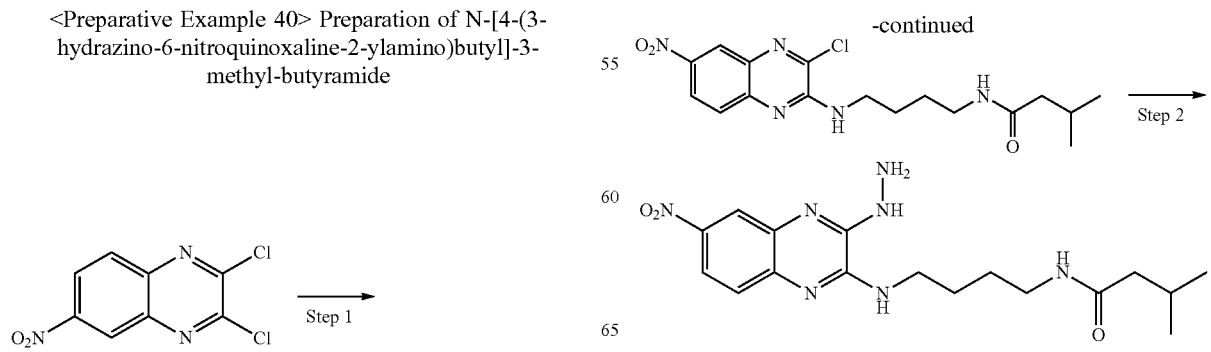

Step 1: Preparation of N-[4-(3-chloro-6-nitroquinoxaline-2-ylamino)-butyl]-3-methyl-butyramide 1.5 g of a target compound was obtained (96% yield) by the same manner as described in step 1 of Preparative Example 20, except that 2,3-dichloro-6-nitroquinoxaline (1 g, 4.1 mmol) and N-(4-aminobutyl)-3-methyl-butyramide ditrifluoroacetic acid (2.46 g, 6.15 mmol) prepared in step 1 of Preparative Example 18 were used.

Mass (M+H⁺): 378.2

¹H NMR (500 MHz, DMSO-d6) δ1.24 (d, 6H), 1.31 (m, 3H), 1.40 (m, 2H), 1.52 (m, 2H), 2.73 (q, 2H), 3.56 (q, 2H), 6.67 (s, 1H), 6.72 (t, 1H), 8.20 (t, 1H), 8.28 (d, 1H), 8.50 (d, 1H).

Step 2: Preparation of N-[4-(3-hydrazino-6-nitro-quinoxaline-2-ylamino) butyl]-3-methyl-butyramide 2.45 g of a target compound was obtained (67% yield) by the same manner as described in step 2 of Preparative Example 20, except that N-[4-(3-chloro-6-nitroquinoxaline-2-ylamino)-butyl]-3-methyl-butyramide (3.7 g, 9.74 mmol) prepared in step 1 of Preparative Example 40 was used. The following reaction was carried out without purification.

Mass (M+H⁺): 376.2

¹H NMR (500 MHz, DMSO-d6) δ0.80 (d, 6H) 1.40 (m, 2H), 1.55 (m, 2H), 1.86 (d, 2H), 1.89 (m, 1H), 3.00 (q, 2H), 3.38 (br, 3H), 3.42 (q, 2H), 7.25 (d, 1H), 7.55 (t, 1H), 7.71 (s, 1H), 7.72 (d, 1H), 7.98 (t, 1H).

<Example 550> Preparation of 3-methyl-N-[4-(1-methyl-8-nitro-[1,2,4]triazolo[4,3-a]quinoxaline-4-ylamino)-butyl]-butyramide

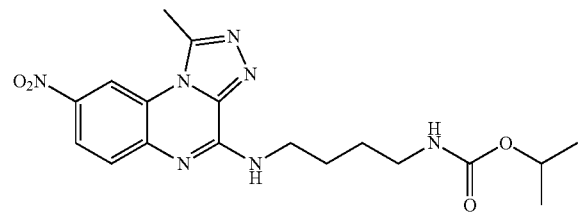 [SMILES: Cc1nnc2c(NCCCCNC(=O)OC(C)C)nc3ccc([N+](=O)[O-])cc3n12]

1.8 g of a target compound was obtained (70% yield) by the same manner as described in step 3 of Preparative Example 5, except that N-[4-(3-hydrazino-6-nitroquinoxaline-2-ylamino) butyl]-3-methyl-butyramide (2.4 g, 6.4 mmol) prepared in step 2 of Preparative Example 40 was used.

Mass (M+H⁺): 400.2

¹H NMR (500 MHz, DMSO-d6) δ0.79 (d, 6H), 1.45 (m, 2H), 1.64 (m, 2H), 1.86 (d, 2H), 1.87 (m, 1H), 3.04 (q, 2H), 3.05 (s, 3H), 3.57 (q, 2H), 7.64 (d, 1H), 7.70 (t, 1H), 8.23 (d, 1H), 8.74 (s, 1H), 8.95 (t, 1H)

<Example 551> Preparation of N-[4-(8-amino-1-methyl-[1,2,4]triazolo[4,3-a]quinoxaline-4-ylamino)-butyl]-3-methyl-butyramide

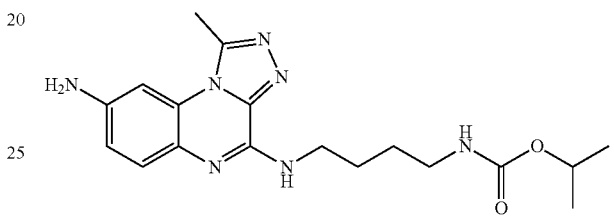

0.72 g of a target compound was obtained (75% yield) by the same manner as described in Example 243, except that 3-methyl-N-[4-(1-methyl-8-nitro-[1,2,4]triazolo[4,3-a]quinoxaline-4-ylamino)-butyl]-butyramide (1 g, 2.50 mmol) prepared in Example 549 was used.

Mass (M+H⁺): 370.0

¹H NMR (500 MHz, DMSO-d6) δ0.80 (d, 6H), 1.43 (m, 2H), 1.59 (m, 2H), 1.86 (d, 2H), 1.87 (m, 1H), 2.94 (s, 3H), 3.04 (q, 2H), 3.43 (q, 2H), 5.32 (s, 2H), 6.70 (t, 1H), 7.29 (m, 2H), 7.35 (t, 1H), 7.70 (t, 1H).

The compounds prepared by using N-[4-(8-amino-1-methyl-[1,2,4]triazolo[4,3-a]quinoxaline-4-ylamino)-butyl]-3-methyl-butyramide prepared in Example 550 are shown in Table 39 below.

TABLE 39

| Example | Structure | Name | Data |
|---|---|---|---|
| Example 552 | 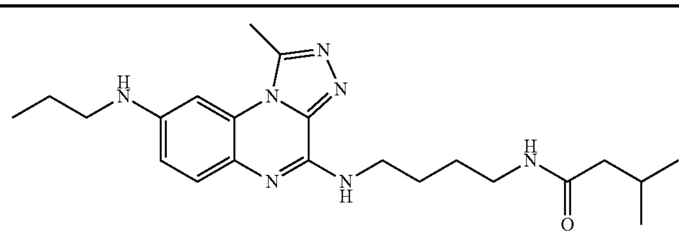 | 3-methyl-N-[4-(1-methyl-8-propylamino-[1,2,4]triazolo[4,3-a]quinoxaline-4-ylamino)-butyl]-butyramide | Mass (M + H⁺): 412.0; ¹H NMR (500 MHz, DMSO-d6): δ0.80 (d, 6H), 0.98 (m, 3H), 1.14 (m, 2H), 1.40 (m, 2H), 1.58 (m, 4H), 1.88 (t, 3H), 2.97 (s, 3H), 3.05 (q, 2H), 3.40 (q, 2H), 5.87 (t, 1H), 6.72 (d, 1H), 7.19 (s, 1H), 7.32 (d, 1H), 7.68 (t, 1H), 8.84 (br, 1H). |

TABLE 39-continued

| Example | Structure | Name | Data |
|---|---|---|---|
| Example 553 | 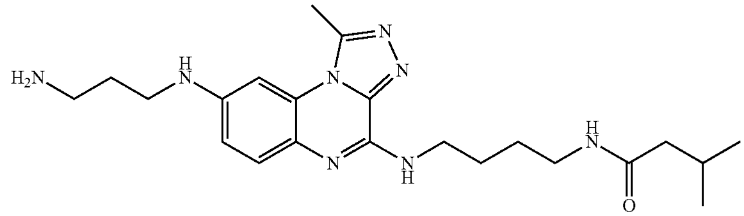 | N-{4-[8-(3-cyano-propylamino)-1-methyl-[1,2,4]triazolo[4,3-a]quinoxaline-4-ylamino]-butyl}-3-methyl-butyramide | Mass (M + H⁺): 437.2; ¹H NMR (500 MHz, DMSO-d6): δ0.80 (d, 6H), 1.43 (m, 2H), 1.70 (m, 2H), 1.82 (m, 4H), 1.87 (m, 4H), 2.46 (m, 2H), 3.02 (m, 4H), 3.41 (m, 5H), 5.71 (s, 1H), 6.93 (d, 1H), 7.20 (s, 1H), 7.43 (d, 1H), 7.55 (t, 1H), 7.69 (t, 1H). |
| Example 554 | 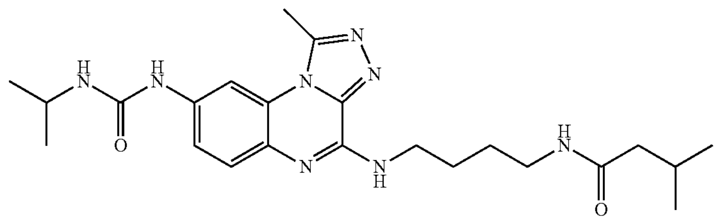 | N-{4-[8-(3-ethyl-thioureido)-1-methyl-[1,2,4]triazolo[4,3-a]quinoxaline-4-ylamino]-butyl}-3-methyl-butyramide | Mass (M + H⁺): 471.3; ¹H NMR (500 MHz, DMSO-d6): δ0.86 (d, 6H), 1.23 (t, 3H), 1.45 (m, 2H), 1.63 (m, 2H), 1.71 (m, 2H), 1.87 (d, 1H), 2.98 (s, 3H), 3.04 (q, 2H), 3.48 (q, 2H), 3.75 (t, 3H), 7.47 (d, 1H), 7.49 (t, 1H), 7.62 (d, 1H), 7.69 (m, 2H), 7.95 (t, 1H). |

<Example 555> Preparation of N-[4-(7-methoxy-1-methyl-8-nitro-[1,2,4]triazolo[4,3-a]quinoxaline-4-ylamino)-butyl]-3-methyl-butyramide

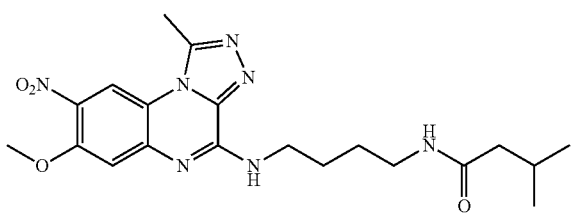 [SMILES: COc1cc2nc(NCCCCNC(=O)CC(C)C)c3nnc(C)n3c2cc1[N+](=O)[O-]]

N-[4-(7-methoxy-1-methyl-[1,2,4]triazolo[4,3-a]quinoxaline-4-ylamino)-butyl]-3-methyl-butyramide (100 mg, 0.26 mmol) prepared in Example 285 was dissolved in 2 ml of 60% nitric acid aqueous solution, to which 1 ml of sulfuric acid was added, followed by reaction at room temperature for 3 hours. Upon completion of the reaction, the reaction mixture was extracted with ethylacetate and water. The organic layer was dried over magnesium sulfate, followed by distillation under reduced pressure. The resulting solid was recrystallized in ethanol, and as a result 25 mg of a target compound was obtained (22% yield).

Mass (M+H⁺): 430.1

¹H NMR (500 MHz, DMSO-d6): δ0.80 (d, 6H), 1.46 (m, 2H), 1.62 (m, 2H), 1.86 (d, 2H), 1.87 (m, 1H), 2.98 (s, 3H), 3.01 (q, 2H), 3.56 (q, 2H), 3.98 (s, 3H), 7.27 (s, 1H), 7.70 (t, 1H), 8.52 (s, 1H), 8.85 (t, 1H)

<Example 556> Preparation of N-[4-(8-amino-7-methoxy-1-methyl-[1,2,4]triazolo[4,3-a]quinoxaline-4-ylamino)-butyl]-3-methyl-butyramide

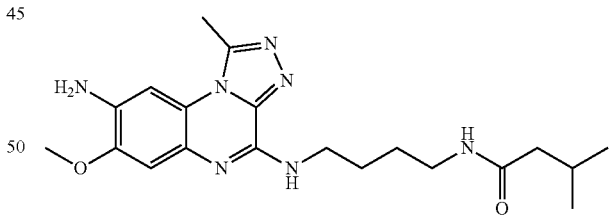

0.56 g of a target compound was obtained (67% yield) by the same manner as described in Example 243, except that N-[4-(7-methoxy-1-methyl-8-nitro-[1,2,4]triazolo[4,3-a]quinoxaline-4-ylamino)-butyl]-3-methyl-butyramide (0.9 g, 2.10 mmol) prepared in Example 555 was used.

Mass (M+H⁺): 400.2

¹H NMR (500 MHz, DMSO-d6): δ0.80 (d, 6H), 1.48 (m, 2H), 1.65 (m, 2H), 1.89 (d, 2H), 1.92 (m, 1H), 2.95 (s, 3H), 3.13 (q, 2H), 3.55 (q, 2H), 3.89 (s, 3H), 7.26 (s, 1H), 7.70 (s, 1H), 7.76 (t, 1H), 9.40 (br, 2H).

The compounds prepared by using N-[4-(8-amino-7-methoxy-1-methyl-[1,2,4]triazolo[4,3-a]quinoxaline-4-ylamino)-butyl]-3-methyl-butyramide prepared in Example 556 are shown in Table 40 below.

TABLE 40

| Example | Structure | Name | Data |
|---|---|---|---|
| Example 557 | 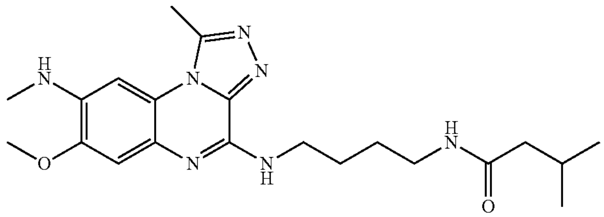 [SMILES: CNc1cc2c(cc1OC)nc(NCCCCNC(=O)CC(C)C)c1nnc(C)n12] | N-[4-(7-methoxy-1-methyl-8-methylamino-[1,2,4]triazolo[4,3-a]quinoxaline-4-ylamino)-butyl]-3-methyl-butyramide | Mass (M + H$^+$): 414.2; $^1$H NMR (500 MHz, DMSO-d6): δ0.79 (d, 6H), 1.20 (d, 3H), 1.45 (m, 2H), 1.61 (m, 2H), 1.87 (d, 2H), 1.90 (m, 1H), 2.80 (q, 2H), 3.02 (q, 2H), 3.05 (s, 3H), 3.40 (q, 1H), 3.85 (s, 3H), 6.98 (s, 1H), 7.03 (s, 1H), 7.44 (t, 1H), 7.70 (t, 1H). |
| Example 558 | 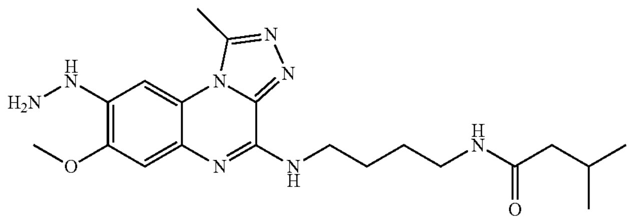 [SMILES: COc1cc2nc(NCCCCNC(=O)CC(C)C)c3nnc(C)n3c2cc1NN] | N-[4-(8-hydroxyamino-7-methoxy-1-methyl-[1,2,4]triazolo[4,3-a]quinoxaline-4-ylamino)-butyl]-3-methyl-butyramide | Mass (M − H$^+$): 414.2; $^1$H NMR (500 MHz, DMSO-d6): δ0.81 (d, 6H), 1.20 (br, 1H), 1.46 (m, 2H), 1.65 (m, 2H), 1.89 (m, 1H), 2.86 (s, 3H), 3.05 (s, 2H), 3.30 (d, 1H), 3.60 (q, 2H), 4.23 (s, 3H), 6.80 (s, 1H), 7.39 (s, 1H), 7.71 (t, 1H), 9.22 (t, 1H). |
| Example 559 | 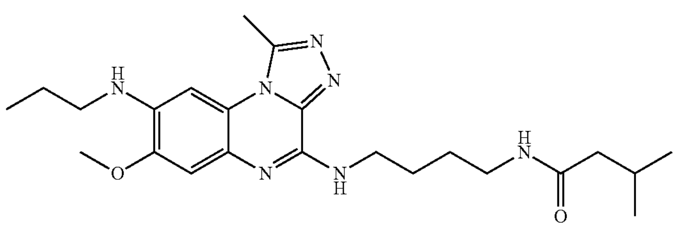 [SMILES: CCCNc1cc2c(cc1OC)nc(NCCCCNC(=O)CC(C)C)c1nnc(C)n12] | N-[4-(7-methoxy-1-methyl-8-propylamino-[1,2,4]triazolo[4,3-a]quinoxaline-4-ylamino)-butyl]-3-methyl-butyramide | Mass (M + H$^+$): 442.3; $^1$H NMR (500 MHz, DMSO-d6): δ0.80 (d, 6H), 0.94 (t, 3H), 1.43 (m, 2H), 1.61 (m, 2H), 1.86 (m, 4H), 1.87 (d, 2H), 3.00 (m, 1H), 3.04 (s, 3H), 3.11 (q, 2H), 3.45 (s, 2H), 3.86 (m, 2H), 5.09 (s, 3H), 6.98 (t, 1H), 7.06 (s, 1H), 7.45 (s, 1H), 7.70 (t, 1H). |
| Example 560 | 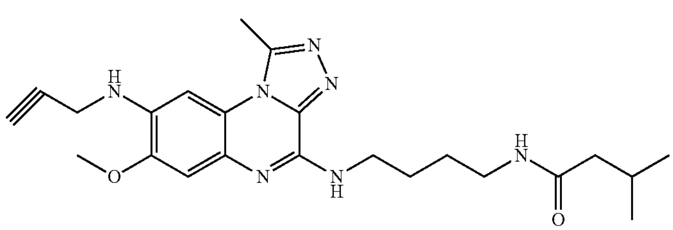 [SMILES: C#CCNc1cc2c(cc1OC)nc(NCCCCNC(=O)CC(C)C)c1nnc(C)n12] | N-[4-(7-methoxy-1-methyl-8-prop-2-ylamino-[1,2,4]triazolo[4,3-a]quinoxaline-4-ylamino)-butyl]-3-methyl-butyramide | Mass (M + H$^+$): 438.3; $^1$H NMR (500 MHz, DMSO-d6): δ0.80 (d, 6H), 1.44 (m, 2H), 1.62 (m, 2H), 1.86 (d, 2H), 1.90 (m, 1H), 3.05 (s, 3H), 3.09 (q, 2H), 3.46 (q, 2H), 3.86 (s, 3H), 4.03 (d, 2H), 5.67 |

TABLE 40-continued

| Example | Structure | Name | Data |
|---|---|---|---|
| | | | (t, 1H), 7.02 (s, 1H), 7.31 (s, 1H), 7.53 (t, 1H), 7.71 (t, 2H). |
| Example 561 | 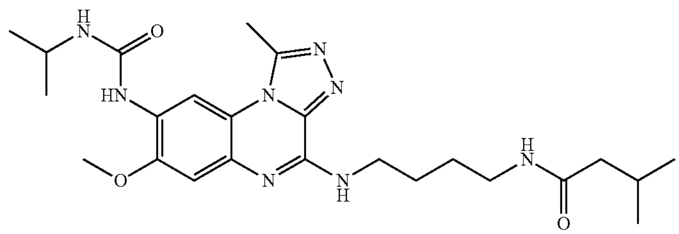 [SMILES: COc1cc2nc(NCCCCNC(=O)CC(C)C)c3nnc(C)n3c2cc1NC(=O)NC(C)C] | N-{4-[8-(3-isopropyl-ureido)-7-methoxy-1-methyl-[1,2,4]triazolo[4,3-a]quinoxaline-4-ylamino]-butyl}-3-methyl-butyramide | Mass (M + H$^+$): 485.2; $^1$H NMR (500 MHz, DMSO-d6): δ0.80 (d, 6H), 1.45 (m, 2H), 1.62 (m, 2H), 1.87 (d, 2H), 2.01 (m, 1H), 2.93 (s, 3H), 3.04 (q, 2H), 3.49 (q, 2H), 3.80 (m, 1H), 3.91 (s, 3H), 6.86 (t, 1H), 7.09 (s, 1H), 7.70 (d, 1H), 7.78 (t, 1H), 8.02 (s, 1H), 9.12 (s, 1H). |
| Example 562 | 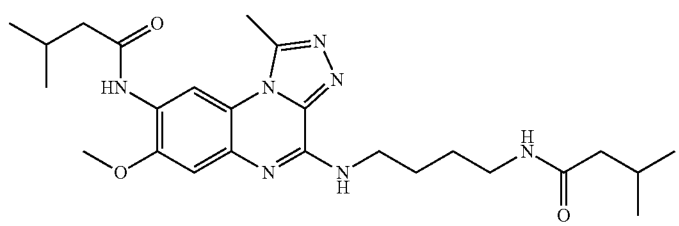 [SMILES: COc1cc2nc(NCCCCNC(=O)CC(C)C)c3nnc(C)n3c2cc1NC(=O)CC(C)C] | N-{4-[7-methoxy-1-methyl-8-(3-methyl-butyrylamino)-[1,2,4]triazolo[4,3-a]quinoxaline-4-ylamino]-butyl}-3-methyl-butyramide | Mass (M + H$^+$): 484.3; $^1$H NMR (500 MHz, DMSO-d6): δ0.81 (d, 6H), 0.92 (d, 6H), 1.46 (m, 2H), 1.64 (m, 2H), 1.87 (d, 2H), 2.06 (m, 1H), 2.15 (m, 1H), 2.25 (d, 2H), 2.94 (s, 3H), 3.10 (q, 2H), 3.67 (q, 2H), 3.94 (s, 3H), 7.34 (t, 1H), 7.74 (t, 1H), 9.07 (s, 1H), 9.27 (s, 1H), 9.50 (t, 1H). |
| Example 563 | 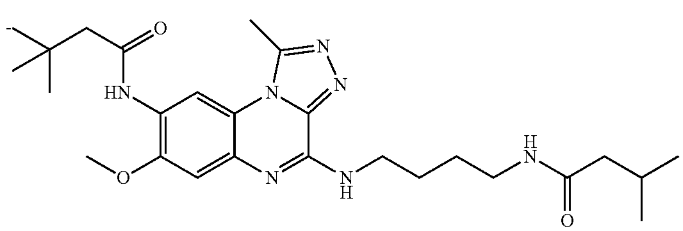 | N-{7-methoxy-1-methyl-4-[4-(3-methyl-butyrylamino)-[1,2,4]triazolo[4,3-a]quinoxaline-8-ylamino]-butyl}-3,3-dimethyl-butyramide | Mass (M + H$^+$): 498.2; $^1$H NMR (500 MHz, DMSO-d6): δ0.78 (d, 6H), 1.01 (d, 9H), 1.45 (m, 2H), 1.63 (m, 2H), 1.86 (d, 2H), 1.88 (m, 1H), 2.31 (s, 2H), 2.92 (s, 3H), 3.05 (q, 2H), 3.48 (q, 2H), 3.89 (s, 3H), 7.12 (t, 1H), 7.69 (s, 1H), 7.95 (s, 1H), 8.98 (t, 1H), 9.09 (s, 1H). |

TABLE 40-continued

| Example | Structure | Name | Data |
|---|---|---|---|
| Example 564 | 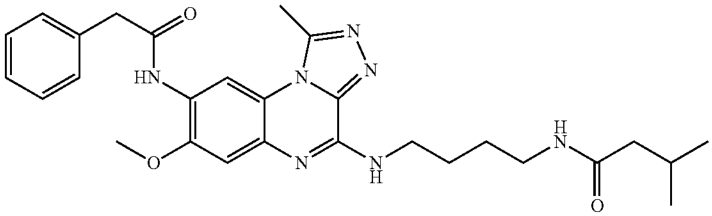 [SMILES: COc1cc2nc(NCCCCNC(=O)CC(C)C)c3nnc(C)n3c2cc1NC(=O)Cc1ccccc1] | N-{4-[7-methoxy-1-methyl-8-(3-phenylureido)-[1,2,4]triazolo[4,3-a]quinoxaline 4-ylamino]-butyl}-3-methyl-butyramide | Mass (M + H$^+$): 518.3; $^1$H NMR (500 MHz, DMSO-d6): δ0.80 (d, 6H), 1.44 (m, 2H), 1.62 (m, 2H), 1.87 (m, 2H), 1.90 (d, 2H), 2.89 (m, 1H), 3.05 (s, 3H), 3.49 (q, 2H), 3.52 (q, 2H), 3.92 (s, 3H), 7.22 (s, 2H), 7.50 (m, 5H), 7.70 (t, 1H), 7.90 (s, 1H), 7.98 (d, 1H), (t, 1H). |
| Example 565 | 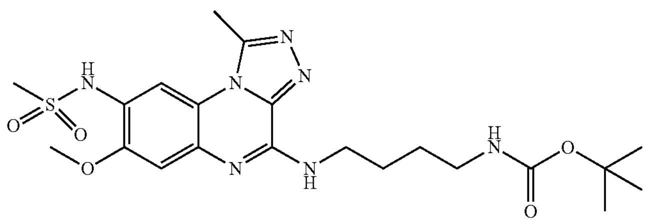 [SMILES: COc1cc2nc(NCCCCNC(=O)OC(C)(C)C)c3nnc(C)n3c2cc1NS(C)(=O)=O] | N-[4-(8-methanesulfonyl-amino-7-methoxy-1-methyl-[1,2,4]triazolo[4,3-a]quinoxaline-4-ylamino)-butyl]-3-methyl-butyramide | Mass (M − H$^+$): 476.2; $^1$H NMR (500 MHz, DMSO-d6): δ0.80 (d, 6H), 1.45 (m, 2H), 1.63 (m, 2H), 1.86 (m, 2H), 1.87 (d, 2H), 2.92 (m, 1H), 2.96 (s, 3H), 3.05 (s, 3H), 3.50 (q, 2H), 3.91 (q, 6H), 7.16 (s, 3H), 7.70 (s, 1H), 7.97 (t, 1H), 8.10 (s, 1H), 9.12 (t, 1H), (s, 1H). |
| Example 566 | 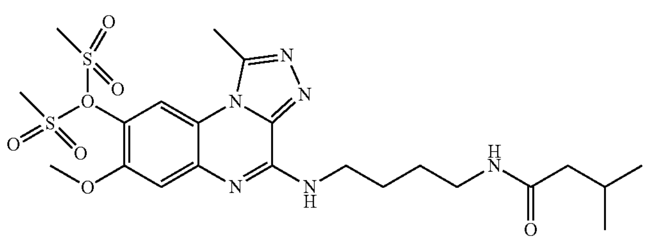 | N-[4-(8-dimethanesulfonyl-amino-7-methoxy-1-methyl-[1,2,4]triazolo[4,3-a]quinoxaline-4-ylamino)-butyl]-3-methyl-butyramide | Mass (M − H$^+$): 556.2; $^1$H NMR (500 MHz, DMSO-d6): δ0.82 (d, 6H), 1.44 (m, 2H), 1.64 (m, 2H), 1.86 (m, 2H), 1.88 (d, 2H), 2.97 (m, 1H), 3.05 (s, 3H), 3.50 (q, 2H), 3.52 (s, 6H), 3.91 (q, 2H), 7.22 (s, 3H), 7.69 (s, 1H), 7.95 (t, 1H), 8.44 (s, 1H), (t, 1H). |
| Example 567 | 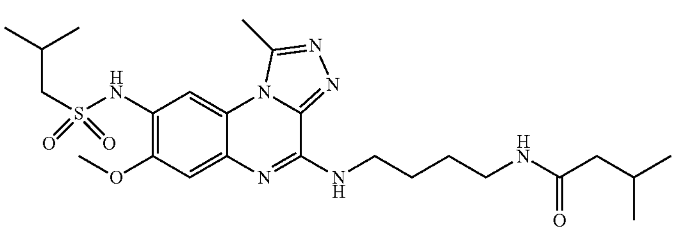 [SMILES: COc1cc2nc(NCCCCNC(=O)CC(C)C)c3nnc(C)n3c2cc1NS(=O)(=O)CC(C)C] | N-{4-[7-methoxy-1-methyl-8-(2-methyl-propane-1-sulfonylamino-[1,2,4]triazolo[4,3-a]quinoxaline-4-ylamino]-butyl}-3-methyl-butyramide | Mass (M + H$^+$): 520.2; $^1$H NMR (500 MHz, DMSO-d6): δ0.79 (d, 6H), 0.97 (d, 6H), 1.45 (m, 2H), 1.63 (m, 2H), 1.86 (d, 2H), 1.90 (m, 1H), 2.15 (m, 1H), 2.91 (d, 2H), 2.93 (s, 3H), 3.10 (q, 2H), 3.50 (q, 2H), 3.88 (s, 3H), 7.14 |

| Example | Structure | Name | Data |
|---|---|---|---|
| | | | (s, 1H), 7.70 (t, 1H), 7.99 (s, 1H), 8.09 (t, 1H), 9.14 (s, 1H). |
| Example 568 | 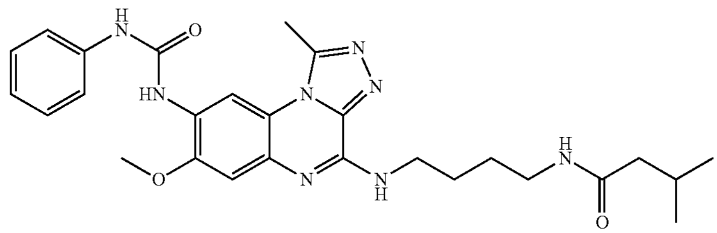 [SMILES: COc1cc2nc(NCCCCNC(=O)CC(C)C)c3nnc(C)n3c2cc1NC(=O)Nc1ccccc1] | N-{4-[7-methoxy-1-methyl-8-(3-phenyl-ureido)-[1,2,4]triazolo[4,3-a]quinoxaline-4-ylamino]-butyl}-3-methyl-butyramide | Mass (M + H⁺): 519.3; ¹H NMR (500 MHz, DMSO-d6): δ0.80 (d, 6H), 1.46 (m, 2H), 1.63 (m, 2H), 1.87 (d, 2H), 1.95 (m, 1H), 2.97 (s, 3H), 3.04 (q, 2H), 3.50 (q, 2H), 3.96 (s, 3H), 6.97 (dd, 1H), 7.15 (s, 1H), 7.27 (dd, 1H), 7.46 (dd, 1H), 7.70 (t, 1H), 7.87 (t, 1H), 8.45 (s, 1H), 9.14 (s, 1H), 9.37 (s, 1H). |
| Example 569 | 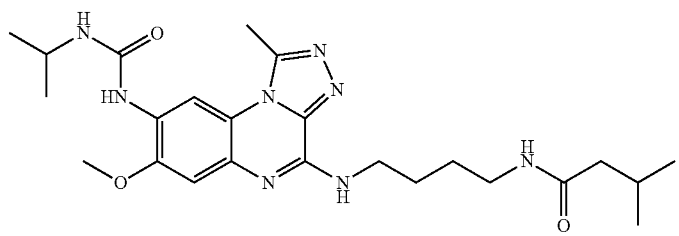 | N-{4-[8-(3-isopropyl-thioureido)-7-methoxy-1-methyl-[1,2,4]triazolo[4,3-a]quinoxaline-4-ylamino]-butyl}-3-methyl-butyramide | Mass (M + H⁺): 501.2; ¹H NMR (500 MHz, DMSO-d6): δ0.80 (d, 6H), 1.15 (d, 6H), 1.45 (m, 2H), 1.63 (m, 2H), 1.86 (d, 2H), 1.90 (m, 1H), 2.95 (s, 3H), 3.05 (q, 2H), 3.50 (q, 2H), 3.91 (s, 3H), 4.38 (m, 1H), 7.13 (s, 1H), 7.70 (t, 1H), 7.97 (t, 1H), 8.23 (d, 1H), 8.97 (s, 1H), 9.26 (s, 1H) |

<Example 570> Preparation of {4-[8-(4-methoxy-benzoyl)-1-methyl-[1,2,4]triazolo[4,3-a]quinoxaline-4-ylamino]-butyl}-carbamic acid-tert-butylester

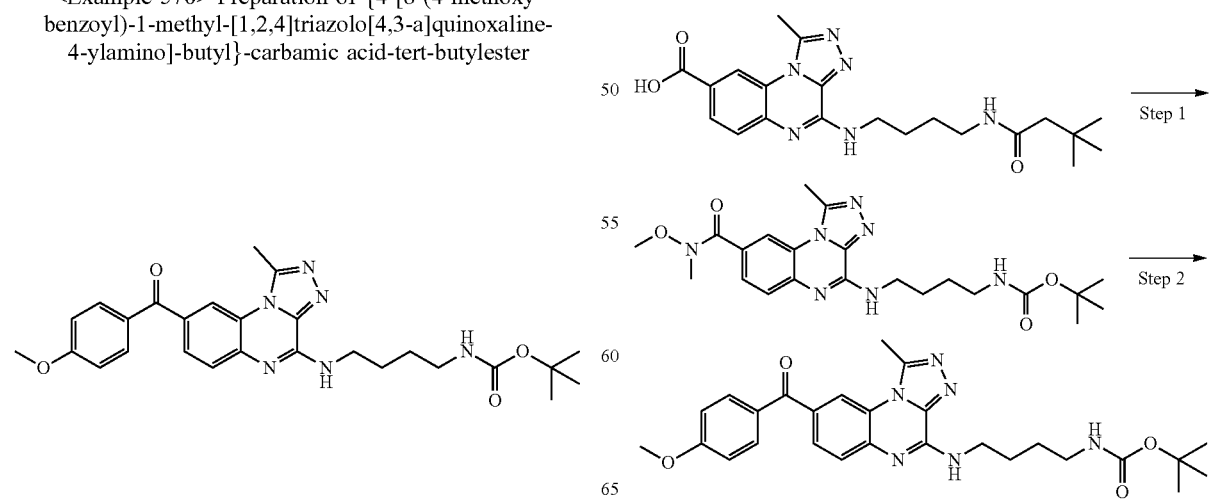

The compound of Example 570 was prepared by the following two-step reaction.

Step 1: Preparation of tert-butyl-{4-[(8-(methoxy(methyl)carbamoyl)-1-methyl-[1,2,4]triazolo[4,3-a]quinoxaline-4-yl)amino]-butyl}-carbamate 4-(4-Tert-butoxycarbonylamino-butylamino)-1-methyl-[1,2,4]triazolo[4,3-a]quinoxaline-8-carboxylic acid (0.30 g, 0.72 mmol) and methoxylmethylamine hydrochloride (0.08 g, 0.86 mmol) prepared in Example 531, HCTU (0.36 g, 0.86 mmol) and DIPEA (0.38 ml, 2.16 mmol) were dissolved in dimethylformamide, followed by stirring at room temperature for 3 hours. Upon completion of the reaction, the reaction mixture was extracted with ethylacetate and sodium bicarbonate aqueous solution. The organic layer was washed with 1 N aqueous hydrochloric acid solution and brine. The reactant was purified by MPLC (isopropyl alcohol/dichloromethane), and as a result, a target compound was obtained (86% yield).

Mass (M+H$^+$): 458.2

$^1$H NMR (500 MHz, DMSO-d6) δ1.36 (s, 9H), 1.44-1.49 (m, 2H), 1.64-1.69 (m, 2H), 2.94-3.01 (m, 2H), 3.03 (s, 3H), 3.58 (s, 3H), 3.62 (s, 3H), 6.80 (brs, 1H), 7.63 (d, J=8.40, 1H), 7.75 (d, J=8.40 Hz, 1H), 8.39 (s, 1H), 8.53 (brs, 1H).

Step 2: Preparation of {4-[8-(4-methoxy-benzoyl)-1-methyl-[1,2,4]triazolo[4,3-a]quinoxaline-4-ylamino]-butyl}-carbamic acid-tert-butylester Tert-butyl-{4-[(8-(methoxy(methyl)carbamoyl)-1-methyl-[1,2,4]triazolo[4,3-a]quinoxaline-4-yl)amino]-butyl}-carbamate (0.10 g, 0.22 mmol) prepared in step 1 above was dissolved in anhydrous tetrahydrofuran, to which excessive 4-methoxyphenylmagnesiumbromide was added in the presence of nitrogen, followed by reflux stirring for 15 minutes. Upon completion of the reaction, the reaction was terminated by adding 1 N aqueous hydrochloric acid solution at room temperature, followed by extraction with ethylacetate. The collected organic layer was washed with brine and dried over magnesium sulfate. The reactant was purified by MPLC (isopropyl alcohol/dichloromethane), and as a result, a target compound was obtained (78% yield).

Mass (M+H$^+$): 505.2

$^1$H NMR (300 MHz, DMSO-d6): δ1.36 (s, 9H), 1.43-1.50 (m, 2H), 1.65-1.70 (m, 2H), 2.94-3.01 (m, 5H), 3.58-3.60 (m, 2H), 3.89 (s, 3H), 6.80 (brs, 1H), 7.11-7.13 (m, 2H), 7.67-7.70 (m, 1H), 7.79-7.87 (m, 3H), 8.41 (s, 1H), 8.60 (brs, 1H).

<Example 571> Preparation of [4-(8-benzoyl-1-methyl-[1,2,4]triazolo[4,3-a]quinoxaline-4-ylamino)-butyl]-carbamic acid-tert-butylester

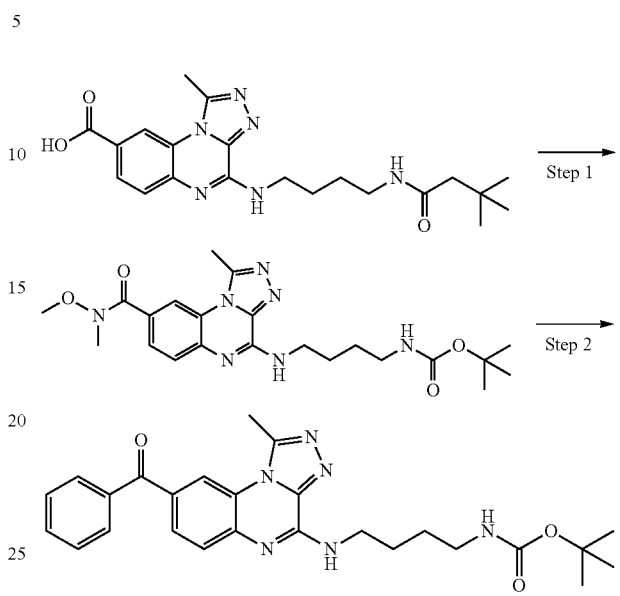

A target compound was obtained by the same manner as described in Example 570, except that phenylmagnesiumbromide was used instead of 4-methoxyphenylmagnesiumbromide in step 2 of Example 570.

Mass (M+H$^+$): 475.2

$^1$H NMR (300 MHz, DMSO-d6): δ1.36 (s, 9H), 1.43-1.50 (m, 2H), 1.63-1.70 (m, 2H), 2.95-3.00 (m, 5H), 3.58-3.60 (m, 2H), 6.80 (brs, 1H), 7.58-7.63 (m, 4H), 7.68-7.84 (m, 3H), 8.45 (s, 1H), 8.67 (t, J=5.10 Hz, 1H)

<Preparative Example 41> Preparation of [4-(3-hydrazino-6-fluoro-7-methoxy-quinoxaline-2-ylamino)-butyl]-carbamic acid-tert-butylester (c) and [4-(3-hydrazino-7-fluoro-6-methoxy-quinoxaline-2-ylamino)-butyl]-carbamic acid-tert-butylester (d)

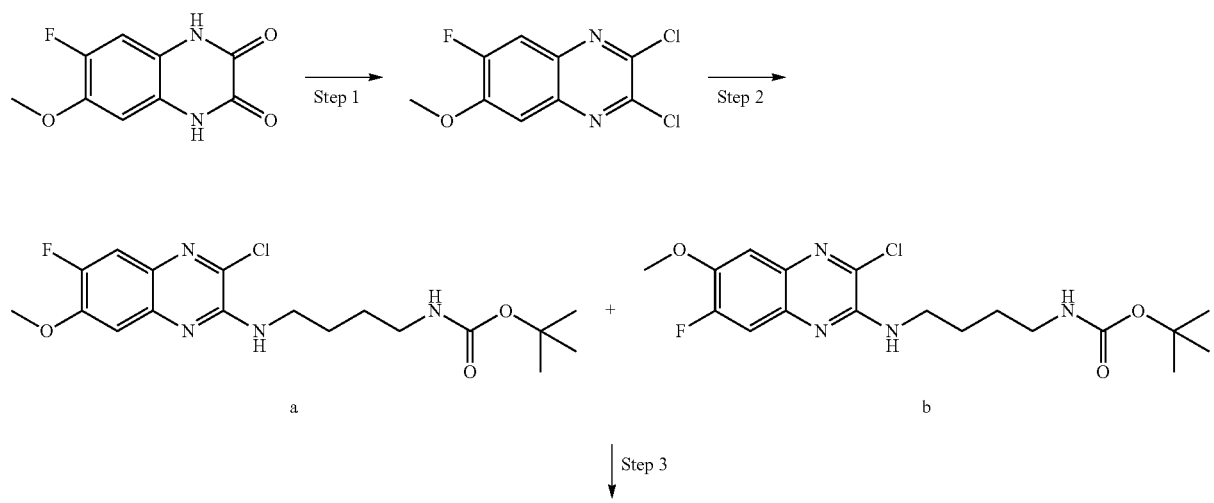

-continued

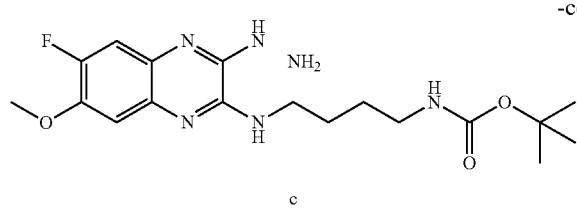

c

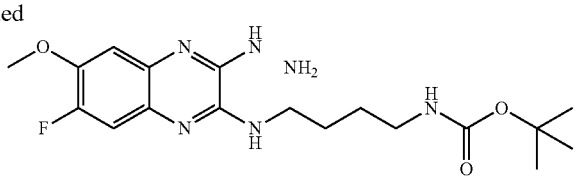

d

Step 1: Preparation of
2,3-dichloro-7-fluoro-6-methoxy-quinoxaline

Mass (M+H⁺): 247.2

Step 2: Preparation of [4-(3-chloro-6-fluoro-7-methoxy-quinoxaline-2-ylamino)-butyl]-carbamic acid-tert-butylester (a) and [4-(3-chloro-7-fluoro-6-methoxy-quinoxaline-2-ylamino)-butyl]-carbamic acid-tert-butylester (b) mixture Mass (M+H⁺): 399.1

Step 3: Preparation of [4-(3-hydrazino-6-fluoro-7-methoxy-quinoxaline-2-ylamino)-butyl]-carbamic acid-tert-butylester (c) and [4-(3-hydrazino-7-fluoro-6-methoxy-quinoxaline-2-ylamino)-butyl]-carbamic acid-tert-butylester (d) mixture Mass (M+H⁺): 395.2

<Example 572> Preparation of [4-(8-fluoro-7-methoxy 1-methyl-[1,2,4]triazolo[4,3-a]quinoxaline-4-ylamino)-butyl]-carbamic acid-tert-butylester

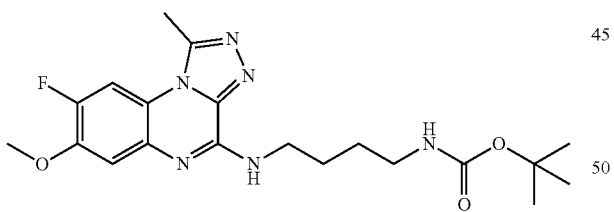

580 mg of a target compound was obtained (39% yield) by the same manner as described in step 3 of Preparative Example 5, except that [4-(3-hydrazino-6-fluoro-7-methoxy-quinoxaline-2-ylamino)-butyl]-carbamic acid-tert-butylester (c) and [4-(3-hydrazino-7-fluoro-6-methoxy-quinoxaline-2-ylamino)-butyl]-carbamic acid-tert-butylester (d) mixture (1.4 g, 3.55 mmol) prepared in step 3 of Preparative Example 41 was used.

Mass (M+H⁺): 419.2

¹H NMR (500 MHz, DMSO-d6) δ1.32 (s, 9H), 1.42 (m, 2H), 1.60 (m, 2H), 2.91 (m, 2H), 2.95 (s, 3H), 3.48 (q, 2H), 3.90 (s, 3H), 6.75 (t, 1H), 7.25 (d, 1H), 7.88 (d, 1H), 8.07 (t, 1H).

<Example 573> Preparation of [4-(7-fluoro-8-methoxy-1-methyl-[1,2,4]triazolo[4,3-a]quinoxaline-4-ylamino)-butyl]-carbamic acid-tert-butylester

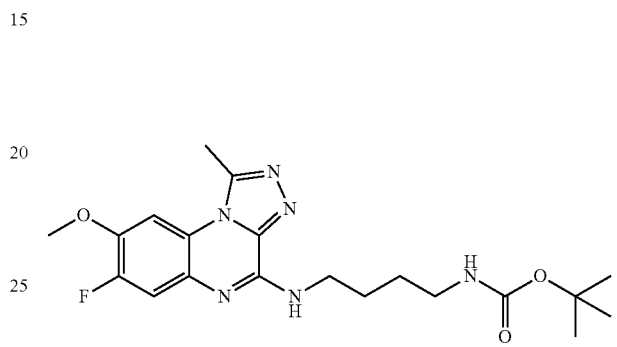

185 mg of a target compound was obtained (12% yield) by separating and purifying the compound produced as a structural isomer in the course of reaction in Example 572.

Mass (M+H⁺): 419.2

¹H NMR (500 MHz, DMSO-d6) δ1.32 (s, 9H), 1.42 (m, 2H), 1.59 (m, 2H), 2.91 (q, 2H), 3.05 (s, 3H), 3.45 (q, 2H), 3.95 (s, 3H), 6.74 (t, 1H), 7.38 (dd, 1H), 7.65 (s, 1H), 8.00 (t, 1H).

The compounds of Examples 574 and 575 were prepared by the same manner as described in Examples 572 and 573, except that N-(4-aminobutyl)-3-methyl-butyramide was used instead of tert-butyl-(N-aminobutyl)carbonate in step 2 of Preparative Example 41.

<Example 574> Preparation of N-[4-(8-fluoro-7-methoxy-1-methyl-[1,2,4]triazolo[4,3-a]quinoxaline-4-ylamino)-butyl]-3-methyl-butyramide

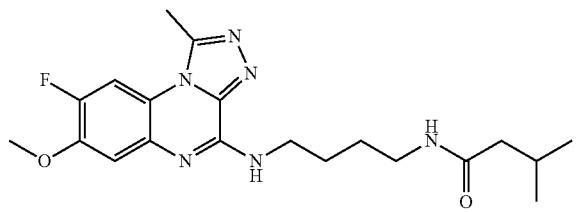 [SMILES: COc1cc2nc(NCCCCNC(=O)CC(C)C)c3nnc(C)n3c2cc1F]

Mass (M+H⁺): 403.2

¹H NMR (500 MHz, DMSO-d6): δ0.80 (d, 6H), 1.44 (m, 2H), 1.62 (m, 2H), 1.86 (d, 2H), 1.89 (m, 1H), 2.95 (s, 3H), 3.04 (q, 2H), 3.48 (q, 2H), 3.90 (s, 3H), 7.25 (d, 1H), 7.70 (t, 1H), 7.87 (d, 1H), 8.08 (t, 1H).

363

<Example 575> Preparation of N-[4-(7-fluoro-8-methoxy-1-methyl-[1,2,4]triazolo[4,3-a]quinoxaline-4-ylamino)-butyl]-3-methyl-butyramide

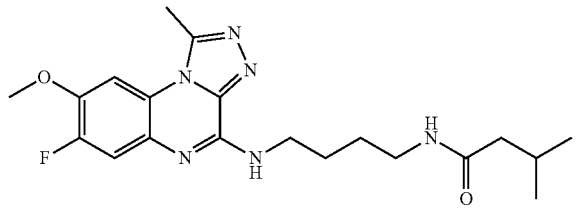 [SMILES: COc1cc2c(cc1F)nc(NCCCCNC(=O)CC(C)C)c1nnc(C)n12]

Mass (M+H$^+$): 403.2
$^1$H NMR (500 MHz, DMSO-d6): δ0.79 (d, 6H), 1.44 (m, 2H), 1.60 (m, 2H), 1.86 (d, 2H), 1.90 (m, 1H), 3.03 (q, 2H), 3.05 (s, 3H), 3.46 (q, 2H), 3.95 (s, 3H), 6.74 (t, 1H), 7.38 (dd, 1H), 7.65 (s, 1H), 8.00 (t, 1H).

<Preparative Example 42> Preparation of N$^1$-[7-methoxy-1-methyl-8-(2-morpholine-4-yl-ethoxy)-[1,2,4]triazolo[4,3-a]quinoxaline-4-yl]-butane-1,4-diamine dihydrochloride (g); and N$^1$-[8-methoxy-1-methyl-7-(2-morpholine-4-yl-ethoxy)-[1,2,4]triazolo[4,3-a]quinoxaline-4-yl]-butane-1,4-diamine dihydrochloride (h) mixture

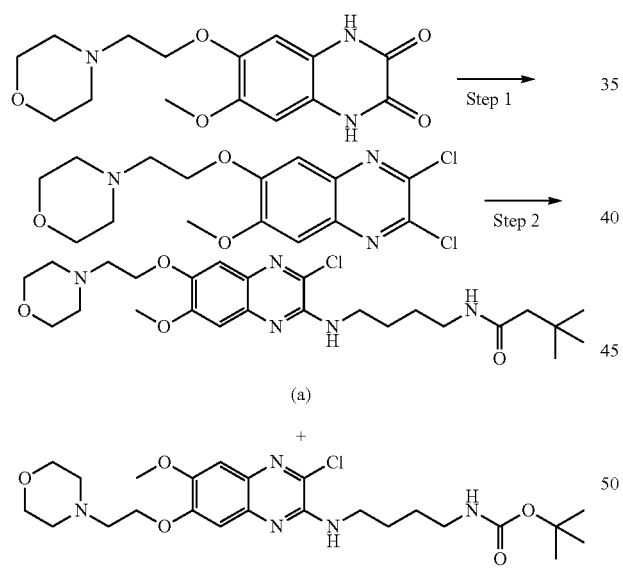

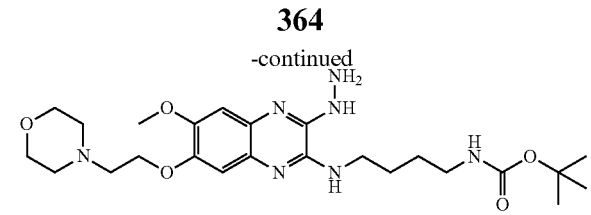

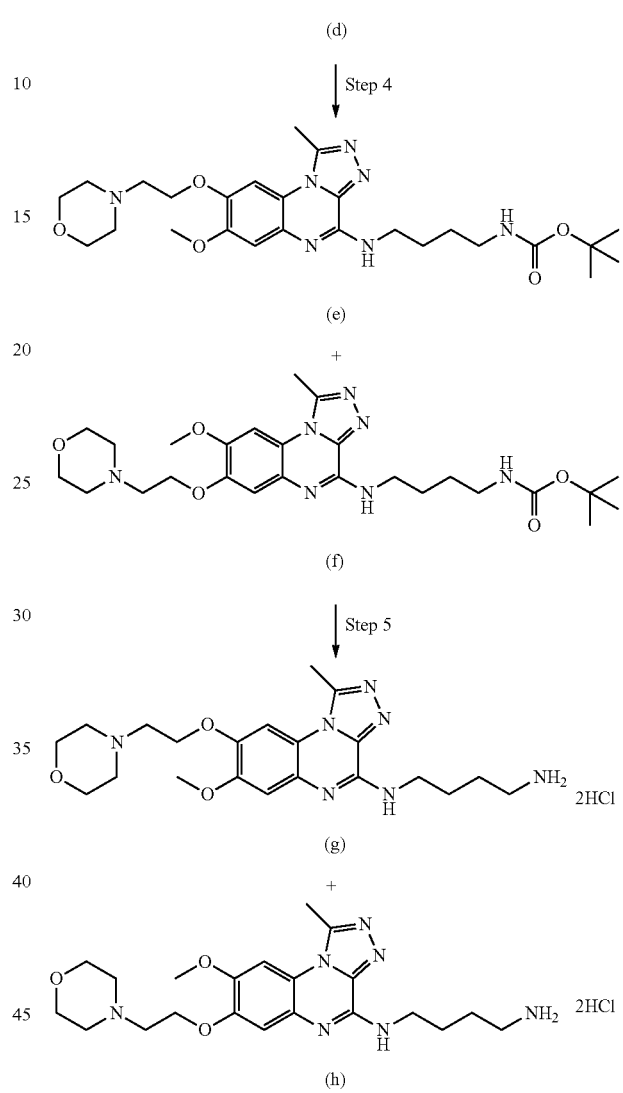

Step 1: Preparation of 2,3-dichloro-6-methoxy-7-(2-morpholine-4-yl-ethoxy)-quinoxaline Mass (M+H$^+$): 358.0
$^1$H NMR (500 MHz, DMSO-d6): δ2.46 (s, 4H), 2.74 (m, 2H), 3.54 (m, 4H), 3.94 (s, 3H), 4.26 (m, 2H), 7.37 (s, 1H), 7.41 (s, 1H).

Step 2: Preparation of {4-[3-chloro-7-methoxy-6-(2-morpholine-4-yl-ethoxy)-quinoxaline-2-ylamino]-butyl}carbamic acid-tert-butylester (a) and {4-[3-chloro-6-methoxy-7-(2-morpholine-4-yl-ethoxy)-quinoxaline-2-ylamino]-butyl}carbamic acid-tert-butylester (b) mixture Mass (M+H$^+$): δ10.2

Step 3: Preparation of {4-[3-hydrazino-7-methoxy-6-(2-morpholine-4-yl-ethoxy)-quinoxaline-2-ylamino]butyl}carbamic acid-tert-butylester (c) and {4-[3-hydrazino-6-methoxy-7-(2-morpholine-4-yl-ethoxy)-quinoxaline-2-ylamino]butyl}carbamic acid-tert-butylester (d) mixture Mass (M+H$^+$): 506.1

Step 4: Preparation of {4-[7-methoxy-1-methyl-8-(2-morpholine-4-yl-ethoxy)-[1,2,4]triazolo[4,3,-a]quinoxaline-4-ylamino]butyl}carbamic acid-tert-butylester (e) and {4-[8-methoxy-1-methyl-7-(2-morpholine-4-yl-ethoxy)-[1,2,4]triazolo[4,3,-a]quinoxaline-4-ylamino]butyl}carbamic acid-tert-butylester (f) mixture Mass (M+H$^+$): 530.3

Step 5: Preparation of N$^1$-[7-methoxy-1-methyl-8-(2-morpholine-4-yl-ethoxy)-[1,2,4]triazolo[4,3-a]quinoxaline-4-yl]-butane-1,4-diamine dihydrochloride (g) and N$^1$-[8-methoxy-1-methyl-7-(2-morpholine-4-yl-ethoxy)-[1,2,4]triazolo[4,3-a]quinoxaline-4-yl]-butane-1,4-diamine dihydrochloride (h) mixture Mass (M+H$^+$): 430.1

<Example 576> Preparation of N-{4-[7-methoxy-1-methyl-8-(2-morpholine-4-yl-ethoxy)-[1,2,4]triazolo[4,3-a]quinoxaline-4-ylamino]-butyl}-3-methyl butyramide

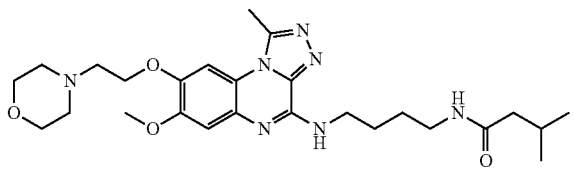 [SMILES: COc1cc2nc(NCCCCNC(=O)CC(C)C)c3nnc(C)n3c2cc1OCCN1CCOCC1]

0.17 g of a target compound was obtained (22% yield) by the same manner as described in Example 37, except that N$^1$-[7-methoxy-1-methyl-8-(2-morpholine-4-yl-ethoxy)-[1,2,4]triazolo[4,3-a]quinoxaline-4-yl]-butane-1,4-diamine dihydrochloride (g) and N$^1$-[8-methoxy-1-methyl-7-(2-morpholine-4-yl-ethoxy)-[1,2,4]triazolo[4,3-a]quinoxaline-4-yl]-butane-1,4-diamine dihydrochloride (h) mixture prepared in step 5 of Preparative Example 42 was used.

Mass (M+H$^+$): 514.3
$^1$H NMR (500 MHz, DMSO-d6): δ0.79 (d, 6H), 1.44 (s, 2H), 1.62 (m, 4H), 1.87 (m, 3H), 2.48 (s, 2H), 3.04 (m, 5H), 3.47 (m, 2H), 3.56 (s, 4H), 3.83 (s, 3H), 4.20 (t, 2H), 7.10 (s, 1H), 7.52 (s, 1H), 7.7 (t, 1H), 7.81 (t, 1H).

<Example 577> Preparation of N-{4-[8-methoxy-1-methyl-7-(2-morpholine-4-yl-ethoxy)-[1,2,4]triazolo[4,3-a]quinoxaline-4-ylamino]-butyl}-3-methyl butyramide

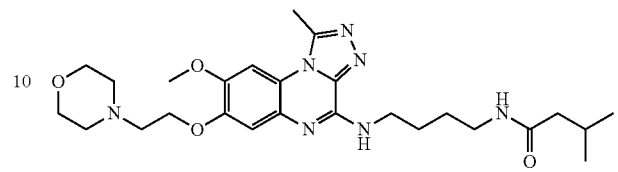

0.42 g of a target compound was obtained (55% yield) by separating the structural isomer produced in the preparation process of Example 576.

Mass (M+H$^+$): 514.3
$^1$H NMR (500 MHz, DMSO-d6): δ0.79 (d, 6H), 1.44 (s, 2H), 1.62 (m, 4H), 1.87 (m, 3H), 2.70 (t, 2H), 3.03 (m, 5H), 3.50 (m, 2H), 3.56 (t, 4H), 3.87 (s, 3H), 4.14 (m, 2H), 7.13 (s, 1H), 7.51 (s, 1H), 7.70 (t, 1H), 7.81 (t, 1H)

<Preparative Example 43> Preparation of {4-[7-(3,5dimethyl-isoxazol-4-yl)-3-hydrazino-quinoxaline-2-ylamino]butyl}carbamic acid-tert-butylester (c) and {4-[6-(3,5-dimethyl-isoxazol-4-yl)-3-hydrazino-quinoxaline-2-ylamino]butyl}carbamic acid-tert-butylester (d)

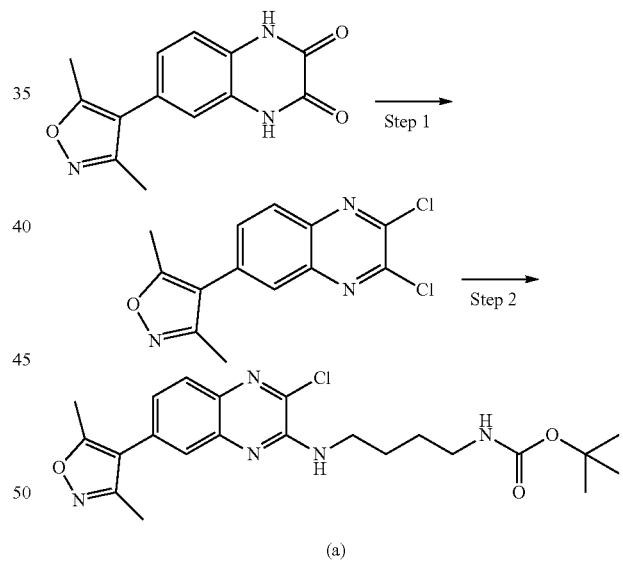

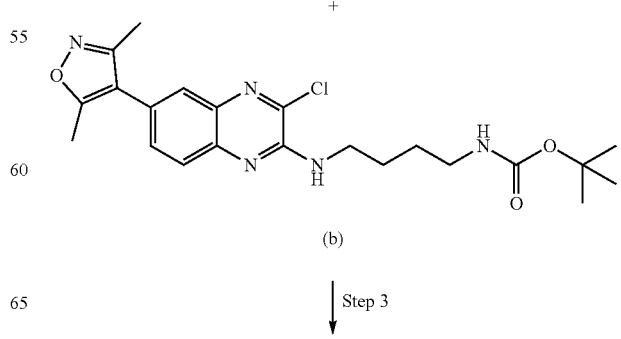

-continued

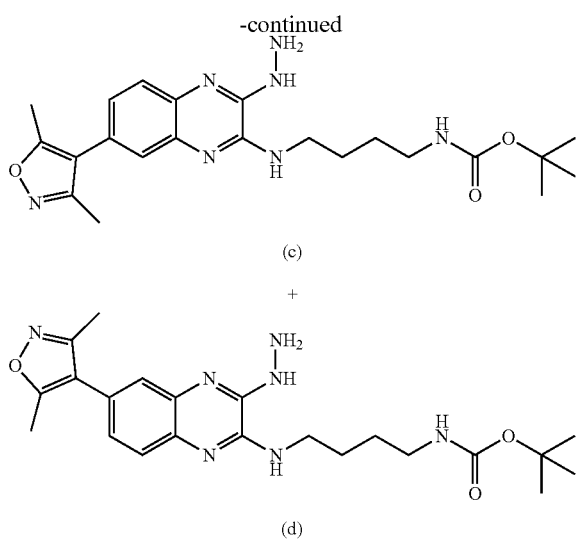

Step 1: Preparation of 2,3-dichloro-6-(3,5-dimethyl-isoxazol-4-yl)-quinoxaline

Mass (M+H⁺): 294.0
¹H NMR (500 MHz, DMSO-d6) δ2.29 (s, 3H), 2.47 (s, 3H), 7.97 (dd, 1H), 8.10 (s, 1H), 8.14 (d, 1H).

Step 2: Preparation of {4-[3-chloro-7-(3,5-dimethyl-isoxazol-4-yl)-quinoxaline-2-ylamino]-butyl}carbamic acid-tert-butylester (a) and {4-[3-chloro-6-(3,5-dimethyl-isoxazol-4-yl)-quinoxaline-2-ylamino]-butyl}carbamic acid-tert-butylester (b)

Mass (M+H⁺): 446.1
¹H NMR (500 MHz, DMSO-d6): δ1.31 (s, 9H), 1.42 (m, 2H), 1.59 (m, 2H), 2.23 (s, 3H), 2.42 (s, 3H), 2.92 (q, 2H), 3.44 (m, 2H), 6.74 (d, 1H), 7.36 (dd, 1H) 7.52 (t, 1H), 7.59 (m, 4H), 7.67 (dd, 1H), 7.71 (s, 1H), 7.78 (d, 1H)

Step 3: Preparation of {4-[7-(3,5dimethyl-isoxazol-4-yl)-3-hydrazino-quinoxaline-2-ylamino]butyl}carbamic acid-tert-butylester (c) and {4-[6-(3,5-dimethyl-isoxazol-4-yl)-3-hydrazino-quinoxaline-2-ylamino]butyl}carbamic acid-tert-butylester (d) mixture Mass (M+H⁺): 442.3

<Example 578> Preparation of {4-[8-(3,5-dimethyl-isoxazol-4-yl)-1-methyl-[1,2,4]triazolo[4,3-a]quinoxaline-4-ylamino]-butyl}-carbamic acid-tert-butylester

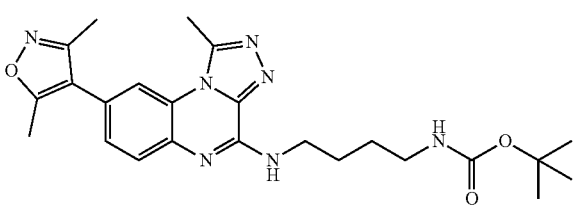 [SMILES: Cc1noc(C)c1-c1ccc2nc(NCCCCNC(=O)OC(C)(C)C)c3nnc(C)n3c2c1]

0.34 g of a target compound was obtained (39% yield) by the same manner as described in step 3 of Preparative Example 5 using {4-[7-(3,5dimethyl-isoxazol-4-yl)-3-hydrazino-quinoxaline-2-ylamino]butyl}carbamic acid-tert-butylester (c) and {4-[6-(3,5-dimethyl-isoxazol-4-yl)-3-hydrazino-quinoxaline-2-ylamino]butyl}carbamic acid-tert-butylester (d) mixture (1.74 g, 3.95 mmol) prepared in step 3 of Preparative Example 43.

Mass (M+H⁺): 466.3
¹H NMR (500 MHz, DMSO-d6): δ1.32 (s, 9H), 1.44 (m, 2H), 1.62 (m, 2H), 2.28 (s, 3H), 2.46 (s, 3H), 2.93 (q, 2H), 3.01 (s, 3H), 3.53 (q, 2H), 6.75 (t, 1H), 7.45 (d, 1H), 7.64 (d, 1H), 7.93 (s, 1H), 8.18 (t, 1H).

<Example 579> Preparation of N¹-[8-(3,5-dimethyl-isoxazol-4-yl)-1-methyl-[1,2,4]triazolo[4,3-a]quinoxaline-4-yl]-butane-1,4-diamine ditrifluoroacetic acid

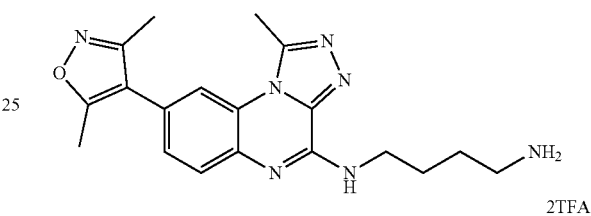

0.4 g of a target compound was obtained (93% yield) by the same manner as described in Example 58, except that {4-[8-(3,5-dimethyl-isoxazol-4-yl)-1-methyl-[1,2,4]triazolo[4,3-a]quinoxaline-4-ylamino]-butyl}-carbamic acid-tert-butylester (0.34 g, 0.73 mmol) prepared in Example 578 was used.

Mass (M+H⁺): 366.2
¹H NMR (500 MHz, DMSO-d6): δ1.61 (m, 2H), 1.71 (m, 2H), 2.25 (s, 3H), 2.47 (s, 3H), 2.82 (q, 2H), 3.02 (s, 3H), 3.57 (q, 2H), 7.46 (d, 1H), 7.64 (br, 2H), 7.66 (s, 1H), 7.95 (d, 1H), 8.29 (t, 1H).

<Example 580> Preparation of N-{4-[8-(3,5-dimethyl-isoxazol-4-yl)-1-methyl-[1,2,4]triazolo[4,3-a]quinoxaline-4-ylamino]-butyl}-3-methyl-butyramide

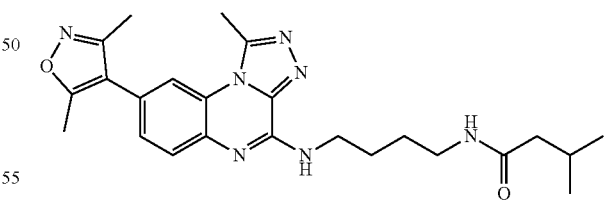

72 mg of a target compound was obtained (95% yield) by the same manner as described in Example 37, except that N¹-[8-(3,5-dimethyl-isoxazol-4-yl)-1-methyl-[1,2,4]triazolo[4,3-a]quinoxaline-4-yl]-butane-1,4-diamine ditrifluoroacetic acid prepared in Example 579 was used.

Mass (M+H⁺): 450.1
¹H NMR (500 MHz, DMSO-d6) δ0.79 (d, 6H), 1.45 (m, 2H), 1.64 (m, 2H), 1.86 (m, 2H), 1.88 (m, 1H), 2.28 (s, 3H), 2.47 (s, 3H), 3.01 (s, 3H), 3.04 (q, 2H), 3.53 (q, 2H), 7.45 (d, 1H), 7.63 (d, 1H), 7.70 (t, 1H), 7.94 (s, 1H), 8.19 (t, 1H).

The compounds prepared by the same manner as described in Example 580 are shown in Table 41.

TABLE 41

| Example | Structure | Name | Data |
|---|---|---|---|
| Example 581 | 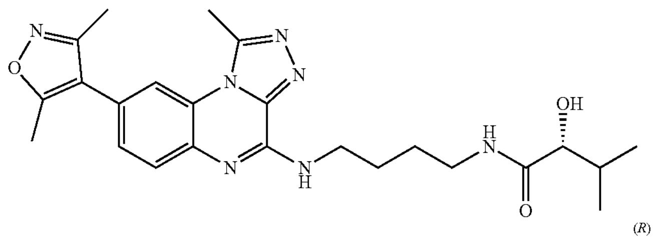 | N-{4-[8-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide | Mass (M + H$^+$): 466.2; $^1$H NMR (500 MHz, DMSO-d6): δ0.68 (d, 3H), 0.83 (d, 3H), 1.48 (m, 2H), 1.63 (m, 2H), 1.90 (m, 1H), 2.28 (s, 3H), 2.46 (s, 3H), 3.01 (s, 3H), 3.14 (q, 2H), 3.53 (q, 2H), 3.60 (m, 1H), 5.23 (d, 1H), 7.45 (d, 1H), 7.64 (d, 1H), 7.67 (t, 1H), 7.93 (s, 1H), 8.19 (t, 1H). |
| Example 582 | 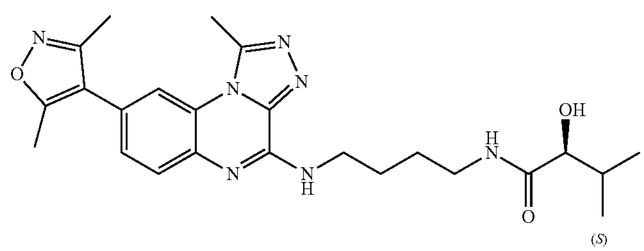 | N-{4-[8-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide | Mass (M + H$^+$): 466.2; $^1$H NMR (500 MHz, DMSO-d6): δ0.68 (d, 3H), 0.83 (d, 3H), 1.48 (m, 2H), 1.63 (m, 2H), 1.90 (m, 1H), 2.28 (s, 3H), 2.46 (s, 3H), 3.01 (s, 3H), 3.13 (q, 2H), 3.53 (q, 2H), 3.60 (m, 1H), 5.23 (d, 1H), 7.45 (d, 1H), 7.63 (d, 1H), 7.65 (t, 1H), 7.93 (s, 1H), 8.19 (t, 1H). |

<Example 583> Preparation of {4-[7-(3,5-dimethyl-isoxazol-4-yl)-1-methyl-[1,2,4]triazolo[4,3-a]quinoxaline-4-ylamino]-butyl}-carbamic acid-tert-butyl-ester

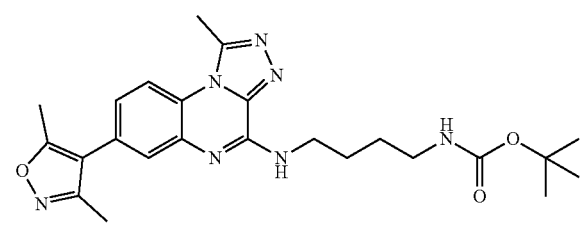 [SMILES: Cc1noc(C)c1-c1ccc2c(c1)nc(NCCCCNC(=O)OC(C)(C)C)c1nnc(C)n12]

0.38 g of a target compound was obtained (44% yield) by separating the structural isomer produced in the preparation process of Example 578.

Mass (M+H$^+$): 466.3

$^1$H NMR (500 MHz, DMSO-d6) δ1.30 (s, 9H), 1.43 (m, 2H), 1.61 (m, 2H), 2.22 (s, 3H), 2.41 (s, 3H), 2.93 (q, 2H), 3.01 (s, 3H), 3.53 (q, 2H), 6.75 (t, 1H), 7.25 (d, 1H), 7.52 (s, 1H), 8.12 (d, 1H), 8.17 (t, 1H).

The compounds prepared by the same manner as described in Example 583 are shown in Table 42.

TABLE 42

| Example | Structure | Name | Data |
|---|---|---|---|
| Example 584 | 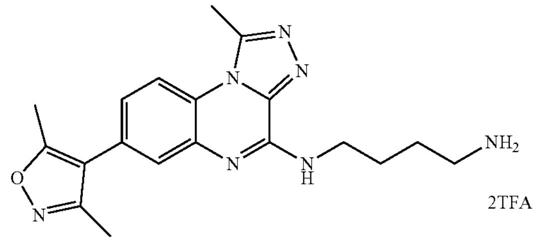 [SMILES: Cc1noc(C)c1-c1ccc2c(c1)nc(NCCCCN)c1nnc(C)n12] | N$^1$-[7-(3,5-dimethyl-isoxazol-4-yl)-1-methyl-[1,2,4]triazolo[4,3-a]quinoxaline-4-yl]-butane-1,4-diamine ditrifluoro-acetic acid | Mass (M + H$^+$): 366.2; $^1$H NMR (500 MHz, DMSO-d6): δ1.61 (m, 2H), 1.69 (m, 2H), 2.23 (s, 3H), 2.41 (s, 3H), 2.83 (q, 2H), 3.02 (s, 3H), 3.56 (q, 2H), 7.29 (d, 1H), 7.52 (s, 1H), 7.63 (br, 2H), 8.15 (d, 1H), 8.32 (t, 1H). |
| Example 585 | 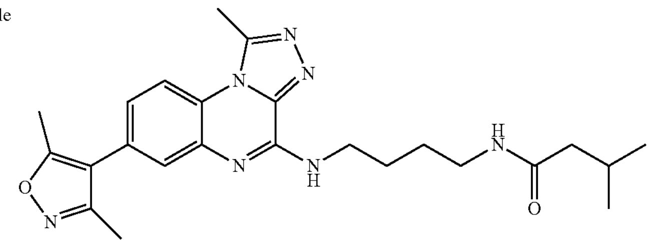 | N-{4-[7-(3,5-dimethyl-isoxazol-4-yl)-1-methyl-[1,2,4]triazolo[4,3-a]quinoxaline-4-ylamino]-butyl}-3-methyl-butyramide | Mass (M + H$^+$): 450.2; $^1$H NMR (500 MHz, DMSO-d6): δ0.77 (d, 6H), 1.44 (m, 2H), 1.64 (m, 2H), 1.86 (m, 2H), 1.88 (m, H), 2.23 (s, 3H), 2.41 (s, 3H), 3.01 (s, 3H), 3.05 (q, 2H), 3.52 (q, 2H), 7.26 (d, 1H), 7.52 (s, 1H), 7.70 (t, 1H), 8.13 (d, 1H), 8.19 (t, 1H). |
| Example 586 | 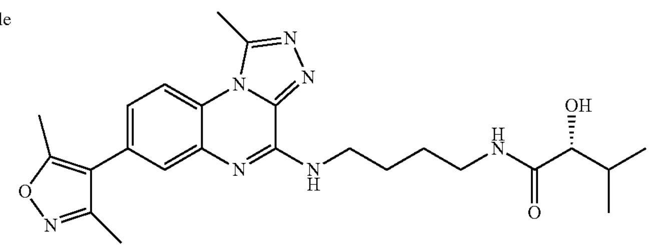 | N-{4-[7-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide | Mass (M + H$^+$): 466.2; $^1$H NMR (500 MHz, DMSO-d6): δ0.66 (d, 3H), 0.81 (d, 3H), 1.48 (m, 2H), 1.63 (m, 2H), 1.89 (m, 1H), 2.23 (s, 3H), 2.41 (s, 3H), 3.01 (s, 3H), 3.13 (q, 2H), 3.52 (q, 2H), 3.60 (m, 1H), 5.23 (d, 1H), 7.26 (d, 1H), 7.52 (s, 1H), 7.65 (t, 1H), 8.13 (d, 1H), 8.19 (t, 1H). |
| Example 587 | 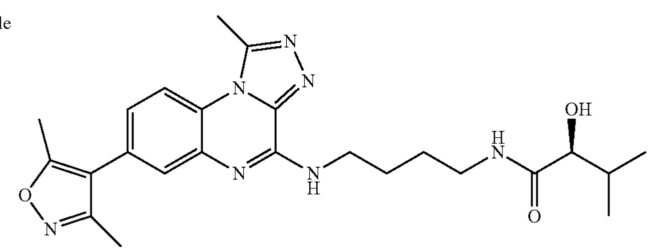 | N-{4-[7-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide | Mass (M + H$^+$): 466.2; $^1$H NMR (500 MHz, DMSO-d6): δ0.66 (d, 3H), 0.82 (d, 3H), 1.47 (m, 2H), 1.63 (m, 2H), 1.88 (m, 1H), 2.23 (s, 3H), 2.41 (s, 3H), 3.01 (s, 3H), 3.13 (q, 2H), 3.52 (q, 2H), 3.60 (m, 1H), 5.23 (d, 1H), 7.26 (d, 1H), |

7.52 (s, 1H),
7.65 (t, 1H),
8.13 (d, 1H),
8.19 (t, 1H).

<Example 588> Preparation of N¹-[7-methoxy-1-trifluoromethyl-[1,2,4]triazolo[4,3-a]quinoxaline-4-yl]-butane-1,4-diamine ditrifluoroacetic acid

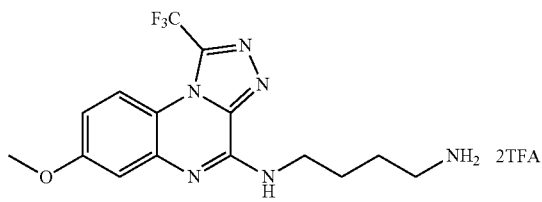 [SMILES: COc1ccc2c(c1)nc(NCCCCN)c1nnc(C(F)(F)F)n12]

[4-(3-Hydrazino-7-methoxy)-quinoxaline-2-ylamino)butyl]-carbamic acid-tert-butylester (0.95 g, 2.2 mmol) prepared in step 2 of Preparative Example 20 was dissolved in trifluoroacetic acid, followed by reflux stirring for 3 hours. Upon completion of the reaction, acid was eliminated by distillation under reduced pressure, followed by recrystallization with methanol and ether. As a result, 1 g of a target compound was obtained (68% yield).

Mass (M+H⁺): 355.1

<Example 589> Preparation of [4-(7-methoxy-1-trifluoromethyl-[1,2,4]triazolo[4,3-a]quinoxaline-4-ylamino)-butyl]-carbamic acid isopropylester

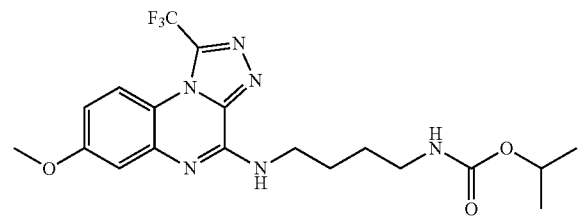 [SMILES: COc1ccc2c(c1)nc(NCCCCNC(=O)OC(C)C)c1nnc(C(F)(F)F)n12]

0.03 g of a target compound was obtained (21% yield) by the same manner as described in Example 60, except that N¹-(7-methoxy-1-trifluoromethyl-[1,2,4]triazolo[4,3-a]quinoxaline-4-ylamino)-butane-1,4-diamine ditrifluoroacetic acid prepared in Example 588 was used.

Mass (M+H⁺): 441.2

¹H NMR (500 MHz, DMSO-d6) δ1.10 (d, 6H), 1.45 (m, 2H), 1.62 (m, 2H), 2.99 (m, 2H), 3.50 (q, 2H), 3.80 (s, 3H), 4.68 (m, 1H), 6.99 (d, 1H), 7.13 (s, 1H), 7.70 (t, 1H), 7.73 (d, 1H), 8.51 (t, 1H).

<Example 590> Preparation of N-[4-(7-methoxy-1-trifluoromethyl-[1,2,4]triazolo[4,3-a]quinoxaline-4-ylamino)-butyl]-3-methyl-butyramide 0.04 g of a target compound was obtained (33% yield) by the same manner as described in Example 74, except that N¹-(7-methoxy-1-trifluoromethyl-[1,2,4]triazolo[4,3-a]quinoxaline-4-ylamino)-butane-1,4-diamine ditrifluoroacetic acid prepared in Example 588 was used.

Mass (M+H⁺): 439.2

¹H NMR (500 MHz, DMSO-d6) δ0.80 (d, 6H), 1.46 (m, 2H), 1.64 (m, 2H), 1.86 (m, 2H), 1.87 (m, 1H), 3.04 (q, 2H), 3.54 (q, 2H), 3.82 (s, 3H), 6.98 (d, 1H), 7.12 (s, 1H), 7.71 (t, 1H), 7.73 (d, 1H), 8.51 (t, 1H).

<Example 591> Preparation of 3-methyl-pentanoic acid-[4-(7-methoxy-1-trifluoromethyl-[1,2,4]triazolo[4,3-a]quinoxaline-4-ylamino)-butyl]-amide 0.06 g of a target compound was obtained (37% yield) by the same manner as described in Example 73, except that N¹-(7-methoxy-1-trifluoromethyl-[1,2,4]triazolo[4,3-a]quinoxaline-4-ylamino)-butane-1,4-diamine ditrifluoroacetic acid prepared in Example 588 was used.

Mass (M+H⁺): 453.2

¹H NMR (500 MHz, DMSO-d6): δ0.79 (m, 6H), 1.08-1.25 (brm, 2H), 1.46 (m, 2H), 1.63 (m, 2H), 1.78 (m, 2H), 1.96 (m, 1H), 3.06 (q, 2H), 3.50 (q, 2H), 3.81 (s, 3H), 6.98 (d, 1H), 7.12 (s, 1H), 7.71 (t, 1H), 7.73 (d, 1H), 8.51 (t, 1H).

<Example 592> Preparation of N¹-(7,8-dimethoxy-1-trifluoromethyl-[1,2,4]triazolo[4,3-a]quinoxaline-4-yl)-butane-1,4-diamine ditrifluoroacetic acid

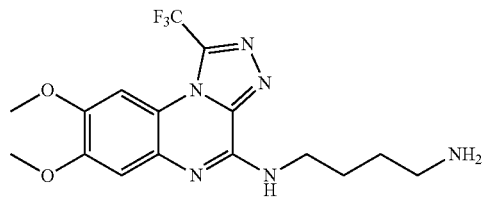 [SMILES: COc1cc2nc(NCCCCN)c3nnc(C(F)(F)F)n3c2cc1OC]

0.35 g of a target compound was obtained (18% yield) by the same manner as described in Example 558, except that [4-(3-hydrazino-7,8-dimethoxy)-quinoxaline-2-ylamino)butyl]-carbamic acid-tert-butylester was used.
Mass (M+H⁺): 385.2
¹H NMR (500 MHz, DMSO-d6): δ1.61 (m, 2H), 1.70 (m, 2H), 2.82 (q, 2H), 3.53 (brs, 3H), 3.57 (q, 2H), 3.81 (s, 3H), 3.86 (s, 3H), 7.17 (s, 1H), 7.24 (s, 1H), 7.67 (brs, 3H), 8.31 (t, 1H).

<Example 593> Preparation of N-[4-(7,8-dimethoxy-1-trifluoromethyl-[1,2,4]triazolo[4,3-a]quinoxaline-4-ylamino)-butyl]-3-methyl-butyramide

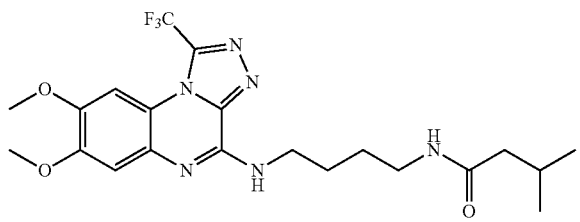 [SMILES: COc1cc2nc(NCCCCNC(=O)CC(C)C)c3nnc(C(F)(F)F)n3c2cc1OC]

0.21 g of a target compound was obtained (93% yield) by the same manner as described in Example 66, except that N¹-(7,8-dimethoxy-1-methyl-[1,2,4]triazolo[4,3-a]quinoxaline-4-ylamino)-butane-1,4-diamine ditrifluoroacetic acid was used.
Mass (M+H⁺): 469.2
¹H NMR (500 MHz, DMSO-d6) δ0.80 (d, 6H), 1.47 (m, 2H), 1.64 (m, 2H), 1.87 (d, 2H), 1.90 (m, 1H), 3.04 (q, 2H), 3.52 (q, 2H), 3.86 (s, 3H), 3.94 (s, 3H), 7.18 (s, 1H), 7.23 (s, 1H), 7.70 (t, 1H), 8.27 (t, 1H).

<Preparative Example 44> Preparation of 4-chloro-7,8-dimethoxy-1-ethyl-[1,2,4]triazolo[4,3-a]quinoxaline

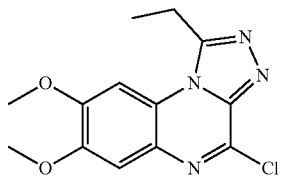 [SMILES: CCc1nnc2c(Cl)nc3cc(OC)c(OC)cc3n12]

1.02 g of a target compound was obtained (89% yield) by the same manner as described in step 3 of Preparative Example 5, except that (3-chloro-6,7-dimethoxy-quinoxaline-2-yl)-hydrazine (1 g, 3.92 mmol) prepared in step 2 of Preparative Example 5 and 6 ml of triethylorthopropionate were used.
Mass (M+H⁺): 293.1
¹H NMR (500 MHz, DMSO-d6): δ1.49 (t, 3H), 2.47 (q, 2H), 3.27 (s, 3H), 3.88 (s, 3H), 3.98 (s, 3H), 7.52 (s, 1H), 7.60 (s, 1H).

Examples of the compounds synthesized using 4-chloro-7,8-dimethoxy-1-ethyl-[1,2,4]triazolo[4,3-a]quinoxaline prepared in Preparative Example 44 are shown in Table 43 below.

TABLE 43

| Example | Structure | Name | Data |
|---|---|---|---|
| Example 594 | 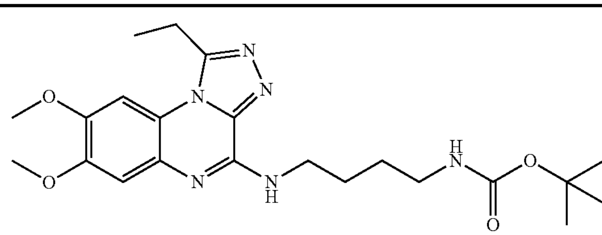 | [4-(1-ethyl-7,8-dimethoxy-[1,2,4]triazolo[4,3-a]quinoxaline-4-ylamino)-butyl]-carbamic acid-tert-butylester | Mass (M + H⁺): 445.2; ¹H NMR (500 MHz, DMSO-d6): δ1.32 (s, 9H), 1.42 (m, 2H), 1.47 (t, 3H), 1.60 (m, 2H), 2.92 (q, 2H), 3.44 (q, 2H), 3.47 (q, 2H), 3.82 (s, 3H), 3.89 (s, 3H), 6.75 (t, 1H), 7.10 (s, 1H), 7.54 (s, 1H), 7.82 (t, 1H) |
| Example 595 | 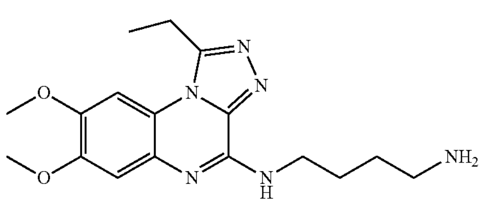 | N¹-(1-ethyl-7,8-dimethoxy-[1,2,4]triazolo[4,3-a]quinoxaline-4-yl)-butane-1,4-diamine ditrifluoro | Mass (M + H⁺): 345.2; ¹H NMR (500 MHz, DMSO-d6): δ1.46 (t, 3H), 1.59 (m, 2H), 1.67 (m, 2H), 2.81 (q, 2H), 3.43 (q, 2H), 3.52 (q, 2H), 3.82 (s, 3H), 3.86 (s, 3H), 7.10 |

TABLE 43-continued

| Example | Structure | Name | Data |
|---|---|---|---|
| | | acetic acid | (s, 1H), 7.46 (s, 1H), 7.68 (brs, 3H), 7.98 (brs, 1H), |
| Example 596 | 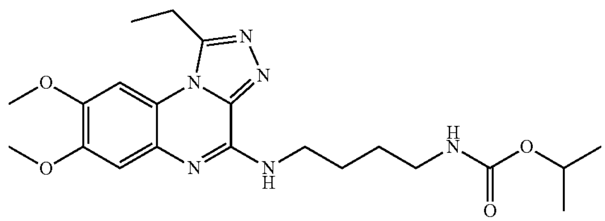 [SMILES: CCc1nnc2c(NCCCCNC(=O)OC(C)C)nc3cc(OC)c(OC)cc3n12] | [4-(1-ethyl-7,8-dimethoxy-[1,2,4]triazolo[4,3-a]quinoxaline-4-ylamino)-butyl]-carbamic acid isopropylester | Mass (M + H$^+$): 431.2; $^1$H NMR (500 MHz, DMSO-d6): δ1.10 (d, 6H), 1.40 (m, 2H), 1.47 (m, 1H), 1.65 (m, 2H), 2.94 (q, 2H), 3.45 (q, 2H), 3.48 (s, 3H), 3.82 (s, 3H), 3.86 (s, 3H), 4.69 (m, 1H), 6.96 (t, 1H), 7.11 (s, 1H), 7.45 (s, 1H), 7.89 (brs, 1H) |
| Example 597 | 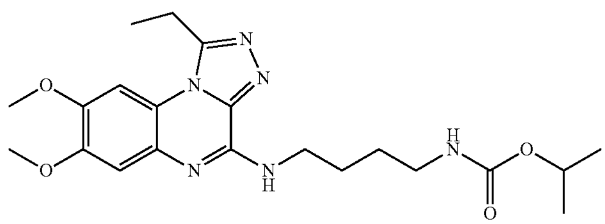 [SMILES: CCc1nnc2c(NCCCCNC(=O)OC(C)C)nc3cc(OC)c(OC)cc3n12] | N-[4-(1-ethyl-7,8-dimethoxy-[1,2,4]triazolo[4,3-a]quinoxaline-4-ylamino)-butyl]-3-methyl-butyramide | Mass (M + H$^+$): 429.2; $^1$H NMR (500 MHz, DMSO-d6): δ0.80 (d, 6H), 1.44 (m, 2H), 1.47 (d, 2H), 1.62 (m, 2H), 1.86 (m, 2H), 1.87 (m, 1H), 3.10 (q, 2H), 3.44 (q, 2H), 3.47 (q, 2H), 3.82 (s, 3H), 3.86 (s, 3H), 7.10 (s, 1H), 7.46 (s, 1H), 7.76 (t, 1H), 7.83 (t, 1H) |
| Example 598 | 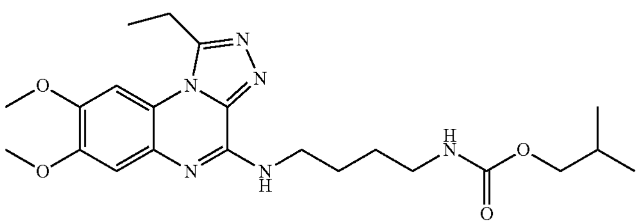 [SMILES: CCc1nnc2c(NCCCCNC(=O)OCC(C)C)nc3cc(OC)c(OC)cc3n12] | [4-(1-ethyl-7,8-dimethoxy-[1,2,4]triazolo[4,3-a]quinoxaline-4-ylamino)-butyl]-carbamic acid isobutylester | Mass (M + H$^+$): 445.2; $^1$H NMR (500 MHz, DMSO-d6): δ0.81 (d, 6H), 1.44 (m, 2H), 1.47 (d, 3H), 1.74 (m, 2H), 1.76 (m, 1H), 3.00 (q, 2H), 3.44 (q, 2H), 3.45 (q, 2H), 3.66 (d, 2H), 3.82 (s, 3H), 3.86 (s, 3H), 7.02 (t, 1H), 7.10 (s, 1H), 7.46 (s, 1H), 7.84 (t, 1H) |

<Preparative Example 45> Preparation of 4-chloro-7,8-dimethoxy-1-isopropyl-[1,2,4]triazolo[4,3-a]quinoxaline

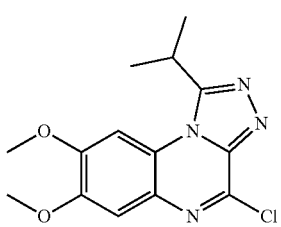 [SMILES: COc1cc2nc(Cl)c3nnc(C(C)C)n3c2cc1OC]

1.02 g of a target compound was obtained (89% yield) by the same manner as described in step 3 of Preparative Example 5, except that (3-chloro-6,7-dimethoxy-quinoxaline-2-yl)-hydrazine (1 g, 3.92 mmol) prepared in step 2 of Preparative Example 5 and isovalerylchloride 5 ml of triethylorthoisobutylate were used.

Mass (M+H$^+$): 307.2

$^1$H NMR (500 MHz, DMSO-d6): δ1.51 (d, 6H), 3.89 (s, 3H), 3.98 (s, 3H), 4.04 (m, 1H), 7.55 (s, 1H), 7.60 (s, 1H).

Examples of the compounds synthesized using 4-chloro-7,8-dimethoxy-1-isopropyl-[1,2,4]triazolo[4,3-a]quinoxaline prepared in Preparative Example 45 are shown in Table 44 below.

TABLE 44

| Example | Name | Data |
|---|---|---|
| Example 599 | [4-(1-isopropyl-7,8-dimethoxy-[1,2,4]triazolo[4,3-a]quinoxaline-4-ylamino)-butyl]-carbamic acid-tert-butylester | Mass (M + H⁺): 459.2; ¹H NMR (500 MHz, DMSO-d6): δ1.31 (S, 9H), 1.42 (m, 2H), 1.48 (d, 6H), 1.61 (m, 2H), 2.92 (q, 2H), 3.47 (q, 2H), 3.83 (s, 3H), 3.85 (s, 3H), 3.93 (m, 1H), 6.75 (t, 1H), 7.11 (s, 1H) 7.45 (s, 1H) 7.83 (t, 1H). |
| Example 600 | N¹-(1-isopropyl-7,8-dimethoxy-[1,2,4]triazolo[4,3-a]quinoxaline-4-yl)-butane-1,4-diamine ditrifluoro acetic acid | Mass (M + H⁺): 359.2; ¹H NMR (500 MHz, DMSO-d6): δ1.47 (d, 6H), 1.59 (m, 2H), 1.67 (m, 2H), 2.82 (q, 2H), 3.53 (q, 2H), 3.83 (s, 3H), 3.94 (m, 1H), 7.11 (s, 1H), 7.46 (s, 1H), 7.63 (brs, 3H), 8.02 (brs, 1H). |
| Example 601 | [4-(1-isopropyl-7,8-dimethoxy-[1,2,4]triazolo[4,3-a]quinoxaline-4-ylamino)-butyl]-carbamic acid isopropylester | Mass (M + H⁺): 445.2; ¹H NMR (500 MHz, DMSO-d6): δ1.21 (d, 6H), 1.78 (m, 2H), 1.79 (m, 6H), 1.80 (m, 2H), 3.26 (q, 2H), 3.73 (m, 1H), 3.76 (q, 2H), 3.97 (s, 3H), 3.99 (s, 3H), 4.72 (t, 1H), 4.90 (t, 1H) 6.21 (s, 1H), 7.46 (s, 1H). |
| Example 602 | [4-(1-isopropyl-7,8-dimethoxy-[1,2,4]triazolo[4,3-a]quinoxaline-4-ylamino)-butyl]-carbamic acid isobutylester | Mass (M + H⁺): 459.2; ¹H NMR (500 MHz, CDCl₃): δ0.90 (d, 6H), 1.65 (d, 6H), 1.68 (m, 2H), 1.78 (m, 2H), 1.80 (m, 1H), 3.28 (q, 2H), 3.74 (q, 2H), 3.82 (m, 1H), 3.83 (d, 2H), 3.97 (s, 3H), 3.99 (s, 3H), 4.84 (brs, 1H), 6.30 (brs, 1H), 7.21 (s, 1H), 7.46 (s, 1H). |
| Example 603 | N-[4-(1-isopropyl-7,8-dimethoxy-[1,2,4]triazolo[4,3-a]quinoxaline-4-ylamino)-butyl]-3-methyl-butyramide | Mass (M + H⁺): 443.3; ¹H NMR (500 MHz, CDCl₃): δ0.93 (d, 6H), 1.65 (d, 6H), 1.66 (d, 2H), 1.79 (m, 2H), 2.01 (m, 2H), 2.10 (m, 1H), 3.33 (q, 2H), 3.73 (q, 2H), 3.76 (m, 1H), 3.97 (s, 3H), 3.99 (s, 3H) 5.54 (brs, 1H), 6.19 (brs, 1H), 7.21 (s, 1H), 7.46 (s, 1H). |

<Preparative Example 46> Preparation of 4-chloro-7,8-dimethoxy-1-phenyl-[1,2,4]triazolo[4,3-a]quinoxaline

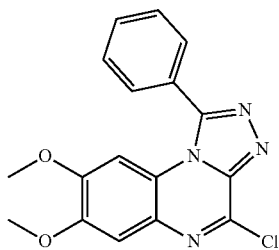 [SMILES: COc1cc2nc(Cl)c3nnc(-c4ccccc4)n3c2cc1OC]

1.02 g of a target compound was obtained (89% yield) by the same manner as described in step 3 of Preparative Example 5, except that (3-chloro-6,7-dimethoxy-quinoxaline-2-yl)-hydrazine (1 g, 3.92 mmol) prepared in step 2 of Preparative Example 5 and 5 ml of triethylorthoisobenzoate were used.

Mass (M+H$^+$): 341.2

$^1$H NMR (500 MHz, DMSO-d6): δ3.27 (s, 3H), 3.33 (s, 3H), 7.54 (s, 1H), 7.69 (m, 3H), 7.70 (m, 3H).

Examples of the compounds synthesized using 4-chloro-7,8-dimethoxy-1-phenyl-[1,2,4]triazolo[4,3-a]quinoxaline prepared in Preparative Example 46 are shown in Table 45 below.

TABLE 45

| Example | Structure | Name | Data |
|---|---|---|---|
| Example 604 | 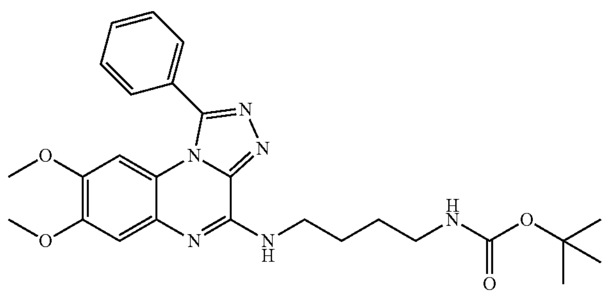 [SMILES: COc1cc2nc(NCCCCNC(=O)OC(C)(C)C)c3nnc(-c4ccccc4)n3c2cc1OC] | [4-(1-phenyl-7,8-dimethoxy-[1,2,4]triazolo[4,3-a]quinoxaline-4-ylamino)-butyl]-carbamic acid-tert-butylester | Mass (M + H$^+$): 493.4; $^1$H NMR (500 MHz, DMSO-d6): δ1.33 (s, 3H), 1.46 (m, 2H), 1.63 (m, 2H), 2.94 (q, 2H), 3.27 (s, 3H), 3.52 (q, 2H), 3.78 (s, 3H), 6.61 (s, 1H), 6.74 (t, 1H), 7.08 (s, 1H), 7.66 (m, 3H) 7.73 (m, 2H), 8.00 (t, 1H). |
| Example 605 | 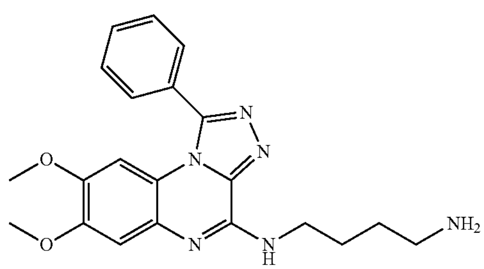 | N$^1$-(1-phenyl-7,8-dimethoxy-[1,2,4]triazolo[4,3-a]quinoxaline-4-yl)-butane-1,4-diamine ditrifluoro acetic acid | Mass (M + H$^+$): 393.2; $^1$H NMR (500 MHz, DMSO-d6): δ1.64 (m, 2H), 1.71 (m, 2H), 2.84 (q, 2H), 3.24 (s, 3H), 3.37 (brs, 2H), 3.56 (q, 2H), 3.78 (s, 3H), 6.62 (s, 1H), 7.07 (s, 1H), 7.65 (m, 2H), 7.73 (m, 3H) 8.07 (t, 1H). |
| Example 606 | 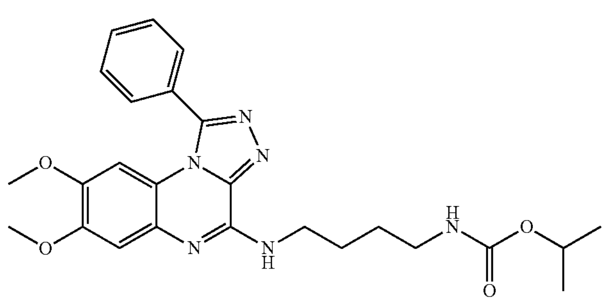 [SMILES: COc1cc2nc(NCCCCNC(=O)OC(C)C)c3nnc(-c4ccccc4)n3c2cc1OC] | [4-(1-phenyl-7,8-dimethoxy-[1,2,4]triazolo[4,3-quinoxaline-4-ylamino)-butyl]-carbamic acid isopropylester | Mass (M + H$^+$): 479.2; $^1$H NMR (500 MHz, DMSO-d6): δ1.11 (d, 6H), 1.48 (m, 2H), 1.64 (m, 2H), 2.99 (q, 2H), 3.23 (s, 3H), 3.52 (q, 2H), 3.79 (s, 3H), 4.70 (m, 1H), 6.61 (s, 1H), 6.98 (t, 1H), 7.09 (s, 1H) 7.66 (m, 3H), 7.75 (m, 2H), 8.01 (m, 1H). |

TABLE 45-continued

| Example | Structure | Name | Data |
|---|---|---|---|
| Example 607 | 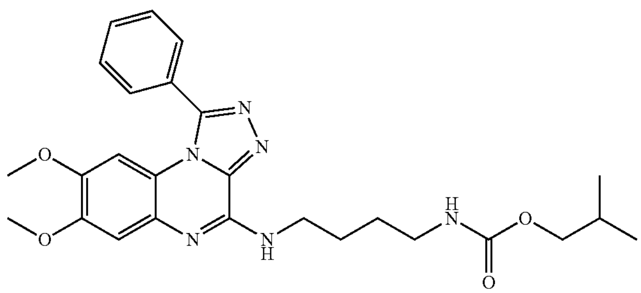 [SMILES: COc1cc2nc(NCCCCNC(=O)OCC(C)C)c3nnc(-c4ccccc4)n3c2cc1OC] | [4-(1-phenyl-7,8-dimethoxy-[1,2,4]triazolo[4,3-a]quinoxaline-4-ylamino)-butyl]-carbamic acid isobutylester | Mass (M + H⁺): 493.2; ¹H NMR (500 MHz, DMSO-d6): δ0.82 (d, 6H), 1.49 (m, 2H), 1.65 (m, 2H), 1.77 (m, 1H), 3.00 (q, 2H), 3.23 (s, 3H), 3.55 (q, 2H), 3.67 (q, 2H), 3.79 (s, 3H), 6.61 (s, 1H), 7.05 (q, 1H) 7.09 (s, 1H), 7.66 (m, 3H), 7.73 (m, 2H), 8.00 (m, 1H). |
| Example 608 | 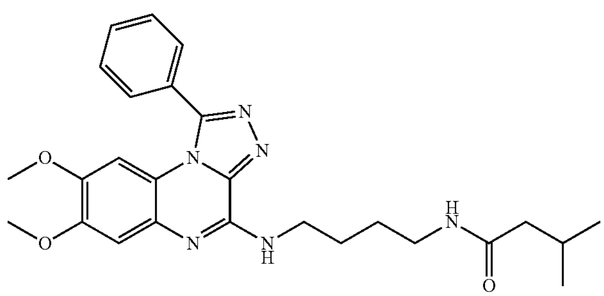 [SMILES: COc1cc2nc(NCCCCNC(=O)CC(C)C)c3nnc(-c4ccccc4)n3c2cc1OC] | N-[4-(1-phenyl-7,8-dimethoxy-[1,2,4]triazolo[4,3-a]quinoxaline-4-ylamino)-butyl]-3-methyl-butyramide | Mass (M + H⁺): 477.2; ¹H NMR (500 MHz, DMSO-d6): δ0.81 (d, 6H), 1.48 (m, 2H), 1.65 (m, 2H), 1.87 (d, 2H), 1.88 (m, 1H), 3.06 (q, 2H), 3.27 (s, 3H), 3.52 (q, 2H), 3.78 (s, 3H), 6.61 (s, 1H), 7.08 (s, 1H) 7.66 (m, 3H), 7.73 (m, 3H), 8.01 (t, 1H). |

Examples of the compounds synthesized by the same manner as described in Preparative Examples 44-46 are shown in Table 46 below.

TABLE 46

| Example | Structure | Name | Data |
|---|---|---|---|
| Example 609 | 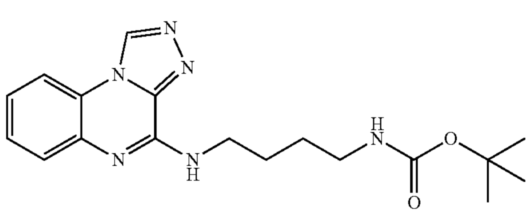 [SMILES: CC(C)(C)OC(=O)NCCCCNc1nc2ccccc2n2cnnc12] | [4-([1,2,4]triazolo[4,3-a]quinoxaline-4-ylamino)-butyl]-carbamic acid-tert-butylester | Mass (M + H⁺): 357.2; ¹H NMR (300 MHz, DMSO-d6): δ1.36 (s, 9H), 1.43-1.52 (m, 2H), 1.62-1.72 (m, 2H), 2.94-3.00 (m, 2H), 3.53-3.59 (m, 2H), 6.79 (t, J = 5.16 Hz, 1H), 7.32 (t, J = 7.26 Hz, 1H), 7.45 (t, J = 7.53 Hz, 1H), 7.60 (d, J = 7.98 Hz, 1H), 8.15 (d, J = 8.04 Hz, 1H), 8.25 (t, J = 5.61 Hz, 1H), 9.95 (s, 1H). |

TABLE 46-continued

| Example | Structure | Name | Data |
|---|---|---|---|
| Example 610 | 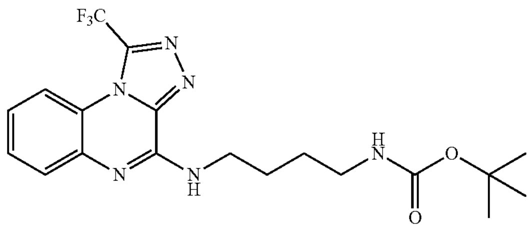 [SMILES: CC(C)(C)OC(=O)NCCCCNc1nc2ccccc2n2c(C(F)(F)F)nnc12] | [4-(1-trifluoro-methyl-[1,2,4]tria-zolo[4,3-a]quinoxaline-4-ylamino)-butyl]-carbamic acid-tert-butylester | Mass (M + H$^+$): 425.2; $^1$H NMR (300 MHz, DMSO-d6): δ1.44-1.54 (m, 2H), 1.63-1.73 (m, 2H), 2.94-3.00 (m, 2H), 3.55-3.61 (m, 2H), 6.78 (t, J = 4.95) Hz, 1H), 7.39-7.44 (m, 1H), 7.56 (t, J = 7.35) Hz, 1H), 7.71 (dd, J = 8.13, 0.93 Hz, 1H), 7.87 (d, J = 8.28 Hz, 1H), 8.51 (t, J = 5.67 Hz, 1H). |
| Example 611 | 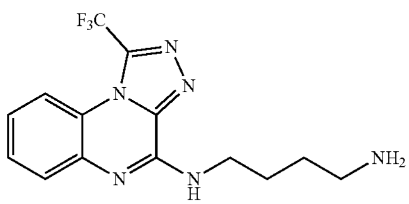 [SMILES: NCCCCNc1nc2ccccc2n2c(C(F)(F)F)nnc12] | N$^1$-(1-trifluoro-methyl-[1,2,4]tria-zolo[4,3-a]quinoxaline-4-yl)-butane-1,4-diamine | Mass (M + H$^+$): 325.1; $^1$H NMR (300 MHz, DMSO-d6): δ1.61-1.84 (m, 2H), 2.83-2.88 (m, 2H), 3.60-3.64 (m, 2H), 7.42-7.47 (m, 1H), 7.57-7.72 (m, 4H), 7.89 (d, J = 8.37 Hz, 1H), 8.61 (t, J = 5.64 Hz, 1H). |
| Example 612 | 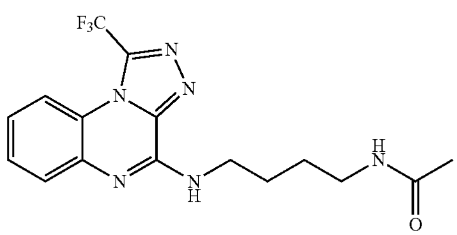 [SMILES: CC(=O)NCCCCNc1nc2ccccc2n2c(C(F)(F)F)nnc12] | N-[4-(1-trifluoro-methyl-(1,2,4]tria-zolo[4,3-a]quinoxaline-4-ylamino)-butyl]-acetamide | Mass (M+H$^+$): 367.2; $^1$H NMR (300 MHz, DMSO-d6): δ1.47-1.54 (m, 2H), 1.65-1.70 (m, 2H), 1.78 (s, 3H), 3.05-3.11 (m, 2H), 3.55-3.62 (m, 2H), 7.42 (t, J = 7.26 Hz, 1H), 7.57 (t, J = 7.71 Hz, 1H), 7.71 (d, J = 8.10 Hz, 1H), 7.80-7.88, (m, 2H), 8.52 (t, J = 5.61 Hz, 1H). |
| Example 613 | 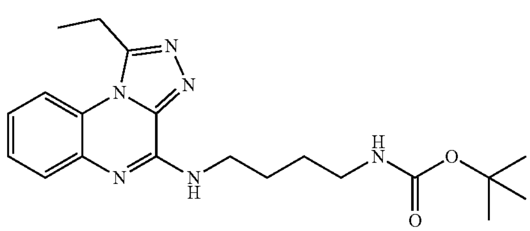 [SMILES: CCc1nnc2c(NCCCCNC(=O)OC(C)(C)C)nc3ccccc3n12] | [4-(1-ethyl-[1,2,4]tria-zolo[4,3-a]quinoxaline-4-ylamino)-butyl]-carbamic acid-tert-butylester | Mass (M + H$^+$): 385.2; $^1$H NMR (300 MHz, DMSO-d6): δ1.36 (s, 9H), 1.42-1.51 (m, 5H), 1.61-1.71 (m, 2H), 2.94-3.00 (m, 2H), 8.11 (t, J = 5.70 Hz, 1H), 3.39-3.46 (m, 2H), 3.51-3.58 (m, 2H), 6.77 (t, J = 4.65 Hz, 1H), 7.27-7.32 (m, 1H), 7.44 (t, J = 7.38 Hz, 1H), 7.59-7.7.62 (m, 1H), 8.04 (d, J = 8.22 Hz, 1H). |

TABLE 46-continued

| Example | Structure | Name | Data |
|---|---|---|---|
| Example 614 | 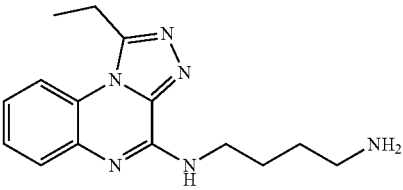 | N[1]-(1-ethyl-[1,2,4]triazolo[4,3-a]quinoxaline-4-yl)-butane-1,4-diamine | Mass (M + H$^+$): 325.1; $^1$H NMR (300 MHz, DMSO-d6): δ1.49 (t, J = 7.29 Hz, 3H), 1.62-1.78 (m, 4H), 2.83-2.90 (m, 2H), 3.45 (q, J = 7.32 Hz, 2H), 3.59-3.65 (m, 2H), 7.34-7.39 (m, 1H), 7.46-7.52 (m, 1H), 7.64-7.71 (m, 3H), 8.09 (d, J = 7.95 Hz, 1H), 8.57 (brs, 1H) |
| Example 615 | 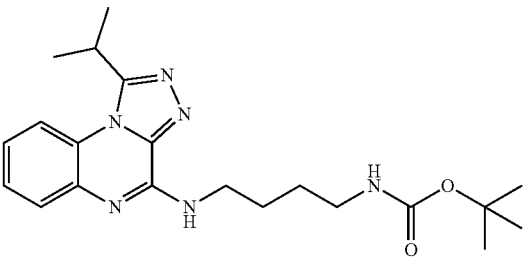 [SMILES: CC(C)c1nnc2c(NCCCCNC(=O)OC(C)(C)C)nc3ccccc3n12] | [4-(1-isopropyl-[1,2,4]triazolo[4,3-a]quinoxaline-4-ylamino)-butyl]-carbamic acid-tert-butylester | Mass (M + H$^+$): 399.2; $^1$H NMR (300 MHz, DMSO-d6): δ1.36 (s, 9H), 1.44-1.51 (m, 8H), 1.61-1.71 (m, 2H), 2.94-3.00 (m, 2H), 3.51-3.58 (m, 2H), 3.90-3.99 (m, 1H), 6.79 (t, J = 5.13 Hz, 1H), 7.29-7.35 (m, 1H), 7.45 (t, J = 7.68 Hz, 1H), 7.62 (d, J = 7.83 Hz, 1H), 8.06-8.13 (m, 2H). |
| Example 616 | 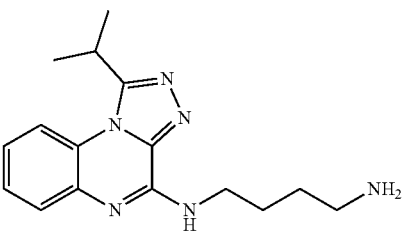 [SMILES: CC(C)c1nnc2c(NCCCCN)nc3ccccc3n12] | N[1]-(1-isopropyl-[1,2,4]triazolo[4,3-a]quinoxaline-4-yl)-butane-1,4-diamine | Mass (M + H$^+$): 299.2; $^1$H NMR (300 MHz, DMSO-d6): δ1.50 (d, J = 6.69 Hz, 6H), 1.55-1.78 (m, 4H), 2.79-2.90 (m, 2H), 3.54-3.64 (m, 2H), 3.92-4.01 (m, 1H), 7.36-7.42 (m, 1H), 7.50 (t, J = 7.59 Hz, 1H), 7.67-7.82 (m, 4H), 8.12 (d, J = 8.19 Hz, 1H), 8.74 (brs, 1H). |
| Example 617 | 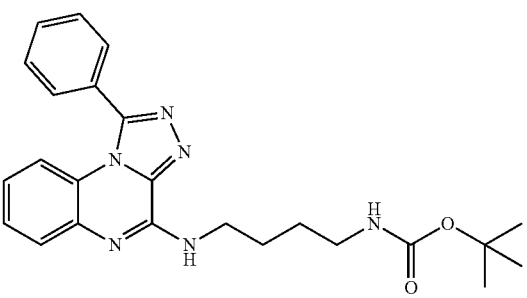 [SMILES: CC(C)(C)OC(=O)NCCCCNc1nc2ccccc2n2c(-c3ccccc3)nnc12] | [4-(1-phenyl-[1,2,4]triazolo[4,3-a]quinoxaline-4-ylamino)-butyl]-carbamic acid-tert-butylester | Mass (M + H$^+$): 432.8; $^1$H NMR (300 MHz, DMSO-d6): δ1.30 (s, 9H), 1.38-1.48 (m, 2H), 1.57-1.65 (m, 2H), 2.89-2.95 (m, 2H), 3.49-3.55 (m, 2H), 6.74 (t, J = 4.86 Hz, 1H), 6.92 (t, J = 7.32 Hz, 1H), 7.08 (d, J = 8.25 Hz, 1H), 7.28 (t, J = 7.35 Hz, 1H), 7.52-7.70 (m, 6H), 8.22 (t, J = 5.64 Hz, 1H). |

TABLE 46-continued

| Example | Name | Data |
|---|---|---|
| Example 618 | N[1]-(1-phenyl-[1,2,4]triazolo[4,3-a]quinoxaline-4-yl)-butane-1,4-diamine | Mass (M + H[+]): 333.2; $^1$H NMR (300 MHz, DMSO-d6): δ1.65-1.70 (m, 2H), 1.76-1.81 (m, 2H), 2.86-2.92 (m, 2H), 3.66-3.67 (m, 2H), 7.04-7.08 (m, 1H), 7.17-7.19 (m, 1H), 7.40-7.43 (m, 1H), 7.65-7.76 (m, 8H), |
| Example 619 | N-[4-(1-phenyl-[1,2,4]triazolo[4,3-a]quinoxaline-4-ylamino)-butyl]-acetamide | Mass (M + H[+]): 375.2; $^1$H NMR (300 MHz, DMSO-d6): δ1.47-1.57 (m, 2H), 1.67-1.77 (m, 2H), 1.80 (s, 3H), 3.07-3.13 (m, 2H), 3.63-3.65 (m, 2H), 7.06 (t, J = 7.47 Hz, 1H), 7.16 (d, J = 8.22 Hz, 1H), 7.41 (t, J = 7.26 Hz, 1H), 7.65-7.88 (m, 6H), 7.87 (t, J = 5.25 Hz, 1H), 9.00 (brs, 1H). |
| Example 620 | [4-(7-methoxy-1-ethyl-[1,2,4]triazolo[4,3-a]quinoxaline-4-ylamino)-butyl]-carbamic acid-tert-butylester | Mass (M + H[+]): 415.2; $^1$H NMR (500 MHz, DMSO-d6): δ1.32 (s, 9H), 1.43 (m, 5H), 1.61 (m, 2H), 2.92 (q, 2H), 3.35 (q, 2H), 3.50 (q, 2H), 3.81 (s, 3H), 6.75 (t, 1H), 6.85 (d, 1H), 7.07 (s, 1H), 7.90 (d, 1H), 8.10 (t, 1H). |
| Example 621 | N[1]-(7-methoxy-1-ethyl-[1,2,4]triazolo[4,3-a]quinoxaline-4-yl)-butane-1,4-diamine ditrifluoroacetic acid | Mass (M + H[+]): 315.1; $^1$H NMR (500 MHz, DMSO-d6): δ1.42 (t, 3H), 1.59 (m, 2H), 1.69 (m, 2H), 2.81 (q, 2H), 3.34 (q, 2H), 3.54 (q, 2H), 3.81 (s, 3H), 6.88 (d, 1H), 7.05 (s. 1H), 7.62 (brm, 2H), 7.93 (d, 1H), 8.19 (t, 1H). |

TABLE 46-continued

| Example | Structure | Name | Data |
|---|---|---|---|
| Example 622 | 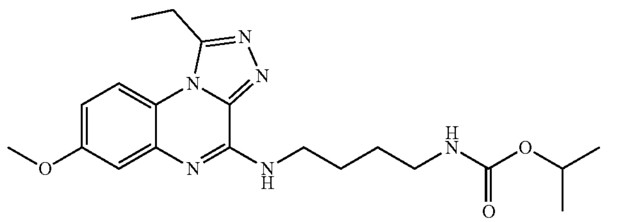 [SMILES: CCc1nnc2c(NCCCCNC(=O)OC(C)C)nc3cc(OC)ccc3n12] | [4-(7-methoxy-1-ethyl-[1,2,4]triazolo[4,3-a]quinoxaline-4-ylamino)-butyl]-3-methyl-butyramide | Mass (M + H$^+$): 399.2; $^1$H NMR (500 MHz, DMSO-d6): δ0.80 (d, 6H), 1.41 (t, 3H), 1.45 (m, 2H), 1.63 (m, 2H), 1.87 (m, 2H), 1.94 (m, 1H), 3.05 (q, 2H), 3.34 (m, 2H), 3.50 (q, 2H), 3.81 (s, 3H), 6.85 (d, 1H), 7.06 (s, 1H), 7.69 (t, 1H), 7.90 (s, 1H), 8.10 (t, 1H). |
| Example 623 | 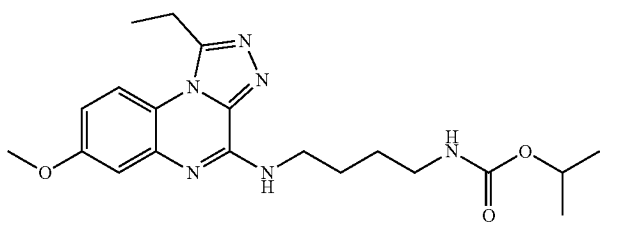 [SMILES: CCc1nnc2c(NCCCCNC(=O)OC(C)C)nc3cc(OC)ccc3n12] | [4-(7-methoxy-1-ethyl-[1,2,4]triazolo[4,3-a]quinoxaline-4-ylamino)-butyl]-carbamic acid isopropylester | Mass (M + H$^+$): 401.2; $^1$H NMR (500 MHz, DMSO-d6): δ1.10 (d, 6H), 1.41 (t, 3H), 1.45 (m, 2H), 1.62 (m, 2H), 1.76 (m, 2H), 2.97 (q, 2H), 3.35 (m, 2H), 3.50 (q, 2H), 3.81 (s, 3H), 4.68 (m, 1H), 6.85 (d, 1H), 6.95 (t, 1H), 7.06 (s, 1H), 7.90 (s, 1H), 8.09 (t, 1H). |
| Example 624 | 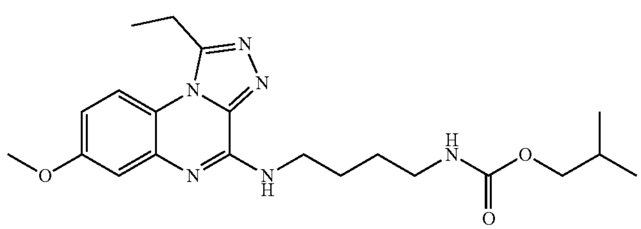 [SMILES: CCc1nnc2c(NCCCCNC(=O)OCC(C)C)nc3cc(OC)ccc3n12] | [4-(7-methoxy-1-ethyl-[1,2,4]triazolo[4,3-a]quinoxaline-4-ylamino)-butyl]-carbamic acid isobutylester | Mass (M + H$^+$): 415.2; $^1$H NMR (500 MHz, DMSO-d6): δ0.81 (d, 6H), 1.42 (t, 3H), 1.47 (m, 2H), 1.62 (m, 2H), 1.76 (m, 2H), 2.99 (q, 2H), 3.34 (m, 2H), 3.51 (q, 2H), 3.67 (q, 2H), 3.80 (s, 3H), 6.85 (d, 1H), 7.00 (t, 1H), 7.06 (s, 1H), 7.90 (s, 1H), 8.09 (t, 1H). |
| Example 625 | 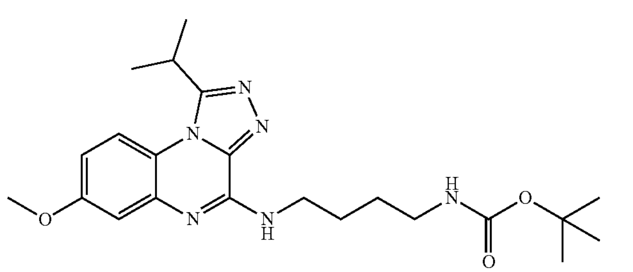 [SMILES: COc1ccc2c(c1)nc(NCCCCNC(=O)OC(C)(C)C)c1nnc(C(C)C)n12] | [4-(7-methoxy-1-isopropyl-[1,2,4]triazolo[4,3-a]quinoxaline-4-ylamino)-butyl]-carbamic acid-tert-butylester | Mass (M + H$^+$): 429.2; $^1$H NMR (500 MHz, DMSO-d6): δ1.32 (s, 9H), 1.43 (d, 6H), 1.54 (m, 2H), 1.61 (m, 2H), 2.93 (q, 2H), 3.50 (m, 2H), 3.81 (s, 3H), 3.85 (m, 1H), 6.74 (t, 1H), 6.86 (d, 1H), 7.07 (s, 1H), 7.93 (d, 1H), 8.10 (t, 1H). |

TABLE 46-continued

| Example | Structure | Name | Data |
|---|---|---|---|
| Example 626 | 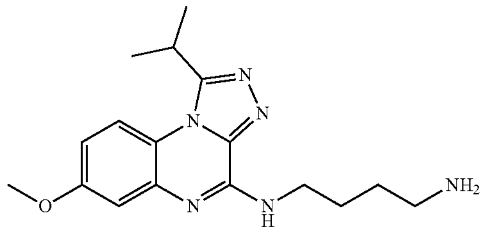 | N¹-(7-methoxy-1-isopropyl-[1,2,4]triazolo[4,3-a]quinoxaline-4-yl)-butane-1,4-diamine ditrifluoroacetic acid | Mass (M + H⁺): 329.1; ¹H NMR (500 MHz, DMSO-d6): δ1.44 (d, 6H), 1.49 (m, 1H), 1.59 (m, 2H), 1.68 (m, 2H), 2.81 (q, 2H), 3.55 (q, 2H), 3.81 (s, 3H), 6.90 (d, 1H), 7.06 (s, 1H), 7.62 (brm, 2H), 7.95 (d, 1H), 8.22 (t, 1H). |
| Example 627 | 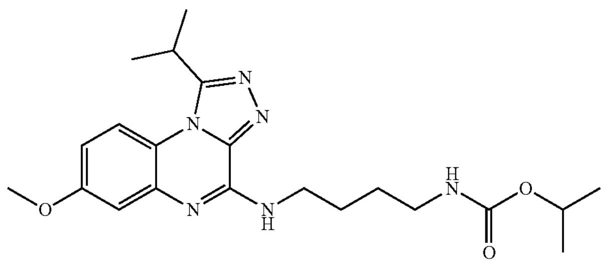 [SMILES: COc1ccc2c(c1)nc(NCCCCNC(=O)OC(C)C)c1nnc(C(C)C)n12] | [4-(1-isopropyl-7-methoxy-[1,2,4]triazolo[4,3-a]quinoxaline-4-ylamino)-butyl]-3-methyl-butyramide | Mass (M + H⁺): 413.2; ¹H NMR (500 MHz, DMSO-d6): δ0.81 (d, 6H), 1.44 (d, 6H), 1.48 (m, 2H), 1.61 (m, 2H), 1.76 (m, 1H), 2.99 (q, 2H), 3.50 (m, 2H), 3.66 (q, 2H), 3.81 (s, 3H), 3.84 (m, 1H), 6.87 (d, 1H), 7.04 (t, 1H), 7.07 (s, 1H), 7.93 (s, 1H), 8.12 (t, 1H). |
| Example 628 | 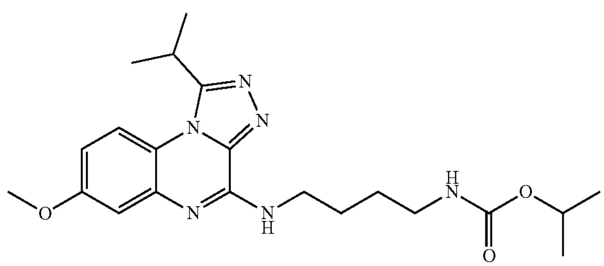 [SMILES: COc1ccc2c(c1)nc(NCCCCNC(=O)OC(C)C)c1nnc(C(C)C)n12] | [4-(1-isopropyl-7-methoxy-[1,2,4]triazolo[4,3-a]quinoxaline-4-ylamino)-butyl]-carbamic acid isopropyl-ester | Mass (M + H⁺): 415.2; ¹H NMR (500 MHz, DMSO-d6): δ1.10 (d, 6H), 1.44 (d 6H), 1.48 (m, 2H), 1.61 (m, 2H), 2.97 (q, 2H), 3.50 (m, 2H), 3.81 (s, 3H), 3.85 (m, 1H), 4.68 (m, 1H), 6.87 (d, 1H), 6.95 (t, 1H), 7.07 (s, 1H), 7.93 (s, 1H), 8.10 (t, 1H). |
| Example 629 | 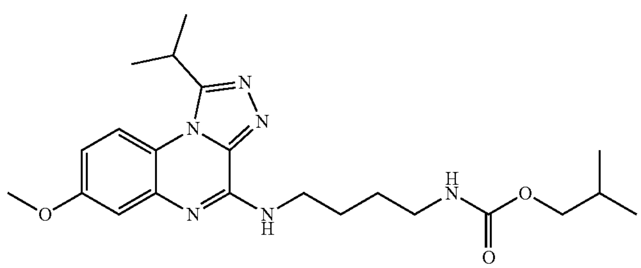 [SMILES: COc1ccc2c(c1)nc(NCCCCNC(=O)OCC(C)C)c1nnc(C(C)C)n12] | [4-(1-isopropyl-7-methoxy-[1,2,4]triazolo[4,3-a]quinoxaline-4-ylamino)-butyl]-carbamic acid isobutylester | Mass (M + H⁺): 429.2; ¹H NMR (500 MHz, DMSO-d6): δ0.81 (d, 6H), 1.44 (d, 6H), 1.48 (m, 2H), 1.61 (m, 2H), 1.76 (m, 1H), 2.99 (q, 2H), 3.50 (m, 2H), 3.66 (q, 2H), 3.81 (s, 3H), 3.84 (m, 1H), 6.86 (d, 1H), 7.03 (t, 1H), 7.07 (s, 1H), 7.93 (s, 1H), 8.12 (t, 1H). |

<Example 630> Preparation of 4-(1-methyl-[1,2,4]triazolo[4,3-a]quinoxaline-4-ylamino)-butan-1-ol

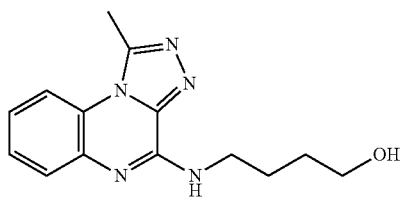 [SMILES: Cc1nnc2c(NCCCCO)nc3ccccc3n12]

1.7 g of a target compound was obtained (68% yield) under the same conditions except that 4-chloro-1-methyl-[1,2,4]triazolo[4,3-a]quinoxaline (2 g, 9.15 mmol) prepared in step 2 of Preparative Example 1 and 4-aminobutanol (1 ml, 11.0 mmol) instead of tert-butyl(4-aminobutyl) carbamate.

Mass (M+H$^+$): 272.1

$^1$H NMR (500 MHz, DMSO-d6) δ1.47 (p, 2H), 1.66 (p, 2H), 2.99 (s, 3H), 3.40 (q, 2H), 3.51 (q, 2H), 4.36 (t, 1H), 7.26 (t, 1H), 7.40 (t, 1H), 7.56 (d, 1H), 8.06 (m, 2H).

<Example 631> Preparation of 2,2-dimethyl-propionic acid-4-(1-methyl-[1,2,4]triazolo[4,3-a]quinoxaline-4-ylamino)-butylester

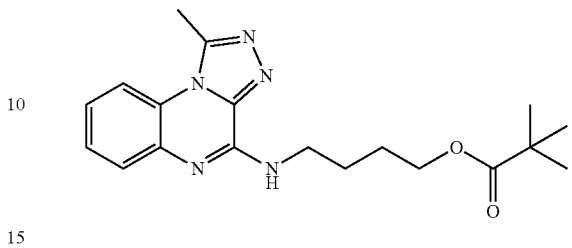

25 mg of a target compound was obtained (10% yield) by the same manner as described in Example 59, except that 4-(1-methyl-[1,2,4]triazolo[4,3-a]quinoxaline-4-ylamino)-butane-1-ol (200 mg, 0.74 mmol) prepared in Example 630 was used.

Mass (M+H$^+$): 356.1

$^1$H NMR (500 MHz, DMSO-d6) δ1.08 (s, 9H), 1.64 (m, 2H), 1.71 (m, 2H), 2.99 (s, 3H), 3.53 (q, 2H), 4.03 (q, 2H), 7.27 (t, 1H), 7.41 (t, 1H), 7.55 (d, 1H), 8.06 (d, 1H), 8.14 (t, 1H).

The compounds shown in Table 47 below were prepared by the same manner as described in Example 631.

TABLE 47

| Example | Structure | Name | Data |
|---|---|---|---|
| Example 632 | 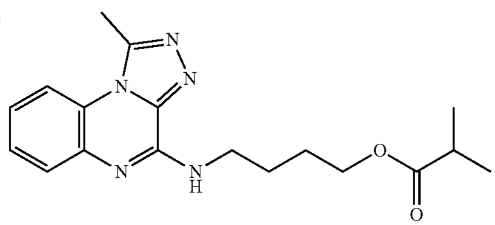 [SMILES: Cc1nnc2c(NCCCCOC(=O)C(C)C)nc3ccccc3n12] | isobutyric acid-4-(1-methyl-[1,2,4]triazolo[4,3-a]quinoxaline-4-ylamino)-butyl]-ester | Mass (M + H$^+$): 342.1; $^1$H NMR (500 MHz, DMSO-d6): δ1.03 (d, 6H), 1.64 (m, 2H), 1.69 (m, 2H), 2.99 (s, 3H), 3.53 (q, 2H), 4.03 (q, 2H), 4.68 (t, 1H), 7.26 (t, 1H), 7.40 (t, 1H), 7.55 (d, 1H), 8.06 (d, 2H), 8.13 (t, 1H) |
| Example 633 | 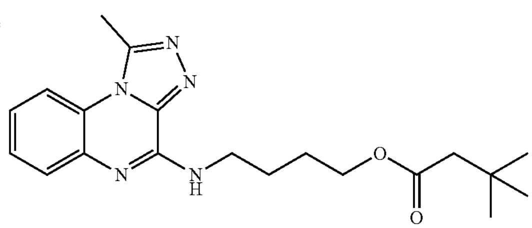 [SMILES: Cc1nnc2c(NCCCCOC(=O)CC(C)(C)C)nc3ccccc3n12] | 3,3-dimethyl butyric acid-4-(1-methyl-[1,2,4]triazolo[4,3-a]quinoxaline-4-ylamino)-butyl]-ester | Mass (M + H$^+$): 370.2; $^1$H NMR (500 MHz, DMSO-d6): δ0.90 (s, 9H), 1.64 (m, 2H), 1.70 (m, 2H), 2.11 (s, 1H), 2.99 (s, 3H), 3.53 (q, 2H), 4.03 (q, 2H), 7.27 (t, 1H), 7.41 (t, 1H), 7.55 (d, 1H), 8.06 (d, 1H), 8.14 (t, 1H). |
| Example 634 | 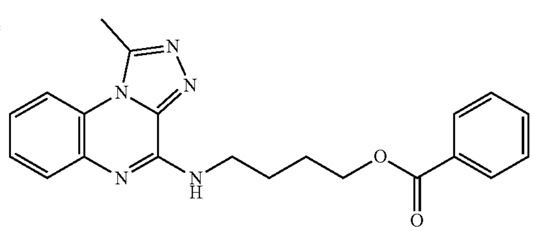 [SMILES: Cc1nnc2c(NCCCCOC(=O)c3ccccc3)nc3ccccc3n12] | benzoic acid-4-(1-methyl-[1,2,4]triazolo[4,3-a]quinoxaline-4-ylamino)-butylester | Mass (M + H$^+$): 376.2; $^1$H NMR (500 MHz, DMSO-d6): δ1.77 (m, 2H), 1.82 (m, 2H), 2.98 (s, 3H), 3.58 (q, 2H), 4.31 (q, 2H), 7.26 (t, 1H), 7.43 (m, 1H), 7.45 (d, 2H), 7.52 (t, 1H), 7.59 (t, 1H), 7.89 (d, 2H), 8.04 (d, 1H), 8.16 (t, 1H). |

TABLE 47-continued

| Example | Structure | Name | Data |
|---|---|---|---|
| Example 635 | 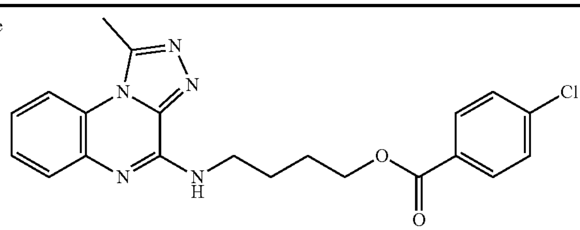 | 4-chlorobenzoic acid-4-(1-methyl-[1,2,4]triazolo[4,3-a]quinoxaline-4-ylamino)-butyl-ester | Mass (M + H$^+$): 410.2; $^1$H NMR (500 MHz, DMSO-d6): δ1.79 (brm, 4H), 2.99 (s, 3H), 3.58 (q, 2H), 4.31 (q, 2H), 7.26 (m, 1H), 7.38 (t, 1H), 7.48 (d, 2H), 7.51 (t, 1H), 7.87 (d, 2H), 8.03 (d, 1H), 8.16 (t, 1H). |
| Example 636 | 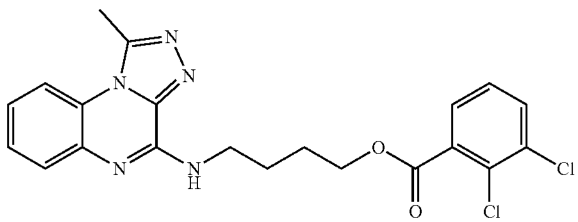 [SMILES: Cc1nnc2c(NCCCCOC(=O)c3cccc(Cl)c3Cl)nc3ccccc3n12] | 2,3-dichlorobenzoic acid-4-(1-methyl-[1,2,4]triazolo[4,3-a]quinoxaline-4-ylamino)-butylester | Mass (M + H$^+$): 444.1; $^1$H NMR (500 MHz, DMSO-d6): δ1.79 (brm, 4H), 2.99 (s, 3H), 3.57 (q, 2H), 4.34 (q, 2H), 7.26 (t, 1H), 7.39 (m, 2H), 7.53 (d, 2H), 7.65 (d, 1H), 7.78 (d, 1H), 8.03 (d, 1H), 8.16 (t, 1H) |
| Example 637 | 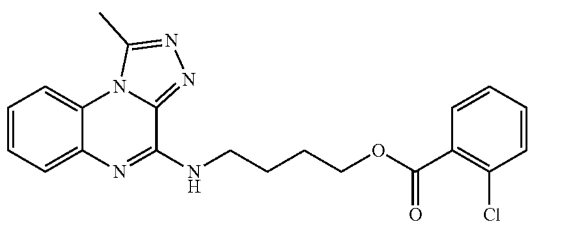 [SMILES: Cc1nnc2c(NCCCCOC(=O)c3ccccc3Cl)nc3ccccc3n12] | 2-chlorobenzoic acid-4-(1-methyl-[1,2,4]triazolo[4,3-a]quinoxaline-4-ylamino)-butylester | Mass (M + H$^+$): 410.2; $^1$H NMR (500 MHz, DMSO-d6): δ1.78 (brm, 4H), 2.99 (s, 3H), 3.57 (q, 2H), 4.32 (q, 2H), 7.26 (t, 1H), 7.41 (m, 2H), 7.51 (m, 3H), 7.73 (d, 1H), 8.05 (d, 1H), 8.16 (t, 1H). |

<Preparative Example 47> Preparation of [4-(3-hydrazino-7-methoxy-quinoxaline-2-yloxy)-butyl]-carbamic acid-tert-butylester

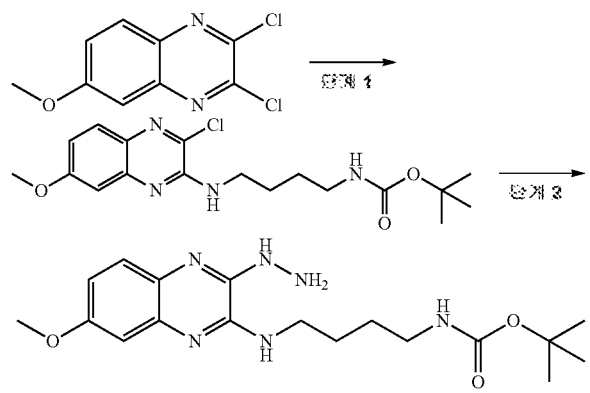

Step 1: Preparation of [4-(3-chloro-7-methoxy-quinoxaline-2-yloxy)-butyl]-carbamic acid-tert-butylester 2,3-Dichloro-6-methoxy-quinoxaline (2 g, 8.73 mmol) prepared in step 1 of Preparative Example 8 was dissolved in 20 ml of dimethylsulfoxide, to which cesiumcarbonate (4.2 g, 13.1 mmol, 1.5 eq) and (4-hydroxy-butyl)-carbamic acid-tert-butyl ester (1.98 g, 10.48 mmol, 1.2 eq) were added stepwise, followed by stirring at 40-50° C. for 18 hours. Upon completion of the reaction, the temperature was lowered to room temperature, and the reactant was extracted with water and ethylacetate. The organic layer was dried over anhydrous magnesium sulfate to eliminate moisture, followed by distillation under reduced pressure. The reactant was purified by column chromatography, and as a result, 1.79 g of a target compound was obtained (54% yield).

Mass (M+H$^+$): 382.2

$^1$H NMR (500 MHz, DMSO-d6) δ1.33 (s, 9H), 1.54 (m, 2H), 1.77 (m, 2H), 2.97 (q, 2H), 3.88 (s, 3H), 4.43 (t, 2H), 6.81 (t, 1H), 7.19 (s, 1H), 7.23 (d, 1H), 7.77 (d, 1H).

Step 2: Preparation of [4-(3-hydrazino-7-methoxy-quinoxaline-2-yloxy)-butyl]-carbamic acid-tert-butylester

[4-(3-Chloro-7-methoxy-quinoxaline-2-yloxy)-butyl]-carbamic acid-tert-butylester (1.7 g, 4.45 mmol) prepared in step 1 of Preparative Example 47 and hydrazine hydrate (6.48 ml, 133 mmol, 30 eq) were dissolved in 20 ml of 1,4-dioxane, followed by reflux stirring for 5 hours. Upon completion of the reaction, the solvent was distilled under reduced pressure. The reactant was extracted with ethylacetate and water. The extract was dried over magnesium sulfate to eliminate moisture, followed by filtering, distillation and drying under reduced pressure. As a result, 13.5 g of a target compound was obtained (94% yield), which proceeded to the next reaction without purification.

Mass (M+H$^+$): 378.2

$^1$H NMR (500 MHz, DMSO-d6) δ1.34 (s, 9H), 1.54 (m, 2H), 1.72 (m, 2H), 2.96 (q, 2H), 3.78 (s, 3H), 4.35 (br, 2H), 4.37 (t, 2H), 6.79 (t, 1H), 6.99 (d, 1H), 7.02 (d, 1H), 7.44 (d, 1H), 8.01 (s, 1H).

<Example 638> Preparation of 4-(7-methoxy-1-methyl-[1,2,4]triazolo[4,3-a]quinoxaline-4-yloxy)-butyl-carbamic acid-tert-butylester

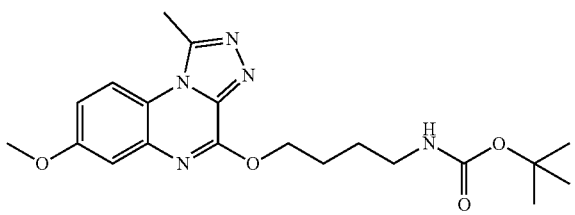 [SMILES: COc1ccc2c(c1)nc(OCCCCNC(=O)OC(C)(C)C)c1nnc(C)n12]

1.34 g of a target compound was obtained (77% yield) by the same manner as described in step 3 of Preparative Example 5, except that [4-(3-hydrazino-7-methoxy-quinoxaline-2-yloxy)-butyl]-carbamic acid-tert-butylester (1.6 g, 4.32 mmol) prepared in step 2 of Preparative Example 47 was used.

Mass (M+H$^+$): 302.2

$^1$H NMR (500 MHz, DMSO-d6): δ1.75 (m, 2H), 1.89 (m, 2H), 2.89 (q, 2H), 2.99 (s, 3H), 3.85 (s, 3H), 4.57 (q, 2H), 7.13 (d, 1H), 7.24 (s, 1H), 7.77 (br, 2H), 8.11 (d, 1H)

<Example 639> Preparation of 4-(7-methoxy-1-methyl-[1,2,4]triazolo[4,3-a]quinoxaline-4-yloxy)-butylamine ditrifluoroacetic acid

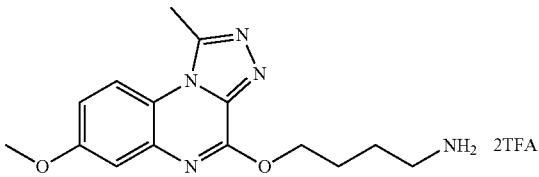 [SMILES: COc1ccc2c(c1)nc(OCCCCN)c1nnc(C)n12]

1.4 g of a target compound was obtained (78% yield) by the same manner as described in Example 58, except that 4-(7-methoxy-1-methyl-[1,2,4]triazolo[4,3-a]quinoxaline-4-yloxy)-butyl-carbamic acid-tert-butylester (1.23 g, 3.26 mmol) prepared in Example 638 was used.

Mass (M+H$^+$): 302.2

$^1$H NMR (500 MHz, DMSO-d6): δ1.75 (m, 2H), 1.89 (m, 2H), 2.89 (q, 2H), 2.99 (s, 3H), 3.85 (s, 3H), 4.57 (q, 2H), 7.13 (d, 1H), 7.24 (s, 1H), 7.77 (br, 2H), 8.11 (d, 1H).

<Example 640> Preparation of N-[4-(7-methoxy-1-methyl-[1,2,4]triazolo[4,3-a]quinoxaline-4-yloxy)-butyl]-3-methyl-butyramide

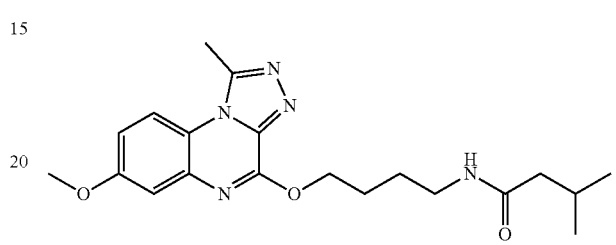

0.3 g of a target compound was obtained (82% yield) by the same manner as described in Example 37, except that 4-(7-methoxy-1-methyl-[1,2,4]triazolo[4,3-a]quinoxaline-4-yloxy)-butylamine ditrifluoroacetic acid (0.5 g, 0.94 mmol) prepared in Example 639 was used.

Mass (M+H$^+$): 386.2

$^1$H NMR (500 MHz, DMSO-d6): δ0.82 (d, 6H), 1.57 (m, 2H), 1.82 (m, 2H), 1.90 (m, 2H), 1.92 (m, 1H), 2.99 (s, 3H), 3.11 (q, 2H), 3.84 (s, 3H), 4.55 (q, 2H), 7.10 (d, 1H), 7.25 (s, 1H), 7.77 (t, 1H), 8.10 (d, 1H).

<Example 641> Preparation of tert-butyl-{2-[(1-methyl-[1,2,4]triazolo[4,3-a]quinoxaline-4-yl)amino]-pentyl}-carbamate

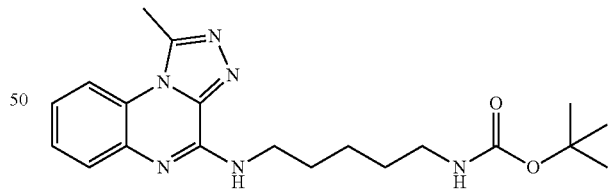

A target compound was obtained (71% yield) by the same manner as described in Example 1, except that 4-chloro-1-methyl-[1,2,4]triazolo[4,3-a]quinoxaline prepared in step 2 of Preparative Example 1 and tert-butyl-(4-aminopentyl)carbamate were used.

Mass (M+H$^+$): 385.2

$^1$H NMR (300 MHz, DMSO-d6): δ1.34-1.45 (m, 13H), 1.61-1.68 (m, 2H), 2.87-2.94 (m, 2H), 3.49-3.56 (m, 2H), 3.02 (s, 3H), 6.76 (t, J=4.59 Hz, 1H), 7.26-7.31 (m, 1H), 7.43 (t, J=7.47 Hz, 1H), 7.59 (d, J=7.41 Hz, 1H), 8.08 (d, J=7.44 Hz, 2H).

Example 642> Preparation of [5-(7,8-dimethoxy-1-methyl-[1,2,4]triazolo[4,3-a]quinoxaline-4-ylamino)-pentyl]-carbamic acid-tert-butylester

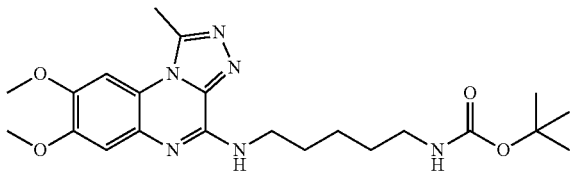 [SMILES: COc1cc2nc(NCCCCCNC(=O)OC(C)(C)C)c3nnc(C)n3c2cc1OC]

590 mg of a target compound was obtained (74% yield) by the same manner as described in Example 57, except that 4-chloro-7,8-dimethoxy-1-methyl-[1,2,4]triazolo[4,3-a]quinoxaline (500 mg, 1.79 mmol) prepared in step 3 of Preparative Example 5 and tert-butyl-(4-aminopentyl)carbamate were used.

Mass (M+H$^+$): 445.3
$^1$H NMR (500 MHz, DMSO-d6): δ1.31 (s, 9H), 1.32 (m, 2H), 1.39 (m, 2H), 1.61 (m, 2H), 2.88 (q. 2H), 3.03 (s, 3H), 3.46 (q, 2H), 3.81 (s, 3H), 3.86 (s, 3H), 6.72 (t, 1H), 7.09 (s, 1H), 7.51 (s, 1H), 7.78 (t, 1H).

Examples of the compounds synthesized using [5-(7,8-dimethoxy-1-methyl-[1,2,4]triazolo[4,3-a]quinoxaline-4-ylamino)-pentyl]-carbamic acid-tert-butylester prepared in Example 642 are shown in Table 48 below.

TABLE 48

| Example | Structure | Name | Data |
|---|---|---|---|
| Example 643 | 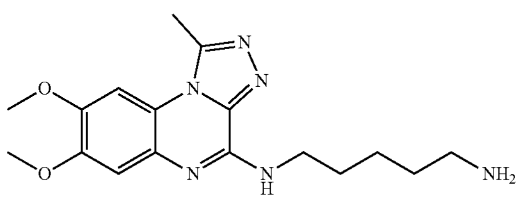 | N$^1$-(7,8-dimethoxy-1-methyl-[1,2,4]triazolo[4,3-a]quinoxaline-4-yl)-pentane-1,5-diamine ditrifluoroacetic acid | Mass (M + H$^+$): 345.1; $^1$H NMR (500 MHz, DMSO-d6): δ1.39 (m, 2H), 1.56 (m, 2H), 1.65 (m, 2H), 2.78 (q, 2H), 3.04 (s, 3H), 3.49 (q, 2H), 3.82(s, 3H), 3.87 (s, 3H), 7.08 (s, 1H), 7.52 (s, 1H), 7.79 (brs, 2H), 7.81 (t, 1H). |
| Example 644 | 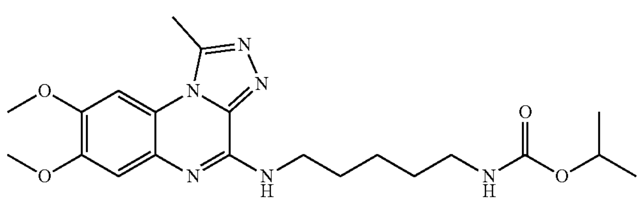 [SMILES: COc1cc2nc(NCCCCCNC(=O)OC(C)C)c3nnc(C)n3c2cc1OC] | [5-(7,8-dimethoxy-1-methyl-[1,2,4]triazolo[4,3-a]quinoxaline-4-ylamino)-pentyl]-carbamic acid isopropylester | Mass (M + H$^+$): 431.2; $^1$H NMR (500 MHz, DMSO-d6): δ1.10 (d, 6H), 1.30 (m, 2H), 1.41 (m, 2H), 1.62 (m, 2H), 2.93 (q, 2H), 3.03 (s, 3H), 3.48 (q, 2H), 3.82 (s, 3H), 3.86 (s, 3H), 4.67 (m, 1H), 6.92 (t, 1H), 7.09 (s, 1H), 7.51 (s, 1H), 7.79 (t, 1H). |
| Example 645 | 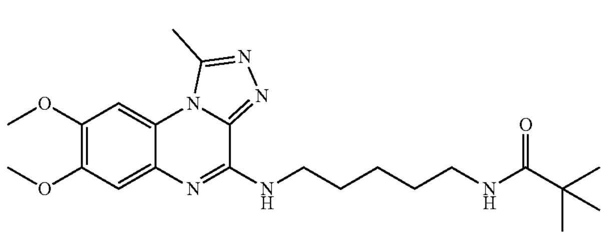 [SMILES: COc1cc2nc(NCCCCCNC(=O)C(C)(C)C)c3nnc(C)n3c2cc1OC] | N-[5-(7,8-dimethoxy-1-methyl-[1,2,4]triazolo[4,3-a]quinoxaline-4-ylamino)-pentyl]-2,2-dimethyl-propionamide | Mass (M + H$^+$): 429.3; $^1$H NMR (500 MHz, DMSO-d6): δ1.02 (s, 9H), 1.30 (m, 2H), 1.42 (m, 2H), 1.64 (m, 2H), 2.98 (q, 2H), 3.03 (s, 3H), 3.46 (q, 2H), 3.82 (s, 3H), 3.87 (s, 3H), 7.10 (s, 1H), 7.34 (t, 1H), 7.51 (s, 1H), 7.77 (t, 1H). |

Example 646: Preparation of 5-(7,8-dimethoxy-1-methyl-[1,2,4]triazolo[4,3-a]quinoxaline-4-ylamino)-pentanoic acid-tert-butyl

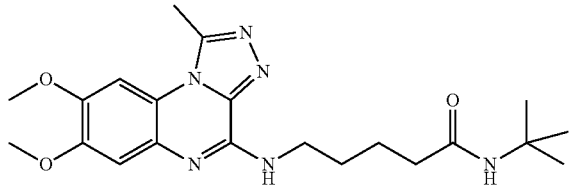 [SMILES: COc1cc2nc(NCCCCC(=O)NC(C)(C)C)c3nnc(C)n3c2cc1OC]

32 mg of a target compound was obtained (15% yield) by the same manner as described in Example 57, except that 5-aminopentanoic acid-tert-butylamide

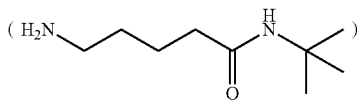

(1.1 g, 2.7 mmol) was used as a substituent for 4-chloro-7,8-dimethoxy-1-methyl-[1,2,4]triazolo[4,3-a]quinoxaline (150 mg, 0.54 mmol) prepared in step 3 of Preparative Example 5.

Mass (M+H$^+$): 415.2

$^1$H NMR (500 MHz, DMSO-d6): δ1.19 (s, 9H), 1.51 (m, 2H), 1.60 (m, 2H), 2.02 (q, 2H), 3.04 (s, 3H), 3.47 (q, 2H), 3.82 (s, 3H), 3.87 (s, 3H), 7.10 (s, 1H), 7.30 (s, 1H), 7.52 (s, 1H), 7.82 (t, 1H).

The compounds shown in Table 49 below were prepared by the same manner as described in Example 646.

TABLE 49

| Example | Structure | Name | Data |
| --- | --- | --- | --- |
| Example 647 | 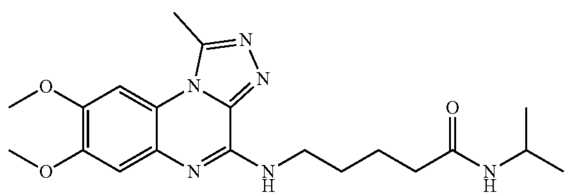 [SMILES: COc1cc2nc(NCCCCC(=O)NC(C)C)c3nnc(C)n3c2cc1OC] | 5-(7,8-dimethoxy-1-methyl-[1,2,4]triazolo[4,3-a]quinoxaline-4-ylamino)-pentanoic acid-isopropyl-amide | Mass (M + H$^+$): 401.2; $^1$H NMR (500 MHz, DMSO-d6): δ0.98 (d, 6H), 1.53 (m, 2H), 1.60 (m, 2H), 2.04 (t, 2H), 3.03 (s. 3H), 3.47 (q, 2H), 3.82 (m, 1H), 3.87 (s, 3H), 3.89 (s, 3H), 7.10 (s, 1H), 7.51 (s, 1H), 7.58 (t, 1H), 7.90 (brs, 1H). |
| Example 648 | 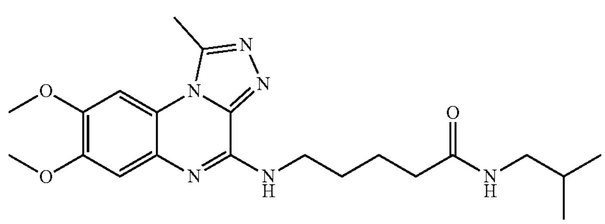 [SMILES: COc1cc2nc(NCCCCC(=O)NCC(C)C)c3nnc(C)n3c2cc1OC] | 5-(7,8-dimethoxy-1-methyl-[1,2,4]triazolo[4,3-a]quinoxaline-4-ylamino)-pentanoic acid-isobutyl-amide | Mass (M + H$^+$): 415.4; $^1$H NMR (500 MHz, DMSO-d6): δ0.77 (d, 6H), 1.51 (m, 1H), 1.59 (m, 2H), 1.61 (d, 2H), 2.11 (q. 2H), 2.81 (q, 2H), 3.04 (s, 3H), 3.48 (m, 2H), 3.82 (s, 3H), 3.87 (s, 3H), 7.10 (s, 1H), 7.52 (s, 1H), 7.70 (t, 1H), 7.81 (t, 1H). |
| Example 649 | 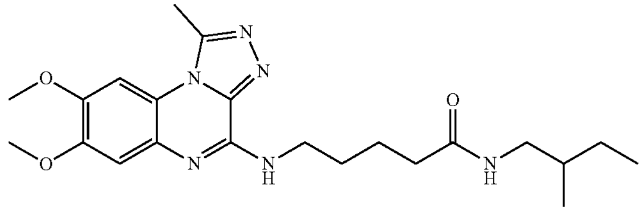 [SMILES: CCC(C)CNC(=O)CCCCNc1nc2cc(OC)c(OC)cc2n2c(C)nnc12] | 5-(7,8-dimethoxy-1-methyl-[1,2,4]triazolo[4,3-a]quinoxaline-4-ylamino)-pentanoic acid-(2-methylbutyl)-amide | Mass (M + H$^+$): 429.2; $^1$H NMR (500 MHz, DMSO-d6): δ0.75 (d, 3H), 0.77 (t, 3H), 1.01 (m, 1H), 1.39 (m, 2H), 1.56 (m, 2H), 1.59 (m, 2H), 2.09 (q, 2H), 2.81 (m, 2H), 3.04 (s, 3H), 3.48 (q. 2H), 3.82 (s, 3H), 3.87 (s, 3H), 7.10 (s, 1H), 7.52 (s, 1H), 7.66 (t, 1H), 7.82 (t, 1H). |

TABLE 49-continued

| Example | Structure | Name | Data |
|---|---|---|---|
| Example 650 | 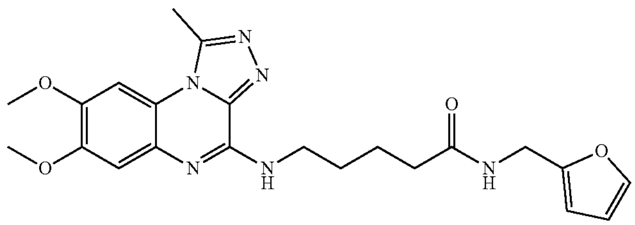 [SMILES: COc1cc2nc(NCCCCC(=O)NCc3ccco3)c3nnc(C)n3c2cc1OC] | 5-(7,8-dimethoxy-1-methyl-[1,2,4]triazolo[4,3-a]quinoxaline-4-ylamino)-pentanoic acid-(furan-2-ylmethyl)-amide | Mass (M + H$^+$): 439.2; $^1$H NMR (500 MHz, DMSO-d6): δ1.58 (m, 4H), 2.13 (m, 2H), 3.07 (s, 3H), 3.48 (q, 2H), 3.82 (q, 2H), 3.87 (s, 3H), 4.20 (d, 2H), 6.16 (d, 1H), 6.30 (d, 1H), 7.10 (s, 1H), 7.49 (s, 1H), 7.52 (s, 1H), 7.80 (t, 1H), 8.20 (t, 1H). |
| Example 651 | 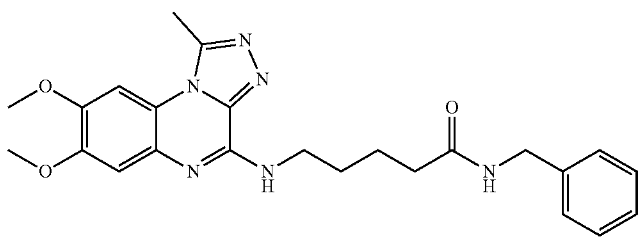 [SMILES: COc1cc2nc(NCCCCC(=O)NCc3ccccc3)c3nnc(C)n3c2cc1OC] | 5-(7,8-dimethoxy-1-methyl-[1,2,4]triazolo[4,3-a]quinoxaline-4-ylamino)-pentanoic acid-benzylamide | Mass (M + H$^+$): 449.2; $^1$H NMR (500 MHz, DMSO-d6): δ1.60 (m, 2H), 1.63 (m, 2H), 2.18 (q, 2H), 3.04 (s, 3H), 3.51 (q, 2H), 3.81 (s, 3H), 3.87 (s, 3H), 4.22 (d, 2H), 7.10 (s, 1H), 7.18 (m, 3H), 7.19 (m, 2H), 7.53 (s, 1H), 7.83 (t, 1H), 8.25 (t, 1H). |
| Example 652 | 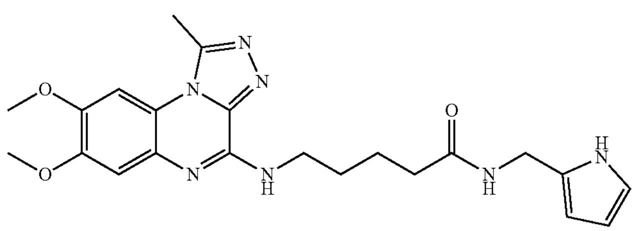 [SMILES: COc1cc2nc(NCCCCC(=O)NCc3ccc[nH]3)c3nnc(C)n3c2cc1OC] | 5-(7,8-dimethoxy-1-methyl-[1,2,4]triazolo[4,3-a]quinoxaline-4-ylamino)-pentanoic acid-(1H-pyrrole-2-ylmethyl)-amide | Mass (M + H$^+$): 438.2; $^1$H NMR (500 MHz, DMSO-d6): δ1.47 (m, 2H), 1.62 (m, 2H), 3.04 (q, 2H), 3.06 (d, 2H), 3.29 (s. 3H), 3.50 (q, 2H), 3.82 (s, 3H), 3.87 (s, 3H), 5.73 (s, 1H), 5.82 (d, 1H), 6.53 (d, 1H), 7.10 (s, 1H), 7.52 (s, 1H), 7.72 (t, 1H), 7.80 (t, 1H), 10.43 (brs, 1H). |

<Example 653> Preparation of 5-(7-methoxy-1-methyl-[1,2,4]triazolo[4,3-a]quinoxaline-4-ylamino)-pentanoic acid-tert-butylamide

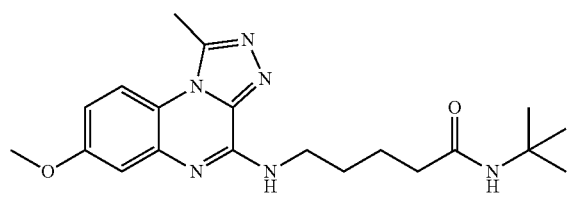 [SMILES: COc1ccc2c(c1)nc(NCCCCC(=O)NC(C)(C)C)c1nnc(C)n12]

Mass (M+H$^+$): 385.2

$^1$H NMR (500 MHz, DMSO-d6) δ1.19 (s, 9H), 1.52 (m, 2H), 1.61 (m, 2H), 2.03 (m, 2H), 2.95 (s, 3H), 3.49 (q, 2H), 3.80 (s, 3H), 6.84 (d, 1H), 7.05 (s, 1H), 7.31 (t, 1H), 7.95 (s, 1H), 8.09 (t, 1H).

The compounds shown in Table 50 below were prepared by the same manner as described in Example 653.

TABLE 50

| Example | Structure | Name | Data |
|---|---|---|---|
| Example 654 | 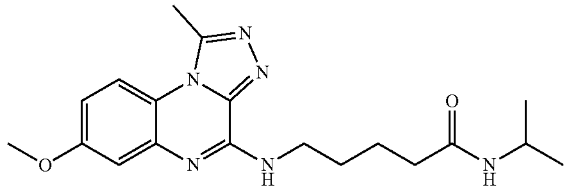 [SMILES: COc1ccc2c(c1)nc(NCCCCC(=O)NC(C)C)c1nnc(C)n12] | 5-(7-methoxy-1-methyl-[1,2,4]triazolo[4,3-a]quinoxaline-4-ylamino)-pentanoic acid isopropylamide | Mass (M + H$^+$): 371.2; $^1$H NMR (500 MHz, DMSO-d6): δ0.98 (d, 6H), 1.54 (m, 2H), 1.61 (m, 2H), 2.04 (m, 2H), 2.95 (s, 3H, 3.50 (q, 2H), 3.77 (m, 1H), 3.81 (s, 3H), 6.85 (d, 1H), 7.06 (s, 1H), 7.57 (t, 1H), 7.95 (s, 1H), 8.09 (t, 1H). |
| Example 655 | 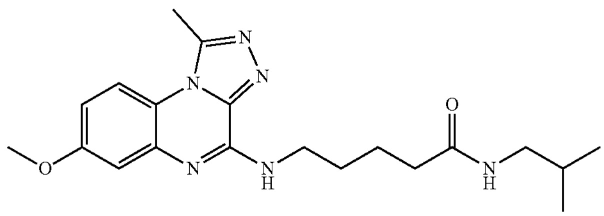 [SMILES: COc1ccc2c(c1)nc(NCCCCC(=O)NCC(C)C)c1nnc(C)n12] | 5-(7-methoxy-1-methyl-[1,2,4]triazolo[4,3-a]quinoxaline-4-ylamino)-pentanoic acid isobutylamide | Mass (M + H$^+$): 385.2; $^1$H NMR (500 MHz, DMSO-d6): δ0.76 (d, 6H), 1.54 (m, 1H), 1.58 (m, 2H), 1.62 (m, 2H), 2.10 (m, 2H), 2.81 (m, 2H), 2.95 (s, 3H), 3.50 (q, 2H), 3.81 (s, 3H), 6.84 (d, 1H), 7.05 (s, 1H), 7.71 (t, 1H), 7.94 (s, 1H), 8.09 (t, 1H). |
| Example 656 | 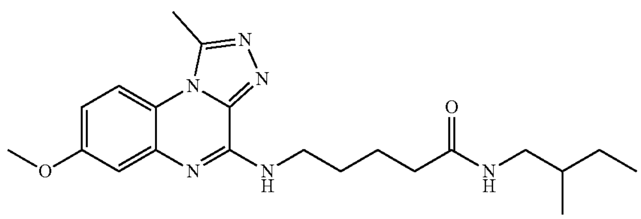 [SMILES: CCC(C)CNC(=O)CCCCNc1nc2cc(OC)ccc2n2c(C)nnc12] | 5-(7-methoxy-1-methyl-[1,2,4]triazolo[4,3-a]quinoxaline-4-ylamino)-pentanoic acid-(2-methyl-butyl)-amide | Mass (M + H$^+$): 399.2; $^1$H NMR (500 MHz, DMSO-d6): δ0.76 (m, 6H), 1.01 (m, 1H), 1.16-1.43 (brm, 2H), 1.55 (m, 2H), 1.60 (m, 2H), 2.09 (m, 2H), 2.81 (m, 2H), 2.95 (s, 3H), 3.50 (q, 2H), 3.81 (s, 3H), 6.84 (d, 1H), 7.05 (s, 1H), 7.66 (t, 1H), 7.94 (s, 1H), 8.09 (t, 1H). |
| Example 657 | 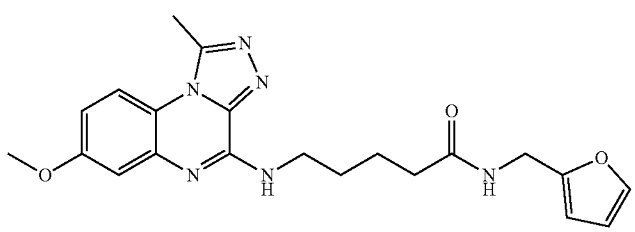 [SMILES: COc1ccc2c(c1)nc(NCCCCC(=O)NCc1ccco1)c1nnc(C)n12] | 5-7-methoxy-1-methyl-[1,2,4]triazolo[4,3-a]quinoxaline-4-ylamino)-pentanoic acid-(furan-2-ylmethyl)-amide | Mass (M + H$^+$): 409.2; $^1$H NMR (500 MHz, DMSO-d6): δ1.61 (m, 2H), 1.64 (m, 2H), 2.14 (m, 2H), 2.95 (s, 3H), 3.51 (q, 2H), 3.81 (s, 3H), 4.20 (d, 2H), 6.15 (t, 1H), 6.30 (t, 1H), 6.85 (d, 1H), 7.06 (s, 1H), 7.49 (s, 1H), 7.96 (d, 1H), 8.09 (t, 1H), 8.20 (t, 1H). |
| Example 658 | 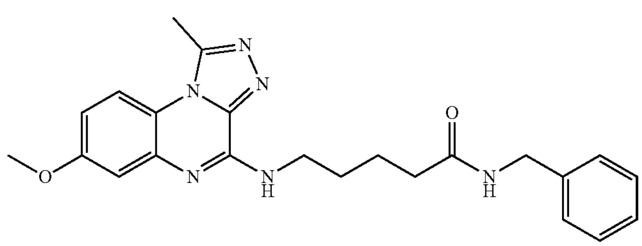 [SMILES: COc1ccc2c(c1)nc(NCCCCC(=O)NCc1ccccc1)c1nnc(C)n12] | 5-(7-methoxy-1-methyl-[1,2,4]triazolo[4,3-a]quinoxaline-4-ylamino)-pentanoic acid benzamide | Mass (M + H$^+$): 419.2; $^1$H NMR (500 MHz, DMSO-d6): δ1.63 (m, 4H), 2.17 (m, 2H), 2.95 (s, 3H), 3.51 (m, 2H), 3.80 (s, 3H), 4.21 (d, 2H), 6.85 (d, 1H), 7.05 (d, 1H), 7.15-7.25 (brm, 5H), 7.94 (d, 1H), 8.09 (t, 1H), 8.25 (t, 1H). |

TABLE 50-continued

| Example | Structure | Name | Data |
|---|---|---|---|
| Example 659 | 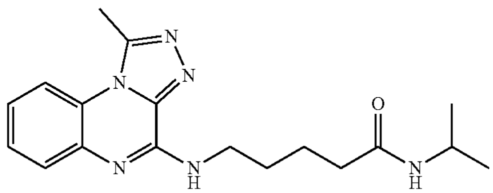 [SMILES: Cc1nnc2c(NCCCCC(=O)NC(C)C)nc3ccccc3n12] | 5-(1-methyl-[1,2,4]triazolo[4,3-a]quinoxaline-4-ylamino)-pentanoic acid isopropylamide | Mass (M + H⁺): 341.1; ¹H NMR (300 MHz, DMSO-d6): δ1.02 (t, J = 6.30 Hz, 6H), 1.60-1.66 (m, 4H), 2.09 (t, J = 6.65 Hz, 2H), 3.30 (s, 3H), 3.54-3.55 (m, 2H), 3.79-3.83 (m, 1H), 7.31 (t, J = 7.20 Hz, 1H), 7.45 (t, J = 7.50 Hz, 1H), 7.60-7.63 (m, 2H), 8.09-8.13 (m, 2H). |
| Example 660 | 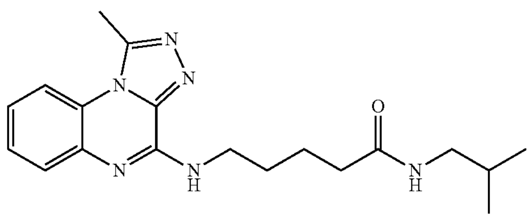 [SMILES: Cc1nnc2c(NCCCCC(=O)NCC(C)C)nc3ccccc3n12] | 5-(1-methyl-[1,2,4]triazolo[4,3-a]quinoxaline-4-ylamino)-pentanoic acid isobutylamide | Mass (M + H⁺): 355.1; ¹H NMR (300 MHz, DMSO-d6): δ0.81 (d, J = 6.65 Hz, 6H), 2.12-2.16 (m, 2H), 1.58-1.68 (m, 5H), 3.04 (s, 3H), 2.84-2.86 (m, 2H), 3.53-3.57 (m, 2H), 7.31 (t, J = 7.70 Hz, 1H), 7.45 (t, J = 7.65 Hz, 1H), 7.61 (d, J = 8.00 Hz, 1H), 7.76 (t, J = 5.40 Hz, 1H), 8.10 (d, J = 8.25 Hz, 1H), 8.14 (brs, 1H). |
| Example 661 | 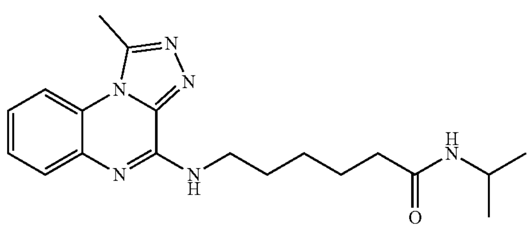 [SMILES: Cc1nnc2c(NCCCCCC(=O)NC(C)C)nc3ccccc3n12] | 6-(1-methyl-[1,2,4]triazolo[4,3-a]quinoxaline-4-ylamino)-hexanoic acid isopropylamide | Mass (M + H⁺): 355.2; ¹H NMR (300 MHz, DMSO-d6): δ1.01 (d, J = 6.60 Hz, 6H), 1.30-1.37 (m, 2H), 1.52-1.58 (m, 2H), 1.65-1.71 (m, 2H), 2.02-2.05 (m, 2H), 3.04 (s, 3H), 3.52-3.56 (m, 2H), 3.78-3.84 (m, 1H), 7.31 (t, J = 7.50 Hz, 1H), 7.45 (t, J = 7.70 Hz, 1H), 7.59-7.62 (m, 2H), 8.09-8.12 (m, 2H). |
| Example 662 | 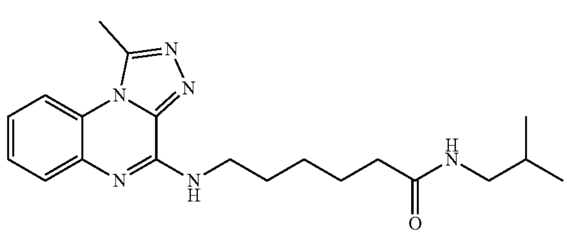 [SMILES: Cc1nnc2c(NCCCCCC(=O)NCC(C)C)nc3ccccc3n12] | 6-(1-methyl-[1,2,4]triazolo[4,3-a]quinoxaline-4-ylamino)-hexanoic acid isobutylamide | Mass (M + H⁺): 369.0; ¹H NMR (300 MHz, DMSO-d6): δ0.80 (d, J = 6.65 Hz, 6H), 1.31-1.37 (m, 2H), 1.53-1.71 (m, 5H), 2.08-2.10 (m, 2H), 2.83-2.86 (m, 2H), 3.52-3.56 (m, 2H), 3.04 (s, 3H), 7.31 (t, J = 7.45 Hz, 1H), 7.45 (t, J = 7.65 Hz, 1H), 7.61 (d, J = 7.85 Hz, 1H), 7.73 (t, J = 5.3 Hz, 1H), 8.09-8.12 (m, 2H). |

Experimental Example 1: Evaluation of BRD4 binding inhibition ability 1-1. Experiment Methods The following experiment was performed to evaluate the ability of [1,2,4]triazolo[4,3-a]quinoxaline derivative of the present invention to inhibit the interaction between BRD4 (BD1+BD2) bromodomain, one of BET protein family, and tetraacetylated histone H4 peptide.

The compound was serially diluted at the ratio of 1:5 in assay buffer from 10 mM stock in DMSO (initial concentration: 100 μM) on white OptiPlate-384 (PerkinElmer). A mixture comprising 100 nM GST-BRD4 (BD1+BD2) and 100 nM biotinylated acetyl-histone H4 (Lys5,8,12,16) peptide was prepared in assay buffer (50 mM HEPES pH 7.4; 25 mM NaCl; 0.05% Tween 20; 0.1% bovine serum albumin (BSA); 10 mM dithiothreitol (DTT)). After adding 6 μl of the mixture to the diluent, 6 μl of the pre-mixed AlphaLISA Glutathione Acceptor Beads and AlphaScreen Streptavidin Donor Beads (PerkinElmer, 10 μg/ml in assay buffer, respectively) was added thereto. The samples were incubated in the dark at room temperature for 30 minutes (shaking at 300 rpm). Then, the signals were measured with PerkinElmer Envision HTS Multilabel Reader using an alpha screen protocol of PerkinElmer. Each plate contained the negative control in which biotinylated acetyl-histone H4 peptide and GST-BRD4 (BD1+BD2) were replaced by assay buffer. In the case of using the software GraphPad Prism for calculation, the negative control point was input as a low standard value. The positive control (probe molecule I-BET762 containing protein/peptide mixture) proceeded to pipetting. $IC_{50}$ value was determined by using GraphPad Prism 3.03 software (or an updated version thereof).

1-2. Experiment Results

The results are shown in Table 51 below.

As shown in Table 51, all the compounds of examples of the present invention demonstrated BRD4 binding inhibition activity.

Among them, the compounds of Examples 3, 4, 7, 8, 9, 10, 14, 15, 16, 19, 20, 30, 31, 37, 39, 45, 47, 51, 54, 57, 59, 60, 62, 63, 64, 65, 66, 67, 68, 70, 71, 72, 73, 74, 75, 76, 77, 78, 79, 80, 81, 82, 83, 84, 85, 86, 87, 88, 89, 92, 93, 95, 96, 97, 98, 99, 102, 106, 108, 110, 120, 123, 124, 125, 126, 127, 128, 129, 130, 133, 134, 136, 137, 139, 144, 145, 150, 153, 158, 159, 160, 161, 162, 164, 165, 166, 167, 168, 169, 170, 171, 172, 173, 175, 176, 177, 178, 179, 180, 181, 182, 183, 184, 185, 186, 187, 188, 189, 190, 191, 192, 196, 197, 201, 202, 203, 210, 211, 212, 215, 216, 217, 218, 220, 222, 223, 224, 226, 227, 228, 229, 230, 231, 232, 233, 234, 235, 236, 237, 238, 239, 240, 241, 245, 246, 247, 249, 250, 251, 253, 254, 257, 258, 266, 267, 268, 272, 273, 274, 275, 279, 280, 281, 284, 285, 286, 288, 289, 290, 292, 293, 294, 295, 296, 297, 298, 299, 300, 301, 302, 305, 307, 309, 310, 311, 312, 313, 315, 316, 317, 318, 319, 320, 321, 322, 323, 324, 327, 328, 329, 330, 332, 333, 335, 336, 339, 340, 343, 344, 345, 346, 347, 350, 358, 363, 365, 366, 367, 368, 369, 370, 371, 372, 373, 375, 376, 377, 378, 379, 380, 381, 382, 383, 384, 385, 388, 389, 390, 391, 392, 393, 394, 396, 397, 398, 399, 400, 401, 402, 403, 404, 405, 406, 407, 408, 409, 410, 411, 413, 414, 415, 418, 420, 422, 423, 424, 425, 426, 427, 428, 430, 432, 434, 435, 436, 437, 438, 439, 440, 442, 443, 444, 445, 446, 447, 448, 449, 450, 451, 453, 454, 455, 457, 458, 459, 460, 461, 462, 463, 467, 468, 474, 476, 477, 478, 479, 480, 482, 488, 489, 490, 492, 493, 494, 495, 496, 497, 499, 500, 501, 502, 504, 505, 506, 507, 508, 511, 513, 515, 516, 517, 519, 520, 525, 528, 529, 530, 541, 546, 547, 548, 550, 551, 552, 553, 556, 557, 559, 560, 562, 563, 564, 567, 568, 569, 574, 578, 579, 581, 582, 583, 585, 586, 587, 589, 590, 591, 596, 597, 598, 603, 620, 622, 623, 624, 627, 628, 629, 631, 632, 633, 647, 648, 649, 650, 651, 652, 653, 654, 655, 656, 657, 658, 660 and 662 exhibited $IC_{50}$ values of 0.05 μM or less, in particular, the compounds of Examples 10, 30, 37, 39, 62, 79, 81, 83, 126, 137, 161, 173, 176, 191, 220, 222, 226, 227, 228, 229, 233, 234, 236, 237, 240, 241, 254, 257, 281, 284, 298, 299, 302, 309, 318, 320, 324, 344, 358, 367, 368, 371, 372, 382, 383, 388, 389, 391, 392, 393, 396, 398, 399, 400, 403, 407, 409, 413, 420, 422, 428, 435, 440, 444, 448, 458, 479, 480, 490, 493, 496, 499, 501, 559, 564, 579, 582, 583, 585 and 587 showed $IC_{50}$ values of 0.01 μM or less, indicating that they inhibited BRD4 binding significantly at a very low concentration.

TABLE 51

| Example | BRD4 $IC_{50}$ (μM) |
|---|---|
| 1 | 0.074 |
| 3 | 0.028 |
| 4 | 0.035 |
| 7 | 0.020 |
| 8 | 0.024 |
| 9 | 0.040 |
| 10 | 0.005 |
| 11 | 0.058 |
| 12 | 0.058 |
| 13 | 0.057 |
| 14 | 0.041 |
| 15 | 0.027 |
| 16 | 0.044 |
| 17 | 0.051 |
| 19 | 0.036 |
| 20 | 0.043 |
| 21 | 0.057 |
| 22 | 0.081 |
| 24 | 0.067 |
| 25 | 0.055 |
| 28 | 0.096 |
| 29 | 0.098 |
| 30 | 0.008 |
| 31 | 0.031 |
| 32 | 0.089 |
| 34 | 0.081 |
| 37 | 0.008 |
| 38 | 0.097 |
| 39 | 0.006 |
| 40 | 0.069 |
| 42 | 0.056 |
| 44 | 0.072 |
| 45 | 0.040 |
| 46 | 0.073 |
| 47 | 0.042 |
| 49 | 0.061 |
| 50 | 0.077 |
| 51 | 0.038 |
| 52 | 0.070 |
| 53 | 0.060 |
| 54 | 0.050 |
| 57 | 0.020 |
| 59 | 0.034 |
| 60 | 0.012 |
| 61 | 0.056 |
| 62 | 0.007 |
| 63 | 0.012 |
| 64 | 0.020 |
| 65 | 0.022 |
| 66 | 0.013 |
| 67 | 0.019 |
| 68 | 0.038 |
| 70 | 0.044 |
| 71 | 0.018 |

TABLE 51-continued

| Example | BRD4 IC$_{50}$ (μM) |
|---|---|
| 72 | 0.021 |
| 73 | 0.015 |
| 74 | 0.028 |
| 75 | 0.028 |
| 76 | 0.038 |
| 77 | 0.022 |
| 78 | 0.020 |
| 79 | 0.005 |
| 80 | 0.028 |
| 81 | 0.010 |
| 82 | 0.012 |
| 83 | 0.002 |
| 84 | 0.014 |
| 85 | 0.027 |
| 86 | 0.017 |
| 87 | 0.027 |
| 88 | 0.018 |
| 89 | 0.047 |
| 90 | 0.063 |
| 92 | 0.041 |
| 93 | 0.039 |
| 94 | 0.057 |
| 95 | 0.036 |
| 96 | 0.015 |
| 97 | 0.024 |
| 98 | 0.047 |
| 99 | 0.021 |
| 100 | 0.069 |
| 101 | 0.051 |
| 102 | 0.019 |
| 105 | 0.060 |
| 106 | 0.028 |
| 108 | 0.017 |
| 110 | 0.035 |
| 114 | 0.091 |
| 117 | 0.064 |
| 118 | 0.054 |
| 119 | 0.079 |
| 120 | 0.034 |
| 121 | 0.055 |
| 123 | 0.042 |
| 124 | 0.029 |
| 125 | 0.031 |
| 126 | 0.004 |
| 127 | 0.046 |
| 128 | 0.033 |
| 129 | 0.017 |
| 130 | 0.036 |
| 133 | 0.034 |
| 134 | 0.019 |
| 135 | 0.061 |
| 136 | 0.058 |
| 137 | 0.006 |
| 138 | 0.051 |
| 139 | 0.040 |
| 140 | 0.052 |
| 144 | 0.038 |
| 145 | 0.047 |
| 150 | 0.048 |
| 151 | 0.052 |
| 152 | 0.096 |
| 153 | 0.016 |
| 154 | 0.078 |
| 155 | 0.077 |
| 158 | 0.018 |
| 159 | 0.024 |
| 160 | 0.028 |
| 161 | 0.004 |
| 162 | 0.024 |
| 164 | 0.037 |
| 165 | 0.026 |
| 166 | 0.020 |
| 167 | 0.040 |
| 168 | 0.016 |
| 169 | 0.041 |
| 170 | 0.038 |
| 171 | 0.026 |
| 172 | 0.040 |
| 173 | 0.004 |
| 175 | 0.026 |
| 176 | 0.002 |
| 177 | 0.050 |
| 178 | 0.017 |
| 179 | 0.035 |
| 180 | 0.017 |
| 181 | 0.017 |
| 182 | 0.022 |
| 183 | 0.011 |
| 184 | 0.030 |
| 185 | 0.019 |
| 186 | 0.022 |
| 187 | 0.024 |
| 188 | 0.025 |
| 189 | 0.017 |
| 190 | 0.028 |
| 191 | 0.010 |
| 192 | 0.034 |
| 195 | 0.069 |
| 196 | 0.032 |
| 197 | 0.028 |
| 199 | 0.058 |
| 200 | 0.071 |
| 201 | 0.026 |
| 202 | 0.044 |
| 203 | 0.042 |
| 205 | 0.075 |
| 210 | 0.018 |
| 211 | 0.034 |
| 212 | 0.035 |
| 215 | 0.022 |
| 216 | 0.031 |
| 217 | 0.016 |
| 218 | 0.025 |
| 219 | 0.068 |
| 220 | 0.009 |
| 221 | 0.062 |
| 222 | 0.001 |
| 223 | 0.017 |
| 224 | 0.013 |
| 226 | 0.004 |
| 227 | 0.001 |
| 228 | 0.007 |
| 229 | 0.003 |
| 230 | 0.013 |
| 231 | 0.014 |
| 232 | 0.033 |
| 233 | 0.002 |
| 234 | 0.006 |
| 235 | 0.011 |
| 236 | 0.002 |
| 237 | 0.0006 |
| 238 | 0.015 |
| 239 | 0.018 |
| 240 | 0.0009 |
| 241 | 0.007 |
| 243 | 0.065 |
| 244 | 0.089 |
| 245 | 0.032 |
| 246 | 0.023 |
| 247 | 0.031 |
| 248 | 0.054 |
| 249 | 0.031 |
| 250 | 0.019 |
| 251 | 0.031 |
| 253 | 0.050 |
| 254 | 0.007 |
| 257 | 0.008 |
| 258 | 0.049 |
| 260 | 0.062 |
| 262 | 0.072 |
| 266 | 0.043 |
| 267 | 0.039 |
| 268 | 0.035 |
| 296 | 0.096 |

TABLE 51-continued

| Example | BRD4 IC$_{50}$ (μM) |
|---|---|
| 270 | 0.085 |
| 272 | 0.025 |
| 273 | 0.049 |
| 274 | 0.027 |
| 275 | 0.038 |
| 278 | 0.051 |
| 279 | 0.018 |
| 280 | 0.014 |
| 281 | 0.0004 |
| 283 | 0.051 |
| 284 | 0.009 |
| 285 | 0.017 |
| 286 | 0.030 |
| 287 | 0.067 |
| 288 | 0.015 |
| 289 | 0.012 |
| 290 | 0.023 |
| 291 | 0.097 |
| 292 | 0.024 |
| 293 | 0.040 |
| 294 | 0.015 |
| 295 | 0.033 |
| 296 | 0.027 |
| 297 | 0.027 |
| 298 | 0.004 |
| 299 | 0.007 |
| 300 | 0.015 |
| 301 | 0.016 |
| 302 | 0.008 |
| 303 | 0.063 |
| 305 | 0.041 |
| 307 | 0.022 |
| 308 | 0.058 |
| 309 | 0.008 |
| 310 | 0.042 |
| 311 | 0.043 |
| 312 | 0.018 |
| 313 | 0.033 |
| 314 | 0.056 |
| 315 | 0.036 |
| 316 | 0.041 |
| 317 | 0.031 |
| 318 | 0.010 |
| 319 | 0.011 |
| 320 | 0.004 |
| 321 | 0.012 |
| 322 | 0.014 |
| 323 | 0.035 |
| 324 | 0.007 |
| 325 | 0.071 |
| 326 | 0.064 |
| 327 | 0.018 |
| 328 | 0.043 |
| 329 | 0.035 |
| 330 | 0.029 |
| 332 | 0.017 |
| 333 | 0.018 |
| 334 | 0.060 |
| 335 | 0.016 |
| 336 | 0.033 |
| 339 | 0.046 |
| 340 | 0.023 |
| 341 | 0.071 |
| 342 | 0.056 |
| 343 | 0.036 |
| 344 | 0.010 |
| 345 | 0.013 |
| 346 | 0.022 |
| 347 | 0.018 |
| 348 | 0.100 |
| 349 | 0.055 |
| 350 | 0.033 |
| 354 | 0.056 |
| 357 | 0.062 |
| 358 | 0.007 |
| 363 | 0.016 |
| 364 | 0.098 |
| 365 | 0.013 |
| 366 | 0.016 |
| 367 | 0.005 |
| 368 | 0.010 |
| 369 | 0.014 |
| 370 | 0.014 |
| 371 | 0.007 |
| 372 | 0.002 |
| 373 | 0.020 |
| 374 | 0.091 |
| 375 | 0.021 |
| 376 | 0.044 |
| 377 | 0.039 |
| 378 | 0.014 |
| 379 | 0.017 |
| 380 | 0.013 |
| 381 | 0.014 |
| 382 | 0.005 |
| 383 | 0.003 |
| 384 | 0.041 |
| 385 | 0.049 |
| 386 | 0.078 |
| 388 | 0.006 |
| 389 | 0.002 |
| 390 | 0.022 |
| 391 | 0.005 |
| 392 | 0.009 |
| 393 | 0.003 |
| 394 | 0.034 |
| 396 | 0.007 |
| 397 | 0.029 |
| 398 | 0.001 |
| 399 | 0.001 |
| 400 | 0.001 |
| 401 | 0.012 |
| 402 | 0.018 |
| 403 | 0.010 |
| 404 | 0.015 |
| 405 | 0.014 |
| 406 | 0.014 |
| 407 | 0.007 |
| 408 | 0.013 |
| 409 | 0.009 |
| 410 | 0.012 |
| 411 | 0.019 |
| 413 | 0.001 |
| 414 | 0.016 |
| 415 | 0.046 |
| 416 | 0.052 |
| 417 | 0.060 |
| 418 | 0.049 |
| 420 | 0.002 |
| 422 | 0.003 |
| 423 | 0.027 |
| 424 | 0.025 |
| 425 | 0.028 |
| 426 | 0.017 |
| 427 | 0.017 |
| 428 | 0.004 |
| 430 | 0.022 |
| 432 | 0.050 |
| 433 | 0.061 |
| 434 | 0.021 |
| 435 | 0.008 |
| 436 | 0.018 |
| 437 | 0.031 |
| 438 | 0.037 |
| 439 | 0.038 |
| 440 | 0.009 |
| 442 | 0.016 |
| 443 | 0.013 |
| 444 | 0.010 |
| 445 | 0.013 |
| 446 | 0.012 |
| 447 | 0.021 |
| 448 | 0.005 |
| 449 | 0.027 |

TABLE 51-continued

| Example | BRD4 IC$_{50}$ (μM) |
|---|---|
| 450 | 0.019 |
| 451 | 0.013 |
| 453 | 0.024 |
| 454 | 0.011 |
| 455 | 0.031 |
| 456 | 0.075 |
| 457 | 0.025 |
| 458 | 0.008 |
| 459 | 0.030 |
| 460 | 0.012 |
| 461 | 0.015 |
| 462 | 0.016 |
| 463 | 0.016 |
| 464 | 0.061 |
| 465 | 0.072 |
| 467 | 0.023 |
| 468 | 0.022 |
| 469 | 0.055 |
| 470 | 0.063 |
| 474 | 0.044 |
| 476 | 0.034 |
| 477 | 0.020 |
| 478 | 0.044 |
| 479 | 0.005 |
| 480 | 0.009 |
| 481 | 0.051 |
| 482 | 0.020 |
| 485 | 0.059 |
| 488 | 0.035 |
| 489 | 0.030 |
| 490 | 0.009 |
| 492 | 0.013 |
| 493 | 0.005 |
| 494 | 0.014 |
| 495 | 0.012 |
| 496 | 0.010 |
| 497 | 0.038 |
| 498 | 0.098 |
| 499 | 0.010 |
| 500 | 0.040 |
| 501 | 0.009 |
| 502 | 0.030 |
| 503 | 0.063 |
| 504 | 0.034 |
| 505 | 0.026 |
| 506 | 0.015 |
| 507 | 0.011 |
| 508 | 0.029 |
| 510 | 0.057 |
| 511 | 0.034 |
| 512 | 0.065 |
| 513 | 0.019 |
| 514 | 0.060 |
| 515 | 0.024 |
| 516 | 0.040 |
| 517 | 0.038 |
| 519 | 0.049 |
| 520 | 0.024 |
| 523 | 0.054 |
| 524 | 0.069 |
| 525 | 0.011 |
| 528 | 0.015 |
| 529 | 0.031 |
| 530 | 0.034 |
| 532 | 0.075 |
| 533 | 0.067 |
| 537 | 0.093 |
| 538 | 0.069 |
| 541 | 0.037 |
| 542 | 0.061 |
| 545 | 0.065 |
| 546 | 0.031 |
| 547 | 0.049 |
| 548 | 0.045 |
| 549 | 0.056 |
| 550 | 0.021 |
| 551 | 0.012 |
| 552 | 0.021 |
| 553 | 0.024 |
| 555 | 0.065 |
| 556 | 0.031 |
| 557 | 0.013 |
| 558 | 0.057 |
| 559 | 0.007 |
| 560 | 0.037 |
| 562 | 0.032 |
| 563 | 0.037 |
| 564 | 0.009 |
| 567 | 0.013 |
| 568 | 0.028 |
| 569 | 0.011 |
| 574 | 0.040 |
| 575 | 0.051 |
| 576 | 0.052 |
| 578 | 0.030 |
| 579 | 0.005 |
| 581 | 0.024 |
| 582 | 0.010 |
| 583 | 0.005 |
| 585 | 0.005 |
| 586 | 0.024 |
| 587 | 0.007 |
| 589 | 0.046 |
| 590 | 0.029 |
| 591 | 0.028 |
| 593 | 0.092 |
| 594 | 0.076 |
| 596 | 0.019 |
| 597 | 0.018 |
| 598 | 0.018 |
| 601 | 0.056 |
| 602 | 0.058 |
| 603 | 0.034 |
| 620 | 0.016 |
| 622 | 0.020 |
| 623 | 0.005 |
| 624 | 0.016 |
| 627 | 0.023 |
| 628 | 0.048 |
| 629 | 0.016 |
| 631 | 0.047 |
| 632 | 0.044 |
| 633 | 0.024 |
| 634 | 0.091 |
| 641 | 0.058 |
| 642 | 0.056 |
| 646 | 0.056 |
| 647 | 0.029 |
| 648 | 0.027 |
| 649 | 0.023 |
| 650 | 0.018 |
| 651 | 0.023 |
| 652 | 0.027 |
| 653 | 0.016 |
| 654 | 0.011 |
| 655 | 0.011 |
| 656 | 0.012 |
| 657 | 0.016 |
| 658 | 0.026 |
| 659 | 0.075 |
| 660 | 0.036 |
| 661 | 0.078 |
| 662 | 0.039 |

Experimental Example 2: Measurement of Cytotoxicity to Thymus Cancer Cells (Ty-82 Cells)

2-1. Experiment Methods

The following experiment was performed to evaluate the cytotoxicity of [1,2,4]triazolo[4,3-a]quinoxaline derivative according to the present invention to thymus cancer cells (Ty-82 cells).

First, thymus cancer cells (Ty-82 cells) were distributed in a 96 well plate at the density of $2.5 \times 10^4$ cells/well. 24 hours later, the plated cells were treated with the compounds of the present invention dissolved in DMSO at the different concentrations ranging from 0.01 μM to 10 μM. 72 hours later, the activities of the compounds were determined using WST-1 reagent.

2-2. Experiment Results

The results are shown in Table 52 below.

As shown in Table 52, the compounds of examples of the present invention demonstrated cytotoxicity against thymus cancer cells at low concentrations. In particular, the compounds of Examples 7, 59, 60, 62, 65, 66, 67, 74, 84, 90, 108, 181, 186, 191, 246, 247, 249, 250, 278, 279, 285, 466, 467, 468 and 469 displayed $IC_{50}$ values of 0.5 μM or less, indicating that they had excellent cytotoxicity at low concentrations.

TABLE 52

| Example | Ty-82 Cytotoxicity $IC_{50}$ (μM) |
| --- | --- |
| IBET762 | 0.5-0.2 |
| OTX015 | 0.08-0.04 |
| 3 | 0.92 |
| 4 | 0.65 |
| 7 | 0.26 |
| 8 | 0.86 |
| 11 | 0.95 |
| 12 | 0.85 |
| 57 | 0.74 |
| 59 | 0.42 |
| 60 | 0.12 |
| 62 | 0.29 |
| 65 | 0.37 |
| 66 | 0.058 |
| 67 | 0.17 |
| 74 | 0.17 |
| 75 | 0.79 |
| 77 | 0.92 |
| 84 | 0.027 |
| 88 | 0.97 |
| 90 | 0.40 |
| 93 | 0.56 |
| 99 | 0.55 |
| 101 | 0.88 |
| 102 | 0.84 |
| 108 | 0.37 |
| 120 | 0.62 |
| 127 | 0.62 |
| 129 | 0.83 |
| 133 | 0.88 |
| 135 | 0.73 |
| 161 | 0.81 |
| 165 | 0.58 |
| 166 | 0.58 |
| 167 | 0.88 |
| 168 | 0.60 |
| 171 | 0.58 |
| 181 | 0.30 |
| 186 | 0.34 |
| 190 | 0.65 |
| 191 | 0.31 |
| 192 | 0.68 |
| 197 | 0.65 |
| 202 | 0.64 |
| 246 | 0.49 |
| 247 | 0.40 |
| 248 | 0.51 |
| 249 | 0.40 |
| 250 | 0.30 |
| 251 | 0.68 |
| 205 | 0.55 |
| 210 | 0.76 |
| 212 | 0.84 |
| 277 | 0.93 |
| 278 | 0.18 |
| 279 | 0.12 |
| 285 | 0.091 |
| 464 | 0.79 |
| 466 | 0.34 |
| 467 | 0.20 |
| 468 | 0.23 |
| 469 | 0.094 |
| 633 | 0.90 |
| 660 | 0.84 |

Experimental Example 3: Measurement of Cytotoxicity of [1,2,4]triazolo[4,3-a]quinoxaline Derivative to Acute Myelogenous Leukemia Cells (MV-4-11 Cells)

3-1. Experiment Methods

The following experiment was performed to evaluate the cytotoxicity of [1,2,4]triazolo[4,3-a]quinoxaline derivative according to the present invention to acute myelogenous leukemia cells (MV-4-11 cells).

Acute myelogenous leukemia cells (MV-4-11 cells) were distributed in a 96 well plate at the density of $5 \times 10^3$ cells/well. The plated cells were treated with the compounds of the present invention dissolved in DMSO at the different concentrations ranging from 0.01 μM to 10 μM. 72 hours later, the activities of the compounds were determined using CCK-8 reagent.

3-2. Experiment Results

The results are shown in Table 53 below.

As shown in Table 53, the compounds of examples of the present invention demonstrated cytotoxicity against acute myelogenous leukemia cells (MV-4-11 cells) at low concentrations. In particular, the compounds of Examples 37, 60, 62, 63, 64, 65, 66, 67, 71, 73, 74, 77, 78, 79, 81, 84, 85, 86, 128, 160, 161, 166, 168, 176, 177, 180, 181, 185, 187, 188, 189, 190, 191, 199, 219, 222, 223, 224, 227, 228, 229, 233, 234, 236, 240, 254, 255, 256, 278, 279, 280, 281, 284, 285, 286, 287, 288, 289, 290, 292, 302, 307, 308, 309, 310, 318, 319, 322, 323, 327, 328, 329, 330, 332, 333, 335, 336, 340, 341, 342, 343, 344, 345, 346, 347, 349, 350, 352, 356, 357, 365, 366, 368, 369, 371, 372, 381, 383, 388, 389, 391, 393, 406, 411, 420, 426, 432, 436, 437, 438, 439, 442, 443, 444, 445, 446, 451, 454, 463, 466, 467, 468, 469, 480, 490, 492, 493, 494, 495, 496, 499, 500, 501, 507, 515, 520, 529, 550, 551, 552, 553, 555, 556, 558, 559, 560, 561, 567, 574, 576, 577, 584, 648, 649, 651, 652, 655, 656 and 657 displayed IC$_{50}$ values of 0.2 μM or less, indicating that they had excellent cytotoxicity at low concentrations.

TABLE 53

| Example | MV-4-11 Cytotoxicity IC$_{50}$ (μM) |
|---|---|
| IBET762 | 0.4-0.2 |
| OTX015 | 0.06-0.01 |
| 1 | 0.980 |
| 10 | 0.160 |
| 11 | 0.710 |
| 37 | 0.121 |
| 39 | 0.190 |
| 57 | 0.760 |
| 59 | 0.310 |
| 60 | 0.010 |
| 61 | 0.380 |
| 62 | 0.120 |
| 63 | 0.070 |
| 64 | 0.120 |
| 65 | 0.130 |
| 66 | 0.110 |
| 67 | 0.140 |
| 68 | 0.450 |
| 70 | 0.370 |
| 71 | 0.110 |
| 72 | 0.470 |
| 73 | 0.010 |
| 74 | 0.110 |
| 75 | 0.340 |
| 76 | 0.870 |
| 77 | 0.150 |
| 78 | 0.140 |
| 79 | 0.070 |
| 81 | 0.100 |
| 83 | 0.211 |
| 84 | 0.010 |
| 85 | 0.050 |
| 86 | 0.060 |
| 88 | 0.510 |
| 90 | 0.300 |
| 93 | 0.340 |
| 95 | 0.590 |
| 96 | 0.630 |
| 97 | 0.510 |
| 98 | 0.830 |
| 99 | 0.230 |
| 102 | 0.360 |
| 105 | 0.650 |
| 106 | 0.310 |
| 108 | 0.510 |
| 117 | 0.370 |
| 124 | 0.700 |
| 128 | 0.170 |
| 135 | 0.360 |
| 137 | 0.370 |
| 138 | 0.860 |
| 140 | 0.680 |
| 150 | 0.460 |
| 151 | 0.380 |
| 153 | 0.460 |
| 158 | 0.610 |
| 159 | 0.530 |
| 160 | 0.070 |
| 161 | 0.080 |
| 162 | 0.640 |
| 164 | 0.570 |
| 165 | 0.220 |
| 166 | 0.070 |
| 167 | 0.510 |
| 168 | 0.090 |
| 169 | 0.860 |
| 170 | 0.530 |
| 172 | 0.280 |
| 173 | 0.360 |
| 175 | 0.260 |
| 176 | 0.110 |
| 177 | 0.110 |

TABLE 53-continued

| Example | MV-4-11 Cytotoxicity IC$_{50}$ (μM) |
|---|---|
| 178 | 0.440 |
| 179 | 0.640 |
| 180 | 0.190 |
| 181 | 0.050 |
| 183 | 0.250 |
| 185 | 0.020 |
| 186 | 0.680 |
| 187 | 0.110 |
| 188 | 0.170 |
| 189 | 0.110 |
| 190 | 0.090 |
| 191 | 0.090 |
| 192 | 0.420 |
| 196 | 0.550 |
| 199 | 0.049 |
| 215 | 0.276 |
| 216 | 0.240 |
| 217 | 0.256 |
| 218 | 0.320 |
| 219 | 0.079 |
| 220 | 0.350 |
| 222 | 0.053 |
| 223 | 0.014 |
| 224 | 0.003 |
| 226 | 0.290 |
| 227 | 0.039 |
| 228 | 0.140 |
| 229 | 0.150 |
| 230 | 0.580 |
| 233 | 0.071 |
| 234 | 0.047 |
| 235 | 0.390 |
| 236 | 0.087 |
| 237 | 0.500 |
| 238 | 0.650 |
| 239 | 0.660 |
| 240 | 0.158 |
| 244 | 0.260 |
| 245 | 0.361 |
| 252 | 0.254 |
| 253 | 0.235 |
| 254 | 0.101 |
| 255 | 0.093 |
| 256 | 0.084 |
| 257 | 0.327 |
| 258 | 0.345 |
| 259 | 0.339 |
| 265 | 0.680 |
| 266 | 0.540 |
| 267 | 0.570 |
| 268 | 0.500 |
| 271 | 0.880 |
| 272 | 0.810 |
| 273 | 0.510 |
| 274 | 0.280 |
| 275 | 0.330 |
| 277 | 0.550 |
| 278 | 0.160 |
| 279 | 0.140 |
| 280 | 0.040 |
| 281 | 0.158 |
| 282 | 0.534 |
| 283 | 0.176 |
| 284 | 0.173 |
| 285 | 0.010 |
| 286 | 0.026 |
| 287 | 0.125 |
| 288 | 0.034 |
| 289 | 0.026 |
| 290 | 0.150 |
| 291 | 0.290 |
| 292 | 0.158 |
| 293 | 0.673 |
| 294 | 0.203 |
| 298 | 0.270 |
| 299 | 0.375 |

TABLE 53-continued

| Example | MV-4-11 Cytotoxicity IC$_{50}$ (μM) |
|---|---|
| 300 | 0.310 |
| 302 | 0.066 |
| 307 | 0.010 |
| 308 | 0.020 |
| 309 | 0.110 |
| 310 | 0.126 |
| 311 | 0.208 |
| 312 | 0.510 |
| 313 | 0.570 |
| 315 | 0.550 |
| 316 | 0.730 |
| 318 | 0.032 |
| 319 | 0.114 |
| 320 | 0.670 |
| 321 | 0.553 |
| 322 | 0.157 |
| 323 | 0.107 |
| 327 | 0.140 |
| 328 | 0.190 |
| 329 | 0.019 |
| 330 | 0.140 |
| 332 | 0.010 |
| 333 | 0.110 |
| 335 | 0.040 |
| 336 | 0.080 |
| 340 | 0.054 |
| 341 | 0.052 |
| 342 | 0.028 |
| 343 | 0.120 |
| 344 | 0.121 |
| 345 | 0.130 |
| 346 | 0.079 |
| 347 | 0.058 |
| 349 | 0.160 |
| 350 | 0.071 |
| 351 | 0.290 |
| 352 | 0.110 |
| 353 | 0.392 |
| 354 | 0.472 |
| 356 | 0.143 |
| 357 | 0.044 |
| 358 | 0.160 |
| 365 | 0.060 |
| 366 | 0.110 |
| 367 | 0.350 |
| 368 | 0.140 |
| 369 | 0.130 |
| 370 | 0.240 |
| 371 | 0.119 |
| 372 | 0.180 |
| 373 | 0.420 |
| 375 | 0.400 |
| 378 | 0.290 |
| 379 | 0.420 |
| 380 | 0.610 |
| 381 | 0.200 |
| 382 | 0.840 |
| 383 | 0.073 |
| 388 | 0.055 |
| 389 | 0.079 |
| 391 | 0.200 |
| 393 | 0.170 |
| 396 | 0.760 |
| 398 | 0.790 |
| 399 | 0.570 |
| 400 | 0.200 |
| 403 | 0.610 |
| 406 | 0.019 |
| 407 | 0.180 |
| 408 | 0.620 |
| 409 | 0.380 |
| 410 | 0.790 |
| 411 | 0.150 |
| 413 | 0.190 |
| 414 | 0.630 |
| 415 | 0.750 |
| 420 | 0.180 |
| 422 | 0.450 |
| 426 | 0.190 |
| 430 | 0.600 |
| 432 | 0.100 |
| 433 | 0.340 |
| 435 | 0.11 |
| 436 | 0.160 |
| 437 | 0.070 |
| 438 | 0.033 |
| 439 | 0.100 |
| 440 | 0.580 |
| 442 | 0.110 |
| 443 | 0.120 |
| 444 | 0.120 |
| 445 | 0.100 |
| 446 | 0.010 |
| 449 | 0.300 |
| 450 | 0.270 |
| 451 | 0.024 |
| 452 | 0.320 |
| 453 | 0.500 |
| 454 | 0.080 |
| 458 | 0.530 |
| 461 | 0.250 |
| 462 | 0.600 |
| 463 | 0.100 |
| 465 | 0.690 |
| 466 | 0.083 |
| 467 | 0.066 |
| 468 | 0.073 |
| 469 | 0.010 |
| 470 | 0.220 |
| 476 | 0.480 |
| 479 | 0.240 |
| 480 | 0.080 |
| 483 | 0.460 |
| 484 | 0.460 |
| 490 | 0.190 |
| 492 | 0.080 |
| 493 | 0.0480 |
| 494 | 0.110 |
| 495 | 0.029 |
| 496 | 0.020 |
| 497 | 0.730 |
| 499 | 0.140 |
| 500 | 0.098 |
| 501 | 0.060 |
| 502 | 0.331 |
| 503 | 0.575 |
| 505 | 0.533 |
| 506 | 0.340 |
| 507 | 0.021 |
| 508 | 0.575 |
| 510 | 0.335 |
| 512 | 0.631 |
| 513 | 0.279 |
| 514 | 0.432 |
| 515 | 0.090 |
| 516 | 0.518 |
| 517 | 0.236 |
| 518 | 0.480 |
| 519 | 0.400 |
| 520 | 0.174 |
| 525 | 0.200 |
| 526 | 0.802 |
| 528 | 0.203 |
| 529 | 0.107 |
| 550 | 0.157 |
| 551 | 0.135 |
| 552 | 0.157 |
| 553 | 0.174 |
| 555 | 0.118 |
| 556 | 0.001 |
| 557 | 0.280 |
| 558 | 0.087 |

TABLE 53-continued

| Example | MV-4-11 Cytotoxicity IC$_{50}$ (μM) |
|---|---|
| 559 | 0.141 |
| 560 | 0.071 |
| 561 | 0.060 |
| 562 | 0.375 |
| 563 | 0.559 |
| 564 | 0.610 |
| 565 | 0.720 |
| 566 | 0.550 |
| 567 | 0.200 |
| 568 | 0.658 |
| 569 | 0.237 |
| 572 | 0.238 |
| 574 | 0.045 |
| 575 | 0.337 |
| 576 | 0.086 |
| 577 | 0.087 |
| 585 | 0.280 |
| 584 | 0.130 |
| 590 | 0.490 |
| 591 | 0.880 |
| 594 | 0.880 |
| 596 | 0.510 |
| 597 | 0.230 |
| 598 | 0.290 |
| 601 | 0.230 |
| 602 | 0.290 |
| 620 | 0.70 |
| 622 | 0.290 |
| 623 | 0.400 |
| 624 | 0.410 |
| 633 | 0.750 |
| 648 | 0.130 |
| 649 | 0.160 |
| 650 | 0.220 |
| 651 | 0.120 |
| 652 | 0.200 |
| 654 | 0.270 |
| 655 | 0.080 |
| 656 | 0.150 |
| 657 | 0.080 |

INDUSTRIAL APPLICABILITY

The novel [1,2,4]triazolo[4,3-a]quinoxaline derivative provided in an aspect of the present invention, inhibits the binding of BRD4, one of BET protein family, at a low concentration, and displays excellent cytotoxicity in tumor cells, so that it can be used as a pharmaceutical composition for the prevention or treatment of BET protein related diseases including cancer and autoimmune disease.

What is claimed is:

1. A compound represented by formula 1, an optical isomer thereof or a pharmaceutically acceptable salt thereof:

[Formula 1]

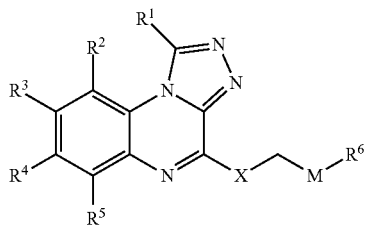

wherein, $R^1$ is $C_{1-20}$ straight or branched alkyl nonsubstituted or substituted with one or more halogens, or $C_{6-20}$ aryl;

$R^2$ is hydrogen, $C_{1-20}$ straight or branched alkyl, or $C_{1-20}$ straight or branched alkoxy;

$R^3$ is hydrogen, nitro, halogen, nonsubstituted or substituted $C_{1-20}$ straight or branched alkyl, nonsubstituted or substituted $C_{1-20}$ straight or branched alkoxy, 5-10 membered heteroaryl nonsubstituted or substituted with one or more methyl groups containing one or more heteroatoms selected from the group consisting of N, O and S,

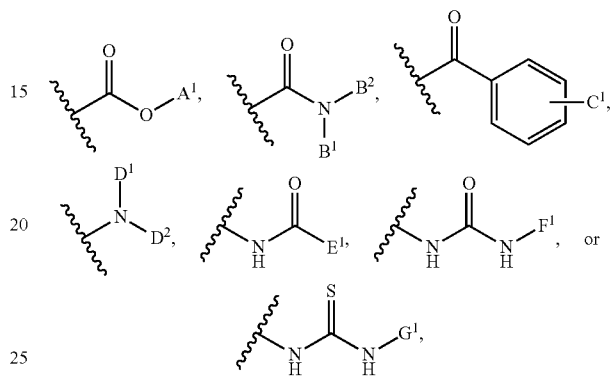

which forms 6 membered cycloalkyl containing one or more heteroatoms selected from the group consisting of S and O along with $R^4$, wherein, the substituted $C_{1-20}$ straight or branched alkyl and the substituted $C_{1-20}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, $A^1$ is hydrogen, or $C_{1-20}$ straight or branched alkyl, $B^1$ and $B^2$ are independently hydrogen, $C_{1-20}$ straight or branched alkyl, di$C_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-20}$ straight or branched alkyl, or $C_{1-20}$ straight or branched alkoxy, $D^1$ and $D^2$ are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl, $E^1$ is $C_{1-20}$ straight or branched alkyl, or $C_{6-10}$ aryl $C_{1-5}$ straight or branched alkyl, $F^1$ is $C_{1-20}$ straight or branched alkyl, or $C_{6-10}$ aryl, $G^1$ is $C_{1-20}$ straight or branched alkyl, or $C_{6-10}$ aryl;

$R^4$ is hydrogen, hydroxy, halogen, nitro, $C_{1-20}$ straight or branched alkyl nonsubstituted or substituted with one or more =S groups, $C_{1-20}$ straight or branched alkylsulfanyl nonsubstituted or substituted with one or more oxo (=O) groups, $C_{1-20}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-20}$ straight or branched alkoxy,

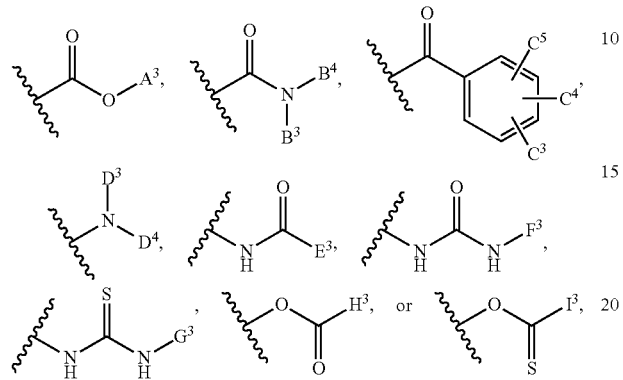

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-20}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

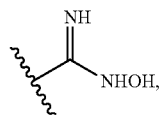

$C_{1-5}$ straight or branched alkoxycarbonyl, and 5-8 membered heteroaryl nonsubstituted or substituted with one or more N groups, $A^3$ is hydrogen, or $C_{1-20}$ straight or branched alkyl, $B^3$ and $B^4$ are independently hydrogen, $C_{1-20}$ straight or branched alkyl, $diC_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-20}$ straight or branched alkyl, or $C_{1-20}$ straight or branched alkoxy, $D^3$ and $D^4$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-20}$ straight or branched alkyl, or $C_{6-10}$ aryl $C_{1-5}$ straight or branched alkyl, $F^3$ is $C_{1-20}$ straight or branched alkyl, or $C_{6-10}$ aryl, $G^3$ is $C_{1-20}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is $diC_{1-3}$ straight or branched alkylamino;

$R^5$ is hydrogen, halogen, $C_{1-20}$ straight or branched alkyl nonsubstituted or substituted with one or more halogens, or $C_{1-20}$ straight or branched alkoxy;

$R^6$ is

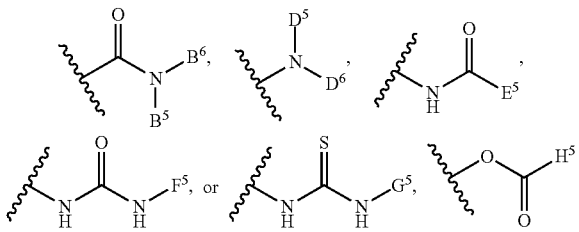

$B^5$ and $B^6$ are independently hydrogen, $C_{1-20}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, $E^5$ is $C_{1-20}$ straight or branched alkyl saturated or containing one or more carbon=carbon unsaturated bonds, $C_{1-20}$ straight or branched alkoxy saturated or containing one or more carbon=carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-20}$ straight or branched alkylsulfanyl, nonsubstituted or substituted $C_{6-10}$ aryl, $diC_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-20}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

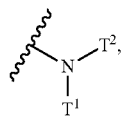

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-20}$ straight or branched alkyl, $C_{3-10}$ cycloalkyl, or $C_{6-10}$ aryl nonsubstituted or substituted with one or more halogens, $G^5$ is $C_{1-20}$ straight or branched alkyl;

M is $C_{1-20}$ straight or branched alkylene; and

X is —NH—.

2. The compound represented by formula 1, the optical isomer thereof or the pharmaceutically acceptable salt thereof according to claim 1, wherein:

$R^1$ is $C_{1-10}$ straight or branched alkyl nonsubstituted or substituted with one or more halogens, or $C_{6-10}$ aryl;

$R^2$ is hydrogen, $C_{1-10}$ straight or branched alkyl, or $C_{1-10}$ straight or branched alkoxy;

$R^3$ is hydrogen, nitro, halogen, nonsubstituted or substituted $C_{1-10}$ straight or branched alkyl, nonsubstituted or substituted $C_{1-10}$ straight or branched alkoxy, 5-10 membered heteroaryl nonsubstituted or substituted with one or more methyl groups containing one or more heteroatoms selected from the group consisting of N, O and S,

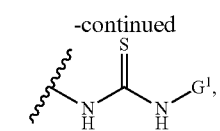

which forms 6 membered cycloalkyl containing one or more heteroatoms selected from the group consisting of S and O along with $R^4$, wherein, the substituted $C_{1-10}$ straight or branched alkyl and the substituted $C_{1-10}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, $A^1$ is hydrogen, or $C_{1-10}$ straight or branched alkyl, $B^1$ and $B^2$ are independently hydrogen, $C_{1-10}$ straight or branched alkyl, $diC_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-10}$ straight or branched alkyl, or $C_{1-10}$ straight or branched alkoxy, $D^1$ and $D^2$ are independently hydrogen, hydroxy, $C_{1-10}$ straight or branched alkyl saturated or containing one or more carbon=carbon unsaturated bonds, $C^{1-10}$ straight or branched alkyl nonsubstituted or substituted with one or more cyano groups, or $C_{1-10}$ straight or branched alkylsulfonyl, $E^1$ is $C_{1-10}$ straight or branched alkyl, or $C_{6-10}$ aryl $C_{1-5}$ straight or branched alkyl, $F^1$ is $C_{1-10}$ straight or branched alkyl, or $C_{6-10}$ aryl, $G^1$ is $C_{1-10}$ straight or branched alkyl, or $C_{6-10}$ aryl;

$R^4$ is hydrogen, hydroxy, halogen, nitro, $C_{1-10}$ straight or branched alkyl nonsubstituted or substituted with one or more =S groups, $C_{1-10}$ straight or branched alkylsulfanyl nonsubstituted or substituted with one or more oxo (=O) groups, $C_{1-10}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-10}$ straight or branched alkoxy,

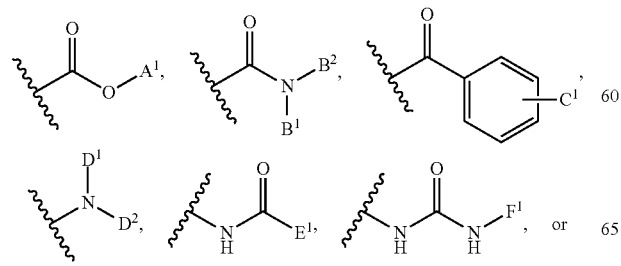

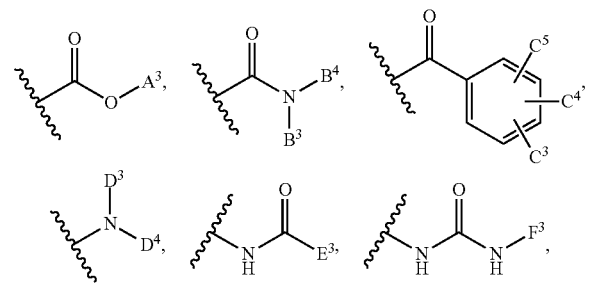

-continued

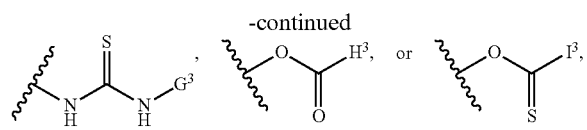

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-10}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

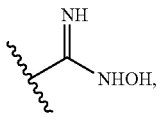

$C_{1-5}$ straight or branched alkoxycarbonyl, and 5-8 membered heteroaryl nonsubstituted or substituted with one or more N groups, $A^3$ is hydrogen, or $C_{1-10}$ straight or branched alkyl, $B^3$ and $B^4$ are independently hydrogen, $C_{1-10}$ straight or branched alkyl, $diC_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-10}$ straight or branched alkyl, or $C_{1-10}$ straight or branched alkoxy, $D^3$ and $D^4$ are independently hydrogen, hydroxy, $C_{1-10}$ straight or branched alkyl saturated or containing one or more carbon≡carbon unsaturated bonds, $C_{1-10}$ straight or branched alkyl nonsubstituted or substituted with one or more cyano groups, or $C_{1-10}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-10}$ straight or branched alkyl, or $C_{6-10}$ aryl $C_{1-5}$ straight or branched alkyl, $F^3$ is $C_{1-10}$ straight or branched alkyl, or $C_{6-10}$ aryl, $G^3$ is $C_{1-10}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is $diC_{1-3}$ straight or branched alkylamino;

$R^5$ is hydrogen, halogen, $C_{1-10}$ straight or branched alkyl nonsubstituted or substituted with one or more halogens, or $C_{1-10}$ straight or branched alkoxy;

$R^6$ is

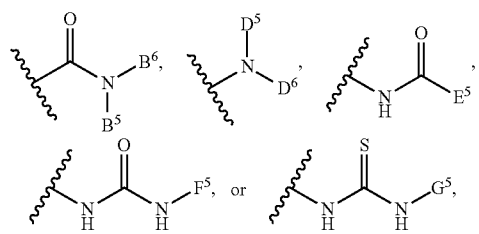

$B^5$ and $B^6$ are independently hydrogen, $C_{1-10}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-10}$ straight or branched alkyl saturated or containing one or more carbon≡carbon unsaturated bonds, $C_{1-10}$ straight or branched alkyl nonsubstituted or substituted with one or more cyano groups, or $C_{1-10}$ straight or branched alkylsulfonyl nonsubstituted or substituted with one or more halogens, $E^5$ is $C_{1-10}$ straight or branched alkyl saturated or containing one or more carbon≡carbon unsaturated bonds, $C_{1-10}$ straight or branched alkoxy saturated or containing one or more carbon≡carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-10}$ straight or branched alkylsulfanyl, nonsubstituted or substituted $C_{6-10}$ aryl, $diC_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-10}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

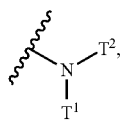

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-10}$ straight or branched alkyl, $C_{3-10}$ cycloalkyl, or $C_{6-10}$ aryl nonsubstituted or substituted with one or more halogens, $G^5$ is $C_{1-10}$ straight or branched alkyl, M is $C_{1-10}$ straight or branched alkylene; and X is —NH—.

3. The compound represented by formula 1, the optical isomer thereof or the pharmaceutically acceptable salt thereof according to claim 1, wherein:

$R^1$ is —CH$_3$, —CH$_2$CH$_3$, —CF$_3$,

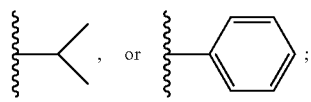, or ;

$R^2$ is —H, —CH$_3$, or —OCH$_3$;

$R^3$ is —H, —Cl, —F, —CH$_3$, —CF$_3$, —OCH$_3$, —OCF$_3$, —NO$_2$, —NH$_2$,

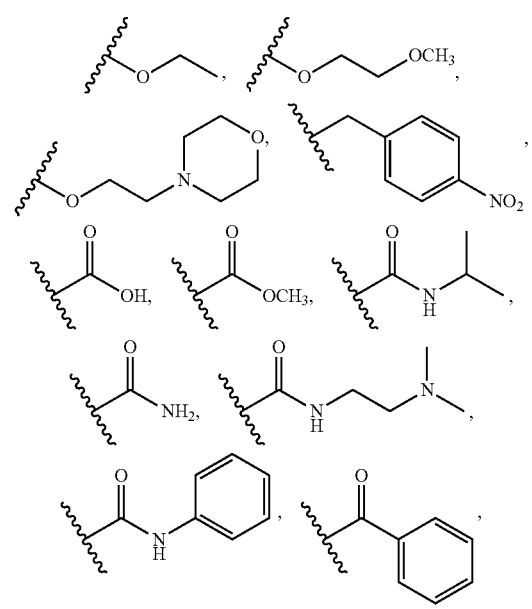

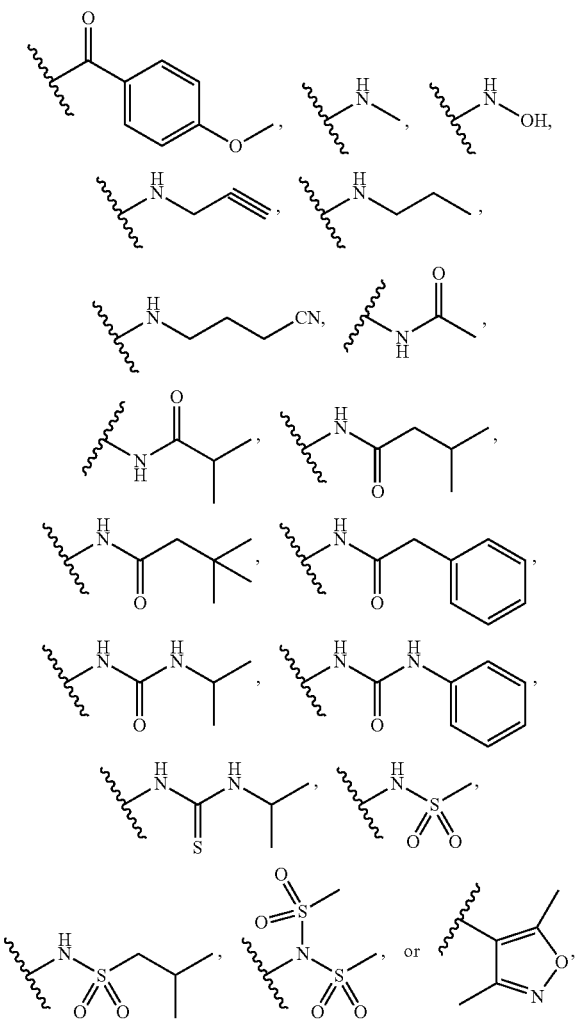

which forms

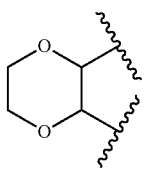

along with $R^4$;

$R^4$ is —H, —OH, —Cl, —F, —CH$_3$, —OCH$_3$, —SCH$_3$, —OCF$_3$, —NO$_2$, —NH$_2$,

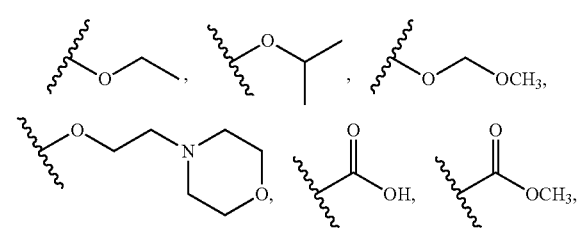

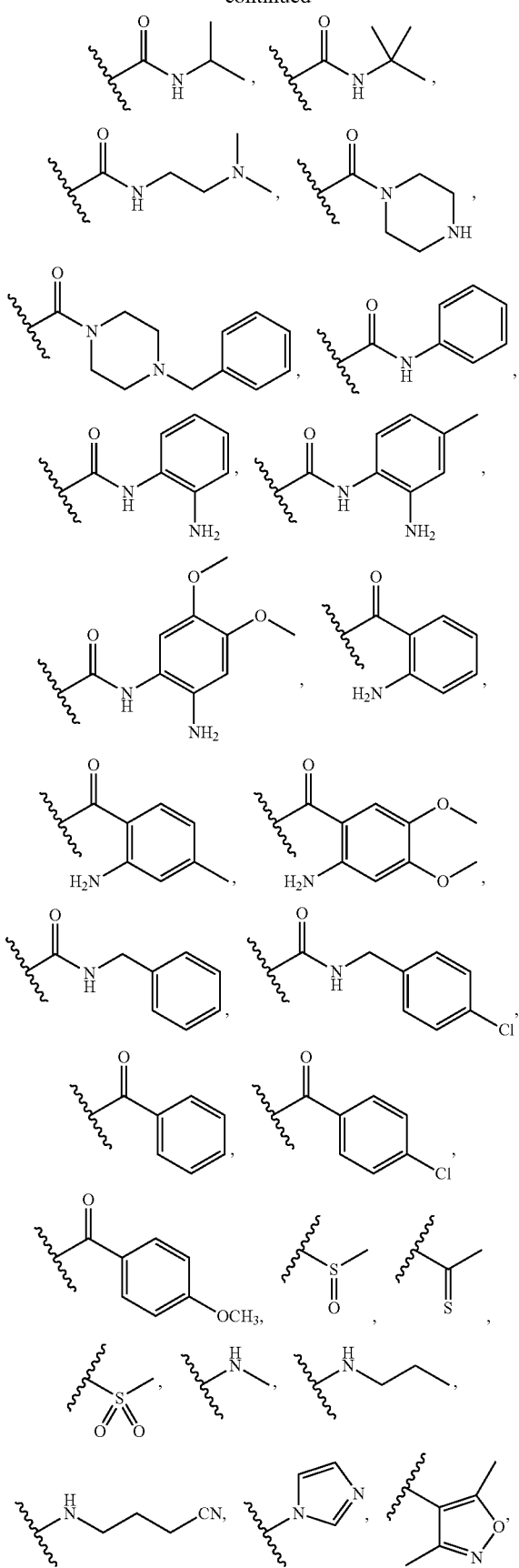
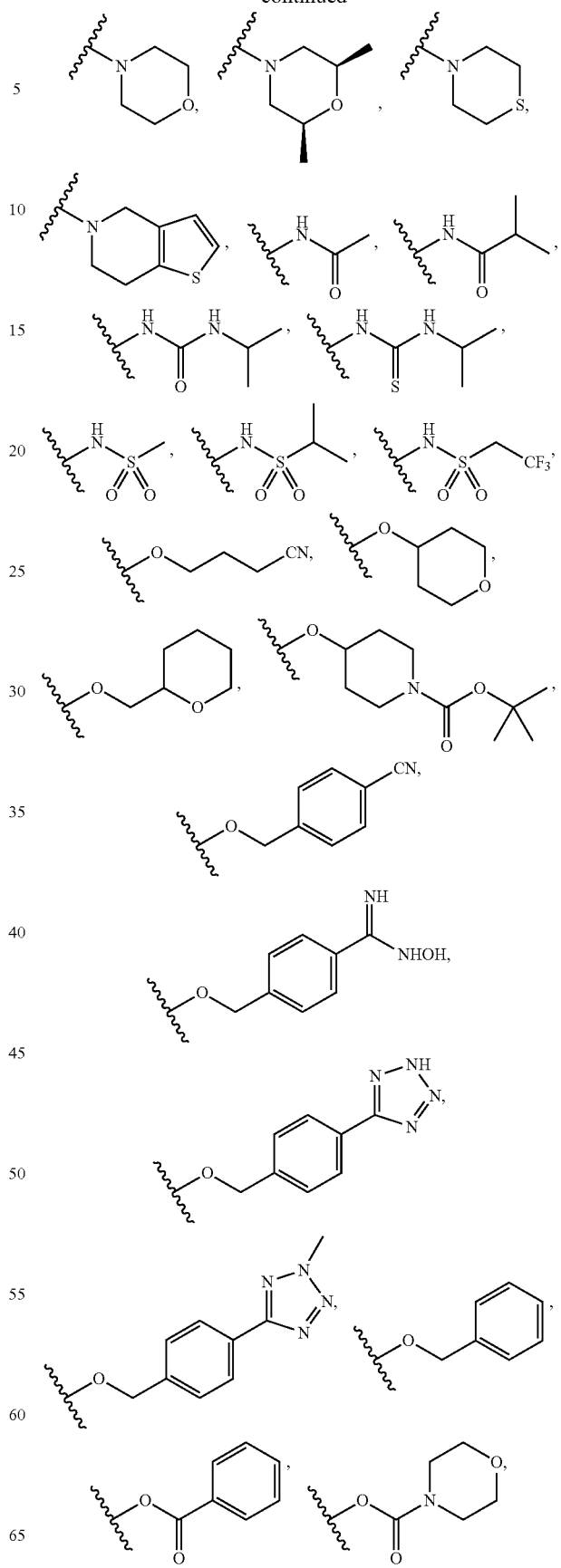

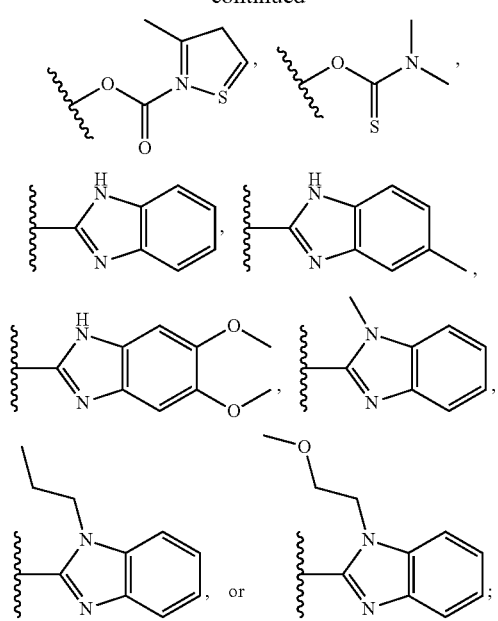
R[5] is —H, —Cl, —CH$_3$, —CF$_3$, or —OCH$_3$;
R[6] is —NH$_2$,
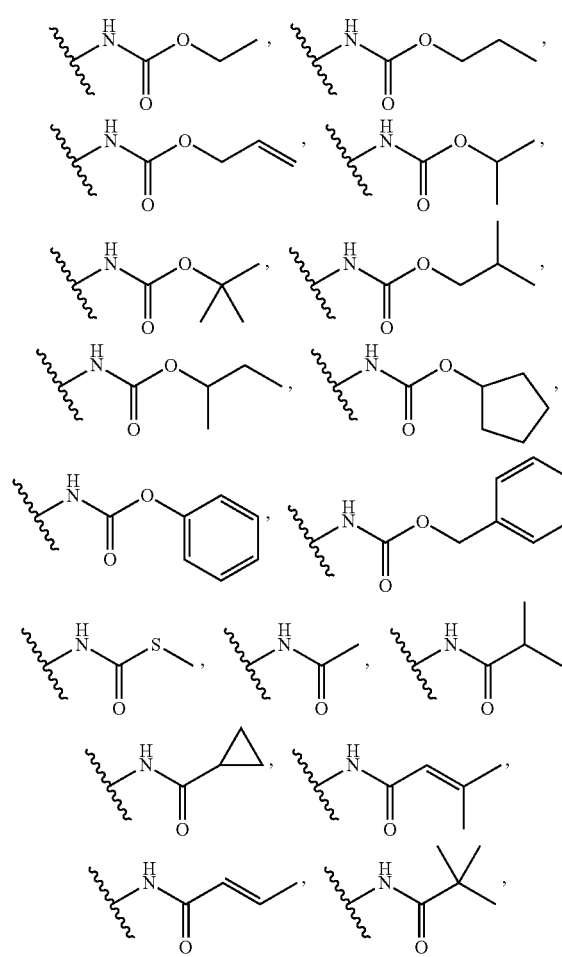
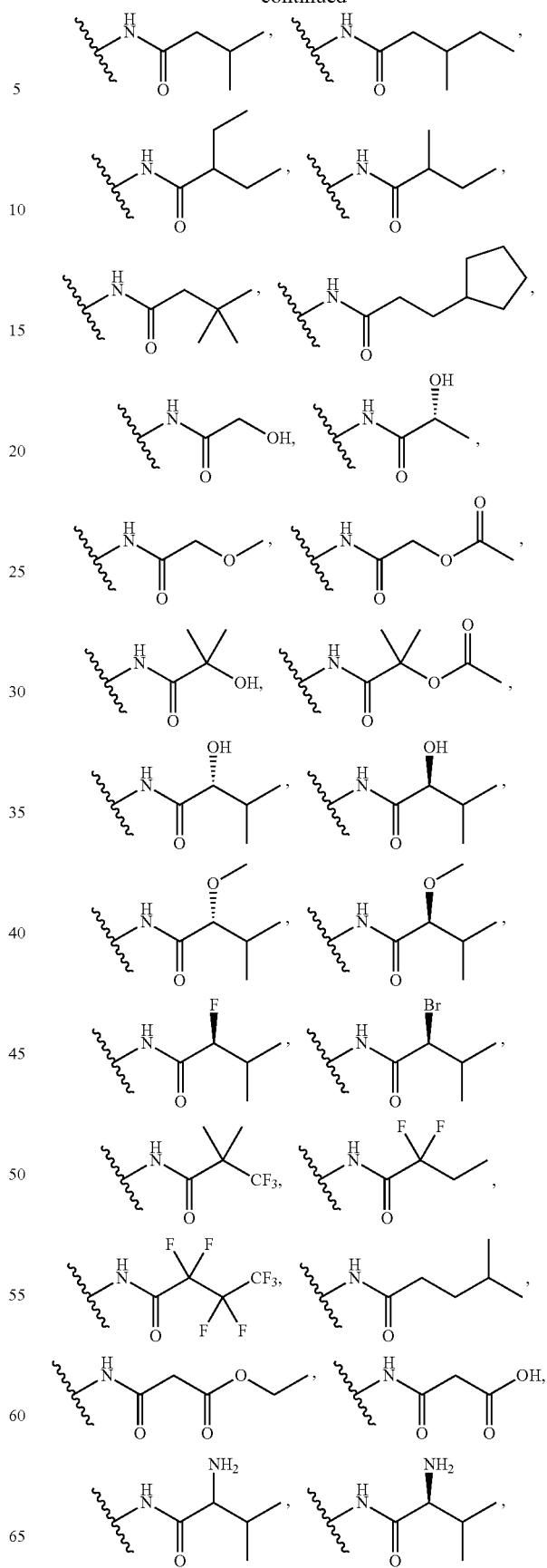

-continued
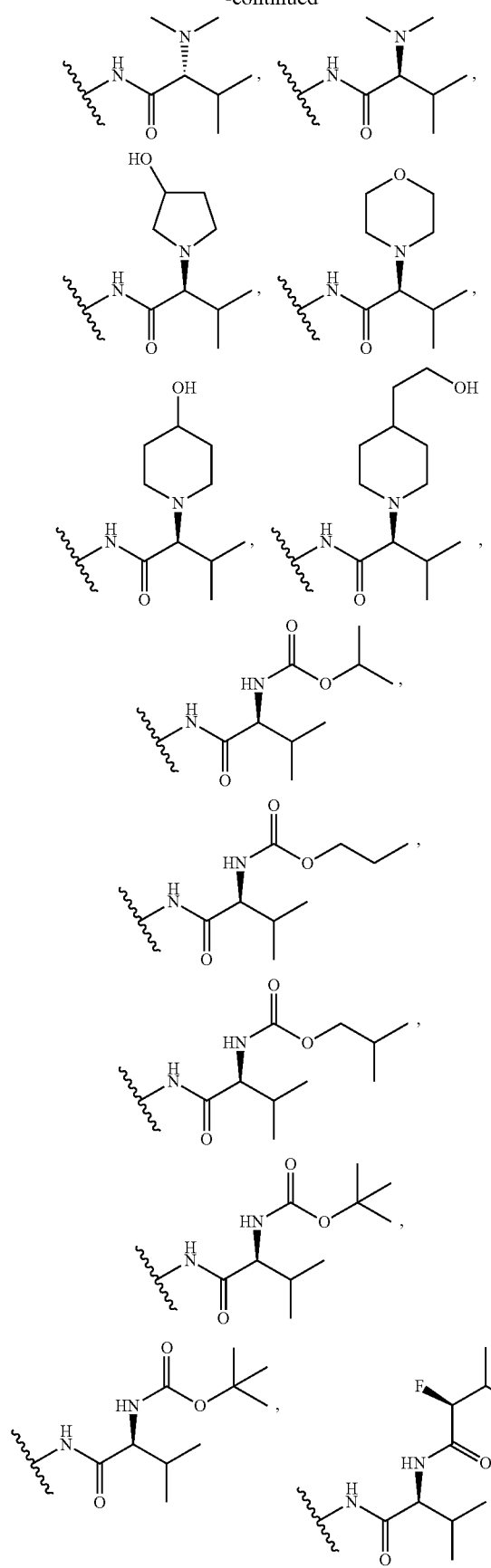
-continued
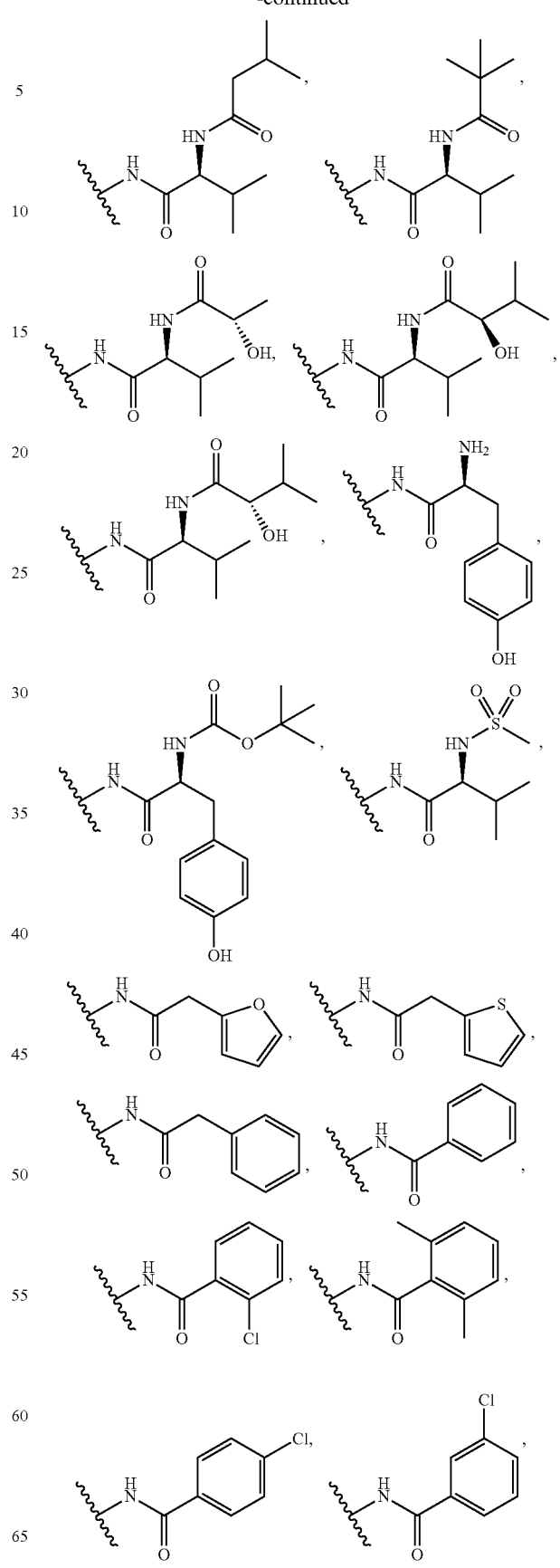

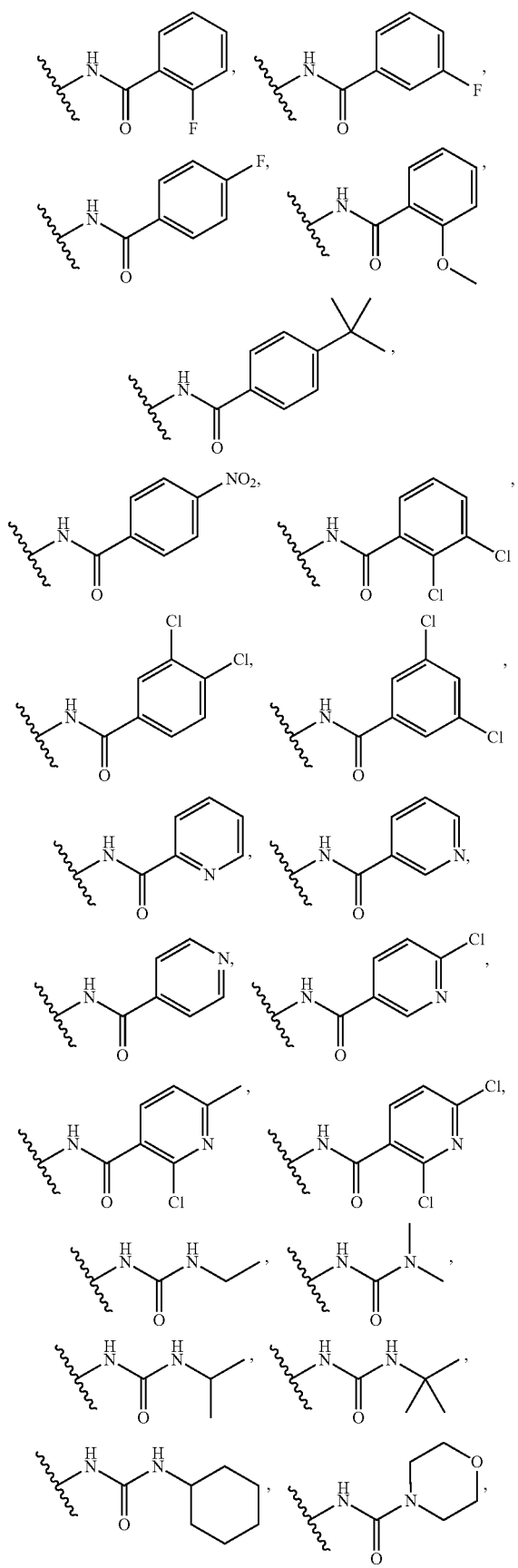
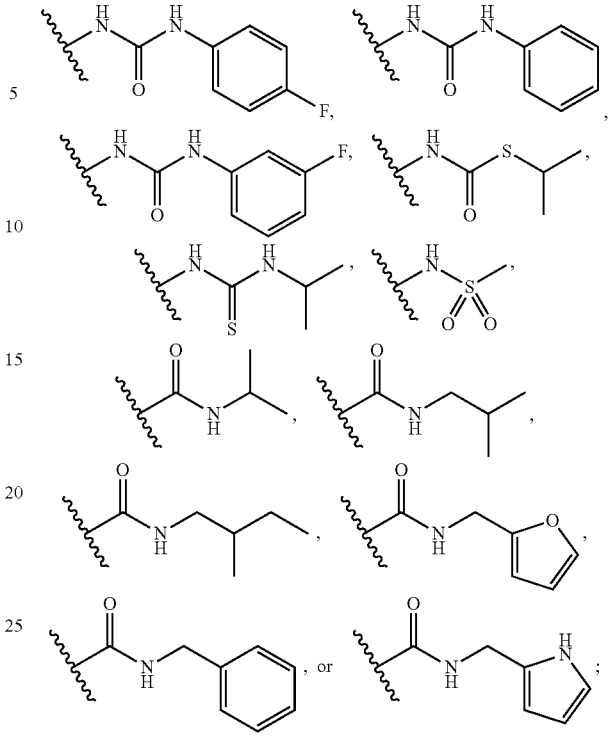

M is C$_{3-4}$ straight or branched alkylene; and
X is —NH—.

4. The compound represented by formula 1, the optical isomer thereof or the pharmaceutically acceptable salt thereof according to claim 1, wherein the compound represented by formula 1 is selected from the group consisting of the following compounds:

(1) [4-(1-methyl-[1,2,4]triazolo[4,3-a]quinoxaline-4-ylamino)-butyl]-carbamic acid-tert-butylester;
(2) N$^1$-(1-methyl-[1,2,4]triazolo[4,3-a]quinoxaline-4-yl)-butane-1,4-diamine dihydrochloride;
(3) 2,2-dimethyl-N-[4-(1-methyl-[1,2,4]triazolo[4,3-a]quinoxaline-4-ylamino)-butyl]-propionamide;
(4) [4-(1-methyl-[1,2,4]triazolo[4,3-a]quinoxaline-4-ylamino)-butyl]-carbamic acid isopropylester;
(5) [4-(1-methyl-[1,2,4]triazolo[4,3-a]quinoxaline-4-ylamino)-butyl]-acetamide;
(6) [4-(1-methyl-[1,2,4]triazolo[4,3-a]quinoxaline-4-ylamino)-butyl]-isobutyramide;
(7) 3-methyl-N-[4-(1-methyl-[1,2,4]triazolo[4,3-a]quinoxaline-4-ylamino)-butyl]-butyramide;
(8) 3,3-dimethyl-N-[4-(1-methyl-[1,2,4]triazolo[4,3-a]quinoxaline-4-ylamino)-butyl]-butyramide;
(9) 2-(R)-hydroxy-N-[4-(1-methyl-[1,2,4]triazolo[4,3-a]quinoxaline-4-ylamino)-butyl]-3-methyl-butyramide;
(10) 2-(S)-hydroxy-N-[4-(1-methyl-[1,2,4]triazolo[4,3-a]quinoxaline-4-ylamino)-butyl]-3-methyl-butyramide;
(11) N-[4-(1-methyl-[1,2,4]triazolo[4,3-a]quinoxaline-4-ylamino)-butyl]-benzamide;
(12) 2-chloro-N-[4-(1-methyl-[1,2,4]triazolo[4,3-a]quinoxaline-4-ylamino)-butyl]-benzamide;
(13) 2,6-dimethyl-N-[4-(1-methyl-[1,2,4]triazolo[4,3-a]quinoxaline-4-ylamino)-butyl]-benzamide;
(14) 4-chloro-N-[4-(1-methyl-[1,2,4]triazolo[4,3-a]quinoxaline-4-ylamino)-butyl]-benzamide;

(15) 3-chloro-N-[4-(1-methyl-[1,2,4]triazolo[4,3-a]quinoxaline-4-ylamino)-butyl]-benzamide;
(16) 3,4-dichloro-N-[4-(1-methyl-[1,2,4]triazolo[4,3-a]quinoxaline-4-ylamino)-butyl]-benzamide;
(17) 2,3-dichloro-N-[4-(1-methyl-[1,2,4]triazolo[4,3-a]quinoxaline-4-ylamino)-butyl]-benzamide;
(18) 3,5-dichloro-N-[4-(1-methyl-[1,2,4]triazolo[4,3-a]quinoxaline-4-ylamino)-butyl]-benzamide;
(19) 2,6-dichloro-N-[4-(1-methyl-[1,2,4]triazolo[4,3-a]quinoxaline-4-ylamino)-butyl]-nicotinamide;
(20) 6-chloro-N-[4-(1-methyl-[1,2,4]triazolo[4,3-a]quinoxaline-4-ylamino)-butyl]-nicotinamide;
(21) 2-chloro-6-methyl-N-[4-(1-methyl-[1,2,4]triazolo[4,3-a]quinoxaline-4-ylamino)-butyl]-nicotinamide;
(22) 1-tert-butyl-3-[4-(1-methyl-[1,2,4]triazolo[4,3-a]quinoxaline-4-ylamino)-butyl]-urea;
(23) 1-(4-fluoro-phenyl)-3-[4-(1-methyl-[1,2,4]triazolo[4,3-a]quinoxaline-4-ylamino)-butyl]-urea;
(24) 1-(3-fluoro-phenyl)-3-[4-(1-methyl-[1,2,4]triazolo[4,3-a]quinoxaline-4-ylamino)-butyl]-urea;
(25) [4-(1-methyl-[1,2,4]triazolo[4,3-a]quinoxaline-4-ylamino)-butyl]-carbamic acid benzylester;
(26) [4-(7,8-dichloro-1-methyl-[1,2,4]triazolo[4,3-a]quinoxaline-4-ylamino)-butyl]-carbamic acid-tert-butylester;
(27) $N^1$-(7,8-dichloro-1-methyl-[1,2,4]triazolo[4,3-a]quinoxaline-4-yl)butane-1,4-diamine ditrifluoroacetic acid;
(28) N-[4-(7,8-dichloro-1-methyl-[1,2,4]triazolo[4,3-a]quinoxaline-4-ylamino)-butyl]-2,2-dimethyl-propionamide;
(29) N-[4-(7,8-dichloro-1-methyl-[1,2,4]triazolo[4,3-a]quinoxaline-4-ylamino)-butyl]-isobutyramide;
(30) N-[4-(7,8-dichloro-1-methyl-[1,2,4]triazolo[4,3-a]quinoxaline-4-ylamino)-butyl]-3-methyl-butyramide;
(31) N-[4-(7,8-dichloro-1-methyl-[1,2,4]triazolo[4,3-a]quinoxaline-4-ylamino)-butyl]-benzamide;
(32) 2-chloro-N-[4-(7,8-dichloro-1-methyl-[1,2,4]triazolo[4,3-a]quinoxaline-4-ylamino)-butyl]-benzamide;
(33) 6-chloro-N-[4-(7,8-dichloro-1-methyl-[1,2,4]triazolo[4,3-a]quinoxaline-4-ylamino)-butyl]-nicotinamide;
(34) [4-(1,7,8-trimethyl-[1,2,4]triazolo[4,3-a]quinoxaline-4-ylamino)-butyl]-carbamic acid-tert-butylester;
(35) [4-(7,8-difluoro-1-methyl-[1,2,4]triazolo[4,3-a]quinoxaline-4-ylamino)-butyl]-carbamic acid-tert-butylester;
(36) $N^1$-(7,8-difluoro-1-methyl-[1,2,4]triazolo[4,3-a]quinoxaline-4-yl)-butane-1,4-diamine ditrifluoroacetic acid;
(37) N-[4-(7,8-difluoro-1-methyl-[1,2,4]triazolo[4,3-a]quinoxaline-4-ylamino)-butyl]-3-methyl-butyramide;
(38) N-[4-(7,8-difluoro-1-methyl-[1,2,4]triazolo[4,3-a]quinoxaline-4-ylamino)-butyl]-2-(R)-hydroxy-3-methyl-butyramide;
(39) N-[4-(7,8-difluoro-1-methyl-[1,2,4]triazolo[4,3-a]quinoxaline-4-ylamino)-butyl]-2-(S)-hydroxy-3-methyl-butyramide;
(40) [4-(1,8-dimethyl-[1,2,4]triazolo[4,3-a]quinoxaline-4-ylamino)-butyl]-carbamic acid-tert-butylester;
(41) [4-(1,8-dimethyl-[1,2,4]triazolo[4,3-a]quinoxaline-4-ylamino)-butane]-1,4-diamine dihydrochloride;
(42) N-[4-(1,8-dimethyl-[1,2,4]triazolo[4,3-a]quinoxaline-4-ylamino)-butyl]-2,2-dimethyl-propionamide;
(43) N-[4-(1,8-dimethyl-[1,2,4]triazolo[4,3-a]quinoxaline-4-ylamino)-butyl]-isobutyramide;
(44) 1-tert-butyl-3-[4-(1,8-dimethyl-[1,2,4]triazolo[4,3-a]quinoxaline-4-ylamino)-butyl]-urea;
(45) N-[4-(1,8-dimethyl-[1,2,4]triazolo[4,3-a]quinoxaline-4-ylamino)-butyl]-benzamide;
(46) 1-[4-(1,8-dimethyl-[1,2,4]triazolo[4,3-a]quinoxaline-4-ylamino)-butyl]-3-phenyl-urea;
(47) [4-(8-fluoro-1-methyl-[1,2,4]triazolo[4,3-a]quinoxaline-4-ylamino)-butyl]-carbamic acid-tert-butylester;
(48) [4-(8-fluoro-1-methyl-[1,2,4]triazolo[4,3-a]quinoxaline-4-ylamino)-butyl]-1,4-diamine dihydrochloride;
(49) N-[4-(8-fluoro-1-methyl-[1,2,4]triazolo[4,3-a]quinoxaline-4-ylamino)-butyl]-2,2-dimethyl-propionamide;
(50) [4-(8-fluoro-1-methyl-[1,2,4]triazolo[4,3-a]quinoxaline-4-ylamino)-butyl]-isobutyramide;
(51) N-[4-(8-fluoro-1-methyl-[1,2,4]triazolo[4,3-a]quinoxaline-4-ylamino)-butyl]-benzamide;
(52) 1-tert-butyl-3-[4-(8-fluoro-1-methyl-[1,2,4]triazolo[4,3-a]quinoxaline-4-ylamino)-butyl]-urea;
(53) 1-[4-(8-fluoro-1-methyl-[1,2,4]triazolo[4,3-a]quinoxaline-4-ylamino)-butyl]-3-phenyl-urea;
(54) [4-(8-chloro-1-methyl-[1,2,4]triazolo[4,3-a]quinoxaline-4-ylamino)-butyl]-carbamic acid-tert-butylester;
(55) $N^1$-(8-chloro-1-methyl-[1,2,4]triazolo[4,3-a]quinoxaline-4-yl)butane-1,4-diamine hydrochloride;
(56) N-[4-(8-chloro-1-methyl-[1,2,4]triazolo[4,3-a]quinoxaline-4-ylamino)-butyl]-benzamide;
(57) [4-(7,8-dimethoxy-1-methyl-[1,2,4]triazolo[4,3-a]quinoxaline-4-ylamino)-butyl]-carbamic acid-tert-butylester;
(58) $N^1$-(7,8-dimethoxy-1-methyl-[1,2,4]triazolo[4,3-a]quinoxaline-4-yl)-butane-1,4-diamine ditrifluoroacetic acid;
(59) N-[4-(7,8-dimethoxy-1-methyl-[1,2,4]triazolo[4,3-a]quinoxaline-4-ylamino)-butyl]-2,2-dimethyl-propionamide;
(60) [4-(7,8-dimethoxy-1-methyl-[1,2,4]triazolo[4,3-a]quinoxaline-4-ylamino)-butyl]-carbamic acid isopropylester;
(61) [4-(7,8-dimethoxy-1-methyl-[1,2,4]triazolo[4,3-a]quinoxaline-4-ylamino)-butyl]-carbamic acid ethylester;
(62) [4-(7,8-dimethoxy-1-methyl-[1,2,4]triazolo[4,3-a]quinoxaline-4-ylamino)-butyl]-carbamic acid isobutylester;
(63) [4-(7,8-dimethoxy-1-methyl-[1,2,4]triazolo[4,3-a]quinoxaline-4-ylamino)-butyl]-carbamic acid-sec-butylester;
(64) [4-(7,8-dimethoxy-1-methyl-[1,2,4]triazolo[4,3-a]quinoxaline-4-ylamino)-butyl]-carbamic acid propylester;
(65) [4-(7,8-dimethoxy-1-methyl-[1,2,4]triazolo[4,3-a]quinoxaline-4-ylamino)-butyl]-carbamic acid allylester;
(66) [4-(7,8-dimethoxy-1-methyl-[1,2,4]triazolo[4,3-a]quinoxaline-4-ylamino)-butyl]-carbamic acid cyclopentylester;
(67) [4-(7,8-dimethoxy-1-methyl-[1,2,4]triazolo[4,3-a]quinoxaline-4-ylamino)-butyl]-carbamic acid phenylester;
(68) [4-(7,8-dimethoxy-1-methyl-[1,2,4]triazolo[4,3-a]quinoxaline-4-ylamino)-butyl]-carbamic acid benzylester;
(69) N-[4-(7,8-dimethoxy-1-methyl-[1,2,4]triazolo[4,3-a]quinoxaline-4-ylamino)-butyl]-acetamide;
(70) N-[4-(7,8-dimethoxy-1-methyl-[1,2,4]triazolo[4,3-a]quinoxaline-4-ylamino)-butyl]-isobutyramide;

(71) 3-methyl-buten-2-oic acid-[4-(7,8-dimethoxy-1-methyl-[1,2,4]triazolo[4,3-a]quinoxaline-4-ylamino)-butyl]-amide;
(72) butene-2-oic acid-[4-(7,8-dimethoxy-1-methyl-[1,2,4]triazolo[4,3-a]quinoxaline-4-ylamino)-butyl]-amide;
(73) 3-methyl-pentanoic acid-[4-(7,8-dimethoxy-1-methyl-[1,2,4]triazolo[4,3-a]quinoxaline-4-ylamino)-butyl]-amide;
(74) N-[4-(7,8-dimethoxy-1-methyl-[1,2,4]triazolo[4,3-a]quinoxaline-4-ylamino)-butyl]-3-methyl-butyramide;
(75) N-[4-(7,8-dimethoxy-1-methyl-[1,2,4]triazolo[4,3-a]quinoxaline-4-ylamino)-butyl]-3,3-dimethyl-butyramide;
(76) cyclopropanecarboxylic acid-[4-(7,8-dimethoxy-1-methyl-[1,2,4]triazolo[4,3-a]quinoxaline-4-ylamino)-butyl]-amide;
(77) N-[4-(7,8-dimethoxy-1-methyl-[1,2,4]triazolo[4,3-a]quinoxaline-4-ylamino)-butyl]-2-methyl-butyramide;
(78) N-[4-(7,8-dimethoxy-1-methyl-[1,2,4]triazolo[4,3-a]quinoxaline-4-ylamino)-butyl]-2-ethyl-butyramide;
(79) 4-methyl-pentanoic acid-[4-(7,8-dimethoxy-1-methyl-[1,2,4]triazolo[4,3-a]quinoxaline-4-ylamino)-butyl]-amide;
(80) N-[4-(7,8-dimethoxy-1-methyl-[1,2,4]triazolo[4,3-a]quinoxaline-4-ylamino)-butyl]-2-methoxy-acetamide;
(81) 3-cyclopentyl-N-[4-(7,8-dimethoxy-1-methyl-[1,2,4]triazolo[4,3-a]quinoxaline-4-ylamino)-butyl]-propionamide;
(82) N-[4-(7,8-dimethoxy-1-methyl-[1,2,4]triazolo[4,3-a]quinoxaline-4-ylamino)-butyl]-2-(R)-hydroxy-3-methyl-butyramide;
(83) N-[4-(7,8-dimethoxy-1-methyl-[1,2,4]triazolo[4,3-a]quinoxaline-4-ylamino)-butyl]-2-(S)-hydroxy-3-methyl-butyramide;
(84) N-[4-(7,8-dimethoxy-1-methyl-[1,2,4]triazolo[4,3-a]quinoxaline-4-ylamino)-butyl]-2-thiophene-2-yl-acetamide;
(85) N-[4-(7,8-dimethoxy-1-methyl-[1,2,4]triazolo[4,3-a]quinoxaline-4-ylamino)-butyl]-2-furan-2-yl-acetamide;
(86) N-[4-(7,8-dimethoxy-1-methyl-[1,2,4]triazolo[4,3-a]quinoxaline-4-ylamino)-butyl]-2-phenyl-acetamide;
(87) acetic acid-[4-(7,8-dimethoxy-1-methyl-[1,2,4]triazolo[4,3-a]quinoxaline-4-ylamino)-butyl-carbamoyl]-methylester;
(88) 1-tert-butyl-3-[4-(7,8-dimethoxy-1-methyl-[1,2,4]triazolo[4,3-a]quinoxaline-4-ylamino)-butyl]-urea;
(89) 1-[4-(7,8-dimethoxy-1-methyl-[1,2,4]triazolo[4,3-a]quinoxaline-4-ylamino)-butyl]-3-ethyl-urea;
(90) 1-[4-(7,8-dimethoxy-1-methyl-[1,2,4]triazolo[4,3-a]quinoxaline-4-ylamino)-3-isopropyl-urea;
(91) 3-[4-(7,8-dimethoxy-1-methyl-[1,2,4]triazolo[4,3-a]quinoxaline-4-ylamino)-butyl]-1,1-dimethyl-urea;
(92) morpholine-4-carboxylic acid-[4-(7,8-dimethoxy-1-methyl-[1,2,4]triazolo[4,3-a]quinoxaline-4-ylamino)-butyl]-amide;
(93) 1-cyclohexyl-3-[4-(7,8-dimethoxy-1-methyl-[1,2,4]triazolo[4,3-a]quinoxaline-4-ylamino)-butyl]-urea;
(94) 1-[4-(7,8-dimethoxy-1-methyl-[1,2,4]triazolo[4,3-a]quinoxaline-4-ylamino)-butyl]-3-phenyl-urea;
(95) N-[4-(7,8-dimethoxy-1-methyl-[1,2,4]triazolo[4,3-a]quinoxaline-4-ylamino)-butyl]-benzamide;
(96) 4-tert-butyl-N-[4-(7,8-dimethoxy-1-methyl-[1,2,4]triazolo[4,3-a]quinoxaline-4-ylamino)-butyl]-benzamide;
(97) N-[4-(7,8-dimethoxy-1-methyl-[1,2,4]triazolo[4,3-a]quinoxaline-4-ylamino)-butyl]-2-methoxy-benzamide;
(98) N-[4-(7,8-dimethoxy-1-methyl-[1,2,4]triazolo[4,3-a]quinoxaline-4-ylamino)-butyl]-4-fluoro-benzamide;
(99) 2-chloro-N-[4-(7,8-dimethoxy-1-methyl-[1,2,4]triazolo[4,3-a]quinoxaline-4-ylamino)-butyl]-benzamide;
(100) 4-chloro-N-[4-(7,8-dimethoxy-1-methyl-[1,2,4]triazolo[4,3-a]quinoxaline-4-ylamino)-butyl]-benzamide;
(101) N-[4-(7,8-dimethoxy-1-methyl-[1,2,4]triazolo[4,3-a]quinoxaline-4-ylamino)-butyl]-4-nitro-benzamide;
(102) 2,3-dichloro-N-[4-(7,8-dimethoxy-1-methyl-[1,2,4]triazolo[4,3-a]quinoxaline-4-ylamino)-butyl]-benzamide;
(103) N-[4-(7,8-dimethoxy-1-methyl-[1,2,4]triazolo[4,3-a]quinoxaline-4-ylamino)-butyl]-isonicotinamide;
(104) N-[4-(7,8-dimethoxy-1-methyl-[1,2,4]triazolo[4,3-a]quinoxaline-4-ylamino)-butyl]-nicotinamide;
(105) pyridine-2-carboxylic acid-[4-(7,8-dimethoxy-1-methyl-[1,2,4]triazolo[4,3-a]quinoxaline-4-ylamino)-butyl]-amide;
(106) N-[4-(7,8-dimethoxy-1-methyl-[1,2,4]triazolo[4,3-a]quinoxaline-4-ylamino)-butyl]-2-fluoro-benzamide;
(107) 6-chloro-N-[4-(7,8-dimethoxy-1-methyl-[1,2,4]triazolo[4,3-a]quinoxaline-4-ylamino)-butyl]-nicotinamide;
(108) 2-chloro-N-[4-(7,8-dimethoxy-1-methyl-[1,2,4]triazolo[4,3-a]quinoxaline-4-ylamino)-butyl]-6-methyl-nicotinamide;
(109) N-[4-(7,8-dimethoxy-1-methyl-[1,2,4]triazolo[4,3-a]quinoxaline-4-ylamino)-butyl]-methanesulfonamide;
(110) [4-(7,8-dimethoxy-1-methyl-[1,2,4]triazolo[4,3-a]quinoxaline-4-ylamino)-butyl]-thiocarbamic acid-S-isopropylester;
(111) [4-(8-fluoro-1-methyl-6-trifluoromethyl-[1,2,4]triazolo[4,3-a]quinoxaline-4-ylamino)-butyl]-carbamic acid-tert-butylester;
(112) $N^1$-(8-fluoro-1-methyl-6-trifluoromethyl-[1,2,4]triazolo[4,3-a]quinoxaline-4-yl)-butane-1,4-diamine dihydrochloride;
(113) N-[4-(8-fluoro-1-methyl-6-trifluoromethyl-[1,2,4]triazolo[4,3-a]quinoxaline-4-ylamino)-butyl]-2,2-dimethyl-propionamide;
(114) [4-(8-fluoro-1-methyl-6-trifluoromethyl-[1,2,4]triazolo[4,3-a]quinoxaline-4-ylamino)-butyl]-carbamic acid isopropylester;
(115) [4-(8-fluoro-1-methyl-6-trifluoromethyl-[1,2,4]triazolo[4,3-a]quinoxaline-4-ylamino)-butyl]-carbamic acid isobutylester;
(116) N-[4-(8-fluoro-1-methyl-6-trifluoromethyl-[1,2,4]triazolo[4,3-a]quinoxaline-4-ylamino)-butyl]-3,3-dimethyl-butyramide;
(117) [4-(6-methoxy-1-methyl-[1,2,4]triazolo[4,3-a]quinoxaline-4-ylamino)-butyl]-carbamic acid-tert-butylester;
(118) $N^1$-(6-methoxy-1-methyl-[1,2,4]triazolo[4,3-a]quinoxaline-4-yl)-butane-1,4-diamine dihydrochloride;
(119) N-[4-(6-methoxy-1-methyl-[1,2,4]triazolo[4,3-a]quinoxaline-4-ylamino)-butyl]-2,2-dimethyl-propionamide;
(120) N-[4-(6-methoxy-1-methyl-[1,2,4]triazolo[4,3-a]quinoxaline-4-ylamino)-butyl]-carbamic acid isobutylester;
(121) [4-(8-methoxy-1-methyl-[1,2,4]triazolo[4,3-a]quinoxaline-4-ylamino)-butyl]-carbamic acid-tert-butylester;

(122) N¹-(8-methoxy-1-methyl-[1,2,4]triazolo[4,3-a]quinoxaline-4-yl)-butane-1,4-diamine ditrifluoroacetic acid;
(123) N-[4-(8-methoxy-1-methyl-[1,2,4]triazolo[4,3-a]quinoxaline-4-ylamino)-butyl]-2,2-dimethyl-propionamide;
(124) [4-(8-methoxy-1-methyl-[1,2,4]triazolo[4,3-a]quinoxaline-4-ylamino)-butyl]-3,3-dimethyl-butyramide;
(125) 2-(R)-hydroxy-N-[4-(8-methoxy-1-methyl-[1,2,4]triazolo[4,3-a]quinoxaline-4-ylamino)-butyl]-3-methyl-butyramide;
(126) 2-(S)-hydroxy-N-[4-(8-methoxy-1-methyl-[1,2,4]triazolo[4,3-a]quinoxaline-4-ylamino)-butyl]-3-methyl-butyramide;
(127) N-[4-(8-methoxy-1-methyl-[1,2,4]triazolo[4,3-a]quinoxaline-4-ylamino)-butyl]-benzamide;
(128) 2-chloro-N-[4-(8-methoxy-1-methyl-[1,2,4]triazolo[4,3-a]quinoxaline-4-ylamino)-butyl]-benzamide;
(129) 2-chloro-N-[4-(8-methoxy-1-methyl-[1,2,4]triazolo[4,3-a]quinoxaline-4-ylamino)-6-methyl-nicotinamide;
(130) {4-[6-methoxy-1,7-dimethyl-[1,2,4]triazolo[4,3-a]quinoxaline-4-ylamino]-butyl}-carbamic acid-tert-butylester;
(131) N¹-(6-methoxy-1,7-dimethyl-[1,2,4]triazolo[4,3-a]quinoxaline-4-yl)-butane-1,4-diamine ditrifluoroacetic acid;
(132) [4-(6-methoxy-1,7-dimethyl-[1,2,4]triazolo[4,3-a]quinoxaline-4-ylamino)-butyl]-2,2-dimethyl-propionamide;
(133) [4-(6-methoxy-1,7-dimethyl-[1,2,4]triazolo[4,3-a]quinoxaline-4-ylamino)-butyl]-carbamic acid isopropylester;
(134) [4-(6-methoxy-1,7-dimethyl-[1,2,4]triazolo[4,3-a]quinoxaline-4-ylamino)-butyl]-carbamic acid isobutylester;
(135) N-[4-(6-methoxy-1,7-dimethyl-[1,2,4]triazolo[4,3-a]quinoxaline-4-ylamino)-butyl]-3-methyl-butyramide;
(136) 2-(R)-hydroxy-N-[4-(6-methoxy-1,7-dimethyl-[1,2,4]triazolo[4,3-a]quinoxaline-4-ylamino)-butyl]-3-methyl-butyramide;
(137) 2-(S)-hydroxy-N-[4-(6-methoxy-1,7-dimethyl-[1,2,4]triazolo[4,3-a]quinoxaline-4-ylamino)-butyl]-3-methyl-butyramide;
(138) N-[4-(6-methoxy-1,7-dimethyl-[1,2,4]triazolo[4,3-a]quinoxaline-4-ylamino)-butyl]-benzamide;
(139) 2-fluoro-N-[4-(6-methoxy-1,7-dimethyl-[1,2,4]triazolo[4,3-a]quinoxaline-4-ylamino)-butyl]-benzamide;
(140) 2-chloro-N-[4-(6-methoxy-1,7-dimethyl-[1,2,4]triazolo[4,3-a]quinoxaline-4-ylamino)-butyl]-benzamide;
(141) 2-chloro-N-[4-(6-methoxy-1,7-dimethyl-[1,2,4]triazolo[4,3-a]quinoxaline-4-ylamino)-butyl]-6-methyl-nicotinamide;
(142) [4-(6-methoxy-1-methyl-8-trifluoromethyl-[1,2,4]triazolo[4,3-a]quinoxaline-4-ylamino)-butyl]-carbamic acid-tert-butylester;
(143) N¹-(6-methoxy-1-methyl-8-trifluoromethyl-[1,2,4]triazolo[4,3-a]quinoxaline-4-yl)-butane-1,4-diamine ditrifluoroacetic acid;
(144) [4-(6-methoxy-1-methyl-8-trifluoromethyl-[1,2,4]triazolo[4,3-a]quinoxaline-4-ylamino)-butyl]-carbamic acid isopropylester;
(145) N-[4-(6-methoxy-1-methyl-8-trifluoromethyl-[1,2,4]triazolo[4,3-a]quinoxaline-4-ylamino)-butyl]-3-methyl-butyramide;
(146) [4-(8-methoxy-1,7-dimethyl-[1,2,4]triazolo[4,3-a]quinoxaline-4-ylamino)-butyl]-carbamic acid-tert-butylester;
(147) N¹-(8-methoxy-1,7-dimethyl-[1,2,4]triazolo[4,3-a]quinoxaline-4-yl)-butane-1,4-diamine ditrifluoroacetic acid;
(148) N-[4-(8-methoxy-1,7-dimethyl-[1,2,4]triazolo[4,3-a]quinoxaline-4-ylamino)-butyl]-2,2-dimethyl-propionamide;
(149) [4-(8-methoxy-1,7-dimethyl-[1,2,4]triazolo[4,3-a]quinoxaline-4-ylamino)-butyl]-carbamic acid isopropylester;
(150) [4-(8-methoxy-1,7-dimethyl-[1,2,4]triazolo[4,3-a]quinoxaline-4-ylamino)-butyl]-carbamic acid isobutylester;
(151) N-[4-(8-methoxy-1,7-dimethyl-[1,2,4]triazolo[4,3-a]quinoxaline-4-ylamino)-butyl]-3-methyl-butyramide;
(152) 2-(R)-hydroxy-N-[4-(8-methoxy-1,7-dimethyl-[1,2,4]triazolo[4,3-a]quinoxaline-4-ylamino)-butyl]-3-methyl-butyramide;
(153) 2-(S)-hydroxy-N-[4-(8-methoxy-1,7-dimethyl-[1,2,4]triazolo[4,3-a]quinoxaline-4-ylamino)-butyl]-3-methyl-butyramide;
(154) N-[4-(8-methoxy-1,7-dimethyl-[1,2,4]triazolo[4,3-a]quinoxaline-4-ylamino)-butyl]-benzamide;
(155) 2-fluoro-N-[4-(8-methoxy-1,7-dimethyl-[1,2,4]triazolo[4,3-a]quinoxaline-4-ylamino)-butyl]-benzamide;
(156) 2-chloro-N-[4-(8-methoxy-1,7-dimethyl-[1,2,4]triazolo[4,3-a]quinoxaline-4-ylamino)-butyl]-benzamide;
(157) 2-chloro-N-[4-(8-methoxy-1,7-dimethyl-[1,2,4]triazolo[4,3-a]quinoxaline-4-ylamino)-butyl]-6-methyl-nicotinamide;
(158) [4-(8-methoxy-1,6-dimethyl-[1,2,4]triazolo[4,3-a]quinoxaline-4-ylamino)-butyl]-carbamic acid-tert-butylester;
(159) N¹-(8-methoxy-1,6-dimethyl-[1,2,4]triazolo[4,3-a]quinoxaline-4-yl)-butane-1,4-diamine difluoroacetic acid;
(160) N-[4-(8-methoxy-1,6-dimethyl-[1,2,4]triazolo[4,3-a]quinoxaline-4-ylamino)-butyl]-3-methyl-butyramide;
(161) [4-(8-methoxy-1,6-dimethyl-[1,2,4]triazolo[4,3-a]quinoxaline-4-ylamino)-butyl]-carbamic acid isopropylester;
(162) {4-[7,8-bis-(2-methoxy-ethoxy)-1-methyl-[1,2,4]triazolo[4,3-a]quinoxaline-4-ylamino]-butyl}-carbamic acid-tert-butylester;
(163) N¹-[7,8-bis-(2-methoxy-ethoxy)-1-methyl-[1,2,4]triazolo[4,3-a]quinoxaline-4-yl]-butane-1,4-diamine ditrifluoroacetic acid;
(164) N-{4-[7,8-bis-(2-methoxy-ethoxy)-1-methyl-[1,2,4]triazolo[4,3-a]quinoxaline-4-ylamino]-butyl}-2,2-dimethyl-propionamide;
(165) {4-[7,8-bis-(2-methoxy-ethoxy)-1-methyl-[1,2,4]triazolo[4,3-a]quinoxaline-4-ylamino]-butyl}-carbamic acid isopropylester;
(166) N-{4-[7,8-bis-(2-methoxy-ethoxy)-1-methyl-[1,2,4]triazolo[4,3-a]quinoxaline-4-ylamino]-butyl}-3-methyl-butyramide;
(167) N-{4-[7,8-bis-(2-methoxy-ethoxy)-1-methyl-[1,2,4]triazolo[4,3-a]quinoxaline-4-ylamino]-butyl}-3,3-dimethyl-butyramide;

(168) {4-[7,8-bis-(2-methoxy-ethoxy)-1-methyl-[1,2,4]triazolo[4,3-a]quinoxaline-4-ylamino]-butyl}-carbamic acid isobutylester;

(169) 1-{4-[7,8-bis-(2-methoxy-ethoxy)-1-methyl-[1,2,4]triazolo[4,3-a]quinoxaline-4-ylamino]-butyl}-3-tert-butyl-urea;

(170) N-{4-[7,8-bis-(2-methoxy-ethoxy)-1-methyl-[1,2,4]triazolo[4,3-a]quinoxaline-4-ylamino]-butyl}-benzamide;

(171) N-{4-[7,8-bis-(2-methoxy-ethoxy)-1-methyl-[1,2,4]triazolo[4,3-a]quinoxaline-4-ylamino]-butyl}-2-chloro-benzamide;

(172) N-{4-[7,8-bis-(2-methoxy-ethoxy)-1-methyl-[1,2,4]triazolo[4,3-a]quinoxaline-4-ylamino]-butyl}-2-chloro-6-methyl-nicotinamide;

(173) [4-(7,8-diethoxy-1-methyl-[1,2,4]triazolo[4,3-a]quinoxaline-4-ylamino)-butyl-carbamic acid-tert-butylester;

(174) $N^1$-(7,8-diethoxy-1-methyl-[1,2,4]triazolo[4,3-a]quinoxaline-4-yl)-butane-1,4-diamine ditrifluoroacetic acid;

(175) [4-(7,8-diethoxy-1-methyl-[1,2,4]triazolo[4,3-a]quinoxaline-4-ylamino)-butyl]-carbamic acid isopropylester;

(176) [4-(7,8-diethoxy-1-methyl-[1,2,4]triazolo[4,3-a]quinoxaline-4-ylamino)-butyl]-carbamic acid isobutylester;

(177) N-[4-(7,8-diethoxy-1-methyl-[1,2,4]triazolo[4,3-a]quinoxaline-4-ylamino)-butyl-3-methyl-butyramide;

(178) [4-(1-methyl-8,9-dihydro-7,10-dioxa-2,3,5,11b-tetraaza-cyclopenta[a]anthracene-4-ylamino)-butyl]-carbamic acid-tert-butylester;

(179) $N^1$-(1-methyl-8,9-dihydro-7,10-dioxa-2,3,5,11b-tetraaza-cyclopenta[a]anthracene-4-yl)-butane-1,4-diamine ditrifluoroacetic acid;

(180) 2,2-dimethyl-N-[4-(1-methyl-8,9-dihydro-7,10-dioxa-2,3,5,11b-tetraaza-cyclopenta[a]anthracene-4-ylamino)-butyl]-propionamide;

(181) 3-methyl-N-[4-(1-methyl-8,9-dihydro-7,10-dioxa-2,3,5,11b-tetraaza-cyclopenta[a]anthracene-4-ylamino)-butyl]-butyramide;

(182) 2-(R)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide;

(183) 2-(S)-hydroxy-3-methyl-N-[4-(1-methyl-8,9-dihydro-7,10-dioxa-2,3,5,11b-tetraaza-cyclopenta[a]anthracene-4-ylamino)-butyl]-butyramide;

(184) acetic acid-[4-(1-methyl-8,9-dihydro-7,10-dioxa-2,3,5,11b-tetraaza-cyclopenta[a]anthracene-4-ylamino)-butyl]-carbamoyl]-methylester;

(185) N-[4-(1-methyl-8,9-dihydro-7,10-dioxa-2,3,5,11b-tetraaza-cyclopenta[a]anthracene-4-ylamino)-butyl]-2-thiophene-2-yl-acetamide;

(186) N-[4-(1-methyl-8,9-dihydro-7,10-dioxa-2,3,5,11b-tetraaza-cyclopenta[a]anthracene-4-ylamino)-butyl]-benzamide;

(187) 2-chloro-N-[4-(1-methyl-8,9-dihydro-7,10-dioxa-2,3,5,11b-tetraaza-cyclopenta[a]anthracene-4-ylamino)-butyl]-benzamide;

(188) [4-(1-methyl-8,9-dihydro-7,10-dioxa-2,3,5,11b-tetraaza-cyclopenta[a]anthracene-4-ylamino)-butyl]-carbamic acid isopropylester;

(189) [4-(1-methyl-8,9-dihydro-7,10-dioxa-2,3,5,11b-tetraaza-cyclopenta[a]anthracene-4-ylamino)-butyl]-carbamic acid isobutylester;

(190) [4-(1-methyl-8,9-dihydro-7,10-dioxa-2,3,5,11b-tetraaza-cyclopenta[a]anthracene-4-ylamino)-butyl]-carbamic acid cyclopentylester;

(191) [4-(1-methyl-8,9-dihydro-7,10-dioxa-2,3,5,11b-tetraaza-cyclopenta[a]anthracene-4-ylamino)-butyl]-carbamic acid phenylester;

(192) 1-isopropyl-3-[4-(1-methyl-8,9-dihydro-7,10-dioxa-2,3,5,11b-tetraaza-cyclopenta[a]anthracene-4-ylamino)-butyl]-urea;

(193) [4-(6,7,8-trimethoxy-1-methyl-[1,2,4]triazolo[4,3-a]quinoxaline-4-ylamino)-butyl]-carbamic acid-tert-butylester;

(194) $N^1$-(6,7,8-trimethoxy-1-methyl-[1,2,4]triazolo[4,3-a]quinoxaline-4-yl)-butane-1,4-diamine ditrifluoroacetic acid;

(195) 3-methyl-N-[4-(6,7,8-trimethoxy-1-methyl-[1,2,4]triazolo[4,3-a]quinoxaline-4-ylamino)-butyl]-butyramide;

(196) 3-methyl-pentanoic acid-[4-(6,7,8-trimethoxy-1-methyl-[1,2,4]triazolo[4,3-a]quinoxaline-4-ylamino)-butyl]-amide;

(197) 4-(4-tert-butoxycarbamoylamino-butylamino)-1-methyl-[1,2,4]triazolo[4,3-a]quinoxaline-7-carboxylic acid methylester;

(198) 4-(4-amino-butylamino)-1-methyl-[1,2,4]triazolo[4,3-a]quinoxaline-7-carboxylic acid methylester ditrifluoroacetic acid;

(199) 1-methyl-4-[4-(3-methyl-butyrylamino)-butylamino]-[1,2,4]triazolo[4,3-a]quinoxaline-7-carboxylic acid methylester;

(200) 4-[(4-tert-butoxycarbamoylamino)-butylamino]-1-methyl-[1,2,4]triazolo[4,3-a]quinoxaline-7-carboxylic acid;

(201) 1-methyl-4-[4-(3-methyl-butyrylamino)-butylamino]-[1,2,4]triazolo[4,3-a]quinoxaline-7-carboxylic acid;

(202) [4-(7-isopropylcarbamoyl-1-methyl-[1,2,4]triazolo[4,3-a]quinoxaline-4-ylamino)-butyl]-carbamic acid-tert-butylester;

(203) [4-(7-tert-butylcarbamoyl-1-methyl-[1,2,4]triazolo[4,3-a]quinoxaline-4-ylamino)-butyl]-carbamic acid-tert-butylester;

(204) 4-(4-isobutyramido-butylamino)-1-methyl-[1,2,4]triazolo[4,3-a]quinoxaline-7-carboxylic acid isopropylamide;

(205) 4-(4-benzoylamino-butylamino)-1-methyl-[1,2,4]triazolo[4,3-a]quinoxaline-7-carboxylic acid isopropylamide;

(206) {4-[7-(2-dimethylamino-ethylcarbamoyl)-1-methyl-[1,2,4]triazolo[4,3-a]quinoxaline-4-ylamino]-butyl}-carbamic acid-tert-butylester;

(207) 4-(4-benzoylamino-butylamino)-1-methyl-[1,2,4]triazolo[4,3-a]quinoxaline-7-carboxylic acid-(2-dimethylamino-ethyl)-amide;

(208) N-{4-[7-(4-benzyl-piperazine-1-carbonyl)-1-methyl-[1,2,4]triazolo[4,3-a]quinoxaline-4-ylamino]-butyl}-benzamide;

(209) N-{4-[1-methyl-7-(piperazine-1-carbonyl)-[1,2,4]triazolo[4,3-a]quinoxaline-4-ylamino]-butyl}-benzamide;

(210) [4-(7-benzylcarbamoyl-1-methyl-[1,2,4]triazolo[4,3-a]quinoxaline-4-ylamino)-butyl]-carbamic acid-tert-butylester;

(211) {4-[7-(4-chloro-benzylcarbamoyl)-1-methyl-[1,2,4]triazolo[4,3-a]quinoxaline-4-ylamino]-butyl}-carbamic acid-tert-butylester;

(212) [4-(1-methyl-7-phenylcarbamoyl-[1,2,4]triazolo[4,3-a]quinoxaline-4-ylamino)-butyl]-carbamic acid-tert-butylester;
(213) {4-[7-(2-amino-phenylcarbamoyl)-1-methyl-[1,2,4]triazolo[4,3-a]quinoxaline-4-ylamino]-butyl}-carbamic acid-tert-butylester;
(214) {4-[7-(2-amino-4-methyl-phenylcarbamoyl)-1-methyl-[1,2,4]triazolo[4,3-a]quinoxaline-4-ylamino]-butyl}-carbamic acid-tert-butylester;
(215) 1-methyl-4-[4-(3-methyl-butyrylamino)-butylamino]-[1,2,4]triazolo[4,3-a]quinoxaline-7-carboxylic acid-(2-amino-phenyl)-amide;
(216) 1-methyl-4-[4-(3-methyl-butyrylamino)-butylamino]-[1,2,4]triazolo[4,3-a]quinoxaline-7-carboxylic acid-(2-amino-4-methyl-phenyl)-amide;
(217) 1-methyl-4-[4-(3-methyl-butyrylamino)-butylamino]-[1,2,4]triazolo[4,3-a]quinoxaline-7-carboxylic acid-(2-amino-4,5-dimethoxy-phenyl)-amide;
(218) {4-[7-(1H-benzoimidazole-2-yl)-1-methyl-[1,2,4]triazolo[4,3-a]quinoxaline-4-ylamino]-butyl}-carbamic acid-tert-butylester;
(219) {4-[1-methyl-7-(5-methyl-1H-benzoimidazole-2-yl)-[1,2,4]triazolo[4,3-a]quinoxaline-4-ylamino]-butyl}-carbamic acid-tert-butylester;
(220) {4-[1-methyl-7-(1-methyl-1H-benzoimidazole-2-yl)-[1,2,4]triazolo[4,3-a]quinoxaline-4-ylamino]-butyl}-carbamic acid-tert-butylester;
(221) $N^1$-[1-methyl-7-(1-methyl-1H-benzoimidazole-2-yl)-[1,2,4]triazolo[4,3-a]quinoxaline-4-yl]-butane-1,4-diamine ditrifluoroacetic acid;
(222) 3-methyl-N-{4-[1-methyl-7-(1-methyl-1H-benzoimidazole-2-yl)-[1,2,4]triazolo[4,3-a]quinoxaline-4-ylamino]-butyl}-butyramide;
(223) 3-methyl-N-{4-[1-methyl-7-(5-methyl-1H-benzoimidazole-2-yl)-[1,2,4]triazolo[4,3-a]quinoxaline-4-ylamino]-butyl}-butyramide;
(224) N-{4-[7-(1H-benzoimidazole-2-yl)-1-methyl-[1,2,4]triazolo[4,3-a]quinoxaline-4-ylamino]-butyl}-3-methyl-butyramide;
(225) N-{4-[7-(1H-benzoimidazole-2-yl)-1-methyl-[1,2,4]triazolo[4,3-a]quinoxaline-4-ylamino]-butyl}-2-(S)-hydroxy-3-methyl-butyramide;
(226) N-{4-[7-(1H-benzoimidazole-2-yl)-1-methyl-[1,2,4]triazolo[4,3-a]quinoxaline-4-ylamino]-butyl}-2-(R)-hydroxy-3-methyl-butyramide;
(227) N-{4-[7-(5,6-dimethoxy-1H-benzoimidazole-2-yl)-1-methyl-[1,2,4]triazolo[4,3-a]quinoxaline-4-ylamino]-butyl}-3-methyl-butyramide;
(228) {4-[1-methyl-7-(1-methyl-1H-benzoimidazole-2-yl)-[1,2,4]triazolo[4,3-a]quinoxaline-4-ylamino]-butyl}-carbamic acid propylester;
(229) {4-[1-methyl-7-(1-methyl-1H-benzoimidazole-2-yl)-[1,2,4]triazolo[4,3-a]quinoxaline-4-ylamino]-butyl}-carbamic acid cyclopentylester;
(230) 2,2-dimethyl-N-{4-[1-methyl-7-(1-methyl-1H-benzoimidazole-2-yl)-[1,2,4]triazolo[4,3-a]quinoxaline-4-ylamino]-butyl}-propionamide;
(231) acetic acid-1-{4-[7-(1-methyl-1H-benzoimidazole-2-yl)-1-methyl-[1,2,4]triazolo[4,3-a]quinoxaline-4-ylamino]-butylcarbamoyl}-1-methyl-ethylester;
(232) 2-hydroxy-N-{4-(7-(1-methyl-1H-benzoimidazole-2-yl)-1-methyl-[1,2,4]triazolo[4,3-a]quinoxaline-4-ylamino]-butyl}-2-methyl-propionamide;
(233) 2,2-difluoro-N-{4-[1-methyl-7-(1-methyl-1H-benzoimidazole-2-yl)-[1,2,4]triazolo[4,3-a]quinoxaline-4-ylamino]-butyl}-butyramide;
(234) 2-(S)-hydroxy-3-methyl-N-{4-[1-methyl-7-(1-methyl-1H-benzoimidazole-2-yl)-[1,2,4]triazolo[4,3-a]quinoxaline-4-ylamino]-butyl}-butyramide;
(235) 2-(R)-hydroxy-3-methyl-N-{4-[1-methyl-7-(1-methyl-1H-benzoimidazole-2-yl)-[1,2,4]triazolo[4,3-a]quinoxaline-4-ylamino]-butyl}-butyramide;
(236) 4-methyl-pentanoic acid-{4-[1-methyl-7-(1-methyl-1H-benzoimidazole-2-yl)-[1,2,4]triazolo[4,3-a]quinoxaline-4-ylamino]-butyl}-amide;
(237) 2-methoxy-N-{4-[1-methyl-7-(1-methyl-1H-benzoimidazole-2-yl)-[1,2,4]triazolo[4,3-a]quinoxaline-4-ylamino]-butyl}-benzamide;
(238) 1-isopropyl-3-{4-[1-methyl-7-(1-methyl-1H-benzoimidazole-2-yl)-[1,2,4]triazolo[4,3-a]quinoxaline-4-ylamino]-butyl}-urea;
(239) 1-cyclohexyl-3-{4-[1-methyl-7-(1-methyl-1H-benzoimidazole-2-yl)-[1,2,4]triazolo[4,3-a]quinoxaline-4-ylamino]-butyl}-urea;
(240) 3-methyl-N-{4-[1-methyl-7-(1-propyl-1H-benzoimidazole-2-yl)-[1,2,4]triazolo[4,3-a]quinoxaline-4-ylamino]-butyl}-butyramide;
(241) N-(4-{7-[1-(2-methoxy-ethyl)-1H-benzoimidazole-2-yl]-1-methyl-[1,2,4]triazolo[4,3-a]quinoxaline-4-ylamino}-butyl)-3-methyl-butyramide;
(242) [4-(1-methyl-7-nitro-[1,2,4]triazolo[4,3-a]quinoxaline-4-ylamino)-butyl]-carbamic acid-tert-butylester;
(243) [4-(7-amino-1-methyl-[1,2,4]triazolo[4,3-a]quinoxaline-4-ylamino)-butyl]-carbamic acid-tert-butylester;
(244) 3-methyl-N-[4-(1-methyl-8-nitro-[1,2,4]triazolo[4,3-a]quinoxaline-4-ylamino)-butyl]-butyramide;
(245) N-[4-(7-amino-1-methyl-[1,2,4]triazolo[4,3-a]quinoxaline-4-ylamino)-butyl]-3-methyl-butyramide;
(246) [4-(7-isobutyramido-1-methyl-[1,2,4]triazolo[4,3-a]quinoxaline-4-ylamino)-butyl]-carbamic acid-tert-butylester;
(247) N-[4-(7-isobutyramido-1-methyl-[1,2,4]triazolo[4,3-a]quinoxaline-4-ylamino)-butyl]-2,2-dimethyl-propionamide;
(248) N-[4-(7-isobutyramido-1-methyl-[1,2,4]triazolo[4,3-a]quinoxaline-4-ylamino)-butyl]-benzamide;
(249) [4-(7-acetylamino-methyl-[1,2,4]triazolo[4,3-a]quinoxaline-4-ylamino)-butyl]-carbamic acid-tert-butylester;
(250) N-[4-(7-acetylamino-methyl-[1,2,4]triazolo[4,3-a]quinoxaline-4-ylamino)-butyl]-2,2-dimethyl-propionamide;
(251) N-[4-(7-acetylamino-methyl-[1,2,4]triazolo[4,3-a]quinoxaline-4-ylamino)-butyl]-benzamide;
(252) 3-methyl-N-[4-(1-methyl-7-methylamino-[1,2,4]triazolo[4,3-a]quinoxaline-4-ylamino)-butyl]-butyramide;
(253) 3-methyl-N-[4-(1-methyl-7-propylamino-[1,2,4]triazolo[4,3-a]quinoxaline-4-ylamino)-butyl]-butyramide;
(254) N-{4-[7-(3-cyano-propylamino)-1-methyl-[1,2,4]triazolo[4,3-a]quinoxaline-4-ylamino]-butyl}-3-methyl-butyramide;
(255) N-{4-[7-(3-isopropyl-ureido)-1-methyl-[1,2,4]triazolo[4,3-a]quinoxaline-4-ylamino]-butyl}-3-methyl-butyramide;
(256) N-{4-[7-(3-isopropyl-thioureido)-1-methyl-[1,2,4]triazolo[4,3-a]quinoxaline-4-ylamino]-butyl}-3-methyl-butyramide;
(257) N-[4-(7-methanesulfonylamino-1-methyl-[1,2,4]triazolo[4,3-a]quinoxaline-4-ylamino)-butyl]-3-methyl-butyramide;

(258) 3-methyl-N-{4-[1-methyl-7-(2,2,2-trifluoro-ethanesulfonylamino)-[1,2,4]triazolo[4,3-a]quinoxaline-4-ylamino]-butyl}-butyramide;
(259) 3-methyl-N-{4-[1-methyl-7-(propane-2-sulfonylamino)-[1,2,4]triazolo[4,3-a]quinoxaline-4-ylamino]-butyl}-butyramide;
(260) [4-(7-benzoyl-1-methyl-[1,2,4]triazolo[4,3-a]quinoxaline-4-ylamino)-butyl]-carbamic acid-tert-butylester;
(261) {4-[7-(4-chloro-benzoyl)-1-methyl-[1,2,4]triazolo[4,3-a]quinoxaline-4-ylamino]-butyl}-carbamic acid-tert-butylester;
(262) {4-[7-(4-methoxy-benzoyl)-1-methyl-[1,2,4]triazolo[4,3-a]quinoxaline-4-ylamino]-butyl}-carbamic acid-tert-butylester;
(263) [4-(1-methyl-8-trifluoromethoxy-[1,2,4]triazolo[4,3-a]quinoxaline-4-ylamino)-butyl]-carbamic acid-tert-butylester;
(264) $N^1$-(1-methyl-8-trifluoromethoxy-[1,2,4]triazolo[4,3-a]quinoxaline-4-yl)-butane-1,4-diamine ditrifluoroacetic acid;
(265) 2,2-dimethyl-N-[4-(1-methyl-8-trifluoromethoxy-[1,2,4]triazolo[4,3-a]quinoxaline-4-ylamino)-butyl]-propionamide;
(266) 3,3-dimethyl-N-[4-(1-methyl-8-trifluoromethoxy-[1,2,4]triazolo[4,3-a]quinoxaline-4-ylamino)-butyl]-butyramide;
(267) N-[4-(1-methyl-8-trifluoromethoxy-[1,2,4]triazolo[4,3-a]quinoxaline-4-ylamino)-butyl]-benzamide;
(268) 2-chloro-N-[4-(1-methyl-8-trifluoromethoxy-[1,2,4]triazolo[4,3-a]quinoxaline-4-ylamino)-butyl]-benzamide;
(269) [4-(1-methyl-7-trifluoromethoxy-[1,2,4]triazolo[4,3-a]quinoxaline-4-ylamino)-butyl]-carbamic acid-tert-butylester;
(270) $N^1$-(1-methyl-7-trifluoromethoxy-[1,2,4]triazolo[4,3-a]quinoxaline-4-yl)-butane-1,4-diamine ditrifluoroacetic acid;
(271) 2,2-dimethyl-N-[4-(1-methyl-7-trifluoromethoxy-[1,2,4]triazolo[4,3-a]quinoxaline-4-ylamino)-butyl]-propionamide;
(272) 3,3-dimethyl-N-[4-(1-methyl-7-trifluoromethoxy-[1,2,4]triazolo[4,3-a]quinoxaline-4-ylamino)-butyl]-butyramide;
(273) N-[4-(1-methyl-7-trifluoromethoxy-[1,2,4]triazolo[4,3-a]quinoxaline-4-ylamino)-butyl]-benzamide;
(274) 2-chloro-N-[4-(1-methyl-7-trifluoromethoxy-[1,2,4]triazolo[4,3-a]quinoxaline-4-ylamino)-butyl]-benzamide;
(275) [4-(7-methoxy-1-methyl-[1,2,4]triazolo[4,3-a]quinoxaline-4-ylamino)-butyl]-carbamic acid-tert-butylester;
(276) $N^1$-(7-methoxy-1-methyl-[1,2,4]triazolo[4,3-a]quinoxaline-4-yl)-butane-1,4-diamine ditrifluoroacetic acid;
(277) N-[4-(7-methoxy-1-methyl-[1,2,4]triazolo[4,3-a]quinoxaline-4-ylamino)-butyl]-2,2-dimethyl-propionamide;
(278) [4-(7-methoxy-1-methyl-[1,2,4]triazolo[4,3-a]quinoxaline-4-ylamino)-butyl]-carbamic acid isopropylester;
(279) [4-(7-methoxy-1-methyl-[1,2,4]triazolo[4,3-a]quinoxaline-4-ylamino)-butyl]-carbamic acid isobutylester;
(280) [4-(7-methoxy-1-methyl-[1,2,4]triazolo[4,3-a]quinoxaline-4-ylamino)-butyl]-carbamic acid-sec-butylester;
(281) N-[4-(7-methoxy-1-methyl-[1,2,4]triazolo[4,3-a]quinoxaline-4-ylamino)-butyl]-isobutyramide;
(282) cyclopropanecarboxylic acid-[4-(7-methoxy-1-methyl-[1,2,4]triazolo[4,3-a]quinoxaline-4-ylamino)-butyl]-amide;
(283) butene-2-oic acid-[4-(7-methoxy-1-methyl-[1,2,4]triazolo[4,3-a]quinoxaline-4-ylamino)-butyl]-amide;
(284) 3-methyl-butene-2-oic acid-[4-(7-methoxy-1-methyl-[1,2,4]triazolo[4,3-a]quinoxaline-4-ylamino)-butyl]-amide;
(285) N-[4-(7-methoxy-1-methyl-[1,2,4]triazolo[4,3-a]quinoxaline-4-ylamino)-butyl]-3-methyl-butyramide;
(286) 2-(S)-fluoro-N-[4-(7-methoxy-1-methyl-[1,2,4]triazolo[4,3-a]quinoxaline-4-ylamino)-butyl]-3-methyl-butyramide;
(287) N-[4-(7-methoxy-1-methyl-[1,2,4]triazolo[4,3-a]quinoxaline-4-ylamino)-butyl]-3,3-dimethyl-butyramide;
(288) 4-methyl-pentanoic acid-[4-(7-methoxy-1-methyl-[1,2,4]triazolo[4,3-a]quinoxaline-4-ylamino)-butyl]-amide;
(289) 3-methyl-pentanoic acid-[4-(7-methoxy-1-methyl-[1,2,4]triazolo[4,3-a]quinoxaline-4-ylamino)-butyl]-amide;
(290) 2-ethyl-N-[4-(7-methoxy-1-methyl-[1,2,4]triazolo[4,3-a]quinoxaline-4-ylamino)-butyl]-butyramide;
(291) N-[4-(7-methoxy-1-methyl-[1,2,4]triazolo[4,3-a]quinoxaline-4-ylamino)-butyl]-2-methyl-butyramide;
(292) 2,2,3,3,4,4,4-heptafluoro-N-[4-(7-methoxy-1-methyl-[1,2,4]triazolo[4,3-a]quinoxaline-4-ylamino)-butyl]-butyramide;
(293) 3,3,3-trifluoro-N-[4-(7-methoxy-1-methyl-[1,2,4]triazolo[4,3-a]quinoxaline-4-ylamino)-butyl]-2,2-dimethyl-propaneamide;
(294) 2,2-difluoro-N-[4-(7-methoxy-1-methyl-[1,2,4]triazolo[4,3-a]quinoxaline-4-ylamino)-butyl]-butyramide;
(295) 2-(R)-hydroxy-N-[4-(7-methoxy-1-methyl-[1,2,4]triazolo[4,3-a]quinoxaline-4-ylamino)-butyl]-propaneamide;
(296) acetic acid-1-[4-(7-methoxy-1-methyl-[1,2,4]triazolo[4,3-a]quinoxaline-4-ylamino)-butylcarbamoyl]-1-methyl-ethylester;
(297) 2-hydroxy-N-[4-(7-methoxy-1-methyl-[1,2,4]triazolo[4,3-a]quinoxaline-4-ylamino)-butyl]-2-methyl-propionamide;
(298) 2-(R)-hydroxy-N-[4-(7-methoxy-1-methyl-[1,2,4]triazolo[4,3-a]quinoxaline-4-ylamino)-butyl]-3-methyl-butyramide;
(299) 2-(S)-hydroxy-N-[4-(7-methoxy-1-methyl-[1,2,4]triazolo[4,3-a]quinoxaline-4-ylamino)-butyl]-3-methyl-butyramide;
(300) 2-(R)-methoxy-N-[4-(7-methoxy-1-methyl-[1,2,4]triazolo[4,3-a]quinoxaline-4-ylamino)-butyl]-3-methyl-butyramide;
(301) 2-(S)-methoxy-N-[4-(7-methoxy-1-methyl-[1,2,4]triazolo[4,3-a]quinoxaline-4-ylamino)-butyl]-3-methyl-butyramide;
(302) 2-(S)-bromo-N-[4-(7-methoxy-1-methyl-[1,2,4]triazolo[4,3-a]quinoxaline-4-ylamino)-butyl]-3-methyl-butyramide;
(303) acetic acid-[4-(7-methoxy-1-methyl-[1,2,4]triazolo[4,3-a]quinoxaline-4-ylamino)-butylcarbamoyl]-methylester;
(304) 2-hydroxy-N-[4-(7-methoxy-1-methyl-[1,2,4]triazolo[4,3-a]quinoxaline-4-ylamino)-butyl]-acetamide;

(305) N-[4-(7-methoxy-1-methyl-[1,2,4]triazolo[4,3-a]quinoxaline-4-ylamino)-butyl]-malonamic acid ethylester;
(306) N-[4-(7-methoxy-1-methyl-[1,2,4]triazolo[4,3-a]quinoxaline-4-ylamino)-butyl]-malonamic acid;
(307) N-[4-(7-methoxy-1-methyl-[1,2,4]triazolo[4,3-a]quinoxaline-4-ylamino)-butyl]-2-thiophene-2-yl-acetamide;
(308) 2-furan-2-yl-N-[4-(7-methoxy-1-methyl-[1,2,4]triazolo[4,3-a]quinoxaline-4-ylamino)-butyl]-acetamide;
(309) 3-cyclopentyl-N-[4-(7-methoxy-1-methyl-[1,2,4]triazolo[4,3-a]quinoxaline-4-ylamino)-butyl]-propionamide;
(310) {1-[4-(7-methoxy-1-methyl-[1,2,4]triazolo[4,3-a]quinoxaline-4-ylamino)-butylcarbamoyl]-2-methyl-propyl}-carbamic acid-tert-butylester;
(311) 2-amino-N-[4-(7-methoxy-1-methyl-[1,2,4]triazolo[4,3-a]quinoxaline-4-ylamino)-butyl]-3-methyl-butyramide;
(312) 2-(R)-dimethylamino-N-[4-(7-methoxy-1-methyl-[1,2,4]triazolo[4,3-a]quinoxaline-4-ylamino)-butyl]-3-methyl-butyramide;
(313) 2-(S)-dimethylamino-N-[4-(7-methoxy-1-methyl-[1,2,4]triazolo[4,3-a]quinoxaline-4-ylamino)-butyl]-3-methyl-butyramide;
(314) N-[4-(7-methoxy-1-methyl-[1,2,4]triazolo[4,3-a]quinoxaline-4-ylamino)-butyl]-3-methyl-2-(S)-morpholine-4-yl-butyramide;
(315) 2-(S)-(3-hydroxy-pyrrolidine-1-yl)-N-[4-(7-methoxy-1-methyl-[1,2,4]triazolo[4,3-a]quinoxaline-4-ylamino)-butyl]-3-methyl-butyramide;
(316) 2-(S)-(4-hydroxy-piperidine-1-yl)-N-[4-(7-methoxy-1-methyl-[1,2,4]triazolo[4,3-a]quinoxaline-4-ylamino)-butyl]-3-methyl-butyramide;
(317) 2-(S)-[4-(2-hydroxy-ethyl)-piperidine-1-yl]-N-[4-(7-methoxy-1-methyl-[1,2,4]triazolo[4,3-a]quinoxaline-4-ylamino)-butyl]-3-methyl-butyramide;
(318) (S)-{1-[4-(7-methoxy-1-methyl-[1,2,4]triazolo[4,3-a]quinoxaline-4-ylamino)-butylcarbamoyl]-2-methyl-propyl}-carbamic acid isobutylester;
(319) (S)-{1-[4-(7-methoxy-1-methyl-[1,2,4]triazolo[4,3-a]quinoxaline-4-ylamino)-butylcarbamoyl]-2-methyl-propyl}-carbamic acid propylester;
(320) (S)-{1-[4-(7-methoxy-1-methyl-[1,2,4]triazolo[4,3-a]quinoxaline-4-ylamino)-butylcarbamoyl]-2-methyl-propyl}-carbamic acid isopropylester;
(321) (S)-2-(S)-fluoro-N-{1-[4-(7-methoxy-1-methyl-[1,2,4]triazolo[4,3-a]quinoxaline-4-ylamino)-butyl carbamoyl]-2-methyl-propyl}-3-methyl-butyramide;
(322) (S)—N-[4-(7-methoxy-1-methyl-[1,2,4]triazolo[4,3-a]quinoxaline-4-ylamino)-butyl]-3-methyl-2-(3-methyl-butyrylamino)-butyramide;
(323) (S)-2-(2,2-dimethyl-propionylamino)-N-[4-(7-methoxy-1-methyl-[1,2,4]triazolo[4,3-a]quinoxaline-4-ylamino)-butyl]-3-methyl-butyramide;
(324) 2-(S)-(2(S)-hydroxy-propionylamino)-N-[4-(7-methoxy-1-methyl-[1,2,4]triazolo[4,3-a]quinoxaline-4-ylamino)-butyl]-3-methyl-butyramide;
(325) {2-(S)-(4-hydroxy-phenyl)-1-[4-(7-methoxy-1-methyl-[1,2,4]triazolo[4,3-a]quinoxaline-4-ylamino)-butylcarbamoyl]-ethyl}-carbamic acid-tert-butylester;
(326) 2-(S)-amino-3-(4-hydroxy-phenyl)-N-[4-(7-methoxy-1-methyl-[1,2,4]triazolo[4,3-a]quinoxaline-4-ylamino)-butyl]-propionamide;
(327) 2-(S)-methanesulfonylamino-N-[4-(7-methoxy-1-methyl-[1,2,4]triazolo[4,3-a]quinoxaline-4-ylamino)-butyl]-3-methyl-butyramide;
(328) 2-fluoro-N-[4-(7-methoxy-1-methyl-[1,2,4]triazolo[4,3-a]quinoxaline-4-ylamino)-butyl]-benzamide;
(329) N-[4-(7-methoxy-1-methyl-[1,2,4]triazolo[4,3-a]quinoxaline-4-ylamino)-butyl]-2-phenyl-acetamide;
(330) 1-isopropyl-3-[4-(7-methoxy-1-methyl-[1,2,4]triazolo[4,3-a]quinoxaline-4-ylamino)-butyl]-urea;
(331) 1-tert-butyl-3-[4-(7-methoxy-1-methyl-[1,2,4]triazolo[4,3-a]quinoxaline-4-ylamino)-butyl]-urea;
(332) [4-(7-methoxy-1-methyl-[1,2,4]triazolo[4,3-a]quinoxaline-4-ylamino)-butyl]-carbamic acid cyclopentylester;
(333) [4-(7-methoxy-1-methyl-[1,2,4]triazolo[4,3-a]quinoxaline-4-ylamino)-butyl]-carbamic acid phenylester;
(334) 3-[4-(7-methoxy-1-methyl-[1,2,4]triazolo[4,3-a]quinoxaline-4-ylamino)-butyl]-1,1-dimethyl-urea;
(335) 1-cyclohexyl-3-[4-(7-methoxy-1-methyl-[1,2,4]triazolo[4,3-a]quinoxaline-4-ylamino)-butyl]-urea;
(336) [4-(7-methoxy-1-methyl-[1,2,4]triazolo[4,3-a]quinoxaline-4-ylamino)-butyl]-thiocarbamic acid-S-isopropylester;
(337) 1-isopropyl-3-[4-(7-methoxy-1-methyl-[1,2,4]triazolo[4,3-a]quinoxaline-4-ylamino)-butyl]-thiourea;
(338) N-[4-(7-methoxy-1-methyl-[1,2,4]triazolo[4,3-a]quinoxaline-4-ylamino)-butyl]-methanesulfonamide;
(339) N-{4-[7-methoxy-1-methyl-8-(4-nitro-benzyl)-[1,2,4]triazolo[4,3-a]quinoxaline-4-ylamino]-butyl}-3-methyl-butyramide;
(340) N-[4-(7-hydroxy-1-methyl-[1,2,4]triazolo[4,3-a]quinoxaline-4-ylamino)-butyl]-3-methyl-butyramide;
(341) N-{4-[7-(4-cyano-benzyloxy)-1-methyl-[1,2,4]triazolo[4,3-a]quinoxaline-4-ylamino]-butyl}-3-methyl-butyramide;
(342) N-{4-[7-(3-cyano-propoxy)-1-methyl-[1,2,4]triazolo[4,3-a]quinoxaline-4-ylamino]-butyl}-3-methyl-butyramide;
(343) 3-methyl-N-{4-[1-methyl-7-(tetrahydro-pyran-2-ylmethoxy)-[1,2,4]triazolo[4,3-a]quinoxaline-4-ylamino]-butyl}-butyramide;
(344) 3-methyl-N-{4-[1-methyl-7-(tetrahydro-pyran-4-yloxy)-[1,2,4]triazolo[4,3-a]quinoxaline-4-ylamino]-butyl}-butyramide;
(345) 4-{1-methyl-4-[4-(3-methyl-butylamino)-butylamino]-[1,2,4]triazolo[4,3-a]quinoxaline-7-yloxy}-piperidine-1-carboxylic acid-tert-butylester;
(346) N-[4-(7-benzyloxy-1-methyl-[1,2,4]triazolo[4,3-a]quinoxaline-4-ylamino)-butyl]-3-methyl-butyramide;
(347) N-(4-{7-[4-(N-hydroxycarbamimidoyl)-benzoyl]-1-methyl-[1,2,4]triazolo[4,3-a]quinoxaline-4-ylamino}-butyl)-3-methyl-butyramide;
(348) 3-methyl-N-(4-{1-methyl-7-[4-(2H-tetrazol-5-yl)-benzyloxy]-[1,2,4]triazolo[4,3-a]quinoxaline-4-ylamino}-butyl)-butyramide;
(349) 3-methyl-N-(4-{1-methyl-7-[4-(2-methyl-2H-tetrazolo-5-yl)-benzyloxy]-[1,2,4]triazolo[4,3-a]quinoxaline-4-ylamino}-butyl)-butyramide;
(350) benzoic acid-1-methyl-4-[4-(3-methyl-butylamino)-butylamino]-[1,2,4]triazolo[4,3-a]quinoxaline-7-yl-ester;
(351) morpholine-4-carboxylic acid-1-methyl-4-[4-(3-methyl-butylamino)-butylamino]-[1,2,4]triazolo[4,3-a]quinoxaline-7-yl-ester;
(352) 3-methyl-thiophene-2-carboxylic acid-1-methyl-4-[4-(3-methyl-butylamino)-butylamino]-[1,2,4]triazolo[4,3-a]quinoxaline-7-yl-ester;
(353) dimethyl-thiocarbamic acid-O-{1-methyl-4-[4-(3-methyl-butylamino)-butylamino]-[1,2,4]triazolo[4,3-a]quinoxaline-7-yl}-ester;

(354) [4-(1-methyl-7-methylsulfanyl-[1,2,4]triazolo[4,3-a]quinoxaline-4-ylamino)-butyl]-carbamic acid-tert-butylester;
(355) N$^1$-(1-methyl-(7-methylsulfanyl-[1,2,4]triazolo[4,3-a]quinoxaline-4-yl)-butane-1,4-diamine ditrifluoroacetic acid;
(356) 3-methyl-N-[4-(1-methyl-7-methylsulfanyl-[1,2,4]triazolo[4,3-a]quinoxaline-4-ylamino)-butyl]-butyramide;
(357) 2-(S)-fluoro-3-methyl-N-[4-(1-methyl-7-methylsulfanyl-[1,2,4]triazolo[4,3-a]quinoxaline-4-ylamino)-butyl]-butyramide;
(358) 2-(S)-hydroxy-3-methyl-N-[4-(1-methyl-7-methylsulfanyl-[1,2,4]triazolo[4,3-a]quinoxaline-4-ylamino)-butyl]-butyramide;
(359) N-[4-(7-methanesulfinyl-1-methyl-[1,2,4]triazolo[4,3-a]quinoxaline-4-ylamino)-butyl]-3-methyl-butyramide;
(360) N-[4-(7-methanesulfonyl-1-methyl-[1,2,4]triazolo[4,3-a]quinoxaline-4-ylamino)-butyl]-3-methyl-butyramide;
(361) [4-(7-fluoro-1-methyl-[1,2,4]triazolo[4,3-a]quinoxaline-4-ylamino)-butyl]-carbamic acid-tert-butylester;
(362) 4-(7-chloro-1-methyl-[1,2,4]triazolo[4,3-a]quinoxaline-4-ylamino)-carbamic acid-tert-butylester;
(363) {4-[7-(2-methoxy-ethoxy)-1-methyl-[1,2,4]triazolo[4,3-a]quinoxaline-4-ylamino]-butyl}-carbamic acid-tert-butylester;
(364) N$^1$-[7-(2-methoxy-ethoxy)-1-methyl-[1,2,4]triazolo[4,3-a]quinoxaline-4-yl]-butane-1,4-diamine ditrifluoroacetic acid;
(365) N-{4-[7-(2-methoxy-ethoxy)-1-methyl-[1,2,4]triazolo[4,3-a]quinoxaline-4-ylamino]-butyl}-3-methyl-butyramide;
(366) {4-[7-(2-methoxy-ethoxy)-1-methyl-[1,2,4]triazolo[4,3-a]quinoxaline-4-ylamino]-butyl}-carbamic acid isopropylester;
(367) {4-[7-(2-methoxy-ethoxy)-1-methyl-[1,2,4]triazolo[4,3-a]quinoxaline-4-ylamino]-butyl}-carbamic acid propylester;
(368) {4-[7-(2-methoxy-ethoxy)-1-methyl-[1,2,4]triazolo[4,3-a]quinoxaline-4-ylamino]-butyl}-carbamic acid-sec-butylester;
(369) {4-[7-(2-methoxy-ethoxy)-1-methyl-[1,2,4]triazolo[4,3-a]quinoxaline-4-ylamino]-butyl}-carbamic acid isobutylester;
(370) {4-[7-(2-methoxy-ethoxy)-1-methyl-[1,2,4]triazolo[4,3-a]quinoxaline-4-ylamino]-butyl}-carbamic acid allylester;
(371) {4-[7-(2-methoxy-ethoxy)-1-methyl-[1,2,4]triazolo[4,3-a]quinoxaline-4-ylamino]-butyl}-carbamic acid cyclopentylester;
(372) {4-[7-(2-methoxy-ethoxy)-1-methyl-[1,2,4]triazolo[4,3-a]quinoxaline-4-ylamino]-butyl}-carbamic acid phenylester;
(373) {4-[7-(2-methoxy-ethoxy)-1-methyl-[1,2,4]triazolo[4,3-a]quinoxaline-4-ylamino]-butyl}-carbamic acid benzylester;
(374) {4-[7-(2-methoxy-ethoxy)-1-methyl-[1,2,4]triazolo[4,3-a]quinoxaline-4-ylamino]-butyl}-acetamide;
(375) {4-[7-(2-methoxy-ethoxy)-1-methyl-[1,2,4]triazolo[4,3-a]quinoxaline-4-ylamino]-butyl}-2,2-dimethyl-propionamide;
(376) {4-[7-(2-methoxy-ethoxy)-1-methyl-[1,2,4]triazolo[4,3-a]quinoxaline-4-ylamino]-butyl}-isobutyramide;
(377) cyclopropanecarboxylic acid-{4-[7-(2-methoxy-ethoxy)-1-methyl-[1,2,4]triazolo[4,3-a]quinoxaline-4-ylamino]-butyl}-amide;
(378) 3-methyl-butene-2-oic acid-{4-[7-(2-methoxy-ethoxy)-1-methyl-[1,2,4]triazolo[4,3-a]quinoxaline-4-ylamino]-butyl}-amide;
(379) butene-2-oic acid-{4-[7-(2-methoxy-ethoxy)-1-methyl-[1,2,4]triazolo[4,3-a]quinoxaline-4-ylamino]-butyl}-amide;
(380) N-{4-[7-(2-methoxy-ethoxy)-1-methyl-[1,2,4]triazolo[4,3-a]quinoxaline-4-ylamino]-butyl}-2-methyl-butyramide;
(381) 2-ethyl-N-{4-[7-(2-methoxy-ethoxy)-1-methyl-[1,2,4]triazolo[4,3-a]quinoxaline-4-ylamino]-butyl}-butyramide;
(382) N-{4-[7-(2-methoxy-ethoxy)-1-methyl-[1,2,4]triazolo[4,3-a]quinoxaline-4-ylamino]-butyl}-3,3-dimethyl-butyramide;
(383) 4-methyl-pentanoic acid-{4-[7-(2-methoxy-ethoxy)-1-methyl-[1,2,4]triazolo[4,3-a]quinoxaline-4-ylamino]-butyl}-amide;
(384) acetic acid-1-{4-[7-(2-methoxy-ethoxy)-1-methyl-[1,2,4]triazolo[4,3-a]quinoxaline-4-ylamino]-butylcarbamoyl}-1-methyl-ethylester;
(385) 2-hydroxy-N-{4-(7-(2-methoxy-ethoxy)-1-methyl-[1,2,4]triazolo[4,3-a]quinoxaline-4-ylamino)-butyl}-2-methyl-propionamide;
(386) acetic acid-{4-[7-(2-methoxy-ethoxy)-1-methyl-[1,2,4]triazolo[4,3-a]quinoxaline-4-ylamino]-butylcarbamoyl}-methylester;
(387) 2-hydroxy-N-{4-[7-(2-methoxy-ethoxy)-1-methyl-[1,2,4]triazolo[4,3-a]quinoxaline-4-ylamino]-butyl}-acetamide;
(388) 2-(R)-hydroxy-N-{4-[7-(2-methoxy-ethoxy)-1-methyl-[1,2,4]triazolo[4,3-a]quinoxaline-4-ylamino]-butyl}-3-methyl-butyramide;
(389) 2-(S)-hydroxy-N-{4-[7-(2-methoxy-ethoxy)-1-methyl-[1,2,4]triazolo[4,3-a]quinoxaline-4-ylamino]-butyl}-3-methyl-butyramide;
(390) 2-(R)-methoxy-N-{4-[7-(2-methoxy-ethoxy)-1-methyl-[1,2,4]triazolo[4,3-a]quinoxaline-4-ylamino]-butyl}-3-methyl-butyramide;
(391) 2,2-difluoro-N-{4-[7-(2-methoxy-ethoxy)-1-methyl-[1,2,4]triazolo[4,3-a]quinoxaline-4-ylamino]-butyl}-butyramide;
(392) 3,3,3-trifluoro-N-{4-[7-(2-methoxy-ethoxy)-1-methyl-[1,2,4]triazolo[4,3-a]quinoxaline-4-ylamino]-butyl}-2,2-dimethyl-propionamide;
(393) 3-cyclopentyl-N-{4-[7-(2-methoxy-ethoxy)-1-methyl-[1,2,4]triazolo[4,3-a]quinoxaline-4-ylamino]-butyl}-propionamide;
(394) N-{4-[7-(2-methoxy-ethoxy)-1-methyl-[1,2,4]triazolo[4,3-a]quinoxaline-4-ylamino]-butyl}-malonamic acid ethylester;
(395) N-{4-[7-(2-methoxy-ethoxy)-1-methyl-[1,2,4]triazolo[4,3-a]quinoxaline-4-ylamino]-butyl}-malonamic acid;
(396) (1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid-tert-butylester;
(397) 2-amino-N-{4-[7-(2-methoxy-ethoxy)-1-methyl-[1,2,4]triazolo[4,3-a]quinoxaline-4-ylamino]-butyl}-3-methyl-butyramide;
(398) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid isobutylester;

(399) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid propylester;
(400) (S)-(1-{4-[7-(2-methoxy-ethoxy)-1-methyl-[1,2,4]triazolo[4,3-a]quinoxaline-4-ylamino]-butylcarbamoyl}-2-methyl-propyl)-carbamic acid isopropylester;
(401) (S)—N-{4-[7-(2-methoxy-ethoxy)-1-methyl-[1,2,4]triazolo[4,3-a]quinoxaline-4-ylamino]-butyl}-3-methyl-2-(3-methyl-butyrylamino)-butyramide;
(402) (S)-2-(2,2-dimethyl-propionylamino)-N-{4-[7-(2-methoxy-ethoxy)-1-methyl-[1,2,4]triazolo[4,3-a]quinoxaline-4-ylamino]-butyl}-3-methyl-butyramide;
(403) 2-(S,R)-hydroxy-N-(1-{4-[7-(2-methoxy-ethoxy)-1-methyl-[1,2,4]triazolo[4,3-a]quinoxaline-4-ylamino]-butylcarbamoyl}-2-methyl-propyl)-3-methyl-butyramide;
(404) 2-(S,S)-hydroxy-N-(1-{4-[7-(2-methoxy-ethoxy)-1-methyl-[1,2,4]triazolo[4,3-a]quinoxaline-4-ylamino]-butylcarbamoyl}-2-methyl-propyl)-3-methyl-butyramide;
(405) 2-(S)-methanesulfonylamino-{4-[7-(2-methoxy-ethoxy)-1-methyl-[1,2,4]triazolo[4,3-a]quinoxaline-4-ylamino]-butyl}-3-methyl-butyramide;
(406) N-{4-[7-(2-methoxy-ethoxy)-1-methyl-[1,2,4]triazolo[4,3-a]quinoxaline-4-ylamino]-butyl}-2-thiophene-2-yl-acetamide;
(407) 2-furan-2-yl-N-{4-[7-(2-methoxy-ethoxy)-1-methyl-[1,2,4]triazolo[4,3-a]quinoxaline-4-ylamino]-butyl}-acetamide;
(408) N-{4-[7-(2-methoxy-ethoxy)-1-methyl-[1,2,4]triazolo[4,3-a]quinoxaline-4-ylamino]-butyl}-benzamide;
(409) 2-fluoro-N-{4-[7-(2-methoxy-ethoxy)-1-methyl-[1,2,4]triazolo[4,3-a]quinoxaline-4-ylamino]-butyl}-benzamide;
(410) 3-fluoro-N-{4-[7-(2-methoxy-ethoxy)-1-methyl-[1,2,4]triazolo[4,3-a]quinoxaline-4-ylamino]-butyl}-benzamide;
(411) 2-chloro-N-{4-[7-(2-methoxy-ethoxy)-1-methyl-[1,2,4]triazolo[4,3-a]quinoxaline-4-ylamino]-butyl}-benzamide;
(412) 2-chloro-N-{4-[7-(2-methoxy-ethoxy)-1-methyl-[1,2,4]triazolo[4,3-a]quinoxaline-4-ylamino]-butyl}-benzamide;
(413) 2,3-dichloro-N-{4-[7-(2-methoxy-ethoxy)-1-methyl-[1,2,4]triazolo[4,3-a]quinoxaline-4-ylamino]-butyl}-benzamide;
(414) 2-methoxy-N-{4-[7-(2-methoxy-ethoxy)-1-methyl-[1,2,4]triazolo[4,3-a]quinoxaline-4-ylamino]-butyl}-benzamide;
(415) N-{4-[7-(2-methoxy-ethoxy)-1-methyl-[1,2,4]triazolo[4,3-a]quinoxaline-4-ylamino]-butyl}-4-nitro-butyramide;
(416) pyridine-2-carboxylic acid-{4-[7-(2-methoxy-ethoxy)-1-methyl-[1,2,4]triazolo[4,3-a]quinoxaline-4-ylamino]-butyl}-amide;
(417) N-{4-[7-(2-methoxy-ethoxy)-1-methyl-[1,2,4]triazolo[4,3-a]quinoxaline-4-ylamino]-butyl}-nicotinamide;
(418) N-{4-[7-(2-methoxy-ethoxy)-1-methyl-[1,2,4]triazolo[4,3-a]quinoxaline-4-ylamino]-butyl}-isonicotinamide;
(419) 6-chloro-N-{4-[7-(2-methoxy-ethoxy)-1-methyl-[1,2,4]triazolo[4,3-a]quinoxaline-4-ylamino]-butyl}-nicotinamide;
(420) N-{4-[7-(2-methoxy-ethoxy)-1-methyl-[1,2,4]triazolo[4,3-a]quinoxaline-4-ylamino]-butyl}-2-phenyl-acetamide;
(421) 3-{4-[7-(2-methoxy-ethoxy)-1-methyl-[1,2,4]triazolo[4,3-a]quinoxaline-4-ylamino]-butyl}-1,1-dimethyl-urea;
(422) 1-isopropyl-3-{4-[7-(2-methoxy-ethoxy)-1-methyl-[1,2,4]triazolo[4,3-a]quinoxaline-4-ylamino]-butyl}-urea;
(423) 1-ethyl-3-{4-[7-(2-methoxy-ethoxy)-1-methyl-[1,2,4]triazolo[4,3-a]quinoxaline-4-ylamino]-butyl}-urea;
(424) 1-tert-butyl-3-{4-[7-(2-methoxy-ethoxy)-1-methyl-[1,2,4]triazolo[4,3-a]quinoxaline-4-ylamino]-butyl}-urea;
(425) morpholine-4-carboxylic acid-{4-[7-(2-methoxy-ethoxy)-1-methyl-[1,2,4]triazolo[4,3-a]quinoxaline-4-ylamino]-butyl}-amide;
(426) 1-cyclohexyl-3-{4-[7-(2-methoxy-ethoxy)-1-methyl-[1,2,4]triazolo[4,3-a]quinoxaline-4-ylamino]-butyl}-urea;
(427) 3-{4-[7-(2-methoxy-ethoxy)-1-methyl-[1,2,4]triazolo[4,3-a]quinoxaline-4-ylamino]-butyl}-1-phenyl-urea;
(428) {4-[7-(2-methoxy-ethoxy)-1-methyl-[1,2,4]triazolo[4,3-a]quinoxaline-4-ylamino]-butyl}-thiocarbamic acid-S-isopropylester;
(429) N-{4-[7-(2-methoxy-ethoxy)-1-methyl-[1,2,4]triazolo[4,3-a]quinoxaline-4-ylamino]-butyl}-methanesulfonamide;
(430) {4-[1-methyl-7-(2-morpholine-4-yl-ethoxy)-[1,2,4]triazolo[4,3-a]quinoxaline-4-ylamino]-butyl}-carbamic acid-tert-butylester;
(431) $N^1$-{4-[1-methyl-7-(2-morpholine-4-yl-ethoxy)-[1,2,4]triazolo[4,3-a]quinoxaline-4-yl]-butane-1,4-diamine trifluoroacetic acid;
(432) 3-methyl-N-{4-[1-methyl-7-(2-morpholine-4-yl-ethoxy)-[1,2,4]triazolo[4,3-a]quinoxaline-4-ylamino]-butyl}-butyramide;
(433) 2,2-dimethyl-N-{4-[1-methyl-7-(2-morpholine-4-yl-ethoxy)-[1,2,4]triazolo[4,3-a]quinoxaline-4-ylamino]-butyl}-propionamide;
(434) 2-(R)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide;
(435) 2-(S)-hydroxy-N-{4-[7-(2-morpholine-4-yl-ethoxy)-1-methyl-[1,2,4]triazolo[4,3-a]quinoxaline-4-ylamino]-butyl}-3-methyl-butyramide;
(436) {4-[1-methyl-7-(2-morpholine-4-yl-ethoxy)-[1,2,4]triazolo[4,3-a]quinoxaline-4-ylamino]-butyl}-carbamic acid isopropylester;
(437) {4-[1-methyl-7-(2-morpholine-4-yl-ethoxy)-[1,2,4]triazolo[4,3-a]quinoxaline-4-ylamino]-butyl}-carbamic acid cyclopentylester;
(438) N-{4-[1-methyl-7-(2-morpholine-4-yl-ethoxy)-[1,2,4]triazolo[4,3-a]quinoxaline-4-ylamino]-butyl}-2-thiophene-2-yl-acetamide;
(439) 2-chloro-N-{4-[1-methyl-7-(2-morpholine-4-yl-ethoxy)-[1,2,4]triazolo[4,3-a]quinoxaline-4-ylamino]-butyl}-benzamide;
(440) [4-(7-ethoxy-1-methyl-[1,2,4]triazolo[4,3-a]quinoxaline-4-ylamino)-butyl]-carbamic acid-tert-butylester;
(441) $N^1$-(7-ethoxy-1-methyl-[1,2,4]triazolo[4,3-a]quinoxaline-4-yl)-butane-1,4-diamine dihydrochloride;
(442) N-[4-(7-ethoxy-1-methyl-[1,2,4]triazolo[4,3-a]quinoxaline-4-ylamino)-butyl]-3-methyl-butyramide;

(443) [4-(7-ethoxy-1-methyl-[1,2,4]triazolo[4,3-a]quinoxaline-4-ylamino)-butyl]-carbamic acid isopropylester;
(444) [4-(7-ethoxy-1-methyl-[1,2,4]triazolo[4,3-a]quinoxaline-4-ylamino)-butyl]-carbamic acid isobutylester;
(445) [4-(7-ethoxy-1-methyl-[1,2,4]triazolo[4,3-a]quinoxaline-4-ylamino)-butyl]-carbamic acid cyclopentylester;
(446) N-[4-(7-ethoxy-1-methyl-[1,2,4]triazolo[4,3-a]quinoxaline-4-ylamino)-butyl]-2-thiophene-2-yl-acetamide;
(447) [4-(7-isopropoxy-1-methyl-[1,2,4]triazolo[4,3-a]quinoxaline-4-ylamino)-butyl]-carbamic acid-tert-butylester;
(448) $N^1$-(7-isopropoxy-1-methyl-[1,2,4]triazolo[4,3-a]quinoxaline-4-yl)-butane-1,4-diamine ditrifluoroacetic acid;
(449) N-[-(7-isopropoxy-1-methyl-[1,2,4]triazolo[4,3-a]quinoxaline-4-ylamino)-butyl]-3-methyl-butyramide;
(450) N-[4-(7-isopropoxy-1-methyl-[1,2,4]triazolo[4,3-a]quinoxaline-4-ylamino)-butyl]-2-methyl-butyramide;
(451) N-[4-(7-isopropoxy-1-methyl-[1,2,4]triazolo[4,3-a]quinoxaline-4-ylamino)-butyl]-2-thiophene-2-yl-acetamide;
(452) [4-(7-isopropoxy-1-methyl-[1,2,4]triazolo[4,3-a]quinoxaline-4-ylamino)-butyl]-carbamic acid isopropylester;
(453) [4-(7-isopropoxy-1-methyl-[1,2,4]triazolo[4,3-a]quinoxaline-4-ylamino)-butyl]-carbamic acid cyclopentylester;
(454) 2-chloro-N-[4-(7-isopropoxy-1-methyl-[1,2,4]triazolo[4,3-a]quinoxaline-4-ylamino)-butyl]-benzamide;
(455) [4-(7-methoxy-1,9-dimethyl-[1,2,4]triazolo[4,3-a]quinoxaline-4-ylamino)-butyl]-carbamic acid-tert-butylester;
(456) $N^1$-(7-methoxy-1,9-dimethyl-[1,2,4]triazolo[4,3-a]quinoxaline-4-yl)-butane-1,4-diamine ditrifluoroacetic acid;
(457) [4-(7-methoxy-1,9-dimethyl-[1,2,4]triazolo[4,3-a]quinoxaline-4-ylamino)-butyl]-carbamic acid isopropylester;
(458) [4-(7-methoxy-1,9-dimethyl-[1,2,4]triazolo[4,3-a]quinoxaline-4-ylamino)-butyl]-3-methyl-butyramide;
(459) [4-(6-chloro-7-methoxy-1-methyl-[1,2,4]triazolo[4,3-a]quinoxaline-4-ylamino)-butyl]-carbamic acid-tert-butylester;
(460) [4-(6-chloro-7-methoxy-1-methyl-[1,2,4]triazolo[4,3-a]quinoxaline-4-yl)-butane-1,4-diamine dihydrochloride;
(461) [4-(6-chloro-7-methoxy-1-methyl-[1,2,4]triazolo[4,3-a]quinoxaline-4-ylamino)-butyl]-3-methyl-butyramide;
(462) [4-(6-chloro-7-methoxy-1-methyl-[1,2,4]triazolo[4,3-a]quinoxaline-4-ylamino)-butyl]-carbamic acid isobutylester;
(463) N-[4-(6-chloro-7-methoxy-1-methyl-[1,2,4]triazolo[4,3-a]quinoxaline-4-ylamino)-butyl]-2-thiophene-2-yl-acetamide;
(464) [4-(7-methoxy-1,8-dimethyl-[1,2,4]triazolo[4,3-a]quinoxaline-4-ylamino)-butyl]-carbamic acid-tert-butylester;
(465) $N^1$-(7-methoxy-1,8-dimethyl-[1,2,4]triazolo[4,3-a]quinoxaline-4-yl)-butane-1,4-diamine ditrifluoroacetic acid;
(466) N-[4-(7-methoxy-1,8-dimethyl-[1,2,4]triazolo[4,3-a]quinoxaline-4-ylamino)-butyl]-2,2-dimethyl-propionamide;
(467) [4-(7-methoxy-1,8-dimethyl-[1,2,4]triazolo[4,3-a]quinoxaline-4-ylamino)-butyl]-carbamic acid isopropylester;
(468) [4-(7-methoxy-1,8-dimethyl-[1,2,4]triazolo[4,3-a]quinoxaline-4-ylamino)-butyl]-carbamic acid isobutylester;
(469) N-[4-(7-methoxy-1,8-dimethyl-[1,2,4]triazolo[4,3-a]quinoxaline-4-ylamino)-butyl]-3-methyl-butyramide;
(470) 2-chloro-N-[4-(7-methoxy-1,8-dimethyl-[1,2,4]triazolo[4,3-a]quinoxaline-4-ylol-□])-butyl]-benzamide;
(471) [4-(7-methoxy-1-methyl-8-trifluoromethyl-[1,2,4]triazolo[4,3-a]quinoxaline-4-ylamino)-butyl]-carbamic acid-tert-butylester;
(472) $N^1$-(7-methoxy-1-methyl-8-trifluoromethyl-[1,2,4]triazolo[4,3-a]quinoxaline-4-yl)-butane-1,4-diamine ditrifluoroacetic acid;
(473) [4-(7-methoxy-1-methyl-8-trifluoromethyl-[1,2,4]triazolo[4,3-a]quinoxaline-4-ylamino)-butyl]-carbamic acid isopropylester;
(474) [4-(7-methoxy-1-methyl-8-trifluoromethyl-[1,2,4]triazolo[4,3-a]quinoxaline-4-ylamino)-butyl]-carbamic acid isobutylester;
(475) [4-(7-methoxy-1-methyl-8-trifluoromethyl-[1,2,4]triazolo[4,3-a]quinoxaline-4-ylamino)-butyl]-carbamic acid cyclopentylester;
(476) N-[4-(7-methoxy-1-methyl-8-trifluoromethyl-[1,2,4]triazolo[4,3-a]quinoxaline-4-ylamino)-butyl]-3-methyl-butyramide;
(477) N-[4-(7-methoxy-1-methyl-8-trifluoromethyl-[1,2,4]triazolo[4,3-a]quinoxaline-4-ylamino)-butyl]-2,2-dimethyl-propionamide;
(478) 2-(R)-hydroxy-N-[4-(7-methoxy-1-methyl-8-trifluoromethyl-[1,2,4]triazolo[4,3-a]quinoxaline-4-ylamino)-butyl]-3-methyl-butyramide;
(479) 2-(S)-hydroxy-N-[4-(7-methoxy-1-methyl-8-trifluoromethyl-[1,2,4]triazolo[4,3-a]quinoxaline-4-ylamino)-butyl]-3-methyl-butyramide;
(480) N-[4-(7-methoxy-1-methyl-8-trifluoromethyl-[1,2,4]triazolo[4,3-a]quinoxaline-4-ylamino)-butyl]-2-thiophene-2-yl-acetamide;
(481) 2-chloro-N-[4-(7-methoxy-1-methyl-8-trifluoromethyl-[1,2,4]triazolo[4,3-a]quinoxaline-4-ylamino)-butyl]-benzamide;
(482) 1-cyclohexyl-3-[4-(7-methoxy-1-methyl-8-trifluoromethyl-[1,2,4]triazolo[4,3-a]quinoxaline-4-ylamino)-butyl]-urea;
(483) {4-[7-methoxy-8-(2-methoxy-ethoxy)-1-methyl-[1,2,4]triazolo[4,3-a]quinoxaline-4-ylamino]-butyl}-carbamic acid-tert-butylester;
(484) $N^1$-[7-methoxy-8-(2-methoxy-ethoxy)-1-methyl-[1,2,4]triazolo[4,3-a]quinoxaline-4-yl]-butane-1,4-diamine ditrifluoroacetic acid;
(485) N-{4-[7-methoxy-8-(2-methoxy-ethoxy)-1-methyl-[1,2,4]triazolo[4,3-a]quinoxaline-4-ylamino]-butyl}-3-methyl-butyramide;
(486) [4-(7,8,9-trimethoxy-1-methyl-[1,2,4]triazolo[4,3-a]quinoxaline-4-ylamino)-butyl]-carbamic acid-tert-butylester;
(487) $N^1$-(7,8,9-trimethoxy-1-methyl-[1,2,4]triazolo[4,3-a]quinoxaline-4-yl)-butane-1,4-diamine ditrifluoroacetic acid;

(488) 3-methyl-N-[4-(7,8,9-trimethoxy-1-methyl-[1,2,4]triazolo[4,3-a]quinoxaline-4-ylamino)-butyl]-butyramide;
(489) 3-methyl-pentanoic acid-[4-(6,8,9-trimethoxy-1-methyl-[1,2,4]triazolo[4,3-a]quinoxaline-4-ylamino)-butyl]-amide;
(490) [4-(7-imidazole-1-yl-1-methyl-[1,2,4]triazolo[4,3-a]quinoxaline-4-ylamino)-butyl]-carbamic acid-tert-butylester;
(491) $N^1$-(7-imidazole-1-yl-1-methyl-[1,2,4]triazolo[4,3-a]quinoxaline-4-yl)-butane-1,4-diamine dihydrochloride;
(492) N-[4-(7-imidazole-1-yl-1-methyl-[1,2,4]triazolo[4,3-a]quinoxaline-4-ylamino)-butyl]-3-methyl-butyramide;
(493) [4-(7-imidazole-1-yl-1-methyl-[1,2,4]triazolo[4,3-a]quinoxaline-4-ylamino)-butyl]-carbamic acid isobutylester;
(494) [4-(7-imidazole-1-yl-1-methyl-[1,2,4]triazolo[4,3-a]quinoxaline-4-ylamino)-butyl]-carbamic acid isopropylester;
(495) 3-methyl-pentanoic acid-[4-(7-imidazole-1-yl-1-methyl-[1,2,4]triazolo[4,3-a]quinoxaline-4-ylamino)-butyl]-amide;
(496) N-[4-(7-imidazole-1-yl-1-methyl-[1,2,4]triazolo[4,3-a]quinoxaline-4-ylamino)-butyl]-2-thiophene-2-yl-acetamide;
(497) [4-(1-methyl-7-morpholine-4-yl-[1,2,4]triazolo[4,3-a]quinoxaline-4-ylamino)-butyl]-carbamic acid-tert-butylester;
(498) $N^1$-(1-methyl-7-morpholine-4-yl-[1,2,4]triazolo[4,3-a]quinoxaline-4-yl)-butane-1,4-diamine dihydrochloride;
(499) 3-methyl-N-[4-(1-methyl-7-morpholine-4-yl-[1,2,4]triazolo[4,3-a]quinoxaline-4-ylamino)-butyl]-butyramide;
(500) 2-(S)-fluoro-3-methyl-N-[4-(1-methyl-7-morpholine-4-yl-[1,2,4]triazolo[4,3-a]quinoxaline-4-ylamino)-butyl]-butyramide;
(501) 3-methyl-pentanoic acid-[4-(1-methyl-7-morpholine-4-yl-[1,2,4]triazolo[4,3-a]quinoxaline-4-ylamino)-butyl]-amide;
(502) (S)-{2-methyl-1-[4-(1-methyl-7-morpholine-4-yl-[1,2,4]triazolo[4,3-a]quinoxaline-4-ylamino)-butylcarbamoyl]-propyl}-carbamic acid-tert-butylester;
(503) 2-(S)-amino-3-methyl-N-[4-(1-methyl-7-morpholine-4-yl-[1,2,4]triazolo[4,3-a]quinoxaline-4-ylamino)-butyl]-butyramide hydrochloride;
(504) (S)-2-(2-(S)-hydroxy-propionylamino)-3-methyl-N-[4-(1-methyl-7-morpholine-4-yl-[1,2,4]triazolo[4,3-a]quinoxaline-4-ylamino)-butyl]-butyramide hydrochloride;
(505) 2-(S)-methanesulfonylamino-3-methyl-N-[4-(1-methyl-7-morphonyl-4-yl-[1,2,4]triazolo[4,3-a]quinoxaline-4-ylamino)-butyl]-butyramide;
(506) [4-(1-methyl-7-morpholine-4-yl-[1,2,4]triazolo[4,3-a]quinoxaline-4-ylamino)-butyl]-carbamic acid isopropylester;
(507) N-[4-(1-methyl-7-morpholine-4-yl-[1,2,4]triazolo[4,3-a]quinoxaline-4-ylamino)-butyl]-2-thiophene-2-yl-acetamide;
(508) {4-[7-(2,6-dimethyl-morphonyl-4-yl)-1-methyl-[1,2,4]triazolo[4,3-a]quinoxaline-4-ylamino]-butyl}-carbamic acid-tert-butylester;
(509) $N^1$-[7-(2,6-dimethyl-morphonyl-4-yl)-1-methyl-[1,2,4]triazolo[4,3-a]quinoxaline-4-yl]-butane-1,4-diamine ditrifluoroacetic acid;
(510) N-{4-[7-(2,6-dimethyl-morpholine-4-yl)-1-methyl-[1,2,4]triazolo[4,3-a]quinoxaline-4-ylamino]-butyl}-3-methyl-butyramide;
(511) N-{4-[7-(2,6-dimethyl-morphonyl-4-yl)-1-methyl-[1,2,4]triazolo[4,3-a]quinoxaline-4-ylamino]-butyl}-2-(S)-fluoro-3-methyl-butyramide;
(512) N-{4-[7-(2,6-dimethyl-morpholine-4-yl)-1-methyl-[1,2,4]triazolo[4,3-a]quinoxaline-4-ylamino]-butyl}-2-(R)-hydroxy-3-methyl-butyramide;
(513) (S)-(2-methyl-1-{4-[1-methyl-7-(2,6-dimethyl-morpholine-4-yl)-[1,2,4]triazolo[4,3-a]quinoxaline-4-ylamino]-butylcarbamoyl}-propyl)-carbamic acid-tert-butylester;
(514) 2-(S)-amino-N-{4-[7-(2,6-dimethyl-morpholine-4-yl)-1-methyl-[1,2,4]triazolo[4,3-a]quinoxaline-4-ylamino]-butyl}-3-methyl-butyramide hydrochloride;
(515) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isobutylester;
(516) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid propylester;
(517) (S)—N-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-2-(S)-fluoro-3-methyl-butyramide;
(518) (S)—N-{4-[7-(2,6-dimethyl-morpholine-4-yl)-1-methyl-[1,2,4]triazolo[4,3-a]quinoxaline-4-ylamino]-butyl}-3-methyl-2-(3-methyl-butyrylamino)-butyramide;
(519) (S)—N-{4-[7-(2,6-dimethyl-morpholine-4-yl)-1-methyl-[1,2,4]triazolo[4,3-a]quinoxaline-4-ylamino]-butyl}-2-(2,2-dimethyl-propionylamino)-3-methyl-butyramide;
(520) (S)-(1-{4-[7-(2,6-dimethyl-morpholine-4-yl)-1-methyl-[1,2,4]triazolo[4,3-a]quinoxaline-4-ylamino]-butylcarbamoyl}-2-methyl-propyl)-carbamic acid isopropylester;
(521) {[4-(1-methyl-7-thiomorpholine-4-yl)-[1,2,4]triazolo[4,3-a]quinoxaline-4-ylamino]-butyl}-carbamic acid-tert-butylester;
(522) N-(1-methyl-7-thiomorphonyl-4-yl-[1,2,4]triazolo[4,3-a]quinoxaline-4-yl)-butane-1,4-diamine ditrifluoroacetic acid;
(523) 3-methyl-N-[4-(1-methyl-7-thiomorpholine-4-yl-[1,2,4]triazolo[4,3-a]quinoxaline-4-ylamino)-butyl]-butyramide;
(524) N-[4-(7-thiomorphonyl-4-yl-1-methyl-[1,2,4]triazolo[4,3-a]quinoxaline-4-ylamino)-butyl]-2-(R)-hydroxy-3-methyl-butyramide;
(525) N-[4-(7-thiomorphonyl-4-yl-1-methyl-[1,2,4]triazolo[4,3-a]quinoxaline-4-ylamino)-butyl]-2-(S)-hydroxy-3-methyl-butyramide;
(526) {4-[7-(6,7-dihydro-4H-thiano[3,2-c]pyridine-5-yl)-1-methyl-[1,2,4]triazolo[4,3-a]quinoxaline-4-ylamino]-butyl}-carbamic acid-tert-butylester;
(527) $N^1$-[7-(6,7-dihydro-4H-thiano[3,2-c]pyridine-5-yl)-1-methyl-[1,2,4]triazolo[4,3-a]quinoxaline-4-yl]-butane-1,4-diamine ditrifluoroacetic acid;
(528) N-{4-[7-(6,7-dihydro-4H-thiano[3,2-c]pyridine-5-yl)-1-methyl-[1,2,4]triazolo[4,3-a]quinoxaline-4-ylamino]-butyl}-3-methyl-butyramide;
(529) N-{4-[7-(6,7-dihydro-4H-thiano[3,2-c]pyridine-5-yl)-1-methyl-[1,2,4]triazolo[4,3-a]quinoxaline-4-ylamino]-butyl}-2-(S)-fluoro-3-methyl-butyramide;

(530) 4-(4-tert-butoxycarbonylamino-butylamino)-1-methyl-[1,2,4]triazolo[4,3-a]quinoxaline-8-carboxylic acid methylester;
(531) 4-(4-tert-butoxycarbonylamino-butylamino)-1-methyl-[1,2,4]triazolo[4,3-a]quinoxaline-8-carboxylic acid;
(532) [4-(8-isopropylcarbamoyl-1-methyl-[1,2,4]triazolo[4,3-a]quinoxaline-4-ylamino)-butyl]-carbamic acid-tert-butylester;
(533) [4-(8-carbamoyl-1-methyl-[1,2,4]triazolo[4,3-a]quinoxaline-4-ylamino)-butyl]-carbamic acid-tert-butylester;
(534) 4-(4-isobutyramido-butylamino)-1-methyl-[1,2,4]triazolo[4,3-a]quinoxaline-8-carboxylic acid isopropylamide;
(535) 4-(4-benzylamino-butylamino)-1-methyl-[1,2,4]triazolo[4,3-a]quinoxaline-8-carboxylic acid isopropylamide;
(536) {4-[8-(2-dimethylamino-ethylcarbamoyl)-1-methyl-[1,2,4]triazolo[4,3-a]quinoxaline-4-ylamino]-butyl}-carbamic acid-tert-butylester;
(537) 4-(4-benzoylamino)-1-methyl-[1,2,4]triazolo[4,3-a]quinoxaline-8-carboxylic acid-(2-dimethylamino-ethyl)-amide;
(538) [4-(1-methyl-8-phenylcarbamoyl-[1,2,4]triazolo[4,3-a]quinoxaline-4-ylamino)-butyl]-carbamic acid-tert-butylester;
(539) N-{4-[8-(4-benzyl-piperazine-1-carbonyl)-1-methyl-[1,2,4]triazolo[4,3-a]quinoxaline-4-ylamino]-butyl}-benzamide;
(540) N-{4-[1-methyl-8-(piperazine-1-carbonyl)-[1,2,4]triazolo[4,3-a]quinoxaline-4-ylamino]-butyl}-benzamide;
(541) [4-(1-methyl-8-nitro-[1,2,4]triazolo[4,3-a]quinoxaline-4-ylamino)-butyl]-carbamic acid-tert-butylester;
(542) [4-(8-amino-1-methyl-[1,2,4]triazolo[4,3-a]quinoxaline-4-ylamino)-butyl]-carbamic acid-tert-butylester;
(543) [4-(8-isobutyramido-1-methyl-[1,2,4]triazolo[4,3-a]quinoxaline-4-ylamino)-butyl]-carbamic acid-tert-butylester;
(544) N-[4-(4-aminobutylamino)-1-methyl-[1,2,4]triazolo[4,3-a]quinoxaline-8-yl]-isobutyramide ditrifluoroacetic acid;
(545) N-[4-(8-isobutyramido-1-methyl-[1,2,4]triazolo[4,3-a]quinoxaline-4-ylamino)-butyl]-2,2-dimethyl-propionamide;
(546) [4-(8-acetamino-1-methyl-[1,2,4]triazolo[4,3-a]quinoxaline-4-ylamino)-butyl]-carbamic acid-tert-butylester;
(547) N-[4-(8-acetamino-1-methyl-[1,2,4]triazolo[4,3-a]quinoxaline-4-ylamino)-butyl]-2,2-dimethyl-propionamide;
(548) N-[4-(8-acetamino-1-methyl-[1,2,4]triazolo[4,3-a]quinoxaline-4-ylamino)-butyl]-benzamide;
(549) N-[4-(8-isobutyramido-1-methyl-[1,2,4]triazolo[4,3-a]quinoxaline-4-ylamino)-butyl]-benzamide;
(550) 3-methyl-N-[4-(1-methyl-8-nitro-[1,2,4]triazolo[4,3-a]quinoxaline-4-ylamino)-butyl]-butyramide;
(551) N-[4-(8-amino-1-methyl-[1,2,4]triazolo[4,3-a]quinoxaline-4-ylamino)-butyl]-3-methyl-butyramide;
(552) 3-methyl-N-[4-(1-methyl-8-propylamino-[1,2,4]triazolo[4,3-a]quinoxaline-4-ylamino)-butyl]-butyramide;
(553) N-{4-[8-(3-cyano-propylamino)-1-methyl-[1,2,4]triazolo[4,3-a]quinoxaline-4-ylamino]-butyl}-3-methyl-butyramide;
(554) N-{4-[8-(3-ethyl-thioureido)-1-methyl-[1,2,4]triazolo[4,3-a]quinoxaline-4-ylamino]-butyl}-3-methyl-butyramide;
(555) N-[4-(7-methoxy-1-methyl-8-nitro-[1,2,4]triazolo[4,3-a]quinoxaline-4-ylamino)-butyl]-3-methyl-butyramide;
(556) N-[4-(8-amino-7-methoxy-1-methyl-[1,2,4]triazolo[4,3-a]quinoxaline-4-ylamino)-butyl]-3-methyl-butyramide;
(557) N-[4-(7-methoxy-1-methyl-8-methylamino-[1,2,4]triazolo[4,3-a]quinoxaline-4-ylamino)-butyl]-3-methyl-butyramide;
(558) N-[4-(8-hydroxyamino-7-methoxy-1-methyl-[1,2,4]triazolo[4,3-a]quinoxaline-4-ylamino)-butyl]-3-methyl-butyramide;
(559) N-[4-(7-methoxy-1-methyl-8-propylamino-[1,2,4]triazolo[4,3-a]quinoxaline-4-ylamino)-butyl]-3-methyl-butyramide;
(560) N-[4-(7-methoxy-1-methyl-8-prop-2-ylamino-[1,2,4]triazolo[4,3-a]quinoxaline-4-ylamino)-butyl]-3-methyl-butyramide;
(561) N-{4-[8-(3-isopropyl-ureido)-7-methoxy-1-methyl-[1,2,4]triazolo[4,3-a]quinoxaline-4-ylamino]-butyl}-3-methyl-butyramide;
(562) N-{4-[7-methoxy-1-methyl-8-(3-methyl-butyrylamino)-[1,2,4]triazolo[4,3-a]quinoxaline-4-ylamino]-butyl}-3-methyl-butyramide;
(563) N-{7-methoxy-1-methyl-4-[4-(3-methyl-butyrylamino)-[1,2,4]triazolo[4,3-a]quinoxaline-8-ylamino]-butyl}-3,3-dimethyl-butyramide;
(564) N-{4-[7-methoxy-1-methyl-8-(3-phenyl-ureido)-[1,2,4]triazolo[4,3-a]quinoxaline-4-ylamino]-butyl}-3-methyl-butyramide;
(565) N-[4-(8-methanesulfonylamino-7-methoxy-1-methyl-[1,2,4]triazolo[4,3-a]quinoxaline-4-ylamino)-butyl]-3-methyl-butyramide;
(566) N-[4-(8-dimethanesulfonylamino-7-methoxy-1-methyl-[1,2,4]triazolo[4,3-a]quinoxaline-4-ylamino)-butyl]-3-methyl-butyramide;
(567) N-{4-[7-methoxy-1-methyl-8-(2-methyl-propane-1-sulfonylamino)-[1,2,4]triazolo[4,3-a]quinoxaline-4-ylamino]-butyl}-3-methyl-butyramide;
(568) N-{4-[7-methoxy-1-methyl-8-(3-phenyl-ureido)-[1,2,4]triazolo[4,3-a]quinoxaline-4-ylamino]-butyl}-3-methyl-butyramide;
(569) N-{4-[8-(3-isopropyl-thioureido)-7-methoxy-1-methyl-[1,2,4]triazolo[4,3-a]quinoxaline-4-ylamino]-butyl}-3-methyl-butyramide;
(570) {4-[8-(4-methoxy-benzoyl)-1-methyl-[1,2,4]triazolo[4,3-a]quinoxaline-4-ylamino]-butyl}-carbamic acid-tert-butylester;
(571) [4-(8-benzoyl-1-methyl-[1,2,4]triazolo[4,3-a]quinoxaline-4-ylamino)-butyl]-carbamic acid-tert-butylester;
(572) [4-(8-fluoro-7-methoxy-1-methyl-[1,2,4]triazolo[4,3-a]quinoxaline-4-ylamino)-butyl]-carbamic acid-tert-butylester;
(573) [4-(7-fluoro-8-methoxy-1-methyl-[1,2,4]triazolo[4,3-a]quinoxaline-4-ylamino)-butyl]-carbamic acid-tert-butylester;
(574) N-[4-(8-fluoro-7-methoxy-1-methyl-[1,2,4]triazolo[4,3-a]quinoxaline-4-ylamino)-butyl]-3-methyl-butyramide;
(575) N-[4-(7-fluoro-8-methoxy-1-methyl-[1,2,4]triazolo[4,3-a]quinoxaline-4-ylamino)-butyl]-3-methyl-butyramide;

(576) N-{4-[7-methoxy-1-methyl-8-(2-morpholine-4-yl-ethoxy)-[1,2,4]triazolo[4,3-a]quinoxaline-4-ylamino]-butyl}-3-methyl-butyramide;
(577) N-{4-[8-methoxy-1-methyl-7-(2-morpholine-4-yl-ethoxy)-[1,2,4]triazolo[4,3-a]quinoxaline-4-ylamino]-butyl}-3-methyl-butyramide;
(578) {4-[8-(3,5-dimethyl-isoxazol-4-yl)-1-methyl-[1,2,4]triazolo[4,3-a]quinoxaline-4-ylamino]-butyl}-carbamic acid-tert-butylester;
(579) $N^1$-[8-(3,5-dimethyl-isoxazol-4-yl)-1-methyl-[1,2,4]triazolo[4,3-a]quinoxaline-4-yl]-butane-1,4-diamine ditrifluoroacetic acid;
(580) N-{4-[8-(3,5-dimethyl-isoxazol-4-yl)-1-methyl-[1,2,4]triazolo[4,3-a]quinoxaline-4-ylamino]-butyl}-3-methyl-butyramide;
(581) N-{4-[8-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide;
(582) N-{4-[8-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide;
(583) {4-[7-(3,5-dimethyl-isoxazol-4-yl)-1-methyl-[1,2,4]triazolo[4,3-a]quinoxaline-4-ylamino]-butyl}-carbamic acid-tert-butylester;
(584) $N^1$-[7-(3,5-dimethyl-isoxazol-4-yl)-1-methyl-[1,2,4]triazolo[4,3-a]quinoxaline-4-yl]-butane-1,4-diamine ditrifluoroacetic acid;
(585) N-{4-[7-(3,5-dimethyl-isoxazol-4-yl)-1-methyl-[1,2,4]triazolo[4,3-a]quinoxaline-4-ylamino]-butyl}-3-methyl-butyramide;
(586) N-{4-[7-(3,5-dimethyl-isoxazol-4-yl)-1-methyl-[1,2,4]triazolo[4,3-a]quinoxaline-4-ylamino]-butyl}-2-(R)-hydroxy-3-methyl-butyramide;
(587) N-{4-[7-(3,5-dimethyl-isoxazol-4-yl)-1-methyl-[1,2,4]triazolo[4,3-a]quinoxaline-4-ylamino]-butyl}-2-(S)-hydroxy-3-methyl-butyramide;
(588) $N^1$-[7-methoxy-1-trifluoromethyl-[1,2,4]triazolo[4,3-a]quinoxaline-4-yl]-butane-1,4-diamine ditrifluoroacetic acid;
(589) [4-(7-methoxy-1-trifluoromethyl-[1,2,4]triazolo[4,3-a]quinoxaline-4-ylamino)-butyl]-carbamic acid isopropylester;
(590) N-[4-(7-methoxy-1-trifluoromethyl-[1,2,4]triazolo[4,3-a]quinoxaline-4-ylamino)-butyl]-3-methyl-butyramide;
(591) 3-methyl-pentanoic acid-[4-(7-methoxy-1-trifluoromethyl-[1,2,4]triazolo[4,3-a]quinoxaline-4-ylamino)-butyl]-amide;
(592) $N^1$-(7,8-dimethoxy-1-trifluoromethyl-[1,2,4]triazolo[4,3-a]quinoxaline-4-yl)-butane-1,4-diamine ditrifluoroacetic acid;
(593) N-[4-(7,8-dimethoxy-1-trifluoromethyl-[1,2,4]triazolo[4,3-a]quinoxaline-4-ylamino)-butyl]-3-methyl-butyramide;
(594) [4-(1-ethyl-7,8-dimethoxy-[1,2,4]triazolo[4,3-a]quinoxaline-4-ylamino)-butyl]-carbamic acid-tert-butylester;
(595) $N^1$-(1-ethyl-7,8-dimethoxy-[1,2,4]triazolo[4,3-a]quinoxaline-4-yl)-butane-1,4-diamine ditrifluoroacetic acid;
(596) [4-(1-ethyl-7,8-dimethoxy-[1,2,4]triazolo[4,3-a]quinoxaline-4-ylamino)-butyl]-carbamic acid isopropylester;
(597) N-[4-(1-ethyl-7,8-dimethoxy-[1,2,4]triazolo[4,3-a]quinoxaline-4-ylamino)-butyl]-3-methyl-butyramide;
(598) [4-(1-ethyl-7,8-dimethoxy-[1,2,4]triazolo[4,3-a]quinoxaline-4-ylamino)-butyl]-carbamic acid isobutylester;
(599) [4-(1-isopropyl-7,8-dimethoxy-[1,2,4]triazolo[4,3-a]quinoxaline-4-ylamino)-butyl]-carbamic acid-tert-butylester;
(600) $N^1$-(1-isopropyl-7,8-dimethoxy-[1,2,4]triazolo[4,3-a]quinoxaline-4-yl)-butane-1,4-diamine ditrifluoroacetic acid;
(601) [4-(1-isopropyl-7,8-dimethoxy-[1,2,4]triazolo[4,3-a]quinoxaline-4-ylamino)-butyl]-carbamic acid isopropylester;
(602) [4-(1-isopropyl-7,8-dimethoxy-[1,2,4]triazolo[4,3-a]quinoxaline-4-ylamino)-butyl]-carbamic acid isobutylester;
(603) N-[4-(1-isopropyl-7,8-dimethoxy-[1,2,4]triazolo[4,3-a]quinoxaline-4-ylamino)-butyl]-3-methyl-butyramide;
(604) [4-(1-phenyl-7,8-dimethoxy-[1,2,4]triazolo[4,3-a]quinoxaline-4-ylamino)-butyl]-carbamic acid-tert-butylester;
(605) $N^1$-(1-phenyl-7,8-dimethoxy-[1,2,4]triazolo[4,3-a]quinoxaline-4-yl)-butane-1,4-diamine ditrifluoroacetic acid;
(606) [4-(1-phenyl-7,8-dimethoxy-[1,2,4]triazolo[4,3-a]quinoxaline-4-ylamino)-butyl]-carbamic acid isopropylester;
(607) [4-(1-phenyl-7,8-dimethoxy-[1,2,4]triazolo[4,3-a]quinoxaline-4-ylamino)-butyl]-carbamic acid isobutylester;
(608) N-[4-(1-phenyl-7,8-dimethoxy-[1,2,4]triazolo[4,3-a]quinoxaline-4-ylamino)-butyl]-3-methyl-butyramide;
(610) [4-(1-trifluoromethyl-[1,2,4]triazolo[4,3-a]quinoxaline-4-ylamino)-butyl]-carbamic acid-tert-butylester;
(611) N-(1-trifluoromethyl-[1,2,4]triazolo[4,3-a]quinoxaline-4-yl)-butane-1,4-diamine;
(612) N-[4-(1-trifluoromethyl-[1,2,4]triazolo[4,3-a]quinoxaline-4-ylamino)-butyl]-acetamide;
(613) [4-(1-ethyl-[1,2,4]triazolo[4,3-a]quinoxaline-4-ylamino)-butyl]-carbamic acid-tert-butylester;
(614) $N^1$-(1-ethyl-[1,2,4]triazolo[4,3-a]quinoxaline-4-yl)-butane-1,4-diamine;
(615) [4-(1-isopropyl-[1,2,4]triazolo[4,3-a]quinoxaline-4-ylamino)-butyl]-carbamic acid-tert-butylester;
(616) $N^1$-(1-isopropyl-[1,2,4]triazolo[4,3-a]quinoxaline-4-yl)-butane-1,4-diamine;
(617) [4-(1-phenyl-[1,2,4]triazolo[4,3-a]quinoxaline-4-ylamino)-butyl]-carbamic acid-tert-butylester;
(618) $N^1$-(1-phenyl-[1,2,4]triazolo[4,3-a]quinoxaline-4-yl)-butane-1,4-diamine;
(619) N-[4-(1-phenyl-[1,2,4]triazolo[4,3-a]quinoxaline-4-ylamino)-butyl]-acetamide;
(620) [4-(7-methoxy-1-ethyl-[1,2,4]triazolo[4,3-a]quinoxaline-4-ylamino)-butyl]-carbamic acid-tert-butylester;
(621) $N^1$-(7-methoxy-1-ethyl-[1,2,4]triazolo[4,3-a]quinoxaline-4-yl)-butane-1,4-diamine ditrifluoroacetic acid;
(622) [4-(7-methoxy-1-ethyl-[1,2,4]triazolo[4,3-a]quinoxaline-4-ylamino)-butyl]-3-methyl-butyramide;
(623) [4-(7-methoxy-1-ethyl-[1,2,4]triazolo[4,3-a]quinoxaline-4-ylamino)-butyl]-carbamic acid isopropylester;

(624) [4-(7-methoxy-1-ethyl-[1,2,4]triazolo[4,3-a]quinoxaline-4-ylamino)-butyl]-carbamic acid isobutylester;
(625) [4-(7-methoxy-1-isopropyl-[1,2,4]triazolo[4,3-a]quinoxaline-4-ylamino)-butyl]-carbamic acid-tert-butylester;
(626) $N^1$-(7-methoxy-1-isopropyl-[1,2,4]triazolo[4,3-a]quinoxaline-4-yl)-butane-1,4-diamine ditrifluoroacetic acid;
(627) [4-(1-isopropyl-7-methoxy-[1,2,4]triazolo[4,3-a]quinoxaline-4-ylamino)-butyl]-3-methyl-butyramide;
(628) [4-(1-isopropyl-7-methoxy-[1,2,4]triazolo[4,3-a]quinoxaline-4-ylamino)-butyl]-carbamic acid isopropylester;
(629) [4-(1-isopropyl-7-methoxy-[1,2,4]triazolo[4,3-a]quinoxaline-4-ylamino)-butyl]-carbamic acid isobutylester;
(641) tert-butyl(2-((1-methyl-[1,2,4]triazolo[4,3-a]quinoxaline-4-yl)amino)pentyl)carbamate;
(642) [5-(7,8-dimethoxy-1-methyl-[1,2,4]triazolo[4,3-a]quinoxaline-4-ylamino)-pentyl]-carbamic acid-tert-butylester;
(643) $N^1$-(7,8-dimethoxy-1-methyl-[1,2,4]triazolo[4,3-a]quinoxaline-4-yl)-pentane-1,5-diamine ditrifluoroacetic acid;
(644) [5-(7,8-dimethoxy-1-methyl-[1,2,4]triazolo[4,3-a]quinoxaline-4-ylamino)-pentyl]-carbamic acid isopropylester;
(645) N-[5-(7,8-dimethoxy-1-methyl-[1,2,4]triazolo[4,3-a]quinoxaline-4-ylamino)-pentyl]-2,2-dimethyl-propionamide;
(646) 5-(7,8-dimethoxy-1-methyl-[1,2,4]triazolo[4,3-a]quinoxaline-4-ylamino)-pentanoic acid-tert-butylamide;
(647) 5-(7,8-dimethoxy-1-methyl-[1,2,4]triazolo[4,3-a]quinoxaline-4-ylamino)-pentanoic acid isopropylamide;
(648) 5-(7,8-dimethoxy-1-methyl-[1,2,4]triazolo[4,3-a]quinoxaline-4-ylamino)-pentanoic acid isobutylamide;
(649) 5-(7,8-dimethoxy-1-methyl-[1,2,4]triazolo[4,3-a]quinoxaline-4-ylamino)-pentanoic acid-(2-methyl-butyl)-amide;
(650) 5-(7,8-dimethoxy-1-methyl-[1,2,4]triazolo[4,3-a]quinoxaline-4-ylamino)-pentanoic acid-(furan-2-yl-methyl)-amide;
(651) 5-(7,8-dimethoxy-1-methyl-[1,2,4]triazolo[4,3-a]quinoxaline-4-ylamino)-pentanoic acid benzylamide;
(652) 5-(7,8-dimethoxy-1-methyl-[1,2,4]triazolo[4,3-a]quinoxaline-4-ylamino)-pentanoic acid-(1H-pyrrole-2-yl-methyl)-amide;
(653) 5-(7-methoxy-1-methyl-[1,2,4]triazolo[4,3-a]quinoxaline-4-ylamino)-pentanoic acid-tert-butylamide;
(654) 5-(7-methoxy-1-methyl-[1,2,4]triazolo[4,3-a]quinoxaline-4-ylamino)-pentanoic acid isopropylamide;
(655) 5-(7-methoxy-1-methyl-[1,2,4]triazolo[4,3-a]quinoxaline-4-ylamino)-pentanoic acid isobutylamide;
(656) 5-(7-methoxy-1-methyl-[1,2,4]triazolo[4,3-a]quinoxaline-4-ylamino)-pentanoic acid-(2-methyl-butyl)-amide;
(657) 5-(7-methoxy-1-methyl-[1,2,4]triazolo[4,3-a]quinoxaline-4-ylamino)-pentanoic acid-(furan-2-yl-methyl)-amide;
(658) 5-(7-methoxy-1-methyl-[1,2,4]triazolo[4,3-a]quinoxaline-4-ylamino)-pentanoic acid-benzamide;
(659) 5-(1-methyl-[1,2,4]triazolo[4,3-a]quinoxaline-4-ylamino)-pentanoic acid isopropylamide;
(660) 5-(1-methyl-[1,2,4]triazolo[4,3-a]quinoxaline-4-ylamino)-pentanoic acid isobutylamide;
(661) 6-(1-methyl-[1,2,4]triazolo[4,3-a]quinoxaline-4-ylamino)-hexanoic acid isopropylamide; and
(662) 6-(1-methyl-[1,2,4]triazolo[4,3-a]quinoxaline-4-ylamino)-hexanoic acid isobutylamide.

5. A preparation method of the compound represented by formula 1 comprising the following steps, as shown in reaction formula 1 below:
preparing the compound represented by formula 4 by reacting the compound represented by formula 2 with the compound represented by formula 3 (step 1); and
preparing the compound represented by formula 1 by reacting the compound represented by formula 4 prepared in step 1 above with the compound represented by formula 5 (step 2):

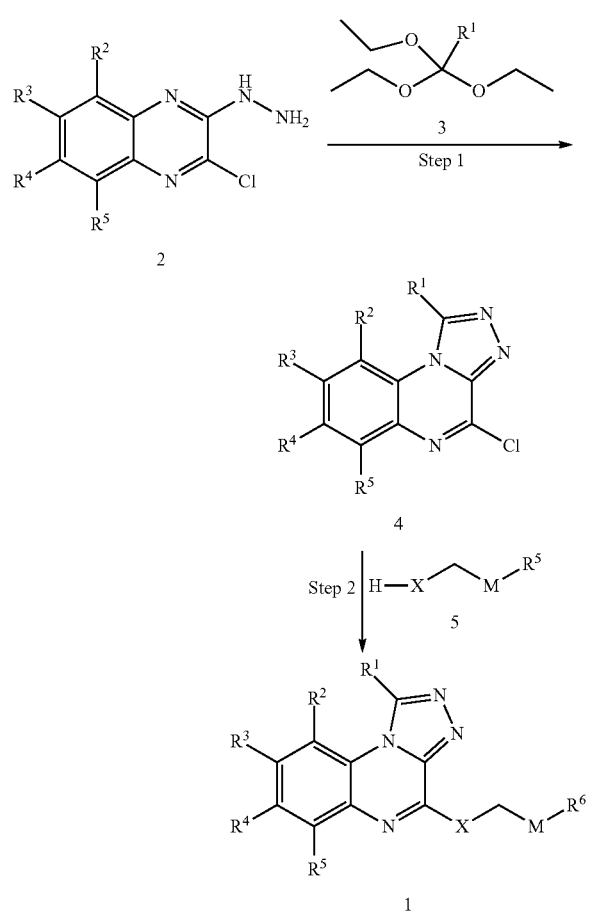

[Reaction Formula 1]

wherein,
$R^1$ is $C_{1-20}$ straight or branched alkyl nonsubstituted or substituted with one or more halogens, or $C_{6-20}$ aryl;
$R^2$ is hydrogen, $C_{1-20}$ straight or branched alkyl, or $C_{1-20}$ straight or branched alkoxy;
$R^3$ is hydrogen, nitro, halogen, nonsubstituted or substituted $C_{1-20}$ straight or branched alkyl, nonsubstituted or substituted $C_{1-20}$ straight or branched alkoxy, 5-10 membered heteroaryl nonsubstituted or substituted with one or more methyl groups containing one or more heteroatoms selected from the group consisting of N, O and S,

471

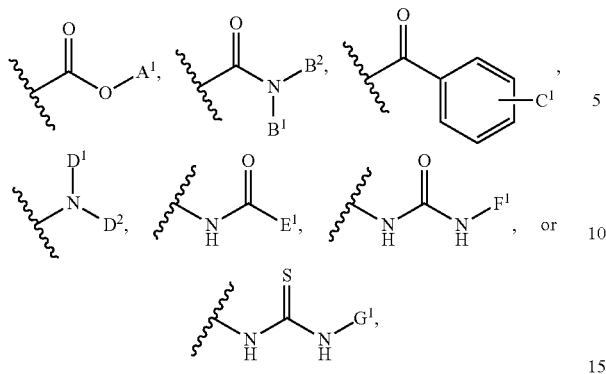

which forms 6 membered cycloalkyl containing one or more heteroatoms selected from the group consisting of S and O along with $R^4$, wherein, the substituted $C_{1-20}$ straight or branched alkyl and the substituted $C_{1-20}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, $A^1$ is hydrogen, or $C_{1-20}$ straight or branched alkyl, $B^1$ and $B^2$ are independently hydrogen, $C_{1-20}$ straight or branched alkyl, $diC_{1-3}$ straight or branched alkylamino $C_{1-3}$ straight or branched alkyl, or $C_{6-10}$ aryl, and $B^1$ and $B^2$ are linked to each other to form 5-10 membered heterocycloalkyl nonsubstituted or substituted with one or more benzyl groups containing one or more heteroatoms selected from the group consisting of N, O and S, $C^1$ is hydrogen, $C_{1-20}$ straight or branched alkyl, or $C_{1-20}$ straight or branched alkoxy, $D^1$ and $D^2$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl, $E^1$ is $C_{1-20}$ straight or branched alkyl, or $C_{6-10}$ aryl $C_{1-5}$ straight or branched alkyl, $F^1$ is $C_{1-20}$ straight or branched alkyl, or $C_{6-10}$ aryl, $G^1$ is $C_{1-20}$ straight or branched alkyl, or $C_{6-10}$ aryl;

$R^4$ is hydrogen, hydroxy, halogen, nitro, $C_{1-20}$ straight or branched alkyl nonsubstituted or substituted with one or more =S groups, $C_{1-20}$ straight or branched alkylsulfanyl nonsubstituted or substituted with one or more oxo (=O) groups, $C_{1-20}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-20}$ straight or branched alkoxy,

472

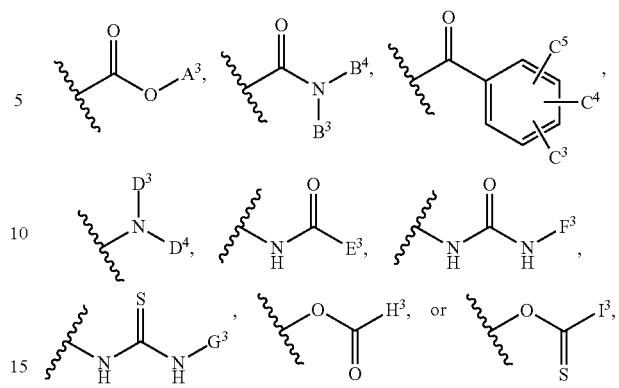

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-20}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

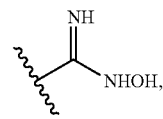

$C_{1-5}$ straight or branched alkoxycarbonyl, and 5-8 membered heteroaryl nonsubstituted or substituted with one or more N groups, $A^3$ is hydrogen, or $C_{1-20}$ straight or branched alkyl, $B^3$ and $B^4$ are independently hydrogen, $C_{1-20}$ straight or branched alkyl, $diC_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-20}$ straight or branched alkyl, or $C_{1-20}$ straight or branched alkoxy, $D^3$ and $D^4$ are independently hydrogen, hydroxy, $C_{1-20}$ straight or branched alkyl saturated or containing one or more carbon=carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-20}$ straight or branched alkyl, or $C_{6-10}$ aryl $C_{1-5}$ straight or branched alkyl, $F^3$ is $C_{1-20}$ straight or branched alkyl, or $C_{6-10}$ aryl, $G^3$ is $C_{1-20}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is $diC_{1-3}$ straight or branched alkylamino;

$R^5$ is hydrogen, halogen, $C_{1-20}$ straight or branched alkyl nonsubstituted or substituted with one or more halogens, or $C_{1-20}$ straight or branched alkoxy;

$R^6$ is

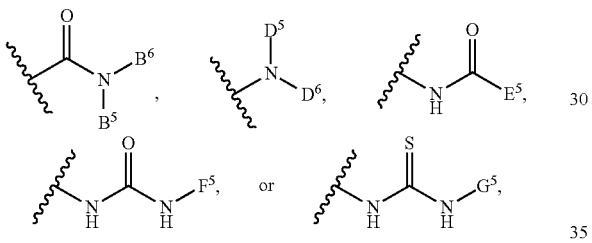

$B^5$ and $B^6$ are independently hydrogen, $C_{1-20}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, $E^5$ is $C_{1-20}$ straight or branched alkyl saturated or containing one or more carbon=carbon unsaturated bonds, $C_{1-20}$ straight or branched alkoxy saturated or containing one or more carbon=carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-20}$ straight or branched alkylsulfanyl, nonsubstituted or substituted $C_{6-10}$ aryl, $diC_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-20}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

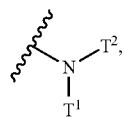

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-20}$ straight or branched alkyl, $C_{3-10}$ cycloalkyl, or $C_{6-10}$ aryl nonsubstituted or substituted with one or more halogens, and $G^5$ is $C_{1-20}$ straight or branched alkyl;

M is $C_{1-20}$ straight or branched alkylene; and

X is —NH—.

6. A preparation method of the compound represented by formula 1 comprising the following steps, as shown in reaction formula 2 below:

preparing the compound represented by formula 8 by reacting the compound represented by formula 7 with the compound represented by formula 5 (step 1);

preparing the compound represented by formula 9 by reacting the compound represented by formula 8 prepared in step 1 above with hydrazine hydrate (step 2); and preparing the compound represented by formula 1 by reacting the compound represented by formula 9 prepared in step 2 above with the compound represented by formula 3 (step 3):

[Reaction Formula 2]

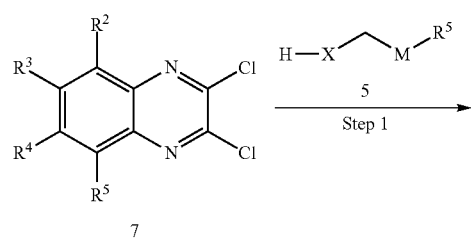

-continued

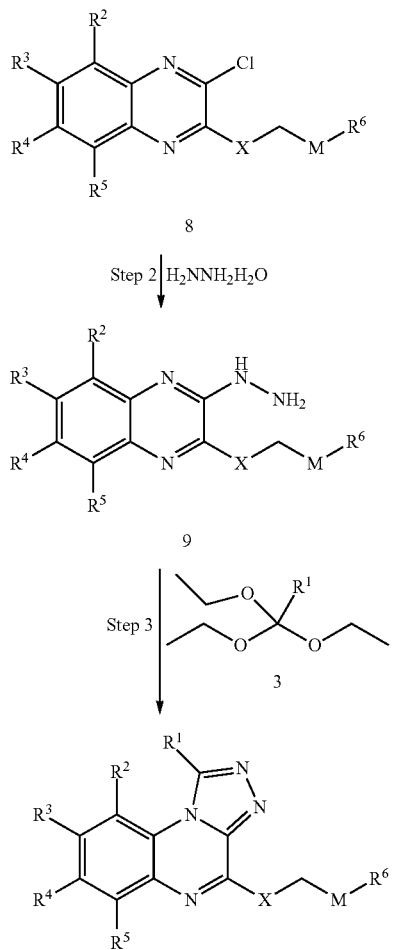

wherein,

R¹ is $C_{1-20}$ straight or branched alkyl nonsubstituted or substituted with one or more halogens, or $C_{6-20}$ aryl;

R² is hydrogen, $C_{1-20}$ straight or branched alkyl, or $C_{1-20}$ straight or branched alkoxy;

R³ is hydrogen, nitro, halogen, nonsubstituted or substituted $C_{1-20}$ straight or branched alkyl, nonsubstituted or substituted $C_{1-20}$ straight or branched alkoxy, 5-10 membered heteroaryl nonsubstituted or substituted with one or more methyl groups containing one or more heteroatoms selected from the group consisting of N, O and S, -continued

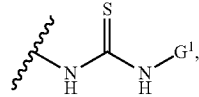

which forms 6 membered cycloalkyl containing one or more heteroatoms selected from the group consisting of S and O along with R⁴, wherein, the substituted $C_{1-20}$ straight or branched alkyl and the substituted $C_{1-20}$ straight or branched alkoxy can be independently substituted with one or more substituents selected from the group consisting of halogen, $C_{1-3}$ straight or branched alkoxy, 5-10 membered heterocycloalkyl containing one or more heteroatoms selected from the group consisting of N, O and S, and $C_{6-10}$ aryl nonsubstituted or substituted with one or more nitro groups, A¹ is hydrogen, or $C_{1-20}$ straight or branched alkyl, B¹ and B² are independently hydrogen, $C_{1-20}$ straight or branched alkyl, $diC_{1-3}$ straight or branched alkylamino $C_{1-3}$ straight or branched alkyl, or $C_{6-10}$ aryl, and B¹ and B² are linked to each other to form 5-10 membered heterocycloalkyl nonsubstituted or substituted with one or more benzyl groups containing one or more heteroatoms selected from the group consisting of N, O and S, C¹ is hydrogen, $C_{1-20}$ straight or branched alkyl, or $C_{1-20}$ straight or branched alkoxy, D¹ and D² are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl, E¹ is $C_{1-20}$ straight or branched alkyl, or $C_{6-10}$ aryl $C_{1-5}$ straight or branched alkyl, F¹ is $C_{1-20}$ straight or branched alkyl, or $C_{6-10}$ aryl, G¹ is $C_{1-20}$ straight or branched alkyl, or $C_{6-10}$ aryl;

R⁴ is hydrogen, hydroxy, halogen, nitro, $C_{1-20}$ straight or branched alkyl nonsubstituted or substituted with one or more =S groups, $C_{1-20}$ straight or branched alkylsulfanyl nonsubstituted or substituted with one or more oxo (=O) groups, $C_{1-20}$ straight or branched alkylsulfonyl, 5-10 membered heterocycloalkyloxy nonsubstituted or substituted with one or more $C_{1-5}$ straight or branched alkoxycarbonyl containing one or more heteroatoms selected from the group consisting of N, O and S, nonsubstituted or substituted 5-10 membered heteroaryl containing one or more heteroatoms selected from the group consisting of N, O and S, nonsubstituted or substituted $C_{1-20}$ straight or branched alkoxy,

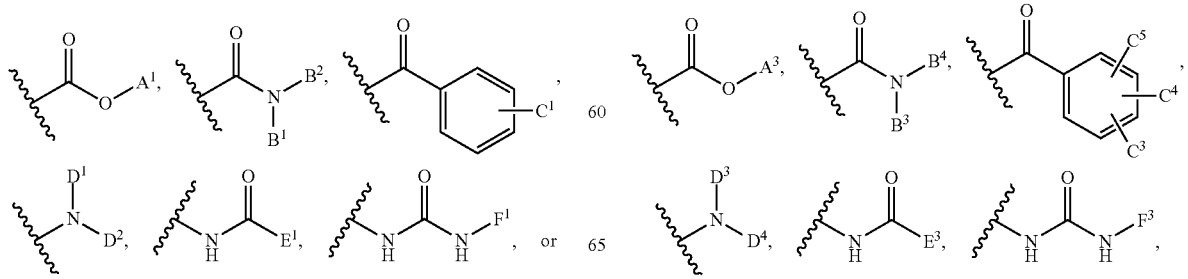

-continued

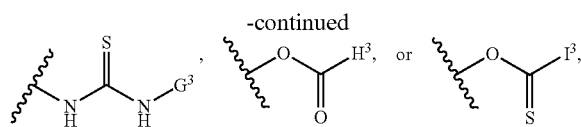

wherein, the substituted 5-10 membered heteroaryl can be substituted with one or more substituents selected from the group consisting of $C_{1-3}$ straight or branched alkyl, $C_{1-3}$ straight or branched alkoxy and $C_{1-3}$ straight or branched alkoxy $C_{1-3}$ straight or branched alkyl, wherein, the substituted $C_{1-20}$ straight or branched alkoxy can be substituted with one or more substituents selected from the group consisting of halogen, cyano, $C_{1-3}$ straight or branched alkoxy, nonsubstituted or substituted 5-10 membered heterocycloalkyl containing one or more heteroatoms selected from the group consisting of N, O and S, and nonsubstituted or substituted $C_{6-10}$ aryl, wherein, the substituted 5-10 membered heterocycloalkyl and the substituted $C_{6-10}$ aryl can be independently substituted with one or more substituents selected from the group consisting of cyano,

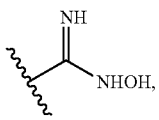

$C_{1-5}$ straight or branched alkoxycarbonyl, and 5-8 membered heteroaryl nonsubstituted or substituted with one or more N groups, $A^3$ is hydrogen, or $C_{1-20}$ straight or branched alkyl, $B^3$ and $B^4$ are independently hydrogen, $C_{1-20}$ straight or branched alkyl, di$C_{1-3}$ straight or branched alkylamino $C_{1-3}$ straight or branched alkyl, nonsubstituted or substituted $C_{6-10}$ aryl, nonsubstituted or substituted $C_{6-10}$ aryl $C_{1-3}$ straight or branched alkyl, and $B^3$ and $B^4$ are linked to each other to form 5-10 membered heterocycloalkyl nonsubstituted or substituted with one or more benzyl groups containing one or more heteroatoms selected from the group consisting of N, O and S, wherein, the substituted $C_{6-10}$ aryl can be substituted with one or more substituents selected from the group consisting of amine, halogen, $C_{1-5}$ straight or branched alkyl and $C_{1-5}$ straight or branched alkoxy, $C^3$, $C^4$ and $C^5$ are independently hydrogen, amine, halogen, $C_{1-20}$ straight or branched alkyl, or $C_{1-20}$ straight or branched alkoxy, $D^3$ and $D^4$ are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, and $D^3$ and $D^4$ are linked to each other to form 5-10 membered heteroaryl containing one or more heteroatoms selected from the group consisting of N, O and S, or 5-10 membered heterocycloalkyl fused with 5 membered heteroaryl nonsubstituted or substituted with one or more methyl groups or containing one S group and one or more heteroatoms selected from the group consisting of N, O and S, $E^3$ is $C_{1-20}$ straight or branched alkyl, or $C_{6-10}$ aryl $C_{1-5}$ straight or branched alkyl, $F^3$ is $C_{1-20}$ straight or branched alkyl, or $C_{6-10}$ aryl, $G^3$ is $C_{1-20}$ straight or branched alkyl, or $C_{6-10}$ aryl, $H^3$ is $C_{6-10}$ aryl, 5-10 membered heterocycloalkyl containing one or more heteroatoms selected from the group consisting of N, O and S, or 5-10 membered heteroaryl nonsubstituted or substituted with one or more methyl groups containing one or more heteroatoms selected from the group consisting of N, O and S, $I^3$ is di$C_{1-3}$ straight or branched alkylamino;

$R^5$ is hydrogen, halogen, $C_{1-20}$ straight or branched alkyl nonsubstituted or substituted with one or more halogens, or $C_{1-20}$ straight or branched alkoxy;

$R^6$ is

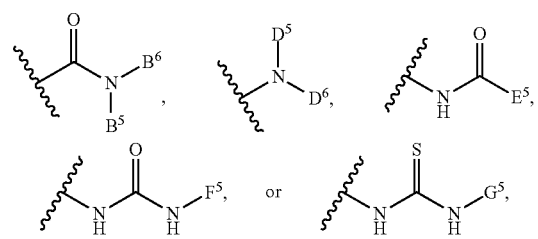

$B^5$ and $B^6$ are independently hydrogen, $C_{1-20}$ straight or branched alkyl, $C_{6-10}$ aryl $C_{1-3}$ straight or branched alkyl, or 5-10 membered heteroaryl $C_{1-3}$ straight or branched alkyl containing one or more heteroatoms selected from the group consisting of N, O and S, $D^5$ and $D^6$ are independently hydrogen, hydroxy, $C_{1-20}$ straight or branched alkyl saturated or containing one or more carbon≡carbon unsaturated bonds, $C_{1-20}$ straight or branched alkyl nonsubstituted or substituted with one or more cyano groups, or $C_{1-20}$ straight or branched alkylsulfonyl nonsubstituted or substituted with one or more halogens, $E^5$ is $C_{1-20}$ straight or branched alkyl saturated or containing one or more carbon≡carbon unsaturated bonds, $C_{1-20}$ straight or branched alkoxy saturated or containing one or more carbon=carbon unsaturated bonds, $C_{3-10}$ cycloalkyloxy, $C_{3-10}$ cycloalkyl $C_{1-3}$ straight or branched alkyl, $C_{3-10}$ cycloalkyl, $C_{6-10}$ aryloxy, $C_{6-10}$ aryl $C_{1-3}$ straight or branched alkoxy, $C_{1-20}$ straight or branched alkylsulfanyl, nonsubstituted or substituted $C_{6-10}$ aryl, di$C_{1-3}$ straight or branched alkylamino, 5-10 membered heterocycloalkyl containing one or more heteroatoms selected from the group consisting of N, O and S, or nonsubstituted or substituted 5-10 membered heteroaryl containing one or more N groups, wherein, the substituted $C_{1-20}$ straight or branched alkyl can be substituted with one or more substituents selected from the group consisting of hydroxy, halogen, $C_{1-3}$ straight or branched alkoxy, $C_{1-3}$ straight or branched alkylcarbonyloxy, $C_{1-3}$ straight or branched alkoxycarbonyl, hydroxycarbonyl, $C_{6-10}$ aryl nonsubstituted or substituted with one or more hydroxyl groups, 5-10 membered heteroaryl containing one or more heteroatoms selected from the group consisting of N, O and S, and

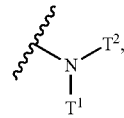

$T^1$ and $T^2$ are independently hydrogen, $C_{1-5}$ straight or branched alkyl, $C_{1-5}$ straight or branched alkoxycarbonyl, $C_{1-5}$ straight or branched alkylcarbonyl nonsubstituted or substituted with one or more halogens or hydroxyl groups, and $T^1$ and $T^2$ are linked to each other to form heterocycloalkyl nonsubstituted or substituted with one or more hydroxyl groups or $C_{1-3}$ straight or branched alkyl groups containing one S group and one or more heteroatoms selected from the group consisting of N, O and S, wherein, the substituted $C_{6-10}$ aryl and the substituted 5-10 membered heteroaryl can be independently substituted with one or more substituents selected from the group consisting of halogen, nitro, $C_{1-5}$ straight or branched alkyl and $C_{1-5}$ straight or branched alkoxy, $F^5$ is $C_{1-20}$ straight or branched alkyl, $C_{3-10}$ cycloalkyl, or $C_{6-10}$ aryl nonsubstituted or substituted with one or more halogens, $G^5$ is $C_{1-20}$ straight or branched alkyl;

M is $C_{1-20}$ straight or branched alkylene; and

X is —NH—.

\* \* \* \* \*